(12) United States Patent
Tomalia et al.

(10) Patent No.: US 7,985,424 B2
(45) Date of Patent: *Jul. 26, 2011

(54) DENDRITIC POLYMERS WITH ENHANCED AMPLIFICATION AND INTERIOR FUNCTIONALITY

(75) Inventors: Donald A. Tomalia, Midland, MI (US); Douglas R. Swanson, Mt. Pleasant, MI (US); Baohua Huang, Mt. Pleasant, MI (US); Veera Reddy Pulgam, Mt. Pleasant, MI (US); Joseph R. Heinzelmann, Saginaw, MI (US); Sonke Svenson, Midland, MI (US); Lori A. Reyna, Midland, MI (US); Michael A. Zhuravel, Mt. Pleasant, MI (US); Abhay Singh Chauhan, Mt. Pleasant, MI (US); Cordell R. DeMattei, Mt. Pleasant, MI (US)

(73) Assignee: Dendritic Nanotechnologies Inc., Midland, MI (US)

( * ) Notice: Subject to any disclaimer, the term of this patent is extended or adjusted under 35 U.S.C. 154(b) by 572 days.

This patent is subject to a terminal disclaimer.

(21) Appl. No.: 11/630,044

(22) PCT Filed: Dec. 21, 2005

(86) PCT No.: PCT/US2005/047635
§ 371 (c)(1),
(2), (4) Date: Dec. 15, 2006

(87) PCT Pub. No.: WO2006/115547
PCT Pub. Date: Nov. 2, 2006

(65) Prior Publication Data
US 2007/0298006 A1 Dec. 27, 2007

Related U.S. Application Data

(63) Continuation-in-part of application No. PCT/US2005/013864, filed on Apr. 20, 2005.

(60) Provisional application No. 60/563,659, filed on Apr. 20, 2004.

(51) Int. Cl.
*A61K 9/14* (2006.01)

(52) U.S. Cl. .......................... 424/486; 424/400; 528/480

(58) Field of Classification Search ................... 424/486, 424/400; 428/480
See application file for complete search history.

(56) References Cited

U.S. PATENT DOCUMENTS

| | | | |
|---|---|---|---|
| 4,568,737 A | 2/1986 | Tomalia et al. | |
| 4,587,329 A | 5/1986 | Tomalia et al. | |
| 4,694,064 A | 9/1987 | Tomalia et al. | |
| 5,338,532 A | 8/1994 | Tomalia et al. | |
| 5,527,524 A | 6/1996 | Tomalia et al. | |
| 5,773,527 A | 6/1998 | Tomalia et al. | |
| 5,919,442 A | 7/1999 | Yin et al. | |
| 6,025,462 A * | 2/2000 | Wang et al. | 528/377 |
| 6,410,680 B1 * | 6/2002 | Kubota | 528/310 |

FOREIGN PATENT DOCUMENTS

| | | |
|---|---|---|
| CA | 2363202 | 9/2000 |
| EP | A 0 271 180 | 6/1988 |
| WO | 9534595 A1 | 12/1995 |
| WO | 9615778 A1 | 5/1996 |
| WO | WO96/12754 | 5/1996 |
| WO | WO97/10281 | 3/1997 |
| WO | WO98/24831 | 6/1998 |
| WO | 0072851 A1 | 12/2000 |
| WO | WO03/033027 | 4/2003 |
| WO | WO2005/100450 | 10/2005 |

OTHER PUBLICATIONS

Balogh L et al., J. Amer. Chem. Soc. US 120(29), 1998, pp. 7355-7356.
Yin, R. et al.,Architectural Copolymers: Rod-Shapes, Cylindrical Dendrimers: J. Am. Chem. Soc. 1998, 120, pp. 2678-2679.
Dave, Paritosch R., et al., Preparation of 'cage molecule' based polyazido core units for dendrimer synthesis: Tetrahedron Letters 2004, 45, pp. 2159-2162.
Lapienis, G. et al., Reaction of Oligoalcohols with Diepoxides: An easy, one-pot way . . . : J. Polymer Sci. Part A: Polymer Chemistry, 2004, 42, 1576-1598.
Xu, Donogmei, et al., Study on dendritic poly(amine-amide) as epoxy hardner: Jingxi Shiyou Huagong, 2004, 5, 21-24 (pub. Sep. 2004) Eng. Abst.
Xu, Dong-Mei, et al., Synthesis of dendritic epoxide hardner containing multiamino groups . . . :, (2004).
Tang, Li-Ming, et al., Polymer J., 37(4), pp. 255-261 (2005).
Xu, Dongmei, et al., Tetrahedron Letters, 46, pp. 2503-2505 (2005).

* cited by examiner

*Primary Examiner* — Edward J Cain
(74) *Attorney, Agent, or Firm* — Technology Law PLLC; Karen L. Kimble

(57) ABSTRACT

Dendritic polymers with enhanced amplification and interior functionality are disclosed. These dendritic polymers are made by use of fast, reactive ring-opening chemistry (or other fast reactions) combined with the use of branch cell reagents in a controlled way to rapidly and precisely build dendritic structures, generation by generation, with cleaner chemistry, often single products, lower excesses of reagents, lower levels of dilution, higher capacity method, more easily scaled to commercial dimensions, new ranges of materials, and lower cost. The dendritic compositions prepared have novel internal functionality, greater stability (e.g., thermal stability and less or no reverse Michael's reaction), and reach encapsulation surface densities at lower generations. Unexpectedly, these reactions of polyfunctional branch cell reagents with polyfunctional cores do not create cross-linked materials. Such dendritic polymers are useful as demulsifiers for oil/water emulsions, wet strength agents in the manufacture of paper, proton scavengers, polymers, nanoscale monomers, calibration standards for electron microscopy, making size selective membranes, and agents for modifying viscosity in aqueous formulations such as paint. When these dendritic polymers have a carried material associated with their surface and/or interior, then these dendritic polymers have additional properties for carrying materials due to the unique characteristics of the dendritic polymer, such as for drug delivery, transfection, and diagnostics.

86 Claims, 25 Drawing Sheets

Branch Cell Structure Resulting from a Tetra Glycidyl Ether

(A)

(B)

Where: $N_b = 3$ (A) (B)

DENDRITIC POLYMERS WITH ENHANCED AMPLIFICATION AND INTERIOR FUNCTIONALITY

CROSS REFERENCE TO RELATED APPLICATIONS

This application is a 371 of PCT/US05/47635, filed Dec. 21, 2005, which is a continuation-in-part of and claims benefit of PCT/US05/13864, filed Apr. 20, 2005, which claims benefit of US Provisional Application 60/563,659, Apr. 20, 2004.

FEDERALLY SPONSORED RESEARCH STATEMENT

This invention was made with U.S. Government support under DAAL-01-1996-02-044 and W911NF-04-2-0030 awarded by The Army Research Laboratory Contract by the U.S. Department of Defense. The U.S. Government has certain rights in this invention.

BACKGROUND OF THE INVENTION

1. Field of the Invention

The present invention concerns the field of dendritic polymers where dendrimers are an example of the preferred polymers. These polymers have void spaces that may entrap molecules and their surface functionalities may undergo further reactions.

2. Description of Related Art

Branched Polymer Ring-Opening Reactions

Various ring-opening reactions to prepare branched polymer systems are known. A few of these processes are described below.

Polymerizations using ring-opening is well known, particularly with using cyclic ethers, amides, aziridines, sulfides, siloxanes and others by either anionic, cationic or other mechanisms. (See George Odian, *Principles of Polymerization*, pub. John Wiley and Sons, 1993, Chapter 7.) However, use of ring-opening polymerizations in the synthesis of highly branched polymers is less well known. One such area where work has been done is in the use of ring-opening polymerizations in the synthesis of various hyperbranched polymers. In most of the cases the ring-opening polymerization is of the traditional tppe, resulting in random hyperbranched polymers with broad polydispersity [see D. A. Tomalia and J. M. J. Fréchet, *J. Polym. Sci. Part A: Polym. Chem.*, 40, 2719-2718 (2002)].

One of the first examples of ring-opening polymerizations to prepare a hyperbranched polymer was the work of Odian and Tomalia [P. A. Gunatillake, G. Odian, D. A. Tomalia, *Macromolecules*, 21, 1556 (1989)] where hyperbranched materials were made from oxazolines.

Ring-opening has been used in the generation of linear or comb-branched polyethers as single ion conductors [X. G. Sun, J. B. Kerr, C. L. Reeder, G. Liu, Y. Han, *Macromolecules*, 37(14), 5133-5135 (2004)].

Ring-opening polymerization of 2-hydroxymethyloxetane under basic conditions was attempted to obtain hyperbranched polyethers [Y. H. Kim, *J. Polym. Sci., Polym. Chem.*, 36, 1685 (1998)].

D. A. Tomalia's work on ring-opening polymerization of oxazolines achieved hyperbranched PEOX or PEI polymers (see U.S. Pat. Nos. 4,690,985, 5,631,329, and 5,773,527).

Hyperbranched dendritic macromolecules have been made using a multi-branching polymerization ("MBP") approach with an initiator at the core, involving ring-opening polymerization including, for example, Pd-catalyzed ring-opening polymerization of cyclic carbamates in the presence of an initiator using oxazinones [M. Suzuki; A. In, T. Saegusa, *Macromolecules*, 25, 7071-7072 (1992), and M. Suzuki, S. Yoshida; K. Shiraga, T. Saegusa, *Macromolecules*, 31, 1716-19 (1998)].

Epoxide ring-opening, involving an $AB_2$ type monomer polymerization, is initiated by addition of a catalytic amount of an initiator, such as hydroxide ion, and goes through a novel propagation mode distinct from other hyperbranched polymer methods involving acid- or base-catalyzed reactions [H. T. Chang, J. M. J. Fréchet, *J. Am. Chem. Soc.*, 121, 2313-2314 (1999)]. $AB_2$ monomer type glycidols are polymerized to hyperbranched "polyglycerols" by controlled anionic ring-opening polymerization to polydispersities below 1.5 [A. Sunder, R. Hanselmann, H. Frey, R. Mulhaupt, *Macromolecules*, 32, 4240-4246 (1999)]. Cationic cyclopolymerization of dianhydro-D-mannitol is used to produce hyperbranched carbohydrate polymers [T. Imai, T. Satoh, H. Kaga, N. Kaneko, T. Kakuchi, *Macromolecules*, 36, 6359-6363 (2003); T. Imai, T. Satoh, H. Kaga, N. Kaneko, T. Kakuchi, *Macromolecules*, 37, 3113-3119 (2004)].

Hyperbranched polymers are obtained by combining ring-opening polymerization and some features of self condensing vinyl polymerization ("SCVP"), ring-opening polymerization of caprolactone to give hyperbranched polyesters having a polydispersity of about 3.2 [M. Liu, N. Vladimirov, J. M. J. Fréchet, *Macromolecules*, 32, 6881-6884 (1999)].

Ring-opening polymerization of bis(hydroxymethyl)caprolactones gave hyperbranched polyesters [M. Trollsas, P. Lowenhielm, V. Y. Lee, M. Moller, R. D. Miller, J. L. Hedrick, *Macromolecules*, 32, 9062-9066 (1999)].

Cationic ring-opening polymerization of ethyl hydroxymethyl oxetanes resulted in hyperbranched polyethers, polydispersities in the range of 1.33-1.61 [Y. Mai, Y. Zhou, D. Yan, H. Lu, *Macromolecules*, 36, 9667-9669 (2003)].

3-Ethyl-3-(hydroxymethyl)oxetane ring-opening is used to generate hyperbranched polyethers [H. Magnusson, E. Malmstrom, A. Hult, *Macromolecules*, 34, 5786-5791 (2001)].

Dendritic polypeptides were obtained by ring-opening polymerization of N-carboxyanhydrides. The method involves repetitive sequences of N-carboxyanhydride ring-opening and end-coupling reactions. This process results in polymeric regions with a statistically driven average chain length per branch, having no precise lengths, and results in a polymer with typical polydispersities of 1.2-1.5.

Precise Dendrimer Ring-Opening Reactions

Polysulfide dendrimers can be formed by reacting a polythiol under basic conditions with epichlorosulfide to form polyepisulfides (see U.S. Pat. Nos. 4,558,120, and 4,587,329). These same patents also discuss the preparation of a polyaminosulfide dendrimer using a reaction of a polyamino core with an excess of ethylene sulfide to form a polysulfide followed by reaction with excess aziridine to form further generations.

Addition of N-tosyl aziridine is discussed as a way to create a partially protected dendrimer surface (U.S. Pat. Nos. 4,361, 337; 4,587,329; and 4,568,737) and is extended to azetidine derivatives.

Precise Dendrimer Ring-Opening Reactions for Attachment of Surface Groups

Ring-opening reactions are discussed as a way to add terminal groups. For example, U.S. Pat. No. 4,568,737 discloses the use of oxiranes to create a polyol surface on a dendrimer.

Processes for Precise Dendrimer Structures

Many specific reactions have been used to create a wide range of precise dendrimer structures. These reactions typically define a core ("C"), branch structure type ("BR") and terminal functionality ("TF"). The synthesis of precise dendrimer structures has been performed using two broad approaches that have been categorized as "convergent synthesis" and "divergent synthesis" [*Dendrimers and other Dendritic Polymers*, eds. J. M. J. Fréchet, D. A. Tomalia, pub. John Wiley and Sons, (2001)]. Within these broad categories there are further variations regarding branch cell construction (i.e., in situ and preformed) or dendron anchoring type construction.

One of the earliest published uses of branch cell reagents involved coupling preformed branch cells around a core to form low molecular weight arborol structures [G. R. Newkome, Z.-Q. Yao, G. R. Baker, V. K. Gupta, *J. Org. Chem.*, 50, 2003 (1985)]. Poly(thioether)dendrimers were synthesized using protected, preformed branch cell reagents based on a pentaerythritol core; $N_c$-4 and 4-acetothiomethyl-2,6,7-trioxabicyclo[2.2.2]octane; $N_b$=3. In this case a protected branch cell reagent was used in the building of the dendrimer branch structure, which requires chemical deprotection as an added step to rapidly build structure. Although the reagent used is a polycyclic type ether (i.e., orthoester), the ether ring is not strained and does not ring-open during polymerization.

Steric Effects in Traditional Small Molecule Chemistry

Steric effects, as defined in small molecule chemistry, are due to the volume of sub-nanoscale space (i.e., 0.05-1 nm) that all fundamental small molecule "building block components" (i.e. atoms, functional groups, hydrocarbon scaffolding, etc.) occupy and their relationship to each other in critical reaction and assembly events. The effect that their relative sizes have on reactivity, displacements, substitutions, chirality, associations, assemblies, specific product formation and attainable architectures have always remained issues of very high importance both in the academic as well as commercial realms. For example the steric effect that decreases reactivity is called "steric hindrance" [See P. Y. Bruice, *Organic Chemistra*, $2^{nd}$ Ed. (1998), p 362, Prentice Hall]. Steric hindrance results from groups getting in the way at a reaction site. Classical examples include the "neopentyl effect", wherein the relative reactivities of increasingly hindered alkyl halides to $S_{N2}$ reactions are increasingly suppressed to a point that a tertiary alkyl halide (i.e. neopentyl bromide) is too slow to measure. It is not just the number of alkyl groups attached to the carbon undergoing nucleophilic attack that determines the reaction rate; the relative sizes of the alkyl groups are also very important.

Cram's Rule is another classical example of a small molecule steric effect. While not wishing to be bound by theory, it is believed that steric effects control the stereo selective reactivity at a carbonyl oxygen resulting in chiral introduction. Cram's Rule states that a nucleophile approaches a carbonyl along the smallest substituent alignment. The largest group aligns itself anti to the carbonyl group to minimize the steric effect such that the nucleophile preferentially attacks from the side of the small substituent. [See D. J. Cram, A. Elhafez, *J. Am. Chem. Soc.* 74, 5828 (1952).]

These above brief examples not only portend the possibility but also the importance that such analogous "steric effects" may offer if discovered and defined for critical construction components at the nanoscale level, (i.e. 1-100 nm). The nanoscale rules for these N-SIS effects are virtually unknown. How N-SIS relates to this invention is described in the Detailed Description of this specification.

Poly(amidoamine) Dendrimer ("PAMAM") Synthesis

Some of the difficulties in the synthesis of dendrimers are inherent in the methods used to make them. For example the preparation of poly(amidoamine) ("PAMAM") dendrimers, one of the key compositional families of these dendritic polymers, currently focuses on Michael addition chemistry with in situ branch cell formation [*Dendrimers and other Dendritic Polymers*, eds. J. M. J. Fréchet, D. A. Tomalia, pub. John Wiley and Sons, (2001), Chapter 25]. The usual process includes an amidation step which involves slow chemistry, long reaction times and non-differentiated difunctional intermediates. These circumstances force the process to require high dilutions resulting in low capacities and high costs, particularly at higher generations. Additionally, PAMAM dendrimers, due to their specific amide structures have access to low energy routes to degradation through reverse Michael addition reactions and hydrolysis reactions.

Clearly, it would be desirable to find a process to make precise dendrimer structures with a faster reaction time, easier separation with fewer by-products, and lower cost of manufacture than that presently used. Additionally, if the dendrimers were more stable and easier to scale, that also would be desired. Such improved characteristics and properties could also provide additional unique uses of these dendritic polymers otherwise not available.

BRIEF SUMMARY OF THE INVENTION

The dendritic polymer structures of the present invention possess several unique components that manifest surprising properties (compared to traditional dendritic structures) and utilize unique ring-opening processes for their preparation.

A structure for these dendritic polymers is shown by Formula (I) below:

Formula (I)

$$[C]\underset{[IF]_q}{\overset{[FF]_x}{\text{—}}}[BR]_p\underset{[IF]_q}{\text{—}}[EX]_m\text{—}[TF]_z]_{N_c\text{-}x}$$

wherein:
(C) means a core;
(FF) means a focal point functionality component of the core;
x is independently 0 or an integer from 1 to $N_c$-1;
(BR) means a branch cell, which, if p is greater than 1, then (BR) may be the same or a different moiety;
p is the total number of branch cells (BR) in the dendrimer and is an integer from 1 to 2000 derived by the following equation $$p = \text{Total \# of } [BR] = \left(\frac{N_b^1}{N_b} + \frac{N_b^2}{N_b} + \frac{N_b^3}{N_b} + \ldots \frac{N_b^G}{N_b}\right)[N_c] = \left(\sum_{i=0}^{i=G-1} N_b^i\right)[N_c]$$

where: G is number of concentric branch cell shells (generation) surrounding the core;
i is final generation G;
$N_b$ is branch cell multiplicity; and
$N_c$ is core multiplicity and is an integer from 1 to 1000;
(IF) means interior functionality, which, if q is greater than 1, then (IF) may be the same or a different moiety;
q is independently 0 or an integer from 1 to 4000;

(EX) means an extender, which, if m is greater than 1, then (EX) may be the same or a different moiety;

m is independently 0 or an integer from 1 to 2000;

(TF) means a terminal functionality, which, if z is greater than 1, then (TF) may be the same or a different moiety;

z means the number of surface groups from 1 to the theoretical number possible for (C) and (BR) for a given generation G and is derived by the following equation $$z = N_c N_b^G;$$

where: G, $N_b$ and $N_c$ are defined as above; and with the proviso that at least one of (EX) or (IF) is present.

Some of the present dendrimers of this invention are represented by Formula (II):

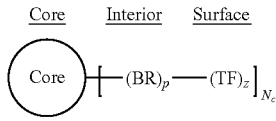

Formula (II)

Core    Interior    Surface $$p = \text{Total \# of } [BR] = \left(\frac{N_b^1}{N_b} + \frac{N_b^2}{N_b} + \frac{N_b^3}{N_b} + \ldots \frac{N_b^G}{N_b}\right)[N_c] = \left(\sum_{i=0}^{i=G-1} N_b^i\right)[N_c]$$

where: core=(C), (TF), G, $N_c$, $N_b$, i, z and p are defined as in Formula (I) above and (BR) must have an (IF) moiety present or be able to generate an (IF) in situ.

The various terms [(C), (FF), (IF), (BR), (EX), (TF)] for Formula (I) and Formula (II) above are more fully explained in the Detailed Description below. Preferably the compounds of Formula (I) have at least one (EX) present which is a piperazine or a triazole derived from a 1,3-cyclo-addition of azides to acetylenes, or a cleavable moiety such as an ester. Also preferred are those compounds of Formula (I) where both (EX) and (IF) are present and may have more than one of each of (BR) and (IF) present.

Processes to Prepare Dendritic Polymers of Formula (D)

These dendritic polymers of Formula (I) are prepared by the processes described later in this specification and illustrated for some of the processes by Flow Charts 1 and 2 provided later below.

One embodiment of this invention provides a process for preparing a dendrimer where a branch cell reagent is contacted with a diamine that is reactive with the branch cell reagent and allowing the branch cell reagent and the diamine to react for a time sufficient (e.g., 0.5 to 30 hours) and a temperature sufficient (e.g. 20° C. to 150° C.) in the presence of a solvent (e.g. alcohols) in preferably an inert atmosphere (e.g. nitrogen) to form a dendrimer that is selected from the group consisting of poly(ester-acrylate)dendrimers and poly(ester-epoxide)dendrimers. Dendrons are also prepared by this method. The initiator cores and the branch cell reagents are contacted with each other in the presence of alcohols or polar/non-polar solvents.

A process to prepare the dendritic polymers of Formula (I) as defined above by an acrylate-amine reaction system which comprises:

A. Reacting an acrylate functional core with an amine functional extender, such as shown below:

(C)+(EX)→(C)(EX)(TF)

where (C)=an acrylate functional core such as TMPTA; (EX)=an amine functional extender such as PIPZ; and (TF)=amine; and B. Reacting an amine functional extended core reagent of (C) (EX) (TF1) with an acrylate functional branch cell reagent (BR) as shown below:

(C)(EX)(TF1)+(BR)→(C)(EX)(BR)(TF2)

where (C)=TMPTA; (EX)=PIPZ; (TF1)=Amine; (BR)=TMPTA; and (TF2)=Acrylate; and wherein for both Steps A and B the addition of an extender (EX) group to a core, the mole ratio of (EX)/(C) is defined as the moles of extender molecules (EX) to the moles of reactive functional groups on the simple core, scaffolding core, super core, or current generation structure (i.e. $N_c$) where an excess of (EX) is used when full coverage is desired;

the addition of a branch cell (BR) to a simple core, scaffolding core, super core, or current generation structure (BR)/(C) is defined as the moles of branch cell molecules (BR) to the moles of reactive functional groups on the simple core, scaffolding core, super core, or current generation structure (i.e. $N_c$) where an excess of (BR) is used when full coverage is desired; and the level of addition of branch cells (BR) or extenders (EX) to a core, scaffolding core, super core or current generational product can be controlled by the mole ratio added or by N-SIS.

A process to prepare the dendritic polymers of Formula (I) as defined above by ring-opening reaction system which comprises:

A. Reacting an epoxy functional core with an amine functional extender, such as shown below:

(C)+(EX)→(C)(IF1)(EX)(TF1)

where (C)=an epoxy functional core such as PETGE; (IF1)=Internal hydroxyl (OH); (EX)=piperazine (PIPZ); (TF1)=Amine; and B. Reacting an amine functional extended core reagent (C) (IF1) (EX) (TF1) with an epoxy functional branch cell reagent such as shown below:

(C)(IF1)(EX)(TF1)+(BR)→(C)(IF1)(EX)(IF2)(BR)(TF2)

where (C)=PETGE; (IF1)=Internal functionality moiety as defined in claim 1 such as OH; (EX)=an extender moiety as defined in claim 1 such as PIPZ; (TF1)=Amine; (BR)=an epoxy functional branch cell reagent such as PETGE; and (IF2)=Internal functionality moiety as defined in claim 1 such as OH; (TF2)=Amine; and wherein for both Steps A and B the addition of an extender (EX) group to a core, the mole ratio of (EX)/(C) is defined as the moles of extender molecules (EX) to the moles of reactive functional groups on the simple core, scaffolding core, super core, or current generation structure (i.e. $N_c$) where an excess of (EX) is used when full coverage is desired;

the addition of a branch cell (BR) to a simple core, scaffolding core, super core, or current generation structure (BR)/(C) is defined as the moles of branch cell molecules (BR) to the moles of reactive functional groups on the simple core, scaffolding core, super core, or current generation structure (i.e. $N_c$) where an excess of (BR) is used when full coverage is desired; and the level of addition of branch cells (BR) or extenders (EX) to a core, scaffolding core, super core or current generational product can be controlled by the mole ratio added or by N-SIS.

Uses of Dendritic Polymers of Formula (f)

These dendritic polymers of Formula (I) may be used as mentioned below and described further in this specification. It is believed that, based on knowledge of these materials and of similar dendritic polymers, these dendritic polymers may display all of these mentioned uses and many others. There are numerous references to dendritic polymers, such as PAMAMs, for a vast variety of uses.

The present dendritic polymers of Formula (I) are believed to be able to be used in most, if not all, of those prior known uses of PAMAM and dendrimers and even more uses because of their unique properties as discussed before. Some examples of such uses include, but are not limited to the following. In the energy and electronics market, these dendritic polymers can have utility in fuel cells (e.g., membranes, catalysts), energy storage (hydrogen), solid state lighting, thermal management for devices, light emitting diodes, displays, electronic inks, interlayer dielectric, photoresist, molecular electronics, telecom devices (waveguides), photonics, photographic materials, quantum dots, and stealth enhancement of materials. Toner compositions can be made by admixing these dendritic polymers of Formula (I) with resin powders, heating, and then either extruding or dispersing the toner resin particles in solution with a suitable surfactant. These dendritic polymers of Formula (I) can be mixed with dyes (such as anionic dyes), salts, surfactants, antioxidants, solvent (such as water) or neat, and other desired components to yield a precipitate free ink that can be deposited on paper or another printing surface. The improvement in the ability of dyes to coat or permeate synthetic and natural fibers make these dendritic polymers useful in many applications for cloth, patterns in cloth, carpets, and other such items. Water-soluble dendritic polymers of Formula (I) can be added to paper-coating formulations to increase the production capacity of paper-coating machines while improving paper quality, Chromatographic supports for use in separations or filtrations can be prepared by mixing the dendritic polymers of Formula (I) with silicas or aluminas. The dendritic polymers of Formula (I) can be used in dental compositions to increase performance, reduce shrinkage, and/or improve adhesion. Low-viscosity, optimal etching behavior, and tuneable glass transition temperatures are properties that make these dendritic polymers useful for manufacturing computer memory systems. Other uses are also possible where such nanoscale dendritic molecules are functioning themselves or as carriers for metal ions or metals. As oil additives and lubricants these dendritic polymers of Formula (I) can display dispersant and antioxidant properties, and as an additive to SAE-30 motor oil can reduce sludge, varnish and clogging.

In the environmental area, these dendritic polymers can have utility as chemical and biosensors, electronic nose (array-based sensors), lab-on-a-chip, nanoencoding of materials for environmental tracking and source identification, amplification technology for environmental sensors, biocidal materials, environmental sensing, remediation, clean water (e.g., ion exchange), clean air (e.g., super absorbers), and catalysts.

In the personal/household area, these dendritic polymers can have utility as environmental upgrading of fuels, coatings and surface modifiers (such as to provide scratch resistance, an antimicrobial surface, color changing, texture modifier, dirt resistance, water resistance), cleansers and lotions, cosmetics, pigments and dyes, UV absorbers, adsorbers, reflectors, carriers of nutritionals, nutritceuticals, sweeteners, artificial sweeteners, surfactants, and functional additives with or without adding color.

In the chemicals and manufacturing market, these dendritic polymers can have utility as improved binders, in inclusion compounds for removing heavy metals or impurities from solution or water purification, chemical catalysts, chemical separation materials, filtration systems, petrochemical processing (nanocatalysts), and toxic leak sensors. Also these dendritic polymers may be used as a monomer in various chemical applications, including making a heteropolymer or homopolymer, and as a polymerization modifier or initiator (such as for nylon 6 by lowering the viscosity for easier injection molding and lower processing pressures).

Also the dendritic polymers for Formula (I) may have various carried materials present in their interior void spaces. These dendritic polymers may have a variety of uses as agents in the pharmaceutical and agricultural fields.

In the human and animal medical and health area, these dendritic polymers can have utility with in vivo diagnostic imaging (e.g., targeted control with increased contrast), diagnostic sensing (e.g., signal booster with simultaneous targeting), drug delivery (e.g., enhanced oral, intravenous, dermal, transdermal, nasal, etc.), drug discovery (e.g., miniaturization, bioarrays), in vitro and ex vivo diagnostics and therapies, hormones, proteins, enzymes, protein resistant coatings for medical devices (e.g., in vivo and ex vivo), anti-biofouling coatings and surfaces for devices, transdermal delivery, chemotherapies for oncology, remote and in vivo devices, polyvalent pharma applications, near infrared absorbers, biomarkers, targeted biomarkers, non-invasive imaging and sensing, targeted therapies, targeted diagnostics, metal containing dendritic polymers such as copper, silver, gold, and magnetic bioreactors (e.g., cell growth and harvesting), drug releasing stents, surface coatings, and controlled release (e.g., therapeutics, nutritionals, etc.). Included are use of these dendritic polymers for encapsulation or adsorption of drugs, prodrugs, antiviral agents, antibacterial agents, antiparasitic agents, proteins, hormones, enzymes, oligonucleotides, genetic materials (e.g., fragments of DNA, RNA, viral particles or fragments, or synthetic genetic particles).

Thus it is clearly possible, based on known prior dendritic polymers and testing done on the present dendritic polymers of Formula (I) that they can be useful as: surface conjugated or surface associated carriers (such as possible from their shape variants of ellipsoids, spheres, rods, random hyperbranched, dendrigrafts, core-shell tecto dendrimers) which can be further modified by the variety of surface groups (TF) present; encapsulated carriers (whether the carried material is associated with the interior of simply entrapped) for use in time release drug delivery, having cleavable linkages in the structure of the dendritic polymer for time release and pH or other desired changes once administered, solubility differences between the interior and surface of the dendritic polymer, quantity of carried material possible per dendritic polymer because of generation or shape; and precision in their size enables use as molecular size standards, calibrating agents, and pore-forming templates.

In the food and agriculture market, these dendritic polymers can have utility as highly selective control sensors, sensory amplification materials (e.g., taste, smell, sound, sight, and feel), biopathway studies and distribution within the plant, targeted, non-toxic biodegradable pesticides, herbicides, time-released fertilizers and pesticides, packaging materials (e.g., microbe resistant plastics), freshness, contamination, and/or tamper sensors, and delivery of drugs to plants and animals.

Additionally, these dendritic polymers may carry other desirable materials as discussed further herein.

Formulations of these dendritic polymers of Formula (I) for these uses are also described later herein.

BRIEF DESCRIPTION OF THE DRAWINGS

FIG. 20(B) shows the diameter dimensions (nm) obtained from CPK models illustrating contracted (by circles) and extended (by squares) values for the classical poly(ether) (PE) dendrimers [(C)=neopentyl; (BR)=neopentyl; (TF)=OH]. The actual SEC values (shown by triangles) correspond closely to the CPK values. This dendrimer family has no (EX) and no (IF). Note, the extended and contracted dimensions are nearly super imposable, indicating that classical poly(ether) dendrimer have virtually no interior void space. Additionally, the absence of (EX) in the classical poly(ether)dendrimers shifts the de Gennes dense packing cross over point by about 2-3 generations earlier to G=3 compared with G=5.5 or PEHAM dendrimers as shown in FIG. 20(B).

DETAILED DESCRIPTION OF THE INVENTION

Glossary

Figure 1:
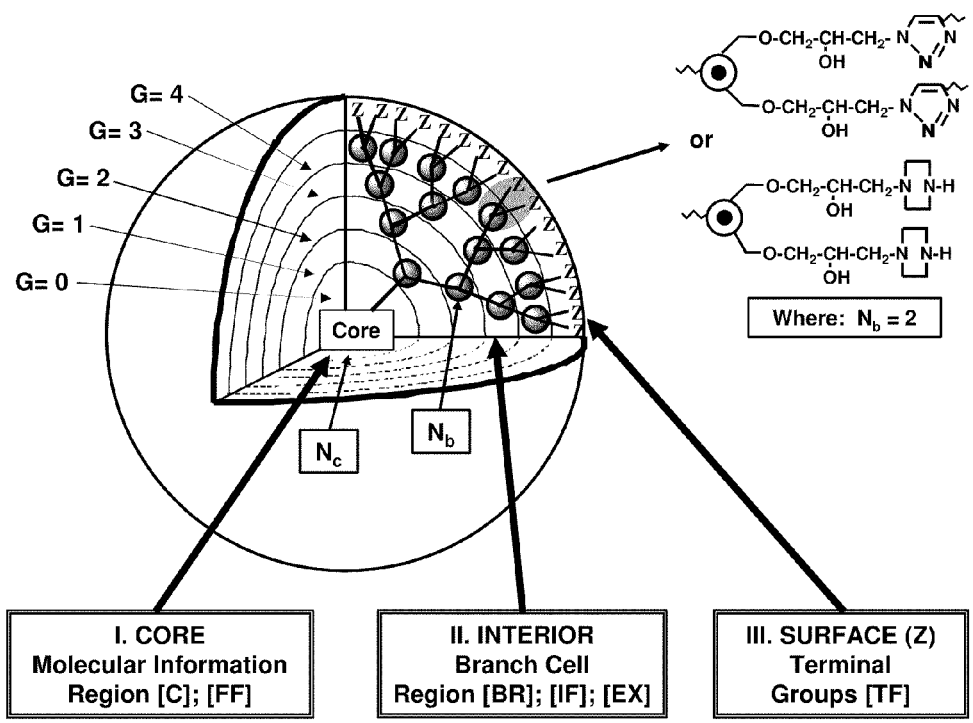
FIG. 1 illustrates a three-dimensional projection of dendrimer core-shell architecture for a dendrimer of Formula (I) with components of a core (C), an interior that has branch cells (BR), interior functionality (IF) and extenders (EX), and number of surface groups (z) that have terminal functionality (TF). Piperazine and triazole as (EX) in this Figure are only for illustration and could be any other (EX).

The following terms as used in this application are to be defined as stated below and for these terms, the singular includes the plural.

AEEA means N-(2-hydroxyethyl)ethylenediamine
AEP means 1-(2-aminoethyl)piperazine
AFM means atomic force microscopy
AIBN means 2,2'-azo-bis(isobutyrolnitrile)
Alkyl means any number of carbon atoms for the term that is used, whether linear or branched, alone or a part of another term such as alkyl substituted, alkylaryl, cycloalkyl, heterocyclic moieties, and others; typically from $C_1$-$C_{100}$, with $C_1$-$C_{50}$ preferred and most preferred $C_1$-$C_{25}$. In a similar manner alkene and alkyne are defined broadly; typically from $C_2$-$C_{200}$, with $C_2$-$C_{100}$ preferred.
AMTS means acryloxymethyltrimethylsilane
APS means ammonium peroxydisulfate
Aptamer means a specific synthetic DNA or RNA oligonucleotide that can bind to a particular target molecule, such as a protein or metabolite
Aryl means any number of carbon atoms containing an aromatic moiety and can be from $C_5$-$C_{100}$ and may be substituted with one or more alkyl (optionally substituted), alkene (optionally substituted), alkyne (optionally substituted), halo, hetero atoms in the ring (such as N, O, S, P, B), azides, and others such as those in the present examples and taught in this specification.
BAA means bis(allyl)amine or diallylamine
BGPM means bis(4-glycidyloxyphenyl)methane
BOC means tert-butoxycarbonyl
BPEDS means bis(2-piperazinylethyl)disulfide
BSA means bovine serum albumin
Celite means diatomaceous earth (Fisher Scientific)
CPK means Corey-Pauling-Koltun molecular models
DAB means diaminobutane
DBA means dibenzylamine
DCC means dicyclohexylcarbodiimide
DCM means dichloromethane
DEA means diethanolamine
DEIDA means diethyliminodiacetate
DETA means diethylenetriamine
DGGA means N,N'-diglycidyl-4-glycidyloxyanaline
DIA means diiminoamine
DI water means deionized water
diglyme means diethylene glycol dimethyl ether
DMDTB means dimethyldithiobutyrate
DME means dimethoxyethane
DMF means dimethylforamide
DMI means dimethylitaconate
DMSO means dimethylsulfoxide; from Acros organics and further distilled prior to use
DNA or RNA or nucleic acids means synthetic or natural, single or double stranded DNA or RNA or PNA (phosphorous nucleic acid) or combinations thereof or aptamers, preferably from 4 to 9000 base pairs or from 500 D to 150 kD
DO3A means 1,4,7,10-tetraazacyclododecane-1,4,7-tris (acetic acid)
DOTA means 1,4,7,10-tetraazacyclododecane-1,4,7,10-tetra (acetic acid)

DTPA means diethylenetriaminepentaacetic acid
DTT means dithiothreitol
EA means ethanolamine
EDA means ethylenediamine; Aldrich
EDTA means ethylenediaminetetraacetic acid
EPC means ethyl-N-piperazinecarboxylate
EPI means epichlorohydrin; from Acros organics and further distilled prior to use equiv. means equivalent(s)
Et means ethyl
EtOH means ethanol
FBS means fetal bovine serum
FITC means fluorescein isothiocyanate
FT-IR means Fourier Transform Infrared Spectroscopy
G means dendrimer generation, which is indicated by the number of concentric branch cell shells surrounding the core (usually counted sequentially from the core)
g means gram(s)
halo means fluoro, chloro, bromo, or iodo atom, ion or radical
HCl means hydrochloric acid
HEDA means (2-hydroxyethyl)ethylenediamine
HEK Cells means human embryonic kidney cells
Hexanes means mixtures of isomeric hexane (Fisher Scientific)
HMDA means hexamethylenediamine
HPLC means high pressure liquid chromatography
HSEt means thioethanol or mercaptoethanol
IDAN means 3,3-iminodiacetonitrile
IMAE means 2-imidazolidyl-1-aminoethane
IMPA means imino bis(methylphosphonic acid)
IR means infrared spectroscopy
KOH means potassium hydroxide; used as 85% pellets from Aldrich, powdered before use
L means liter(s)
Lipofectamine means Lipofectamine™ 2000 (Invitrogen)
mA means milliamphere(s)
MALDI-TOF means matrix-assisted laser desorption ionization time of flight mass spectroscopy
MBDGA means 4,4'-methylene bis(N,N'-diglycidyl aniline)
MBP means multi-branching polymerization
m-CPDA means meta-chloroperoxy benzoic acid
MDCK Cells means Madin-Darby canine kidney cells
MEM means minimal essential media
MeOH means methanol
MES means 2-(4-morpholino)ethane sulfonic acid
mg means milligram(s)
MIA means 2-methyl-2-imidazoline
MIBK means methylisobutylketone
mins. means minutes
MIPIEP means methylisopropyliminoethylpiperazine
mL means milliliter(s)
NMR means nuclear magnetic resonance
N-SIS means nanoscale sterically induced stoichiometry
Oligonucleotides means synthetic or natural, single or double stranded DNA or RNA or PNA (peptide nucleic acid) or combinations thereof or aptamers, preferably from 4 to 100 base pairs
Orthogonal Chemistry means the chemical transformations that may be performed either in parallel or in sequence on a multi-functional reagent or substrate without cross-reactions or interference by other components of the reactants
PAGE means poly(acrylamide) gel electrophoresis
PAMAM means poly(amidoamine), including linear and branched polymers or dendrimers with primary amine terminal groups
PBS means phosphate buffered saline
PCR means polymerase chain reaction
PEA means methyl isobutyl protected 1-(2-aminoethyl)piperazine
PEHAM means poly(etherhydroxylamine); dendrimers of Formula (I)
PEI means poly(ethyleneimine)
PEOX means poly(2-ethyl-2-oxazoline)—partially and fully hydrolyzed
Percent or % means by weight unless stated otherwise
PETAE means pentaerytlritol tetraallyl ether
PETAZ means pentaerythritol tetrazide
PETGE means pentaerythritol tetraglycidyl ether
PETriAE means pentaerythritol triallyl ether
PETriGE means pentaeiythritol triglycidyl ether
PGA means poly(glycidyl) aniline
PGE means poly(glycidyl)ether
PIPZ means piperazine or diethylenediamine
PPI means poly(propyleneimine)dendrimer
Pyrrol means 2-pyrrolidone
$R_f$ means relative flow in TLC
RT means ambient temperature or room temperature, about 20-25° C.
SCVP means self-condensing vinyl polymerization
SDS means sodium dodecylsulfate
SEC means size exclusion chromatography
SIS means sterically induced stoichiometry
TBAB means tetrabutyl ammonium bromide
TBE buffer means tris(hydroxymethyl)amidomethane, boric acid and EDTA disodium buffer
TBS means TRIS-buffered saline
TEA means triethylamine
TEMED means N,N,N',N'-tetramethylethylenediamine
TEPC means tetra(epoxypropyl)cyanurate
TES means tetraepisulfide or tetrathiorane
TETA means triethylenetetramine
TGA means thermal gravimetric analysis
TGIC means tris(2,3-epoxypropyl)isocyanurate
THF means tetrahydrofuran
TLC means thin layer chromatography
TMPTA means trimethylolpropane triacrylate
TMPTGE means trimethylolpropane triglycidyl ether; Aldrich; [first distilled and purified by column chromatography (1.75'×10') over silica gel (200-400 mesh) with 1:2:2 ratio of hexanes, ethyl acetate and chloroform as elutes. Purification of 5 g of TMPTGE gave 3.2 g (64% yield) of pure (>98%) material. Reaction was kept for 60 hours as precaution or done overnight. Elsewhere?]
TMS means tetramethylsilane
TPEGE means tetraphenylolethane glycidyl ether
TPMTGE means triphenylolmethane triglycidyl ether
TREN means tris(2-aminoethyl)amine
TRIS means tris(hydroxymethyl)aminomethane
Tween means polyoxyethylene (20) sorbitan mono-oleate
UF means ultrafiltration
UV-vis means ultraviolet and visible spectroscopy Chemical Structure The dendritic polymer structures of the present invention possess several unique components that manifest surprising properties (compared to traditional dendritic structures) and utilize unique ring-opening processes for their preparation. A structure for these dendritic polymers is shown by Formula (I) below:

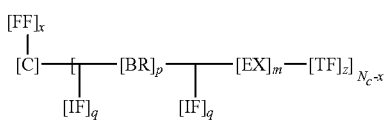

Formula (I)

wherein:
(C) means a core;
(FF) means a focal point functionality component of the core;
x is independently 0 or an integer from 1 to $N_c-1$;
(BR) means a branch cell, which, if p is greater than 1, then (BR) may be the same or a different moiety;
p is the total number of branch cells (BR) in the dendrimer and is an integer from 1 to 2000 derived by the following equation $$p = \text{Total \# of } [BR] = \left(\frac{N_b^1}{N_b} + \frac{N_b^2}{N_b} + \frac{N_b^3}{N_b} + \ldots \frac{N_b^G}{N_b}\right)[N_c] = \left(\sum_{i=0}^{i=G-1} N_b^i\right)[N_c]$$

where: G is number of concentric branch cell shells (generation) surrounding the core;
i is final generation G;
$N_b$ is branch cell multiplicity; and
$N_c$ is core multiplicity and is an integer from 1 to 1000;
(IF) means interior functionality, which, if q is greater than 1, then (IF) may be the same or a different moiety;
q is independently 0 or an integer from 1 to 4000;
(EX) means an extender, which, if m is greater than 1, then (EX) may be the same or a different moiety;
m is independently 0 or an integer from 1 to 2000;
(TF) means a terminal functionality, which, if z is greater than 1, then (TF) may be the same or a different moiety;
z means the number of surface groups from 1 to the theoretical number possible for (C) and (BR) for a given generation G and is derived by the following equation $$z = N_c N_b^G;$$

where: G, $N_b$ and $N_c$ are defined as above; and
with the proviso that at least one of (EX) or (IF) is present.
Preferred compounds of Formula (I) above are those where $N_c$ is an integer from 1 to 20; q is 0 or an integer from 1 to 250; p is an integer from 1 to 250; and m is 0 or an integer from 1 to 250; and one of q or m must be at least 1; and when both q and m are greater than 1, (BR) and (EX) may occur alternately with the other moiety or sequentially with multiple groups of (BR) or (EX) occurring in succession.

Other preferred dendritic polymers of Formula (I) are those where one or more of the following moieties are present: where (C) is PETriGE, PETAZ, TPEGE, or TPMTGE; or where (BR) is IDAN, IMEA, IMPA, BAA, DETA, PEA, TREN, AEEA, or MIA; or where (TF) is TMS; or where (EX) is triazole.

In the above Formula (I) the terms used are further explained as follows.
(C) includes the following:
A core includes a simple core, a scaffolding core, and a super core. These cores may be electrophilic (E), nucleophilic (N) or other (O) moiety as described before and hereafter. The core must be capable of further reaction. If desired, the core may be cleavable by acids or bases and yield a dendron or dendritic polymer of lower core $N_c$ value. Additionally one or more but less than all of the core functionalities $N_c$ may be temporarily or permanently capped with a non-reactive group (e.g., t-BOC, esters, acetals, ketals, etc.).

Simple cores are well known in this art. Some examples of a simple core include, but are not limited to, poly(glycidyl ethers) [e.g., bis-phenol glycidyl ether, PETGE, TPEGE, TPMTGE, TMPTGE, BGPM, tris(2-acryloyloxyethyl)isocyanurate, TGIC, MBDGA, diglycidyl aniline, DGGA, sorbitol, glycerol, neopentyl, oligoneopentyl diglycidyl ether, tertbutylglycidylether, allylglycidyl ether), aminoethanol, ammonia, polyamines [e.g., EDA, PAMAM, HMDA, diethylenetriamine, methylisopropylidine, alkylene bis(2-haloethylamines), arylmethyl halides (e.g., benzylic halides), piperazine, aminoethylpiperazine, hyperbranched (e.g., polylysine, polyethyleneimine, poly(propyleneimine), tris-2-(aminoethylamine))], linear poly(ethyleneimine), water, hydrogen sulfide, alkylene/arylene dithiols, BPEDS, cystamine, 4,4'-dithiodibutyric acid, DMDTB, mercaptoalkylamines, thioether alkylamines, isocyanurate, heterocycles (e.g., DO3A, DOTA), macrocycles (e.g., crown ethers), multicarbon cores (ethylene, butane, hexane, dodecane), polyglycidylmethacrylate, poly(functional acrylates) (e.g., TMPTA, diallyl amine), diethylaminodiacetate, tris(hydroxymethyl)aminomethane, phosphine, porphines (e.g., porphyrins), oxiranes, thioranes (e.g., TES), oxetanes, aziridines, azetidines, multiazido functionalities, siloxanes, oxazolines (e.g., PEOX), carbamates, or caprolactones. Preferred cores are disulfide containing structures (e.g., cystamine and other diamines possessing disulfide moieties, such as diazido disulfides, disulfide diacetylene), isocyanurate, heterocycles, propargyl PETAE, propargyl PETriGE, pentaerythritol tetraazide, PETGE, tetraphenylolethane glycidyl ether, triphenylolmethane triglycidyl ether, PETAZ, TMPTGE, TGIC, TMPTA, poly(2-ethyl-2-oxazoline), multicarbon cores (ethylene, butane, hexane, dodecane), phosphine, linear, branched or cyclic moieties with single or multiple functional epoxides, multifunctional alkenes, alkynes or aryls, or multiazido functionalities (e.g., tetra-azido adduct derived from PETGE). Simple cores are illustrated by those discussed in U.S. Pat. Nos. 4,568,77; 4,587,329; 4,631,337; 4,558,120; 5,714,166; 5,338,532, and in *Dendrimers and other Dendritic Polymers*, eds. by J. M. J. Fréchet, D. A. Tomalia, pub. John Wiley and Sons, (2001). Virtually any core with at least two reactive ends can be used, provided that when there are only two such reactive ends, a (BR) group is reacted at some point during the formation of the dendritic polymer and either a (IF) or (EX) or both are also present in the final dendritic polymer.

A scaffolding core is one where the simple core has other moieties or entities attached which then serve as the platform for the dendritic polymer growth to the first generation. Examples of scaffolding cores include, but are not limited to, capped materials, such as trimethylolpropane triacrylate capped with piperazine, PETGE, TMPTGE, TPEGE, or TPMTGE each capped with one or more aminoethylpiperazine, azides, propargyl functionalities, piperazine, di-imminodiacetic acids, or epoxide surface PEHAMS or mixtures thereof.

A super core is where a dendrimer serves as the core functionality and other dendritic structures may be attached or grown from its surface or zero valent metal particles (e.g., Au, Ag, Cu, Pd, Pt), gold nanoparticles, gold nanorods, colloids, latex particles, metal oxides, micelles, vesicles, liposomes, buckyballs, carbon nanotubes (single and multi wall), carbon fibers, silica or bulk metal surfaces, and where other structures are attached to or grown from the core surface. Some examples of super cores are: PAMAM as the core with PEHAM grown on or attached to its surface; PEHAM as the core with PEHAM grown on or attached to its surface; PEHAM as the core with PEHAM and PAMAM grown on or attached to its surface; PAMAM as the core with PEHAM and PAMAM grown on or attached to its surface; PEHAM as the core with PAMAM grown on or attached to its surface; polylysine dendritic polymer as the core and PEHAM is grown on or attached to its surface, PPI as the core and PEHAM grown on or attached to its surface; or polyols as the core and PEHAM grown on or attached to its surface. After these various cores have the other dendritic polymers grown on or attached to them, they are a super core.

Cores have at least one nucleophilic (Nu) or one electrophilic (E) moiety; or a polyvalent core bonded to at least two ordered dendritic branches (O); or a core atom or molecule that may be any monovalent or monofunctional moiety or any polyvalent or polyfunctional moiety, preferably a polyfunctional moiety having 2-2300 valence bonds of functional sites available for bonding with dendritic branches.

Nucleophilic core examples include ammonia, water, hydrogen sulfide, phosphine, poly(alkylenediamines) such as EDA, HMDA, dodecyl diamines, polyalkylene polyamines such as DETA, TETA, tetraethylenepentaamine, pentaethylenehexamine, poly(propyleneimine), linear and branched poly(ethyleneimine) and poly(amidoamines), primary amines such as methylamine, hydroxyethylamine, octadecylamine, poly(methylenediamines), macrocyclic/cryptand polyamines, poly(aminoalkylarenes), tris(aminoalkyl) amines, methylisopropylidine, alkylene bis(2-haloethylamines), arylmethyl halides (e.g., benzylic halides), hyperbranched (e.g., polylysine), poly(propyleneimine), tris-2-(aminoethylamine), heterocyclic amines, star/comb-branched polyamines, piperazine and its derivatives (e.g., aminoalkyl piperazines), and other various amines. Other nucleophilic cores are polyvinyl alcohols, polyvinyl amines, ethylene glycol, polyalkylene polyols, polyalkylene polymercaptans, thiophenols and phenols. Any of these cores may be as capped cores [e.g., tert-butoxycarbonyl (BOC)] where at least one $N_c$ valence is uncapped.

Examples of electrophilic cores include those where the core is converted to an (E) with Brönsted/Lewis acids or alkylation/acylation agents and is cyclic ethers (e.g., epoxides), oxiranes, cyclic sulfides (epichlorosulfide), aziridines, azetidines, siloxanes, oxetanes, oxazolines, oxazines, carbamates, caprolactones, carboxyanhydrides, thiolactones, sultones, β-lactams, α,β-ethylenically unsaturated carboxylic esters such as methyl acrylate, ethyl acrylate, $(C_2-C_{18}$ alkyl)methacrylate esters, acrylonitrile, methyl itaconate, dimethyl fumarates, maleic anhydride, and amides such as acrylamide or any of these cores as capped cores where at least one $N_c$ valence is uncapped.

There are also polyfunctional initiator cores (core compound) for (O) as (C) that are compounds capable of generating a polyvalent core or free-radical receptor groups (e.g., olefinics), or 1,3-dipolar cyclo-addition moieties (e.g., polyalkynes and polyazides). Also included are star/comb-branched polyamines.

Cores are known from dendritic polymers as described in U.S. Pat. Nos. 4,507,466; 4,558,120; and 4,631,337 and many other literature and patent citations.

Also preferred moieties of these cores are triacrylate, tetraacrylates, triaziridine, tetraaziridine, triazide, tetraazide, trithiorane, tetrathiorane, trioxazoline, tetraoxazoline, triepoxide, tetraepoxide, diglycidyl aniline, aminoalkylol such as aminoethanol, alkylenediamine such as ethylenediamine, triphenylmethane, neopentyl alcohols, triglycidylether, triarylmethane, tetraarylmethane, tetraglycidylether, bis(glycidoxyphenyl)alkane, methylene bis(diglycidylaniline), tetraepisulfide, trisglycidlyisocyanurate, tris(2,3-epoxypropyl) isocyanurate.

Figure 2:
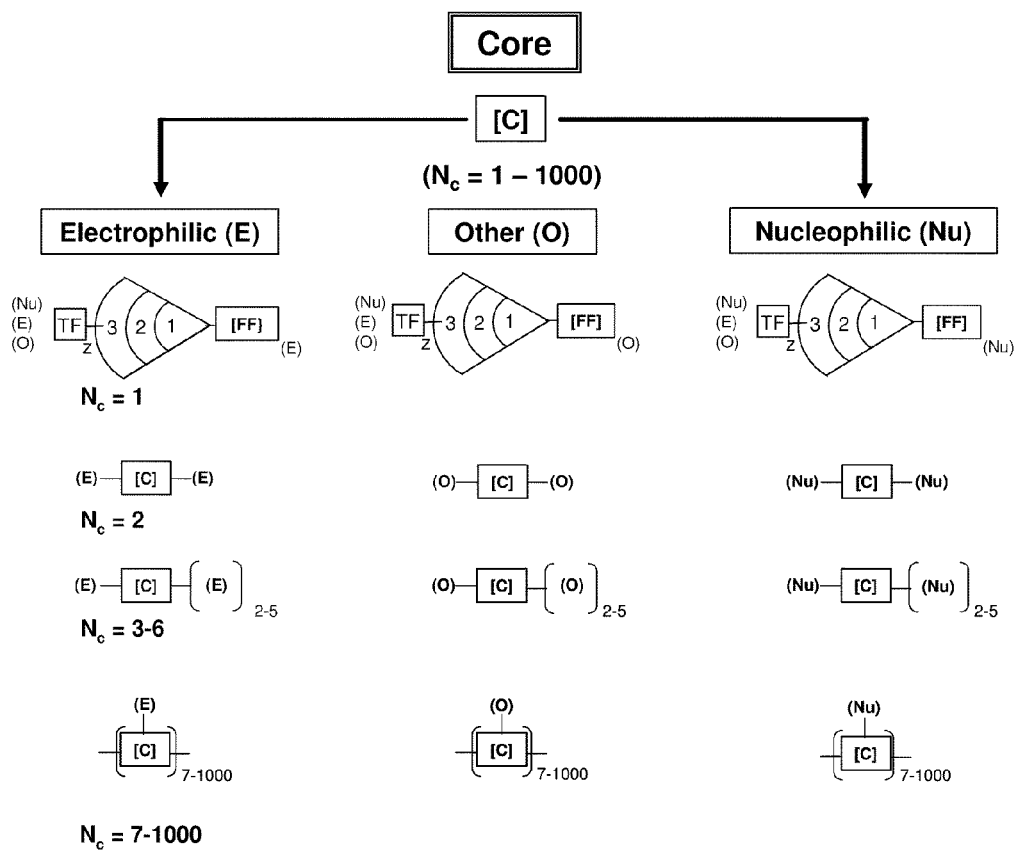
FIG. 2 illustrates the various core components (C) that may consist of one or more of an electrophilic moiety (E), a nucleophilic moiety (Nu), or other reactive moiety (O), or a combination of these moieties. The multiplicity of the core is defined as $N_c$. Included within these three terms (E), (Nu), and (O), in addition to the customary moieties for these moieties, are groups such as a dendron with focal point functionality (FF) as illustrated.

FIG. 2 illustrates these cores.

(FF) means the following:

The focal point functionality (FF) moieties serve to enable a dendron to be used as a core whereby the core may later be further reacted, including but not limited to joining two or more dendrons together or reacting with another (C), (BR), or (EX) and (BR). When Formula (I) is a dendrimer with a fully reacted core (e.g., all $N_c$ valences are dendritic), then (FF) becomes a part of the core so that (FF) is not separately observed (thus x=0 and a dendrimer is formed). The maximum (FF) moieties possible are $N_c-1$. When all core reactive entities are not reacted, then (FF) is present and observed (a dendron is formed). Preferably x is from 1 to 3 (FF) moieties; and more preferably x is 1 (FF) moiety. Especially preferred for certain fully dendritic polymers (FF) is a part of the core and not noticeably present; thus x is 0.

Preferred (FF) moieties are hydrogen, thiols, amines, carboxylic acids, esters, ethers, cyclic ethers (e.g., crown ethers, cryptands), porphyrins, hydroxyl, maleimides, alkyls, alkenyls, alkynyls, alkyl halides, arylalkyl halides, phosphinos, phosphines, boranes, alcohols, aldehydes, acrylates, cyclic anhydrides, aziridines, pyridines, nitriles, itaconates, cyclic thiolactones, thioranes, azetidines, cyclic lactones, macrocyclics (e.g., DOTA, DO3A), chelating ligands (e.g., DTPA) isocyanates, isothiocyanates, oligonucleotides, amino acids, peptides, cyclopeptides, proteins, antibodies, or fragments, aptamers, imidazoles, azides, mercaptoamines, silanes, oxazolines, oxirane, oxetane, oxazines, imines, tosylates, metals, biotin, streptavidin, avidin, protecting groups (e.g., BOC or ketone solvent protected), siloxanes or its derivatives, or substituted derivatives or combinations thereof, or groups suitable for click chemistry (e.g., polyazido or polyalkyne functionality). The number of carbons present in each of these hydrocarbon moieties, when present, is from at least 1 to 25; halo means chloro, bromo, fluoro, or iodo; hetero means S, N, O, Si, B, or P. Preferred are mercapto, amino, carboxyl and carboxyl esters, oxazoline, isothiocyanates, isocyanates, hydroxyl, epoxy, orthoester, acrylates, methacrylates, styrenyl, and vinylbenzylic moieties. The ability of the (FF) group(s) to react further can be estimated by N-SIS, as discussed later.

FIG. 2 illustrates these (FF) moieties.

(BR) means the following:

Any nucleophilic (Nu), electrophilic (E) or other (O) reagent that is capable of reacting with the (C), an extender (EX), with another branch cell or branch cell reagent (BR) or terminal functional group (TF). Additionally, the (BR) reagent may be formed in situ from a precursor of a (BR). These (BR) moieties must be able to undergo such a reaction and result in a covalent presentation of a multiplicity or amplification of reactive groups that (BR) of the lower generation product to grow the dendrimer to the next generation. (See U.S. Pat. No. 4,737,550.) The (BR) may react with a co-reactant to form a core adduct and further reacted with a second co-reactant. The co-reactants can be (C), (FF), (BR) or (EX). Also the (BR) can be selected to react and form bonds with the core or terminal functionalities (TF) groups of the prior lower generation dendrimer which is now being further reacted to grow the next higher generation. Thus, any multifunctional (C) may also serve as a (BR). When (BR) occurs in more than one generation, it may be the same or different (BR) moiety.

Examples of co-reactants for bonding with the electrophilic cores include nucleophilic moieties such as uncapped or partially protected polyamines both branched and linear, primary and secondary, DETA, IMAE, DEA, DBA, TETA, tetraethylenepentaamine, poly(ethyleneimine), methylamine, BAA, hydroxyethylamine, octadecylamine, DEIDA, poly(methylenediamines) such as HMDA, polyaminoalkylarenes, tris(aminoalkyl)amines such as TREN, TRIS, linear and branched poly(ethyleneimines), linear and branched poly(amidoamines), heterocyclic amines such as imidazolines, piperidines, aminoalkyl piperazines, PEA, PETGE, and various other amines such as hydroxyethylaminoethylamine, HEDA, mercaptoalkylamines, mercaptoethylamine, iminodialkynes, iminodiakenes, substituted piperazine, amino derivatives of polyvinylbenzyl chloride and other benzylic amines such as tris(1,3,5-aminomethyl)benzene. Other suitable nucleophilic reactants include polyols such as pentaerythritol, ethylene glycol, polyalkylene polyols such as polyethylene glycol, polypropylene glycol, 1,2-dimercaptoethane and polyalkylene polymercaptans; thiophenols and phenols. Also suitable nucleophilic reactants are acetylenic polyepoxides, hydroxyalkyl azides, alkyl azides, tri- and tetra-aziridines, tri- and tetra-oxazolines, thiol alkyls, thiol (FF) dendrons, allyl groups, acrylates, methacrylates. Any of the above moieties may have olefinic functionality or capped moieties. Preferred are the triacrylate, tetraacrylates, triepoxide, tetraepoxide, diallyl amine, diethanol amine, diethyliminodiacetate, bis(2-haloalkyl)amine, tris(hydroxymethylamine), protected DETA, or methyl acrylate may be used, including in situ. Also preferred are one or more of cyclic ethers (epoxides), oxiranes, sulfides (epichlorosulfide), aziridines, azetidines, siloxanes, oxetanes, oxazolines, oxazines, carbamates, caprolactones, carboxyanhydrides, thiolactones, P-lactams, or derivatives thereof. More preferred are triacrylate, tetraacrylates, triepoxide, tetraepoxide, triazides, tetraazides, BAA, DEA, DEIDA, PETGE, PETriGE, PETriAE, HEDA, PEA, TREN, TRIS, dimethyliminodiacetate, protected DETA (with ketonic solvents), or methyl acrylate, including in situ.

Alternatively, a nucleophilic moiety can be reacted with an electrophilic reactant to form a core adduct which is then reacted with a suitable second coreactant to form the dendrimer.

When (BR) is an other (O) moiety then some suitable reagents are those that may undergo free radical additions or participate in 1,3-cyclo-addition reactions, that is "click" chemistry that include but are not limited to acetylenic polyepoxides, hydroxyalkyl azides, alkyl azides, triazoles, thiol alkyls, thio (FF) dendrons, allyl groups, acrylates, methyacrylates, or olefinic functionality.

When the (BR) moiety is part of a ring-opening reaction such (BR) may be cyclic ethers (epoxides), oxiranes, sulfides (epichlorosulfide), aziridines, azetidines, siloxanes, oxetanes, oxazolines, oxazines, carbamates, caprolactones, carboxyanhydrides, thiolactones, and beta-lactams. When this reaction occurs, in addition to the branching function, the (BR) may also form an (IF) in situ as a result of unreacted groups left on the (BR).

Preferred (BR) moieties are triacrylate, tetraacrylates, triepoxide, tetraepoxide, diallyl amine (BAA), diethanol amine (DEA), diethyliminodiacetate (DEIDA), tris(hydroxymethylamine), PETGE, HEDA, PEA, TREN, TRIS, dimethyliminodiacetate, and protected DETA (with ketonic solvents). Additionally, methyl acrylate may be used, as an electrophilic reagent to generate (BR) in situ by addition to amines or thiols.

Figure 3:
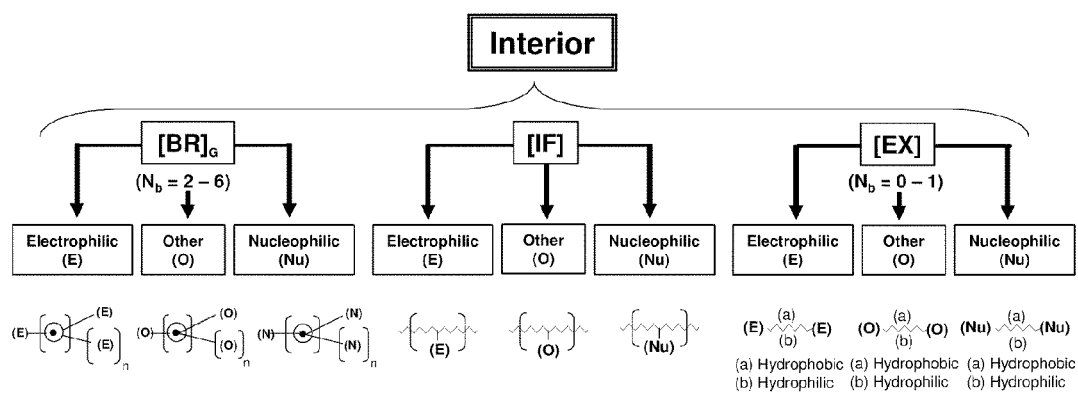
FIG. 3 illustrates the interior portion of a dendrimer of Formula (I) that has branch cells (BR), which have one or more of the following: electrophilic moieties (E), nucleophilic moieties (Nu), or other reactive moieties (O), (i.e., free radical or 1,3-dipolar cyclo-addition) or a combination of these moieties. Additionally, the interior may optionally have groups that provide interior functionalities (IF), usually derived from a ring-opening reaction which may have one or more of the following: an electrophilic moiety (E), a nucleophilic moiety (Nu), or other reactive moieties (O), or a combination of these moieties. Also optionally present in the interior are extender moieties (EX), which have one or more of the following: an electrophilic moiety (E), a nucleophilic moiety (Nu), or other reactive moieties (O), or a combination of these moieties. These interior moieties may be repeated for each generation of the dendrimer.
Figure 4:
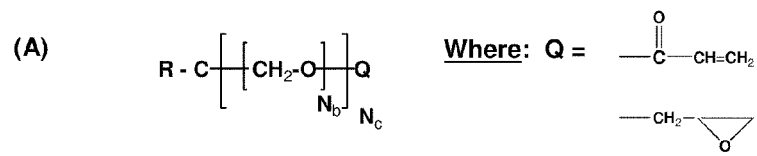
FIG. 4 illustrates in part (A) a branch cell or core where Q can be an epoxide moiety or an acrylate moiety. When the epoxide is ring-opened a branch cell, part (B), showing the (BR) moiety, the (IF) moiety, the (EX) moiety and the (TF) moiety for a tetraglycidyl ether branch cell reagent; where $N_b=3$ is formed as illustrated. Similarly, when $N_b=2$ is illustrated on FIG. 1. When the acrylate is Q, then an ester is integrated that can be cleaved.
Figure 4:
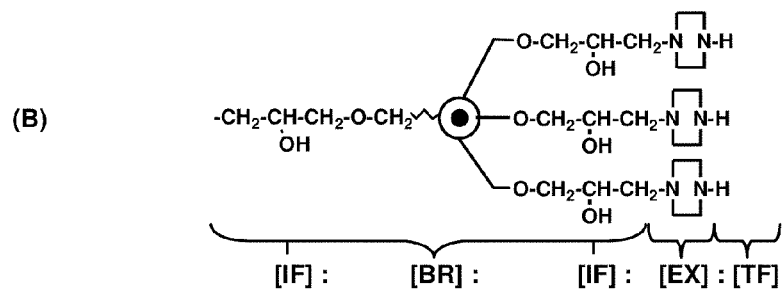

FIGS. 3 and 4 illustrate these (BR) moieties.

(IF) means the following:

This interior functionality (IF) is a unique feature of these dendrimers created by the reaction of appropriate branch cell reagents leading to the (BR) that are growing from generation to generation. The interior reactive sites, (i.e. hydroxyl, sulfhydryl, amine, phosphine, alkylsilane, silane, boranes, carboxyl, carboxyl ester, chloro, bromo, alkene, alkyne, or alkyl- or aryl-amide, etc.) result from the ring-opening reactions. This provides an interior covalent chemistry handle which may be further reacted, while maintaining the important internal functionality suitable for association with a further group, chelation or encapsulation. (IF) also provide unique attachment sites for adjusting the hydrophobic/hydrophilic features of the interior of the dendritic polymer, for introduction of polymerization initiators or sites, or for attachment of or association with therapeutic entities as pro-drugs.

Preferred (IF) moieties are hydroxyl, thiol, an alkylene ester and amine.

FIG. 3 illustrates these (IF) moieties.

(EX) means the following:

Extenders (EX) may be present in the interior of the dendrimer. They provide a means to lengthen the distance and thereby increase the space between the core (C) and subsequent generations G of the dendrimer and preferably must have two or more reactive sites, unless the (EX) is in the last G when it can have one reactive site and effectively terminates further G growth or caps the dendritic polymer for (TF) or only partially caps it. These enhancements in interior space volume increase the capacity for the dendrimer to encapsulate carrier materials (M) further described below. These (EX) may occur prior to or after the (BR) moiety or both prior to and after the (BR) moiety. These (EX) may also have an (IF) moiety present. These (EX) have at least two reactive sites and optionally may contain an (IF) or may form (IF) in situ. It is possible to consecutively react (EX) before any other reaction in any G; and in that case (EX) may be the same or different.

Preferred extenders (EX) are poly(amino acids) such as polylysine, other poly(amino acids), lysine, other amino acids, oligoethyleneglycols, diethylenetetraamine and higher amine analogs, oligoalkylenamines protected as 5-membered imidazolidyl derivatives [see Araki et al., 21(7), 1995-2001 (1988)], fatty acids with di- or greater heterogeneous or homogenous functionality, unsaturated aliphatic and aromatic difunctional or polyfunctional moieties, EA, morpholine, dicarboxylic acids, EPC, 1,2,3-triazoles, IMAE, aryl dimercaptans, dimercaptoalkanes, DMI, diazides, diacetylenes, pyrrolidone, pyrrolidone esters, aminoalkyl imidazolines, imidazolines, poly(alkyleneimidazolidines), mercaptoalkylamines, hydroxyalkylamines, and heterogeneous unsaturated aliphatic and aromatic difunctional or polyfunctional moieties (e.g., imidazolidyl moieties).

Additional preferred (EX) are diaminoalkanes, diphenols, dithiophenols, aromatic poly(carboxylic acids), mercaptoamines, mercaptoethanol, allylamines, PEA, piperazine, polypiperazines, AEP, EPC, cyclic pyrrolidine derivatives, EDA, DEIDA, and hyperbranched dendritic polymers such as those derived from polylysine, poly(esteramide), hyperbranched dendritic polymers such as those derived from polylysine, poly(esteramide), poly(amidoamine), poly(ethyleneimine) or poly(propyleneimine) moieties. More preferred are PEA, DMI, methyl acrylate, EPC, 1,2,3-triazoles, IMAE, PIPZ, aminoalkyl piperazines, poly(alkylenepiperazines), diamines possessing disulfide moieties, MIPIEP, bis(piperazinoalkyl)disulfides, and piperazine derivatives.

FIG. 3 illustrates these (EX) moieties.

(TF) means the following:

Terminal functional groups (TF) sufficiently reactive to undergo addition or substitution reactions, or ring-opening, or any functionally active moiety that can be used to propagate the dendritic branch to the next generation including but not limited to free radical and 1,3-dipolar cyclo-addition reactive moieties. Some but not all (TF) moieties may react to form the next generation G dendrimer and the (TF) groups may be the same or different. The (TF) can be polymer initiation groups. When the (TF) moiety is the last G, then that (TF) may be unreactive. The (z) term refers to the number of surface groups mathematically defined by the G.

Some examples of such terminal groups are, including but not limited to, amino groups [including primary and secondary, which may be capped, but has at least one uncapped amino group present (e.g., methylamino, ethylamino, hydroxyethylamino, hydrazino groups, benzylamino, glucosamine, an amino acid, mercaptoethylamino), tertiary amino (e.g., dimethylamino, diethylamino, bis(hydroxyethyl)amino), quaternary amino groups, trialkyl ammonium, bis (hydroxyethyl)amino, bis(2-haloethyl)amino, N-alkylated, N-arylated, N-acylated derivatives]; hydroxyl, mercpato, carboxyl, alkenyl, allyl, aryl, methalkyl, vinyl, amido, halo, urea, oxiranyl, aziridinyl, oxazolinyl, azalactone, lactam, lactone, imidazolinyl, sulfonato, phosphonato, boronato, organosilanes, isocyanato, isothiocyanate, hydroxy alkylazido, and α-haloacyl groups. The number of carbons present for these hydrocarbon groups is from 1 to 25. Terminal groups may be substituted with other groups using conventional procedures. [See U.S. Pat. Nos. 4,507,466; 4,558,120; 4,631,337.]

Preferred surface groups (TF) are polyethyleneglycol, pyrrolidone, pyrrolidone esters, carboxypiperidines, piperidines, piperazines, substituted piperazines, aminoalkyl piperazines, hexylamides, aldehydes, azides, oxetanes, dyes (e.g., near infared fluorchromes such as cyanine derivatives, FITC), colorimetric (e.g., Nile red), tris(hydroxymethyl)amidomethane, photochromic moieties (e.g., sydnones, phorphines), amidoethylethanolamines, carbomethoxypyrrolidinone, succinamic acid, amidoethanol, amino acids, protected amino acids, antibodies and fragments, proteins, peptides, cyclopeptides, cationic steroids, macrocyclic groups, azacrown ethers, antibiotics/antibacterials [e.g., aminoglycosides, amphenicols, ansamycins, P-lactams (such as penicillin, cephalosporins, cephamycins, oxacephems, carbapenems), tetracyclines, macrolides, lincosamides, 2,4-diaminopyrimidines, nitrofurans, quinolones, sulfonamides, sulfones], antineoplastics [e.g., alkyl sulfonates, aziridines, epoxides, ethylenimines and methylmelamines, nitrogen mustards, nitroureas, purine analogs, androgens, antiadrenals, antiandrogens, antiestrogens, estrogens, LH-RH analogs, progestogens and others], folic acid and analogs, epoxides, acrylates, methacrylates, amines, carboxylates, cationic, anionic, neutral, aromatic, glucosamine or other amino sugars, biotin, avidin, streptavidin, growth factors, hormones, aptamers, DOTA, DTPA, metal chelates, naphthyl sulfonates, alkyl sulfonates, aryl sulfonates, targeting groups (e.g., CD19, CD22, aptamers), hyaluronic acid, polyoxometalates, organic chromophores, polyvalent attached compounds, carbon nanotubes, fullerenes, nanocomposites, all metal nanoparticles, all semiconductor nanoparticles with all varieties of cores and shells, radioactive materials and their chelated analogues, fluorescent molecules (metal salts, organic compounds), electrically conductive molecules, light or electromagnetic energy absorbing or emitting molecules (such as UV, VIS (visible), IR and microwave), radioactive analogues of drugs or diagnostic agents, silanes, siloxanes, silsesquioxane, poly(aryl-alkyl) poly(iodides), quantum dots, nanocrystals (e.g., Au, Ag, Cu, etc.), polyfluorinated molecules, surfactants, dendrons, differentiated dendrons, dendrimers, methoxy ethoxy ethoxy, polyimides (e.g., maleimide), herbicides (e.g., trifluralin, 2-phosphonomethylamino acetic acid), polyazo compounds, polyphosphazine, polyfluorinated sulfonates, heteroatoms chains and branches, lipids, starches, simple sugars (e.g., mannose, dextrose), oligonucleotides, complex sugars, drugs, such as anti-cancer agents (e.g., doxorubicin, methotrexate, others), acetylsalicylic acid, salicylic acid, vitamins (e.g. vitamin E, C), cofactors (e.g. NADH), or antioxidants. (TF) can be further reacted with any carried material (M) that can be associated with the (TF) entity and may be from one (M) to the maximum possible z present on the surface, only limited by N-SIS. Additionally some (TF) can be further reacted with (BR) or (EX) to grow the surface more.

Also, preferred (TF) groups are piperazine and its derivatives, alkyl piperazine, aminoalkyl piperazine, 1,2,3-triazoles, IMEA, acrylate, methacrylate, acrylamides, alkynes, hydroxyl, epoxide, oxazoline, alkyleneimines, lactones, azalactones, polyethylene oxides, amino, ethyl imines, carboxylates, alkyl, aziridine, azides, ethyl imines, alkyl esters, epoxides, alcohol groups, alkylthiols, thiols, thioranes, morpholines, amines, hydrazinyl, carboxyl, allyl, azidyl, alkenyl, alkynyl, hydroxylalkylamino, protected DETA, carboxyalkyl, pyrrolidone (and its esters), and succimidyl esters. Especially preferred are piperidines, aminoalkyl piperazines, alkyl piperazines, piperazine derivatives, and triazoles.

Figure 5:
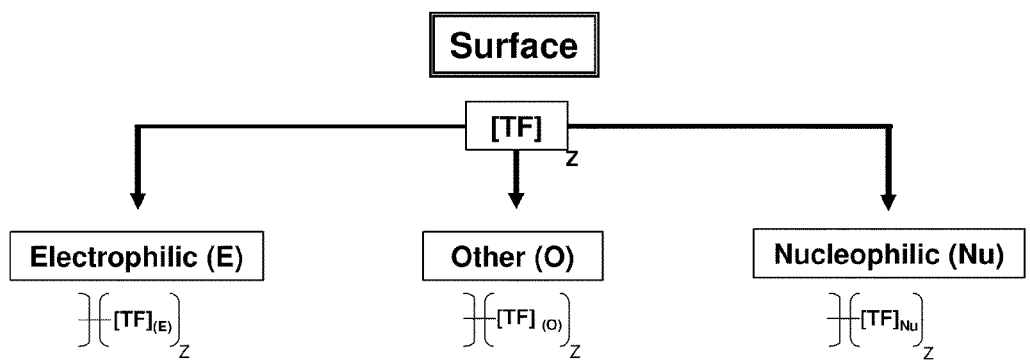
FIG. 5 illustrates the number of surface groups (z) that have terminal functionality (TF). These (TF)s may be the same or different. Also these (TF)s have one or more of the following features: an electrophilic moiety (E), a nucleophilic moiety (Nu), other reactive moiety (O), a non-reactive terminal group (e.g., a hydrocarbon), or a combination of these possible moieties.

FIG. 5 illustrates these (TF) groups.

The moieties (C), (BR), (IF), (FF) and (EX) can contain atoms that are radioactive isotopes when desired. For example, $^3H$ or $^{14}C$ can be used to trace the location of the dendrimer or dendron in a biopathway or location of by-product or metabolite of the dendritic polymer.

The dendritic polymers of Formula (I) must have at least one of (EX) or (IF) present in their desired structure. It is possible to have more then 1 of both (EX) and (IF) present.

Thus prepared, the dendrimer of Formula (I) can be reacted with a wide variety of compounds to produce polyfunctional compounds with unique characteristics. For example, a dendrimer having terminal amine moieties may be reacted with unsaturated nitriles to yield a polynitrile, or with an α, β-ethylenically unsaturated amide to form a polyamide, α, β-ethylenically unsaturated ester to form an ester terminated dendrimer, an oxirane to form a polyol, ethylenically unsaturated sulfide to form a thiol terminated dendrimer. A dendrimer having terminal hydroxyl moieties may be reacted with a carboxylic acid to form an ester terminated dendrimer, with an alcohol or alkylhalide to form an ether terminated dendrimer, with isocyanate to form a urethane terminated dendrimer, with thionyl chloride to a chloride terminated dendrimer, and with tosylate to form a tosyl-terminated dendrimer. As an example, preferred generalized structure is shown by Formula (III) below:

Formula (III)

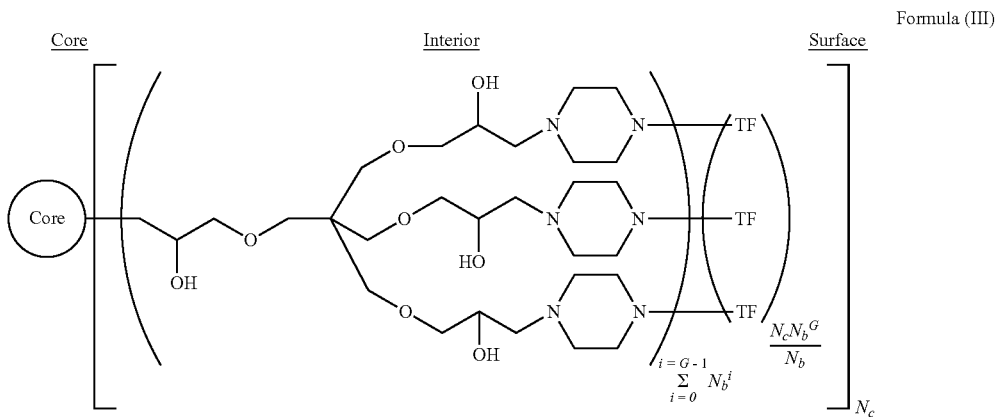

Where:
$N_c$=Core Multplicity; $N_b$=Branch Multiplicity

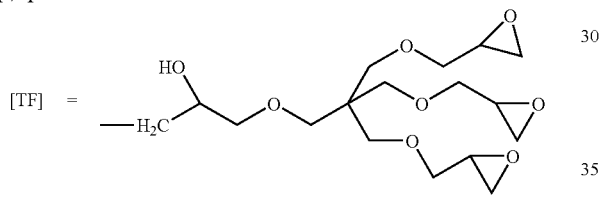

1p;1p

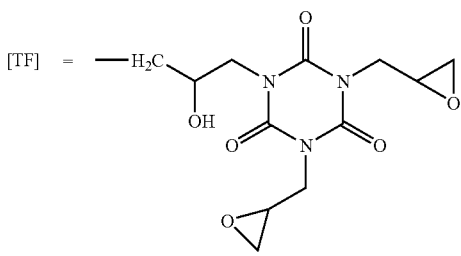

[TF] = —CO$_2$CH$_2$CH$_3$, H, —CH$_2$—CH$_2$—NH$_2$

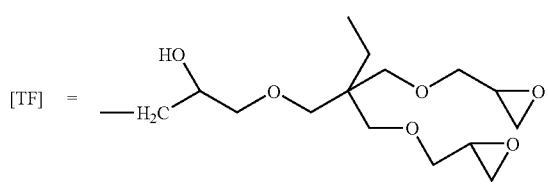

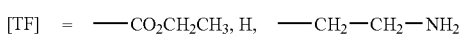

Figure 6:
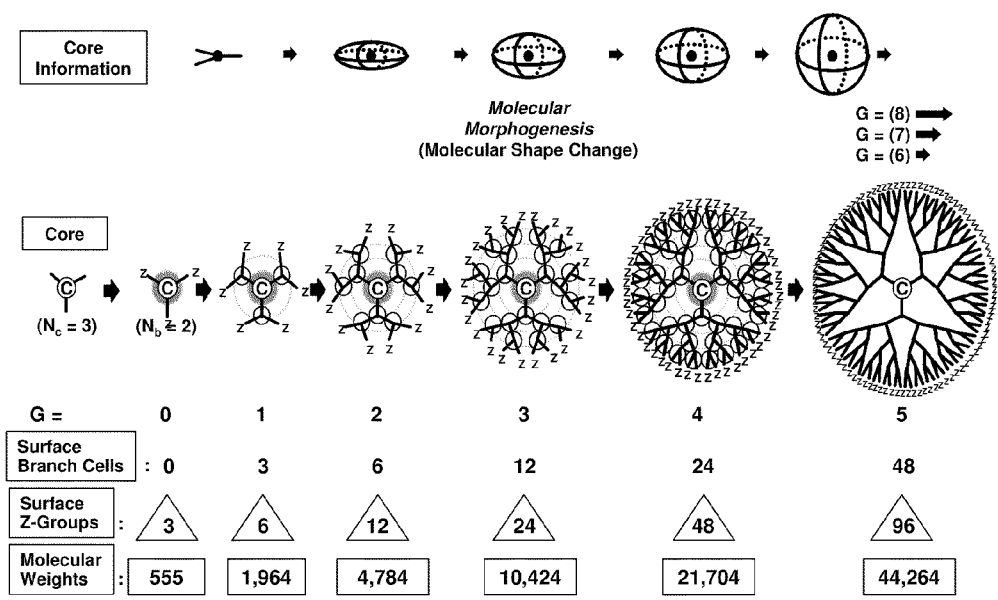
FIG. 6 illustrates the divergent growth of the dendritic polymer (i.e., dendrimer architecture) from one generation to the next. As the dendritic polymer grows, it changes nanoscale molecular shape and molecular weight as a function of generation as it amplifies mathematically. In this Figure the inclusion of (IF), (EX) and (BR) moieties is intended.
Figure 7:
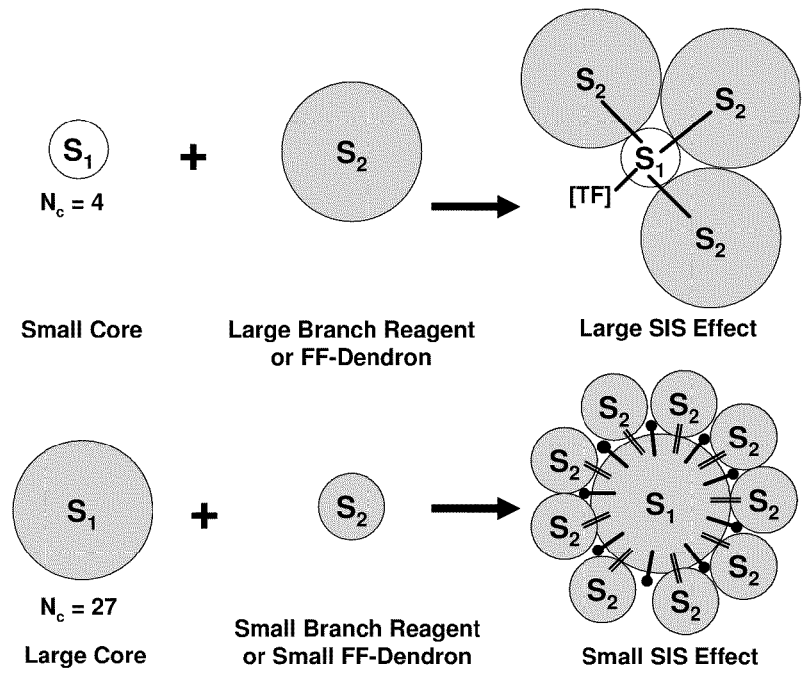
FIG. 7 illustrates the N-SIS characteristics of the dendrimers/dendrons of Formula (I) to show reactivities of various moieties when the (BR) is either larger or smaller than the (C) and the N-SIS effect on the number of reactive groups that are accessible for reaction.
Figure 8:
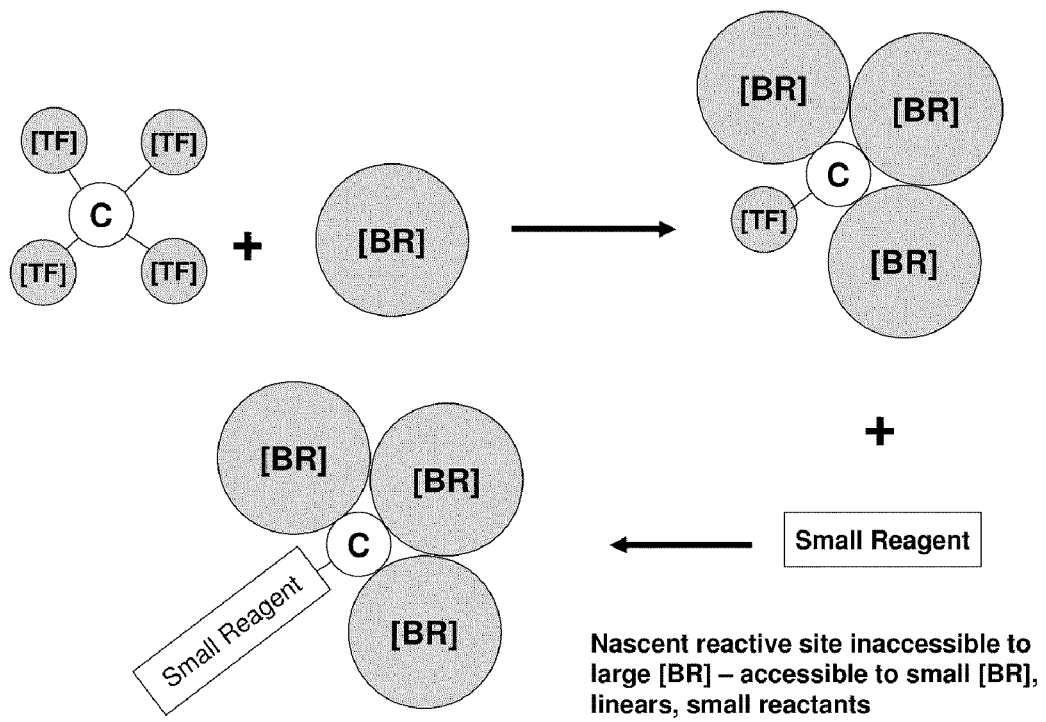
FIG. 8 illustrates the N-SIS characteristics of the dendrons/dendrimers of Formula (I) to show reactivities of various moieties when the (BR) is larger than the (C) showing that further reaction by smaller reactants is still possible.

The method where each generation of the dendrimer is grown is well known. FIG. 6 illustrates such growth and amplification in the number of (z) groups and the increased molecular weight.

Some of the present dendrimers of this invention are represented by the Formula (II):

Formula (II)

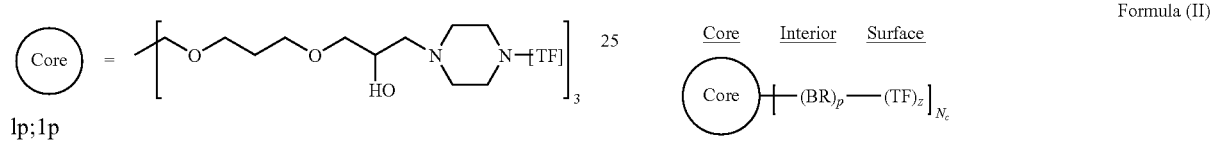

$$p = \text{Total \# of } [BR] = \left(\frac{N_b^1}{N_b} + \frac{N_b^2}{N_b} + \frac{N_b^3}{N_b} + \ldots \frac{N_b^G}{N_b}\right)[N_c] = \left(\sum_{i=0}^{i=G-1} N_b^i\right)[N_c]$$

where: core (C), (IF), G, $N_c$, $N_b$, i, z and p are defined as above for Formula (I) and (BR) must have an (IF) moiety present or be able to generate an (IF) in situ.

Some preferred embodiments of Formula (I) have (FF) forming a dendron where $_c$ of from 3-4; (IF)=OH, NH or SH; (EX)=PIPZ; (BR) has a multiplicity $N_b$ of 24; and (TF) is as defined before. In another embodiment, (M) is associated with the dendritic polymer of Formula (I). Yet another embodiment of the dendritic polymers of Formula (I) are the poly(ester-acrylate) and poly(ester-epoxide)dendrimers.

Nanoscale Sterically Induced Stoichiometry ("N-SIS")

Briefly, N-SIS may be presently defined as a specific nanoscale steric effect that changes or affects the reactivity (i.e. valency/stoichiometry) of a nanoscale reagent or reactive substrate. These N-SIS properties are virtually unknown and at best ill defined in the nanoscale realm. They appear to be manifested whenever certain combinations or permutations of nanoscale reagents, nanoscale substrates, sub-nanoscale reagents or sub-nanoscale substrates are brought together to form chemical bonds or form supramolecular associations or assemblies. Additionally, micron-sized substrates and nanoscale reagents may provide similar effects. A present preliminary view of this concept presumes that as the summation of certain nanoscale reacting component volumes approach or exceed available nanoscale space surrounding a reaction site, such N-SIS effects begin to emerge. For example, when certain dendrimer surface-group volumes and incoming reagent volumes approach the available exterior volume surrounding a collection of reactive dendrimer surface groups (TF), reaction rates are dramatically suppressed and reactivities of certain groups are substantially affected. [D. A. Tomalia; A. M. Naylor; W. A. Goddard III, *Angew. Chem. Int. Ed Engl.*, 29, 138-175 (1990)]. Thus it should be possible to use this N-SIS effect to influence reaction parameters involved for synthesizing various cores, branch cell reagents, dendrons, dendrimers and other dendritic polymer structures based on the relative sizes, bulkiness, electronic/hydrophilic/hydrophobic features, etc. of specific nanoscale and sub-nanoscale reagents and substrates used in these constructions.

While not wishing to be bound by theory, further discussion of this N-SIS result and predications for the formation of the dendritic polymer of Formula (I) are provided below after the Roman numeral comparative examples.

Methods of Making the Dendritic Polymers of Formula (I)

The vast majority of references discussed above are to ring-opening reactions resulting in polymerizations to hyperbranched polymers, rather than use of a highly energetic ring-opening reaction for the controlled addition of reagents toward branch cell amplification. There is no teaching by these references of the combination or to produce the use of reactive ring-opening reactions with highly functional branch cell reagents as is now reported by the present invention. None of these references teach the use of ring-opening, or other highly reactive, precise chemistry for the stepwise controlled addition of a branch cell reagent.

The traditional process for PAMAM dendrimers includes an amidation step which involves thermodynamically driven, lower reaction rate, slow chemistry, accompanied by long reaction times involving non-differentiated, difunctional intermediates (i.e., ethylene-diamine and methyl acrylate). These process features require high excesses of reagents and high dilutions resulting in low production capacities per reactor volume and thus high costs, particularly at higher generations.

The current invention involves building the dendrimer branch structure using branch cell reagents, which are typically bulky, multifunctional molecules compared to the smaller reagents (i.e., ethylenediamine and methyl acrylate) described in typical divergent PAMAM synthesis processes.

The invention herein involves the use of faster, kinetically driven, reactive ring-opening chemistry (i.e., "click type" or other fast reactions) combined with the use of more bulky, polyfunctional branch cell reagents (BR) in a controlled way to rapidly and precisely build dendrimer structures, generation by generation. This present process provides precise structures with cleaner chemistry, typically single products, requires lower excesses of reagents, lower levels of dilution, thus offering a higher capacity method which is more easily scaled to commercial dimensions, new ranges of materials, and lower cost. The dendrimer compositions prepared possess novel internal functionality, greater stability, e.g., thermal stability and exhibit less or no reverse Michael's reaction (compared with traditional PAMAM dendrimer structures). Furthermore, they reach encapsulation surface densities (i.e., acquire nano-container properties) at lower generations (and therefore at less cost) than traditional PAMAM dendrimer structures (see FIGS. 20A and 21). Unexpectedly, these present reactions of poly-functional branch cell reagents (BR), possessing highly functionalized surfaces do not lead to gelled, bridged/cross-linked systems/materials even at lower stoiochiometries/excesses than normally required for traditional PAMAM dendrimer systems.

Methods of preparing the dendritic polymers of Formula (I) can be further described by the following discussion of the reaction from the (C).

One-pot reactions are commercially desirable for speed of process and separation of the desired product. The process uses reactive (C) combined with reactive (BR) precursors (for example iminodiacetic acid, primary amine protected DETA, iminodialkyl nitriles, iminodialkyl phosphonic acids, imino dialkyl halides (e.g. bis(2-chloroethyl)amine), diethanol amine, secondary diamines such as dialkylamines, diallylamines, diarylamines, iminoalkyleneamines (e.g., bis(hexamethylenetriamine)) or preformed (BR) reagents (for example TREN, TRIS, acetylene di- or tri-epoxy moieties), in a solvent, at a temperature from about 0° to 100° C. until completion of the reaction, which forms the dendritic polymers of Formula (I) but without an (EX) moiety present. Formula (IV) below illustrates these dendritic polymers where (C), (FF), (IF), (BR), (TF), q, p, x, z, and $N_c$ are defined as before.

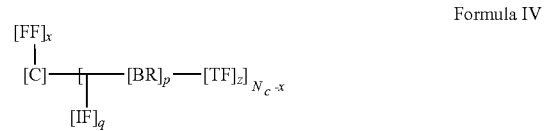

Formula IV

The product of the one-pot reaction from Formula (IV) above can be further reacted by using orthogonal chemistry on the (TF) to add additional (BR) moieties to the first dendritic structure made. This allows the synthesis of higher generations of homo/hetero compositional (BR) containing dendritic polymers of Formula (I) which may or may not have (EX). If (EX) are present, they are introduced with this second step involving orthogonal chemistry. The following Formula (V) shows those dendritic polymers made that do not have (EX) present and where (C), (FF), (IF), (BR), (TF), q, p, x, z, and $N_c$ are defined as before. The subscript of "n" is only to distinguish that the (BR) moieties were added in different steps in the total reaction as described above and that enough of the second (BR) must be present to react with the multiplicity of the first (BR) reagent. This is the method of all (BR) reactions for amount present.

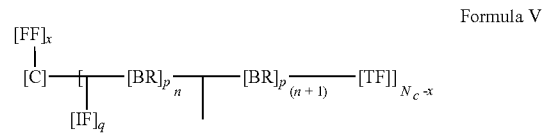

Formula V

One orthogonal chemical approach is to use ketone solvent protection of either reactive (BR) precursors or (BR) possessing secondary and/or primary amines [e.g., Frédéric Laduron et al., Org. Proc. Res. & Devel., 9, 102-104 (2005)]. In this manner primary amines may be protected in the presence of secondary amines, thus allowing reaction of secondary amine sites with reactive (C) or reactive (TF). When only primary amines are present in the preformed (BR), one or more of these primary amine moieties may be protected with ketone solvent and the other unprotected primary amines may be allowed to react with appropriate (C) or (TF).

Another orthogonal chemical approach may involve nucleophilic reaction (Michael's addition) of an alkylamine with an alkyl acrylate (such as methyl acrylate) to form amino ethyl ester linkages, followed by reaction of the ester with alkleneamines or (EX) or other (BR).

A further orthogonal chemical approach may involve conversion of either (C) or (BR) possessing primary amine (TF) groups into pyrrolidone ester groups by reaction with DMI. Subsequent reaction of this ester with primary amines or partially protected primary polyamines can provide linkages to new (BR) or (TF) moieties.

Another orthogonal chemical approach is the free radical addition of thiol containing preformed (BR) reagents or reactive (BR) precursors to (C) or (BR) possessing allylic or olefinic groups.

Another orthogonal chemical approach is the 1,3-dipolar cyclo-addition of azides containing (C) and (BR) to alkynes containing (C) and (BR). The alkyne containing (C) may have from 1 to $N_c$ alkyne moieties present and alkyne containing (BR) may have from 1 to $N_b-1$ alkyne moieties. The other reactive groups present in (C) or (BR) can be any of the (BR) groups listed herein before. Azide containing (C) and (BR) are produced by nucleophilic ring-opening of epoxy rings with azide ions. Subsequent reaction of these reactive groups can provide triazole linkages to new (BR) or (TF) moieties using "click" chemistry as described by Michael Malkoch et al., in *J. Am. Chem. Soc.* 127, 14942-14949 (2005).

When the (EX) is desired, any of the above reactions for orthogonal chemical approaches can be modified to have an (EX) inserted after any (BR) or (C). This addition of (EX) is done by the approaches discussed herein.

The terminal surface groups (TF) may be reacted in a variety of ways. For example, when (TF) is an amine moiety it may be reacted with: an unsaturated nitrile to yield a nitrile-terminated dendrimer; an α,β-ethylenically unsaturated amide to form an amide-terminated dendrimer; an α,β-ethylenically unsaturated ester to form an ester-terminated dendrimer; an oxirane to form a hydroxyl-terminated dendrimer; or an ethylenically unsaturated sulfide to form a thiol-terminated dendrimer. Additionally, the dendrimer terminal groups may be reacted with difunctional or trifunctional compounds such as alkyl dihalides or an aromatic diisocyanate to form a poly(dendrimer) or bridged dendrimers having a plurality of dendrimers linked together through the residues of the polyhalide or polyisocyanate. The bridged dendrimers can also be formed by reaction of an electrophilic surface dendrimer with a nucleophilic surfaced dendrimer such as an amine-terminated surface with an ester-terminated surface. When this reaction occurs, a linking group may optionally be present to space the dendrimers apart. Thus sheets or aggregates of dendrimers that are joined (associated with one another) may be prepared.

The Michael's addition reaction, when used for dendrimer synthesis, is an example of a thermodynamically driven addition of a multifunctional nucleophilic reagent (i.e. an amine to an unsaturated Michael's acceptor). These reactions are known to be reversible, even under moderate conditions, and do not yield pendant interior functionality. Therefore they produce dendrimer structural connectivity that lacks high thermal robustness and stability as determined by thermal gravimetric analyses (TGA) (See FIG. 18 for comparison to PEHAMs obtained by this present invention). On the other hand, small strained ring-opening reactions with the same or similar polyfunctional reagents are driven by kinetically controlled processes to produce more thermally robust dendritic structures which are more resistant to thermal degradation and thermal rearrangement. A further advantage in using these kinetic controlled ring-opening reactions is that they create pendant interior functionality (IF) which does not occur with Michael's addition reactions.

N-SIS appears to affect the reactivity of a (C) with a (BR) or focal point functionalized (FF) dendron due to the relative sizes and the dimensions of the reactants concerned. If the (BR) is larger than the (C), then fewer (BR) can physically find space to allow chemical bonding and there results a large definable N-SIS effect. On the other hand, if the (C) is substantially larger than the (BR), then a smaller N-SIS effect results and more (BR) will be able to bond with the (C) due to enhanced space around the core, thus lessening SIS effects. To mitigate the effects of N-SIS, the present invention uses (EX). Such (EX) allow more physical room between the (C) and the (BR) so the N-SIS effect is lessened.

Figure 9:
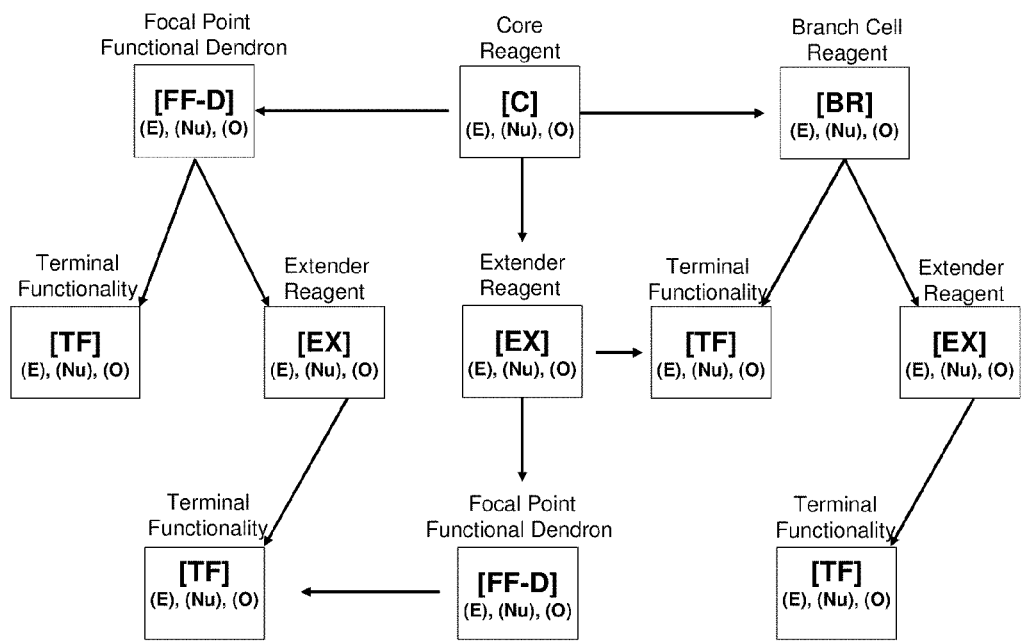
FIG. 9 illustrates the combinatorial reactivities of (Nu), (O), and (E) reactions for (BR), (EX), (C), (FF) and (TF) to form the dendrons/dendrimers for Formula (I) for one generation. These reactions may be repeated to form the higher generations or used in other orthogonal chemistry growth strategies.

FIG. 9 illustrates the various reactions that are a part of this invention to prepare dendrimers of Formula (I).

Another use of N-SIS is to form differentiated dendritic polymers (i.e. dendrons/dendrimers). For example, N-SIS can be used to control the reaction of a single, focal point functional (FF) dendron with a polyfunctional (C), branch cell (BR), extender (EX), dendron or dendrimer terminal groups (TF), to form orthogonally reactive, differentiated dendritic structures. Thus, a dendron having a (FF) can be reacted with a core and (EX) that is joined to a (BR). The (BR) can be further reacted and the dendron has its own surface terminal groups (TF).

Divergent dendritic growth can be precisely controlled to form ideal dendritic polymers which obey mathematical formulas, at least through the first several generations of growth. However, because the radii of dendrimer molecules increase in a linear manner as a function of generation during ideal divergent growth, whereas the surface cells amplify according to a geometric progression law, ideal dendritic growth does not extend indefinitely. There is a critical generation at which the reacting dendrimer surface does not have enough space to accommodate incorporation of all of the mathematically required new units. This stage in digression from ideal dendritic growth is referred to as the de Gennes dense-packed stage. At this stage, the surface becomes so crowded with terminal functional groups that, although the terminal groups are chemically reactive, they are sterically prohibited from participating further in ideal dendritic growth. In other words, the de Gennes dense-packed stage is reached in divergent dendrimer synthesis when the average free volume available to the reactive terminal group decreases below the molecular volume required for the transition state of the desired reaction to extend the dendritic growth to the next generation. Nevertheless, the appearance of the de Gennes dense-packed stage in divergent synthesis does not preclude further dendritic growth beyond this point. It has been demonstrated by mass spectrographic studies that further increase in the molecular weight can occur beyond the de Gennes dense-packed stage. However, this occurs in a non-ideal fashion that no longer adheres to values predicted by dendritic mathematics.

Products resulting from continuation of dendritic growth beyond the dense-packed stage are "imperfect" in structure, because some of the surface groups in the precursor generation are sterically precluded from undergoing further reaction. The number of functional groups on a dendrimer which has been grown past the de Gennes dense-packed stage will not correspond to the ideal, mathematically predicted value for that generation. This discontinuity is interpreted as a signature for the de Gennes dense-packed stage.

Differences in Reactivity

In the following reaction scheme, the behavior and reactivity of the various reactants are briefly reviewed.

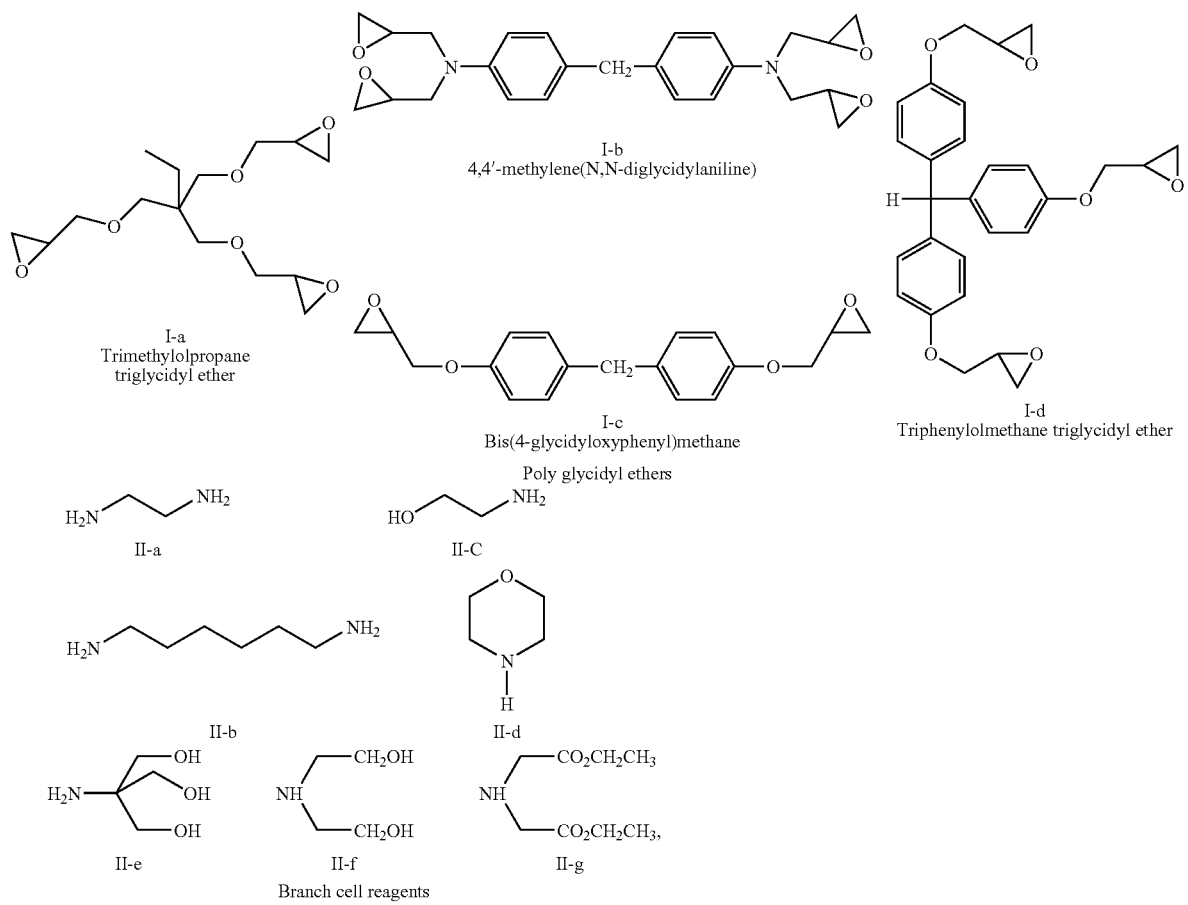

Branch cell reagents

In the following discussion, the bold numerals refer to the structures in these above Schemes.

1. Effect of Electron Density on Ring-Opening Reaction

The reaction of amine reagents (IIe-IIg) with poly(glycidyl)ethers (Ia & Ic-d) (PGE) was faster than with poly(glycidyl)aniline (Ib) (PGA). Addition of TRIS (II-e) to glycidyl aniline (Ib) was not completed even after 3 days at 60° C. and the observed product contained substantial amounts of both bis- and tri-adducts. Prolonged heating caused extensive decomposition of the starting material. Reaction with diethanolamine (II-f) gave tetra- and tri-adducts; reaction with II-g gave a tetra-adduct, but prolonged reaction led to decomposition of the product.

While not wishing to be bound by theory, it is believed that this reactivity difference in the PGE's and PGA's can be explained on the basis of their relative electronegativities of their oxygen and nitrogen substituents, respectively. Since oxygen is more electronegative than nitrogen, the electron density on the epoxide ring (in PGE's) is less than epoxide (PGA's) (i.e. through an inductive effect), thus facilitating the nucleophilic ring-opening of the PGE's verses the PGA's. Thus the PGE's have a faster reaction time. These data show that the dendrimers of Formula (I) are more electronegative and have a faster reaction time.

2. Effect of pKa on Reactivity of Amines

Reactivity of branch cell reagents (IIe-IIg) with PGE's and PGA's was also found to be different. The observed reactivity was IIf>IIg>IIe. The difference in reactivity of the three branch cell reagents can be explained on the basis of their pKa values. The pKa value of tris(hydroxymethyl)amino methane (TRIS) is 8.10 and diethanolamine (DEA) is 8.88. The higher the pKa values the stronger the base. DEA posses a stronger basic character than TRIS, i.e. reactions with DEA are faster. This rationale was supported by the experimental evidence. Thus the higher the pKa for the (BR) the faster the reaction.

3. Effects of Protic Solvents and Temperature

There is a difference in the reactivity of PGE's and PGA's with various nucleophilic branch cell (BR) reagents. Reactions were studied in various solvents and temperature. Initially, reactions with substrate Ia tri(glycidyl ether) were studied in methanol at room temperature and found to be slow with reaction times requiring up to 10 days. These reactions were reexamined in various solvents and at higher temperatures. Addition of branch cell reagents (IIe-g) (BR) to all glycidyl ethers was studied at a small scale (up to 3 g) at 60° C. Surprisingly, all the reactions go to completion in 12-24 hours in methanol at 60° C. However, in contrast reactions with poly(glycidyl aniline) (Ib) were very slow even at 60° C. Thus the (BR) was not the rate determining factor, but the electronegativity of the substrate was a rate determining factor, with PGE's being the fastest.

These reactions were studied in various solvents namely, methanol, dichloromethane (DCM)/methanol (MeOH) mixtures and dimethoxyethane (DME). Reactions were slow in DCM and DME and in MeOH at room temperature. These results show that use of protic solvents is preferred to promote the rapid nucleophilic ring-opening.

Cram's Rule

While not wishing to be bound by theory, it is believed that steric effects control the stereo selective reactivity at a carbonyl oxygen resulting in chiral introduction. Cram's Rule states that a nucleophile approaches a carbonyl along the smallest substituent alignment. The largest group aligns itself anti to the carbonyl group to minimize the steric effect such that the nucleophile preferentially attacks from the side of the small substituent. [See D. J. Cram, A. Elhafez, *J. Am. Chem. Soc.* 74, 5828 (1952).]

Typical Reaction Conditions

The invention includes but is not limited to several major reaction types including (1) nucleophilic addition reactions, (2) nucleophilic ring-opening reactions, (3) 1,3-cyclo-addition reaction types involving azides and acetylenes, and (4) free radical additions of thio to olefins. The addition reaction examples include but are not limited to Michael's addition reactions where acrylates are reacted with amines. The ring-opening reactions examples include but are not limited to ring-opening reactions where amines react with epoxy, thiorane, aziridine or oxazoline functional groups. In all of these cases the amines, acrylates, epoxies, thioranes, aziridines or oxazoline groups can be functional parts of the core (C), including simple core, scaffolding core, or supercore, extender (EX), branch cell reagent (BR) or terminal functional group (TF). Reaction conditions for these two classes of reactions, addition reactions and ring-opening reactions, can be described by the range of conditions established in the literature for addition to a carbon-carbon double bond [See for example, R. T. Morrison, R. N. Boyd, *Organic Chemistry*, Chapter 6, pub. Allyn and Bacon, Inc, New York, N.Y., (1966) or general nucleophilic ring-opening reactions also at Chapter 6]. Typical ranges of reaction conditions are further described.

Acrylate-Amine Reaction System

An example of the acrylate-amine reaction system is the reaction of an acrylate functional core with an amine functional extender, such as shown below:

$$(C)+(EX) \rightarrow (C)(EX)(TF) \quad (1)$$

where (C)=Trimethylolpropane triacrylate (TMPTA); (EX)= piperazine (PIPZ); (TF)=Secondary Amine.

Another example of an acrylate-amine reaction is the reaction of an amine functional extended core reagent (C) (EX) (TF1) with an acrylate functional branch cell reagent, such as shown below:

$$(C)(EX)(TF1)+(BR) \rightarrow (C)(EX)(BR)(TF2) \quad (2)$$

where (C)=Trimethylolpropane triacrylate (TMPTA); (EX)= piperazine (PIPZ); (TF1)=Secondary Amine; (BR)=Trimethylolpropane triacrylate (TMPTA); and (TF2)=Acrylate.

Flow Chart 1

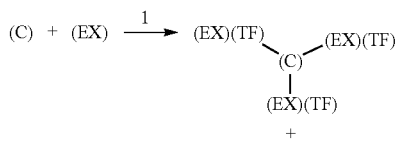

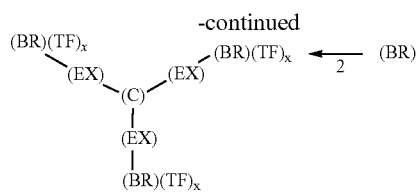

For the addition of a reactive branch cell (BR), extender (EX), or terminal functional group (TF) to a simple core, scaffolding core, super core or current generation product, the mole ratio of the molecule to be added to the moles of reactive functional groups on the simple core, scaffolding core, super core or current generation product is an important parameter. For example, in the addition of an extender group to a core, the mole ratio of (EX)/(C) is defined as the moles of extender molecules (EX) to the moles of reactive functional groups on the simple core, scaffolding core, super core, or current generation structure (i.e. $N_c$). Similarly the addition of a reactive branch cell reagent to a simple core, scaffolding core, super core, or current generation structure (BR)/(C) is defined as the moles of branch cell molecules (BR) to the moles of reactive functional groups on the simple core, scaffolding core, super core, or current generation structure (i.e. $N_c$). Depending on the structure desired, the level of addition of branch cells or extenders to a core, scaffolding core, super core or current generational product can be controlled by the mole ratio added or by sterically induced stoichiometry (e.g., N-SIS). Preferred for this reaction is using an excess of the molecules of the group being added, such as the extender or branch cell reagent to the functional groups on the simple core, scaffolding core or super core, if full surface coverage is desired.

Order of addition of these various reactants can be addition of the simple core, scaffolding core, super core or current generation product to the branch cell or extender, or addition of the branch cell or extender to the simple core, scaffolding core, super core or current generation product. Preferred steps are addition of the simple core, scaffolding core, super core or current generation product to the extender or branch cell reagent.

Reaction times vary depending on the reaction conditions, solvent, temperature, activity of the reagents and other factors but can be generally classified by typical reaction conditions known in the art sufficient to achieve addition reactions to an unsaturated organic functional group. Reaction times can range from 1 minute to several days, with longer reaction times needed for reaction of more sterically bulky groups or for reactions to crowded surfaces, such as addition of surface groups to higher generation dendrimers.

Reaction temperatures can be in the range typical for carbon-carbon double bond addition reactions or nucleophilic epoxy ring-opening reactions. The temperature range is limited by the thermal stability of the reagents in the reactions and the length of time at that temperature required for the reaction. Typical reactions temperatures are shown below.

Any organic solvents or water suitable for these addition reactions can be used including typical solvents for addition reactions to a carbon-carbon double bond, nucleophilic ring-opening reactions of epoxys, aziridines, oxazolines, 1,3-cyclo-additions to acetylenes or conditions for free radical addition of thiol to olefins. Any solvent mixture sufficient to dissolve the reagents to concentrations suitable to allow reaction can be used. Preferred solvents are polar, protic solvents. Also useful are mixtures of solvents containing both polar and nonpolar solvents, and protic and aprotic solvents or combinations thereof. Solvent mixtures can be predominantly nonprotic solvents with sufficient catalytic quantities of protic solvent to catalyze the reaction. In the case of 1,3-cyclo-addition of azides to acetylenes appropriate copper catalysts are use as described in the literature [e.g., B. Helms et al., *J. Amer. Chem. Soc.* 126, 15020-15021 (2004); P. Wu et al., *Angew. Chem. Int. Ed.* 43, 3928-3932 (2004)]. This provides for conditions which allow the dissolution and reaction of less polar or non polar simple cores, scaffolding cores, super cores, extenders or branch cell reagents, for example the difference in the reactivity of poly(glycidyl)ethers and poly (glycidyl)aniline with various nucleophilic branch cell reagents. Reactions were studied in various solvents and temperatures. Initially, reactions with substrate Ia tri(glycidyl ether) were studied in methanol at RT and found to be slow with reaction times requiring up to 10 days. These reactions were reexamined in various solvents and higher temperature. Addition of branch cell reagents (IIe-g) to all glycidyl ethers was studied in small scale (up to 3 g) at 60° C. and interestingly all the reactions go to completion in 12-24 hours in methanol at 60° C. However, in contrast reactions with poly (glycidyl aniline) (Ib) were substantially slower, even at 60° C.

Catalysts can be added to facilitate the addition reaction. Suitable catalysts include any commonly used for catalysis of addition reactions to a carbon-carbon double bond. Typical catalysts are free radical initiators for example AIBN, metal salts, titanium, magnesium, zinc, copper and lithium salts, as well as any other catalysts suitable for organic addition reactions, nucleophilic ring-opening of 3, 4, 5 member heterocyclic rings or 1,3-cyclo-additions of azides to acetylenes as well as for free radical addition of thiols to olefins.

For these and other reactions involving the reaction of an amine functional component with an acrylate functional component, typical reaction conditions can be summarized as shown in the table below:

| Amine-Acrylate Reactions | | |
|---|---|---|
| Mol Ratio range of amine/acrylate or acrylate/amine | Useful | 0.1/1 to 20,000/1 |
| | Preferred | 1/1 to 100/1 |
| | Most preferred | 1/1 to 6/1 |
| Reaction Times | Useful | 1 minute-Several days |
| | Preferred | 1 minute to 24 hours |
| | Most preferred | 1 minute to 6 hours |
| Reaction Temperatures | Useful | 0° C.-180° C. |
| | Preferred | 0° C.-80° C. |
| | Most preferred | 0° C.-35° C. |
| Solvents | Useful | Solvent mixtures containing some protic and polar solvents |
| | Preferred | Protic, polar solvents and mixtures |
| | Most preferred | Alcohols, methanol, ethanol, propanol, butanol, glycols, mixtures containing alcohols, methylene chloride/methanol, chloroform/methanol, DME/methanol, DMSO/MeOH |
| Catalysts | Useful | Catalysts for typical organic addition reactions |
| | Preferred | Metal salts |
| | Most preferred | Titanium, magnesium, and lithium salts |

Nucleophilic Ring-Opening Reaction System

An example of the ring-opening reaction system is the reaction of an epoxy functional core with an amine functional extender, such as $$(C)+(EX) \rightarrow (C)(IF1)(EX)(TF1) \tag{3}$$

where (C)=Pentaerythritol tetraglycidyl ether (PETGE); (IF1)=Internal hydroxyl (OH); (EX)=piperazine (PIPZ); (TF1)=Secondary Amine.

Another example of an epoxy-amine reaction is the reaction of an amine functional extended core reagent (C) (IF1) (EX) (TF1) with an epoxy functional branch cell reagent such as $$(C)(IF1)(EX)(TF1)+(BR) \rightarrow (C)(IF1)(EX)(IF2)(BR) \atop (TF2) \tag{4}$$

where (C)=Pentaerythritol tetraglycidyl ether (PETGE); (IF1)=Internal hydroxyl (OH); (EX)=piperazine (PIPZ); (IF2)=Internal hydroxyl (OH); (BR)=Pentaerythritol tetraglycidyl ether (PETGE) and; (TF2)=Epoxy.

Flow Chart 2

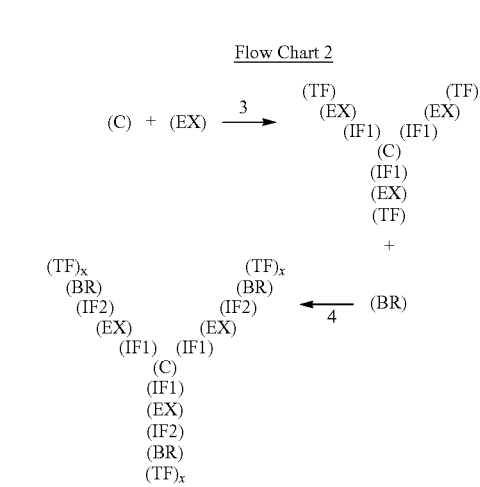

For the addition of a branch cell (BR), extender (EX), or functional group (TF) to a simple core, scaffolding core, super core or current generation product, the mole ratio of the molecule to be added to the moles of reactive functional groups on the simple core, scaffolding core, super core or current generation product is an important parameter. For example, in the addition of an extender group to a core, the mole ratio of (EX)/(C) is defined as the moles of extender molecules (EX) to the moles of reactive functional groups on the simple core, scaffolding core, super core, or current generation structure (i.e. $N_c$). Similarly for addition of a branch cell to a simple core, scaffolding core, super core, or current generation structure (BR)/(C) is defined as the moles of branch cell molecules (BR) to the moles of reactive functional groups on the simple core, scaffolding core, super core, or current generation structure (i.e. $N_c$). Depending on the structure desired, the level of addition of branch cells or extenders to a simple core, scaffolding core, super core or current generational product can be controlled by the mole ratio added or by sterically induced stoichiometry (N-SIS). Preferred is using a excess of the molecules of the group being added, such as the extender or branch cell reagent to the functional groups on the simple core, scaffolding core or super core if full surface coverage is desired.

Order of addition can be addition of the simple core, scaffolding core, super core or current generation product to the branch cell or extender, or addition of the branch cell or extender to the simple core, scaffolding core, super core or current generation product. Preferred is addition of the simple core, scaffolding core, super core or current generation product to the extender or branch cell reagent.

Reaction times vary depending on the reaction conditions, solvent, temperature, activity of the reagents and other factors, but can be generally classified by the breadth of reaction conditions sufficient to achieve nucleophilic ring-opening reactions of a strained epoxy, aziridine or other ring functional group. Reaction times can range from 1 minute to several days with longer reaction times needed for reaction of sterically bulky groups or reactions to crowded surfaces, such as addition of surface groups to higher generation dendrimers.

Reaction temperatures can be in the range typical for strained ring-opening addition reactions. The temperature range is limited by the thermal stability of the reagents in the reactions and the time of reaction. Typical reactions temperatures are shown below.

Any organic solvents or water suitable for ring-opening addition reactions include typical solvents for nucleophilic ring-opening reactions. Any solvent mixture sufficient to dissolve the reagents to concentrations suitable to allow reaction can be used. Preferred solvents are polar, protic solvents. Also useful are mixtures of solvents containing both polar and nonpolar solvents, and protic and aprotic solvents or combinations thereof. Solvents can be a nonprotic solvent with sufficient catalytic quantities of protic solvent to allow reaction. The concentration of the reagents in the solvent can range significantly. In some cases the excess reagents for the reaction may be used as the solvent. Solvent mixtures can be predominantly nonprotic solvents with sufficient catalytic quantities of protic solvent to catalyze the reaction. This provides for conditions which allow the dissolution and reaction of less polar or non-polar simple cores, scaffolding cores, super cores, extenders or branch cell reagents. For example, difference in the reactivity of poly(glycidyl)ethers and poly (glycidyl)aniline with various nucleophilic branch cell reagents required investigation of various solvents and temperatures. For reactions which require higher temperatures, less volatile solvents may be required.

These reactions were studied in various solvents namely, methanol, dichloromethane (DCM)/methanol mixtures and dimethoxyethane (DME). Reactions were slow in DCM and DME and in methanol at room temperature. These results show that use of protic solvents are necessary to promote the nucleophilic addition.

Catalysts can be added to facilitate the addition, 1,3-cyclo-addition or ring-opening reactions. Suitable catalysts include any commonly used catalysis for ring-opening reactions. Typical catalysts are Lewis acids and Lewis acid salts such as LiBF$_4$, BF$_3$, zinc salts or other catalysts in this category. Suitable catalysts for 1,3-cyclo-addition reactions also include copper and zinc salts.

For these and other reactions involving the reaction of an amine functional component with an acrylate functional component, typical reaction conditions can be summarized as shown below:

| Nucleophilic-Ring-Opening Reactions | | |
|---|---|---|
| Mol Ratio range of amine/ring or ring/amine | Useful | 0.1/1 to 20,000/1 |
| | Preferred | 1/1 to 100/1 |
| | Most preferred | 1/1 to 6/1 |
| Reaction Times | Useful | 1 minute-Several days |
| | Preferred | 1 minute to 24 hours |
| | Most preferred | 1 minute to 6 hours |
| Reaction Temperatures | Useful | 0° C.-300° C. |
| | Preferred | 0° C.-120° C. |
| | Most preferred | 0° C.-60° C. |

| Nucleophilic-Ring-Opening Reactions | | |
|---|---|---|
| Solvents | Useful | Solvent mixtures containing some protic and polar solvents |
| | Preferred | Protic, polar solvents and mixtures |
| | Most preferred | Alcohols, methanol, ethanol, propanol, butanol, glycols, mixtures containing alcohols, methylene chloride/methanol, chloroform/methanol, DME/methanol, DMSO/MeOH |
| Catalysts | Useful | Catalysts for typical strained ring-opening reactions |
| | Preferred | Lewis acids and Lewis acid salts |
| | Most preferred | LiBF$_4$, BF$_3$ zinc salts and others in this category |

Methods of isolation and purification of the products for both of these classes of reactions include typical methods of isolation for carbon-carbon double bond addition reactions and strain ring-opening addition reactions. Additionally, known methods of isolation of typical dendrimeric molecules are used. Preferred are ultrafiltration, dialysis, column separations using silica gels or Sephadex™, precipitation, solvent separation or distillation. The method of isolation may vary with the size and generation of the product. As the polymer particle grows in size, more preferred methods of dendrimer separation include ultrafiltration and dialysis. In some cases the differential solubility between the reacted and unreacted species can be used to assist in separation and isolation of the products. For example, the solubility differences between the epoxides, which are fairly non polar, and the ring-opened polyols, which are more polar, can be utilized in the separation process.

Methods to accelerate the reactions may include use of microwave assisted or ultrasound assisted reactions.

1,3-Dipolar Cyclo-addition of Azides to Alkynes to Form Formula (I) Dendrimers/Dendrons As early as 1968, Huisgen, et al., [*Angew. Chem., Int. Ed. Engl.* 7, 321-328 (1968)] reported the facile, high yield, chemo-selective cyclo-addition of organic azides to alkynes, generally catalyzed by Cu$^{+1}$ salts to form structures containing covalent 1,4-disubstituted-1,2,3-triazole linkages. Because of the high chemo-selectivity of these reactions, these reactions may be selectively performed in the presence of a wide variety of competing or parallel reactions/functionalities without interference. These reactions are significant for preparing dendritic polymers of the present invention in that it allows the synthesis of dendrimers/dendrons of the Formula (I) type by either (a) combination of polyazide, terminally functionalized (TF) cores, dendrons or dendrimers possessing internal functionality (IF) (e.g. hydroxyl, and others listed before) with mono-alkyne (TF) functionalized polyepoxy branch cell reagents/dendrons; (b) by direct combination of polyazide, terminally functionalized (TF) cores, dendrons or dendrimers, possessing internal functionality (IF) with a slight excess of polyalkyne terminally functionalized (TF) branch cell reagents. (i.e., where the ratio of alkynes equivalent:azide equivalent is greater than one). The mixing of the azides and alkynes can be done either concurrently or sequentially in the process. No cross-linking or gel formation occurs with the slight equivalent excesses as described above due to N-SIS effect advantages. Alternatively, various "orthogonal chemistry" strategies (c) (more fully discussed below) may be used for constructing these dendrons/dendrimers either in parallel or sequentially with approaches (a) and (b) above. The following Flow Chart 3 shows the series of possible process steps with these methods.

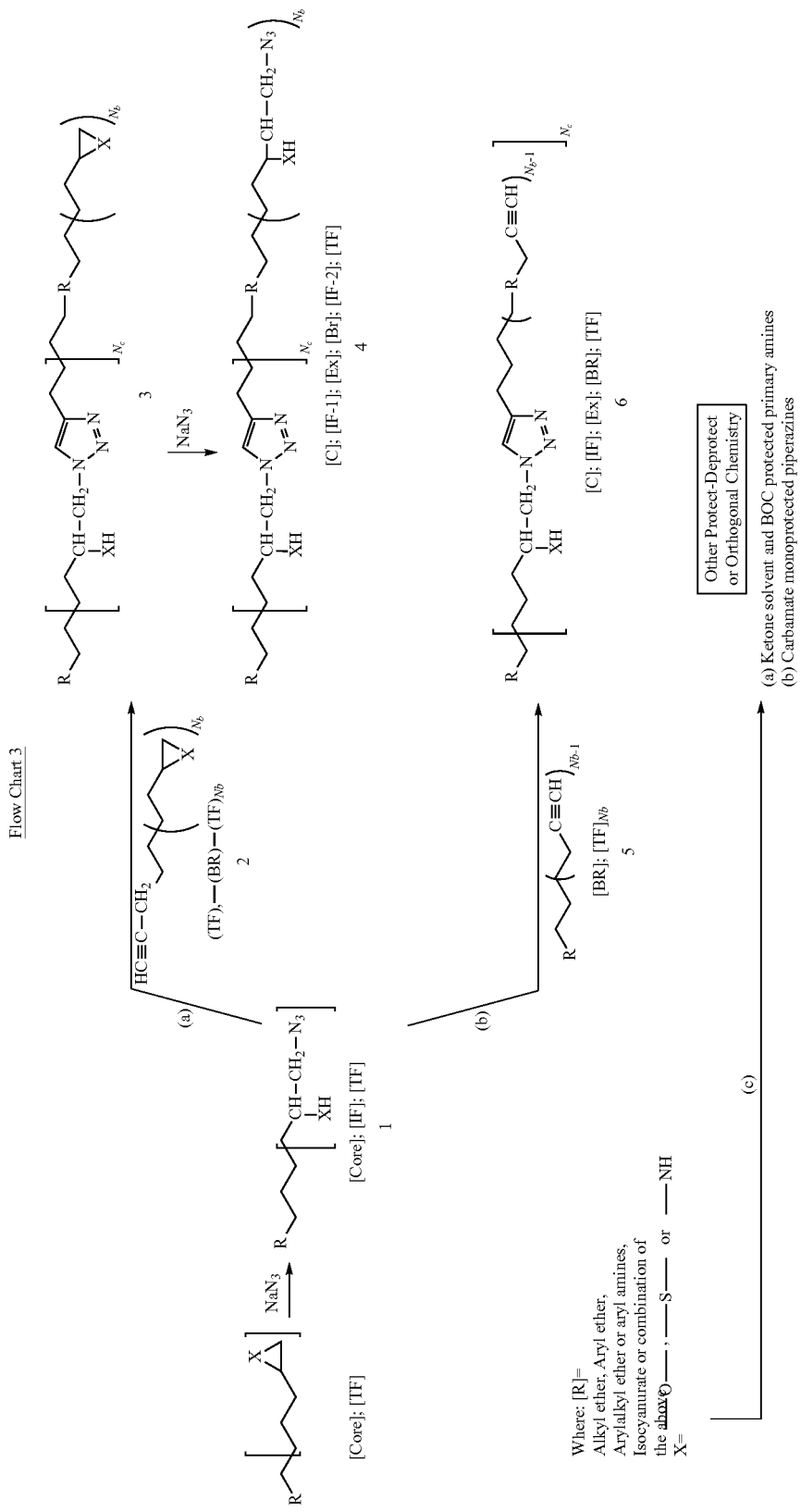

More recently, Sharpless [P. Wu, et al., *Angew. Chem. Int. Ed.*, 43, 3928-3932 (2004)], Frechet [B. Helms, et al., *J. Am. Chem. Soc.*, 126, 15020-15021 (2004)] and Hawker [M. J. Joralemon, et al., *Macromolecules*, 38, 5436 (2005)] have prepared dendrimers possessing no internal functionality (i.e. (IF) moieties) by the addition of mono-azide reagents to polyalkyne substrates. This synthesis strategy has been referred to as a "click chemistry" approach. However, in no case did these references report the use of the reagent types, reaction sequences or strategies described in (a), (b) or (c) above.

Route (a): "Double Click" Chemist Using ($A_{Nc}$) Type Cores and (B-$C_{Nb}$) Type Branch Cell Reagents to form Formula (I) Type Dendritic Structures; where: (A) is Reactive with (B), but not (C): However, (C) can be Converted to (A).

Synthesis of Formula (I) dendritic structures by Route (a) involves the ring-opening reaction of various epoxy core reagents, i.e. (C), (TF); where $N_c$=2-1000, with inorganic azide salts (e.g. $NaN_3$) to produce the corresponding polyfunctional organic azides designated by structure (1) with (C); (IF); (TF). This transformed core reagent structure is allowed to react with an $AB_3$ type acetylene-epoxide functionalized, branch cell (BR) reagent, with general structure (2); ($TF_1$); BR); ($TF_2$). This reaction occurred in very high yield to produce a 1,3-cyclo-addition type product with 1,2,3-triazole structure (3). This structure possesses the following components; i.e. (C); ($IF_1$); (EX); (BR); (TF), where the (EX)=1,2,3-triazole ring. Subsequent addition of sodium azide to this product yielded the ring-opened polyazide product with structure (4); possessing the following components: (C); ($IF_1$); (EX); (BR); ($IF_2$); (TF). Reiteration of these steps allows one to grow and amplify the terminal functionality of these dendritic structures according to traditional mathematical expressions published earlier for traditional dendrimers [*Dendrimers and other Dendritic Polymers*, eds. J. M. J. Fréchet, D. A. Tomalia, pub. John Wiley and Sons, (2001)].

Route (b): "Double Click" Chemistry Using ($A_{Nc}$) Core and ($B_{Nb-1}$) Branch Cell Reagents to form Formula (I) Dendritic Structures; where: (A) is Reactive with (B); However N-SIS Suppresses Gel Formation.

Synthesis of Formula (I) dendritic structures by Route (b) involves the 1,3-cycloaddition reaction of poly-acetylene functionalized branch cell reagents with poly-functional poly-azide cores to produce the desired structures without gel formation due to the N-SIS effects of the highly congested core and branch cell reagents.

Other Orthogonal Synthesis Strategies (c)

Other orthogonal synthesis strategies that may be performed in parallel or sequenced after 1,3-dipolar cyclo-addition type "click chemistry" growth/modification steps described above, may include the following:

(1) Selective epoxy ring-opening with secondary amine moieties in the presence of primary amine moieties by using ketone solvent protection reagents (e.g., methyl isopropyl ketone) that selectively protects primary amines by forming Schiff's base type adducts in the presence of secondary amine functionality [e.g., Frederic Laduron et al., *Org. Proc. Res. & Devel.*, 9, 102-104 (2005)].

(2) A further epoxy ring-opening reaction with olefinic secondary amines (e.g. diallyl amine) followed by free radical assisted addition of single site thiol functionalized reagents, branch cell reagents or dendrons.

(3) Another orthogonal strategy involves conversion of dendron/dendrimer, primary amine terminal groups (TF) to ester functionalized pyrrolidinones that react selectively with the primary amine component of extenders/branch cell reagents/dendrons possessing both primary and secondary amine moieties.

Theory of the Invention

While not wishing to be bound by theory, it is believed that some of the advantageous results of the present invention are obtained because N-SIS controls the number of branch cell reagents (BR), extenders (EX), or terminal functional groups (TF) that may react with a specific size core or dendrimer scaffolding at any given generation level. The stoichiometries of these reactions appear to be nano-sterically controlled by the relative sizes (i.e., $S_1$ vs. $S_2$) of the nano substrate (i.e., the cores or the various dendrimer/dendron generation surfaces) and the steric size of the reacting reagent (i.e., the branch cell reagents (BR) or focal point (FF) reactive dendron). N-SIS may be relevant to this invention since the bulky branch cell reagents (BR) that are used in this invention and their addition products exhibit unexpected behaviors. Most notably, they do not cause cross linking between neighboring moieties during reaction despite the fact that they are highly reactive polyfunctional entities. This is counterintuitive but may be related to a shift in balance between branch cell reagent reactivity (these are much more reactive than amine acrylate reactions or amidation of esters typical of traditional PAMAM dendrimer reactions) and mobility (the larger branch cell reagents move slower (i.e., slower diffusion constants) than a small amine reagent, for example). Further description of this theory may be found after the Roman numeral comparative examples below.

Utility

Uses for the dendrimers of Formula (I) are as numerous as for the traditional PAMAM dendrimers and other dendritic polymers. The following listing of uses is not all inclusive, but illustrative only. Because these dendrimers of Formula (I) exhibit precise nanoscale dimensions (i.e., size), they can be used as size selective membranes, as high efficiency proton scavengers, and as calibration standards for electron microscopy and as quantized nanoscale building blocks for the construction of more complex nanodevices/structures. These dendrimers of Formula (I) may be used as demulsifiers for oil/water emulsions, as wet strength agents in the manufacture of paper, and as agents for modifying viscosity in aqueous formulations such as paints, and in other similar solutions, suspensions and emulsions.

The unique properties exhibited by these dendrimers of Formula (I) are: they are more stable to hydrolysis, thermal degradation. They are not subject to reverse Michael's reactions when derived from nucleophilic ring-open reactions; and they possess (IF) moieties (from the ring-opening reactions) which may be further reacted and provide further binding of (M) or association with (M). Furthermore they exhibit narrow polydispersity ranges and because of simplified processing have a lower cost of manufacture (e.g., because of faster reaction times with less reagent needed and fewer steps).

In addition to the uses for the dendrimers of Formula (I) given above, these dendrimers of Formula (I) are suitable for use in a variety of applications where specific delivery of material (M) is desired.

These dendrimers of Formula (I) possess interior void spaces which can be used to encapsulate materials (M). Examples of such carried materials (M) are provided in U.S. Pat. No. 5,338,532. These materials may have agricultural, pharmaceutical, biological or other activities.

After sufficient generations of reacting branch cells, de Gennes dense packing of the surface groups (Z) occurs and the surface becomes congested and encloses the interior void spaces wherein the characteristics and sizes of the (TF) may function as molecular level gates or orifices suitable for controlling diffusion of materials (M) into or out of the dendrimer interior. The increased functional group density of these dendrimers may allow a greater quantity of material to be carried per dendrimer. Since the number of dendrimer functional groups on the surface (Z) and within the interior (IF) may be controlled, it also provides a means for controlling, for example, the amount of material (M) to be delivered per dendrimer and the release profile of the material (M). For example, these dendrimers may be targeted carriers of bioactive agents capable of delivering the bioactive agents to a particular target site, i.e., disease or cancer site or a particular determinant (receptor) or locus in a target organism, such as an animal, human, plant, algae, virus, fungi, mold or pest.

The surface groups (TF) can have the chemistry controlled in a predetermined fashion by selecting a repeating unit which contains the desired chemical functionality or by chemically modifying all or a portion of these (TF) groups to create new surface functionalities. These surfaces may either be targeted toward specific sites or made to resist uptake by particular cells, e.g., reticuloendothelial cells. The number of (TF) groups present is z.

In addition, when bridged dendrimers are prepared containing one or more of the dendrimers of Formula (I) these polydendritic moieties are also suitable as carriers of such desired materials (M).

The interior of the present dendrimers has possible interior functionality (IF) where these interior groups have the ability to react with materials and serve as a more strongly bonded system for carrying material. Alternatively, the 2-aminoethyl ester linkages derived from polyacrylate-amine addition products may be selectively cleaved in low pH domains, for example endosomal domains, to release desired drugs or other materials as a release mechanism for controlled delivery from the dendrimer interior. The material is associated with the interior, surface or both the interior and surface of these dendrimers and the groups may be the same or different. As used herein "associated with" means that the carried material(s) (M) can be physically encapsulated or entrapped within the interior of the dendrimer, dispersed partially or fully throughout the dendrimer, or attached or linked to the dendrimer or any combination thereof, whereby the attachment or linkage is by means of covalent bonding, hydrogen bonding, adsorption, absorption, metallic bonding, van der Walls forces or ionic bonding, or any combination thereof. The association of the carried material(s) and the dendrimer(s) may optionally employ connectors and/or spacers or chelating agents to facilitate the preparation or use of these conjugates. Suitable connecting groups are groups which link a targeting director (i.e., T) to the dendrimer (i.e., D) without significantly impairing the effectiveness of the director or the effectiveness of any other carried material(s) (i.e., M) present in the combined dendrimer and material ("conjugate"). These connecting groups may be cleavable or non-cleavable and are typically used in order to avoid steric hindrance between the target director and the dendrimer; preferably the connecting groups are stable (i.e., non-cleavable) unless the site of delivery would have the ability to cleave the linker present (e.g., an acid-cleavable linker for release at the cell surface or in the endosomal compartment). Since the size, shape and functional group density of these dendrimers can be rigorously controlled, there are many ways in which the carried material can be associated with the dendrimer. For example, (a) there can be covalent, coulombic, hydrophobic, or chelation type association between the carried material(s) and entities, typically functional groups, located at or near the surface of the dendrimer; (b) there can be covalent, coulombic, hydrophobic, or chelation type association between the carried material(s) and moieties located within the interior of the dendrimer; (c) the dendrimer can be prepared to have an interior which is predominantly hollow (i.e., solvent filled void space) allowing for physical entrapment of the carried materials within the interior (void volume), wherein the release of the carried material can optionally be controlled by congesting the surface of the dendrimer with diffusion controlling moieties, (d) where the dendrimer has internal functionality groups (IF) present which can also associate with the carrier material, possesses a cleavable (IF) which may allow for controlled (i.e., pH dependent) exiting from the dendrimer interior or (e) various combinations of the aforementioned phenomena can be employed.

The material (M) that is encapsulated or associated with these dendrimers may be a very large group of possible moieties that meet the desired purpose. Such materials include, but are not limited to, pharmaceutical materials for in vivo or in vitro or ex vivo use as diagnostic or therapeutic treatment of animals or plants or microorganisms, viruses and any living system, which material can be associated with these dendrimers without appreciably disturbing the physical integrity of the dendrimer.

In a preferred embodiment, the carried materials, herein represented by "M", are pharmaceutical materials. Such materials which are suitable for use in the present dendrimer conjugates include any materials for in vivo or in vitro use for diagnostic or therapeutic treatment of mammals which can be associated with the dendrimer without appreciably disturbing the physical integrity of the dendrimer, for example: drugs, such as antibiotics, analgesics, hypertensives, cardiotonics, steroids and the like, such as acetaminophen, acyclovir, alkeran, amikacin, ampicillin, aspirin, bisantrene, bleomycin, neocardiostatin, chloroambucil, chloramphenicol, cytarabine, daunomycin, doxorubicin, cisplatin, carboplatin, fluorouracil, taxol, gemcitabine, gentamycin, ibuprofen, kanamycin, meprobamate, methotrexate, novantrone, nystatin, oncovin, phenobarbital, polymyxin, probucol, procarbabizine, rifampin, streptomycin, spectinomycin, symmetrel, thioguanine, tobramycin, trimethoprim, and valbanl; toxins, such as diphtheria toxin, gelonin, exotoxin A, abrin, modeccin, ricin, or toxic fragments thereof; metal ions, such as the alkali and alkaline-earth metals; radionuclides, such as those generated from actinides or lanthanides or other similar transition elements or from other elements, such as $^{47}$Sc, $^{67}$Cu, $^{67}$Ga, $^{82}$Rb, $^{89}$Sr, $^{88}$Y, $^{90}$Y, $^{99m}$Tc, $^{105}$Rh, $^{109}$Pd, $^{111}$In, $^{115m}$In, $^{125}$I, $^{131}$I, $^{140}$Ba, $^{140}$La, $^{149}$Pm, $^{153}$Sm, $^{59}$Gd, $^{166}$Ho, $^{175}$Yb, $^{177}$Lu, $^{186}$Re, $^{188}$Re, $^{194}$Ir, and $^{199}$Au, preferably $^{88}$Y, $^{90}$Y, $^{99m}$Tc, $^{125}$I, $^{131}$I, $^{153}$Sm, $^{166}$Ho, $^{177}$Lu, $^{186}$Re, $^{67}$Ga, $^{111}$In, $^{115m}$In, and $^{140}$La; signal generators, which includes anything that results in a detectable and measurable perturbation of the system due to its presence, such as fluorescing entities, phosphorescence entities and radiation; signal reflectors, such as paramagnetic entities, for example, Fe, Gd, or Mn; chelated metal, such as any of the metals given above, whether or not they are radioactive, when associated with a chelant; signal absorbers, such as near infared, contrast agents (such as imaging agents and MRI agents) and electron beam opacifiers, for example, Fe, Gd or Mn; antibodies, including monoclonal or polyclonal antibodies and anti-idiotype antibodies; antibody fragments; aptamers; hormones; biological response modifiers such as interleukins, interferons, viruses and viral fragments; diagnostic opacifiers; and fluorescent moieties. Carried pharmaceutical materials include scavenging agents such as chelants, antigens, antibodies, aptamers, or any moieties capable of selectively scavenging therapeutic or diagnostic agents.

In another embodiment, the carried materials, herein represented by "M", are agricultural materials. Such materials which are suitable for use in these conjugates include any materials for in vivo or in vitro treatment, diagnosis, or application to plants or non-mammals (including microorganisms) which can be associated with the dendrimer without appreciably disturbing the physical integrity of the dendrimer. For example, the carried materials can be toxins, such as diphtheria toxin, gelonin, exotoxin A, abrin, modeccin, ricin, or toxic fragments thereof; metal ions, such as the alkali and alkaline earth metals; radionuclides, such as those generated from actinides or lanthanides or other similar transition elements or from other elements, such as $^{47}$Sc, $^{67}$Cu, $^{67}$Ga, $^{82}$Rb, $^{89}$Sr, $^{88}$Y, $^{90}$Y, $^{99m}$Tc, $^{105}$Rh, $^{109}$Pd, $^{111}$In, $^{115m}$In, $^{125}$I, $^{131}$I, $^{140}$Ba, $^{140}$La, $^{149}$Pm, $^{153}$Sm, $^{159}$Gd, $^{166}$Ho, $^{175}$Yb, $^{177}$Lu, $^{186}$Re, $^{188}$Re, $^{194}$Ir, and $^{199}$Au; signal generators, which includes anything that results in a detectable and measurable perturbation of the system due to its presence, such as fluorescing entities, phosphorescence entities and radiation; signal reflectors, such as paramagnetic entities, for example, Fe, Gd, or Mn; signal absorbers, such contrast agents and as electron beam opacifiers, for example, Fe, Gd, or Mn; hormones; biological response modifiers, such as interleukins, interferons, viruses and viral fragments; pesticides, including antimicrobials, algicides, arithelmetics, acaricides, II insecticides, attractants, repellants, herbicides and/or fungicides, such as acephate, acifluorfen, alachlor, atrazine, benomyl, bentazon, captan, carbofuran, chloropicrin, chlorpyrifos, chlorsulfuron cyanazine, cyhexatin, cypermithrin, 2,4-dichlorophenoxyacetic acid, dalapon, dicamba, diclofop methyl, diflubenzuron, dinoseb, endothall, ferbam, fluazifop, glyphosate, haloxyfop, malathion, naptalam; pendimethalin, permethrin, picloram, propachlor, propanil, sethoxydin, temephos, terbufos, trifluralin, triforine, zineb, and the like. Carried agricultural materials include scavenging agents such as chelants, chelated metal (whether or not they are radioactive) or any moieties capable of selectively scavenging therapeutic or diagnostic agents.

In another embodiment, the carried material, herein represented by (M), are immuno-potentiating agents. Such materials which are suitable for use in these conjugates include any antigen, hapten, organic moiety or organic or inorganic compounds which will raise an immuno-response which can be associated with the dendrimers without appreciably disturbing the physical integrity of the dendrimers. For example, the carried materials can be synthetic peptides used for production of vaccines against malaria (U.S. Pat. No. 4,735,799), cholera (U.S. Pat. No. 4,751,064) and urinary tract infections (U.S. Pat. No. 4,740,585), bacterial polysaccharides for producing antibacterial vaccines (U.S. Pat. No. 4,695,624) and viral proteins or viral particles for production of antiviral vaccines for the prevention of diseases such as AIDS and hepatitis.

The use of these conjugates as carriers for immuno-potentiating agents avoids the disadvantages of ambiguity in capacity and structure associated with conventionally known classical polymer architecture or synthetic polymer conjugates used to give a macromolecular structure to the adjuvant carrier. Use of these dendrimers as carriers for immuno-potentiating agents, allows for control of the size, shape and surface composition of the conjugate. These options allow optimization of antigen presentation to an organism, thus resulting in antibodies having greater selectivity and higher affinity than the use of conventional adjuvants. It may also be desirable to connect multiple antigenic peptides or groups to the dendrimer, such as attachment of both T- and B-cell epitopes. Such a design would lead to improved vaccines.

It may also be desirable to conjugate pesticides or pollutants capable of eliciting an immune response, such as those containing carbamate, triazine or organophosphate constituents, to a dendrimer. Antibodies produced to the desired pesticide or pollutant can be purified by standard procedures, immobilized on a suitable support and be used for subsequent detection of the pesticide or pollutant in the environment or in an organism.

In a further embodiment, the carried materials, herein represented by "M", which are suitable for use in these conjugates include any materials other than agricultural or pharmaceutical materials which can be associated with these dendrimers without appreciably disturbing the physical integrity of the dendrimer, for example: metal ions, such as the alkali and alkaline-earth metals; signal generators, which includes anything that results in a detectable and measurable perturbation of the system due to its presence, such as fluorescing entities, phosphorescence entities, infrared, near infrared, and radiation; signal reflectors, such as paramagnetic entities, for example, Fe, Gd, or Mn; signal absorbers, such as contrast agents and an electron beam opacifiers, for example, Fe, Gd, or Mn; pheromone moieties; fragrance moieties; dye moieties; and the like. Carried materials include scavenging agents such as chelants or any moieties capable of selectively scavenging a variety of agents.

Preferably the carried materials (M) are bioactive agents. As used herein, "bioactive" refers to an active entity such as a molecule, atom, ion and/or other entity which is capable of detecting, identifying, inhibiting, treating, catalyzing, controlling, killing, enhancing or modifying a targeted entity such as a protein, glycoprotein, lipoprotein, lipid, a targeted disease site or targeted cell, a targeted organ, a targeted organism [for example, a microorganism, plant or animal (including mammals such as humans)] or other targeted moiety. Also included as bioactive agents are genetic materials (of any kind, whether oligonucleotides, fragments, or synthetic sequences) that have broad applicability in the fields of gene therapy, siRNA, diagnostics, analysis, modification, activation, anti-sense, silencing, diagnosis of traits and sequences, and the like. These conjugates include effecting cell transfection and bioavailability of genetic material comprising a complex of a dendritic polymer and genetic material and making this complex available to the cells to be transfected.

These conjugates may be used in a variety of in vivo, ex vivo or in vitro diagnostic or therapeutic applications. Some examples are the treatment of diseases such as cancer, autoimmune disease, genetic defects, central nervous system disorders, infectious diseases and cardiac disorders, diagnostic uses such as radioimmunossays, electron microscopy, PCR, enzyme linked immunoadsorbent assays, nuclear magnetic resonance spectroscopy, contrast imaging, immunoscintography, and delivering pesticides, such as herbicides, fungicides, repellants, attractants, antimicrobials or other toxins. Non-genetic materials are also included such as interleukins, interferons, tumor necrosis factor, granulocyte colony stimulating factor, and other protein or fragments of any of these, antiviral agents.

These conjugates may be formulated into a tablet using binders known to those skilled in the art. Such dosage forms are described in *Remington's Pharmaceutical Sciences, 18$^{th}$* ed. 1990, pub. Mack Publishing Company, Easton, Pa. Suitable tablets include compressed tablets, sugar-coated tablets, film-coated tablets, enteric-coated tablets, multiple compressed tablets, controlled-release tablets, and the like.

Ampoules, ointments, gels, suspensions, emulsions, injections (e.g., intramuscular, intravenous, intraperitoneal, subcutaneous), transdermal formulation (e.g., patches or application to the skin surface, suppository compositions), intranasal formulations (e.g., drops, sprays, inhalers, aerosol spray, chest rubs), ocular application (e.g., sterile drops, sprays, ointments), or application in a gauze, wipe, spray or other means at site of surgical incision, near scar formation sites, or site of a tumor growth or removal, may also be used as a suitable formulation. Kits for bioassays as biomarkers, molecular probes are possible, including use with other reagents for the assay, and instructions for their use. Customary pharmaceutically-acceptable salts, adjuvants, binders, desiccants, diluents and excipients may be used in these formulations. For agricultural uses these conjugates may be formulated with the usual suitable vehicles and agriculturally-acceptable carrier or diluent, such as granular formulations, emulsifiable concentrates, solutions, and suspensions as well as combined with one or more than one active agent.

For the following examples the various equipment and methods were used to run the various described tests for the results reported in the examples described below.

Equipment and Methods

Size Exclusion Chromatography (SEC)

A methanolic solution of Sephadex™ (Pharmacia) purified dendrimer was evaporated and reconstituted with the mobile phase used in the SEC experiment (1 mg/mL concentration). All the samples were prepared fresh and used immediately for SEC.

Dendrimers were analyzed qualitatively by the SEC system (Waters 1515) operated in an isocratic mode with refractive index detector (Waters 2400 and Waters 717 Plus Auto Sampler). The analysis was performed at RT on two serially aligned TSK gel columns (Supelco), G3000PW and G2500PW, particle size 10 µm, 30 cm×7.5 mm. The mobile phase of acetate buffer (0.5M) was pumped at a flow rate of 1 mL/min. The elution volume of dendrimer was observed to be 11-16 mL, according to the generation of dendrimer.

High Pressure/Performance Liquid Chromatography (HPLC)

High pressure liquid chromatography (HPLC) was carried out using a Perkin Elmer™ Series 200 apparatus equipped with refractive index and ultraviolet light detectors and a Waters Symmetry® $C_{18}$ (5 µm) column (4.6 mm diameter, 150 mm length). A typical separation protocol was comprised of 0.1% aqueous acetic acid and acetonitrile (75:25% v/v) as the eluant and UV light at $\lambda$=480 nm as the detector.

Thin Layer Chromatography (TLC)

Thin Layer Chromatography was used to monitor the progress of chemical reactions. One drop of material, generally 0.05M to 0.4M solution in organic solvent, is added to a silica gel plate and placed into a solvent chamber and allowed to develop for generally 10-15 mins. After the solvent has been eluted, the TLC plate is generally dried and then stained (as described below). Because the silica gel is a polar polymer support, less polar molecules will travel farther up the plate. "$R_f$" value is used to identify how far material has traveled on a TLC plate. Changing solvent conditions will subsequently change the $R_f$ value. This $R_f$ is measured by the ratio of the length the product traveled to the length the solvent traveled.

Materials: TLC plates used were either (1) "Thin Layer Chromatography Plates—Whatman®" PK6F Silica Gel Glass backed, size 20×20 cm, layer thickness: 250 µm or (2) "Thin Layer Chromatography Plate Plastic sheets—EM Science" Alumina backed, Size 20×20 cm, layer thickness 200 µm.

Staining conditions were: (1) Ninhydrin: A solution is made with 1.5 g of ninhydrin, 5 mL of acetic acid, and 500 mL of 95% ethanol. The plate is submerged in the ninhydrin solution, dried and heated with a heat gun until a color change occurs (pink or purple spots indicate the presence of amine). (2) Iodine Chamber: 2-3 g of $I_2$ is placed in a closed container. The TLC plate is placed in the chamber for 15 mins. and product spots will be stained brown. (3) $KMnO_4$ Stain: A solution is prepared with 1.5 g of $KMnO_4$, 10 g of $K_2CO_3$, 2.5 mL of 5% NaOH, and 150 mL of water. The TLC plate is submerged in $KMnO_4$ solution and product spots turn yellow. (4) UV examination: An ultraviolet (UV) lamp is used to illuminate spots of product. Short wave (254 nm) and long wave (365 nm) are both used for product identification.

MALDI-TOF Mass Spectrometry

Mass spectra were obtained on a Bruker Autoflex™ LRF MALDI-TOF mass spectrometer with Pulsed Ion Extraction. Mass ranges below 20 kDa were acquired in the reflector mode using a 19 kV sample voltage and 20 kV reflector voltage. Polyethylene oxide was used for calibration. Higher mass ranges were acquired in the linear mode using a 20 kV sample voltage. The higher mass ranges were calibrated with bovine serum albumin.

Typically, samples were prepared by combining a 1 µL aliquot of a 5 mg/mL solution of the analyte with 10 µL of matrix solution. Unless otherwise noted, the matrix solution was 10 mg/mL of 2,5-dihydroxybenzoic acid in 3:7 acetonitrile:water. Aliquots (2 µL) of the sample/matrix solution were spotted on the target plate and allowed to air dry at RT.

Dialysis Separation

In a typical dialysis experiment about 500 mg of product is dialyzed through a dialysis membrane with an appropriate pore size to retain the product and not the impurities. Dialyses are done in most examples in water (other appropriate dialyzates used were acetone and methanol) for about 21 hours with two changes of dialyzate. Water (or other dialyzate) is evaporated from the retentate on a rotary evaporator and the product dried under high vacuum or lyophilized to give a solid.

Ultrafiltration Separation (UF)

A typical ultrafiltration separation protocol was as follows: A mixture of product and undesired compounds was dissolved in the appropriate volume of a solvent for this mixture (e.g., 125 mL of MeOH) and ultrafiltered on a tangential flow UF device containing 3K cut-off regenerated cellulose membranes at a pressure of 20 psi (137.9 kPa) at 25° C. The retentate volume as marked in the flask was maintained at 100-125 mL during the UF collection of 1500 mL permeate (~5 hours). The first liter of permeate was stripped of volatiles on a rotary evaporator, followed by high vacuum evacuation to give the purified product. Depending on the specific separation problem, the cut-off size of the membrane (e.g., 3K, 2K or 1K) and the volume of permeate and retentate varied.

Sephadex™ Separation

The product is dissolved in the minimum amount of a solvent (water, PBS, or MeOH) and purified through Sephadex™ LH-20 (Pharmacia) in the solvent. After eluting the void volume of the column, fractions are collected in about 2-20 mL aliquots, depending on the respective separation concerned. TLC, using an appropriate solvent as described before, is used to identify fractions containing similar product mixtures. Similar fractions are combined and solvent evaporated to give solid product.

Nuclear Magnetic Resonance (NMR)—$^1H$ and $^{13}C$

Sample preparation: To 50-100 mg of a dry sample was add 800-900 µL of a deuterated solvent to dissolve. Typical reference standards are used, i.e., trimethylsilane. Typical solvents are $CDCl_3$, $CD_3OD$, $D_2O$, DMSO-$d_6$, and acetone-$d_6$. The dissolved sample was transferred to an NMR tube to a height of ~5.5 cm in the tube.

Equipment: (1) 300 MHz NMR data were obtained on a 300 MHz 2-channel Varian™ Mercury Plus NMR spectrometer system using an Automation Triple Resonance Broadband (ATB) probe, H/X (where X is tunable from $^{15}N$ to $^{31}P$). Data acquisition was obtained on a Sun Blade™ 150 computer with a Solaris™ 9 operating system. The software used was VNMR v6.1C. (2) 500 MHz NMR data were obtained on a 500 MHz 3-channel Varian™ Inova 500 MHz NMR spectrometer system using a Switchable probe, H/X (X is tunable from $^{15}N$ to $^{31}P$). Data acquisition was obtained on a Sun Blade™ 150 computer with a Solaris™ 9 operating system. The software used was VNMR v6.1C.

Atomic Force Microscopy (AFM) or Scanning Probe Microscopy (SPM)

All images were obtained with a Pico-SPM™ LE AFM (Molecular Imaging, USA) in DI water with tapping mode, using Multi-purpose large scanner and MAC mode Tips [Type II MAClevers, thickness: 3 μm, length: 225 μM, width: 28 μm, resonance frequency: ca 45 KHz and force constant: ca 2.8 N/m (Molecular Imaging, USA)]. Typically, 3 lines/sec. scan speed was used for scanning different areas, with a set point of 0.90 of the cantilever oscillation amplitude in free status. To avoid hydrodynamic effect of thin air gaps, the resonance was carefully measured at a small tip—sample distance.

Solubility and Physical Property

The dendrimers of Formula (I) are generally solid materials (in contrast to PAMAM dendrimers that are gel-like solids). These dendrimers do not usually absorb water as easily as do the PAMAM dendrimers. Currently the dendrimers are stored either in solid form or in MeOH as a solution. No difference in stability of the dendrimer between these two storage methods has been observed. In general, the dendrimers of Formula (I) dissolve in water more rapidly than PAMAM dendrimers. PAMAM dendrimers are all soluble in water, but are generally more difficult to dissolve due to their gel-like state. These dendrimers of Formula (I) also dissolve in a number of organic solvents, including but not limited to the following: MeOH, EtOH, isopropanol, DME, chloroform, methylene chloride, 1,2-dichloroethane, methoxypropanol, MIBK, and DMSO.

Thermal Gravimetric Analysis (TGA)

Thermal gravimetric data were obtained on a Universal V3.9A™ (TA Instrument). Temperature scan range was from 20 to 520° C., or within this range, with a ramp rate of typically 10 degrees per minute. Sample sizes were typically about 10 mg of solid product.

Polyacrylamide Gel Electrophoresis (PAGE)

Dendrimers that were stored in solvent are dried under vacuum and then dissolved or diluted with water to a concentration about 100 mg in 4 mL of water. The water solution is frozen using dry ice and the sample dried using a lyophilizer (freeze dryer) (LABCONCO Corp. Model number is Free Zone 4.5 Liter, Freeze Dry System 77510) at about −47° C. and $60 \times 10^{-3}$ mBar. Freeze dried dendrimer (1-2 mg) is diluted with water to a concentration of 1 mg/mL. Tracking dye is added to each dendrimer sample at 10% v/v concentration and includes (1) methylene blue dye (1% w/v) for basic compounds (2) bromophenol blue dye (0.1% w/v) for acid compounds (3) bromophenol blue dye (0.1% w/v) with 0.1% (w/v) SDS for neutral compounds.

Pre-cast 4-20% gradient gels were purchased from ISC BioExpress. Gel sizes were 100 mm (W)×80 mm (H)×1 mm (Thickness) with ten pre-numbered sample wells formed in the cassette. The volume of the sample well is 50 μL. Gels not obtained commercially were prepared as 10% homogeneous gels using 30% acrylamide (3.33 mL), 4×TBE buffer (2.5 mL), water (4.17 mL), 10% APS (100 μL), TEMED (3.5 μL). TBE buffer used for gel electrophoresis is prepared using tris(hydroxymethyl)aminomethane (43.2 g), boric acid (22.08 g), disodium EDTA (3.68 g) in 1 L of water to form a solution of pH 8.3. The buffer is diluted 1:4 prior to use.

Electrophoresis is done using a PowerPac™ 300 165-5050 power supply and BIO-RAD™ Mini Protean 3 Electrophoresis Cells. Prepared dendrimer/dye mixtures (5 μL each) are loaded into separate sample wells and the electrophoresis experiment run. Dendrimers with amine surfaces are fixed with a glutaraldehyde solutions for about one hour and then stained with Coomassie Blue R-250 (Aldrich) for about one hour. Gels are then destained for about one hour using a glacial acetic acid solution. Images are recorded using an hp Scanjet™ 5470C scanner.

Infrared Spectrometry (IR or FTIR)

Infrared spectral data were obtained on a Nicolet Fourier™ Transform Infrared Spectrometer, Model G Series Omnic, System 20 DXB. Samples were run neat using potassium bromide salt plates (Aldrich).

Ultraviolet/Visible Spectrometry (UV/Vis)

UV-VIS spectral data were obtained on a Perkin Elmer™ Lambda 2 UV/VIS Spectrophotometer using a light wavelength with high absorption by the respective sample, for example 480 or 320 nm.

Inductively Coupled Plasma (ICP) Optical Emission

The Gd(III) content of samples was determined on a sequential, radially viewed Varian™ Liberty Series II ICPOES inductively coupled plasma optical emission spectrophotometer.

Proton Relaxivity

Relaxivity analysis was performed using a variable field T1-T2 analyzer. The field strength was varied from 1-64 MHz.

Fluorescence Microscopy and Phase Contrast Microscopy

Fluorescence microscopy and phase contrast microscopy studies were performed using a Nikon Diaphot™ TMD microscope equipped with Nikon™ TMD-EF for fluorescence, along with a Nikon™ CoolPix 990 digital camera to capture the results.

The invention will be further clarified by a consideration of the following examples, which are intended to be purely exemplary of the present invention. The lettered examples are synthesis of starting materials, except that Examples G and H are also examples of the present invention; the numbered examples are those examples of the present invention; and the Roman numbered examples are comparative examples.

Starting Materials

TMPTGE used as starting materials may be obtained from Aldrich, albeit it has a purity level of about 70%. Synthesis and/or purification of tetra-glycidyl ethers were based on the procedure found in "*Synthesis*" p 487 (1993), using epichlorohydrin, KOH and DMSO.

EXAMPLE A

Preparation of Pentaerythritol Tetraglycidyl Ether from Pentaerythritol and Epichlorohydrin (EPI)

[(C)=PETGE; (TF)=Epoxy]

To a 100-mL round bottom flask containing a large stir bar was added pentaerythritol (4.1 g, 30.1 mmols, 120 mmols OH) (Aldrich) and 30 mL of a mixture of DMSO (15.85 g) and KOH (13.47 g, 240.0 mmol, 2 equiv. per OH). To this rapidly stirred mixture in a water bath at RT was added dropwise (about 1 drop per 10-15 sec) epichlorohydrin (34.0 g, 367.0 mmols, 3 equiv. per OH) (Aldrich) over 60 to 90 mins. The temperature was monitored every 10 mins. to maintain the temperature below 35° C. After another hour the exotherm had subsided and the mixture was heated to 35° C. for 5-6 hours. The reaction was monitored by TLC (7:3 toluene-acetone). Spots were visualized from $KMnO_4$ stain. Aliquots were added to the ether-brine mixture to remove DMSO and the ether layer dried with $Na_2SO_4$. The TLC of the reaction mixture showed 5 spots after the addition was complete, then 2 spots after 7 hours. The mixture was filtered through a course fritted funnel and washed with diethyl ether (2×60 mL). The filtered liquid was mixed with 150 mL diethyl ether and combined with the washes. This ether layer was washed with 80 mL brine. The brine layer was washed with another 150 mL diethyl ether. The combined ether layers were dried with anhydrous magnesium sulfate, filtered and evaporated to give the crude product (12 g). This crude product was dissolved in a mixture of 9:1 toluene-acetone and purified over silica gel (140 g, 60 angstrom, 230-400 mesh) in the same solvent. The first two fractions were 200 mL each, containing a very high $R_f$ material (TLC). The next 30 fractions were 50 mL each with pure product in fractions 7-10. The product fractions were combined and evacuated to give the desired product (4.0 g; 37% yield); and has the following spectra:

$^1$H NMR (500 MHz, $CDCl_3$): δ 2.593 (dd, J=6.5 Hz, 4H), 2.773 (t, J=6.5 Hz), 2.922 (m, 4H), 3.10 (m, 4H), 3.37 (ddd, I=7.0, 3.7, 1.5 Hz, 4H), 3.475 (d, J=12 Hz, 4H), 3.515 (d, J=12 Hz, 4H), 3.70 (dd, J=12 and 7.0 Hz, 4H); and $^{13}$C NMR (125 MHz, $CDCl_3$): δ 44.17, 45.75, 50.822, 69.93, 72.013, 72.036, 72.055, 72.078; and MALDI-TOF: Calc. 360.47; found 360 amu.

EXAMPLE B

Synthesis of Pentaerythritol Tetraglycidyl Ether from Pentaerythritol and Epichlorohydrin (EPI)

[(C)=PETGE; (TF)=Epoxy]

This process was performed according to Mitsuo et al., *Synthesis*, 487 (1993). Pentaerythritol I (13.6 g, 400 mmol) and 100 mL DMSO were taken in a 1-L 3-necked round bottom flask and then KOH (52.7 g, 800 mmol, 2 equiv. per OH) added all at once. The reaction mixture was stirred vigorously with a mechanical stirrer and cooled to 15-20° C. with an ice bath. Epichlorohydrin II (110.4 g or 93.55 mL, 1.2 mol, 3 equiv. per OH) in a pressure-equalizing funnel was added dropwise over a period of 150 min. The temperature was maintained at 15-20° C. during the addition of epichlorohydrin. The color of the reaction mixture turned from colorless to pale yellow. After completing the addition, the reaction mixture was allowed to warm to RT and stirring continued overnight. Progress of the reaction was monitored by TLC. After 3 hours, TLC indicated spots for pentaerythritol tetraglycidyl ether (PETGE) II and pentaerythritol triglycidyl ether IV. By continuing reaction, triglycidyl ether IV was expected to be converted into product III; however, some dimerization of III was observed, which gave product V.

Reaction mixture was filtered through a Büchner funnel and solids were washed with 100 mL of DCM. Volatile fractions of DCM were removed on a rotary evaporator. The crude reaction mixture was treated with saturated brine (2×100 mL) and extracted with diethyl ether (2×100 mL). The combined ethereal layers were dried over $Na_2SO_4$ and concentrated on a rotary evaporator to give a dark yellow/light brown liquid. Crude was divided into two equal portions and subjected to column chromatography over silica gel. Silica gel (300 g) was loaded onto column (25 cm height×5.5 cm width). After eluting 500 mL of solvents, fractions were collected in 40 mL. First off fractions were epichlorohydrin followed by PETGE (III) ($R_f$=0.62), then dimer (V) ($R_f$=0.44), and finally triglycidyl ether (IV) ($R_f$=0.33). Isolated pure PETGE yields were 45-60% (some amount will be contaminated with other side products). Spectral analysis was in agreement with reported data for III and analysis on products IV & V were also satisfactory.

The following Scheme A illustrates this reaction.

Scheme A

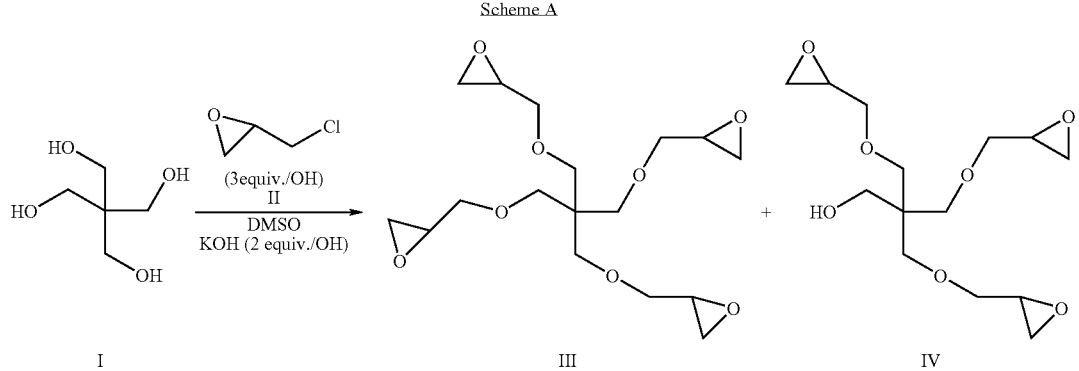

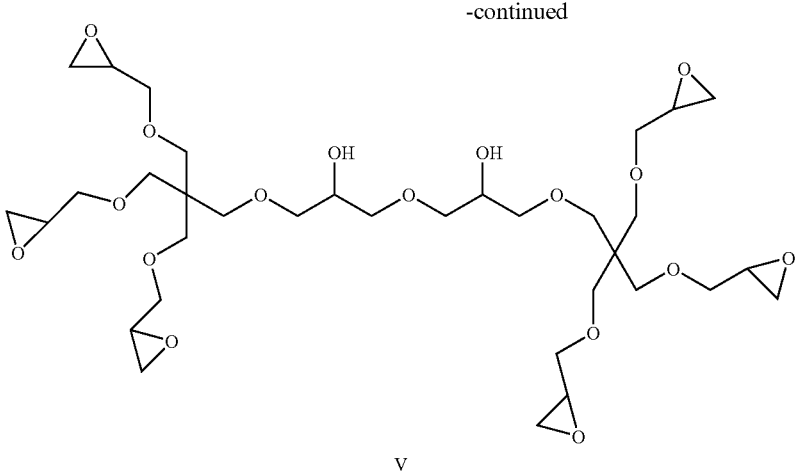

V

EXAMPLE C

Synthesis of Pentaerythritol Tetraglycidyl Ether from Pentaerythritol Using Allylbromide and m-Chloroperyoxy Benzoic Acid (m-CPBA)

[(C)=PETGE; (TF)=Epoxy]

Pentaerythritol, I (15.03 g, 110 mmol) (Acros Organics) and 250 mL of THF were mixed in a 1-L round bottom flask. KOH (85.93 g 1.35 mol 3.0 equiv. per OH), and tetrabutyl ammonium bromide (TBAB) (0.460 g, 1.23% mol) (Acros Organics) were added via powder funnel, followed by addition of allyl bromide, H (106.6 g, 1.35 mol, 3.0 equiv. per OH) via a 125-mL addition funnel over 10 mins. The reaction was then immediately placed into an oil bath at 70° C. for 24 hours. The reaction was monitored by TLC (110:1 hexanes: ethyl acetate), showing the product spot at $R_f$=0.4 and no spots for tri-, di-, or mono-allyl-substituted pentaerythritol. The reaction mixture was vacuum-filtered through a 150-mL coarse glass-fritted Büchner funnel. The organic layer was diluted with diethyl ether (2×250 mL). The organic layer was washed with 5% $K_2CO_3$ (5×300 mL) and dried over $MgSO_4$. Volatiles were removed by a rotary evaporator (40° C. bath temperature) to yield the pentaerythritol tetraallyl ether, III (30.07 g; 92% yield); and has the following spectra:

IR (Neat): $v_{max}$ 3080, 2867, 1646, 1478, 1422, 1350, 1264, 1137, 992, 922 $cm^{-1}$; and $^{13}$C NMR: (75 MHz, $CDCL_3$): δ 45.33, 69.25, 72.15, 115.95, 135.16; and $^1$H NMR: (300 MHz, $CDCL_3$): δ 3.39 (4H, s), 3.84 (4H, q, J=2.3 Hz), 5.04 (2H, q, J=13.8 Hz), 5.80 (1H, septuplet, J=7.78 Hz).

PETAE, III (3.29 g, 11.0 mmol) and 50 mL of chloroform were added to a 500-mL round bottom flask equipped with a magnetic stir bar. Then m-CPBA, IV (70%) (12.51 g, 51.0 mmol, 1.14 equiv. per alkene) (Acros Organics) was added over 10 minutes via an addition funnel. The reaction flask became warm within 30 mins. of the peracid addition. The reaction was stirred for 72 hours at 22° C., then diluted with 100 mL DCM and transferred to a 500-mL separatory funnel. The organic layer was washed with 3% $Na_2S_2O_5$ (3×150 mL) and 3% $NaHCO_3$ (3×150 mL). The organic layer was dried with $Na_2SO_4$, filtered and volatile materials were removed by a rotary evaporator (40° C. bath temperature). TLC (7:3 toluene:acetone) on silica showed one spot at $R_f$=0.48. Further drying of the product overnight at high vacuum yielded PETGE, V as a clear colorless viscous liquid (3.86 g; 92% yield); and has the following spectra:

IR (Neat): $v_{max}$ 3055, 2997, 2876, 1724, 1480, 1340, 1258, 1163, 1018, 908, 845, 799, 760 $cm^{-1}$; and $^{13}$C NMR (75 MHz, $CDCl_3$): δ 43.96, 45.54 50.62, 69.80, 71.90; and $^1$H NMR: (300 MHz, $CDCl_3$): δ 2.55 (1H, q, J=2.05 Hz), 2.72 (1H, t, J=2.33 Hz), 3.09 (1H, q, J=3.06 Hz) 3.32 (1H, q, J=4.43 Hz), 3.45 (2H, d, J=1.65 Hz), 3.64 (1H, q, J=3.675 Hz); and MALDI-TOF: 383 [M+Na]$^+$ amu.

These reactions are represented in Scheme B.

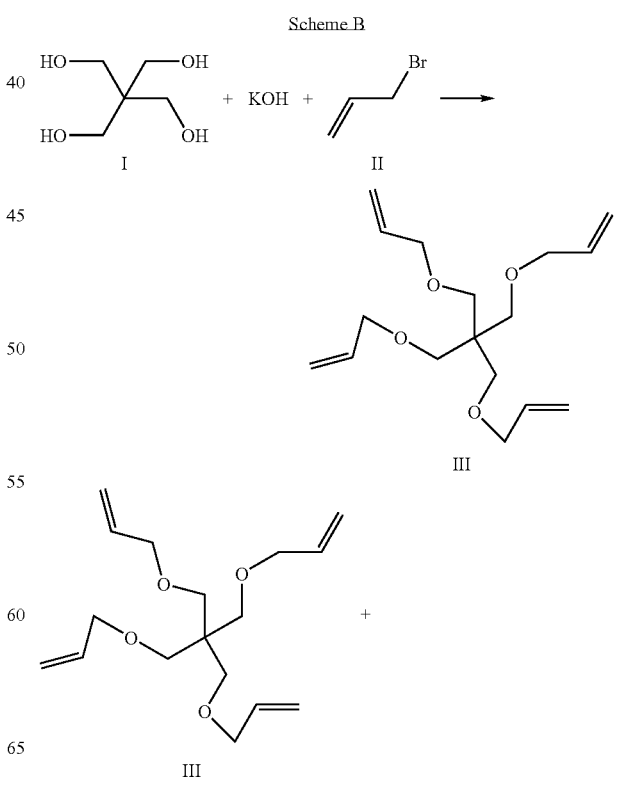

Scheme B

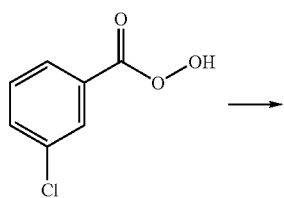

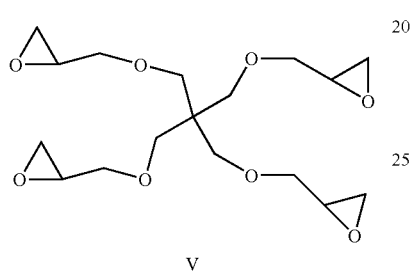

V

EXAMPLE D

Tetra(episulfide) from PETGE: Making the Episulfide Branched Cell

[(C)=Tetrathiorane; (TF)=Thiorane]

An oven-dried, 100-mL round bottom flask was charged with PETGE 1 (1.8 g, 5.0 mmol) and 40 mL dry acetonitrile. Thiourea (3.04 g, 40.0 mmol) was added to the above reaction mixture all at once followed by LiBF$_4$ (0.372 g). The flask was arranged with a refluxing condenser and heated at 60° C. After being heated for 5 hours, TLC indicated traces of PETGE 1 and two other new spots with higher R$_f$. Heating was continued overnight under a N$_2$ atmosphere. The reaction mixture was then quenched with 50 mL water and extracted with CHCl$_3$ (3×50 mL). Combined extracts were washed with brine (2×30 mL), dried over Na$_2$SO$_4$, and concentrated on a rotary evaporator to give a liquid. The crude reaction mixture was purified through column chromatography using silica gel with hexanes:ethyl acetate:chloroform (1:2:2), which gave the pure tetra(episulfide) as a colorless liquid (0.610 g; 29% yield). Its spectra are as follows:

$^1$H NMR: (300 MHz, CDCl$_3$): δ 2.17 (dd, J=1.20 & 5.40 Hz, 4H), 2.50 (d, J=6.00 Hz, 4H), 3.05 (quintet, J=6.00 Hz, 4H), 3.43-3.50 (m, 14H), 3.56 (quintet, J=6.00 Hz, 4H); and $^{13}$C NMR: (75 MHz, CDCl$_3$): δ 23.90, 32.56, 45.99, 69.67, 76.85; and MALDI-TOF: C$_{17}$H$_{28}$O$_4$S$_4$; Calc. 424, found 447 (M$^+$Na) amu.

The following Scheme C illustrates this reaction:

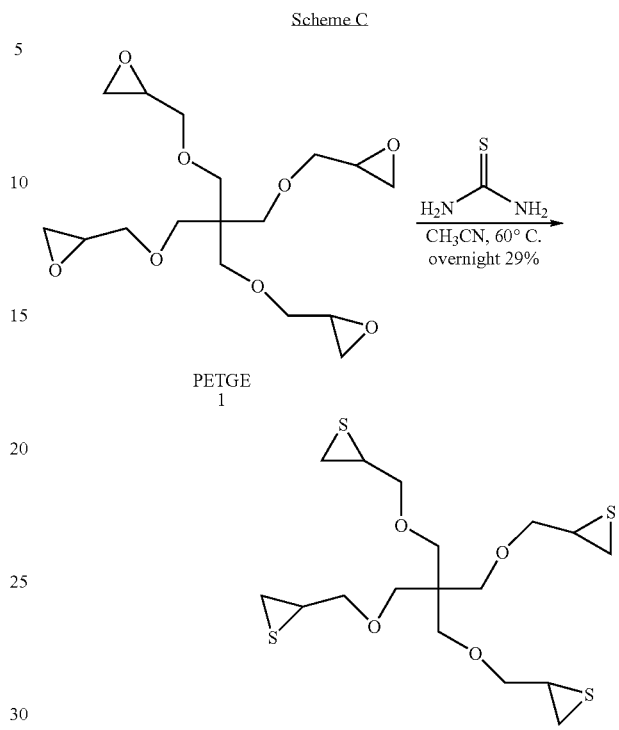

EXAMPLE E

Reaction of Pentaerythritol Triallyl Ether (PETriAE) with m-chloroperbenzoic Acid (m-CPBA)

[(C)=PETriGE; (FF)=OH; (TF)=Epoxide]

A 100-mL round bottom flask was charged with PETriAE (2.56 g, 10.0 mmol, 30 olefin mmol) (Aldrich) and 50 mL chloroform (Fisher Scientific). To this solution was added under mechanical stirring m-CPBA (8.84 g, 36.0 mmol) (Acros Organics) in portions at RT. The mixture was stirred for 3 days, then first washed with 3% aqueous sodium metabisulfite (Na$_2$S$_2$O$_5$) solution (3×100 mL) (Aldrich), followed by 3% aqueous sodium hydrogen carbonate (NaHCO$_3$) solution (3×100 mL). The organic layer was dried over sodium sulfate, concentrated by rotary evaporation to give pale yellow colored liquid (2.58 g, 84.8% yield). Its spectra are as follows:

$^1$H NMR (300 MHz, CDCl$_3$): δ 2.57 (q, J=2.70 Hz, 3H), 2.76 (t, J=4.50 Hz, 4H), 3.07-3.12 (m, 3H), 3.33 (dd, J=1.50 & 1.20 Hz, 2H), 3.37 (dd, J=1.50 & 1.20 Hz, 2H), 3.51 (q, J=9.00 Hz, 6H), 3.66 (s, H), 3.69 (d, J=2.70 Hz, 2H), 3.73 (d, J=2.40 Hz, 2H); and $^{13}$C NMR (75 MHz, CDCl$_3$): δ 44.34, 45.51, 50.97, 65.33, 71.61, 71.67, 71.73, 72.18, 72.20, 72.23; and IR (Neat): 3507, 3056, 2999, 2922, 2870, 1476, 1450, 1424, 1336, 1248, 1160, 1098, 1051, 953, 901, 855, 834, 751 cm$^{-1}$; and MALDI-TOF MS: C$_{14}$H$_{24}$O$_7$; Calc. 304.3; found 327.05 [M+Na]$^+$ amu.

The following Scheme D illustrates this reaction.

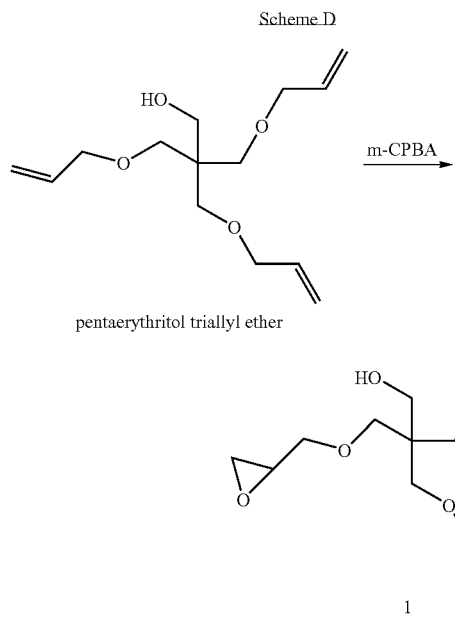

pentaerythritol triallyl ether

EXAMPLE F

Reaction of Pentaerythritol Triglycidyl Ether (PETriGE) with Propargyl Bromide

[(C)=Pentaerythritol triglycidyl ether (PETriGE); (FF)= alkyne; (TF)=Epoxide]

To a 250-mL oven-dried round bottom flask was added PETriGE (made by Example E) and 120 mL dry DMF (Aldrich). The reaction flask was flushed with $N_2$ gas, closed with a septum and cooled to 0° C. with an ice bath. To this solution was added, under mechanical stirring, sodium hydride (1.35 g, 33.8 mmol, 60% dispersion in mineral oil) (Aldrich) in portions over a period of 20 mins. After additional stirring at 0° C. for 40 mins., propargyl bromide (3.73 mL, 90% wt % in toluene) was added. Cooling continued for 90 mins., and then the mixture was allowed to gradually warm to RT. The mixture was stirred overnight at this temperature. The reaction mixture was then cooled to 10° C. using an ice bath, diluted with 70 mL water, extracted with ethyl acetate (3×70 mL), and washed with saturated brine solution (2×50 mL). The combined extracts were dried over sodium sulfate and concentrated by rotary evaporation to give a dark brown colored liquid, which was purified through column chromatography on silica gel, using initially ethyl acetate in hexanes (20:80% v/v), which was gradually changed to ethyl acetate in hexanes (40:60% v/v). Fractions giving a TLC (ethyl acetate:hexanes 1:1) spot at $R_f$=0.31 were combined and found to be the pure propargylated pentaerythritol triglycidyl ether (3.79 g, 82% yield). Its spectra are as follows:

$^1$H NMR (300 MHz, $CDCl_3$): δ 2.43 (t, J=2.10 Hz, 1H), 2.61 (q, J=2.70 Hz, 3H), 2.79 (t, J=4.20 Hz, 3H), 3.13 (sextet, J=3.00 Hz, 3H), 3.37 (d, J=6.00 Hz, 1H), 3.41 (d, J=5.70 Hz, 1H), 3.51 (d, J=3.90 Hz, 6H), 3.54 (s, 2H), 3.70 (d, J=3.00 Hz, 2H), 3.74 (d, J=2.70 Hz, 2H), 4.13 (dd, J=2.10 & 0.30 Hz, 2H); and $^{13}$C NMR (75 MHz, $CDCl_3$): δ 44.44, 45.69, 51.06, 58.84, 69.05, 70.15, 72.24, 74.34, 80.25; and IR (Neat): 3267, 3057, 2991, 2924, 2878, 2755, 1480, 1434, 1367, 1337, 1260, 1168, 1096, 1014, 963, 906, 840, 758, 666 $cm^{-1}$.

The following Scheme E illustrates this reaction.

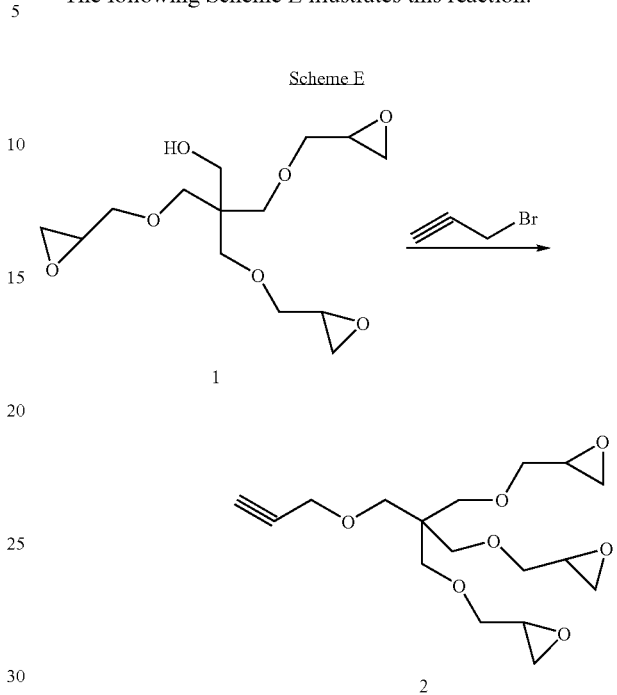

EXAMPLE G

Reaction of Pentaerythritol Tetraglycidyl Ether (PETGE) with Sodium Azide; Modified Core

[(C)=Pentaerythritol tetraazide (PETAZ); (IF)=OH; (TF)= Azide]

A 50-mL round bottom flask was charged with PETGE (3.6 g, 10 mmol) (made by Example C), 27 mL DMF and 3 mL water. To this solution was added sodium azide (7.8 g, 120 mmol, 3 equiv. per epoxide), followed by ammonium chloride (6.36 g, 3 equiv.). The reaction flask was equipped with a stir bar and refluxing condenser and heated at 50° C. overnight. Progress of the reaction was monitored by TLC. After this time, the reaction mixture was allowed to cool to RT, then solid materials were filtered off through a Büchner funnel, and the solids were washed with ethyl acetate (1×50 mL). The filtrate was diluted with 70 mL water and extracted with ethyl acetate (3×50 mL). The combined organic layers were washed with saturated brine, dried over sodium sulfate and filtered through a silica gel bed. The filtrate was concentrated by rotary evaporation to give colorless liquid (5.1 g, 95% yield). Its spectra are as follows.

$^1$H NMR (300 MHz, $CDCl_3$): δ 3.04 (bs, 4H, OH), 3.33 (t, J=5.70 Hz, 8H), 3.47 (s, 8H), 3.49 (t, J=2.40 Hz, 8H), 3.93 (pentate, J=5.10 Hz, 4H); and $^{13}$C NMR (75 MHz, $CDCl_3$): δ 45.75, 53.52, 69.68, 71.09, 73.12; and MALDI-TOF MS: $C_{17}H_{32}N_{12}O_8$; Calc. 532.5, found 555.3 $[M+Na]^+$ amu.

The following Scheme F illustrates this reaction.

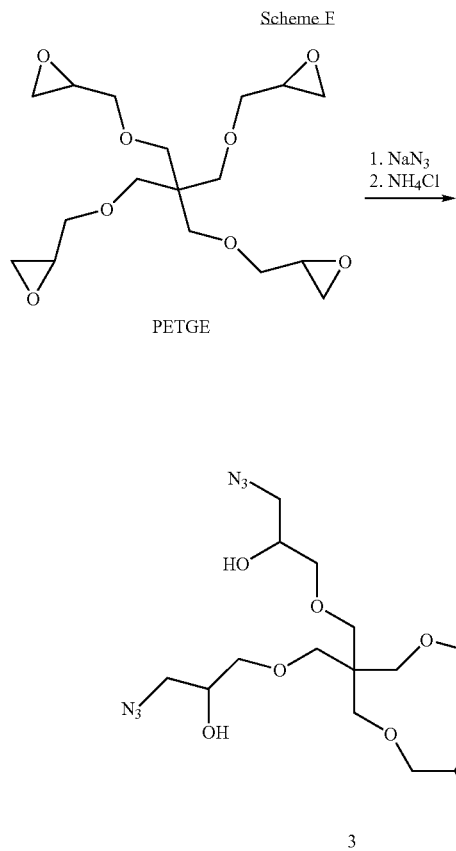

The following Scheme G illustrates this reaction.

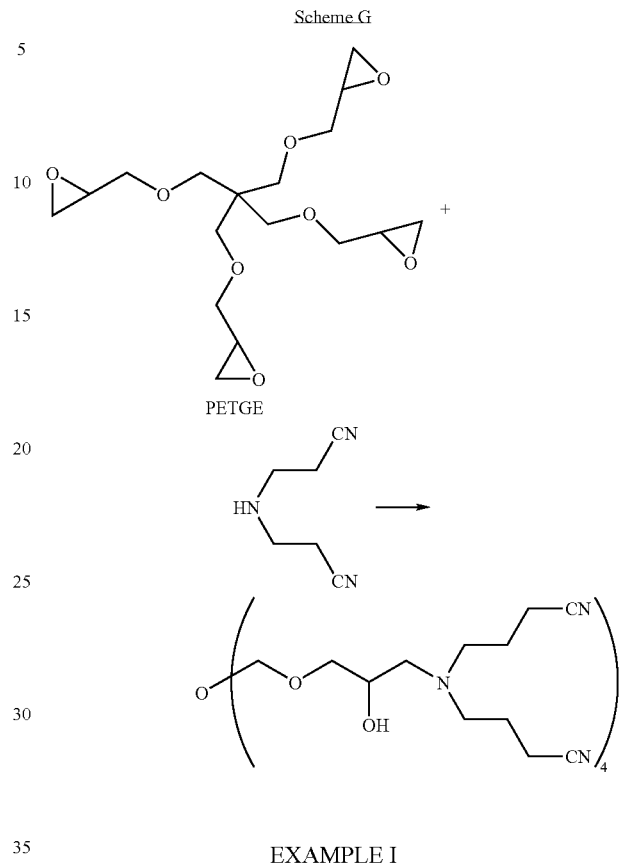

EXAMPLE H

Reaction of pentaerythritol tetraglycidyl ether (PETGE) with iminodiacetonitrile (IDAN). This material will be used as starting core for the production of oxazoline-based PEHAM dendrimers.

[(C)=PETGE; (IF1)=OH; (BR1)=IDAN; (TF)=CN]

To a 250-mL round bottom flask containing a stir bar was added 3,3-IDAN (12.0 g, 97.4 mmol, 2.2 equiv. per epoxide) (Aldrich) and 30 mL of MeOH. To this mixture was added pentaerythritol tetraglycidyl ether (4.0 g, 11.1 mmol, 44.4 mmol epoxide) in 10 mL of MeOH. The flask was fitted with a reflux condenser and the mixture heated and stirred for 3 days at 60° C. under a $N_2$ atmosphere. Volatile materials were removed by rotary evaporation to give a crude weight of 16.5 g. Excess nitrite was removed by bulb-to-bulb distillation at 200-220° C. at high vacuum, leaving the pot residue (10.3 g, 9.45 g theory). This crude product was dissolved in 20 mL of MeOH and passed through a plug of silica gel (75.0 g, 60 angstrom, 200-430 mesh), using MeOH as the eluant. Volatile materials were removed from the eluant by rotary evaporation to give the desired product (8.5 g, 90% yield). TLC (MeOH) of this mixture indicated an intense spot at $R_f$=0.85 with a much lighter spot at $R_f$=0.7. Its spectra are as follows:

$^{13}$C NMR (125 MHz, CDCl$_3$): δ 16.96, 17.33, 44.45, 45.45, 49.49, 50.31, 56.27, 68.23, 71.06, 73.46, 118.56, 119.11.

EXAMPLE I

Synthesis of 2-Imidazolidyl-1-Aminoethane (IMAE)

[(EX)=IMEA]

To an ice-cooled aqueous solution of DETA (1.037 g, 0.01 mmol) in 5 mL DI water, 0.85 mL of 37% formaldehyde was added dropwise over 10 mins. with stirring. After being stirred for one 1 hour, the reaction mixture was concentrated by rotary evaporation. Then KOH pellets were added carefully to the condensate under ice-cooling until a two phase solution was obtained. The oily upper phase was extracted with CHCl$_3$ and dried over Na$_2$SO$_4$. Volatile materials were removed by rotary evaporation, giving the desired IMAE as a clear oil (1.0 g, 95% yield). Its spectra are as follows:

$^1$H NMR (CDCl$_3$, 300 MHz, ppm), 2H (1.7, s, br), 8H (2.42-3.2, m), 2H (3.42, s). $^{13}$C NMR (CDCl$_3$, 75 MHz, ppm), 41.30, 45.53, 52.49, 56.93, 71.06 ppm.

The following Scheme H illustrates this reaction.

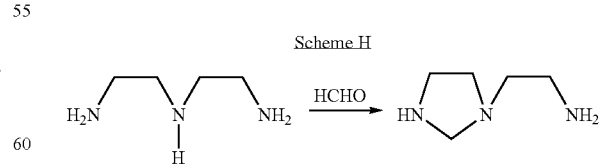

PEHAM Generation 0 and 0.5 (G=0 and G=0.5) with a PIPZ Surface

The PIPZ surface has been found to be advantageous in encapsulation studies, and therefore, will provide encapsulation properties to low generation dendrimers as demonstrated in later examples. The following examples (Examples 1-3, 4B-8, 10B, and 13A) illustrate the attachment of PIPZ to various cores with multiplicities of 2, 3 and 4. Examples 4A, 7A, 9, 13B and 14 illustrate a carboxylate or its ester as the surface with various cores, (IF) and (EX) moieties. Other surfaces are illustrated in Examples 12 and 15.

EXAMPLE 1

Michael's Addition Reactions

Capping the Trimethylolpropane Triacrylate (TMPTA) with Piperazine to Produce the Triamine Functional Core

[(C)=TMPTA; (FF)=Et; (EX1)=PIPZ; (TF)=Secondary NH; G=0.5]

To a 250-mL round bottom flask containing a stir bar was added 13 g of anhydrous PIPZ (151 mmol, 5 equiv. per acrylate) (Aldrich) and 45 g of MeOH. This mixture was made homogeneous and cooled to 4° C. under a $N_2$ atmosphere. To this stirred mixture was added 3 g of TMPTA (10.12 mmol, 30.4 mmol acrylate) (Aldrich) in 20 g of MeOH over about 10 mins. using a dropping funnel. This mixture was stirred at 4° C. for one hour, then for one hour at 25° C. This mixture was evaporated of volatiles on a rotary evaporator. The resulting residue was dissolved in chloroform and extracted with water (4×20 mL). A TLC (5% $NH_4OH$ in MeOH) indicated the complete removal of PIPZ. The organic layer was dried over sodium sulfate, filtered and evaporated of volatiles to give the desired product as a viscous, colorless solid (3.2 g; 60% yield); and its spectra are as follows:

$^1$H NMR (500 MHz, $CDCl_3$): δ 0.89 (qt, 3H, $CH_3$), 1.49 (t, 2H, $CH_2$), 2.42 (bs, 12H, $CH_2$), 2.52 (t, 6H, $CH_2$), 2.66 (t, 6H, $CH_2$), 2.86 (t, 12H, $CH_2$), 4.05 (s, 6H, $CH_2$); and $^{13}$C NMR (125 MHz, $CDCl_3$): δ 7.49, 22.77, 32.16, 40.91, 45.93, 54.03, 54.93, 63.57, 63.57, 172.04; and MALDI-TOF: Calc. 554.4; found 556 amu.

The above reaction is further illustrated by the following Scheme 1:

Scheme 1

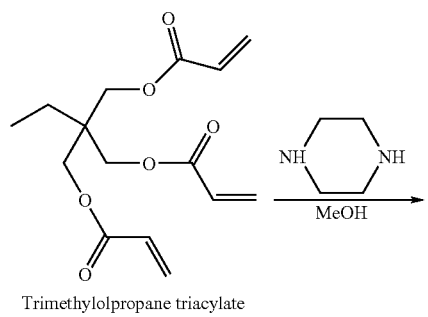

Trimethylolpropane triacylate

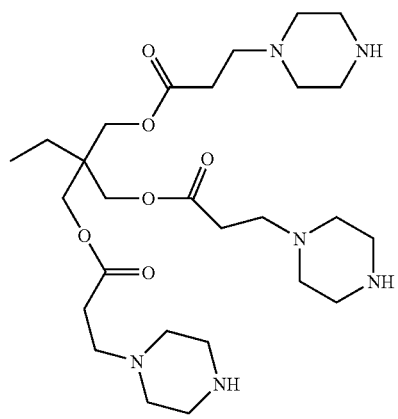

EXAMPLE 2

Addition Using Epoxide Ring-Opening Reactions

Reaction of Capping the Triepoxide TMPTGE with Piperazine to Produce Triamine Functional Core: Trimethylolpropane Tris(2-Hydroxypropyl-3-Piperazine)

[(C)=TMPTGE; (FF)=Et; (IF1)=OH; (EX1)=PIPZ; (TF)= Secondary NH; G=0.5]

To a 250-mL round bottom flask containing a stir bar was added 17 g of PIPZ (198 mmol, 5 equiv. per epoxide) (Aldrich) and 50 g of MeOH. This mixture was made homogeneous. To this mixture was added 4.0 g of TMPTGE (13.2 mmol, 39.6 mmol epoxide) in 20 g of MeOH over about 5 mins. This mixture was heated for 20 hours at 50° C. under a $N_2$ atmosphere. A TLC of this crude mixture (5% $NH_4OH$ in MeOH) and developing with $K_2MnO_4$ solution indicated the absence of epoxide. This mixture was evaporated of volatiles on a rotary evaporator. The resulting residue was distilled of PIPZ using a bulb-to-bulb distillation apparatus using high vacuum and heating the mixture at 140° C. for 30 mins. A TLC of this mixture (5% $NH_4OH$ in MeOH) indicated residual PIPZ remaining in the mixture. The residue was dissolved in 20 g of MeOH and mixed with 60 g toluene. This homogeneous mixture was distilled on a rotary evaporator to azeotrope PIPZ. This procedure was repeated three times to give a PIPZ free product by TLC. High vacuum evacuation overnight at 25° C. gave 6.8 g (92% yield) of the desired product; and its spectra are as follows:

$^1$H NMR (500 MHz, $CDCl_3$): δ 0.84 (t, J=7.5 Hz, 3H), 1.40 (qt, J=7.5 Hz, 2H), 2.3-2.5 (bm, 122H), 2.7-3.0 (bm, 112H), 3.3-3.5 (m, 514), 3.88 (m, 6H); and $^{13}$C NMR (125 MHz, $CDCl_3$): δ 7.71, 23.14, 43.40, 46.03, 54.61, 61.48, 66.35, 71.96, 73.14, and MALDI-TOF: Calc. 560.4; found 560 amu.

Scheme 2 below illustrates the above reaction:

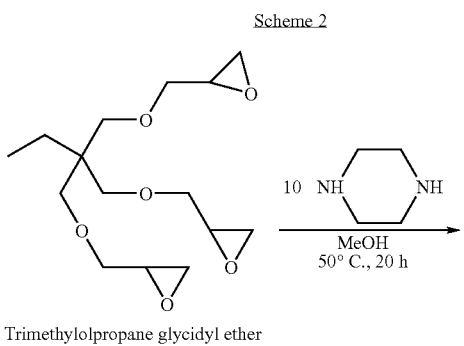

Trimethylolpropane glycidyl ether

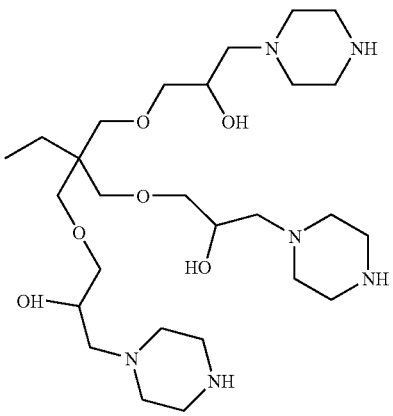

EXAMPLE 3

Divergent PEHAM Dendrimer Synthesis Using Iterative Reaction Sequences Tetrafunctional PETGE with a PIPZ Extender

[(C)=PETGE; (IF1)=OH; (EX1)=PIPZ; (TF)=Secondary NH; G=0.5]

To a 500-mL round bottom flask containing a large stir bar was added 26 g of PIPZ (310 mmol, 8 equiv. per epoxide) (Aldrich) and 45 g of MeOH. To this homogeneous solution was added a mixture of 3.5 g of PETGE (9.71 mmol, 38.8 mmol epoxide) (made by Example A) in 10 g of MeOH in a dropwise manner over 5 mins. This mixture was stirred for 24 hours at 25° C. under a $N_2$ atmosphere. The volatiles were removed with a rotary evaporator to give a white solid residue. This residue was distilled to remove PIPZ using a bulb-to-bulb distillation apparatus at high vacuum and 140° C. for 30-40 mins. The resulting pot residue contained a small amount of PIPZ as determined by TC (30% $NH_4OH$ in MeOH). This residual PIPZ was removed by three azeotropic distillations using 30 mL of MeOH and 90 mL of toluene. The crude product was dried under high vacuum at 25° C. overnight (6.7 g; 97% yield). A TLC of this mixture (30% $NH_4OH$ in MeOH) indicated a small amount of oligomers. An aliquot of this mixture (700 mg) was purified by SEC using Sephadex™ LH-20 in MeOH. After the void volume was taken, 48 fractions of 8 mL each were collected. Fractions 1-3 were empty, fractions 4-7 contained oligomers only and fraction 8 was a mixture of product and oligomers. Fractions 9-48 contained only desired product and were collected and stripped of volatiles to give 400 mg of product. Its spectra are as follows:

$^1$H NMR (500 MHz, $CDCl_3$): δ 2.36-2.44 (bm, 2H), 2.53-2.60 (bm, 2H), 2.82 (m, 4H), 3.45 (m, 4H), 3.88 (m, 2H); and $^{13}$C NMR (125 MHz, $CDCl_3$): δ 45.62, 46.02, 46.02, 54.72, 61.52, 66.18, 70.49, 74.27 and MALDI-TOF: Calc. 704.5; found 705 amu.

EXAMPLE 4

Tetrafunctional Core with Trifunctional Branching Using Mono-Protected Amines in Epoxide Ring-Opening Reaction A. Capping the Tetraepoxide with Mono-Protected Piperazine, Core: Poly(ether-hydroxyamines) Dendrimer, G=0.5, from Pentaerythritol Tetraglycidylether (PETGE) and Ethyl-N-piperazinecarboxylate

[(C)=PETGE; (IF1)=OH; (EX1)=Ethyl Piperazine Carboxylate; (TF)=Carboxylate; G=0.5]

EPC (6.32 g, 40 mmol, 1 equiv. per epoxide) and 40 mL of MeOH were taken in a 100-mL round bottom flask and flask was equipped with stir bar. PETGE (3.6 g, 10 mmol) (made by Example B) was dissolved in 10 mL of MeOH and added to the above stirring solution dropwise over a period of 20 min. through a dropping funnel. After being stirred for 2 hours, TLC showed complete consumption of PETGE, $R_f$=0.80 (3:1 of DCM: MeOH) and iodine vapors were used to visualize the spots. Stirring was continued at RT overnight and solvent was evaporated on a rotary evaporator, which gives a colorless liquid. Traces of EPC were distilled out by Kugelrohr distillation at 180° C. in 20 min., which gave an ester surface (G=0.5)dendrimer 2 as viscous liquid (9.47 g; 95%). Its spectra are as follows:

$^1$H NMR: (300 MHz, $CD_3OD$): δ 1.24 (t, J=6.90 Hz, 12H), 2.36-2.55 (m, 24H), 3.29-3.49 (m, 36H), 3.89 (quintet, J=4.80 Hz, 4H), 4.10 (q, J=7.20 Hz, 8H); and $^{13}$C NMR: (75 MHz, $CD_3OD$): δ 13.80, 43.50, 45.80, 53.42, 61.31, 61.53, 67.55, 70.15, 74.30, 155.95; and IR (Neat): $\lambda_{max}$ 3446, 2975, 2863, 2801, 1695, 1536, 1456, 1424, 1378, 1352, 1244, 1116, 1034, 876, 830, 758 $cm^{-1}$; and MALDI-TOF: $C_{45}H_{84}N_8O_{16}$ Calc. 993; found 1017 ($M^+Na$) amu.

The following Scheme 3 illustrates this above reaction:

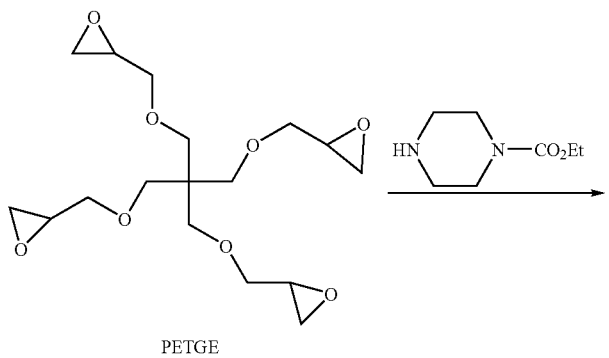

Scheme 3

PETGE

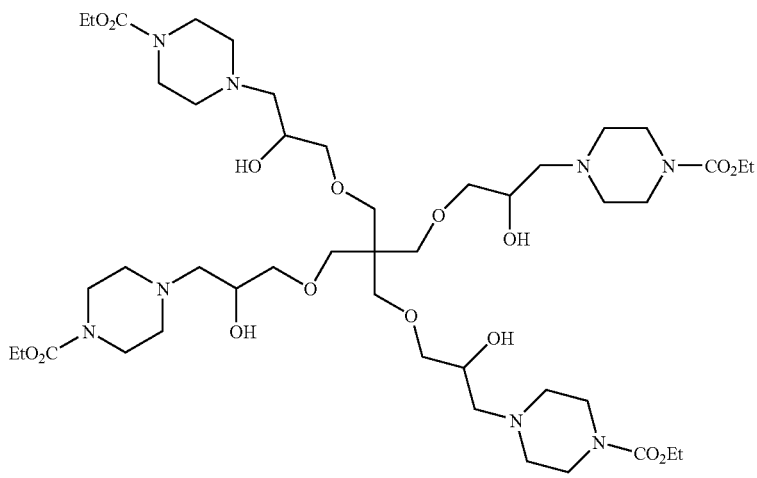

2

B. Deprotection of the Capped Tetraepoxide Core from Example 4A, Hydrolysis of the Ester Surface, G=0.5, Dendrimer with KOH

[(C)=PETGE; (IF1)=OH; (EX1)=PIPZ; (TF)=Secondary NH; G=0.5]

Dendrimer 2 (9.4 g, 9.46 mmol) (made by Example 4A) was taken in a 250-mL round bottom flask and dissolved in 85 mL of MeOH. The flask was equipped with a stir bar. Potassium hydroxide solution (28.2 g of KOH was dissolved in 56.4 mL of water) was added to the above stirring solution at RT. The flask was arranged with a refluxing condenser and kept in a pre-heated oil bath at 85-90° C. Progress of the reaction was monitored by TLC. After 2 hours, TLC indicated three spots and heating was continued overnight. The product showed a pink spot upon exposure to ninhydrin solution at $R_f$=0.17 (50% $NH_4OH$ in MeOH). Solvent and water were removed on a rotary evaporator under reduced pressure, giving a viscous liquid. This liquid was transferred into a separatory funnel and extracted with DCM (3×50 mL). Combined DCM layers were dried over $Na_2SO_4$ and filtered through Celite (1 cm height) and Celite was washed thoroughly with DCM. DCM was removed on a rotary evaporator, which gave the dendrimer 3 as a colorless viscous liquid (6.01 g, 90% yield). It gave a hygroscopic solid upon drying under high vacuum for 2 hours. This material was found to be very pure from its spectroscopic data and used in subsequent synthesis without further purification. Its spectra are as follows:

$^1$H NMR: (300 MHz, $CD_3OD$): δ 3.46 (s, 8H), 3.39 (d, J=2.10 Hz, 8H), 2.84 (t, J=4.80 Hz, 16H), 2.51 (bs, 16H), 2.41 (d, J=3.90 Hz, 8H), 2.40 (s, 4H, NH), 2.37 (s, 4H, OH), 3.89 (sextet, J=4.80 Hz, 4H); and $^{13}$C NMR: (75 MHz, $CD_3OD$): δ 45.06, 45.80, 54.33, 62.07, 67.37, 70.14, 74.41; and IR (Neat): $\lambda_{max}$ 3456, 2936, 2817, 1595, 1457, 1319, 1111, 1005, 859, 732, 697 cm$^{-1}$; and MALDI-TOF: $C_{33}H_{68}N_8O_8$ Calc. 704; found 727 ($M^+Na$), 743 ($M^+K$) amu.

The following Scheme 4 illustrates the above reaction:

Scheme 4

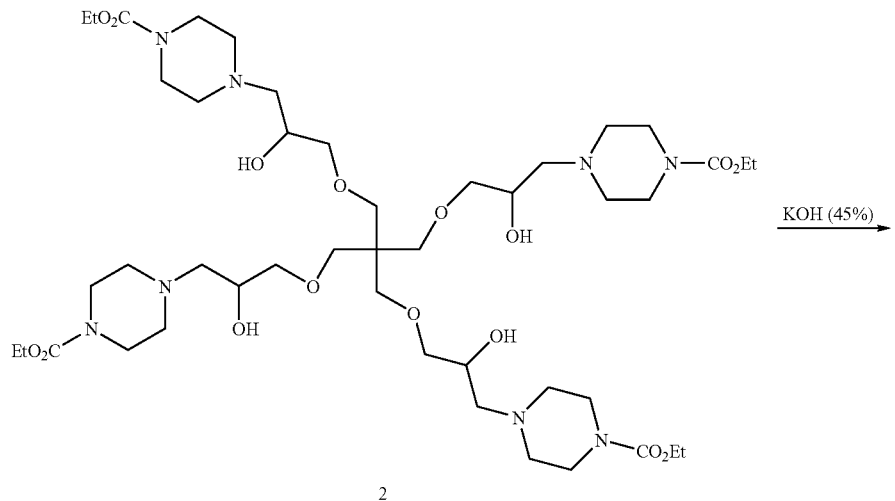

2

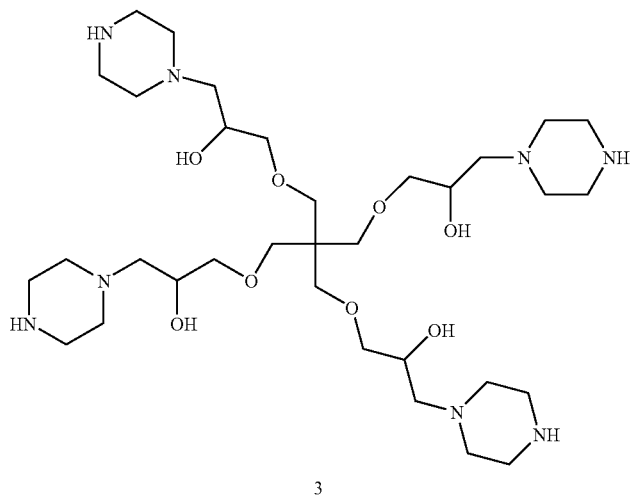

3

EXAMPLE 5

Reaction of Tetraphenylolethane Glycidylether with Piperazine

[(C)=TPEGE; (IF1)=OH; (EX1)=PIPZ; (TF)=Secondary NH; G=0.5]

A. Synthesis of Tetraphenylolethane tetra(2-hydroxypropyl-3-piperazine-1-ethyl carboxylate)ether To a 50-mL round bottom flask containing a stir bar was added TPEGE (Aldrich) (2.0 g, 3.2 mmol, 12.9 mmol epoxide) and 8 mL of DME under mechanical stirring. To this mixture was added EPC (4.5 g, 28.4 mmol, 2.2 equiv. per epoxide) and 4 mL of MeOH. This mixture was stirred at 25° C. for 60 hours sealed under a $N_2$ atmosphere. A MALDI-TOF mass spectrum of an aliquot of this mixture indicated the complete disappearance of the starting material at 622 amu and the formation of the product signals at 1255 amu and 1371 amu. The volatiles of this mixture were removed using a rotary evaporator to give a crude weight of 7.6 g. This mixture was dissolved in 125 mL of MeOH and ultrafiltered on a tangential flow UF device containing 3K cut-off regenerated cellulose membranes at a pressure of 20 psi (137.9 kPa) at 25° C. The retentate volume as marked in the flask was maintained at 100-125 mL during the UF collection of 1500 mL of permeate (~5 hours). The first liter of permeate was stripped of volatiles on a rotary evaporator, followed by high vacuum evacuation at 40° C. to give 4.3 g of material. A MALDI-TOF mass spectrum of this material indicated low molecular weight material ranging from 300-1200 amu along with some product that had permeated through the membrane. The final 500 mL of permeate was distilled of volatiles to give 500 mg of material showing only an $R_f$ 0.75 by TLC and a mass spectrum with peaks for the desired product. The retentate was stripped of volatiles to give 1.9 g of material with a TLC (ethyl acetate-MeOH 1:1) at $R_f$=0.75. The total yield of this product is 47%. Its spectra are as follows:

MALDI-TOF MS: $C_{67}H_{96}N_8O_{16}$ Calc. 1252.7; found 1277 [M+Na]$^+$ amu.

B. Hydrolysis of Carboxylate Protecting Groups to Yield Tetraphenylolethane tetra(2-hydroxypropyl-3-piperazine) ether To a 50-mL round bottom flask containing a stir bar and fitted with a condenser was added KOH (3.6 g, 54.5 mmol, 18 equiv. per carbamate), 7.5 g of DI water and 12 g of MeOH. To this homogeneous mixture was added tetraphenylolethane (2-hydroxypropyl-3-piperzine-1-ethyl carboxylate)ether (1.2 g, 0.95 mmol) (made by Example 5A) in 4 g of MeOH. This mixture was heated at 80° C. for 0.16 hours under a $N_2$ atmosphere. This mixture was cooled to RT and the volatiles were removed using a rotary evaporator followed by high vacuum to give a yellow solid. This mixture was extracted with DCM (5×30 mL). The collected DCM extractions were dried with anhydrous sodium sulfate. The filtered solvent was stripped of volatiles to give 1.2 g of material. This material was dissolved in hot MeOH and filtered through a plug of Celite. The volatiles were removed by high vacuum to give 800 mg of a solid, which was dissolved in a minimum of MeOH and purified on a Sephadex™ LH-20 column in MeOH, taking 30 fractions of 2 mL each. Fractions 11-20 contained the desired product (440 mg, 55% yield) as verified by MALDI-TOF mass spectroscopy and $^{13}$C NMR spectroscopy. Its spectra are as follows:

$^{13}$C NMR (75 MHz, $D_2O$): δ 46.16, 54.50, 62.95, 69.29, 72.17, 117.29, 131.69, 140.04, 159.16; and MALDI-TOF MS: $C_{54}H_{78}O_8$ Calc. 967.25; found 968 [M]$^+$, 990 [M+Na]$^+$ amu.

The following Scheme 5 illustrates the above reactions.

Scheme 5

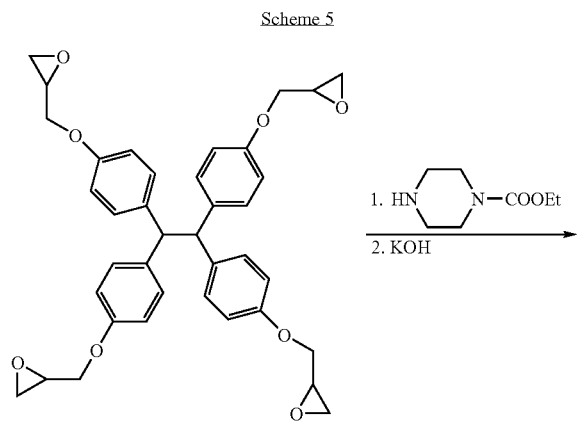

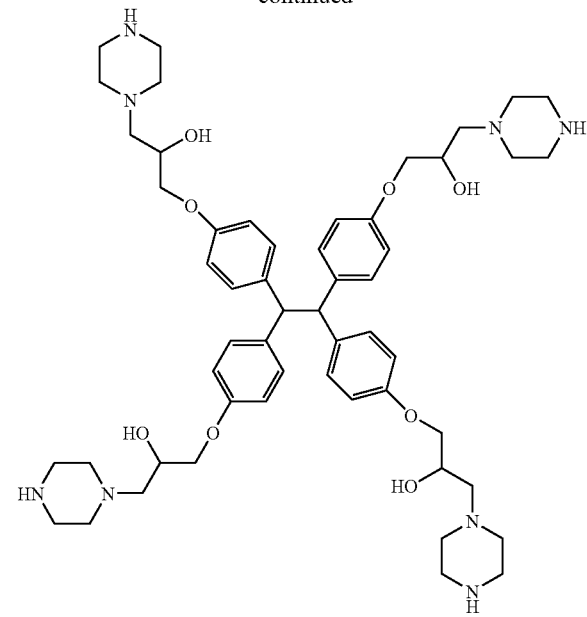

EXAMPLE 6

Reaction of Triphenylolmethane Triglycidylether with Piperazine

[(C)=TPMTGE; (IF1)=OH; (EX1)=PIPZ; (TF)=Secondary NH; G=0.5]

A. Synthesis of Triphenylolmethane tri(2-hydroxypropyl-3-piperazine-1-ethyl carboxylate)ether To a solution of TPMTGE, 1 (2.3 g, 5.0 mmol) in 20 mL of DME and 10 mL of MeOH was added a solution of EPC, 2 (3.55 g, 22.5 mmol, 1.5 equiv. per epoxide) dissolved in 10 mL of MeOH over a period of 10 mins. The flask was closed with a stopper and the mixture stirred at 25° C. for 2 days. The solvent was removed on a rotary evaporator and excess EPC was removed by Kugelrohr distillation at 165° C. to give product 3 as a highly viscous liquid (4.56 g, 97.6%). After distillation, TLC (15 drops of MeOH in 5 mL of DCM, potassium permanganate stain) showed three spots at $R_f$ 0.28 (major), 0.22 and 0.11 (minor). Its spectra are as follows:

MALDI-TOF MS: $C_{40}H_{70}N_6O_{12}$ Calc. 935.1100; found 935.6 [M]$^+$ and 957.5 [M+Na]$^+$ amu.

B. Hydrolysis of Carboxylate Protecting Groups to Yield Triphenylolmethane tri(2-hydroxypropyl-3-piperazine)ether To a 250-mL round bottom flask was added triphenylolmethane tri(2-hydroxypropyl-3-piperazine-1-ethyl carboxylate)ether (4.46 g, 4.77 mmol) (made by Example 6A) and dissolved in 40 mL of MeOH under mechanical stirring. Aqueous KOH (13.38 g of 90% KOH was dissolved in 26.76 mL of water) solution was added into the above stirring reaction mixture dropwise at 25° C. After complete addition, the round bottom flask was equipped with a refluxing condenser and placed in an oil-bath and heated at 85-90° C. After heating for 24 hours, the solvent was removed on a rotary evaporator under reduced pressure. The resulting crude reaction mixture was extracted with DCM (3×50 mL). Combined extracts were filtered through Celite bed and dried over anhydrous sodium sulfate. TLC (30% $NH_4OH$ in MeOH) showed two spots at $R_f$=0.46 and 0.27 (stained with ninhydrin solution). The solvent was removed on a rotary evaporator and the residue dried under high vacuum to give the desired product 3 as a colorless solid (3.37 g, 98.3% yield). Its spectra are as follows:

MALDI-TOF MS: $C_{40}H_{58}N_6O_6$ Calc. 718.9; found 719.5 [M]$^+$, 741.5 [M+Na]$^+$, 757.5 [M+K]$^+$ amu.

The following Scheme 6 illustrates this reaction.

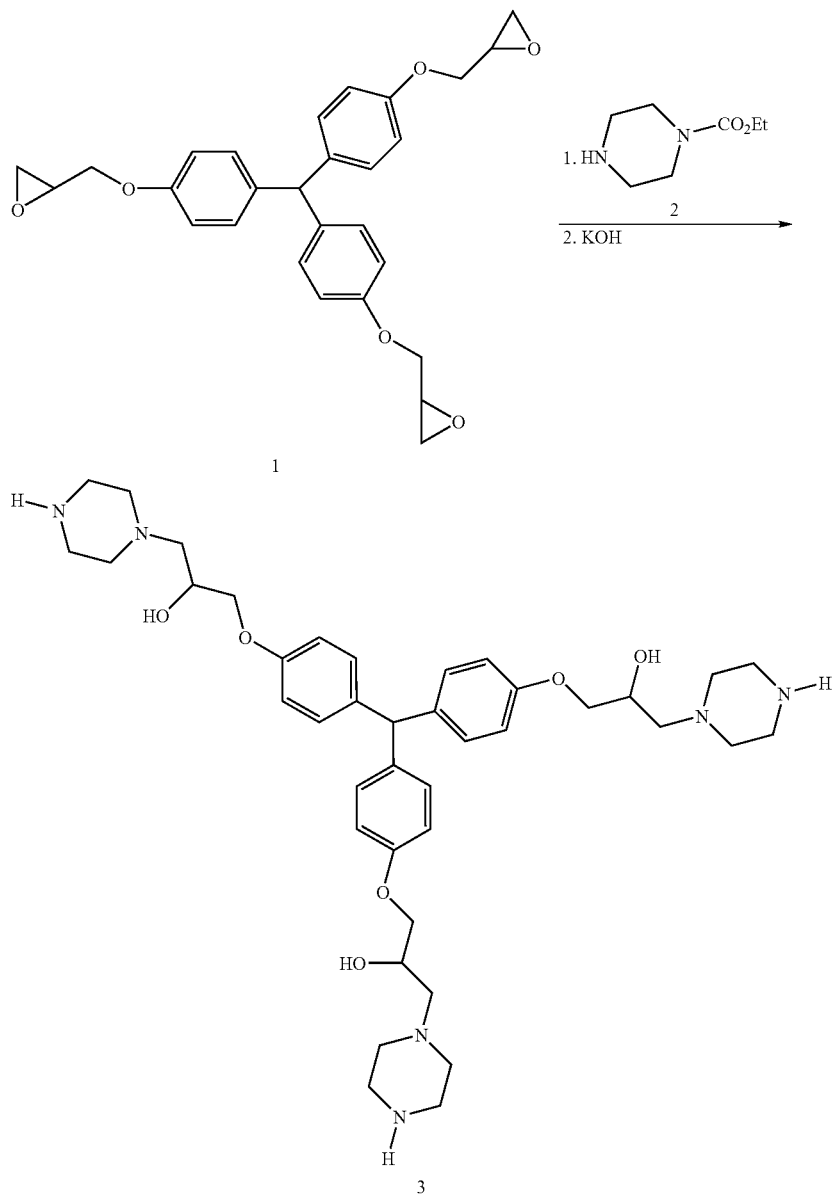

EXAMPLE 7

Reaction of tris(2,3-epoxypropyl)isocyanurate with ethyl-N-piperazine-carboxylate

[(C)=TGIC; (IF1)=OH; (EX1)=PIPZ; (TF)=Secondary NH; G=0.5]

A. Synthesis of Carboxylate Protected tris(2,3-epoxypropyl) isocyanurate

To a stirred solution of EPC (1.42 g, 9 mmol) in 6 mL of MeOH was added TGIC (0.594 g, 2 mmol) all at once, followed by 4 mL of DCM. After stirring for about 3 hours, the isocyanurate was completely dissolved. The reaction mixture was stirred for an additional 48 hours at 25° C. TLC (1:2:2 of hexanes:ethyl acetate:chloroform) showed complete consumption of isocyanurate, and MALDI-TOF on the crude product showed only peaks for the desired product. Solvents were removed using a rotary evaporator to give a colorless transparent liquid. Removal of excess EPC by Kugelrohr distillation at 170° C. for 15 mins. gave compound 2 as a pale yellow colored, highly viscous liquid (1.54 g, 100% yield). Its spectra are as follows:

$^1$H NMR (300 MHz, CD$_3$OD): δ 1.24 (t, J=7.20 Hz, 9H), 2.41-2.54 (m, 18H), 3.45 (bs, 12H), 3.90-4.04 (m, 6H), 4.07-4.16 (m, 3H), 4.11 (q, J=7.20 Hz, 6H); and $^{13}$C NMR (75 MHz, CD$_3$OD): δ 13.79, 43.52, 46.96, 53.28, 61.54, 62.15, 65.54, 150.11, 155.94; and IR (Neat): λ$_{max}$ 3344, 2986, 2934, 2858, 2806, 1685, 1465, 1434, 1388, 1357, 1383, 1244, 1173, 1127, 1096, 1034, 1004, 881, 835, 768 cm$^{-1}$; and MALDI-TOF: C$_{33}$H$_{57}$N$_9$O$_{12}$ Calc. 771; found 794 [M+Na]$^+$ amu.

The following Scheme 7 illustrates this reaction:

B. Hydrolysis of Carboxylate Protecting Groups and Degradation of Isocyanurate Core A round bottom flask was charged with the carboxylate-protected isocyanurate, 2 (made by Example 7A) dissolved in 14 mL of MeOH. Then aqueous KOH (4.5 g of KOH dissolved in 9 mL of water) was added to the above solution at 25° C. over 5 mins. under mechanical stirring. The flask was placed in a pre-heated oil bath (85-90° C.) and heated overnight. TLC (3:1 of DCM:MeOH) indicated the absence of starting material (positive ninhydrin test with $R_f$=0.41 in 50% $NH_4OH/MeOH$). MeOH was removed on a rotary evaporator and the aqueous layer extracted with DCM (2×30 mL). The combined extracts were dried over $Na_2SO_4$, filtered through a pad of Celite, concentrated on a rotary evaporator, and dried under high vacuum, resulting in a transparent liquid. It was found from analysis that compound 2 not only lost the protecting groups to yield the desired product 3, but in addition the core was ring-opened by the base during the hydrolysis step, resulting in the degradation product 4. From MALDI-TOF product 4 was identified as a urea derivative with a multiplicity of 2, which was the main product. Its spectra are as follows:

$^{13}C$ NMR (75 MHz, $CD_3OD$): δ 45.13, 45.81, 54.27, 63.02, 68.48, 160.40; and IR (Neat): $\lambda_{max}$ 3272, 2929, 2847, 2811, 1659, 1567, 1454, 1367, 1321, 1270, 1132, 1065, 1009, 855, 794, 702 $^{cm-1}$; and MALDI-TOF: $C_{15}H_{32}N_6O_3$ Calc. 344; found 367 $[M+Na]^+$ amu.

The following Scheme 8 illustrates this reaction.

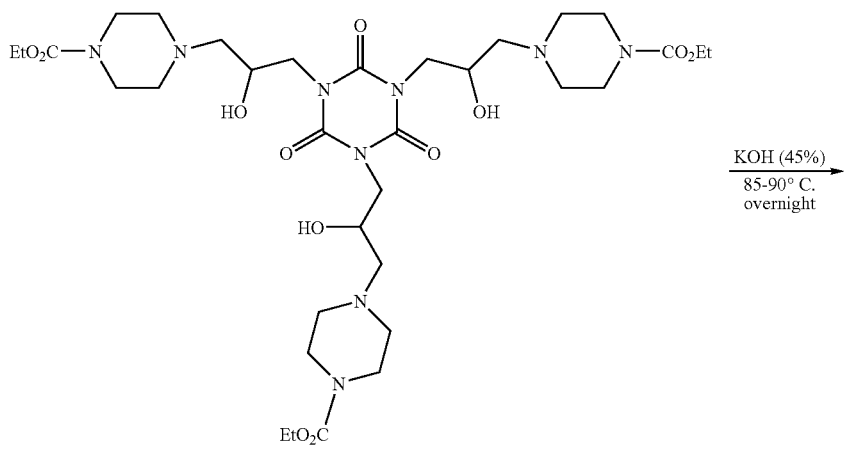

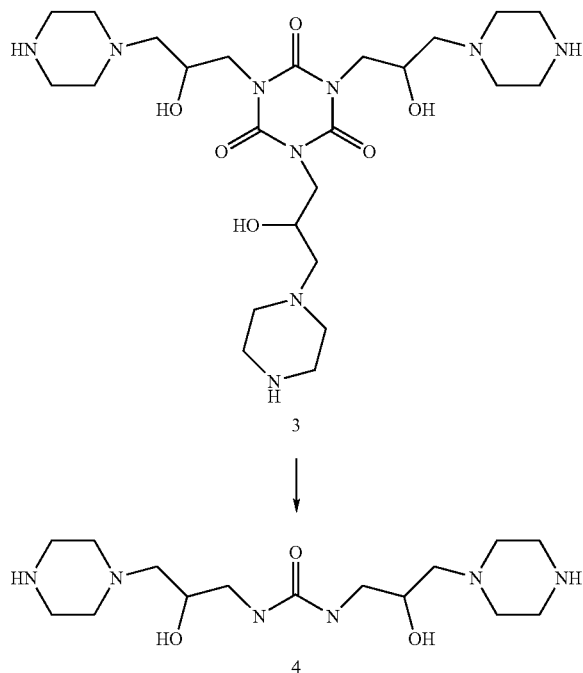

3

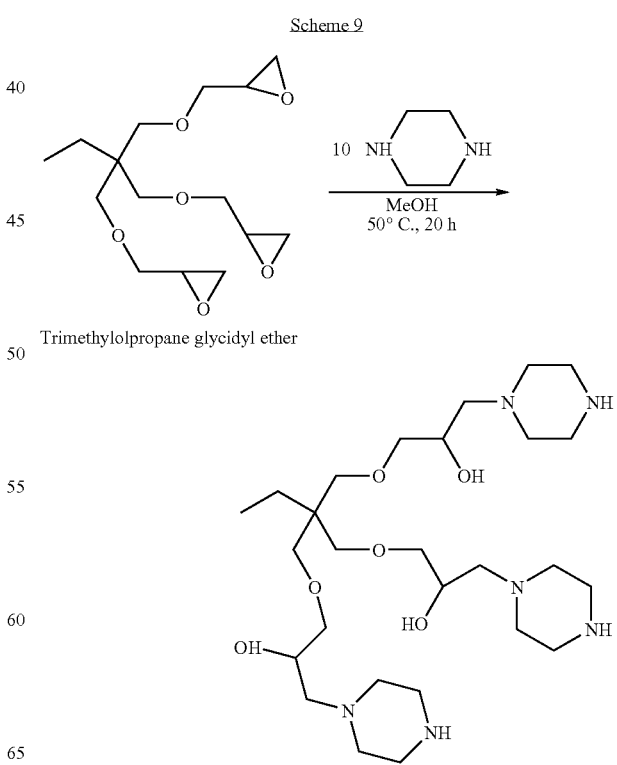

4

EXAMPLE 8

Reaction of Trimethylolpropane Triglycidylether with Piperazine

[(C)=TMPTGE; (IF1)=OH; (EX1)=PIPZ; (TF)=Secondary NH; G=0.5]

To a 250-mL round bottom flask was added 17 g of PIPZ (198 mmol, 5 equiv. per epoxide) (Aldrich) and 50 g of MeOH under mechanical stirring. To this mixture was added 4.0 g of TMPTGE (13.2 mmol, 40 mmol epoxide) in 20 g of MeOH over about 5 mins. This mixture was heated at 50° C. for 20 hours under a $N_2$ atmosphere. A TLC of this crude mixture (5% $NH_4OH$ in MeOH, stained with potassium permanganate solution) indicated the absence of epoxide. Volatiles were removed by rotary evaporation, and the excess PIPZ removed by a bulb-to-bulb Kugelrohr distillation using high vacuum at 140° C. for 30 mins. A TLC of this mixture (5% $NH_4OH$ in MeOH) indicated residual PIPZ remaining in the mixture, which was removed as an azeotropic mixture using 20 g of MeOH and 60 g toluene as the solvent. This procedure was repeated three times to give a piperazine-fee product. High vacuum evacuation overnight at 25° C. gave the desired product (6.8 g, 92% yield). Its spectra are as follows:

$^1$H NMR (500 MHz, $CDCl_3$): δ 0.84 (t, J=7.5 Hz, 3H), 1.40 (qt, J=7.5 Hz, 2H), 2.3-2.5 (bm, 12H), 2.7-3.0 (bm, 12H), 3.3-3.5 (m, 5H), 3.88 (m, 6H); and $^{13}$C NMR (125 MHz, $CDCl_3$): δ 7.71, 23.14, 43.40, 46.03, 54.61, 61.48, 66.35, 71.96, 73.14, and MALDI-TOF: Calc. 560.4; found 560 [M]$^+$ amu.

The following Scheme 9 illustrates the reaction.

EXAMPLE 9

Capping Tetraepisulfide Branch Cell with Blocked Piperazine, Core G=0

[(C)=Tetrathiorane; (TF1)=SH; (EX1)=EPC; (TF)=Carboxylate; G=0.5]

EPC (0.91 g, 5.76 mmol, 1 equiv. per episulfide) and 5 mL of MeOH were taken in a 50-mL round bottom flask equipped with a stir bar and cooled to 4° C. TES (0.610 g, 1.44 mmol) (made by Example D) was dissolved in 5 mL of chloroform (TES is not soluble in MeOH) and added to the above stirring solution dropwise over a period of 5 min. The reaction mixture was stirred for 36 hours. The solvents were evaporated on a rotary evaporator and the crude reaction mixture was purified through column chromatography on silica gel with 3:1 ratio of DCM and MeOH, which gives the pure tetraester 2 that has the following spectra:

$^1$H NMR: (300 MHz, $CD_3Cl$): δ 1.24 (J=6.90 Hz, 12H), 2.44 (m, 26H), 2.61 (4H, SH), 3.22 (quintet, J=6.00 Hz, 4H), 3.44-3.59 (m, 30H), 4.09 (q, J=7.20 Hz, 8H); and $^{13}$C NMR: (75 MHz, $CD_3Cl$): δ 13.79, 37.53, 43.64, 53.08, 61.54, 62.08, 69.39, 74.42, 76.10, 155.95; and MALDI-TOF: $C_{45}H_{84}O_{12}S_4$ Calc. 1057; found 1079 ($M^+$Na) amu.

The following Scheme 10 illustrates this reaction:

EXAMPLE 10

Reaction of Pentaerythritol Tetraglycidylether with Ethyl-N-piperazine Carboxylate

[(C)=PETGE; (IF1)=OH; (EX1)=PIPZ; (TF)=Secondary NH; G=0.5]

A. Capping of PETGE with EPC

EPC (6.32 g, 40 mmol, 1 equiv. per epoxide) and 40 mL of MeOH were mixed in a 100-mL round bottom flask and flask under mechanical stirring. PETGE (3.6 g, 10 mmol) was dissolved in 10 mL of MeOH and added to the above solution dropwise over a period of 20 mins. through a dropping funnel. After additional stirring for 2 hours, TLC (3:1 of DCM: MeOH) showed the complete consumption of PETGE ($R_f$=0.80, staining with iodine vapors). Stirring was continued at 25° C. overnight, and the solvent was evaporated on a rotary evaporator, giving a colorless liquid. Remaining traces of EPC were removed by Kugelrohr distillation at 180° C. in 20 mins., giving the desired mono-protected product as a viscous liquid (9.47 g, 95% yield). Its spectra are as follows:

$^1$H NMR (300 MHz, $CD_3OD$): δ 1.24 (t, J=6.90 Hz, 12H), 2.36-2.55 (m, 24H), 3.29-3.49 (m, 36H), 3.89 (quintet, J=4.80 Hz, 4H), 4.10 (q, J=7.20 Hz, 8H); and $^{13}$C NMR (75 MHz, $CD_3OD$): δ 13.80, 43.50, 45.80, 53.42, 61.31, 61.53, 67.55, 70.15, 74.30, 155.95; and Scheme 10

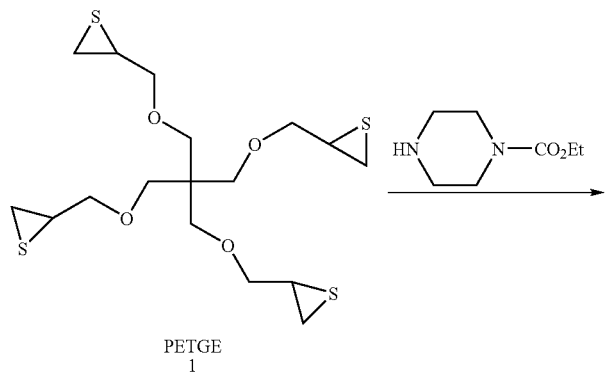

PETGE
1

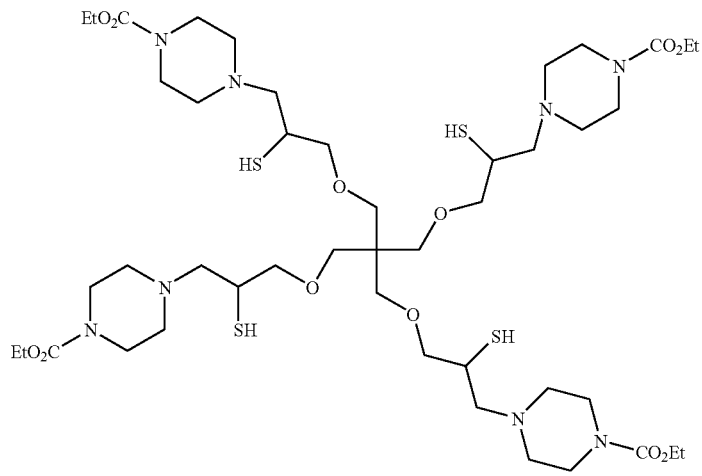

2

IR (Neat): $\lambda_{max}$ 3446, 2975, 2863, 2801, 1695, 1536, 1456, 1424, 1378, 1352, 1244, 1116, 1034, 876, 830, 758 cm$^{-1}$; and MALDI-TOF: $C_{45}H_{84}N_8O_{16}$ Calc. 993; found 1017 [M+Na]$^+$ amu.

B. Deprotection of the Carbamate-Protected Piperazine Surface

The mono-protected product (made by Example 10A) was taken in a 250-mL round bottom flask and dissolved in 85 mL of MeOH under mechanical stirring. KOH solution (28.2 g of KOH dissolved in 56.4 mL of water) was added to the above solution at 25° C. The flask was arranged with a refluxing condenser and kept in a pre-heated oil bath at 85-90° C. Progress of the reaction was monitored by TLC. After 2 hours, TLC indicated three spots and heating was continued overnight. The product showed a pink spot upon exposure to ninhydrin solution at $R_f$=0.17 (50% NH$_4$OH in MeOH). Solvent and water were removed on a rotary evaporator under reduced pressure, giving a viscous liquid. This liquid was transferred into a separation funnel and extracted with DCM (3×50 mL). The combined organic layers were dried over sodium sulfate and filtered through Celite (1 cm height). The solvent was removed on a rotary evaporator. Drying of the remaining colorless viscous liquid under high vacuum for 2 hours gave the desired dendrimer 2 as a hygroscopic solid (6.01 g, 90% yield). Its spectra are as follows:

$^1$H NMR (300 MHz, CD$_3$OD): δ 3.46 (s, 8H), 3.39 (d, J=2.10 Hz, 8H), 2.84 (t, J=4.80 Hz, 16H), 2.51 (bs, 16H), 2.41 (d, J=3.90 Hz, 8H), 2.40 (s, 4H, NH), 2.37 (s, 4H, OH), 3.89 (sextet, J=4.80 Hz, 4H); and $^{13}$C NMR (75 MHz, CD$_3$OD): δ 45.06, 45.80, 54.33, 62.07, 67.37, 70.14, 74.41; and IR (Neat): $\lambda_{max}$ 3456, 2936, 2817, 1595, 1457, 1319, 1111, 1005, 859, 732, 697 cm$^{-1}$; and MALDI-TOF: $C_{33}H_{68}N_8O_8$ Calc. 704; found 727 [M+Na]$^+$, 743 [M+K]$^+$ amu.

The following Scheme 11 illustrates the above reactions:

Scheme 11

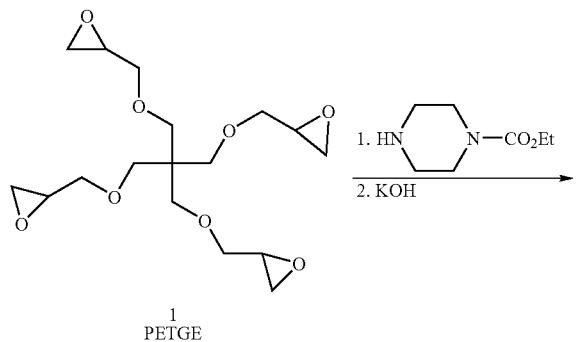

1
PETGE

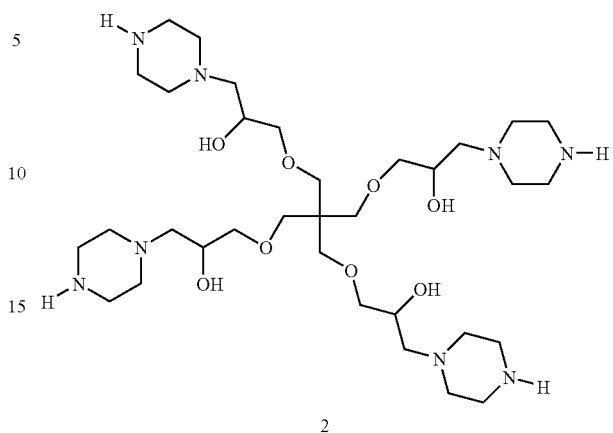

2

EXAMPLE 11

Aminoethyl Piperazine Protection Using Epoxide Ring-Opening Protecting Aminoethyl Piperazine Using to Cap the Tetrafunctional Epoxide: One Primary Amine

[(C)=PETGE; (IF1)=OH; (EX1)=AEP; (TF)=Primary NH$_2$; G=0.5]

In a 250-mL round bottom flask equipped with a Dean-Stark trap and condenser, a mixture of AEP (8.08 g, 0.0625 mol) (Acros) in 4-methyl-2-pentanone (Aldrich) was heated to reflux under an argon atmosphere. After the theoretical amount of water (1.12 mL) water was distilled out as an azeotrope, the reaction was cooled to RT. The reaction mixture (4 mL) was put into a 25-mL round bottom flask and PETGE (1.5 equiv. secondary amine per epoxide) (made by Example B) in 4 mL of MeOH was added. The mixture was heated to 60° C. overnight, followed by solvent removal under vacuum. The residue was treated with 20 mL of 2-propanol and 3 mL of water. Then the mixture was heated to 50° C. for 2.5 hours, followed by solvent removal to give the product as a yellow oil. Its spectra are as follows:

MALDI-TOF: found 877.759 (M$^+$H), 899.752 (M$^+$Na), 748.621 (tri-substitute product) amu.

The following Scheme 12 illustrates the above reaction:

Scheme 12

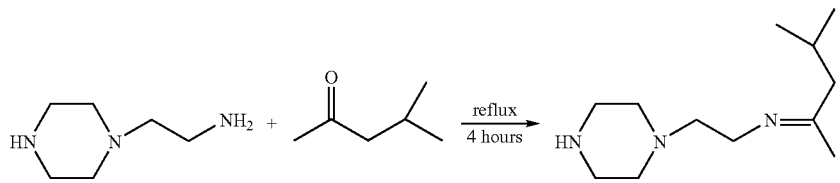

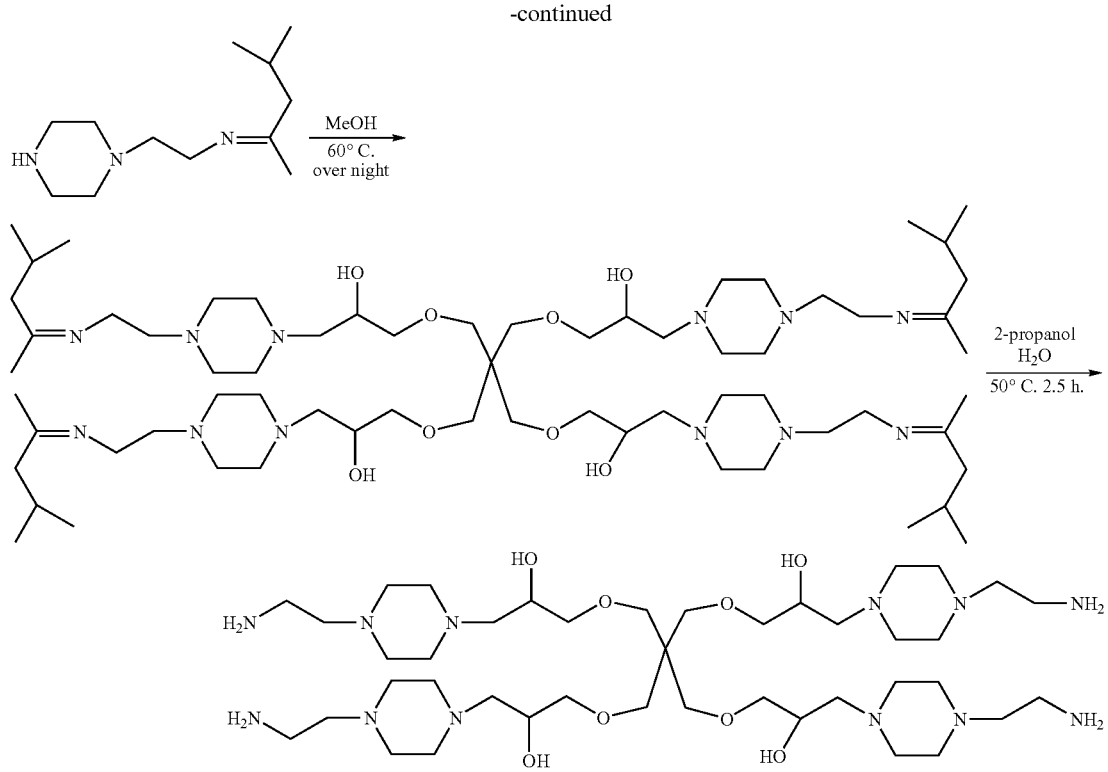

EXAMPLE 12

Reaction of Tetraepoxide with Aziridine: Reaction of Secondary Amine

[(C)=PETGE; (IF)=OH; (TF)=Aziridine; G=0.5]

To a solution of 2-methylaziridine (913 mg, 16 mmol) (Aldrich) in 2 mL of MeOH was added a solution of PETGE (360 mg, 1.0 mmol) (made by Example B) in 1 mL of MeOH. The mixture was stirred at RT overnight. Then the solvent was removed to give the product, a clear colorless oil (550 mg, 93% yield).

MALDI-TOF: Calc. 588; found 589.430(M$^+$H), 611.422 (M$^+$Na) amu.

The following Scheme 13 illustrates the above reaction:

Scheme 13

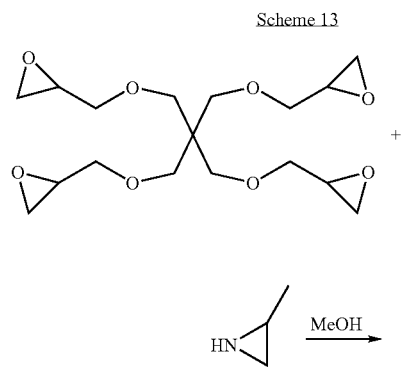

-continued

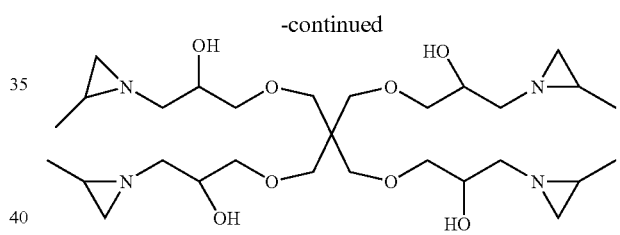

EXAMPLE 13

Preparation of PEHAM Dendrimer, Di(2-amidoethylpiperazine)-4',4-dithiobutyramide (DMDTB) Core, $N_c=2$, $N_b=3$, G=0.5, Piperazine Surface

[(C)=DMDTB; (EX1)=AEP; (IF1)=OH; (BR1)=PETGE; (EX2)=EPC; (TF)=Carboxylate; G=0.5]

A. To a 25-mL round bottom flask containing a stir bar was added AEP (1.0 g, 7.75 mmol, 2 equiv. per ester) and 5 g of MeOH. To this homogeneous mixture was added DMDTB (500 mg, 1.88 mmol, 3.76 mmol ester). A TLC (10% NH$_4$OH in MeOH) of this mixture, after 24 hours at 25° C., indicated considerable diester remaining and some product formed. Heating this mixture at 65° C. for 16 hours indicated the complete conversion of diester to one spot by TLC. This mixture was concentrated and chromatographed by silica gel using 30% NH$_4$OH in MeOH. The collected fractions containing the product were stripped of volatiles to give the desired di(2-amidoethylpiperazine)-4,4'-dithiobutyramide (840 mg; 97% yield); and it spectra are as follows:

$^1$H NMR (500 MHz, CDCl$_3$): δ 2.04 (t, J=7 Hz, 4H), 2.32 (t, J=7 Hz, 4H), 2.38-2.52 (m, 16H), 2.74 (t, J=7 Hz, 4H), 2.89 (t, J=7 Hz, 4H), 3.34 (dt, J=7 Hz, 4H); and $^{13}$C NMR (125 MHz, CDCl$_3$): δ 24.79, 34.60, 35.81, 37.98, 45.97, 54.20, 57.22, 172.06; and MALDI-TOF: Calc. 461; found 460 amu.

The following Scheme 14 illustrates the above reaction:

Scheme 14

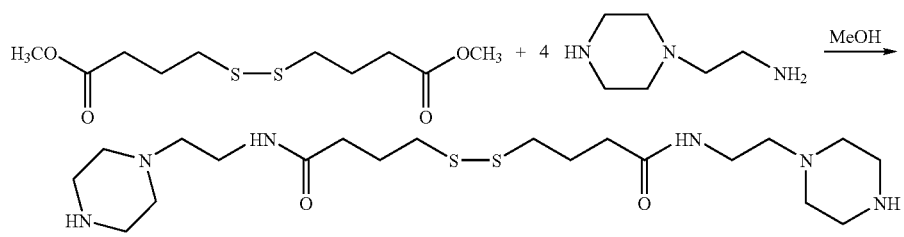

B. To a 25-mL round bottom flask containing a stir bar was added PETGE (660 mg, 1.83 mmol, 3 equiv. per NH) and 2 g of MeOH. To this homogeneous mixture was added dropwise over 5 mins. a mixture of di(2-amidoethylpiperazine)-4,4'-dithiobutyramide (140 mg, 0.3 mmol) (made by Example 13A) in 2 g of MeOH. This mixture was stirred for 24 hours at 25° C. sealed under a $N_2$ atmosphere. This mixture was added dropwise to a mixture of EPC (1.8 g, 11.4 mmol, 1.6 equiv. per epoxide) in a 25-mL round bottom flask containing a stir bar. This resulting mixture was stirred for 24 hours at RT sealed under a $N_2$ atmosphere. This mixture was concentrated on a rotary evaporator to give 3 g of crude material. An aliquot of this mixture (900 mg) was dissolved in MeOH to give a 50% w/w solution and added to a Sephadex™ LH-20 column in MeOH with a void volume of 525 mL. After the void volume was taken, 37 fractions of 4 mL each were collected. A TLC (30% $NH_4OH$ in MeOH) of each fraction indicated the pure product was contained in fractions 2-10. These fractions were collected and stripped by a rotary evaporator followed by high vacuum to give the desired product (172 mg; 98% yield); and its spectra are as follows:

$^{13}C$ NMR (125 MHz, $CDCl_3$): δ 14.66, 24.77, 34.57, 36.01, 38.00, 43.63, 45.59, 52.90, 53.18, 56.61, 60.81, 60.81, 61.34, 66.36, 66.46, 70.56, 74.12, 74.26, 155.42, 172.06; and MALDI-TOF: Calc. 2130; found 1065 (from cleavage of disulfide bond).

The following Scheme 15 illustrates the above reaction:

Scheme 15

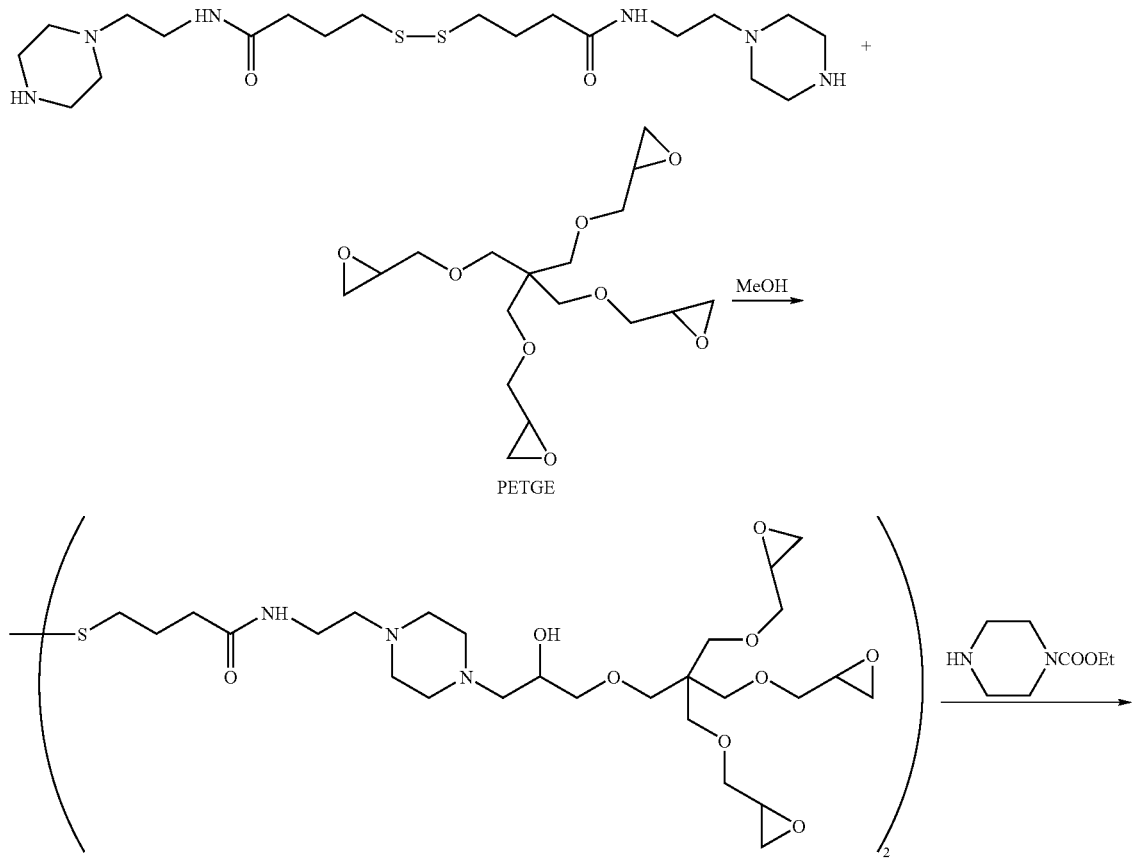

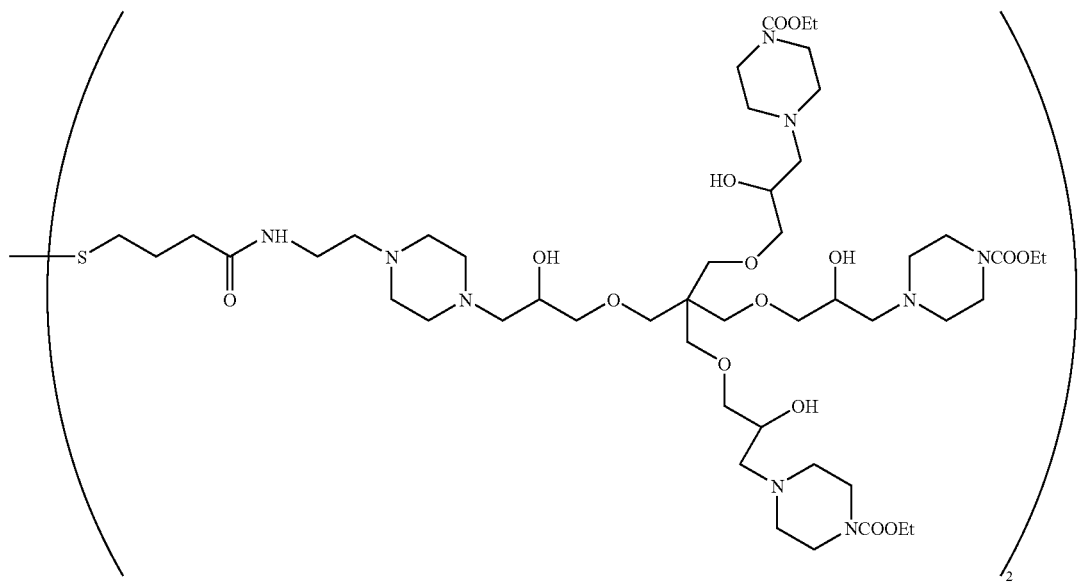

EXAMPLE 14

Acetylation of Pentaerythritol tetra(2-hydroxy-3-piperazine-N-ethyl carboxylate)

[(C)=PETGE; (IF1)=Acetyl; (EX1)=EPC; (TF)=Carboxylate; G=0.5]

To a 10-mL round bottom flask containing a stir bar was added pentaerythritol tetra(2-hydroxy-3-piperazine-N-ethyl carboxylate) (800 mg, 0.81 mmol, 3.2 mmol OH) (made by Example 10A), dimethylaminopyridine (23 mg, 0.19 mmol, 3 mole % based on anhydride) (Acros) and 6 mL of DCM. To this homogeneous mixture, cooled to 4° C., was added dropwise over 2-3 mins. acetic anhydride (550 mg, 5.4 mmol, 1.7 equiv. per OH). This mixture was stirred for 16 hours at 25° C. sealed under $N_2$ atmosphere. This mixture was diluted with 20 mL of methylene chloride and washed with saturated $NaHCO_3$ (2×3 mL). The organic layer was dried over $Na_2SO_4$, filtered and stripped of volatiles to give the desired product (930 mg; 99% yield); and $^1H$ NMR (500 MHz, $CDCl_3$): δ 1.25 (t, J=7 Hz, 12H), 2.06 (s, 9H), 2.38-2.43 (m, 8H), 2.5-2.7 (m, 16H), 3.5-4.0 (m, 8H), 4.1-4.5 (m, 16H), 3.5-3.7 (m, 8H), 4.127 (qt, J=7 Hz, 8H), 5.12 (pt, J=6.5 Hz, 4H); and $^{13}C$ NMR (125 MHz, $CDCl_3$): δ 14.67, 21.23, 39.01, 43.74, 45.77, 53.34, 58.52, 61.29, 70.04, 71.41, 155.45, 170.25; and MALDI-TOF: $C_{53}H_{92}N_8O_{20}$ Calc. 1160; found 1160 amu.

The following Scheme 16 illustrates the above reaction:

Scheme 16

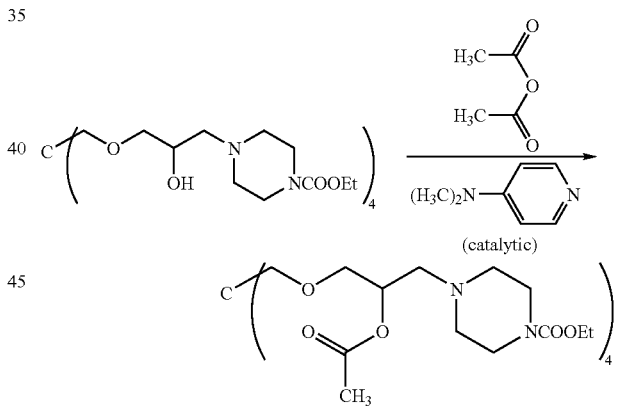

EXAMPLE 15

Reaction of PETGE with Piperazine Surface with Acryloxymethyl-trimethylsilane (AMTS). This example discloses the production of PEHAM dendrimers having a biocompatible phosphonic surface

[(C)=PETGE; (IF1)=OH; (EX1)=PIPZ; (EX2)=Acryloxymethyl; (TF)=TMS; G=0.5]

To a 25-mL round bottom flask with a stir bar was added acryloxymethyl-trimethylsilane (1.6 g, 10.2 mmol, 1.2 equiv. per NH) and 5 g of MeOH. To this mixture at 25° C. was added PETGE dendrimer with piperazine surface (1.5 g, 2.1 mmol, 8.5 mmol NH) (made by Example 4B) in 4 g of MeOH. This mixture was stirred for 24 hours at 25° C. sealed under a blanket of a $N_2$ atmosphere. The reaction mixture was purified as a 5% solution in MeOH using a tangential flow ultra-filtration device containing 1K regenerated cellulose membranes to give 500 mL of permeate (~8 recirculations). Volatile material from the retentate were filtered through a Whitman No. 1 filter paper and the resulting filtrate condensed using a rotary evaporator followed by high vacuum to give the desired product (2.7 g; 95% yield); and its spectra are as follows:

$^{13}$C NMR (125 MHz, CDCl$_3$): δ −3.50, 33.42, 45.17, 47.38, 55.32, 56.14, 57.23, 60.71, 67.37, 70.14, 74.41, 172.61; and MALDI-TOF MS: C$_{60}$H$_{116}$N$_8$O$_{12}$Si$_4$ Calc. 1337; found 1338 [M+1]$^+$ amu.

The following Scheme 17 illustrates the above reaction:

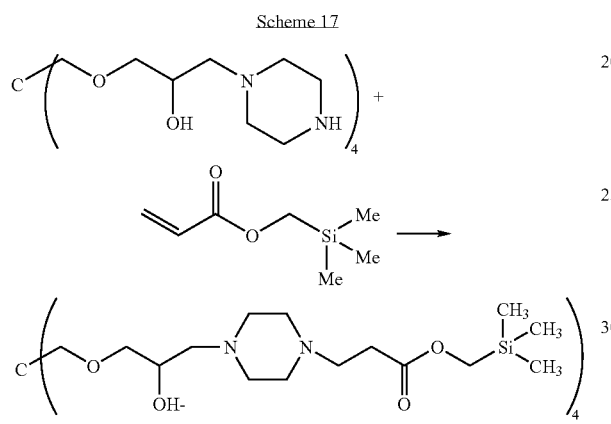

EXAMPLE 16

Reaction of PETGE with Sodium meta-Bisulfite.
This example discloses the production of PEHAM dendrimers with an antimicrobial sulfonic acid surface

[(C)=PETGE; (IF1)=OH; (TF)=Sulfonic acid; G-0.5]

To a 25-mL round bottom flask containing a stir bar was added DI water (15.0 g). This mixture was deoxygenated by bubbling N$_2$ gas through the solution for 20 mins. To this solution was added sodium meta-bisulfite, Na$_2$S$_2$O$_5$, (2.6 g, 13.7 mmol, 27.4 mmol NaHSO$_3$) and the resulting mixture made homogeneous by stirring. To this mixture was added dropwise over 2-3 mins. PETGE (1.0 g, 2.7 mmol, 11 mmol epoxide) in 1 g of MeOH. This mixture was rapidly stirred for 24 hours at 25° C. under a N$_2$ atmosphere. The volatiles of this homogeneous mixture were removed by rotary evaporation to give a white solid. This solid was further evacuated at high vacuum at 30° C. for 3 hours to give the crude product (3.8 g). The product was stirred for 30 mins. at 60° C. with 100 ml of 95% EtOH, then filtered through Whitman™ No. 1 filter paper to give a clear colorless solution. Volatile materials were removed by a rotary evaporation, followed by drying at high vacuum, to give the purified product (300.0 mg; 15% yield). Its spectra are as follows:

$^{13}$C NMR (125 MHZ, D$_2$O): δ 47.58, 48.01, 54.47, 72.58, 74.60.

The following Scheme 18 illustrates the above reaction:

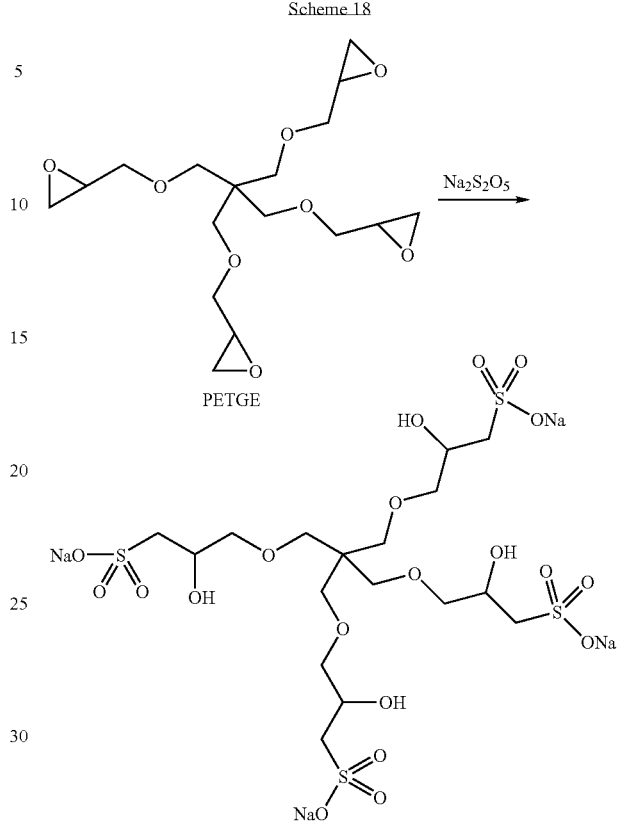

PEHAM Generation 1 and 1.5 (G=1 and G=1.5) with Various Surfaces

The PIPZ as (EX) has been found to be advantageous in encapsulation studies, and therefore, will provide encapsulation properties to low generation dendrimers as demonstrated in later examples. A variety of (BR) and (EX) are illustrated by these examples and various dendrons (FF) moieties.

EXAMPLE 17

Ring-Opening Using Ethylenediamine, Difunctional Primary Amine: 3 Epoxides

[(C)=EDA; (IF1)=OH; (FF)=H; (BR1)=TMPTGE; (TF)= Epoxide; G=1]

To a stirred solution of TMPTGE (1.81 g; 6 mmol) in 12 mL of MeOH was added EDA (0.06 g; 1 mmol) in 3 mL of MeOH dropwise over 15 min. Stirring was continued at RT for 24 hours and MALDI-TOF mass spectrometry showed dendrimer III-a together with trace amounts of dendrimer IV-a. Stirring was continued for a total of 3 days. The solvent was evaporated on a rotary evaporator under reduced pressure to give a colorless transparent liquid, which was dried under high vacuum. The entire reaction mixture was dissolved in 15 mL of ethyl acetate, then 40 mL of hexane was added dropwise with occasional shaking. During this time, precipitate formation was observed. The flask was kept at RT for 2 hours, the solution separated by decantation, and the precipitate washed with hexanes to give a light yellow solid (0.716 g; the % yield could not be calculated due to the unknown ratio of III-a and IV-a). The spectra for III-a are as follows:

$^{13}$C NMR (75 MHz, CDCl$_3$): δ 7.92, 14.36, 22.87, 23.07, 31.80, 43.60, 44.32, 51.22, 71.81, 72.19, 73.87; and MALDI-TOF: C$_{30}$H$_{56}$N$_2$O$_{12}$ Calc. 642; found 666 (M$^+$Na) amu.

The following Scheme 19 illustrates this reaction:

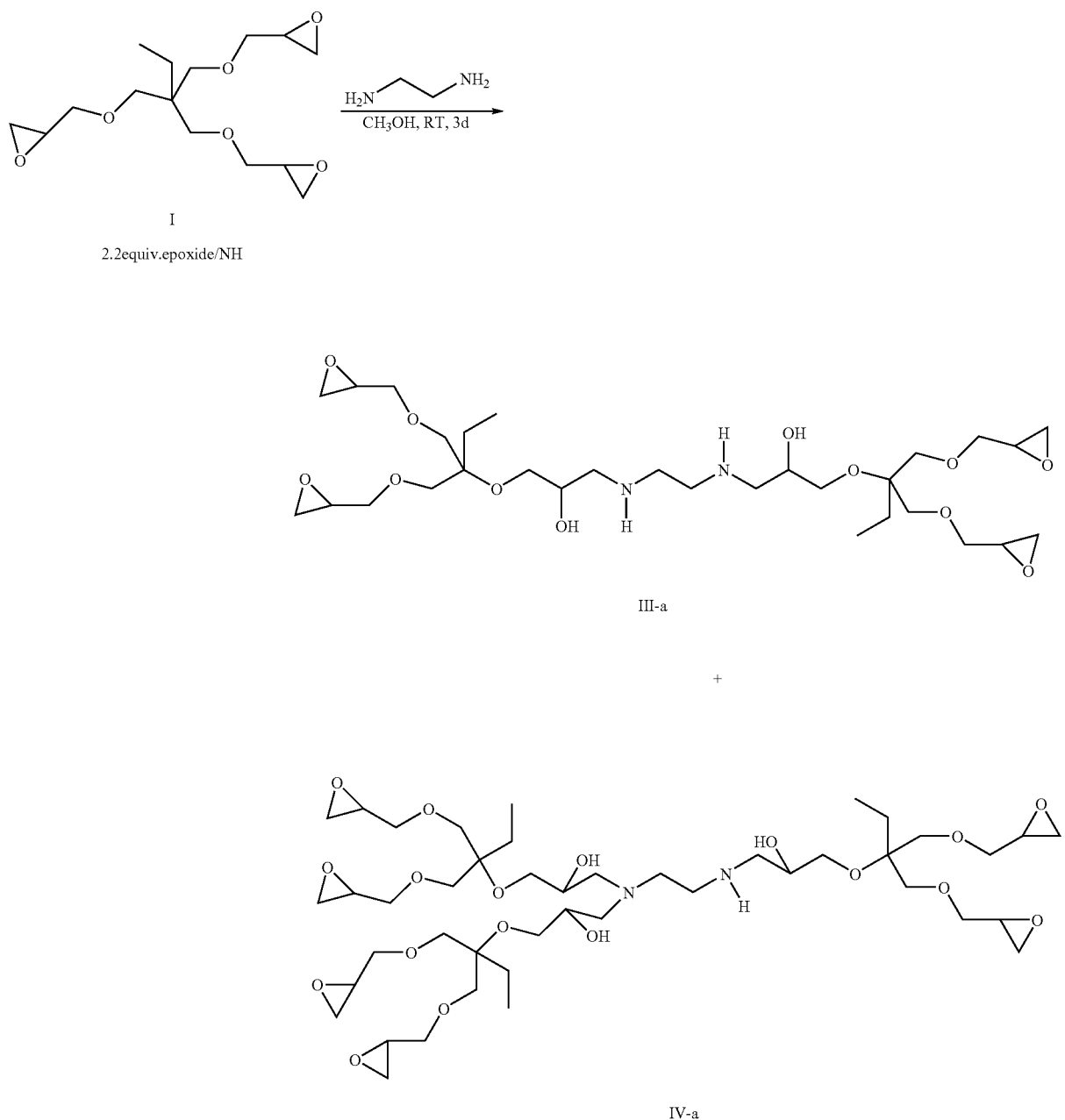

EXAMPLE 18

Reaction of TMPTGE with Amino bis(methylphosphonic acid) (IMPA)

This example discloses the production of PEHAM dendrimers with biocompatible phosphonic surface.

[(C)=TMPTGE; (FF)=Et; (IF1)=OH; (BR1)=IMPA; (TF)= $PO_2Na$; G=1.5]

To a 25-mL round bottom flask containing a stir bar was added IMPA (1.0 g, 4.9 mmol, 2 equiv. per epoxide) (Aldrich) and 15 mL of DI water. To this heterogeneous mixture was added ~10% aqueous NaOH to adjust the solution to pH 8 as determined by a pH meter. To this homogeneous mixture at 25° C. was added neat TMPTGE (250 mg, 0.83 mmol, 2.5 mmol epoxide). This mixture was stirred for 3 days at 25° C. sealed under a blanket of a $N_2$ atmosphere, then dialyzed in DI water using a 1K dialysis membrane as a ~5% solution with four changes of dialyzate at 13, 16, 19 and 22 hours. The volatiles of the retentate were removed by rotary evaporator followed by high vacuum to give the desired product (290 mg; 33% yield); and its spectra are as follows:

$^{13}C$ NMR (125 MHz, $D_2O$) δ 9.63, 25.05, 45.91, 47.76, 50.22, 51.24, 54.56, 56.97, 57.96, 61.27, 67.25, 74.27, 74.68, 75.95.

The following Scheme 20 illustrates the above reaction:

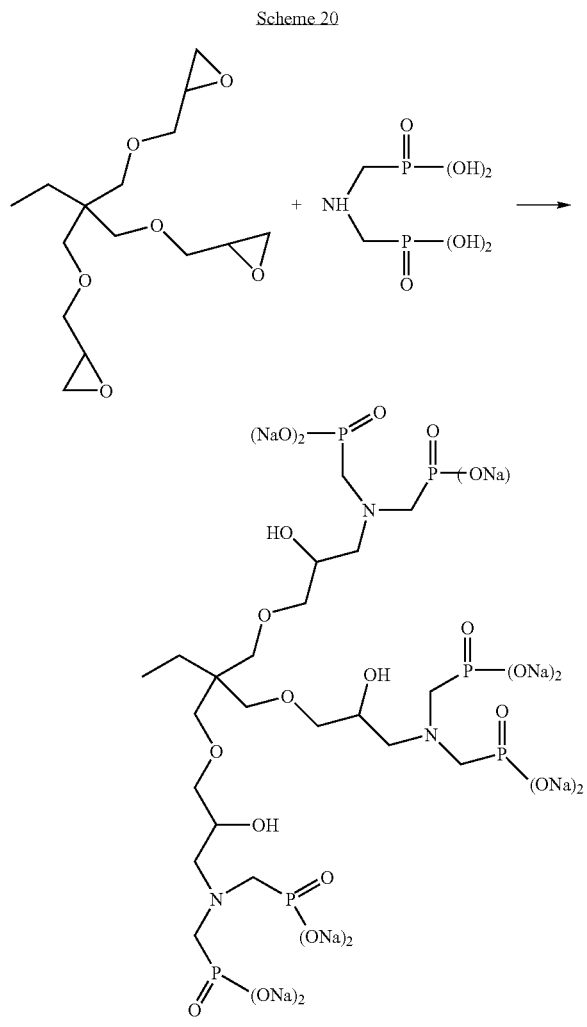

The following Scheme 21 illustrates the above reaction:

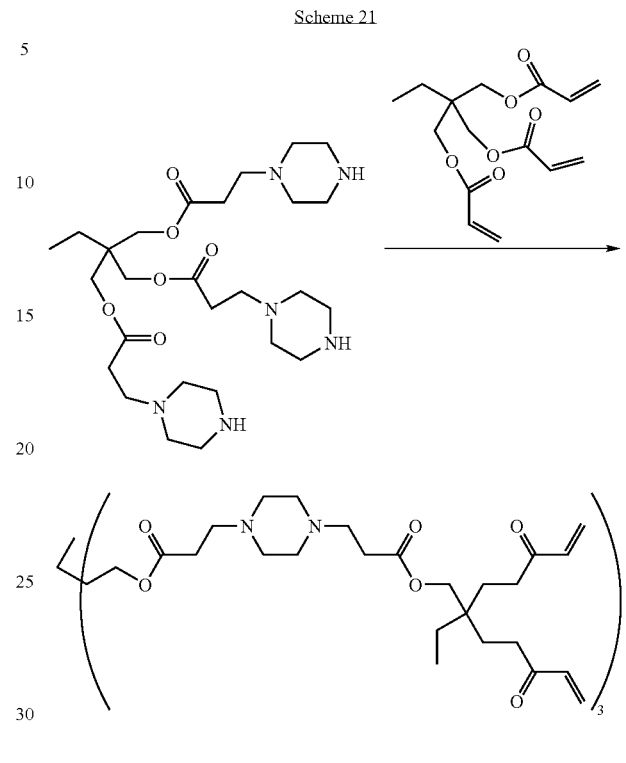

EXAMPLE 19

Addition of Acrylate Branch Cell Reagent to the Trifunctional Piperazine Core from Example 1: Poly(esteramine) TMPTA Core

[(C)=TMPTA; (FF)=Et; (EX1)=PIPZ; (BR1)=TMPTA; (TF)=Acrylate; G=1]

To a 25-mL round bottom flask containing a stir bar was added 6.4 g of TMPTA (21.7 mmol, 2 equiv. per NH) (Aldrich) and 5 g of MeOH. To this mixture, cooled to 4° C., was added 2.0 g of piperazinyl surface TMPTA (3.6 mmol, 10.8 mmol NH) (made by Example 1) in 2 g of MeOH over about 5 mins. This mixture was stirred at 25° C. for 20 hours in the dark. The mixture was extracted with hexanes (3×30 mL) and the resulting MeOH layer was stripped of volatiles on a rotary evaporator. Evacuation with high vacuum for 30 mins. gave 4.9 g of product. Its spectra are as follows:

(TF) for the product has six acrylates on the surface; and
$^{13}$C NMR (125 MHz, CDCl$_3$) δ 7.42, 7.47, 23.11, 23.25, 32.27, 32.32, 40.92, 50.59, 52.76, 53.44, 64.14, 127.97, 128.01, 131.31, 165.79, 165.80, 171.96, 172.04 and
MALDI-TOF: Calc. 1442; found 1443 amu.

EXAMPLE 20

Capping of the Poly(esteramine) Core Possessing an Acrylate Surface from Example 19 with Piperazine to Give Poly(esteramine) Dendrimer, G=1

[(C)=TMPTA; (FF)=Et; (EX1)=PIPZ; (BR1)=TMPTA; (EX2)=PIPZ; (TF)=Secondary NH; G=1.5]

To a 250-mL round bottom flask containing a stir bar was added PIPZ (8.8 g, 102 mmol, 5 equiv. per acrylate) (Aldrich) and 38 g of MeOH. To this mixture, cooled to 4° C., was added poly(esteramine) core possessing an acrylate surface (4.9 g, 3.4 mmol, 21 mmol acrylate) (made by Example 19) in 10 g of MeOH. This mixture was stirred for one hour at 4° C. and then one hour at 25° C. The volatiles of this mixture were removed by a rotary evaporator. This resulting crude mixture was bulb-to-bulb distilled to remove PIPZ at high vacuum to give the crude desired material (5.5 g). A gram of this material was dialyzed with a 1K regenerated cellulose membrane in MeOH with four changes of dialyzate to give, upon evacuation of volatiles, the purified product (400 mg). A PAGE of this material indicated a tight band corresponding to a G=1; tris-hydroxyl surfaced PAMAM dendrimer; and its spectra are as follows:

$^1$H NMR (500 MHz, CDCl$_3$): δ 0.89 (bt, 12H), 1.47 (bqt, 8H), 2.3-2.6 (bm, 72H), 2.65 (t, J=7 Hz, 24H), 2.86 (t, J=7 Hz, 24H), 4.04 (s, 24H); and $^{13}$C NMR (125 MHz, CDCl$_3$): δ 7.41, 7.42, 22.54, 22.78, 32.25, 32.33, 40.85, 40.91, 45.92, 52.65, 52.82, 53.45, 54.09, 54.14, 54.19, 63.60, 64.16, 171.99, 172.08, 172.40, 172.50, 172.88.

The following reaction Scheme 22 shows this step of the above reaction:

Scheme 22

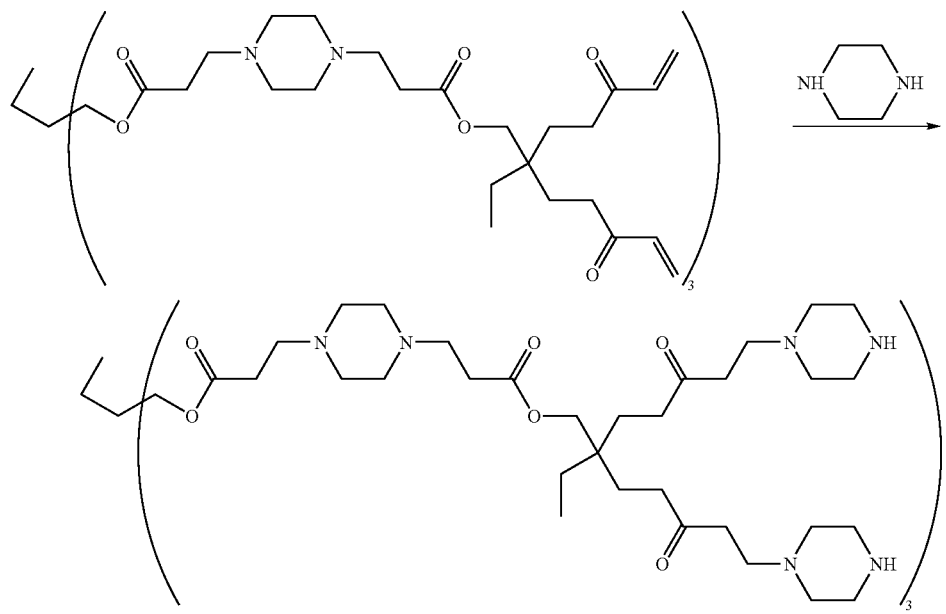

EXAMPLE 21

Addition of Trifunctional Epoxide Branch Cell TMPTGE to Trifunctional Piperazine Core to Give

[(C)=TMPTGE; (FF)=Et; (IF1)=OH; (EX1)=PIPZ; (IF2)=OH; (BR1)=TMPTGE; (TF)=OMe; G=1]

To a 100-mL round bottom flask containing a stir bar was added TMPTGE (4.4 g, 14.6 mmol, 3.9 equiv. per NH) (Aldrich) and 20 mL of MeOH. To this mixture trimethylolpropane tris(2-hydroxypropyl-3-piperazine) (700 mg, 1.25 mmol, 3.75 mmol NH) (made by Example 2) was added in 10 mL of MeOH. This mixture was heated for 3 days at 50° C. under a $N_2$ atmosphere. The volatiles were removed by a rotary evaporator and high vacuum to give the crude product (6.3 g). An aliquot of 600 mg was purified by Sephadex™ LH-20 in MeOH. Fractions 1-14 were collected and stripped of volatiles to give purified product (220 mg; 92% yield). Analysis by $^{13}C$ and $^1H$ NMR spectroscopy indicated the product was the desired product with the epoxide ring-opened with MeOH. A PAGE of this material indicated a tight band corresponding to a G=1, [EDA core], TRIS terminated PAMAM dendrimer; and its spectra are as follows:

$^1H$ NMR (500 MHz, $CDCl_3$): δ 0.84 (bs, 12H), 1.38 (bs, 8H), 2.3-2.9 (m, 12H), 3.37 (s, 18H), 3.4-3.7 (bm, 48H), 3.93 (bs, 18H); and $^{13}C$ NMR (125 MHz, $CDCl_3$): δ 8.13, 23.95, 44.62, 54.12, 59.49, 61.23, 62.28, 65.83, 68.20, 68.94, 70.49, 71.89, 72.68, 73.88, 75.15, 75.40, 80.20.

The following reaction Scheme 23 shows this step of the above reaction:

Scheme 23

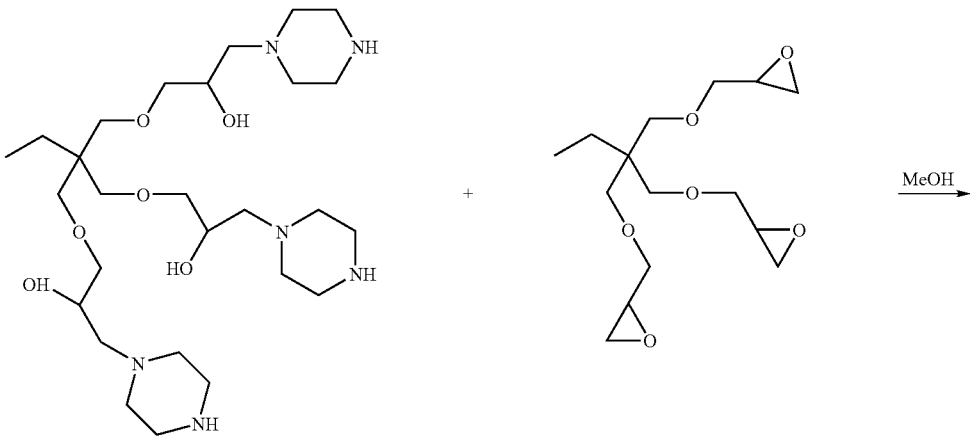

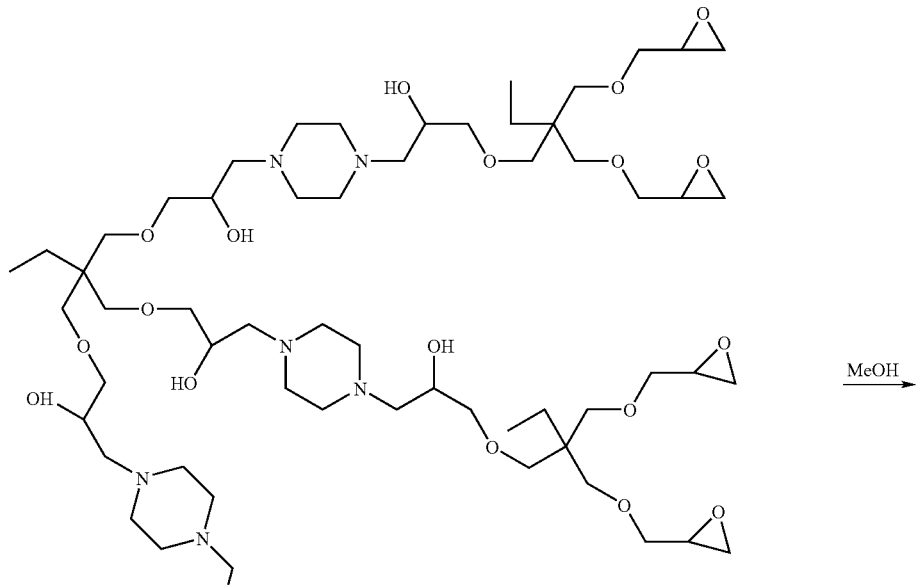
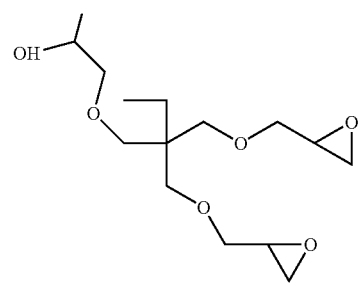
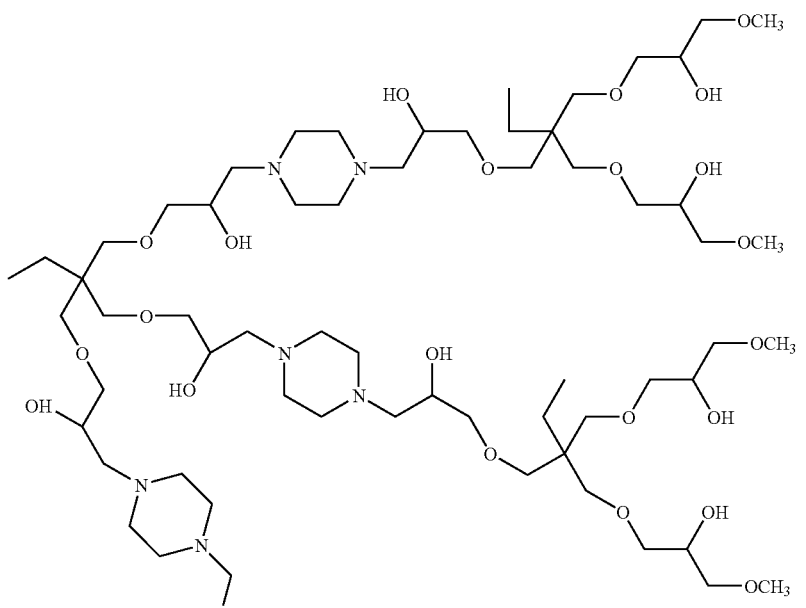

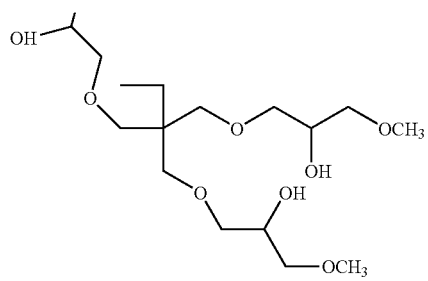

EXAMPLE 22

Addition of Trifunctional Epoxide Branch Cell Reagent to Trifunctional Piperazine Core, Followed by Capping with Piperazine

[(C)=TMPTGE; (FF)=Et; (IF1)=OH; (EX1)=PIPZ; (IF2)= OH; (BR1)=TMPTGE; (IF3)=OH; (EX2)=PIPZ; (TF)= Secondary NH; G=1.5]

To a 25-mL round bottom flask containing a stir bar was added TMPTGE (873 mg, 2.9 mmol, 3 equiv. per epoxide) and 5 g of MeOH. This mixture was made homogeneous and cooled to 4° C. To this mixture was added trimethylopropane tris(2-hydroxypropyl-3-piperazine) (180 mg, 0.32 mmol, 0.96 mmol NH) (made by Example 2) in 3 g of MeOH over 5 mins. A TLC (30% NH$_4$OH in MeOH) of the reaction mixture after one hour at 25° C. indicated a streak from the baseline to $R_f$ about 0.6 along with the excess epoxide at $R_f$=0.9. After 8 hours at 25° C., a TLC of this mixture showed no starting amine remaining (no baseline spot) and a spot at $R_f$=0.9. The reaction mixture was added over 10 mins. to PIPZ (14.5 g, 168 mmol, 20 equiv. per epoxide) in 28 g of MeOH. This mixture was stirred for 24 hours at 25° C. The volatiles were removed on a rotary evaporator to give a white solid. Excess PIPZ was removed by bulb-to-bulb distillation at high vacuum and 160° C. for 30 mins. to give a clear, colorless product (2.2 g). This product was dialyzed as a 5% w/w solution in MeOH using a 1K regenerated cellulose membrane with 3×4 L changes of MeOH over 24 hours, followed by rotary evaporation of volatile materials, to give the desired product (508 mg; 80% yield). A PAGE of this material showed a tight band corresponding to G=1, [EDA core], TRIS terminated PAMAM dendrimer; and its spectra are as follows:

$^1$H NMR (500 MHz, CD$_3$OD): δ 0.86 (t, J=7 Hz, 12H), 1.41 (q, J=7 Hz, 8H), 2.34 (m, 60H), 2.84 (m, 12H), 3.34 (bs, 12H), 3.36 (bs, 6H), 3.37 (bs, 6H), 3.89 (bs, 12H); and $^{13}$C NMR (125 MHz, CD$_3$OD): δ 8.04, 8.07, 23.91, 44.59, 46.21, 49.82, 54.61, 55.49, 62.66, 63.28, 68.49, 68.67, 72.68, 75.43.

The following Scheme 24 illustrates the above reaction:

Scheme 24

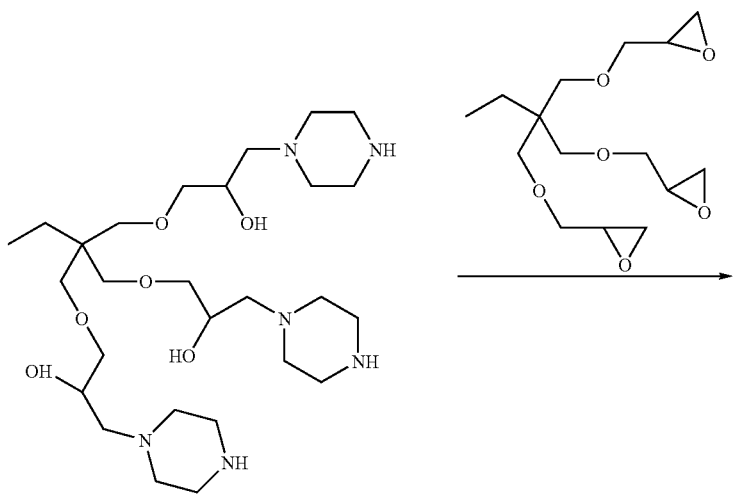

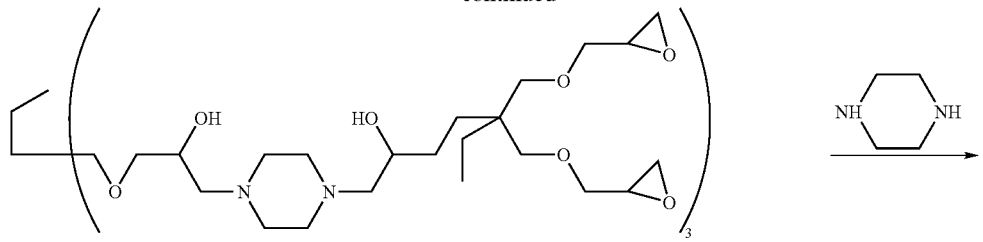

Polyetheramine dendrimer G = 1

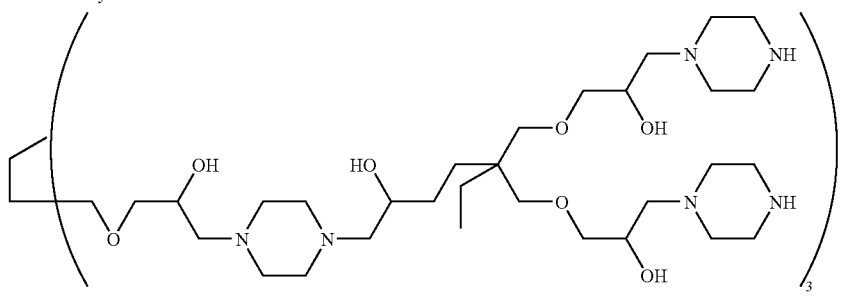

Polyetheramine dendrimer G = 1

EXAMPLE 23

PEHAM Dendrimer Synthesis Using Difunctional Reagents for In Situ Formation of Branch Cells A. Ring-Opening Using a Dihydroxyl Amino Branch Cell Reagent: Hydroxyl Terminated PEHAM Dendrimer (G=1) from Trimethylolpropane Triglycidyl Ether and Diethanolamine

[(C)=TMPTGE; (FF)=Et; (IF1)=OH; (BR1)=DEA; (TF)=OH; G=1]

DEA II (7.82 g, 74.47 mmol) (Aldrich) and 120 mL of dry MeOH (Aldrich), both without further purification, were placed in an oven dried 250-mL single necked round bottom flask. The flask was equipped with stir bar and septum. TMPTGE I (5 g, 16.55 mmol) was dissolved in 40 mL of dry MeOH and added dropwise to the above stirring solution through a pressure equalizing funnel over a period of one hour at RT. The funnel was replaced with a refluxing condenser and heated at 60° C. for 60 hours under a $N_2$ atmosphere. Solvent was removed with a rotary evaporator under reduced pressure to give a colorless transparent liquid. The entire reaction mixture was transferred into a 100-mL single necked round bottom flask. Excess DEA H was separated by Kugelrohr distillation under reduced pressure at 180-190° C. The product, m, (9.76 g; 95.53% yield) was recovered as a transparent viscous liquid. Its spectra are as follows:

$^1$H NMR: (300 MHz, $CD_3OD$): δ 0.87 (t, J=7.50 Hz, 3H, $CH_3$), 1.43 (q, $CH_2$, J=7.20 Hz, 2H), 2.52-2.79 (m, 18H), 3.32 (s, 3H, 3×OH), 3.50 (s, 6H), 3.40 (d, J=5.10 Hz, 6H), 3.54-3.67 (m, 12H), 3.93 (sextet, J=5.10 Hz, 3H), 4.85 (s, 6H, 6×OH); and $^{13}$C NMR: (75 MHz, $CD_3OD$): 36.93, 22.76, 43.43, 57.42, 58.51, 59.47, 68.32, 71.56, 73.72; and IR (Neat): $\lambda_{max}$ 3354, 2939, 2817, 1454, 1408, 1367, 1321, 1280, 1111, 1081, 1070, 871, 778 cm$^{-1}$; and MALDI-TOF MS: $C_{27}H_{59}N_3O_{12}$ Calc. 617; found 641 ($M^+Na$) amu.

The following Scheme 25 illustrates this reaction:

Scheme 25

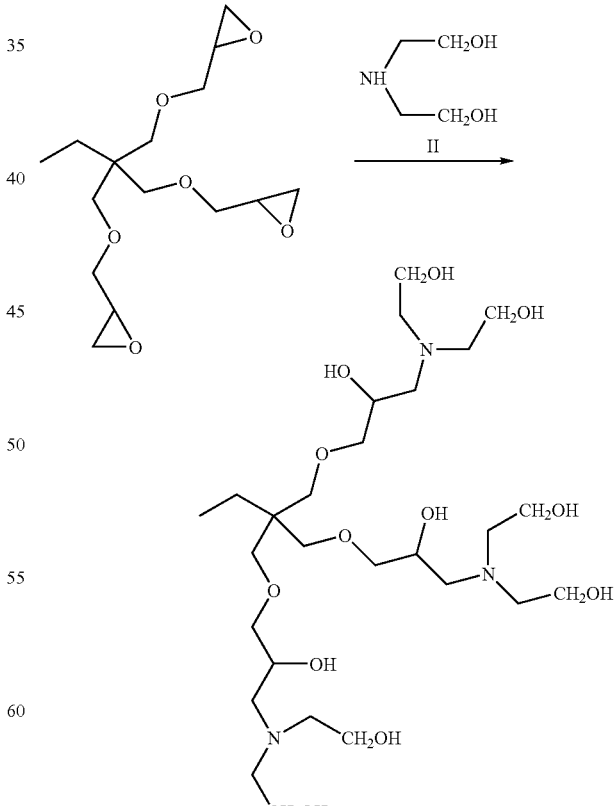

III

B. Ring-Opening Using an Diester Amino Branch Cell Reagent Precursor: Ester Terminated PEHAM Dendrimer, G=1, from Trimethylolpropane Triglycidyl Ether (TMPTGE) and Diethyl Iminodiacetate (DEIDA)

[(C)=TMPTGE; (FF)=Et; (IF1)=OH; (BR1)=DEIDA; (TF)=Ethyl ester; G=1.5]

DEIDA II (14.07 g, 74.47 mmol) (Aldrich) and 120 mL of dry MeOH were placed in an oven dried 250-mL single necked round bottom flask. The flask was equipped with a stir bar and septum. TMPTGE I (5.0 g, 16.55 mmol) (Aldrich) was dissolved in 40 mL of dry MeOH and then added to the above stirring solution through a pressure equalizing funnel dropwise over a period of one hour at RT. The funnel was replaced with refluxing condenser and the flask heated at 60° C. for 60 hours under a $N_2$ atmosphere. The solvent was removed on a rotary evaporator under reduced pressure, which gave a colorless transparent liquid. The entire reaction mixture was transferred into a 100-mL single necked round bottom flask. Excess of DEIDA H was removed by Kugelrohr distillation under reduced pressure at 150-160° C. Undistilled product II (12.59 g; 87.5% yield) was recovered as a pale yellow color, viscous liquid. Compound III is stored in ethyl alcohol at 0° C. Its spectra are as follows:

$^1$H NMR: (300 MHz, $CD_3OD$): δ 4.65 (sextet, J=4.20 Hz, 3H), 4.16 (m, 12H), 3.59 (s, 12H), 3.36 (s, 6H), 3.30 (s, 6H), 3.05 (dd, J=3.60 Hz, 3H), 2.95 (dd, J=3.90 Hz, 2H), 2.81 (dt, J=1.80 Hz & 9.90 Hz, 3H), 2.67 (dd, J=8.40 & 8.10 Hz, 2H), 1.37 (q, J=7.50 Hz, 2H), 1.26 (t, J=7.20 Hz, 6H, 2×$CH_3$), 1.25 (J=7.20 Hz, 12H, 6×$CH_3$), 0.85 (t, J=7.50 Hz, 3H, $CH_3$); and $^{13}$C NMR: (75 MHz, $CD_3OD$): δ 6.81, 13.36, 13.40, 22.66, 43.48, 49.85, 53.62, 55.76, 56.21, 58.00, 60.55, 60.68, 68.72, 71.17, 71.33, 71.50, 73.40, 78.43, 78.48, 168.67, 170.25, 172.31; and IR (Neat): $λ_{max}$ 2980, 2934, 2904, 2868, 1741, 1460, 1408, 1378, 1342, 1250, 1198, 1111, 1065, 1024, 983, 927, 860, 784 cm$^{-1}$; and MALDI-TOF MS: $C_{39}H_{71}N_3O_{18}$ Calc. 869; found 893 (M$^+$Na) and 847, 801, 779, 775 amu. (The mass spectrum shows a typical fragmentation pattern for elimination of $OC_2H_5$ group.)

The following Scheme 26 illustrates this reaction:

Scheme 26

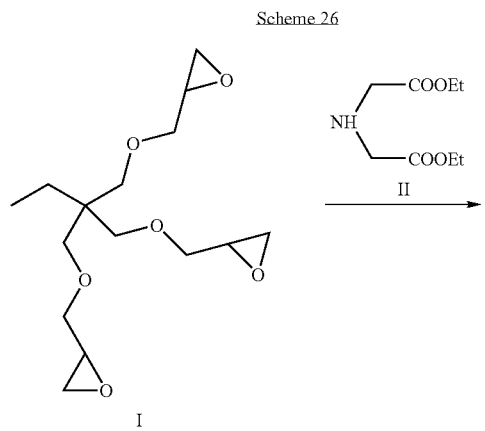

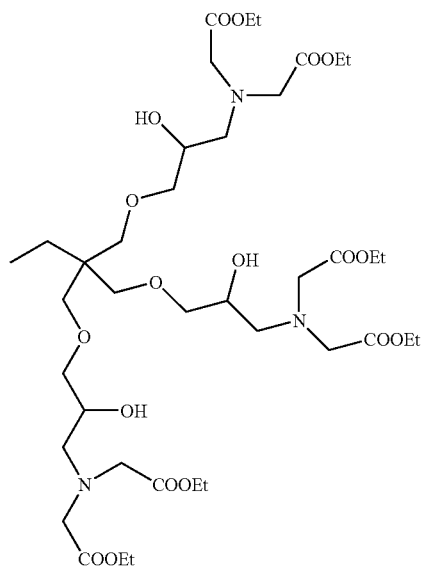

III

C. Amidation of an Ester Terminated PEHAM Dendrimer; G=1 with EDA to give a G=1 Hexamine Dendrimer

[(C)=TMPTGE; (FF)=Et; (IF1)=OH; (BR1)=DEIDA; (EX1)=EDA; (TF)=Primary $NH_2$; G=1]

EDA (180 mL, 77% in MeOH, 200 mol equiv. per ester) was added to a 500-mL single necked round bottom flask. The flask was flushed with $N_2$ gas, equipped with a stir bar, pressure equalizing funnel and cooled to 0° C. with ice bath. Hexaethylester terminated dendrimer III-g (0.869 g, 1 mmol in 10 mL of MeOH) (made by Example 23B) was added over a period of 20 mins. The pressure equalizing was removed from the round bottom flask and was closed with a septum followed by storing at 4° C. for 40 hours. The flask was allowed to warm to RT and excess EDA and MeOH were removed on a rotary evaporator to give a colorless, transparent liquid, hexamino terminated (G=1)dendrimer V, which was further dried under high vacuum. Residual EDA was separated by azeotropic distillation using methanol and toluene, which gave the desired product (0.95 g; >99% yield). The spectra for dendrimer V are:

$^1$H NMR (300 MHz, $CD_3OD$): δ 0.8-0.9 (t, J=5.40, 3H), 1.30-1.42 (q, J=6.6, 2H), 1.94 (s, 3H, 30H), 2.64-2.80 (m, 24H), 3.26-3.40 (m, 30H), 3.82 (m, 3H); and $^{13}$C NMR (75 MHz, $CD_3OD$): δ 6.70, 6.95, 21.42, 40.77, 40.81, 41.70, 41.94, 43.41, 43.71, 59.41, 59.59, 68.05, 71.58, 73.79, 172.86; and IR (Neat): $ν_{max}$ 3290, 3068, 2930, 2863, 1659, 1542, 1437, 1360, 1292, 1110, 919, 603 cm$^{-1}$.

MALDI-TOF MS: $C_{39}H_{83}N_{15}O_{12}$ Calc. 954; found 977 (M$^+$Na) amu.

The following Scheme 27 illustrates this reaction:

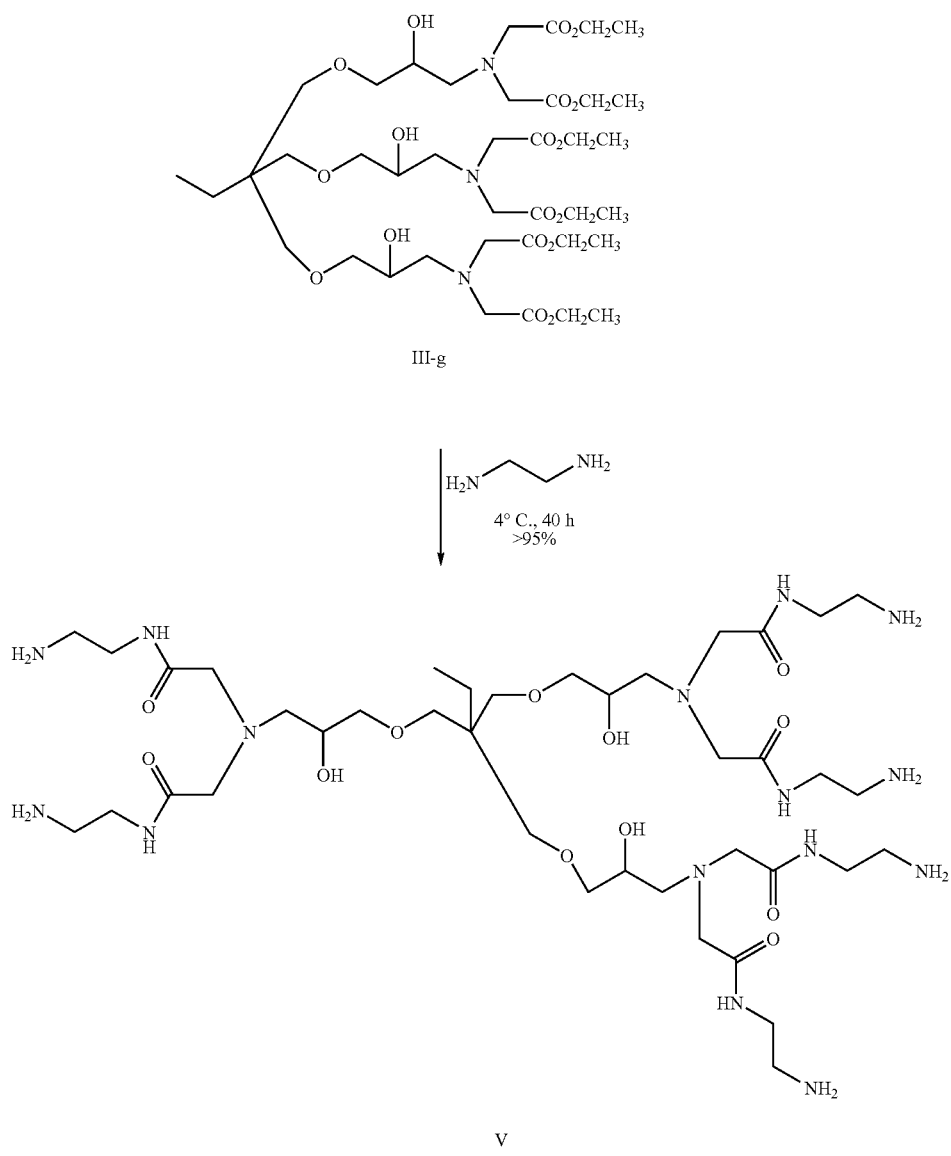

EXAMPLE 24

Ring-Opening Using a Preformed Tris(hydroxymethylamine) (TRIS) Branch Cell Reagent Nona-Hydroxyl Surface Dendrimer, G=1, from TMPTGE and TRIS

[(C)=TMPTGE; (FF)=Et; (IF1)=OH; (BR1)=TRIS; (TF)=OH; G=1]

TMPTGE I (2.66 g, 8.8 mmol) and 50 mL of MeOH were placed in an oven dried 100-mL round bottom flask. The flask was equipped with a stir bar and stopper. TRIS II (4.79 g, 39.6 mmol) (Fisher Scientific) was added to the above stirring reaction mixture in one portion at RT. The flask was arranged with a refluxing condenser and heated at 60° C. for 60 hours under a $N_2$ atmosphere. TRIS dissolves completely after heating for about 15 min. The reaction mixture was cooled to RT and transferred into a 500-mL Erlenmeyer flask. Then first 120 mL of chloroform was added, followed by slow addition of 300 mL of hexanes under constant stirring using a spatula. Formation of a white precipitate was observed during the hexanes addition. The mixture was mixed thoroughly once again and allowed to stand at RT overnight. The precipitate was observed as solid flakes on the walls and bottom of the flask. The solution was mixed gently to separate the solid from the glass, followed by filtration of the mixture through a Büchner funnel, giving the desired product (1.7 g). On the bottom of the flask a colorless paste remained, even after separating the solid. This paste weighed 5.2 g ($^1$H and $^{13}$C NMR showed signals for dendrimer III along with trace amounts of TRIS). The paste was dissolved in 5 mL of MeOH, followed by rinsing the flask with MeOH (2×2 mL). The methanol solution was loaded onto a Sephadex™ LH-20 column. After eluting 600 mL of MeOH, fractions were collected in 15 mL aliquots. The desired dendrimer was found in fractions 18-47; whereas, TRIS was found in fractions 48-58. Fractions 1847 were combined and the solvent was evaporated on a rotary evaporator under reduced pressure to give a hygroscopic solid (4.2 g; 71.82%), (G=1) PEHAM dendrimer III. Evaporation of solvents from 48-58 gave TRIS II (0.592 g) as a colorless solid. Its spectra are as follows:

$^1$H NMR: (300 MHz, CD$_3$OD): δ 0.86 (t, J=7.20 Hz, 3H), 1.42 (q, J=6.90 Hz, 2H), 2.64 (dd, J=7.80 & 8.10 Hz, 3H), 2.78 (dd, J=3.60 & 3.60 Hz, 3H), 3.34 (s, 6H), 3.35 (s, 6H), 3.41 (d, 5.10 Hz, 6H), 3.48 (s, 1H, OH), 3.50 (s, 1H, OH), 3.53 (d, J=3.00 Hz, 12H), 3.58 (s, 1H, OH), 3.67 (bt, J=3.00 Hz 3H, 3×NH), 3.79 (sextet, J=3.60 Hz, 3H), 4.81 (s, 9H, 9×OH); and $^{13}$CNMR: (75 MHz, CD$_3$OD): δ6.91, 22.72, 43.41, 44.34, 59.83, 61.49, 70.07, 71.57, 74.27; and IR (Neat): ν$_{max}$ 3354, 2919, 2873, 1460, 1424, 1408, 1367, 1296, 1234, 1106, 1029, 866, 773 cm$^{-1}$; and MALDI-TOF MS: C$_{27}$H$_{59}$N$_3$O$_{15}$ Calc. 665; found 689 (M$^+$Na) amu.

The following Scheme 28 illustrates this reaction:

Scheme 28

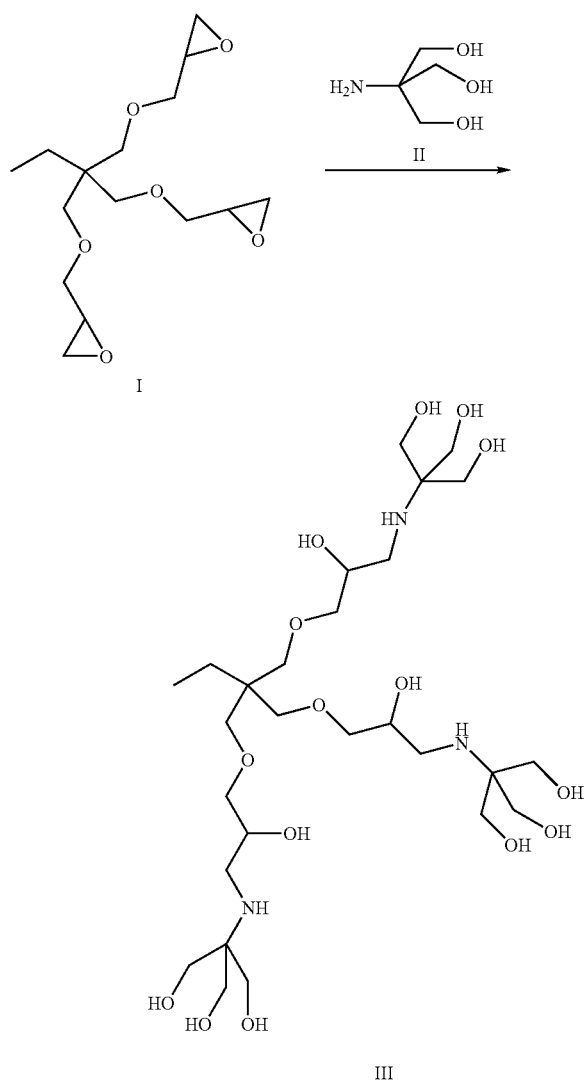

EXAMPLE 25

Addition of Tetrafunctional Epoxide Branch Cell Reagent PETGE to Tetrafunctional Piperazine Core (G=0.5) and Piperazine Capping PEHAM Dendrimer G=1.5

[(C)=PETGE; (IF1)=OH; (EX1)=PIPZ; (IF2)=OH; (BR1)= PETGE; (IF3)=OH; (EX2)=PIPZ; (TF)=2°-Amine; G=1.5]

To a 25-mL round bottom flask containing a stir bar was added PETGE (2.45 g, 6.8 mmol, 5.44 equiv. per NH) (made by Example A) in 8 mL of MeOH. To this mixture was added a solution of pentaerythritol tetra(2-hydroxypropyl-3-piperazine) (200 mg, 0.31 mmol, 1.25 mmol NH) (made by Example 3) in 3 mL of MeOH dropwise over about 5 mins. This mixture was stirred for 8.5 hours at 25° C. under a N$_2$ atmosphere. This mixture was added dropwise over about 5 mins. to a 250-mL round bottom flask containing a stir bar, PIPZ (35.0 g, 406 mmol, 15 equiv. per epoxide) and 70 mL of MeOH. The resulting mixture was stirred at 25° C. for 18 hours under a N$_2$ atmosphere. Volatile materials were removed from this mixture using a rotary evaporator to give a white solid residue. Excess PIPZ was removed from the reaction crude material using bulb-to-bulb Kugelrohr distillation at high vacuum and a pot temperature of 140° C. until the residue in the pot was a clear homogeneous film on the inside of the flask. This crude residue weighed 5.0 g.

This material was dissolved in 100 mL of MeOH, placed in a 1K regenerated cellulose membrane and dialyzed for 48 hours in a 2-L vessel with four changes of dialyzate. A TLC (30% NH$_4$OH in MeOH) indicated some lower molecular weight material present in the mixture. Volatile materials were removed from the retentate to give crude product (1.3 g, theory: 992 mg). Therefore, the material was dialyzed another 24 hours. A TLC of this material showed an almost complete removal of lower molecular weight residue. The retentate was stripped of volatiles to give purified product (900 mg). To completely remove all low molecular weight impurities, the product was further dialyzed in DI water for 24 hours, giving the pure product (360 mg. 36% yield). A TLC of the retentate showed one spot, indicating complete removal of low molecular weight residues. A TLC of the aqueous dialyzate stripped of volatiles indicated that a significant amount of product had migrated through the membrane together with low molecular weight impurities (520 mg; ~45% yield); and its spectra are as follows:

$^1$H NMR (500 MHz, CD$_3$OD): δ 2.3-2.7 (m, 21H), 2.7-2.8 (bt, 43H), 3.34 (s, H), 3.38 (s, H), 3.45 (bt, 43H), 3.89 (bm, 22H); and $^{13}$C NMR (125 MHz, CD$_3$OD): δ 46.21, 46.78, 46.92, 54.61, 55.46, 62.58, 63.19, 68.55, 68.65, 71.27, 75.54, and MALDI-TOF: Calc. 3180; found 3143 amu.

The following Scheme 29 illustrates this reaction:

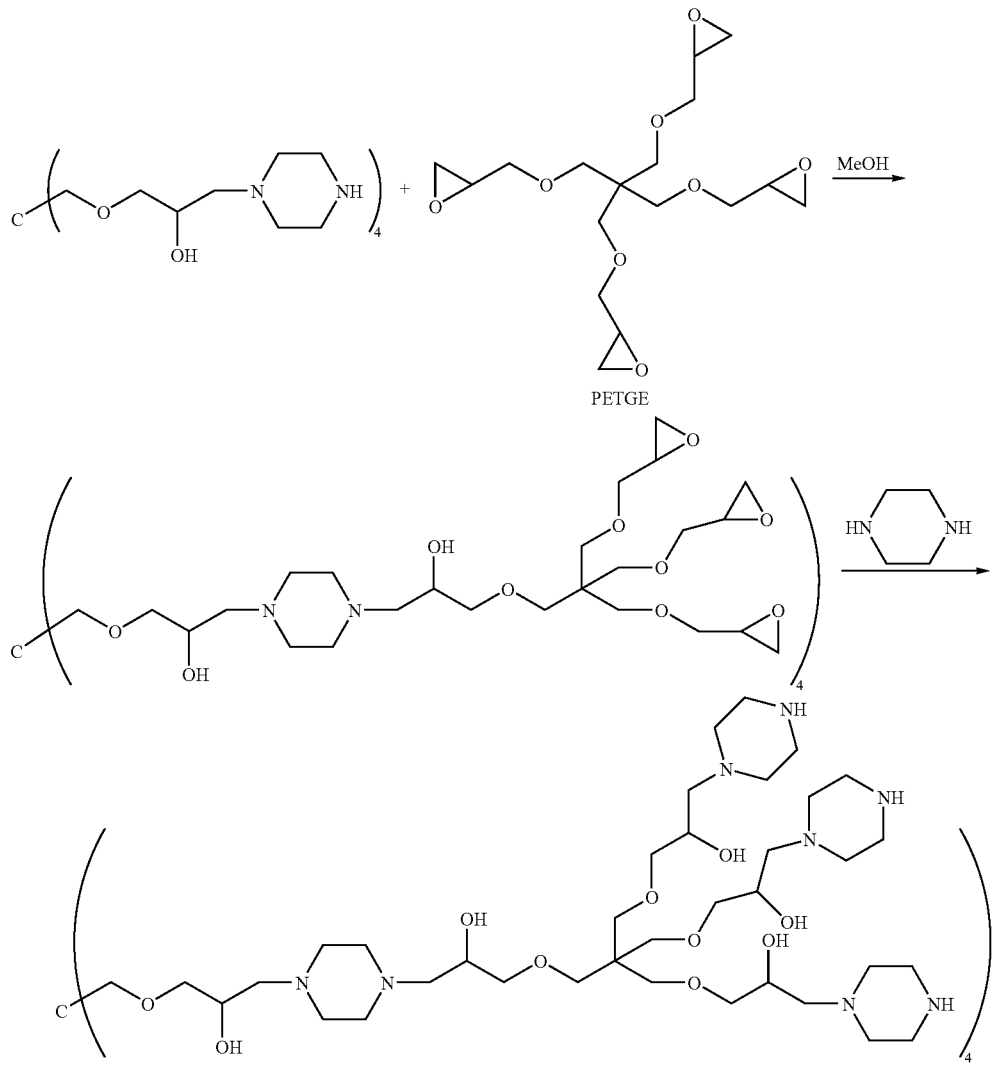

EXAMPLE 26

Addition of Tetrafunctional Epoxide Branch Cell Reagent to Piperazine

A. Functional G=0 and Mono-Protected Piperazine Capping: Poly(etherhydroxyamine) Dendrimer (G=1.5)
[(C)=PETGE; (IF1)=OH; (EX1)=PIPZ; (IF2)=OH; (BR1)= PETGE; (IF3)=OH; (EX2)=piperazine Carboxylate; (TF)=Carboxylate; G=1.5]

PETGE 1 (5.05 g, 14.04 mmol) (made by Example B) and 35 mL of MeOH were taken in a 100-mL round bottom flask and equipped with a stir bar. The flask was cooled to 4° C. with an ice-bath. Dendrimer (G=0) (1.65 g, 2.34 mmol) (made by Example 4B) was dissolved in 10 mL of MeOH and added into the above stirring solution dropwise over a period of 20 mins. through a dropping funnel. The ice-bath was removed and the reaction mixture allowed to stir at RT for 20 hours. MALDI-TOF showed signals for bis-, tri- and tetra-addition products. The reaction mixture was stirred at RT for 2 days. The above reaction mixture was then subjected to UF (1K) to remove excess PETGE while maintaining the temperature at 25° C. After six recycles (6×120 mL), TLC indicated only traces of PETGE remained with the retentate. The retentate was transferred into a 250-mL round bottom flask and quenched with EPC (1.5 equiv. per epoxide). The reaction mixture was concentrated to 50 mL on a rotary evaporator under reduced pressure with minimal heat (45° C.). The reaction mixture was stirred overnight at RT. Excess EPC was removed by UF (1K) at RT (6×120 mL). Solvent was removed from the retentate on a rotary evaporator under reduced pressure and the residue dried under high vacuum, giving a hygroscopic solid (5.2 g).

B. Deprotection of the Capped Carboethoxy Group: Hydrolysis of the Ester Surface (G=1) Dendrimer with KOH
[(C)=PETGE; (IF1)=OH; (EX1)=PIPZ; (IF2)=OH; (BR1)= PETGE; (IF3)=OH; (EX2)=PIPZ; (TF)=Secondary NH; G=1.5]

Ester surface dendrimer (5.2 g) (made by Example 26A) was taken in a 250-mL round bottom flask and dissolved in 47 mL of MeOH. The flask was equipped with a stir bar. KOH (15.6 g) was dissolved in 31 mL of water and added into the above stirring solution at RT over 5 mins. The flask was kept in a pre-heated oil bath (85-90° C.) and heated for 22 hours. TLC indicated no ester surface dendrimer (G=0) was left at this time. Excess MeOH was removed on a rotary evaporator and the aqueous phase was extracted with DCM (3×150 mL). Combined filtrates were dried over $Na_2SO_4$ and filtered through a Celite bed. Celite was thoroughly washed with DCM. The solvent was evaporated on a rotary evaporator, giving a hydroscopic solid, which was dried under high vacuum to give the PIPZ surface dendrimer 4 (1.7 g; 27% yield). In a second run, this above workup protocol was improved by acidifying the reaction mixture with 6N HCl, followed by filtration of KCl and UF through 1K, which enhanced the yield to >90%. Its spectra are as follows:

$^1$H NMR (300 MHz, $CD_3OD$): δ 2.37-2.46 (m, H), 2.51 (bs, H), 2.59 (bs, H), 2.84 (t, J=3.90 Hz, H), 3.30 (m, H), 3.35 (bs, H), 3.45 (bs, H), 3.83-3.90 (quintet, J=5.40 Hz, 20H); and $^{13}$C NMR (75 MHz, $CD_3OD$+D2O (two drops): δ 44.97, 45.79, 53.40, 54.29, 58.37, 61.43, 62.06, 67.34, 67.54, 69.20, 70.11, 72.83, 74.16, 74.43; and IR (Neat): $\lambda_{max}$ 3385, 2939, 2873, 2811, 1649, 1634, 1454, 1367, 1321, 1301, 1111, 1009, 963, 860, 830, 789 $cm^{-1}$; and MALDI-TOF: $C_{149}H_{300}N_{32}O_{40}$ Calc. 3180; found 3202.4 ($M^+Na$) amu.

The following Scheme 30 illustrates the above reactions:

Scheme 30
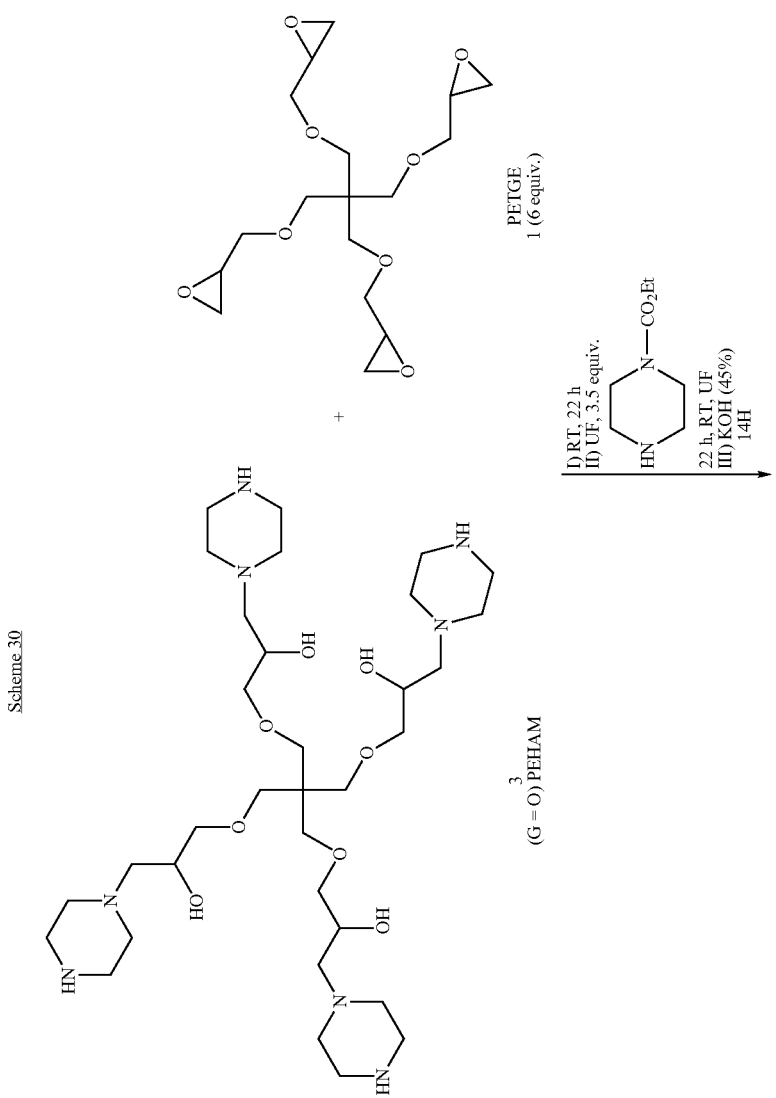

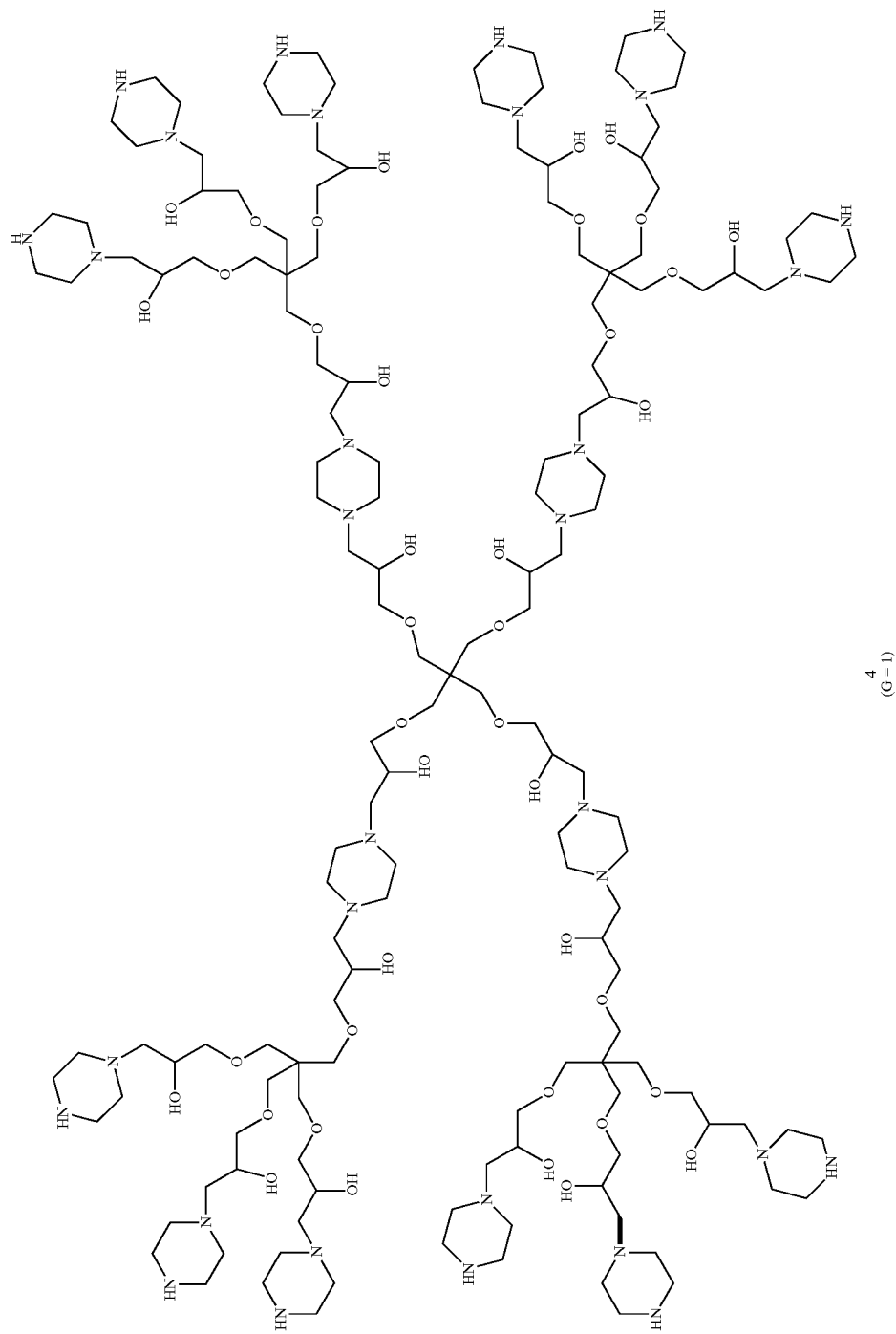
$4$
$(G=1)$

EXAMPLE 27

Protecting the Primary Amines of Diethylenetriamine and Using to Secondary Amine to Cap the Tetrafunctional Epoxide: Two Primary Amines

[(C)=PETGE; (IF1)=OH; (BR1)=DIA; (TF)=Primary NH$_2$; G=1]

DETA (6.56 g, 63.6 mmol) (Acros) and 125 mL of 4-methyl-2-pentanone (Aldrich) were put into a 250-mL round bottom flask, equipped with a Dean-Stark trap, and heated to 140° C. under argon atmosphere. After the theoretical amount of water (2.2 mL) was azeotroped out, the reaction was cooled to RT. The weight of the mixture was 77.37 g, containing 63.6 mmol of secondary amine. The mixture (12.16 g) was transferred to a 50-mL round bottom flask. Solvent was removed by rotary evaporation to give an oil. To this oil was added a solution of PETGE (360 mg, 1.0 mmol) (made by Example B) in 5.5 mL of dry MeOH. The reaction was heated to 75° C. for 23 hours. The solvent was removed and 25 mL of 2-propanol and 3.0 mL of water were added to the residue. The mixture was heated to 50° C. for 2 hours. The solvent was removed using a rotary evaporator. Excess DETA was removed by Kugelrohr distillation (150° C.) to give the product as a slightly yellow sticky oil that has the following spectra:

MALDI-TOF: Calc. 773; found 795.784 (M$^+$Na) amu.

The following Scheme 31 illustrates this above reaction:

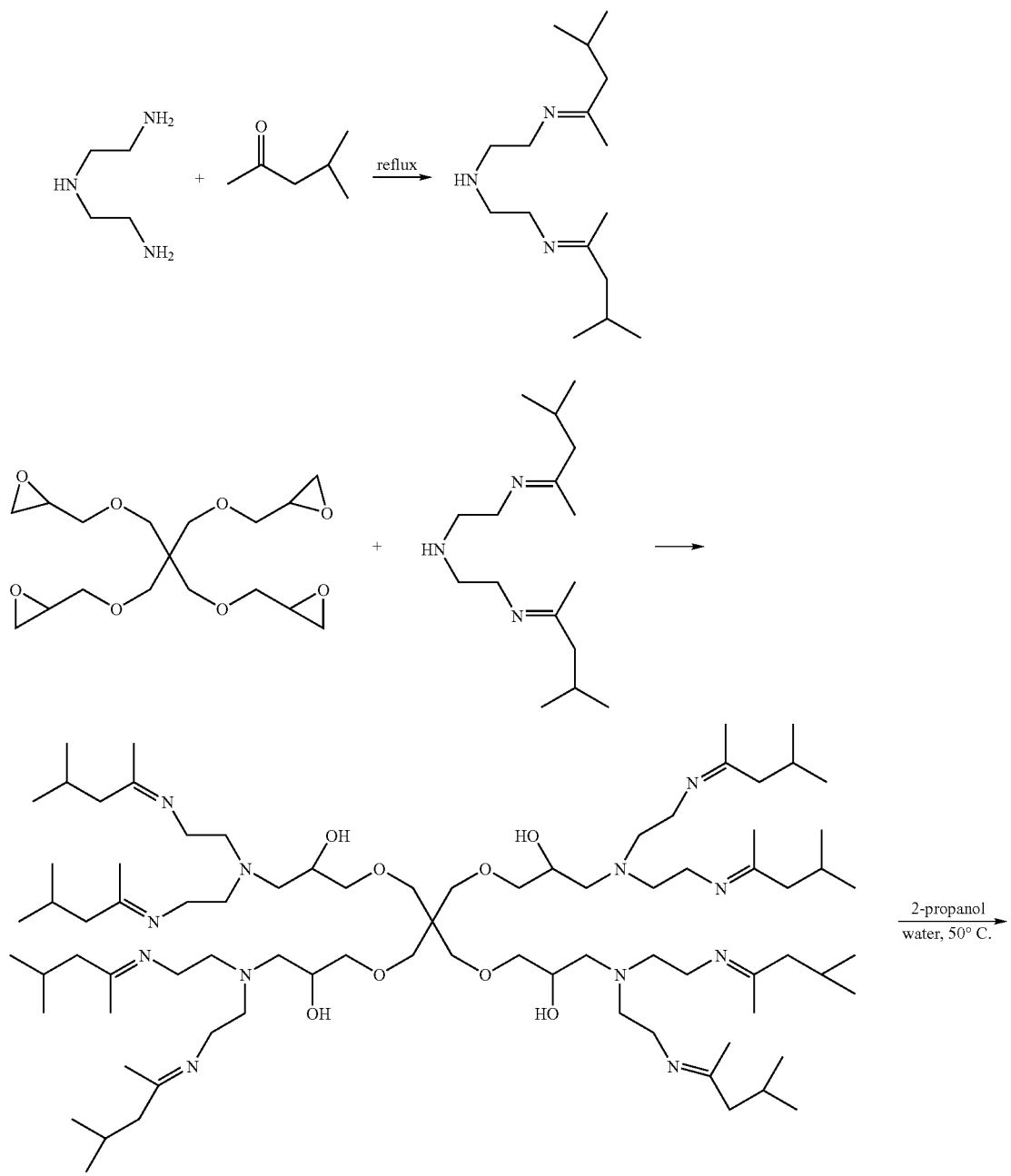

Scheme 31

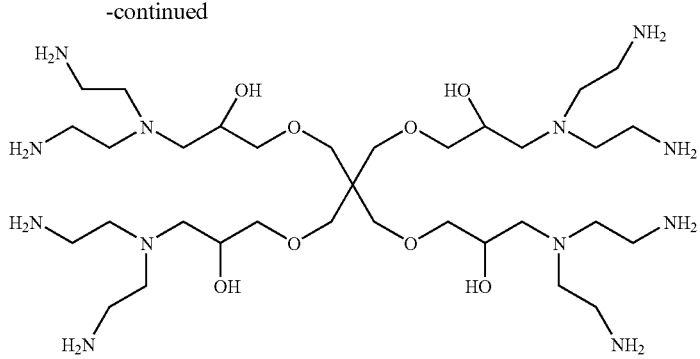

EXAMPLE 28

Combining Epoxy Ring-Opening Reactions/Reagents with Michael's Addition Reactions/Reagents Reaction of Tetraepoxide with Diallyl Amine (BAA): Surface Allylation

[(C)=PETGE; (IF1)=OH; (BR1)=BAA; (TF)=Allyl; G=1]

To a solution of BAA (816 mg, 8.40 mmol) (Aldrich) in 4 mL of MeOH was added a solution of PETGE (360 mg, 11.0 mmol) (made by Example B) in 1 mL of MeOH. The mixture was heated to 60° C. for 64 hours. Then the solvent was removed to give the product as a clear colorless oil (657 mg, 89% yield) that has the following spectra:

$^1$H NMR (500 MHz, CDCl$_3$): δ 2.47 (m, 8H), 3.06 (q, 8H), 3.21 (q, 8H), 3.39 (m, 20H), 3.83 (4H), 5.15 (m, 16H), 5.81 (m, 8H); and $^{13}$C NMR (125 MHz, CDCl$_3$): δ 45.54, 55.63, 56.86, 66.75, 70.54, 74.11, 117.73, 135.12, and MALDI-TOF: Calc. 748; found 749.588(M$^+$H), 771.583 (M$^+$Na) amu.

The following Scheme 32 illustrates this reaction:

Scheme 32

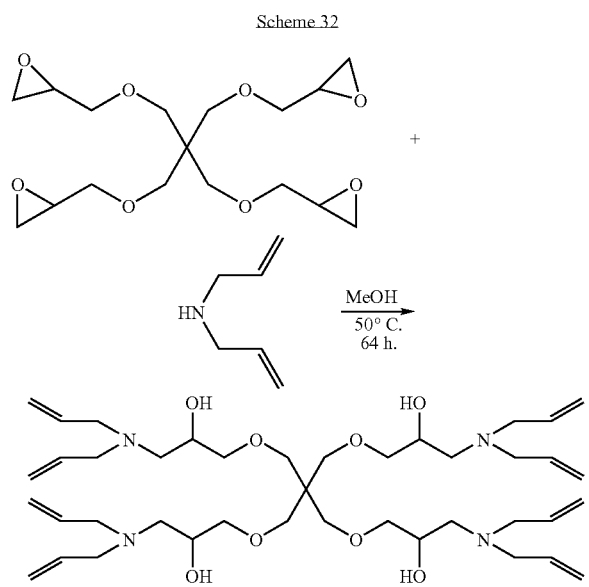

EXAMPLE 29

Phenyl Containing Glycidylether Class of Poly(epoxides) Reacted with Various Amines Reaction of Triphenylmethane Triglycidyl Ether (TPMTGE) (1-d) with Tris(hydroxymethyl)methylamine (TRIS) (II-e)

[(C)=TPMTGE; (FF)=H; (IF1)=OH; (BR1)=TRIS; (TF)=OH; G=1]

TPMGE I-d (0.46 g, 1 mmol) (Aldrich) and 30 mL of MeOH were placed in a 100-mL single necked round bottom flask. TRIS (0.726 g, 6 mmol) (Aldrich) was added to the above reaction mixture all at once. Initially, these two starting materials were not soluble completely but will dissolve after heating for about 10-15 min. Heating continued at 60° C. overnight. TLC indicated complete consumption of starting glycidyl ether during that time. Solvent was removed on a rotary evaporator, to give a colorless solid. The entire reaction mixture was dissolved in a mixture of solvents (CHCl$_3$ and CH$_3$OH, 60 mL, 3:1 v/v) under hot conditions (by heating with a heating gun), then cooled to RT, and hexanes added to form a precipitate. The solid was filtered through a Büchner funnel to remove the excess TRIS. Evaporation of the filtrate gave hydroxyl terminated (G=1)dendrimer, III-e (yield, 0.815 g, 99%) that has the following spectra:

$^1$H NMR (300 MHz, DMSO-d6): δ1.28-1.171 (t, J=6.00 Hz, 3H), 1.48 (bs, 9H), 2.47 (s, 3H), 3.77-3.84 (m, 6H), 4.22 (m, 18H), 4.98 (bs, 3H), 5.72 (s, 1H), 6.62-6.88 (m, 8H), 6.92 (m, 4H); and $^1$H NMR (75 MHz, DMSO-d$_6$): δ 44.72, 55.59, 60.08, 61.64, 69.86, 71.31, 114.74, 114.87, 128.02, 130.48, 137.17, 157.51; and MALDI-TOF: C$_{40}$H$_{61}$N$_3$O$_{15}$ Calc. 823; found 847 (M$^+$Na) amu.

Scheme 33 illustrats this reaction:

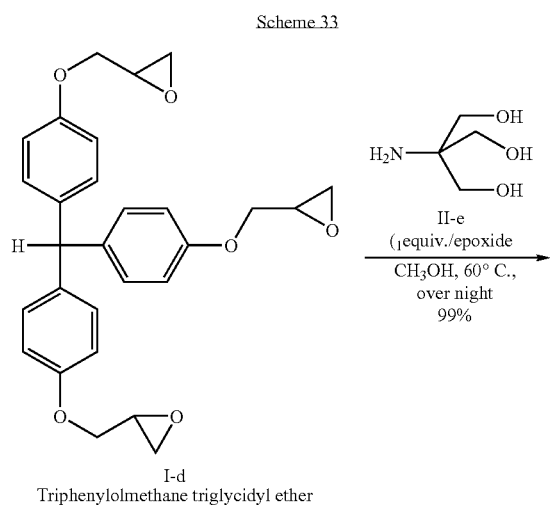

Scheme 33

I-d
Triphenylolmethane triglycidyl ether

III-e

Formation of a colorless precipitate was observed during the addition of ethyl acetate. The flask was allowed to stand at RT for 2 hours. After 2 hours, separation of oil in the bottom of the flask was observed. The mixture was then separated by decantation and the oil washed with ethyl acetate (2×1 mL). The oil was solidified by drying under high vacuum and gave a solid (1.24 g). Analysis by $^{13}C$ NMR indicated the excess of the DEA was separated and spectral data was in agreement with dendrimer III. Concentration of the solution on a rotary evaporator gave a colorless transparent liquid (0.522 g), which was a mixture of product III-f and DEA. The spectra for III-f are:

$^1H$ NMR (300 MHz, $CD_3OD$): δ 2.92-2.58 (m, 6H), 2.60-2.77 (m, 12H), 3.29-3.31 (quintet, J=1.50 Hz, 3H), 3.46-3.67 (m, 6H), 3.57-3.67 (m, 6H), 3.80-4.00 (m, 10H), 4.84 (s, 6H), 6.02-6.86 (m, 6H), 6.90-6.97 (m, 4H), 7.08-7.20 (m, 2H); and $^{13}CNMR$ (75 MHz, $CD_3OD$): δ57.51, 58.28, 59.64, 67.97, 68.13, 70.23, 114.12, 130.10, 137.27, 157.52; and MALDI-TOF: $C_{40}H_{61}N_3O_{12}$ Calc. 775; found 799 ($M^+Na$) amu.

Scheme 34 illustrates this reaction:

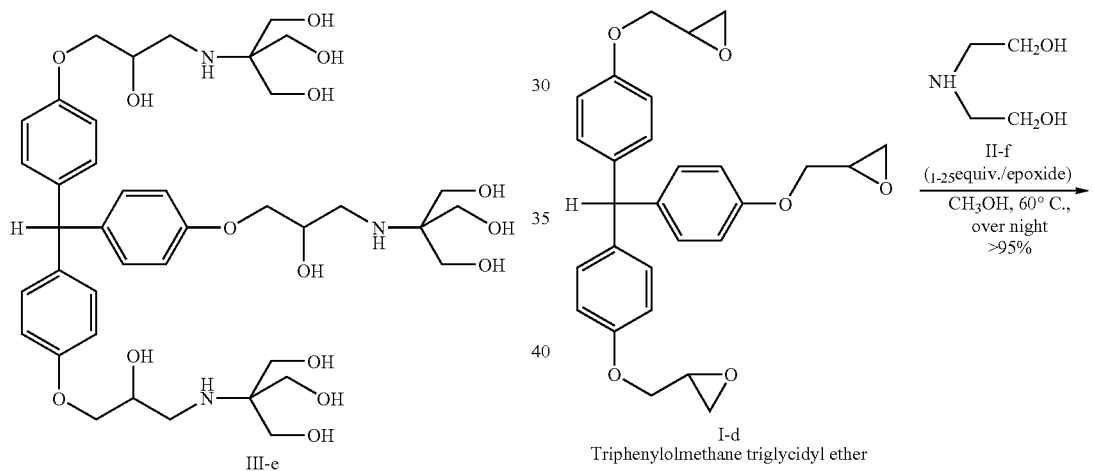

Scheme 34

I-d
Triphenylolmethane triglycidyl ether

EXAMPLE 30

Reaction of TPMTGE with Diethanolamine (DEA)

[(C)=TPMTGE; (FF)=H; (IF1)=OH; (BR1)=DEA; (TF)= OH; G=1]

TPMTGE, I-d (0.92 g, 2 mmol) and 30 mL of MeOH were placed in a 100-mL round bottom flask, followed by the addition of a solution of DEA (0.785 g, 7.5 mmol) in 10 mL of MeOH. The flask was equipped with a stir bar and refluxing condenser and then heated at 60° C. The progress of the reaction was monitored by TLC. After 3 hours, TLC indicated some amount of unreacted triglycidyl ether. Heating was continued at the same temperature overnight. At this time, analysis by MALDI-TOF mass spectrometry showed a molecular ion peak for dendrimer III-f. The solvent was then removed on a rotary evaporator under reduced pressure, which gave a transparent liquid. The entire reaction mixture (1.75 g) was dissolved in 10 mL of MeOH, followed by the addition of 50 mL of ethyl acetate with occasional shaking.

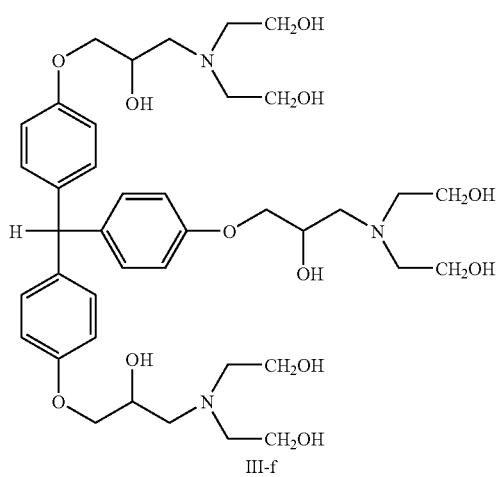

III-f

EXAMPLE 31

Reaction of TPMTGE with Diethyliminodiacetate (DEIDA)

[(C)=TPMTGE; (FF)=H; (IF1)=OH; (BR1)=DEIDA; (TF)=Ethyl ester; G=1.5]

TPMTGE I-d (0.92 g, 2 mmol) and 30 mL of MeOH were placed in a 100-mL round bottom flask followed by addition of a solution of DEIDA (1.42 g, 7.5 mmol) (Aldrich) in 10 mL of MeOH all at once. The flask was equipped with a stir bar and reflux condenser and heated at 60° C. overnight. MALDI-TOF mass spectrometry showed peaks for dendrimer III-g. Heating was continued for 24 hours and the solvent was removed on a rotary evaporator under reduced pressure, giving reaction mixture was purified by column chromatography on silica gel (22 cm height×3 cm width). First, 30% ethyl acetate/hexanes was used to elute the excess of DEIDA, followed by 5% MeOH/CHCl$_3$ used to elute the product III-g (1.93 g; 93.9% yield). The spectra for III-g are:

$^1$H NMR (300 MHz, CDCl$_3$): δ 1.26 (t, J=6.90 Hz, 18H), 3.34-3.55 (m, 12H), 3.61 (s, 3H), 3.65-3.79 (m, 6H), 3.88-4.04 (m, 9H), 4.13-4.22 (m, 13H), 6.71-6.35 (m, 6H), 6.89-6.99 (m, 6H); and $^{13}$C NMR (75 MHz, CDCl$_3$): δ 14.44, 48.91, 50.09, 50.26, 50.36, 51.05, 52.11, 54.38, 56.34, 57.03, 58.28, 58.74, 61.16, 67.44, 69.85, 77.05, 111.45, 114.44, 120.69, 127.79, 130.21, 130.40, 130.48, 130.55, 157.30, 169.61, 172.18, 172.59; and MALDI-TOF: C$_{52}$H$_{73}$N$_3$O$_{15}$ Calc. 1027; found 1050 (M$^+$Na) amu.

The following Scheme 35 illustrates this reaction:

Scheme 35

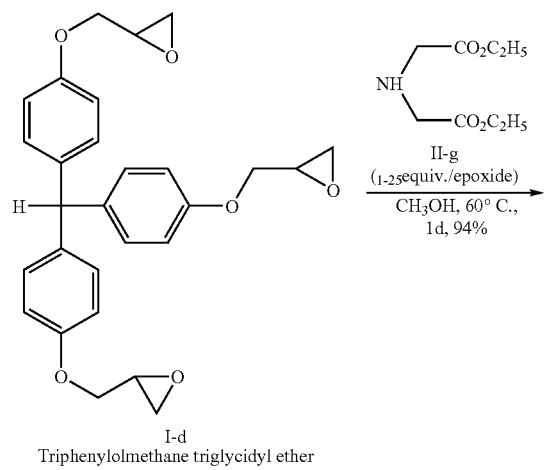

I-d
Triphenylolmethane triglycidyl ether

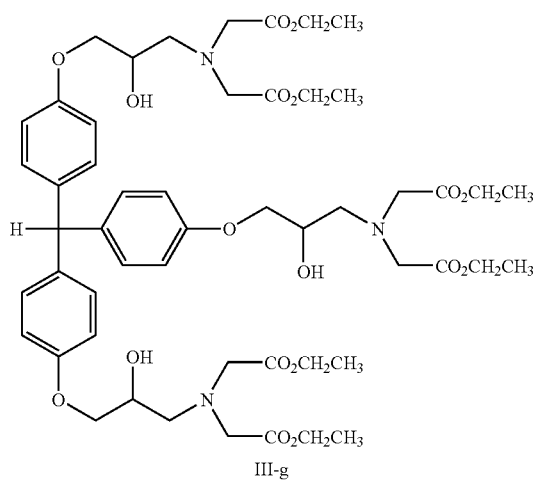

III-g

EXAMPLE 32

Synthesis of Hexamine Terminated, G=1, Dendrimer from Ester Terminated, G=1, Dendrimer

[(C)=TPMTGE; (FF)=H; (IF1)=OH; (BR1)=DEIDA; (EX1)=EDA; (TF)=Primary NH$_2$; G=1]

EDA (168.3 g, 2.244 mol) was placed in an oven dried 500-mL round bottom flask, which was equipped with a stir bar, and cooled to 0° C. with an ice bath. Ester terminated (G=1) dendrimer III-g, (1.93 g, 1.87 mmol) (made by Example 31) was taken in 10 mL of MeOH and added to the above stirring, cooled solution over 15 min. through a pressure equalizing funnel. The flask was flushed with N$_2$ gas and closed with a septum. The reaction mixture was stirred at that temperature for 1 hour and stored at 0° C. for 2 days. The reaction mixture was allowed to stir at RT for 1 hour. Analysis of the sample by MALDI-TOF mass spectrometry showed a molecular ion peak for the hexamine surface (G=1) dendrimer, IV-d. Excess EDA was removed on a rotary evaporator under reduced pressure, which gives a pale yellow color liquid. The entire reaction mixture was dissolved in 30 mL of MeOH and 70 mL of toluene was added in order to remove the remaining EDA by forming an azeotrope. This process was repeated three times. The mixture was then dried under high vacuum, giving a pale yellow color hygroscopic solid (2.07 g; 99% yield). Analytical data (IR, $^1$H and $^{13}$C) were in agreement with hexamine terminated (G=1) dendrimer, IV-d. Its spectra are as follows:

$^1$H NMR (300 MHz, CD$_3$OD): δ 2.68-2.84 (m, 12H), 2.84-2.90 (m, 3H), 3.11-3.18 (m, 6H, NH), 3.22-3.30 (m, 18H), 3.31-3.35 (m, 12H), 3.80-4.14 (m, 10H), 4.82 (s, 12H, NH2), 6.58-6.98 (m, 12H); and $^{13}$C NMR (75 MHz, CD$_3$OD): δ 40.74, 41.58, 51.99, 59.20, 59.52, 67.69, 70.30, 114.13, 127.57, 130.14, 136.77, 137.35, 157.43, 172.74, 172.89; and IR (Neat): ν$_{max}$ 3303 (br), 2933, 2863, 1652, 1543, 1508, 1451, 1242, 1176, 1109, 1033, 968, 829, 757 cm$^{-1}$; and MALDI-TOF: C$_{52}$H$_{55}$N$_5$O$_{12}$ Calc. 1111; found 1134 (M$^+$Na) amu.

Scheme 36 illustrates this reaction:
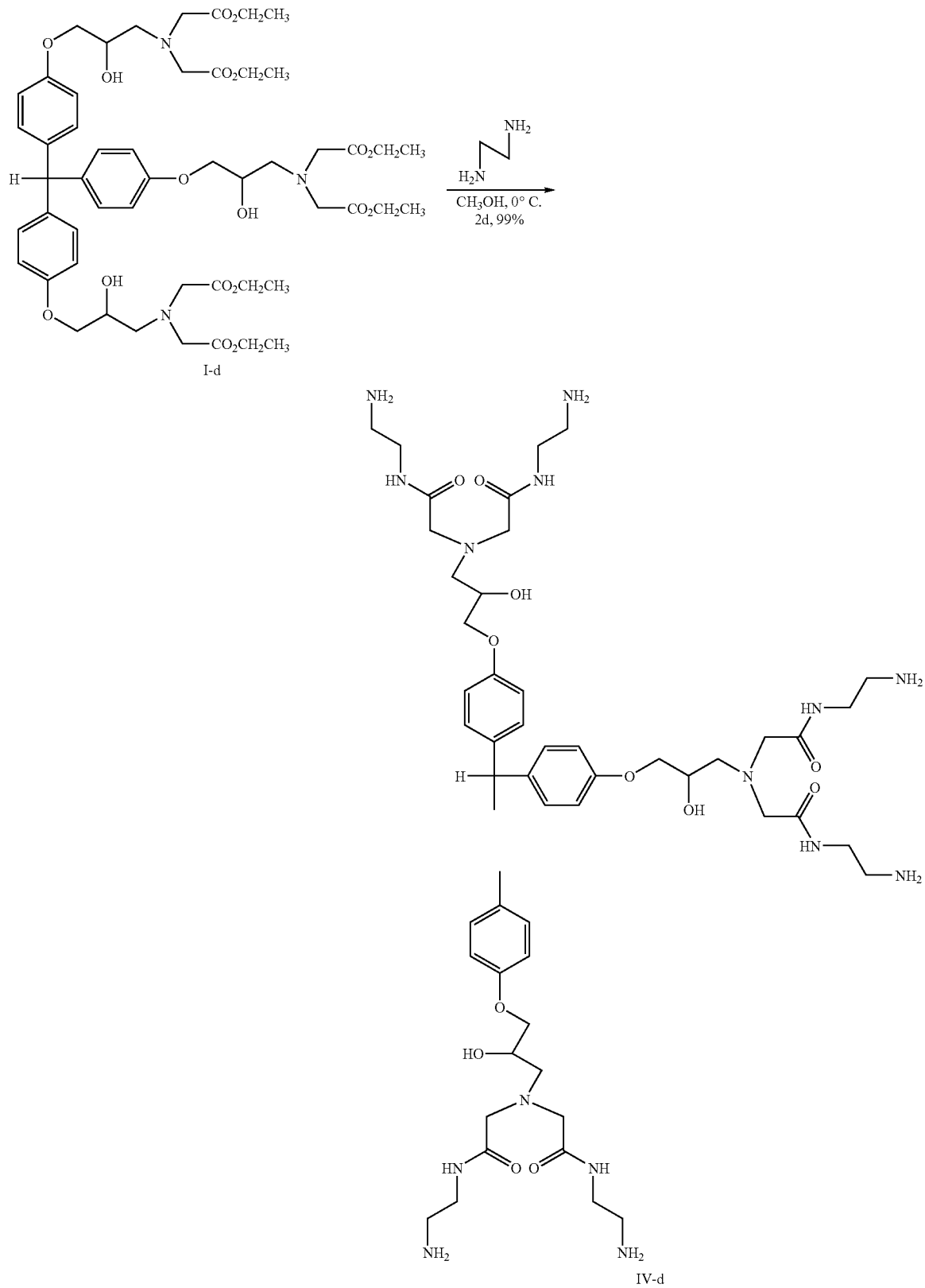

EXAMPLE 33

Reaction of Bis(4-glycidyloxyphenyl)methane (BGPM) with tris(hydroxymethyl)methylamine (TRIS)

[(C)=BGPM; (IF1)=OH; (BR1)=TRIS; (TF)=OH; G=1]

BGPM, I-c (0.624 g, 2.0 mmol) and 20 mL of MeOH were placed in a 100-mL round bottom flask. TRIS (0.605 g, 5.0 mmol) was added to the above reaction all at once. After stirring at 50° C. for 5-10 min. both the starting materials were dissolved completely. Heating was continued at 50° C. for 42 hours after which TLC indicated complete consumption of BGPM I-c; however stirring was continued for another 6 hours. Solvent was removed on a rotary evaporator, to give a colorless solid. The entire crude reaction mixture was dissolved in 60 mL of $CHCl_3$ and 15 mL of MeOH under heating with a heating gun, and was then allowed to cool to RT. Then 30 mL of hexanes was added, resulting in the formation of a precipitate during the hexanes addition. The flask was kept on a bench top and solid was filtered off. Concentration of the solution gives a hygroscopic solid, III-e (1.044 g, 94% yield) that has the following spectra:

MALDI-TOF: $C_{27}H_{42}N_2O_{10}$ Calc. 554.63; found 578.608 ($M^+Na$) amu.

Scheme 37 illustrates this reaction:

equipped with a stir bar. DEIDA (1.965 g, 10.4 mmol) (Aldrich) was dissolved in 10 mL of MeOH and added to the above reaction mixture all at once. The flask was arranged with a refluxing condenser and heated at 60° C. for 36 hours. After heating overnight, MALDI-TOF mass spectrometry indicated peaks for bis- and mono-addition products. TLC also indicated two corresponding spots. Heating continued at that temperature for 36 hours and TLC showed only one spot. Solvent was removed on a rotary evaporator, giving a transparent liquid. The reaction mixture was subjected to column chromatography on silica gel (22 cm height, 3 cm width). First, 40% ethyl acetate in hexanes was used to elute excess of DEIDA (0.447 g, 98% recovery) followed by 5% methanol in chloroform used to elute the tetra ester surfaced (G=1) dendrimer III-g (2.57 g, 93% yield) that has the following spectra:

$^1$H NMR (300 MHz, $CD_3Cl$): δ 1.20-1.30 (m, 12H), 2.60-2.74 (m, 2H), 3.13-3.24 (m, 2H), 3.34 (s, 2H), 3.45-3.72 (m, 8H), 3.80-4.00 (m, 6H), 4.07-4.22 (m, 8H), 4.75-4.83 (m, 2H), 6.76-6.84 (m, 4H), 7.01-7.09 (m, 4H); and $^{13}$C NMR (75 MHz, $CD_3Cl$): δ 14.43, 35.59, 35.72, 40.31, 50.36, 52.09, 54.39, 56.36, 57.03, 58.74, 61.15, 67.45, 67.61,

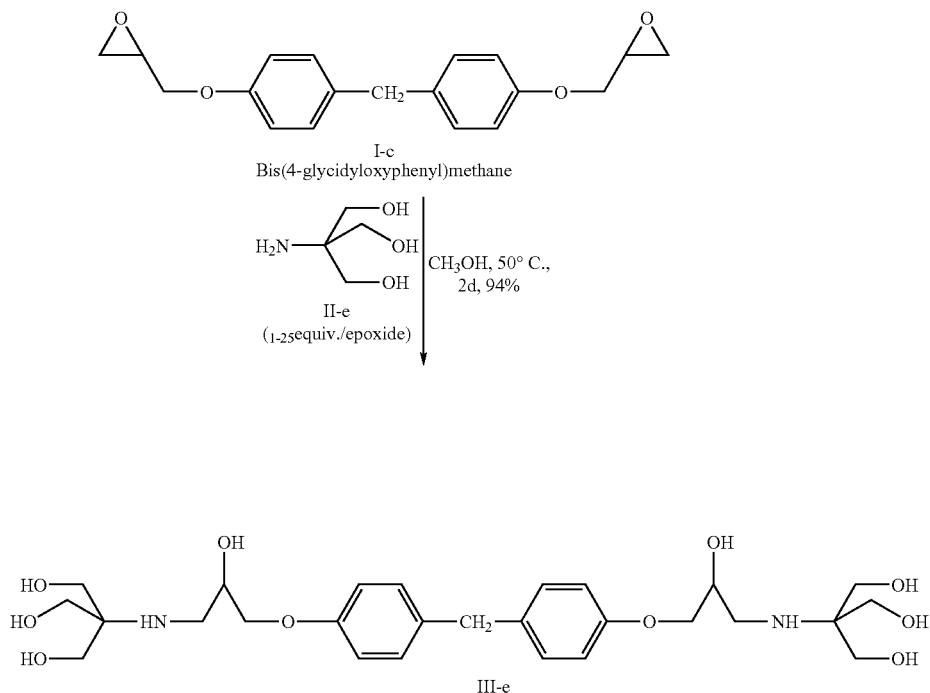

EXAMPLE 34

Reaction of Bis(4-glycidyloxyphenyl)methane (BGPM) with Diethyliminodiacetate (DEIDA)

[(C)=BGPM; (IF1)=OH; (BR1)=DEIDA; (TF)=Ethyl ester; G=1.5]

BGPM, I-c (1.25 g, 4.0 mmol) (Aldrich) and 30 mL of MeOH were placed in a 100-mL round bottom flask, 69.77, 69.90, 77.07, 111.35, 111.50, 114.58, 114.70, 120.96, 121.49, 127.65, 127.84, 129.76, 129.93, 130.02, 130.09, 130.57, 131.09, 130.57, 131.01, 134.16, 156.50, 157.27, 166.97, 169.61, 172.16; and MALDI-TOF: $C_{35}H_{50}N_2O_{12}$ Calc. 690; found 714 ($M^+Na$) amu.

The following Scheme 38 illustrates this reaction:

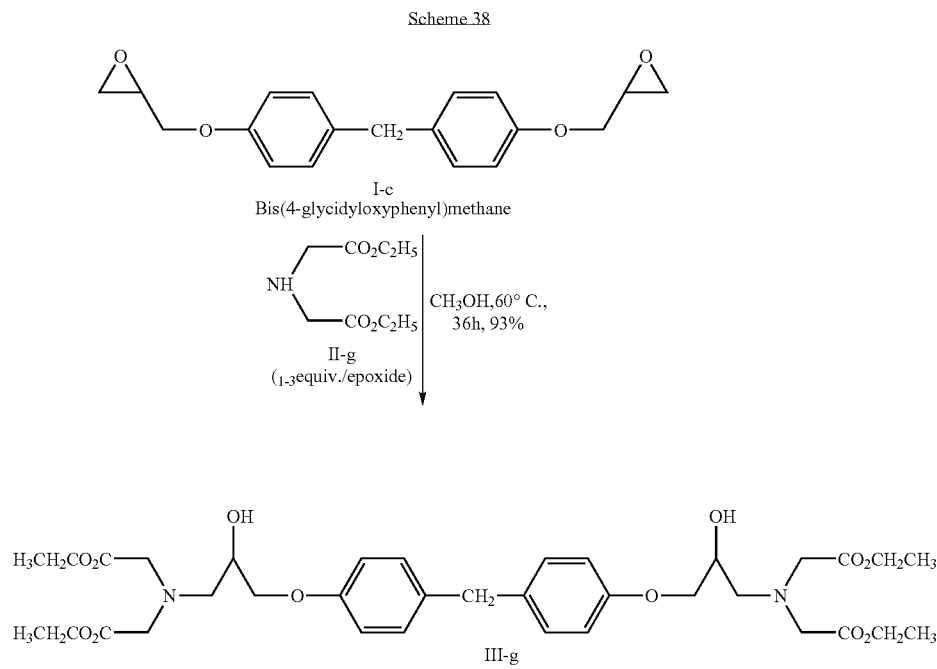

EXAMPLE 35

Synthesis of Tetraamine Terminated (G=1) Dendrimer from Ester Terminated (G=1) Dendrimer

[(C)=BGPM; (IF1)=OH; (BR1)=DEIDA; (EX1)=EDA; (TF)=Primary $NH_2$; G=1]

EDA (111.6 g, 1.49 mol) was placed in an oven-dried 500-mL round bottom flask and cooled to 0° C. Ester terminated (G=1) dendrimer (III-g) (2.57 g, 3.72 mmol) (made by Example 34) was dissolved in 10 mL of MeOH and added to the above cold solution dropwise over a period of 20 min. through a dropping funnel. The flask was flushed with $N_2$ gas, stirred at this temperature for one hour, and stored at 0° C. for 2 days. The flask was allowed to warm to RT and stirred for one hour. Analysis of the sample showed molecular ion peaks for hexamine surface (G=1) dendrimer IV-g. Excess of EDA was removed on a rotary evaporator under reduced pressure, giving a pale yellow color liquid. The entire reaction mixture was dissolved in 30 mL of MeOH. Then 70 mL of toluene was added to the mixture in order to remove residual EDA by forming an azeotrope. This process was repeated three times, and the mixture dried under high vacuum, giving a pale yellow color hygroscopic solid (2.69 g, 96.8% yield). Analytical data (IR, $^1H$ and $^{13}C$) was in agreement with hexamine terminated (G=1) dendrimer, IV-g that has the following spectra:

$^1H$ NMR (300 MHz, $CD_3OD$): δ 2.54-2.62 (m, 4H, NH), 2.67-2.75 (m, 8H), 2.83-2.88 (m, 4H), 3.22-3.31 (m, 8H), 3.33-3.36 (m, 8H), 3.80 (s, 2H), 3.88-4.02 (m, 8H), 4.80 (s, 8H, $NH_2$), 6.79-6.94 (m, 4H), 7.03-7.19 (m, 4H); and $^{13}C$ NMR (75 MHz, $CD_3OD$): δ40.76, 41.66, 59.21, 59.53, 67.55, 67.69, 70.27, 111.32, 114.25, 114.36, 120.65, 127.51, 129.49, 129.61, 129.92, 130.50, 133.87, 134.44, 156.64, 157.22, 157.366, 172.78, 172.85; and IR (Neat): $v_{max}$ 3286 (br), 3071, 2932, 2872, 1653, 1541, 1509, 1452, 1242, 1175, 1114, 966, 822, 756, 602 $cm^{-1}$; and MALDI-TOF: $C_{35}H_{58}N_{10}O_8$ Calc. 746; found 770 ($M^+Na$) amu.

Scheme 39 illustrates this reaction:

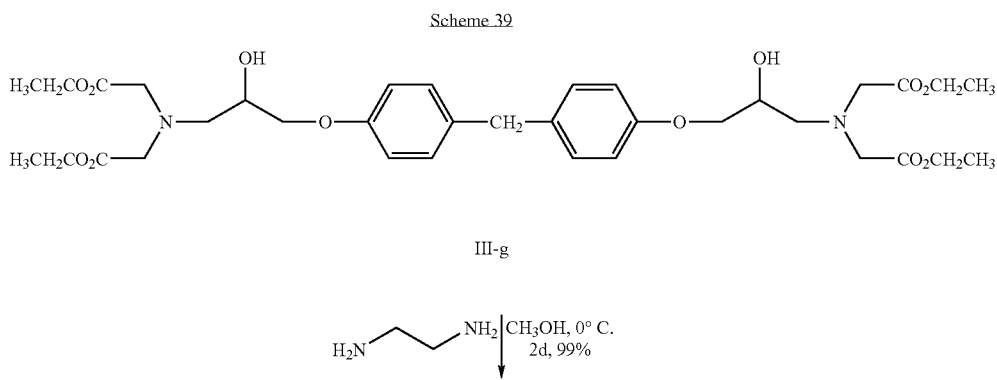

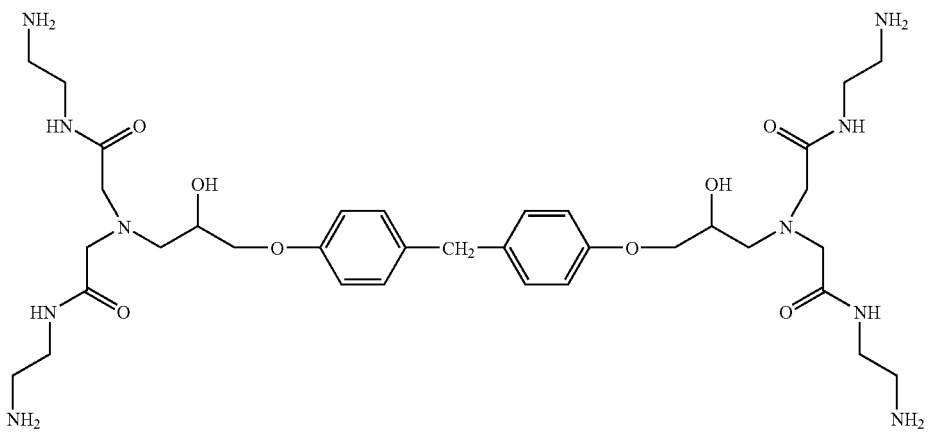

IV-g

EXAMPLE 36

Ring-Opening of a Diepoxide: 4,4'-Methylene-bis(N, N-di-2-hydroxypropyl-3-piperazinylaniline) (MBDGA)

[(C)=DGGA; (IF1)=OH; (EX1)=PIPZ; (TF)=Secondary NH; G=1.5]

To a 250-mL round bottom flask containing a stir bar was added PIPZ (16.0 g 189.0 mmol, 5 equiv. per epoxide) and MBDGA (4.0 g, 9.5 mmol, 37.8 mmol epoxide) (Aldrich) dissolved in 85 g of diglyme. The mixture was made homogeneous by adding 45 g of MeOH. This mixture was heated at 60° C. for 65 hours under a $N_2$ atmosphere. This mixture was cooled and volatile materials removed on a rotary evaporator. PIPZ was distilled from the mixture using a bulb-to-bulb Kugelrohr distillation with high vacuum and a temperature ranging from 140-180° C. A TLC (5% $NH_4OH$ in MeOH) of this mixture indicated residual PIPZ. Residual PIPZ was azeotroped with a 70:30 toluene:MeOH (wt %) mixture by dissolving the residue in a weighed amount of MeOH, adding toluene and distilling on a rotary evaporator. This PIPZ free product was evacuated overnight at 25° C. at high vacuum to give the desired product (6.8 g; 94% yield). Its spectra are as follows:

$^1$H NMR (500 MHz, $CDCl_3$): δ 2.3-2.6 (bm, 8H), 2.8-2.9 (bs, 8H), 3.35 (dd, J=7 Hz, 1H), 3.15 (dd, J=7 Hz, 1H), 3.65 (d, J=7 Hz, 1H), 3.79 (my 2H), 4.04 (bd, 2H), 6.44 (d, J=7 Hz, 1H), 6.74 (d, J=7 Hz, 1H), 7.02 (t, J=7 Hz, 2H); and $^{13}$C NMR (125 MHz, $CDCl_3$): δ 39.78, 46.08, 46.13, 54.81, 54.99, 57.20, 59.32, 62.52, 65.33, 65.79, 111.98, 113.34, 129.29, 129.34, 129.44, 129.47, 129.69, 129.75, 130.28, 130.32, 146.18, 147.22; and MALDI-TOF: Calc. 768.6; found 767 amu.

The following Scheme 40 illustrates this reaction:

Scheme 40

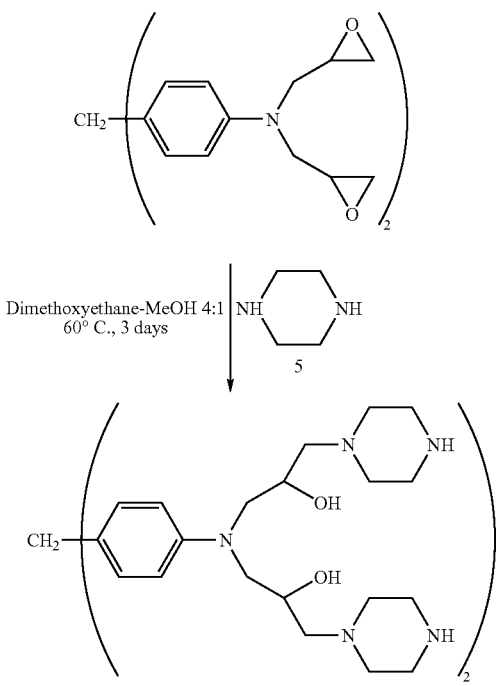

EXAMPLE 37

A. Preparation of Ethylenediamine, G=1, dendri{$CH_2$—$CH_2$—$CO_2$—$CH_2C(CH_3CH_2)(CH_2OC$=$(O)CH$=$CH_2)_2$}$_2$ (hexa-acrylate adduct)

[(C)=EDA; (FF)=H; (BR1)=TMPTA; (TF)=Acrylate; G=1]

To a 100-mL. round bottomed flask equipped with a stir bar was added TMPTA (29.6 g, 0.10 mol) (Aldrich) in 5 ml of MeOH cooled to about 4° C., and EDA (1.2 g, 0.02 mol) in 5 ml of MeOH over about a 5 min. period. This mixture was stirred at 30° C. for 18 hours. This mixture was cooled to 20° C. and poured into 150 g of stirred MeOH. The product phased out after allowing the mixture to stand without stirring for 1 hour at RT. The supernatant MeOH layer was decanted and this process was repeated two more times. The resulting clear, viscous phase was evacuated at high vacuum for 3 hours while protecting the reaction mass from light with aluminum foil wrapped around the reaction vessel, to give the desired product (20 g; 100% yield based on tri-adduct and 80% yield based on tetra-adduct). The isolated product weight suggests that most of the material was the hexa-acrylate (tri-adduct) product, consisting of three TMPTA added to one EDA. A MALDI-TOF mass spectrum of this product indicated a major peak at 950 amu corresponding to a hexa-acrylate tri-adduct product with a theoretical molecular weight of 949. A small peak at 1245 amu was observed consistent with the octa-acrylate (tetra-adduct) product. The spectra of the major peak are as follows:

$^{13}$C-NMR (500 MHz, CDCl$_3$): δ 7.45, 23.00, 23.14, 32.38, 40.77, 40.86, 49.48, 63.88, 64.05, 128.04, 131.26, 165.69, 172.10.

B. Preparation of Hexa-mercaptoethanol Surface

[(C)=EDA; (FF)=H; (BR1)=TMPTA; (EX1)=Mercaptoethanol; (TF)=OH; G=1]

To a 250-mL round bottom flask with a stir bar was added the EDA core polyesteramine (19.0 g, 20.0 mmol, 120 mmol acrylate in 50 ml of DME) (made by Example 37A) and mercaptoethanol (10.4 g, 132 mmol, 1.1 equiv. per acrylate group) (Aldrich) in 20 mL of DME. This mixture was stirred for 2 days at RT, then volatile materials were removed on a rotary evaporator. The resulting material was mixed with 150 mL of ethyl acetate and rapidly stirred with a stir bar. This heterogeneous mixture was allowed to settle for about 1 hour. The clear ethyl acetate layer was decanted. This process was repeated two more times. A PAGE of this material on a 15% cross-linked homogeneous polyacrylamide gel, using G=2-6 EDA core PAMAM dendrimers with EA surfaces as standards G=2 to 6, revealed a sharp, tight band corresponding to a G=1 PAMAM dendrimer.

The following Scheme 41 illustrates the above reactions:

Scheme 41

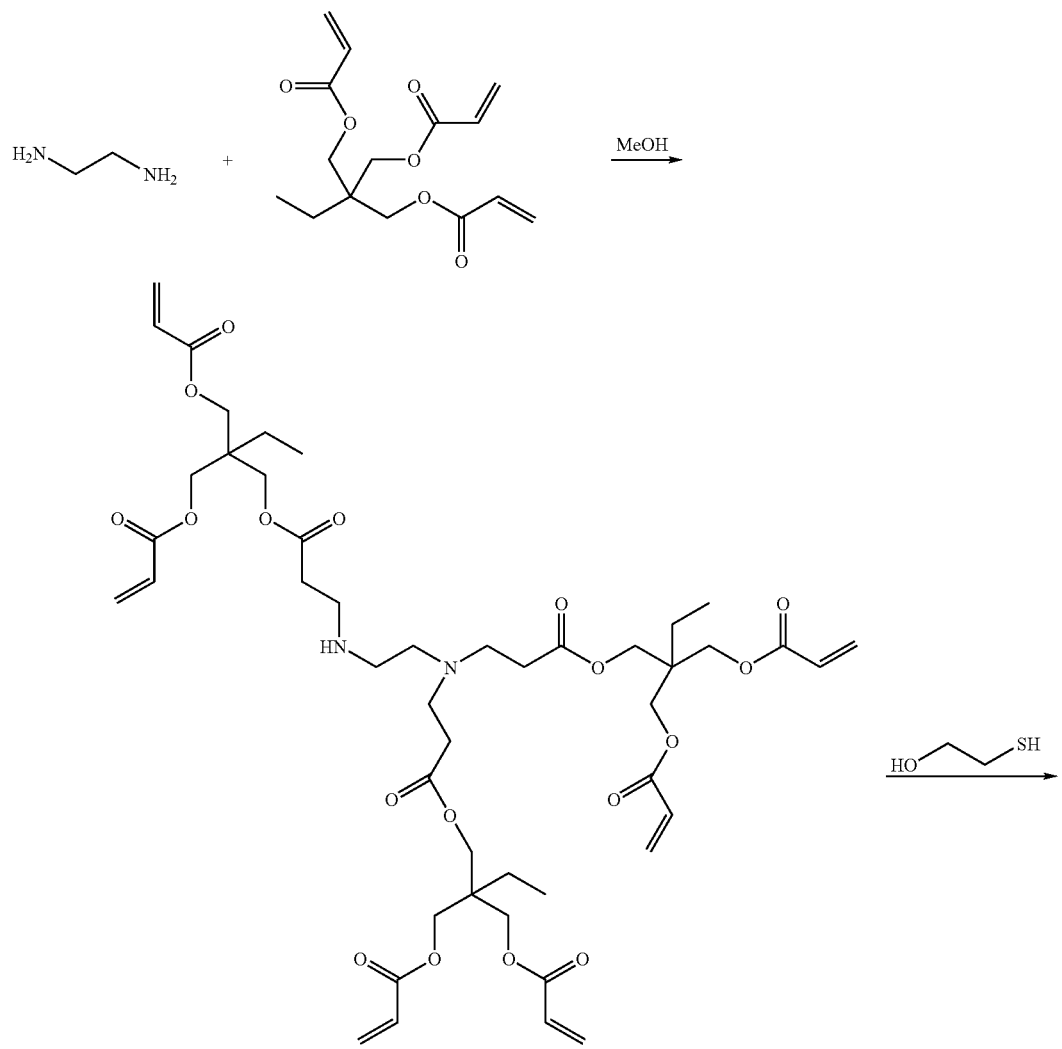

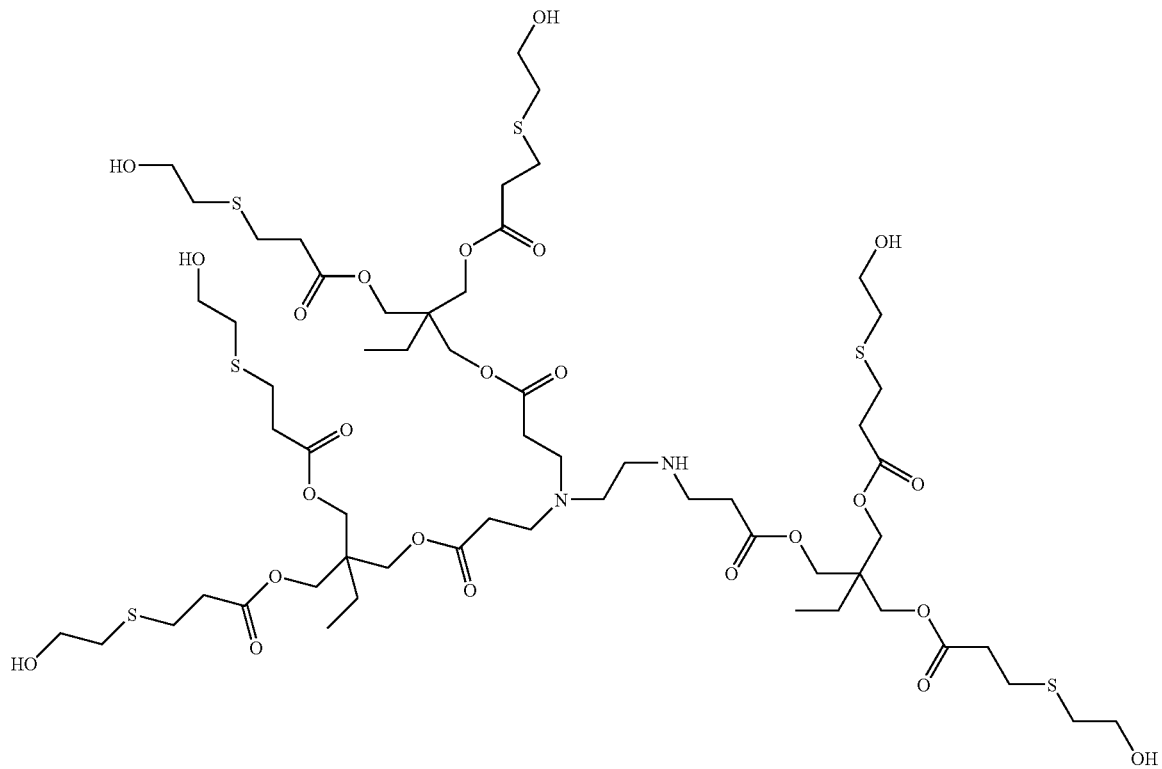

EXAMPLE 38

A. Preparation of Hexamethylenediamine (HMDA), G=1, dendri{CH$_2$—CH$_2$—CO$_2$—CH$_2$C(CH$_3$CH$_2$)(CH$_2$OC=(O)CH=CH$_2$)$_2$}$_2$

[(C)=HMDA; (BR)=TMPTA; (TF)=Acrylate; G=1]

To a 100-mL round bottom flask equipped with a stir bar was added TMPTA (29.6 g, 0.10 mol) (Aldrich) and 10 mL of MeOH. To this mixture, cooled at 4° C., was added HMDA (2.32 g, 0.02 mol) (Aldrich) in 20 mL of MeOH. This mixture was heated at 30° C. for 18 hours under a N$_2$ atmosphere. This mixture was cooled to about 15° C. and poured into 150 mL of stirred MeOH. The product phased out by allowing this mixture to stand without stirring for 1 hour while protecting the flask from light by wrapping the reaction vessel with aluminum foil. The methanol layer was decanted and this operation was repeated two more times to give a clear, colorless, viscous liquid. This immiscible phase was devolatilized by evacuation at high vacuum for 3 to 5 hours to give the crude product (24 g; 92% yield), whose isolated weight is consistent with an octa-acrylate (tetra-adduct) structure. A MALDI-TOF mass spectrum of this product indicated a small peak at 1301 amu consistent with the tetra-adduct and several lower molecular weight peaks, presumably derived from the "in-situ mass spectrometer decomposition" of the tetra-adduct structure. Allowing this product to stand in solution for prolonged periods of time or any attempt to remove solvent at RT, led to the formation of a white, insoluble cross-linked product. Therefore, this product was immediately converted to a more stable Michael's adduct by allowing it to react with stoichiometric amounts of appropriate amine or thiol reagent as described in Example 38B below.

B. Preparation of Octa-monoethanolamine Adduct via Michael's Addition of Amine to the Product of Example 38A

[(C)=HMDA; (BR)=TMPTA; (EX)=EA; (TF)=OH; G=1]

To a 250-mL round bottom flask containing a stir bar was added EA (27.0 g, 442.0 mmol, 3 equiv. per acrylate) in 50 mL of DME. To this mixture, cooled to 4° C., was added hexamethylenediamine core polyesteramine, G=1, octa-acrylate (24.0 g, 18.4 mmol, 8 acrylates per dendrimer) (made by Example 38A) in 50 mL of DME dropwise over about 10 mins. This mixture was stirred at 25° C. for 2 days under a N$_2$ atmosphere. Then volatile materials were removed with a rotary evaporator. This crude material was poured into rapidly stirred ethyl acetate. After a few mins. of stirring, the mixture was allowed to stand for 1 hour to allow separation of the two layers, and the ethyl acetate layer was decanted. The same volume of ethyl acetate was added, the mixture rapidly stirred and separated as before. This was repeated a second time for a total of three washes. The clear, colorless viscous oil was evacuated at high vacuum overnight at RT to give the desired product (29.7 g; 90% yield). An analysis by PAGE on a 15% cross-linked homogeneous polyacrylamide gel using PAMAM dendrimers as standards (G=2 to 6) revealed a sharp, tight band corresponding to a G=1 PAMAM dendrimer.

The following Scheme 42 illustrates the above reactions:
Scheme 42
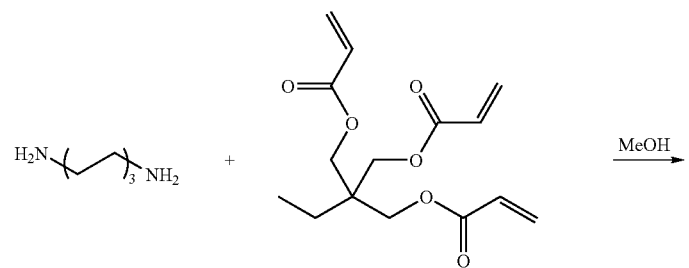
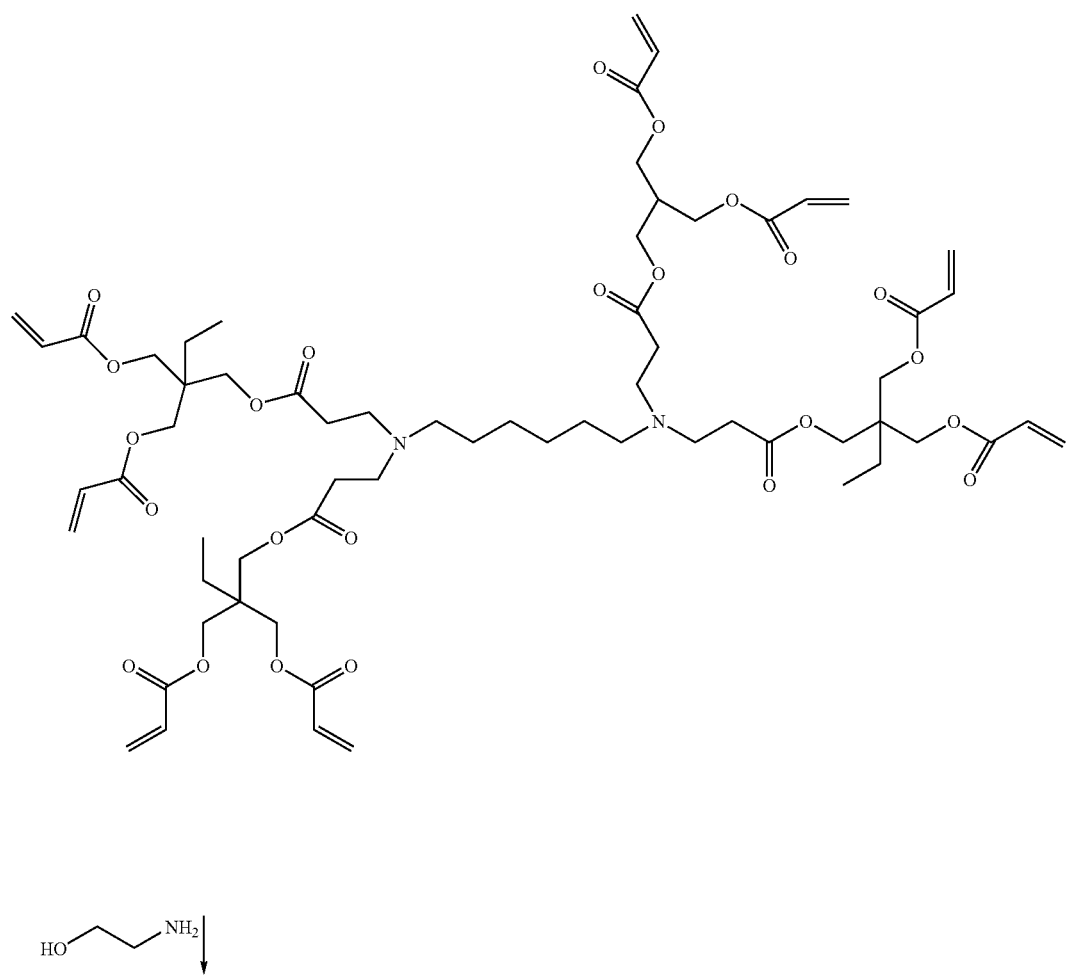

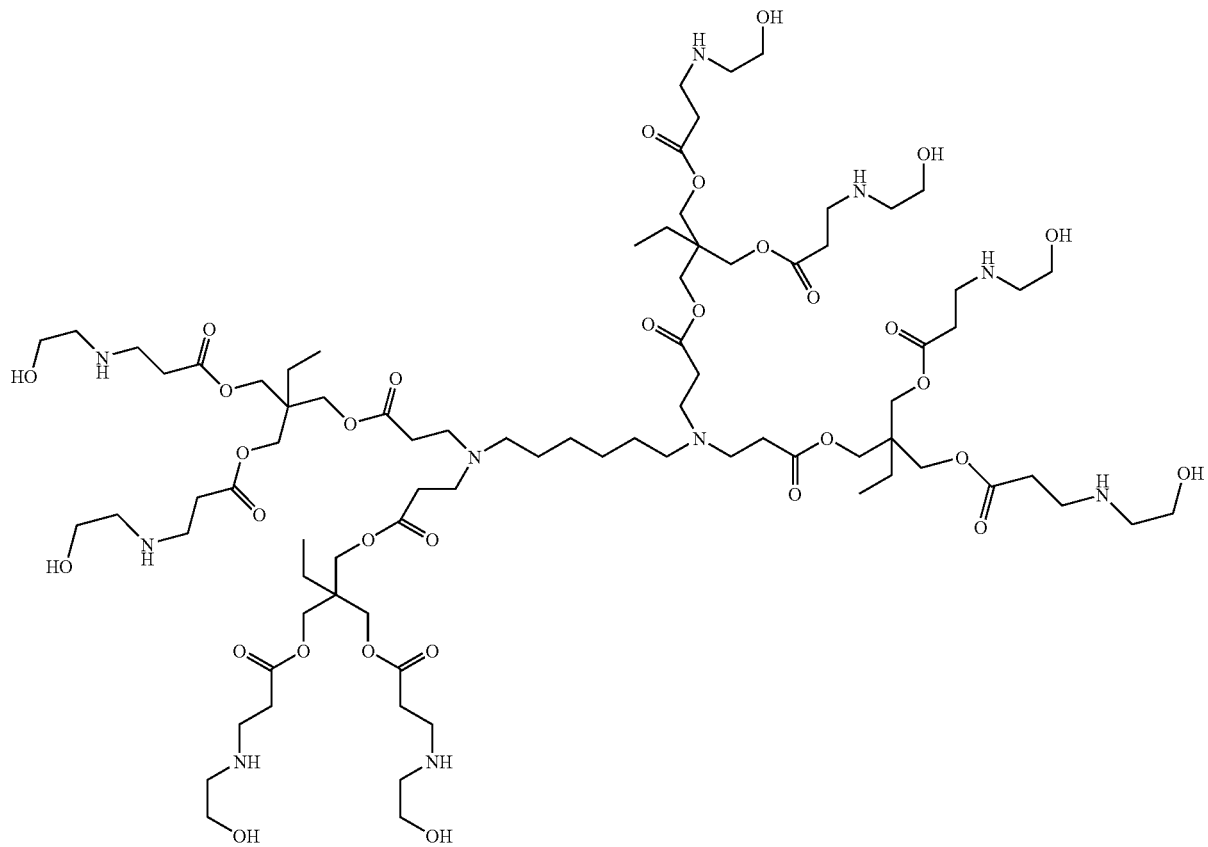

EXAMPLE 39

Preparation of the Octa-morpholine adduct of the material from Example 38A

[(C)=HMDA; (BR1)=TMPTA; (EX1)=Morpholine; (TF)= Cyclic ether; G=1]

To a 250-mL round bottom flask containing a stir bar was added polyesteramine, G=1, HMDA core (24.0 g, 18.4 mmol, 147 mmol acrylate) (made by Example 38A) in 50 mL of diglyme. To this mixture, cooled to about 4° C., was added morpholine (14.0 g, 160.0 mmol, 1.1 equiv. per acrylate) in 50 mL of DME over about 5 to 10 mins. This mixture was warmed to RT and stirred for 24 hours. This mixture was stripped of volatiles on a rotary evaporator and high vacuum at 30° C. for 18 hours to give the product (34.0 g; 94% yield). A MALDI-TOF mass spectrum of this material showed a peak corresponding to the theoretical molecular weight of 1998 amu together with several lower peaks derived from fragmentation of the 1998 amu peak. A $^{13}$C NMR spectrum of this material shows the product is very clean and consistent, with the correct number of carbons for the desired product. Its spectra are as follows:

$^{13}$C NMR (500 MHz, CDCl$_3$): 7.42, 22.82, 27.21, 27.54, 32.15, 40.78, 40.89, 48.97, 53.40, 53.94, 55.85, 59.04, 63.56, 71.79, 171.86, 172.16.

All of the PAGEs were run on 15% cross-linked homogeneous gels and exhibit very tight bands that are the most mobile entities compared to the calibration ladders, i.e. EDA core PAMAM dendrimers with EA surface, G=2 to 6. This mobility indicates a smaller size, consistent for this adduct versus the large octa-monoethanolamine adduct. The octa-morpholine adducts are comparable in mobility to the octa-monoethanolamine adducts. However, the marginal solubility of the morpholine adduct in water exhibit smeared columns rather than the tight bands observed for the mercaptoethanol and the ethanolamine adducts that are more soluble in water.

The following Scheme 43 illustrates this reaction:
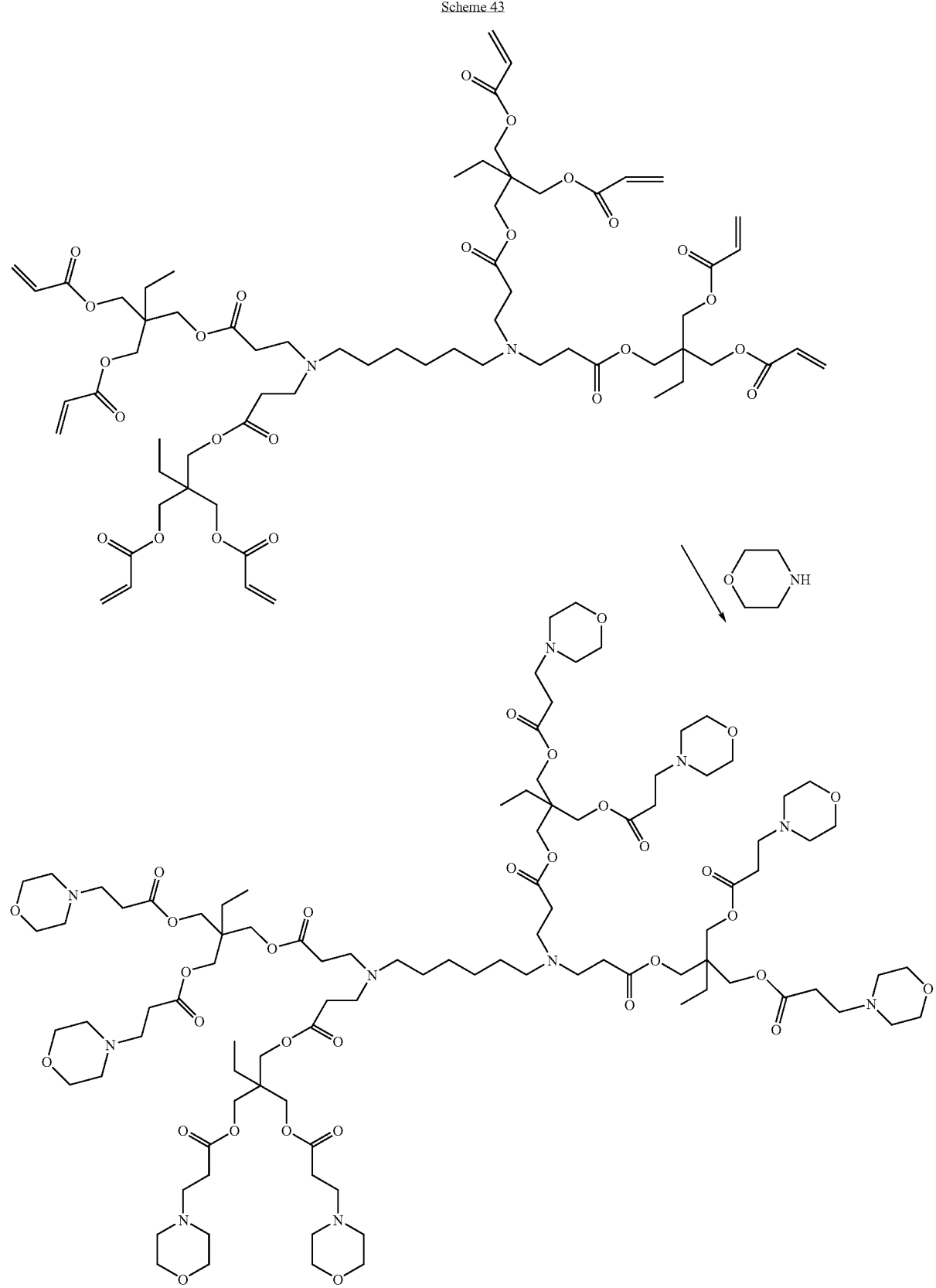

EXAMPLE 40

Reactions with Ethanolamine (EA): Primary Amine that Adds Two Trifunctional Epoxides per Primary Amine

[(C)=EA; (FF)=OH; (IF1)=OH; (BR1)=TMPTGE; (TF1)= Epoxide; G=1]

To a solution of TMPTGE I (1.81 g, 6.0 mmol) in 8 mL of MeOH was added a solution of EA II-c (122.0 mg) in 2 mL of MeOH. Stirring continued at RT for 45 hours, while the progress of the reaction was monitored by TLC. Solvent was evaporated on a rotary evaporator under reduced pressure and the resulting reaction mixture dried under high vacuum, giving a transparent liquid. MALDI-TOF Mass spectrometry indicated the mass for the products III-c and IV-c. This reaction mixture was subjected to purification by precipitation. First, hexanes were added to the reaction mixture, followed by ethyl acetate. While shaking the round bottom flask, formation of a colorless precipitate was observed. The flask was kept at RT for some time, the supernatant decanted, the precipitate washed with hexanes and dried under the high vacuum, to give the product mixture of III-c & IV-c (902 mg; % yield could not be calculated because of unknown mixing ratio).

Scheme 44 illustrates this reaction:

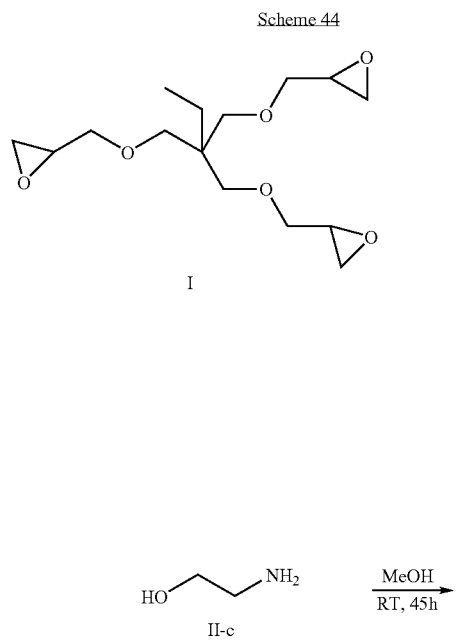

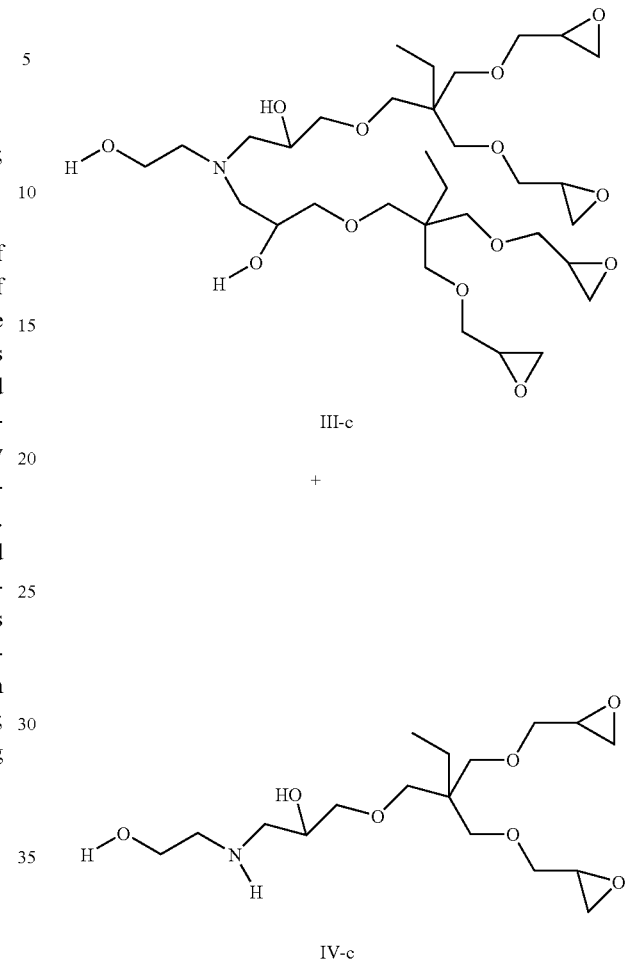

EXAMPLE 41

Reaction of Propargyl Pentaerythritol Triglycidyl Ether with Pentaerythritol Tetrazide (PETAZ) to Produce PEHAM Dendrimer G=1 with a Four-Arm Core and Epoxide Surface

[(C)=PETGE; (IF1)=OH; (EX1)=Triazole; (BR1)=PETriGE; (TF)=Epoxide; G=1]

To an oven-dried 50-mL round bottom flask was added propargyl pentaerythritol triglycidyl ether 2 (0.39 g, 1.14 mmol, 1.05 equiv. per $N_3$; made from Example F), pentaerythritol tetraazide 3 (0.144 g, 0.271 mmol; made from Example G), 1.2 g of 1-butanol and 1.2 g of water. The flask was equipped with a stir bar and sealed with a stopper. To this mixture was added sodium ascorbate (0.026 g, 0.114 mmol, 0.10 equiv.), followed by copper(II) sulfate pentahydrate ($CuSO_4.5H_2O$) (0.014 g, 0.057 mmol, 0.05 equiv.). The progress of the reaction was monitored by TLC. After stirring for 3 days at RT, the reaction was found to be completed. Product 4 was used for the next reaction in Example 76 without isolation because of the high reactivity of the epoxide groups.

The following Scheme 45 illustrates this reaction,

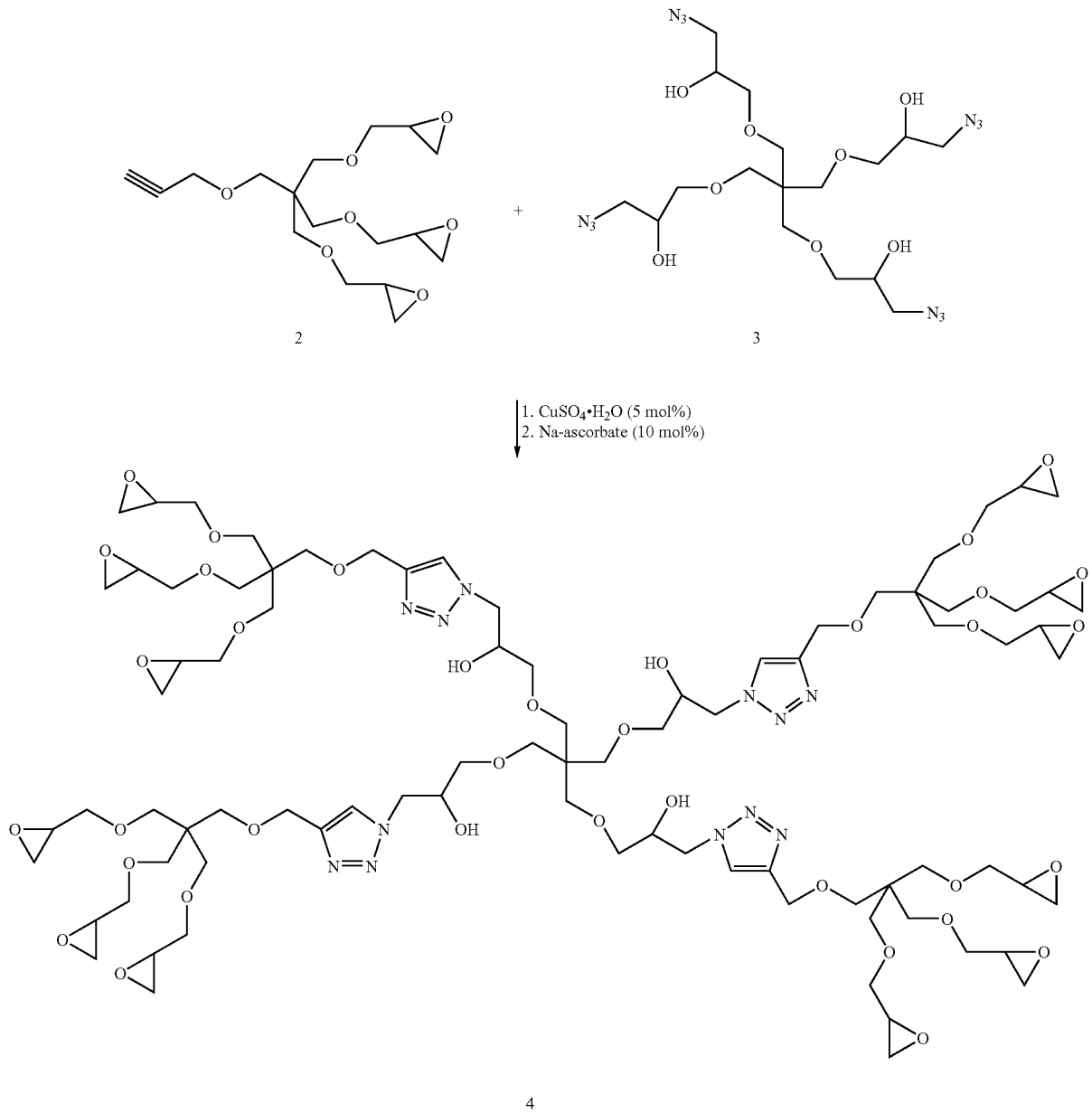

EXAMPLE 42

Reaction of Dimethylacetylene Dicarboxylate with Pentaerythritol Tetrazide (PETAZ) to Produce PEHAM Dendrimer G=1.5 with a Four-Arm Core and Methyl Ester Surface in One Step

[(C)=PETGE; (IF1)=OH; (BR1)=Triazole; (TF)=methyl ester; G=1.5]

Dimethylacetylene dicarboxylate (411.3 mg, 2.894 mmol) (Acros Organics) was mixed with PETAZ (385.0 mg, 0.724 mmol) (made from Example G). To this mixture was first added 1.5 mL of 1:1 t-BuOH:H$_2$O, followed by the addition of sodium ascorbate (55.0 mg, 0.28 mmol) as a solid, followed by the addition of CuSO$_4$ 5H$_2$O (36.0 mg, 0.14 mmol). The reaction was stirred at RT for 48 hours. MALDI-TOF analysis revealed the presence of a small amount of tri-substituted product PETAZ. Therefore, additional dimethylacetylene dicarboxylate (70.0 mg) was added to the reaction mixture, and the reaction was stirred overnight. The solvent was removed by rotary evaporation, and the residue dried on high vacuum overnight. The residue was re-dissolved in DCM, leaving a solid material that was removed by filtration. Volatile materials were removed by rotary evaporation, giving the desired product as a light yellow oil (700.0 mg; 90% yield). Its spectra are as follows:

MALDI-TOF: C$_{41}$H$_{56}$N$_{12}$O$_{24}$; Calc. 1101.0, found 1101.6 [M+H]$^+$ and 1123.6 [M+Na]$^+$ amu.

The following Scheme 46 illustrates this reaction.

Scheme 46.

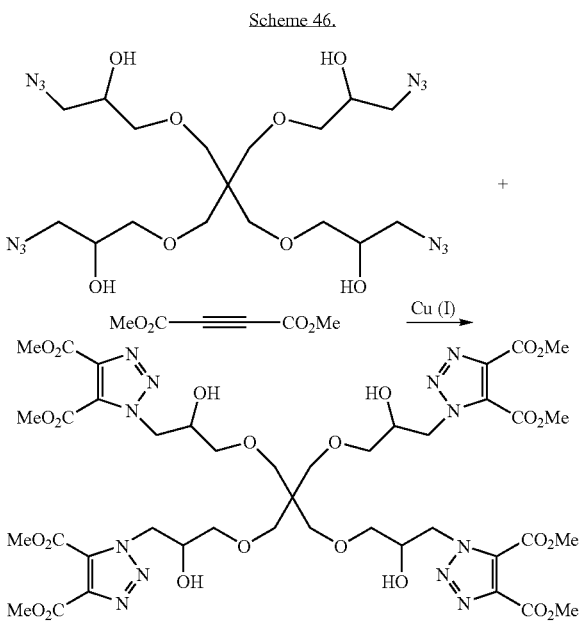

EXAMPLE 43

Alkylation of Amine

[(C)=PETGE; (IF1)=OH; (EX1)=Ethyl PIPZ; (BR1) in situ=Methylacrylate; (TF)=Methyl ester; G=1.5]

Methyl acrylate (861.0 mg, 10.0 mmol) (Acros) was dissolved in 1 mL of MeOH and cooled to 0° C. Then a solution of the previously made tetraamine (489.0 mg, 0.56 mmol) (made by Example 11) in 4 mL of MeOH was added dropwise. After the addition, the reaction was allowed to warm to RT. The mixture was then heated to 40° C. for 48 hours. Solvent was removed and give the product as a pale yellow oil (820 mg, 89% yield) that has the following spectrum:

MALDI: Calc. 1565; found 1566.67 ($M^+H$), 188.69 ($M^+Na$) amu.

Scheme 47 illustrates this reaction:

Scheme 47

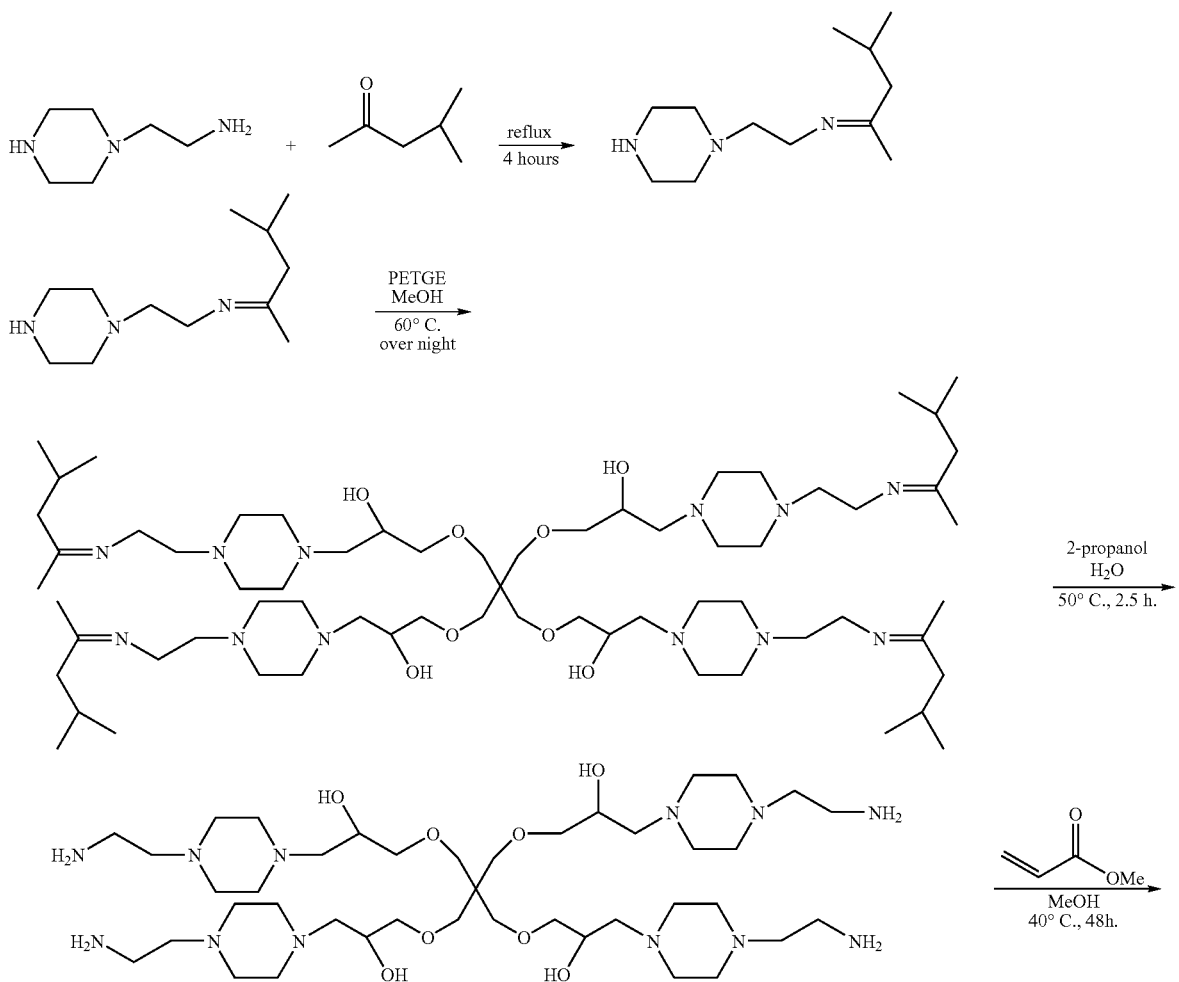

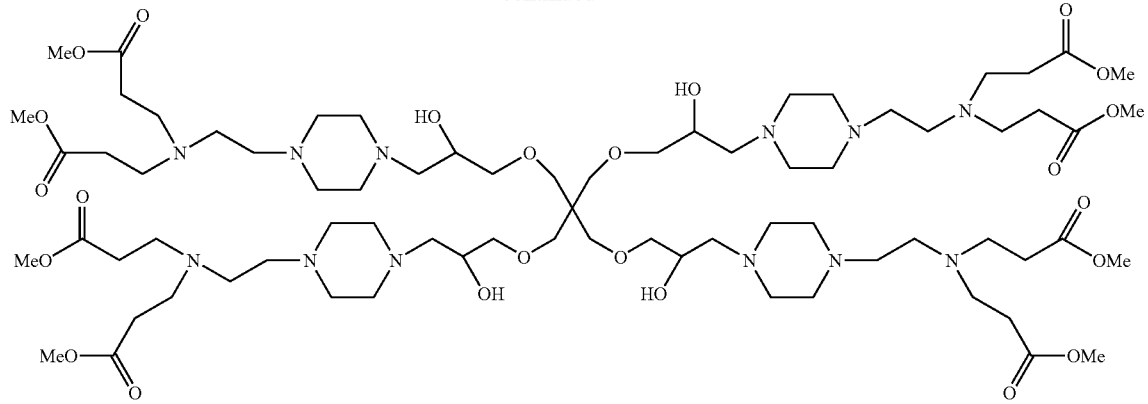

EXAMPLE 44

Pyrrolidone Derivative from Primary Amine

[(C)=PETGE; (IF1)=OH; (BR1)=DETA; (EX1)=Pyrrolidone; (TF)=Methyl ester; G=1.5]

DMI (1.0 g, 6.32 mmol) (Acros) was dissolved in 2.5 mL of MeOH and cooled to 0° C. Then a solution of the octa amine (made by Example 27) in 7 mL of MeOH was added to the previous solution. After the addition, the reaction was allowed to warm to RT and stirred for 24 hours. After removal of solvent, the MALDI-TOF was determined and its spectra is as follows:

MALDI-TOF: Calc. 1771; found 1804.246 (M$^+$Na) amu.

Scheme 48 illustrates this reaction:

Scheme 48

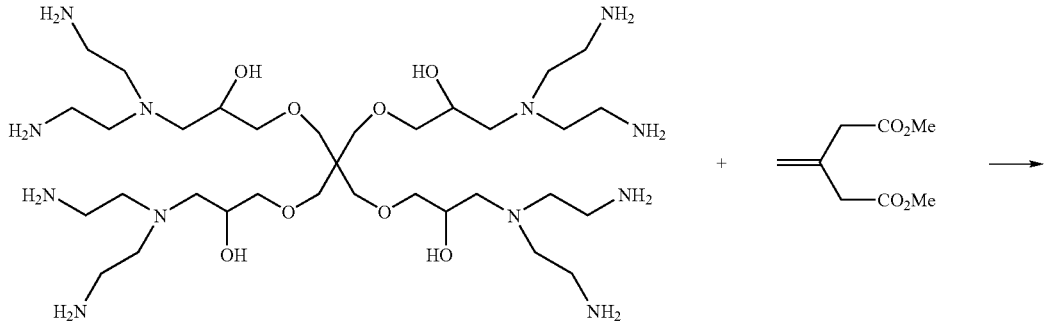

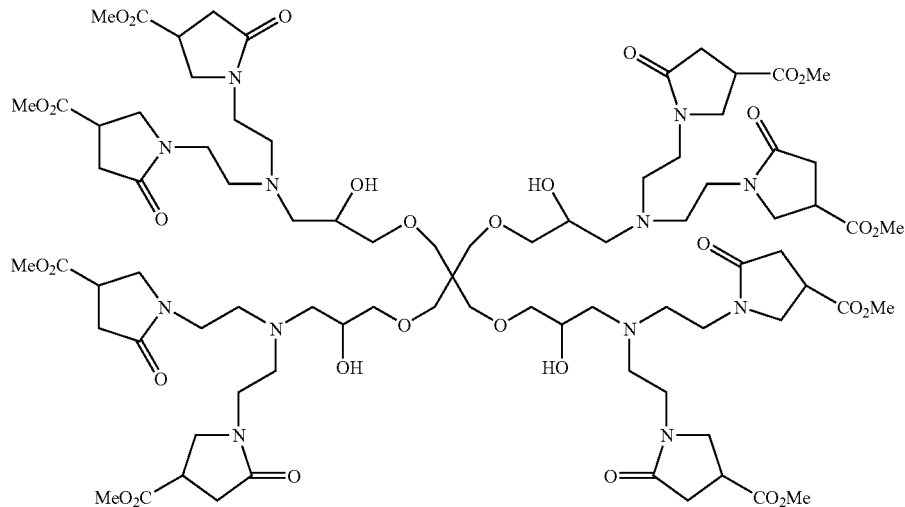

EXAMPLE 45

Isocyanurate with Protected Diethylenetriamine

[(C)=TEPC; (IF1)=OH; (BR1)=DIA; (EX1)=Pyrrolidone; (TF)=Methyl ester; G=1.5]

A. To a stirring solution of 1,7-bis(methyl-isopropylidine) diethylenetriamine (2.15 g, 9.0 mmol) [made from the procedure in F. Laduron et al., *Org. Process Res. & Develop.* 9, 102-104 (2005)] in 15 mL of MeOH was added TGIC (0.594 g, 2 mmol) (Aldrich) all at once at RT. Isocyanurate is not soluble initially but dissolved after heating for about 3 hours at 50° C. Heating continued for 2 days. TLC (1:2:2 of hexanes:ethyl acetate:chloroform) indicated that isocyanurate was consumed completely. Solvent was removed on a rotary evaporator and then dried under high vacuum, which gives a yellow liquid. MALDI-TOF mass spectrometry indicated mass for compound 3 but not compound 2 and few other compounds.

B. The above reaction mixture was dissolved in 30 mL of a mixture of 10:90 water:isopropanol (% v/v) and heated at 50° C. for 1 day. Isopropanol and water were removed on a rotary evaporator, and the residue distilled by Kugelrohr distillation to give a yellow colored, viscous liquid (1.83 g; 1.21 g theoretical yield). MALDI-TOF showed mass for compound 3 and its spectra are as follows:

MALDI-TOF: $C_{24}H_{54}N_{12}O_6$ Calc. 606; found 607 ($M^+H$) & 629 ($M^+Na$) amu.

C. To a 4° C. cold solution in an ice-bath of DMI (1.9 g, 12.0 mmol) was added a solution of compound 3 (606 mg, 1.0 mmol; prepared in Example 45B) in 4 mL of MeOH dropwise over a period of 10 mins. The ice-bath was removed and the mixture stirred at RT. After 1 day, MALDI-TOF mass spectrometry indicated masses at 1364 and 1386 amu. Stirring continued for 2 days. Then the solvent was removed on a rotary evaporator and the crude reaction mixture subjected to column chromatography on silica gel. Initially, excess of DMI was eluted with 1:2:2 of hexanes:ethyl acetate:chloroform, followed by elution with 5:1 DCM:$CH_3OH$, giving hexa-pyrrolidone surface dendrimer 4 as a hygroscopic solid that has the following spectra:

$^1$H NMR: (300 MHz, $CD_3OD$): δ 2.52-2.60 (m, 18H), 2.66 (d, J=8.70 Hz, 6H), 2.73 (d, J=4.80 Hz, 6H), 3.47-3.34 (m, 12H), 3.72 (s, 18H), 3.76-3.90 (m, 12H), 3.64-3.70 (m, 12H), 4.00 (quintet, J=3.30 Hz, 3H); and $^{13}$C NMR: (75 MHz, $CD_3OD$): δ 33.90, 35.85, 40.53, 40.58, 47.02, 49.79, 51.79, 58.10, 66.93, 150.20, 173.91, 174.17; and IR (Neat): $\lambda_{max}$ 3374, 3052, 2952, 2842, 2822, 1735, 1686, 1495, 1461, 1363, 1271, 1203, 1072, 1024, 937, 847, 766, 732, 700 cm$^{-1}$; and MALDI-TOF: $C_{60}H_{90}N_{12}O_{24}$ Calc. 1363; found 1364 ($M^+H$) & 1386 ($M^+Na$) amu.

Scheme 49 illustrates the above reactions:

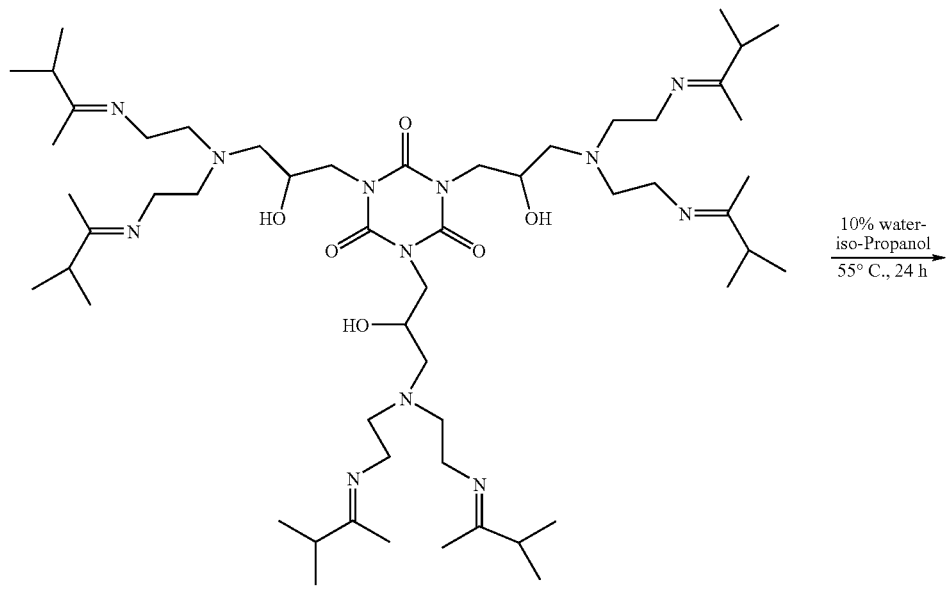

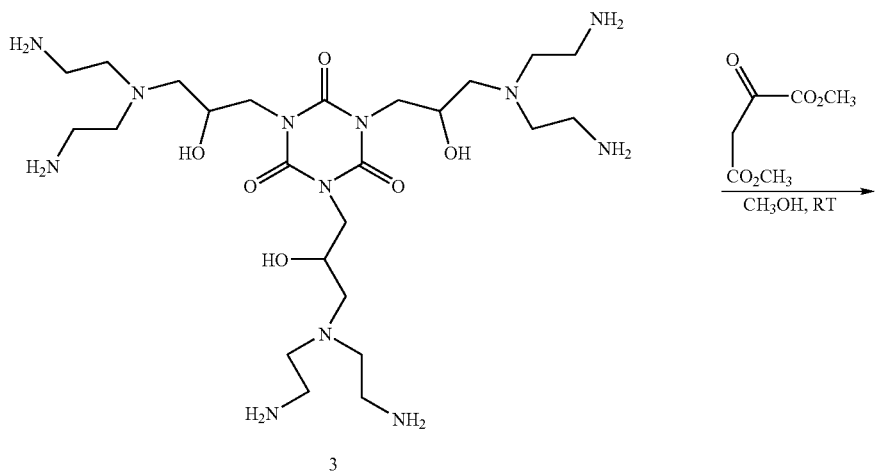

3

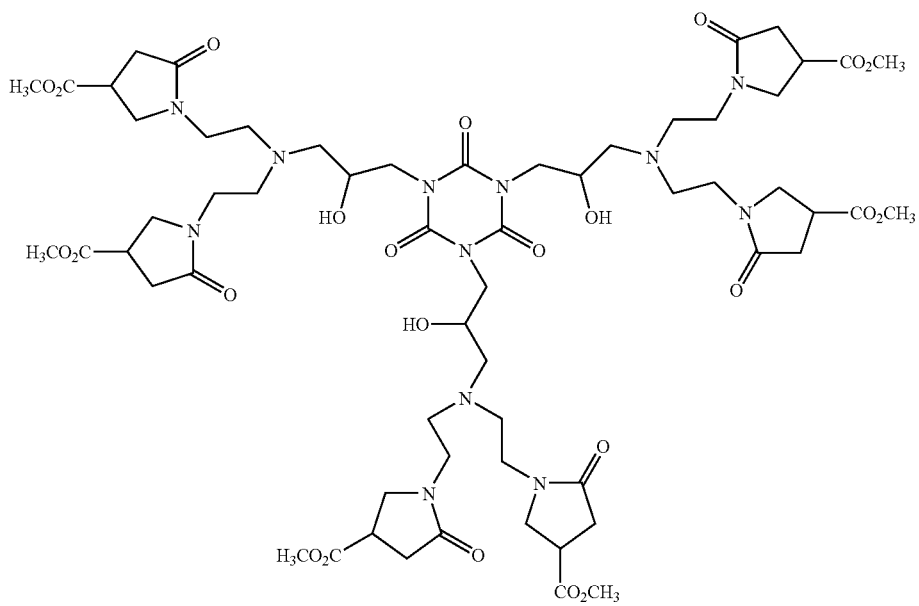

4

EXAMPLE 46

Reaction of Tetraphenylolethane Glycidylether (TPEGE) with tris(hydroxymethylaminomethane (TRIS)

[(C)=TPEGE; (IF1)=OH; (BR1)=TRIS; (TF)=OH; G=1]

To a 100-mL round bottom flask was added TPEGE (5.0 g, 80.0 mmol, 32 mmol epoxide) and 20 mL of diglyme under mechanical stirring. To this mixture was added TRIS (8.0 g, 66.0 mmol, 2 equiv. per epoxide) and 20 mL of MeOH. The mixture was heated at 55° C. for 48 hours under a $N_2$ atmosphere. Then volatile material was removed by rotary evaporation, and the crude residue dissolved in a ~1:1 methanol-water mixture and purified in a tangential flow UF device using 3K regenerated cellulose membranes at a pressure of 20 psi (137.9 kPa). The retentate was adjusted with an appropriate volume of MeOH or water to keep the mixture homogeneous. A total of 850 mL of permeate were obtained. The retentate was concentrated by rotary evaporation, followed by drying of the residue on high vacuum to give the desired product (5.6 g, 88% yield) and its spectra are as follows:

$^{13}$C NMR (125 MHz, DMSO-d6): δ 68.94, 70.59, 78.71, 80.08, 80.23, 123.46, 138.48, 146.60, 165.82; and MALDI-TOF MS: $C_{54}H_{82}N_4O_{20}$ Calc. 1107.2; found 1130 [M+Na]$^+$ amu.

The following Scheme 50 illustrates this reaction.

Scheme 50

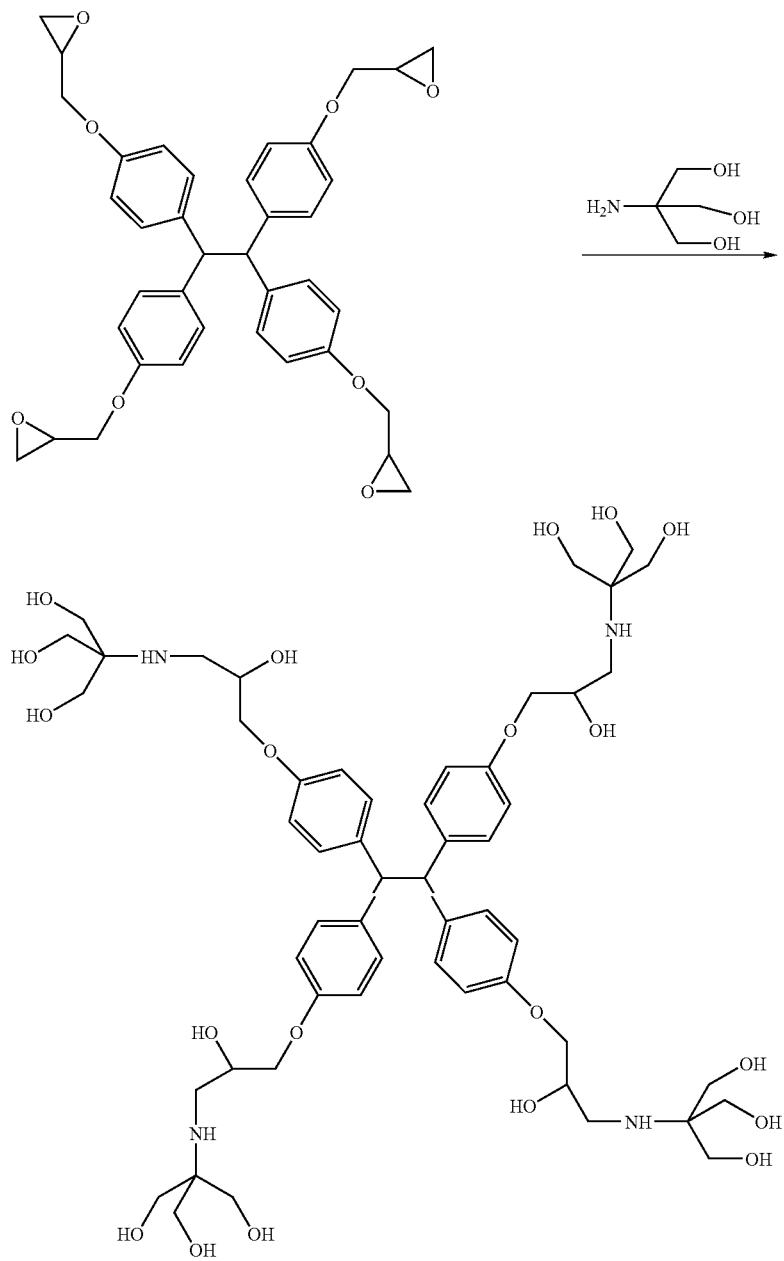

EXAMPLE 47

Reaction of Triphenylolmethane Triglycidylether (TPMTGE) with tris(hydroxymethyl)aminomethane (TRIS)

[(C)=TPMTGE; (FF)=H; (IF1)=OH; (BR1)=TRIS; (TF)=OH; G=1]

TPMTGE, I-d (0.46 g, 1.0 mmol) (Aldrich) and 30 mL of MeOH were placed in a 100-mL round bottom flask under mechanical stirring. TRIS (0.726 g, 6.0 mmol) (Aldrich) was added to the above reaction mixture all at once. Initially, these two starting materials were not soluble completely but dissolved after heating for 10-15 mins. Heating continued at 60° C. overnight. TLC indicated complete consumption of starting glycidyl ether during that time. Solvent was removed on a rotary evaporator to give a colorless solid. The solid was dissolved in a 60 mL 3:1 chloroform:MeOH (% v/v) under heating. After cooling to RT, hexanes were added to precipitate the excess TRIS, which was removed by filtration through a Büchner funnel. Evaporation of the filtrate gave hydroxyl terminated (G=1) dendrimer, III-e (yield, 0.815 g, 99%). Its spectra are as follows:

$^1$H NMR (300 MHz, DMSO-d6): δ1.28-1.171 (t, J=6.00 Hz, 3H), 1.48 (bs, 9H), 2.47 (s, 3H), 3.77-3.84 (m, 6H), 4.22 (m, 18H), 4.98 (bs, 3H), 5.72 (s, 1H), 6.62-6.88 (m, 8H), 6.92 (m, 4H); and $^{13}$C NMR (75 MHz, DMSO-d6): δ44.72, 55.59, 60.08, 61.64, 69.86, 71.31, 114.74, 114.87, 128.02, 130.48, 137.17, 157.51; and MALDI-TOF: $C_{40}H_{61}N_3O_{15}$ Calc. 823; found 847 [M+Na]$^+$ amu.

The following Scheme 51 illustrates this reaction.

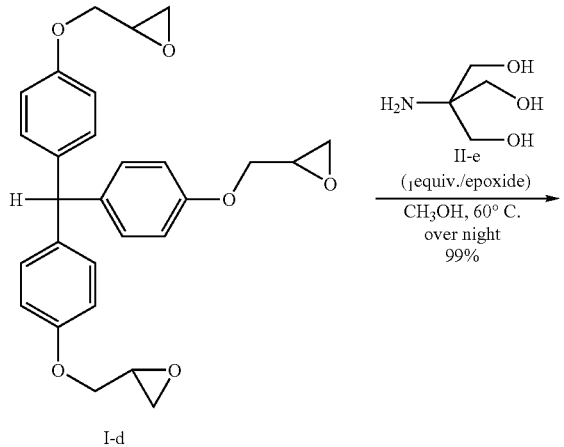

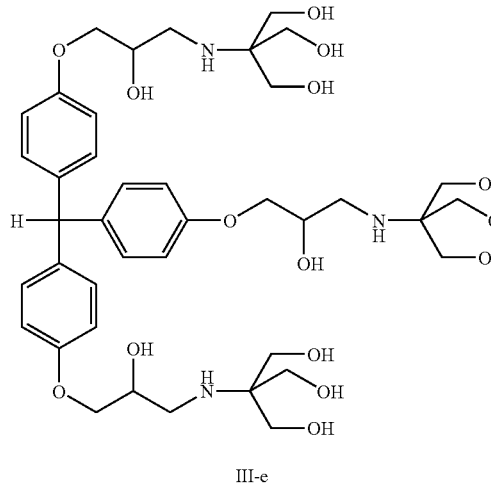

EXAMPLE 48

Reaction of Pentaerythritol Tetraglycidylether (PETGE) with tris(hydroxymethyl)aminomethane (TRIS)

[(C)=PETGE; (IF1)=OH; (BR1)=TRIS; (TF)=OH; G=1]

In a 250-mL round bottom flask, PETGE (3.16 g, 8.78 mmol) was dissolved into 70 mL of MeOH under mechanical stirring. The solution was placed into a 60° C. oil bath, and TRIS (6.41 g, 52.8 mmol, 1.50 equiv./epoxide) (Fisher Scientific) was added via a powder funnel. The flask was then arranged with a reflux condenser and allowed to react for 48 hours. The reaction was monitored by TLC (3:1 CH$_2$Cl$_2$:MeOH) and no PETGE was observed (R$_f$=0.80) after that time. The mixture was diluted with 120 mL of chloroform, then 300 mL of hexanes were added slowly under stirring. A white precipitate formed and the mixture was allowed to stand for 16 hours. The solution was filtered through a Büchner funnel to yield a clear, white paste at the bottom of the flask. The paste was dried under vacuum to yield 6.98 g of crude product. The product was re-dissolved into 40 mL of MeOH and 60 mL of chloroform and remaining TRIS was separated by crystallization from 300 mL of hexanes. The mixture was filtered and the remaining semisolid dried under high vacuum for 24 hours to yield 5.35 g product (72.0% yield, 7.43 g theoretical mass). For further purification, the material was loaded onto a 36"×4" (91 cm×10 cm) LH-20 Sephadex™ column. After the void volume of 575 mL was collected, 48 fractions each of 12 mL of MeOH were collected and analyzed by TLC (7:3 MeOH:NH$_4$OH). 2.29 g (31% yield) of purified product was recovered. Its spectra are as follows:

$^1$H NMR (500 MHz, D$_2$O): δ 2.644 (1H, q, J=4.88 Hz), 2.76 (1H, q, J=3.625), 3.34 (2H, s) 3.44 (2H, d, J=9.0 Hz), 3.54 (2H, q, J=6.75 Hz), 3.79 (1H, s), 4.80 (4H, s); and $^{13}$C NMR (75 MHz, D$_2$O): δ 45.43, 46.91, 49.85, 61.01, 62.69, 71.14, 75.43, 79.42; and MALDI-TOF: $C_{33}H_{72}N_4O_{20}$ Calc. 845; found 867 [M+Na]$^+$ amu.

The following Scheme 52 illustrates this reaction.

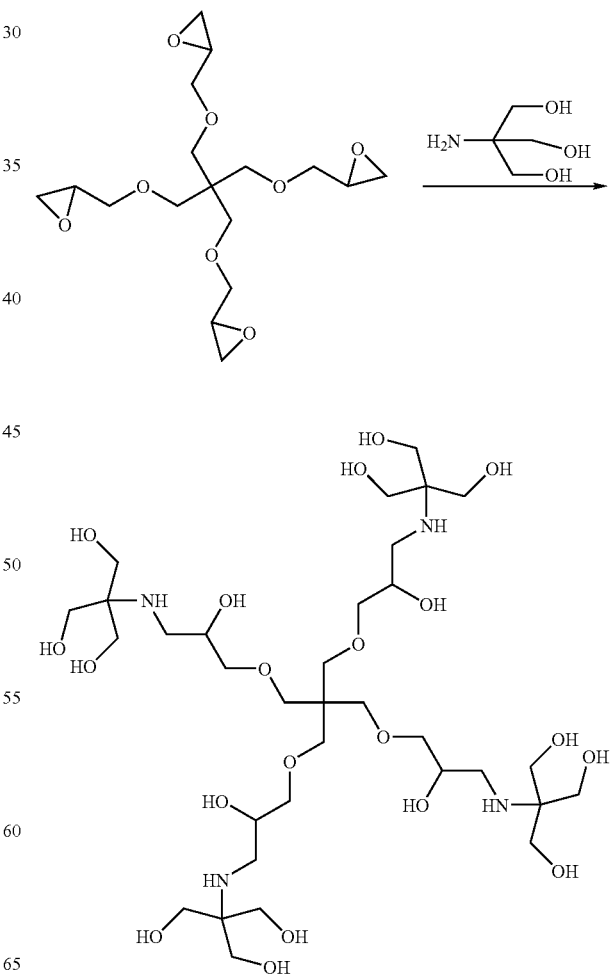

EXAMPLE 49

Reaction of Tetraphenylolethane Glycidylether with Diethyliminodiacetate (DEIDA)

[(C)=TPEGE; (IF1)=OH; (BR1)=DEIDA; (TF)=Ethyl ester; G=1.5]

To a 100-mL round bottom flask was added TPEGE (5.0 g, 8.0 mmol, 32 mmol epoxide) and 20 g of diglyme under mechanical stirring. To this mixture was added DEIDA (12.0 g, 63.4 mmol, 2 equiv. per epoxide) and 20 mL of MeOH. The mixture was stirred at 45° C. for 3.5 days under a blanket of $N_2$ gas. After cooling to RT, volatile material was removed by rotary evaporation to give 13.0 g of crude material that was purified in MeOH using a tangential flow UF device containing 3K regenerated cellulose membranes at a pressure of 20 psi (137.9 kPa) to give 1.2 liters of permeate. TLC (MeOH, $R_f$=0.85) of this mixture indicated complete consumption of DEIDA. The crude product was further purified by dissolution in 15 mL of acetone and chromatography using silica gel (150 g, 60 angstrom, 200-400 mesh) and MeOH in a wide bore column. A total of 1.5 liters of MeOH was eluted to remove impurities. The purified product was eluted with acetone by taking 100-mL fractions and monitoring for product and purity by TLC. Fractions 7-12 were collected and concentrated by rotary evaporation to give the desired product (2.81 g, 43% yield based on a 60% purity of the commercially available starting material). Its spectra are as follows:

$^{13}$C NMR (125 MHz, CDCl$_3$): δ 14.19, 29.28, 30.90, 31.73, 50.09, 51.81, 53.83, 54.13, 55.91, 56.12, 56.79, 58.44, 60.96, 67.26, 114.24, 114.66, 129.38, 136.87, 156.01, 166.71, 169.34, 169.78, 171.86, 172.28; and MALDI-TOF MS: $C_{71}H_{99}N_4O_{24}$ Calc. 1378.6; found 1379 [M]$^+$ amu.

The following Scheme 53 illustrates this reaction.

Scheme 53

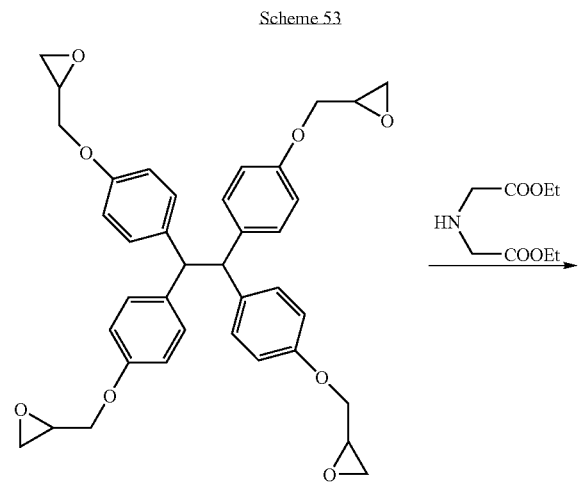

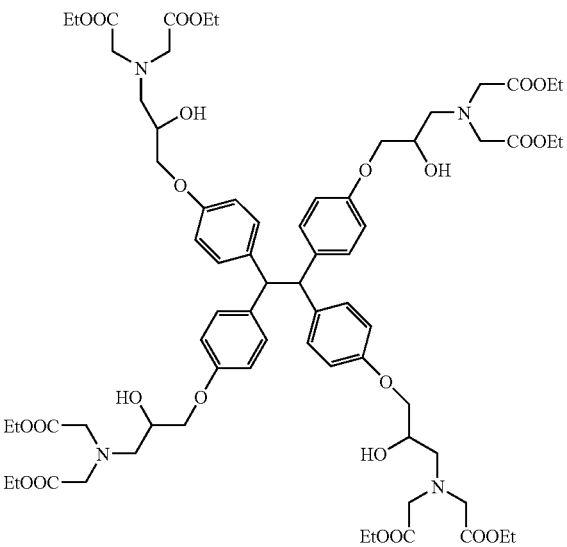

EXAMPLE 50

Reaction of Triphenylolmethane Triglycidylether with Diethyliminodiacetate (DEIDA)

[(C)=TPMTGE; (FF)=H; (IF1)=OH; (BR1)=DEIDA; (TF)=Ethyl ester; G=1.5]

TPMTGE, I-d (0.92 g, 2.0 mmol) and 30 mL of MeOH were placed in a 100-mL round bottom flask, followed by addition of a solution of DEIDA (1.417 g, 7.5 mmol) (Aldrich) in 10 mL of MeOH. The flask was equipped with a stir bar and refluxing condenser and heated at 60° C. for 36 hours. The solvent was removed on a rotary evaporator under reduced pressure, leaving a pale yellow colored liquid. The liquid was purified by column chromatography on silica gel (9' height×1.5' width) (2.7 m×0.45 m). First, 30% ethyl acetate/hexanes was used to elute the excess of DEIDA, followed by 5% MeOH/chloroform used to elute the product III-g (1.929 g, 93.91% yield). Its spectra are as follows:

$^1$H NMR (300 MHz, CDCl$_3$): δ 1.26 (t, J=6.90 Hz, 18H), 3.34-3.55 (m, 12H), 3.61 (s, 3H), 3.65-3.79 (m, 6H), 3.88-4.04 (m, 9H), 4.13-4.22 (m, 13H), 6.71-6.35 (m, 6H), 6.89-6.99 (m, 6H); and $^{13}$C NMR (75 MHz, CDCl$_3$): δ 14.44, 48.91, 50.09, 50.26, 50.36, 51.05, 52.11, 54.38, 56.34, 57.03, 58.28, 58.74, 61.16, 67.44, 69.85, 77.05, 111.45, 114.44, 120.69, 127.79, 130.21, 130.40, 130.48, 130.55, 157.30, 169.61, 172.18, 172.59; and MALDI-TOF: $C_{52}H_{73}N_3O_{15}$ Calc. 1027; found 1050 [M+Na]$^+$ amu.

The following Scheme 54 illustrates this reaction.

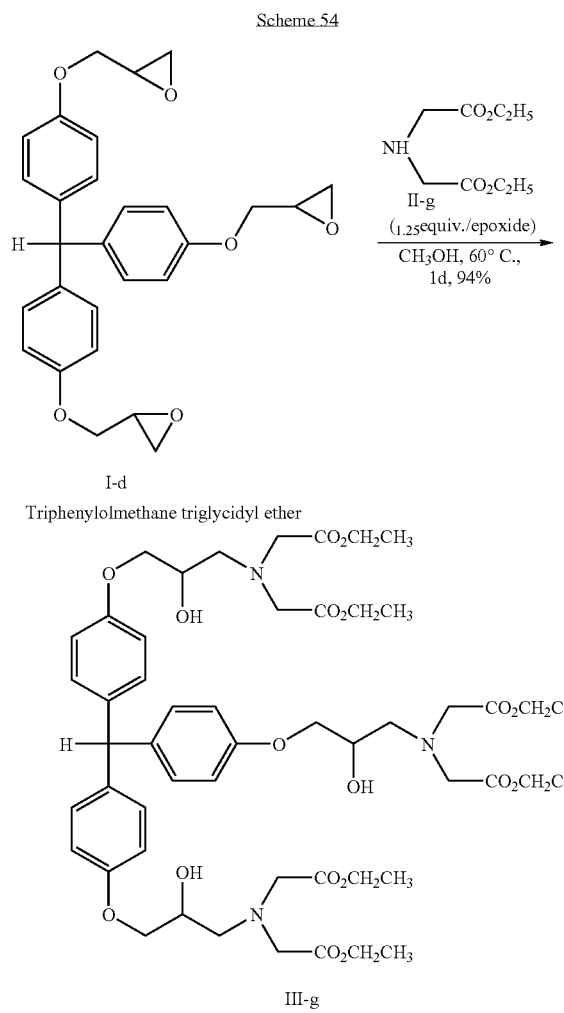

EXAMPLE 51

Reaction of Pentaerythritol Tetraglycidylether with Diethyliminodiacetate (DEIDA)

[(C)=PETGE; (IF1)=OH; (BR1)=DEIDA; (TF)=Ethyl ester; G=1.5]

To a solution of DEIDA, 2 (5.67 g, 30 mmol) (Aldrich) in 35 mL of EtOH (Aldrich) was added a solution of PETGE, 1 (1.8 g, 5 mmol, 20 epoxy mmol) in 20 mL of EtOH (Aldrich) dropwise over a period of 30 mins. through an addition funnel. The flask was arranged with a refluxing condenser, $N_2$ gas inlet and placed in a pre-heated oil bath at 60° C. After heating for 1 day, MALDI-TOF MS analysis showed the calculated mass for the perfect structure and the three-substituted products. Heating was continued for 36 hours, then the solvent was removed on a rotary evaporator, giving a tight brown colored liquid. Excess of DEIDA was distilled off by Kugelrohr distillation apparatus at 175° C. to give a viscous liquid, which was identified as the desired product 3 (4.99 g, 89.4%). Its spectra are as follows:

$^1$H NMR (300 MHz, CD$_3$OD): δ 1.24-1.29 (24H, t, J=7.20 Hz), 3.03-3.09 (4H, dd, J=3.60 Hz), 2.78-2.85 (4H, bt, J=9.0 Hz), 3.41 (12H, s), 3.45 (8H, s), 3.61 (8H, d, J=5.40 Hz), 4.14-4.21 (16H, q, J=6.60 Hz), 4.61-4.67 (4H, sextet, J=4.20 Hz); and $^{13}$C NMR (75 MHz, CD$_3$OD): δ 13.41, 13.45, 45.89, 49.79, 53.65, 55.77, 56.21, 57.97, 60.57, 60.69, 68.71, 69.79, 69.93, 71.31, 73.55, 78.43, 78.46, 168.62, 170.26, 172.30; and IR (Neat): ν$_{max}$ 3457, 2980, 2934, 2904, 2868, 1741, 1675, 1460, 1378, 1250, 1198, 1163, 1106, 1065, 1029, 927, 860, 819, 732 cm$^{-1}$; and MALDI-TOF MS: C$_{49}$H$_{88}$N$_4$O$_{24}$ Calc. 1117.2; found 1117.7 [M]$^+$, 1139.7 [M+Na]$^+$ amu.

The following Scheme 55 illustrates this reaction.

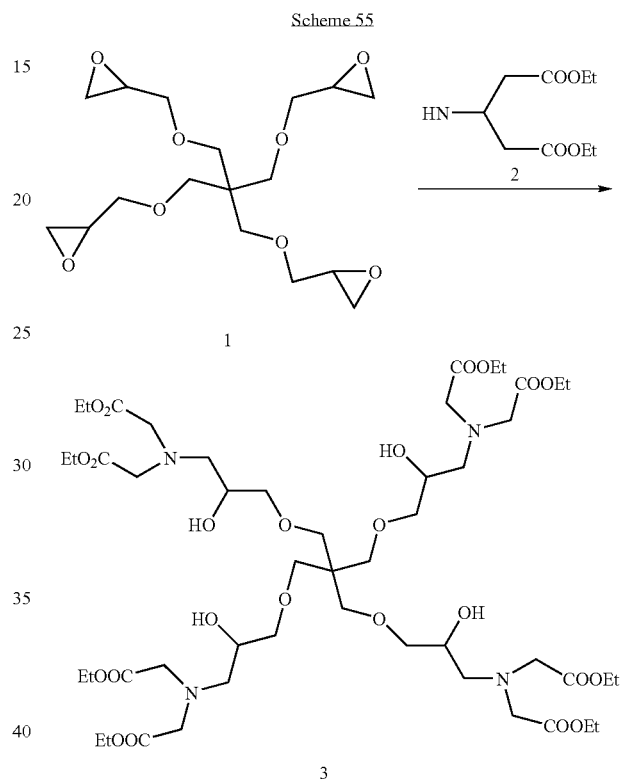

EXAMPLE 52

Reaction of tris(2,3-epoxypropyl)isocyanurate with bis(allylamine)

[(C)=TGIC; (IF1)=OH; (BR1)=BAA; (TF)=(=CH$_2$); G=1]

A 50-mL round bottom flask was charged with BAA (5.82 g or 737 mL, 60 mmol) (Aldrich) and 20 mL of MeOH (Fisher Scientific). Then TGIC (2.97 g, 10 mmol, 30 epoxy mmol) (Aldrich) was added under mechanical stirring. The flask was arranged with a refluxing condenser, and the mixture heated for one day. MALDI-TOF analysis indicated the calculated mass for product 3. The solvent and excess BAA was removed on a rotary evaporator, and the residue dried under high vacuum, giving the desired product 3 as a pale yellow colored, viscous liquid (5.8 g, 98.6%). Its spectra are as follows:

$^1$H NMR (500 MHz, CDCl$_3$): δ 2.47-2.53 (6H, m), 3.06 (6H, dd, J=7.00 & 7.00 Hz) 3.22 (6H, dd, J=6.00 & 6.00 Hz), 3.84-3.87 (3H, m), 3.99 (4.00 (3H, m), 4.05-4.10 (3H, m), 5.14-5.18 (12H, m), 5.76-5.84 (6H, m); and $^{13}$C NMR (125 MHz, CDCl$_3$): δ 47.16, 56.84, 56.89, 56.93, 57.17, 65.80, 111.37, 135.13, 149.88, 149.91; and IR (Neat): v$_{max}$ 3421, 3083, 3006, 2975, 2924, 2806, 1695, 1644, 1460, 1413, 1357, 1311, 1255, 1157, 1065, 999, 968, 917, 860, 835, 763 cm$^{-1}$; and MALDI-TOF MS: C$_{30}$H$_{48}$N$_6$O$_6$ Calc. 588.7; found 589.4 [M]$^+$, 611.4 [M+Na]$^+$ amu.

The following Scheme 56 illustrates this reaction.

Scheme 56

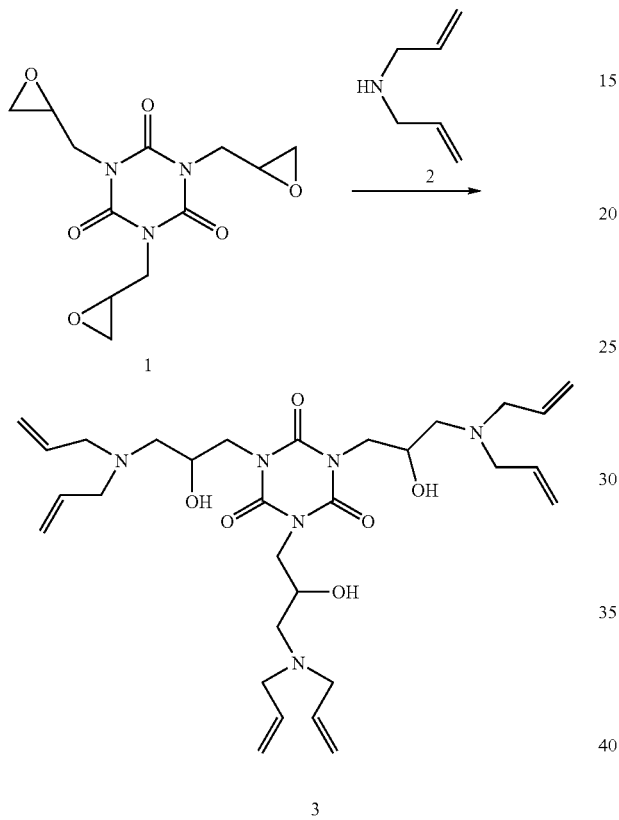

3

EXAMPLE 53

Reaction of Pentaerythritol Tetraglycidylether with bis(allylamine)

[(C)=PETGE; (IF1)=OH; (BR1)=BAA; (TF)=(=CH$_2$); G=1]

In a 250-mL round bottom flask BAA (4.68 g, 48.2 mmol, 1.5 equiv. per PETGE) (Aldrich) was dissolved into 30 mL of MeOH under mechanical stirring. PETGE (2.87 g, 7.97 mmol) dissolved in 10 mL of MeOH was added via a 60-mL addition funnel over a period of 20 mins. An additional 20 mL of MeOH was used for washing. The reaction was purged and blanketed with N$_2$ gas, then continued to stir for 48 hours. The reaction was followed by TLC (7:3 toluene:acetone, R$_f$=0.12) and stopped upon consumption of PETGE (R$_f$=0.60). MeOH was removed via rotary evaporator, followed by Kuglrohr distillation for 45 mins. at 1.5 hours at 110° C., which gave the desired product (5.44 g, 91.3% yield; 5.96 g theoretical yield). Its spectra are as follows:

$^1$H NMR (500 MHz, CDCL$_3$): δ 2.46 (1H, q, J=5.25 Hz), 2.2.55 (1H, q, J=4.5 Hz), 3.15 (4H, d, J=3.5 Hz), 3.36 (2H, q, J=3.4 Hz); 3.44 (2H, q, 6.0 Hz); 3.85 (1H, q, J=4.5 Hz); 4.83 (1H, s); 5.16 (4H, m, J=8.6 Hz); and 5.88 (2H, m, 5.1 Hz); and $^{13}$C NMR (75 MHz, CDCl$_3$): δ 46.90, 51.34, 58.52, 69.25, 71.24, 75.435, 118.45, 136.48; and IR (Neat): v$_{max}$ 3429, 3075, 3006, 2976, 2875, 2812, 1642, 1450, 1419, 1329, 1260, 1106, 996, 920, 869 cm$^{-1}$; and MALDI-TOF: C$_{41}$H$_{72}$N$_4$O$_8$ Calc. 749; found 771 [M+Na]$^+$ amu.

The following Scheme 57 illustrates this reaction.

Scheme 57

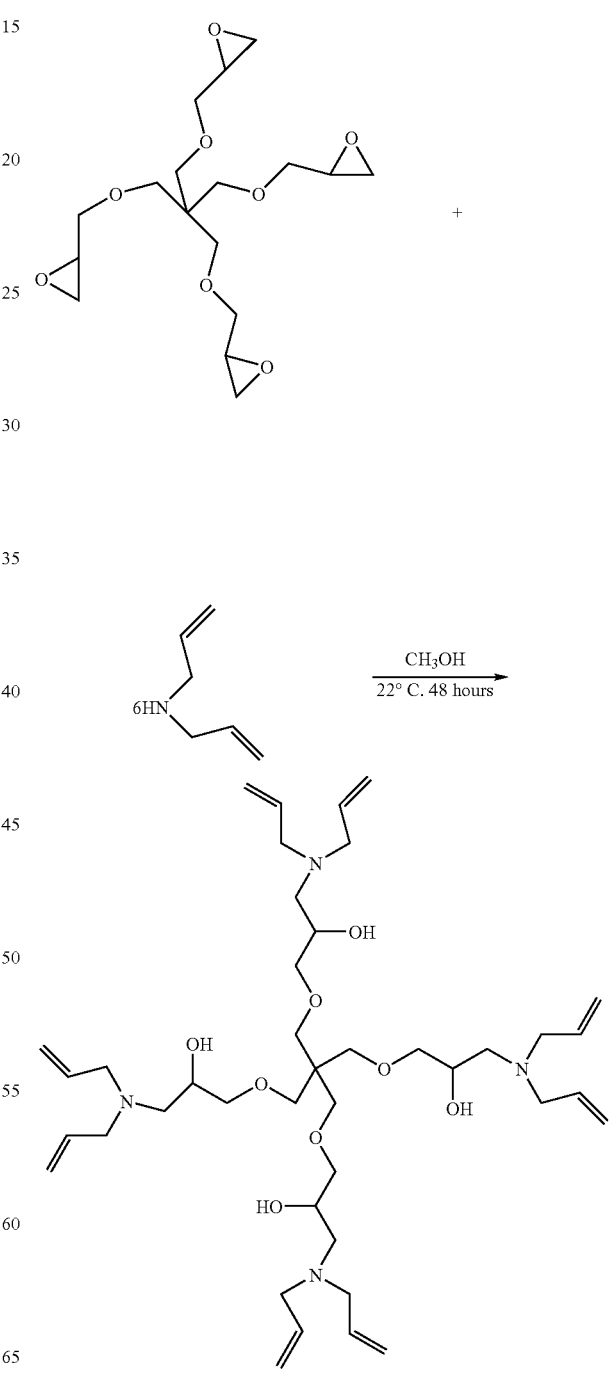

EXAMPLE 54

Reaction of Triphenylolmethane Triglycidylether with Diethanolamine

[(C)=TPMTGE; (FF)=H; (IF1)=OH; (BR1)=DEA; (TF)=OH; G=t]

TPMTGE, I-d (0.92 g, 2.0 mmol) and 30 mL of MeOH were placed in a 100-mL round bottom flask, followed by the addition of a solution of DEA (0.785 g, 7.5 mmol) in 10 mL of MeOH under mechanical stirring. The flask was equipped with a refluxing condenser and heated at 60° C. overnight. The progress of the reaction was monitored by TLC. Then the solvent was removed on a rotary evaporator under reduced pressure, giving a transparent liquid. The residue (1.746 g) was dissolved in 10 mL Of MeOH, followed by addition of 50 mL of ethyl acetate under occasional shaking. Formation of a colorless precipitate was observed during the addition of ethyl acetate. The flask was allowed to remain for 2 hours, while oil separated at the bottom of the flask. The mixture was separated by decantation, and the oil washed with ethyl acetate (2×1 mL). The oil was solidified by drying under high vacuum and gave 1.242 g of the desired product as a solid. Concentration of the solution on a rotary evaporator gave 0.522 g of a colorless transparent liquid, which was a mixture of product III-f and diethanolamine. Its spectra are as follows:

$^1$H NMR (300 MHz, CD$_3$OD): δ 2.92-2.58 (m, 6H), 2.60-2.77 (m, 12H), 3.29-3.31 (quintet, J=1.50 Hz, 3H), 3.46-3.67 (m, 6H), 3.57-3.67 (m, 6H), 3.80-4.00 (m, 10H), 4.84 (s, 6H), 6.02-6.86 (m, 6H), 6.90-6.97 (m, 4H), 7.08-7.20 (m, 2H); and $^{13}$C NMR (75 MHz, CD$_3$OD): δ 57.51, 58.28, 59.64, 67.97, 68.13, 70.23, 114.12, 130.10, 137.27, 157.52; and MALDI-TOF: C$_{40}$H$_{61}$N$_3$O$_{12}$ Calc. 775; found 799 [M+Na]$^+$ amu.

The following Scheme 58 illustrates this reaction.

Scheme 58

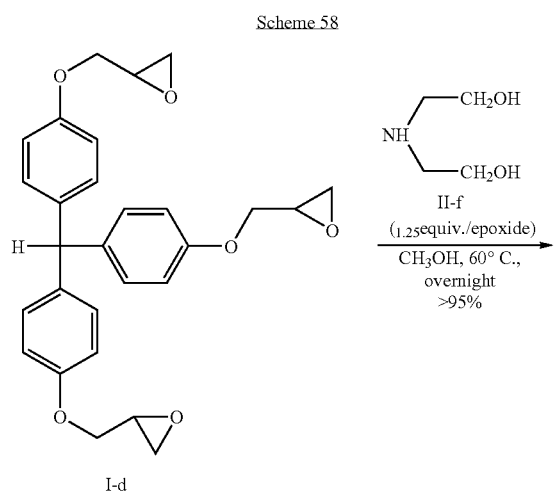

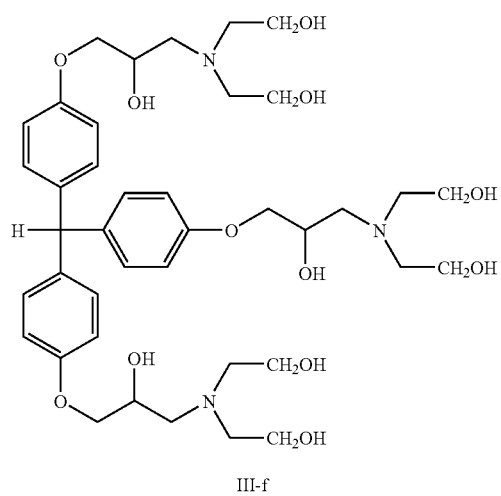

III-f

EXAMPLE 55

Reaction of Tetraphenylolethane Glycidylether with Protected di(ethylamino)amine

[(C)=TPEGE; (IF1)=OH; (BR1)=DETA; (TF)=Primary NH$_2$; G=1]

To a 100-mL round bottom flask containing a stir bar was added bis(methylisobutyliminoethyl)amine (62 mL of a 0.63 M solution in MIBK, 10.0 g, 38 mmol, 2 equiv. per epoxide) and 25 mL of MeOH. To this mixture was added TPEGE (5.0 g, 8.0 mmol, 32 mmol epoxide) (Aldrich) in 25 mL of diglyme. This homogeneous mixture was heated at 70° C. for 3 days under a N$_2$ atmosphere. Volatile material was removed on a rotary evaporator, and the resulting residue was bulb-to-bulb distilled using a Kugelrohr apparatus at 180-220° C. at high vacuum to give 9.0 g residue. An aliquot (830 mg) of this material was purified on a Sephadex™ LH-20 column in MeOH, taking 40 fractions of 2 mL each. TLC (10% NH$_4$OH in MeOH) indicated that fractions 1-20 contained the product. These fractions were collected and concentrated on a rotary evaporator to give 481 mg (62% yield) of the product. Its spectra are as follows:

$^{13}$C NMR: (125 MHz, CD$_3$OD) δ 40.08, 58.36, 58.87, 69.20, 71.40, 79.57, 115.14, 130.54, 138.30, 158.14; and MALDI-TOF MS: C$_{54}$H$_{90}$N$_{12}$O$_8$ Calc. 1035.4; found 1036 [M]$^+$, 1058 [M+Na]$^+$ amu.

The following Scheme 59 illustrates this reaction.

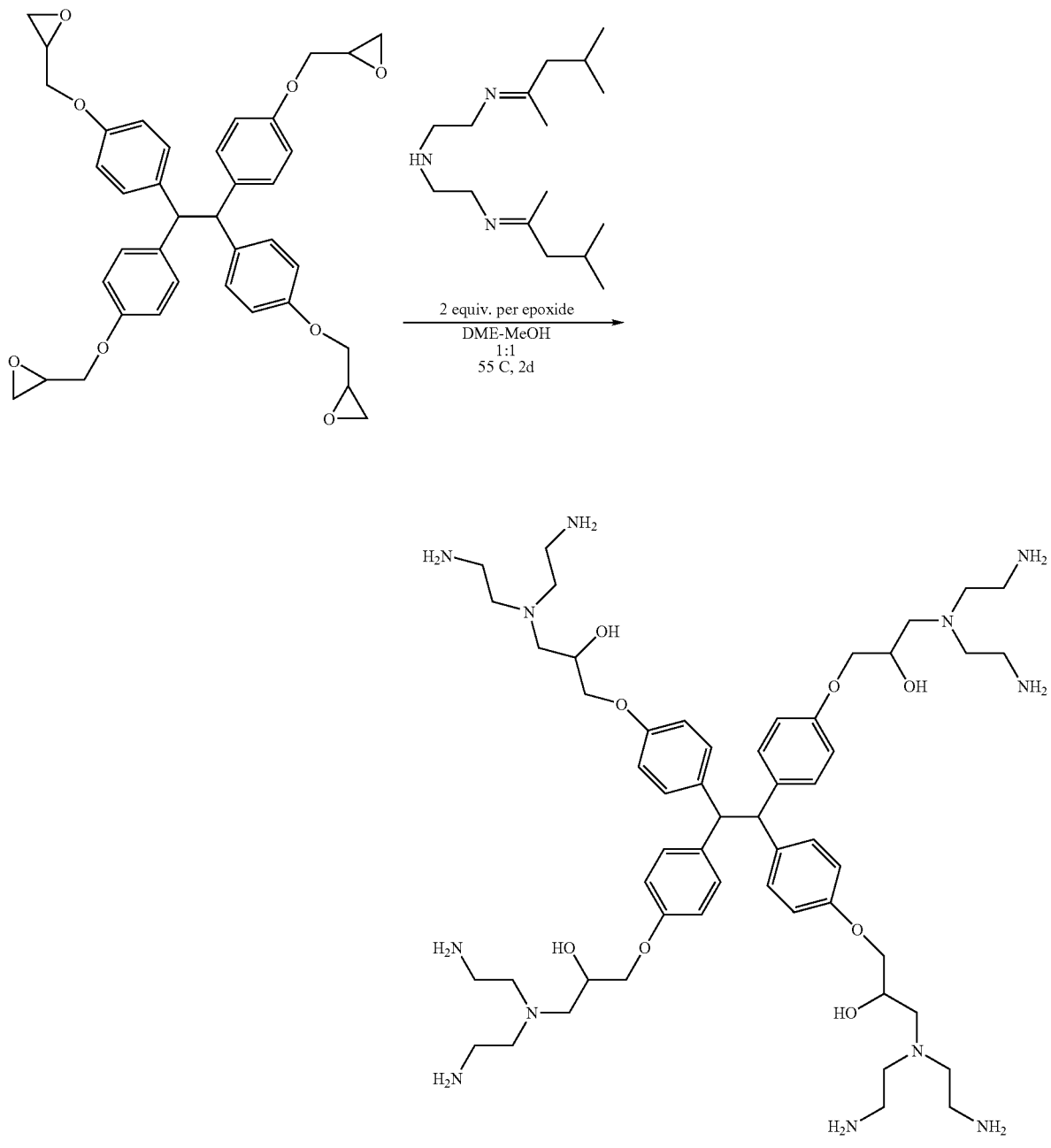

EXAMPLE 56

Reaction of the Product from Tetraphenylolethane Glycidylether with bis(methylisobutyl-iminoethyl)amine with Dimethylitaconate to Produce PEHAM Dendrimer G=1 with a Biocompatible Pyrrolidone Surface

[(C)=TPEGE; (IF1)=OH; (BR1)=DETA; (EX1)=DMI; (TF)=Methyl ester; G=1.5]

In a 250-mL round bottom flask DMI (2.19 g, 13.86 mmol, 1.24 equiv. per amine) (Acros Organics) was dissolved in 10 mL of MeOH under mechanical stirring, and the solution cooled to 4° C. Then G=1 dendrimer F1 (1.45 g, 1.40 mmol; made from Example 55) was dissolved in 15 mL of MeOH and added dropwise to the stirred solution over 30 mins. The addition funnel was washed with 5 mL of MeOH and allowed to warm to 22° C. overnight. The reaction progress was monitored by ninhydrin staining on a TLC plate. Upon complete consumption of the primary amine after 24 hours, the reaction was poured into two dialysis bags (24 mm diameter, 5 cm in length, 1,000 Dalton Spectra/Por®; Spectrum Laboratories) and placed into 1,000 mL of MeOH. The bulk MeOH was changed twice, each time after a 90-mins. dialysis. Then the product was transferred to a 500-mL round bottom flask, the solvent removed by rotary evaporation, and the residue placed under high vacuum for 24 hours to yield the G=1 dendrimer with pyrrolidone surface (1.80 g, 2.8% yield, 2.87 g theoretical yield). Its spectra are as follows:

$^1$H NMR (500 MHz, CDCl$_3$): δ 2.63 (1H, s), 2.76 (1H, s), 3.22 (2H, s), 3.42 (2H, s), 3.68 (4H, d, J=3.17), 3.85 (2H, m), 6.61 (1H, m), 6.96 (1H, m); and $^{13}$C NMR (75 MHz, CDCl$_3$): δ 33.97, 35.74, 37.38, 40.65, 51.82, 52.32, 67.00, 70.01, 114.03, 128.47, 129.18, 133.55, 136.39, 156.43, 172.73, 173.35; and FT-IR (Neat): ν$_{max}$ 3364, 2952, 1736, 1687, 1608, 1509, 1437, 1323, 1248, 1207, 1178, 1148, 1021, 937, 836, 751 cm$^{-1}$; and MALDI-TOF: C$_{102}$H$_{136}$N$_{12}$O$_{32}$ Calc. 2044.3; found 2067 [M+Na]$^+$ amu.

The following Scheme 60 illustrates this reaction.

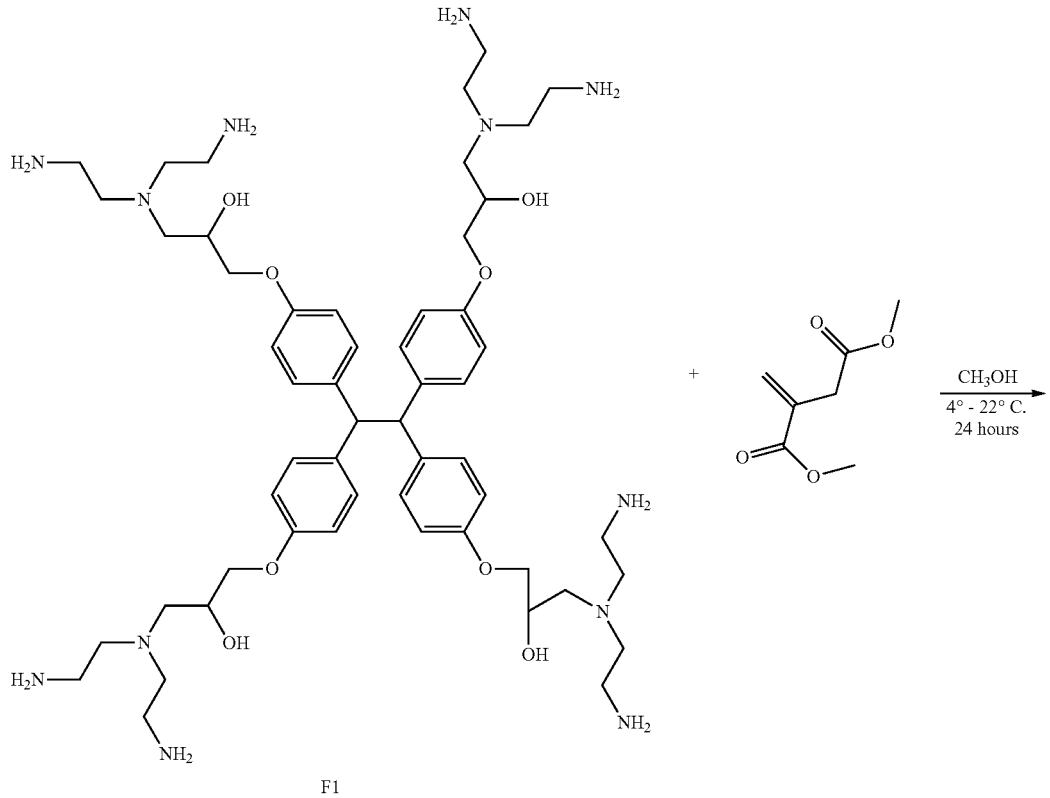

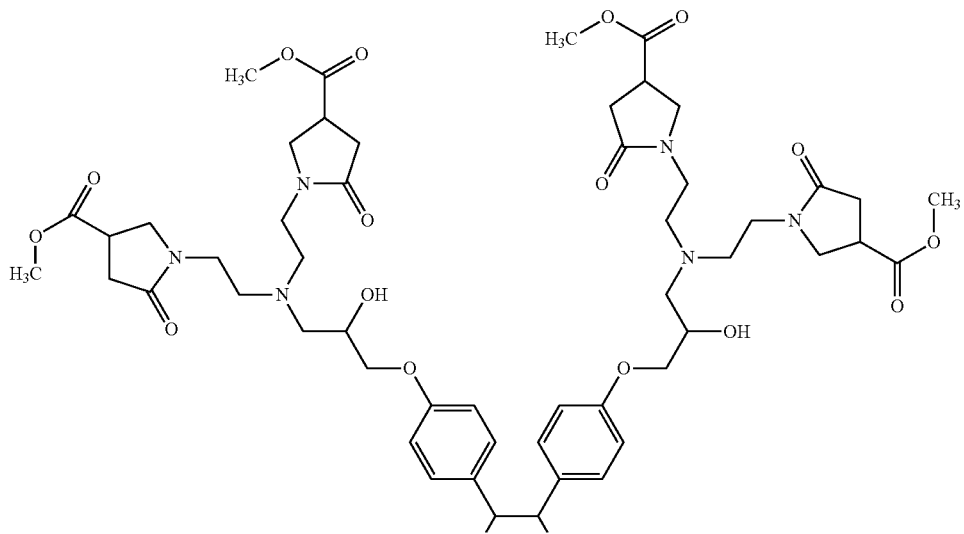

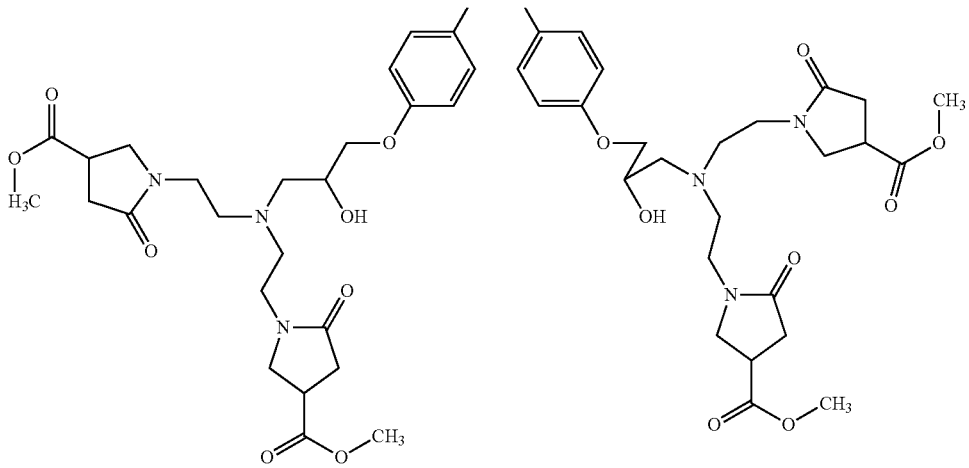

EXAMPLE 57

Preparation and Acetylation of PEHAM Dendrimer, G=1, $N_c$=4, $N_b$=2, Carboethoxy Surface

[(C)=PETGE; (IF1)=Acetyl; (EX1)=PIPZ; (IF2)=Acetyl; (BR1)=TMPTGE; (IF3)=Acetyl; (EX2)=EPC; (TF)= Carboxylate; G=1.5]

A. Preparation of PEHAM Dendrimer, G=1, $N_c$=4, $N_b$=2, Carboethoxy Surface

To a 50-mL round bottom flask containing a stir bar was added TMPTGE (7.2 g, 23.8 mmol, 6 equiv. per NH) and 30 g of MeOH. To this mixture at 25° C. was added dropwise over ~5 minutes pentaerythritol tetra(2-hydroxypropyl-3-piperazine)ether (690.0 mg, 0.98 mmol, 3.9 mmol NH) in 3 g of MeOH. This mixture was stirred for 36 hours at 25° C., sealed under a blanket of a $N_2$ atmosphere. Analysis of this mixture by TLC (MeOH with ninhydrin stain) showed no positive test for the presence of unreacted PIPZ-NH group. This mixture was purified of excess epoxide using a tangential flow ultrafiltration apparatus containing 1K regenerated cellulose membranes, maintaining the temperature at 25-26° C., to give 800 mL of permeate (~7 recirculations). A TLC (MeOH) of the retentate indicated complete removal of excess epoxide. Volatile materials were removed by rotary evaporation and high vacuum drying to give the desired product (2.4 g; 93% yield) that has the following spectrum:

$^{13}$C NMR (125 MHz, CD$_3$OD) δ 8.08, 14.98, 23.95, 44.61, 54.58, 62.53, 62.69, 68.74, 70.46, 71.31, 72.64, 73.32, 74.01, 75.37, 157.12.

The following Scheme 61 illustrates this reaction.

Scheme 61

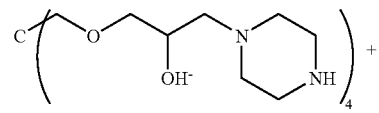

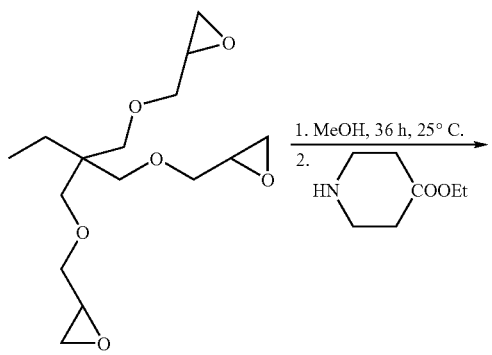

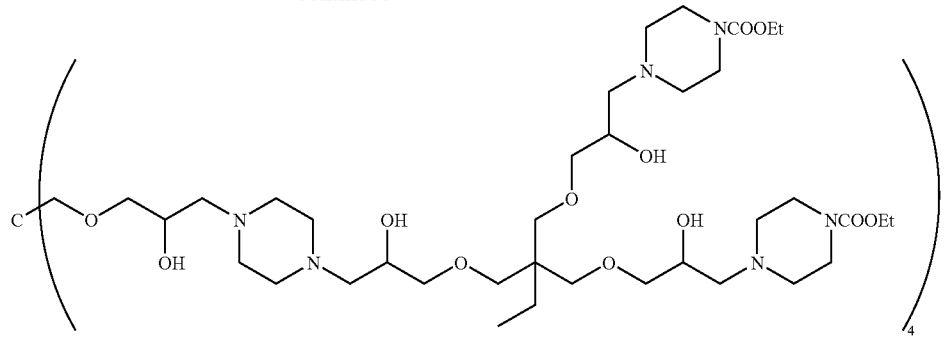

B. Acetylation of Pentaerythritol tetra(2-hydroxy-3-piperazine-N-ethyl Carboxylate)

To a 25-mL round bottom flask containing a stir bar was added PEHAM dendrimer, G=1, $N_c$=4, $N_b$=2, carboethoxy surface (500.0 mg, 0.155 mmol, 1.8 mmol OH) (made by Example 57A), dimethylaminopyridine (23.0 mg, 0.19 mmol) (Acros) and 15 mL of DCM. To this homogeneous solution, cooled at 4° C. was added 500 mg of acetic anhydride. This mixture was stirred at 25° C. for 24 hours seated under a $N_2$ atmosphere. This mixture was diluted with 25 mL of DCM and washed with sat. $NaHCO_3$ solution (2×5 mL).

The organic layer was dried with anhydrous $Na_2SO_4$, filtered and volatiles removed by rotary evaporation to give the crude product (260 mg). This material was chromatographed with silica gel using 3:1 DCM:MeOH (% v/v). The first two fractions contained the product. Removal of volatile materials gave the purified product (570 mg; 95% yield) that has the following spectrum:

$^{13}$C NMR (125 MHz, $CDCl_3$): δ 7.71, 14.69, 21.25, 22.96, 39.39, 43.46, 43.75, 53.34, 53.66, 58.48, 59.26, 61.29, 69.74, 70.08, 70.24, 71.24, 71.36, 71.64, 155.49, 169.75, 170.41.

The following Scheme 62 illustrates this reaction.

Scheme 62

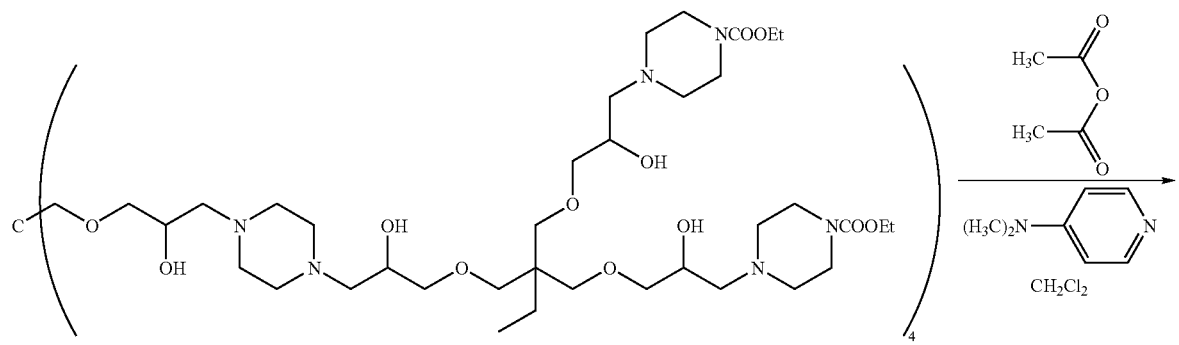

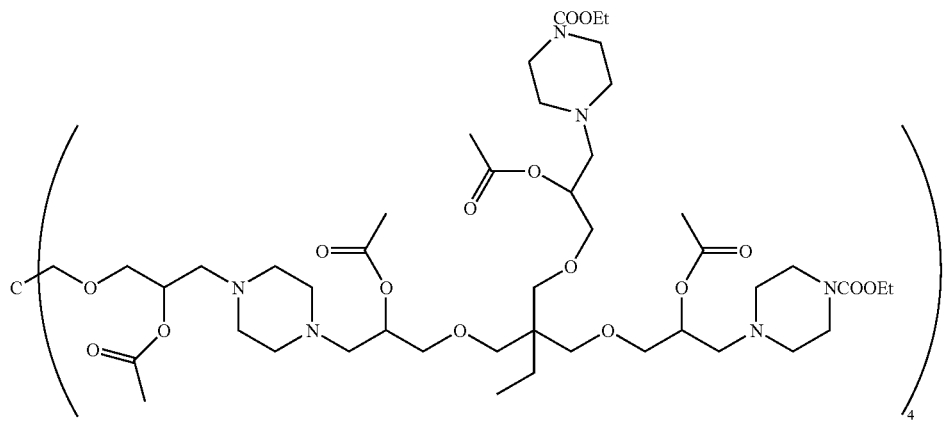

EXAMPLE 58

Reaction of Tetraphenylolethane Glycidylether with tris(2-aminoethyl)amine to Produce Primary Amine Surface for DNA Compaction and Antibacterial Activity

[(C)=TPEGE; (IF)=OH; (BR1)=TREN; (TF)=Primary $NH_2$; G=1]

In a 250-mL round bottom flask TREN (10.35 g, 77.23 mmol, 9.0 equiv) (Dow Chemical) was dissolved into 20 mL of MeOH and 10 mL of DME. The TPEGE (EPON 1031) (2.0 g, 1.93 mmol) (EPON) was dissolved into 25 mL of DME and 10 mL of MeOH and transferred into a 60-mL addition funnel. The TPEGE solution was added dropwise over 30 mins. Upon completion the addition funnel was washed with DME (2×7.5 mL) and the reaction allowed to react at 22° C. for 48 hours. TLC (7:3 $CH_3OH:NH_4OH$) showed complete consumption of the TPEGE (0.55). An aliquot of 55.22 g (49.7%) of the reaction mixture was removed, concentrated by evaporation using a rotary evaporator, and purified by Kugelrohr distillation for 1.5 hours at 210° C. The distillation recovered 4.49 g of TREN and 1.68 g of crude product. The product was then dissolved into 8 g of MeOH and added to a LH-20 Sephadex™ size exclusion column. After the void volume (575 mL), 50 13-mL fractions were collected. TLC (7:3 $CH_3OH:NH_4OH$) analysis showed product in fractions 5-17. These fractions were combined, and MeOH was removed by rotary evaporator. The remaining product was placed under high vacuum for 24 hours (0.7 g, 20.0% yield, 3.61 g theoretical mass balance). Its spectra are as follows:

$^1$H NMR (500 MHz, $CD_3OD$): δ 2.54 (4H, m), 3.811 (2H, m), 4.81 (2H, s) 6.87 (2H, m); and $^{13}$C NMR (75 MHz, $CD_3OD$): δ 40.16, 53.15, 54.21, 55.74, 57.88, 69.55, 72.99, 115.15, 130.53, 158.06; and MALDI-TOF: $C_{62}H_{110}N_{16}O_8$ Calc. 1207.64; found 1208 $[M]^+$ amu.

The following Scheme 63 illustrates this reaction.

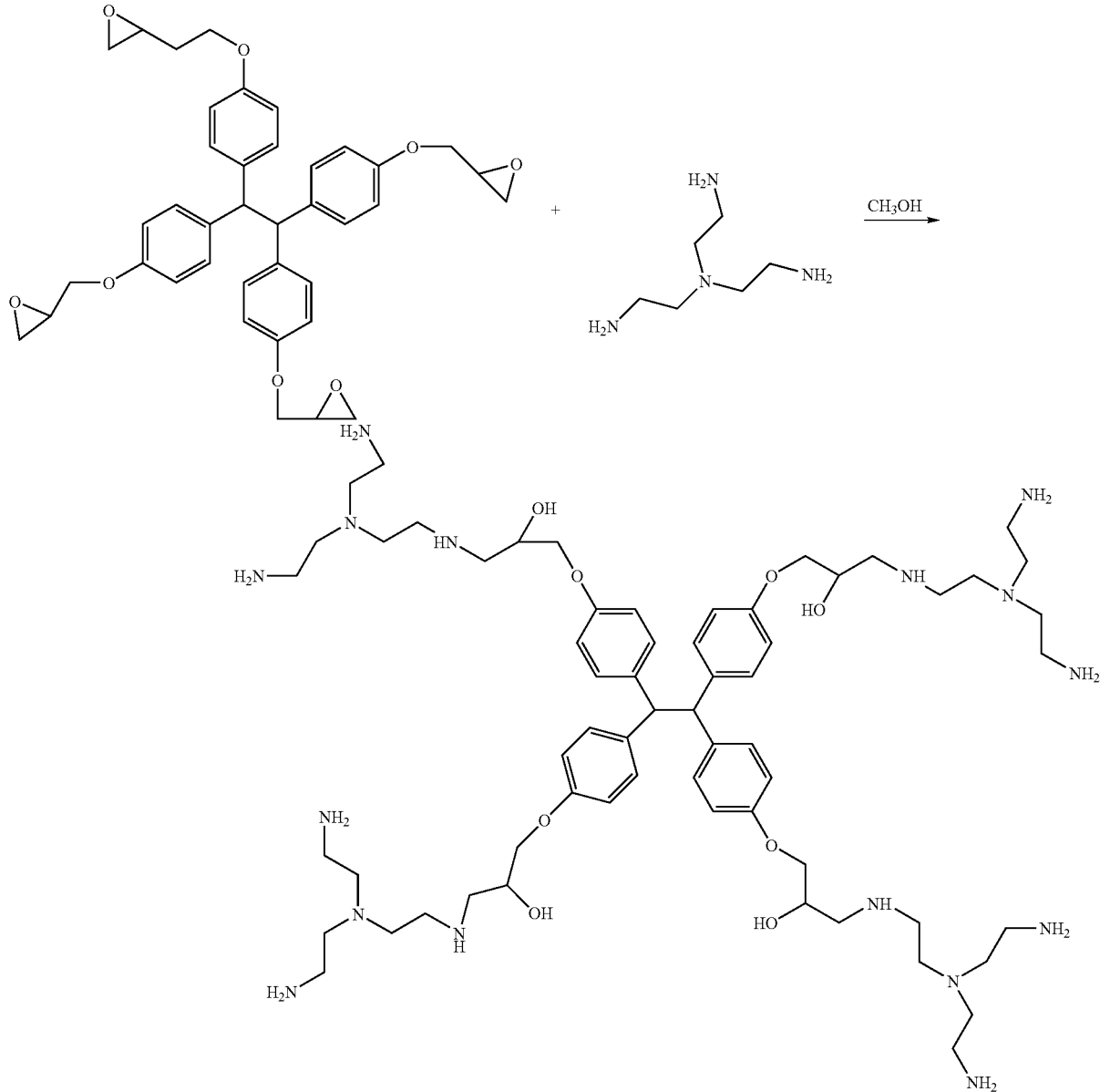

Scheme 63

EXAMPLE 59

Reaction of Pentaerythritol Tetraglycidylether with tris(2-aminoethyl)amine (TREN) to Produce Primary Amine Surface for DNA Compaction and Antibacterial Activity

[(C)=PETGE; (IF1)=OH; (BR1)=TREN; (TF)=Primary $NH_2$; G=1]

To a 50-mL round bottom flask containing a stir bar was added tris(2-aminoethyl)amine (16.0 g, 109 mmol, 10 equiv. per epoxide) and 4 mL of MeOH and cooled to ~25° C. To this stirred mixture was added dropwise a solution of PETGE (1.0 g, 2.78 mmol, 11.1 mmol epoxide) in 2 mL of MeOH. This mixture was stirred for 24 hours at 25° C. under a $N_2$ atmosphere. Volatile material was distilled by rotary evaporation to give a crude residue that was bulb-to-bulb distilled using a Kugelrohr apparatus at 200-230° C. at high vacuum to give 2.4 g residue. MALDI-TOF mass spectrum of this material showed a clean spectrum for the desired 4:1 adduct at a mass of 967 amu $[M+Na]^+$ and a smaller signal for the 3:1 adduct at 799 amu $[M+Na]^+$. TLC (50% $NH_4OH$ in MeOH) showed the absence of TREN. $^{13}C$ NMR spectrum showed the expected peaks for a clean product (2.4 g, 92% yield). Its spectra are as follows:

$^{13}C$ NMR: (125 MHz, $CDCl_3$) δ 39.63, 35.36, 47.30, 52.64, 54.01, 57.24, 68.10, 70.33, 74.64; and MALDI-TOF MS: $C_{42}H_{101}N_{16}O_8$; Calc. 944.3, found 967 $[M+Na]^+$ amu.

The following Scheme 64 illustrates this reaction.

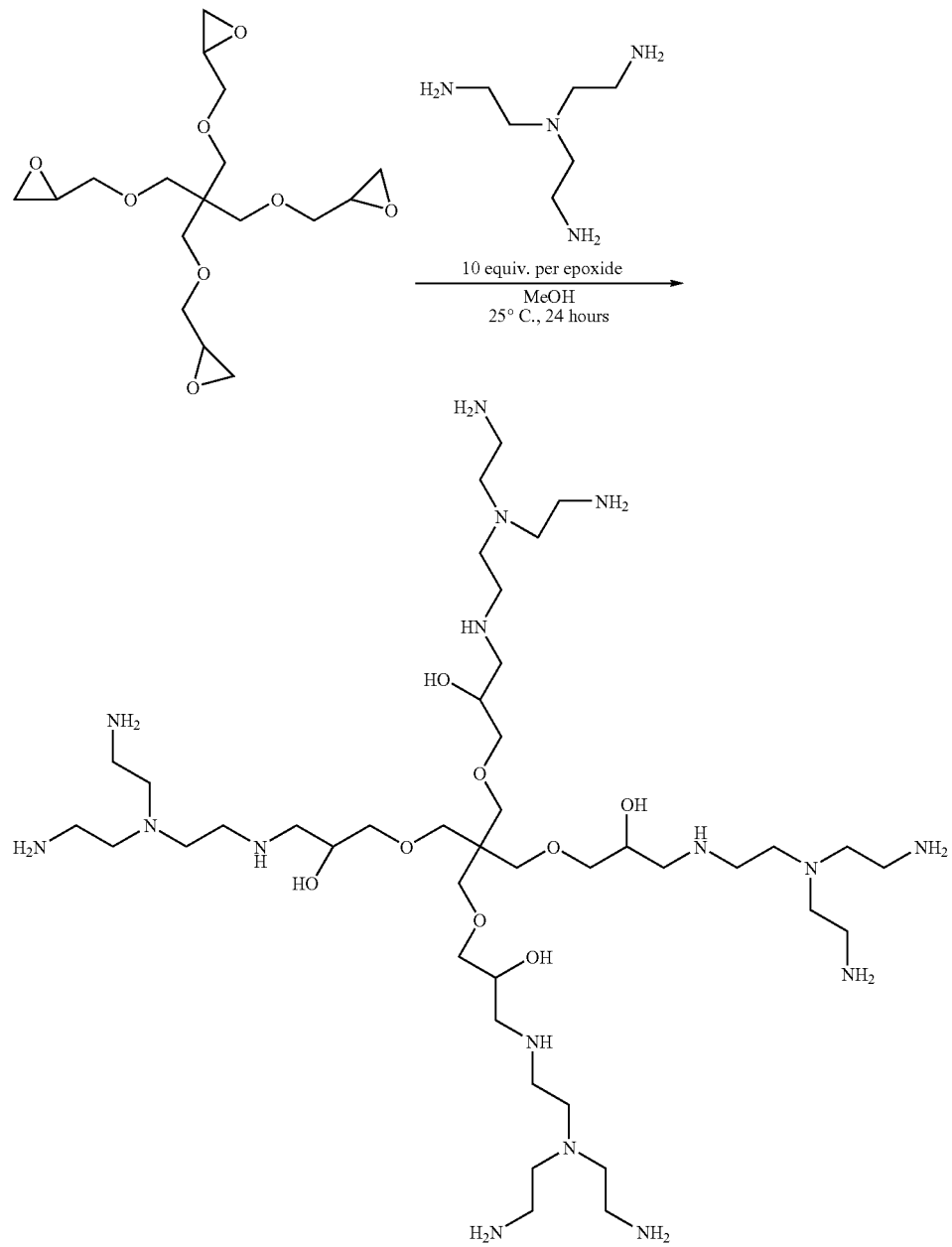

Scheme 64

EXAMPLE 60

Reaction of Tetraphenylolethane Glycidylether with Methylisobutyl-Protected 1-(2-aminoethyl)piperazine (PEA) to Produce a Primary Amine Surface for DNA Compaction and Antibacterial Activity (H1)

[(C)=TPEGE; (IF1)=OH; (BR1)=PEA; (TF)=Primary $NH_2$; G=1]

To a 250-mL round bottom flask containing a stir bar was added PEA as a 0.84 M solution in MIBK (50.0 mL, 42.0 mmol, 2.2 equiv. per epoxide) and 25 mL of MeOH. To this mixture was added TPEGE (5.0 g, 8.0 mmol, 32 mmol epoxide) dissolved in 25 g diglyme. This mixture was heated at 70° C. for 65 hours under a $N_2$ atmosphere. Then 25 mL of DI water were added and the mixture heated at 55° C. for 24 hours. Volatile material was removed by rotary evaporator to give a crude residue that was bulb-to-bulb distilled using a Kugelrohr apparatus at 140-190° C. at high vacuum to give 8.58 g of residue. A portion (600 mg) of this material was purified by Sephadex™ LH 20 column in MeOH. Fractions 1-9 contained pure product as determined by TLC (30% $NH_4OH$ in MeOH), giving a mass of 250 mg (70% yield based on 60% purity of the starting material). Its spectra are as follows:

$^{13}C$ NMR: (125 MHz, $CDCl_3$) δ 38.59, 60.83, 53.19, 60.64, 65.63, 70.27, 114.14, 129.25, 136.46, 156.56; and MALDI-TOF MS: $C_{62}H_{98}N_{12}O_8$; Calc. 1139.5, found 1140 $[M+H]^+$ amu.

The following Scheme 65 illustrates this reaction.

Scheme 65

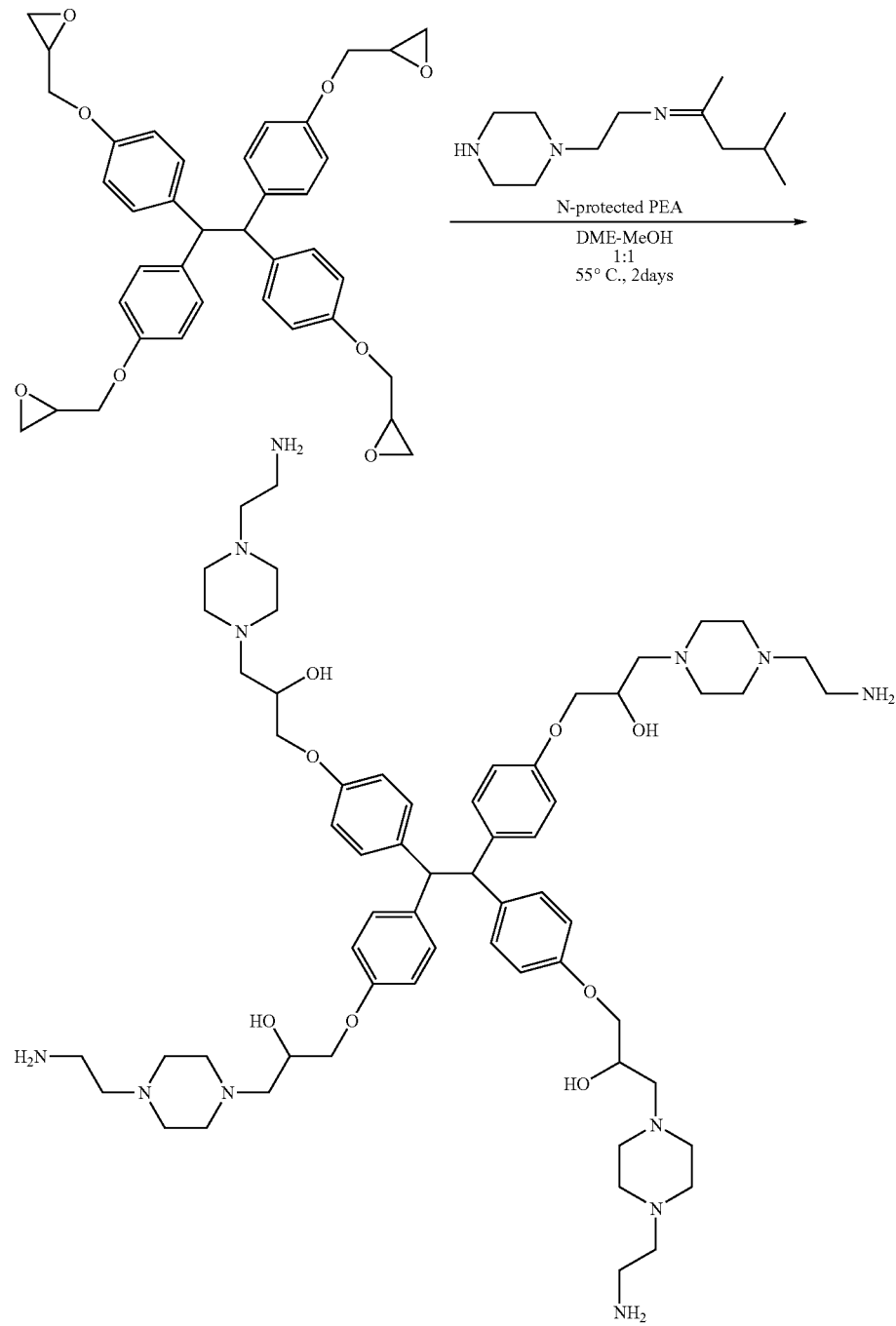

EXAMPLE 61

Reaction of the Product from Pentaerythritol Tetraglycidylether Reacting with Diethyliminodiacetate with 1(2-aminoethyl)piperazine (PEA) to Produce a Secondary Amine Surface for DNA Compaction and Antibacterial Activity

[(C)=PETGE; (IF1)=OH; (EX1)=PEA; (TF)=Secondary NH; G=1.5]

A 100-mL round bottom flask was charged with AEP (2.06 g, 16.0 mmol) (Acros Organics) and dissolved in 20 mL of EtOH (Aldrich). Then a solution of ester C5 (2.23 g, 2.0 mmol, 16 ester mmol; made from Example 51) in 20 mL of EtOH was added at RT under mechanical stirring. The flask was arranged with a refluxing condenser and heated at 70-75° C. After 1 day, MALDI-TOF MS analysis showed the expected mass for the desired product and few by-compounds. Progress of the reaction was monitored by IR, showing the amide vibration (C=O) at 1660 cm$^{-1}$ being more intense than the ester vibration (C=O) at 1742 cm$^{-1}$. Heating was continued for 36 hours and the resulting reaction mixture allowed to cool to RT. The mixture was diluted with MeOH to yield a 5% solution and subjected to UF with a 1K size exclusion membrane at a pressure of 20-22 psi (about 137.9 kPa). After collecting 480 mL permeate, the retentate was withdrawn from UF and the solvent removed by rotary evaporation. The remaining light brown colored solid was dried under high vacuum, yielding the desired PEHAM dendrimer (G=1) 5 (3.53 g, 99% yield). Its spectra are as follows:

$^1$H NMR (300 MHz, CD$_3$OD): δ 2.48-2.51 (64H, t, J=3.90 Hz), 2.83-2.85 (32H, t, J=2.70 Hz), 3.30-3.37 (24H, m), 3.38 (32H, bs), 3.78-3.81 (4H, m); and $^{13}$C NMR (75 MHz, CD$_3$OD): δ 35.76, 45.02, 45.81, 53.66, 57.73, 59.49, 59.76, 68.12, 70.20, 74.22, 172.38; and IR (Neat): ν$_{max}$ 3288, 3078, 2939, 2817, 1654, 1536, 1454, 1444, 1352, 1321, 1301, 1265, 1132, 1029, 999, 912, 845, 758, 666 cm$^{-1}$; and MALDI-TOF MS: C$_{81}$H$_{160}$N$_{28}$O$_{16}$; Calc. 1782.3; found 1803.9 [M+Na]$^+$ amu.

The following Scheme 66 illustrates this reaction.

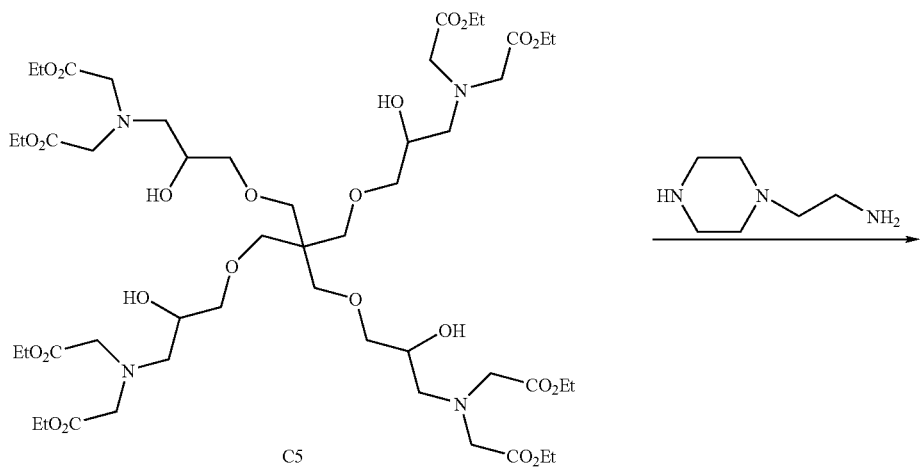

Scheme 66

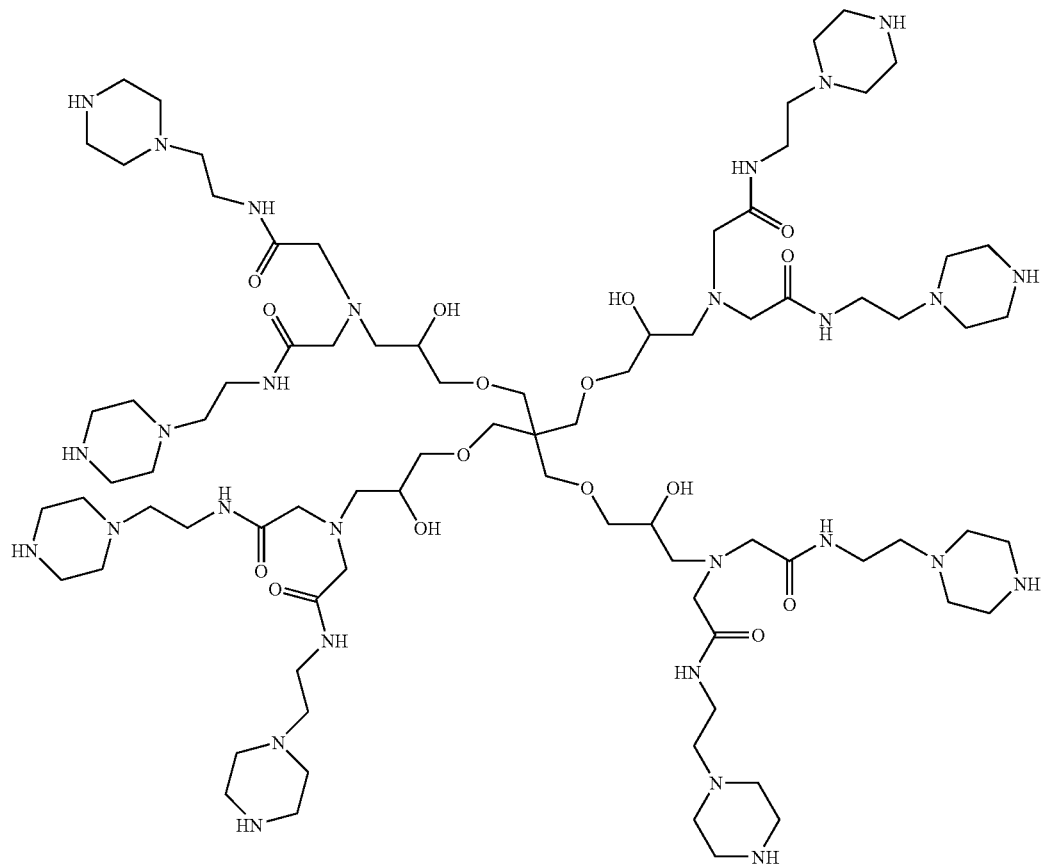

5

EXAMPLE 62

Reaction of Pentaerythritol Tetraglycidylether with Dibenzylamine (DBA) to Produce a Hydrophobic, Inert Surface

[(C)=PETGE; (IF1)=OH; (EX1)=DBA; (TF)=Benzyl; G=1]

In a 250-mL round bottom flask DBA (7.23 g, 36.6 mmol, 1.3 equiv. per epoxide) (Aldrich) was dissolved into 25 mL of MeOH under mechanical stirring. PETGE (2.52 g, 7.0 mmol) was dissolved into 5 mL of MeOH and added dropwise into the reaction mixture at 22° C. over 10 min. under stirring and a N₂ atmosphere. The reaction was monitored by TLC (2:1 hexanes:ethyl acetate), initially giving two spots at $R_f$=0.15 (DBA) and $R_f$=0.26 (product). After 24 hours, the flask was equipped with a reflux condenser and the mixture placed into a 45° C. oil bath to drive the reaction to completion. After an additional 24 hours, MeOH was removed by rotary evaporation and the remaining material (9.52 g) dissolved into 50 mL of DCM, followed by three washings with 75 mL 1.5% potassium carbonate. The organic layer was dried over sodium sulfate, and the DCM removed by rotary evaporation to yield the desired product as a yellow, clear viscous liquid (7.99 g, 99.0% yield, 8.07 g theoretical mass). Its spectra are as follows:

¹H NMR (500 MHz, CDCl₃): δ 2.46 (1H, q, J=5.25 Hz), 3.27 (1H, q, J=2.75 Hz), 3.56 (1H, d, J=6.75 Hz), 3.74 (1H, d, J=7.0 Hz); 3.865 (2H, s); 7.35 (12H, m, J=5.8 Hz); and ¹³C NMR (75 MHz, CDCl₃): δ 45.32, 53.03, 58.59, 67.03, 70.32, 73.90, 126.88, 128.09, 128.27, 128.32, 128.90, 138.79, 140.14; and MALDI-TOF: C₇₃H₈₈O₈; Calc. 1149, found 1172 [M+Na]⁺ amu.

The following Scheme 67 illustrates this reaction.

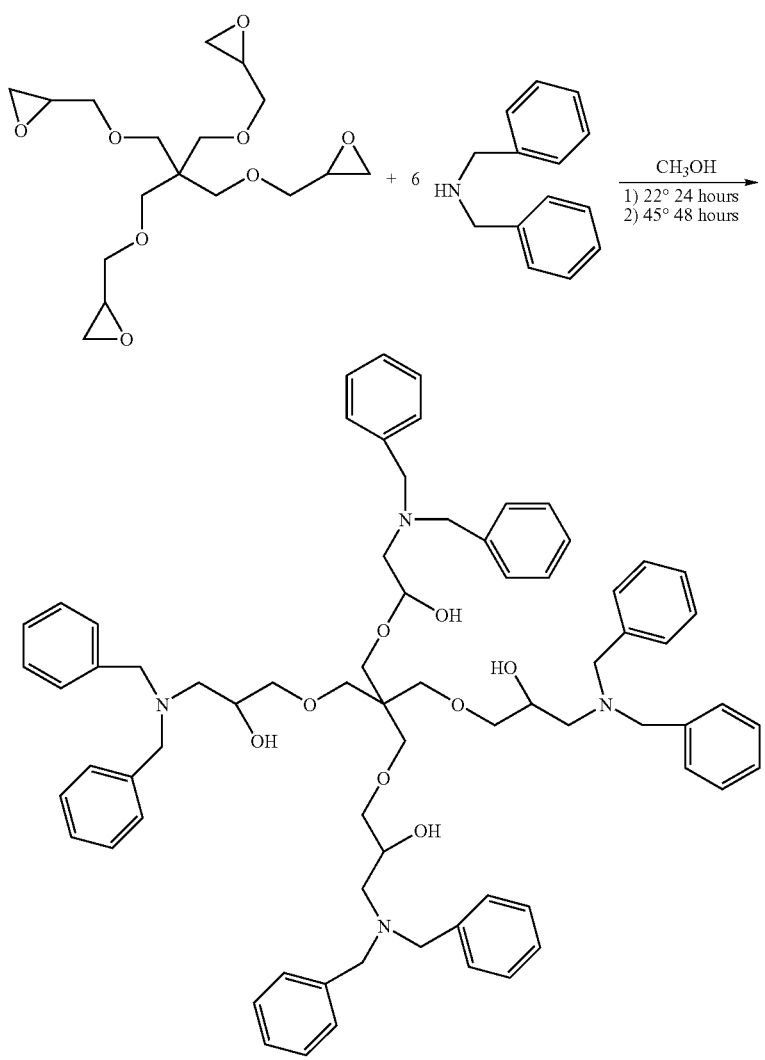

EXAMPLE 63

Reaction of Pentaerythritol Tetraglycidylether with (2-hydroxyethyl)ethylenediamine (AEEA) to Produce a Mixed Primary Amine and Hydroxyl Surface

[(C)=PETGE; (IF1)=OH; (BR1)=AEEA; (TF)=Primary NH$_2$ and OH; G=1]

A 100-mL oven-dried round bottom flask was equipped with a stir bar, flushed with N$_2$ gas and closed with a septum. To it was added MIBK-protected AEEA (30.1 mL, 56.0 mmol, 1.86 M solution in MIBK, 2 equiv. per epoxide) through a syringe, followed by the addition of 20 mL dry MeOH. PETGE (2.52 g, 7.0 mmol, 28 epoxy mmol) in 10 mL dry MeOH was added to the reaction mixture at RT. After stirring for 30 min., the flask was arranged with a refluxing condenser and placed in an oil-bath and heated at 50° C. for 24 hours under a N$_2$ atmosphere. The progress of the reaction was monitored by MALDI-TOF mass spectrometry. The solvent was removed by rotary evaporation and 40 mL of 2-propanol and 4 mL of water were added. The mixture was then heated at 55° C. for overnight. The solvent was removed by rotary evaporation and the resultant reaction mixture subjected to Kugelrohr distillation at 170-195° C. to give a light brown colored, viscous liquid (6.85 g, 5.43 g theoretical). $^1$H and $^{13}$C NMR spectra revealed incomplete removal of the protecting groups. The reaction mixture was therefore redissolved in 40 mL of MeOH and 4 mL of water and heated at 55° C. for 3 days. The solvent was removed as before and Kugelrohr distillation at 170-195° C. gave a light brown colored, viscous liquid with the expected analytical data for compound 4 (5.58 g, 5.43 g theoretical). Its spectra are as follows:

$^1$H NMR (300 MHz, CD$_3$OD): δ 2.46-2.62 (12H, m), 2.64-2.81 (12H, m), 3.36-3.41 (8H, d, J=4.50 Hz), 3.46 (8H, s), 3.53-3.66 (8H, m), 3.81 (4H, bs); and $^{13}$C NMR (75 MHz, CD$_3$OD): δ 39.04, 45.80, 57.40, 57.50, 58.45, 59.66, 68.48, 70.19, 73.99; and IR (Neat): ν$_{max}$ 3354, 2945, 2863, 1572, 1552, 1541, 1454, 1367, 1306, 1101, 876, 825, 773 cm$^{-1}$; and MALDI-TOF MS: C$_{33}$H$_{79}$N$_8$O$_{12}$; Calc. 777.0, found 777.7 [M]$^+$, 799.6 [M+Na]$^+$ amu.

The following Scheme 68 illustrates this reaction.
Scheme 68
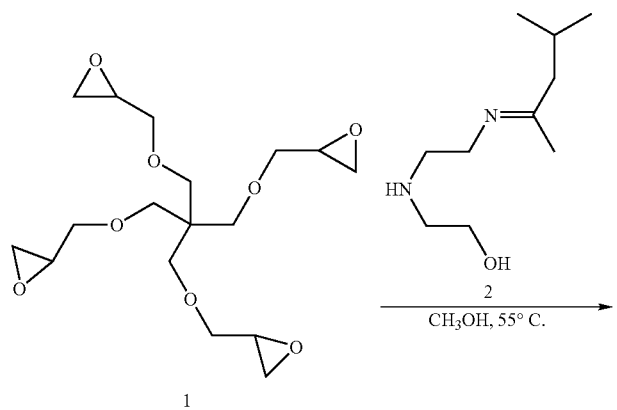
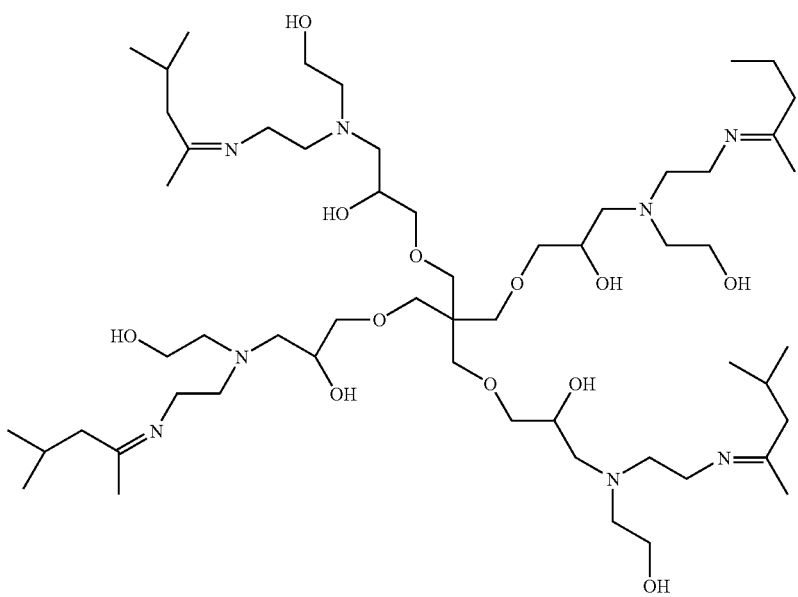

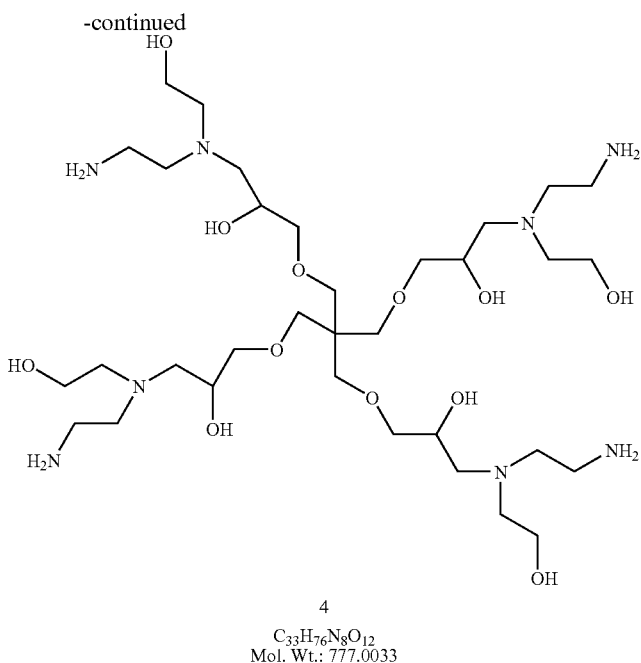

4
C₃₃H₇₆N₈O₁₂
Mol. Wt.: 777.0033

EXAMPLE 64

Reaction of Pentaerythritol Tetraglycidylether with 2-methyl-2-imidazoline (MIA) to Produce a Mildly Basic Surface

[(C)=PETGE; (IF1)=OH; (EX1)=MIA; (TF)=Imidazoline; G=1]

A 50-mL oven-dried round bottom flask was charged with MIA (2.69 g, 32.0 mmol) (Aldrich) and 6 mL of dry MeOH (Aldrich). To it was added a solution of PETGE in 1 mL of MeOH, and the mixture was stirred for 3 days at RT. The reaction mixture was diluted to 2.5-5% solution w/w in MeOH and subjected to UF using a 1K size exclusion filter at a pressure of 20-22 psi (137.9 kPa). After collecting 1 liter of permeate, the retentate was withdrawn from the UF, and the UF washed with MeOH (3×50 mL). The solvent was removed from the retentate by rotary evaporation to give a viscous liquid, which was further dried under high vacuum, giving a pale colored solid (0.61 g, 87.64% yield). $^{13}$C NMR spectrum on this sample indicated that it had less than <5% of the three-arm by-product. Its spectra are as follows:

$^1$H NMR (300 MHz, CD₃OD): δ 1.90 (12H, s), 3.23 (8H, s), 3.41-3.42 (8H, d, 4.50 Hz), 3.30-3.62 (16H, m), 3.57-3.60 (8H, d, J=9.30 Hz), 3.86 (4H, m); and $^{13}$C NMR (75 MHz, CD₃OD): δ 45.73, 48.90, 49.54, 50.40, 50.59, 68.36, 70.20, 73.29, 165. 87; and IR (Neat): $\nu_{max}$ 3308, 2924, 2868, 1608, 1490, 1429, 1372, 1265, 1178, 1101, 1014, 983, 942 cm$^{-1}$; and MALDI-TOF MS: C₃₃H₆₀N₈O₈; Calc. 696.9, found 697.6 [M]⁺ amu.

The following Scheme 69 illustrates this reaction.

Scheme 69

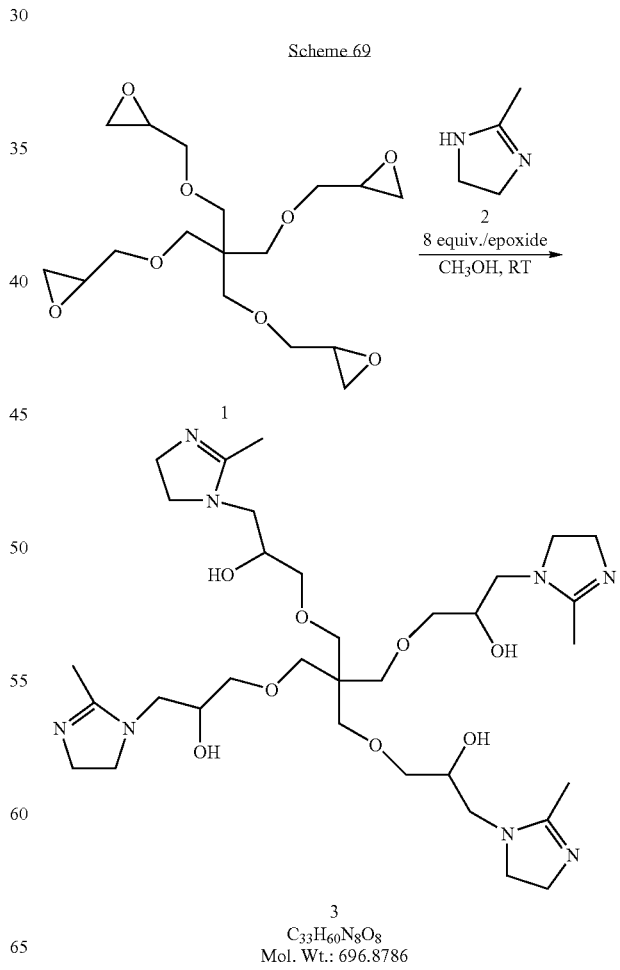

3
C₃₃H₆₀N₈O₈
Mol. Wt.: 696.8786

EXAMPLE 65

Ring Opening Using Morpholine: Alternative Secondary Amine

[(C)=TMPTGE; (FF)=Et; (IF1)=OH; (EX1)=Morpholine; (TF)=Cyclic ether; G=1]

To a stirred solution of 1.044 g of morpholine II-d (12 mmol) in 8 mL of dry MeOH at RT, 0.604 g of TMPTGE I (2 mmol) in 2 mL of dry MeOH was added all at once. Progress of the reaction was monitored by TLC. After being stirred for 3 hours, TLC showed the complete consumption of TMPTGE. Stirring was continued at RT overnight. The solvent was removed on a rotary evaporator under reduced pressure and dried under high vacuum to remove excess morpholine to give a colorless, transparent liquid. The crude reaction mixture was purified through silica gel column chromatography (8.5" height×1.25" width) (21.25 cm×3.18 cm) by increasing the amount of methanol in chloroform (5-10% MeOH in $CHCl_3$). Yield for IIId+IVd 25% and 800 mg, which also contains products IIId and IVd along with some unidentified material (71% yield). Overall yield is 96%. IIId+IVd (mixture of two compounds)=221 mg III-d (pure fraction)= 66 mg.

The spectra for IIId are:

$^1$H NMR (500 MHz, $CDCl_3$): δ 0.81 (t, J=7.50 Hz, 3H), 1.36 (q, J=7.50 Hz, 2H), 2.32-2.43 (m, 12H), 2.52-2.59 (quintet, J=4.50 Hz, 6H), 3.28-3.47 (m, 12H), 3.52 (s, 3H, OH), 3.64-3.71 (m, 12H), 3.87 (quintet, J=4.50 Hz, 3H); and $^{13}$C NMR (125 MHz, $CDCl_3$): δ 7.91, 23.39, 43.61, 54.10, 61.54, 66.41, 67.09, 72.22, 74.02; and MALDI-TOF: Calc. for $C_{27}H_{53}N_3O_9$ 563, found 587 ($M^+Na$) amu.

The spectra for IV-d are:

MALDI-TOF: Calc. for $C_{23}H_{44}N_2O_8$ 476, found 500 ($M^+Na$) amu (Fraction-II).

Scheme 70 illustrates this reaction:

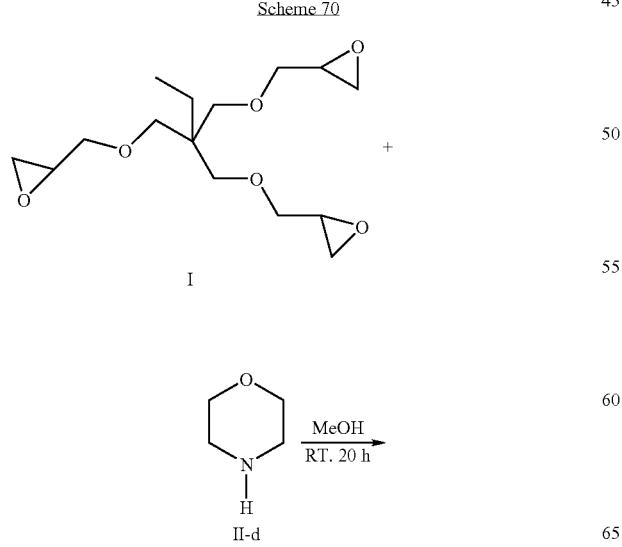

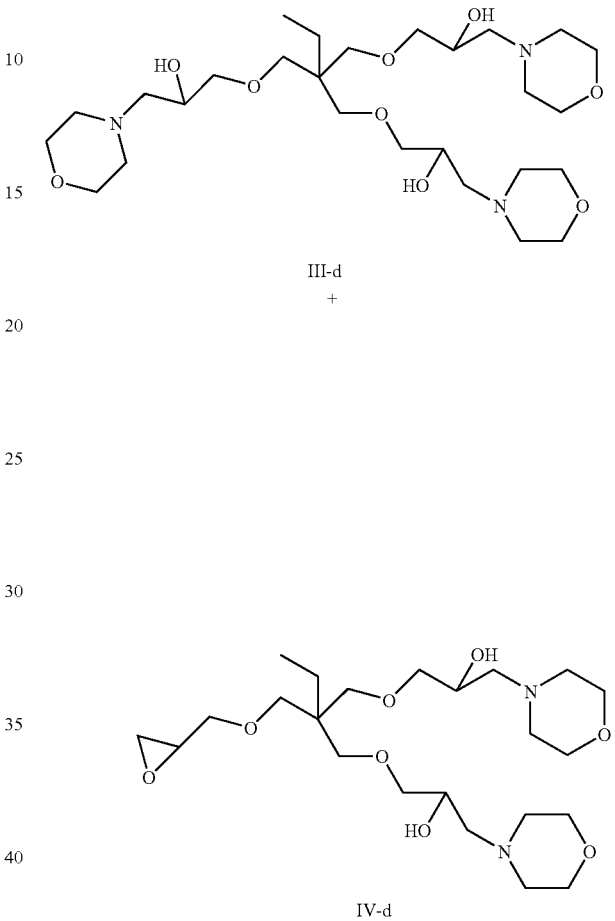

EXAMPLE 66

Reaction of 4,4'-methylene bis(N,N'-diglycidyl aniline) (MBDGA) with tris(hydroxymethyl)methylamine (TRIS)

[(C)=MBDGA; (IF1)=OH; (BR1)=TRIS; (TF1)=OH; (TF1)=Epoxide; G=1]

Tetra glycidyl aniline, I-b (0.422 g, 1 mmol) was weighed in a 50 mL single necked round bottom flask and 15 mL of MeOH and 5 mL of DCM were added. TRIS (0.121 g, 1 mmol) was added to the above reaction mixture. The flask was fitted with a refluxing condenser and heated at 40° C. for 3 days. Solvents were evaporated on a rotary evaporator, which gives a colorless waxy solid, which was further dried under high vacuum. The entire reaction mixture was dissolved in a mixture of solvents (CHCl$_3$+CH$_3$OH; 50 mL, 3:1) under hot conditions using a heat gun. The flask was allowed to warm to RT and 30 mL of hexanes added. Formation of a precipitate was observed while adding hexanes. After 3 hours, a solid was filtered off through a Büchner funnel and evaporation of the solvent on rotary evaporator gives a viscous liquid, which was subjected to column chromatography over silica gel. First, 40% ethyl acetate/hexanes were used to elute traces of tetra glycidyl aniline followed by 5% MeOH/CHCl$_3$ to elute compound-III. Pure fractions (determined by TLC) were evaporated, which gives 37 mg of a hygroscopic solid. Analytical data, MALDI-TOF, $^1$H and $^{13}$C NMR revealed that it was compound-III. This reaction was also studied with 2 equivalents of TRIS/epoxide in the mixture of MeOH and DCM and gives compound-III in good yield. The reaction did not proceed in DME, and, with 2 equiv. of TRIS in MeOH at 60° C. for over night gives bis- and tri-addition products. Reaction with 2 equiv. of TRIS at 60° C. for 3 days also gives bis- and tri-addition products with traces of tetra addition product. The spectra for III-e are:

$^1$H NMR (500 MHz, CDCl$_3$): δ 2.50 (q, J=2.40 Hz, 2H), 2.70 (q, J=4.50 Hz, 2H), 2.82 (bs, 1H), 3.07 (s, 4H), 3.24-3.37 (m, 7H), 3.58-3.66 (m, 9H), 3.95 (s, 2H), 4.59 (s, 6H), 6.65 (d, J=8.40 Hz, 4H), 6.98 (d, J=8.10 Hz, 4H); and $^{13}$C NMR (125 MHz, CDCl$_3$): δ 39.98, 45.58, 45.71, 50.92, 51.03, 53.35, 55.08, 57.84, 63.40, 71.03, 112.85, 112.93, 129.84, 131.02, 146.76, 148.08; and MALDI-TOF: Calc. for C$_{29}$H$_{41}$N$_3$O$_7$, 543; found 567 (M$^+$Na) amu.

Scheme 71 illustrates this reaction:

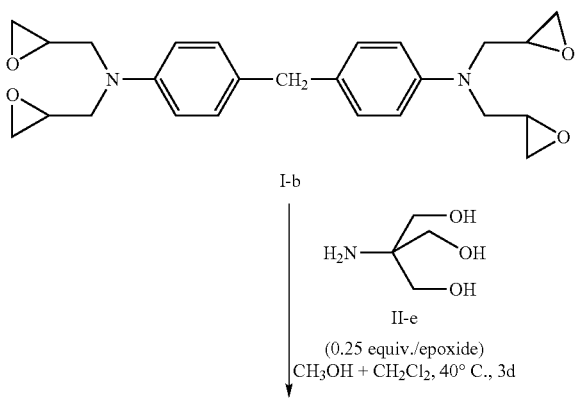

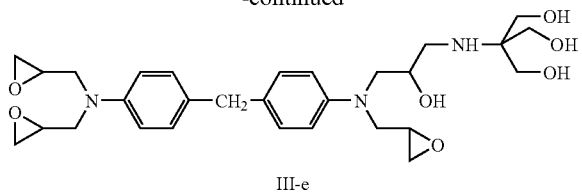

III-e

EXAMPLE 67

Reaction of Hetero Glycidyl Ethers with Ethyl-N-piperazinecarboxylate

[(C)=DGGA; (IF1)=OH; (EX1)=PIPZ; (TF1)=Secondary NH; G=1.5]

Reaction of DGGA 1 (Aldrich) is studied with 0.33 equiv. of EPC (Aldrich) per epoxide at RT. After 1 day, MALDI-TOF mass spectrometry indicated peaks for mono-addition product 2 as major, along with some amount of bis-addition product 2a (ratio is 11:1 from $^1$H NMR). Studies with 1.1 equiv. of EPC per epoxide at RT gives all three epoxides reacted to give product 3 in excellent yield (92%). Alkaline hydrolysis on compound 3 gave compound 4 in 89% isolated yield.

A. To a stirring solution of DGGA 1 (1.38 g, 5 mmol) in 5 mL of MeOH was added a solution of EPC (0.79 g, 5 mmol) in 5 mL of MeOH and stirred for 1 day at RT. However, isolation of this product by column chromatography on silica gel gives ring open product 2 that has the following spectra:

MALDI-TOF: C$_{22}$H$_{33}$N$_3$O$_6$ Calc. 435, found 436 (M$^+$H) and 458 (M$^+$Na) amu.

B. To a stirring solution of DGGA 1 (2.77 g, 10 mmol) in 15 mL of MeOH was added a solution of EPC (5.21 g, 33 mmol) and stirred for 2 days at RT. The starting material was completely consumed. The solvent was removed on a rotary evaporator under reduced pressure. Excess EPC was removed by Kugelrohr distillation, which gave pure compound 3 (6.91 g, 92% yield) that has the following spectra:

MALDI-TOF: C$_{36}$H$_{61}$N$_7$O$_{10}$ Calc. 751, found 774 (M$^+$Na) amu.

C. A round bottom flask (250 mL, single necked) was charged with compound 3 (6.91 g, 9.2 mmol) and dissolved in 42 mL of MeOH. Aqueous KOH (45%) (20.73 g of 90% KOH was dissolved in 42 mL of water) was added to the above stirring solution at RT over 5 mins. The flask was arranged with a refluxing condenser and placed in a pre-heated oil-bath (85-90° C.) and heated for overnight. Progress of the reaction was monitored by TLC. Methanol was removed on a rotary evaporator and aqueous layer was extracted with DCM (3×50 mL). Combined extracts were dried over Na$_2$SO$_4$, filtered through Celite, and concentrated on rotary evaporator, then dried under high vacuum, which gives pale yellow color piperazine surface, dendrimer 4 as a solid (4.86 g, 89% yield) that has the following spectra:

MALDI-TOF: C$_{27}$H$_{49}$N$_7$O$_4$ Calc. 535, found 536 (M$^+$H), 558 (M$^+$Na) amu.

Scheme 72 illustrates this reaction:
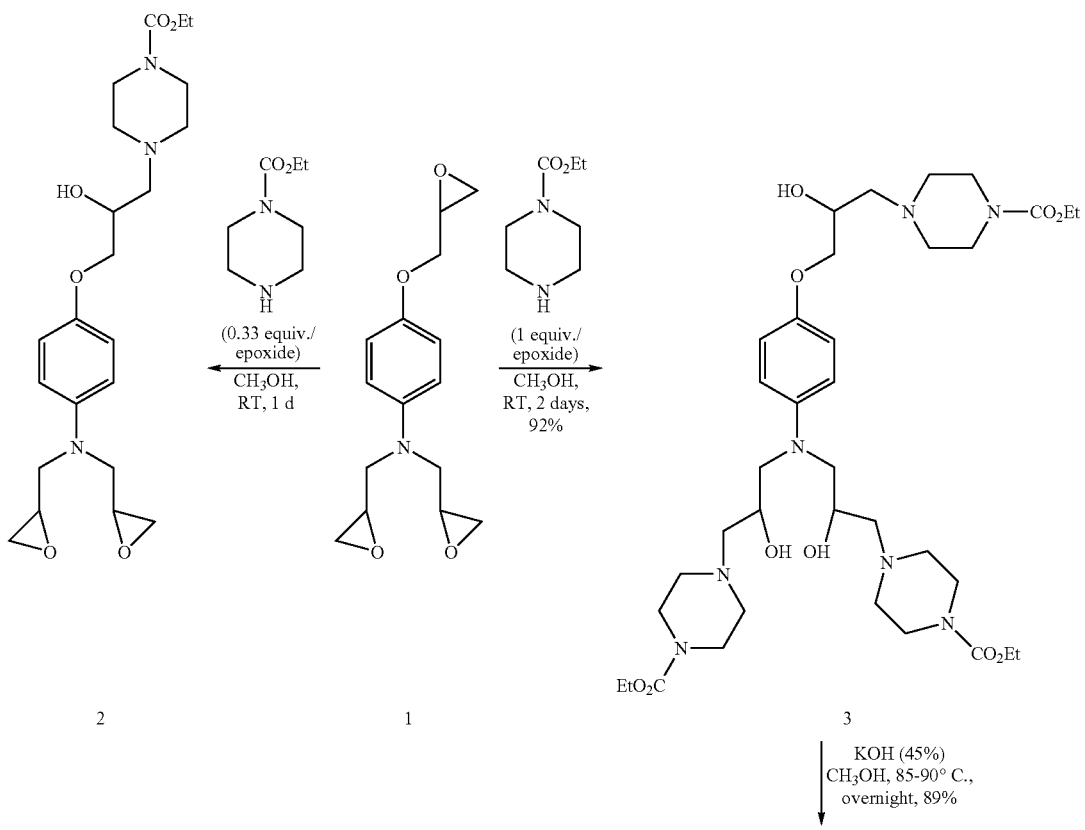
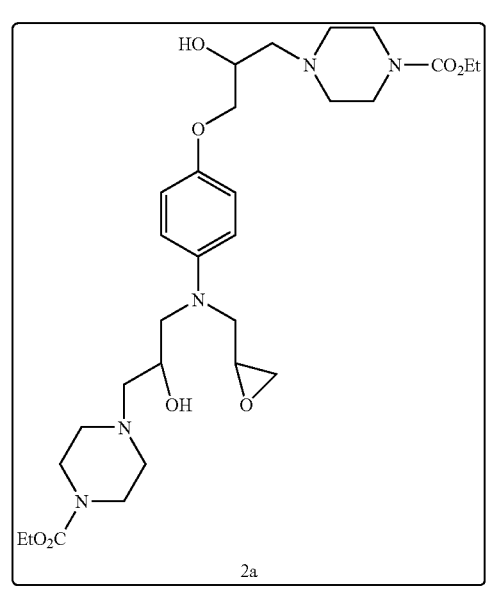
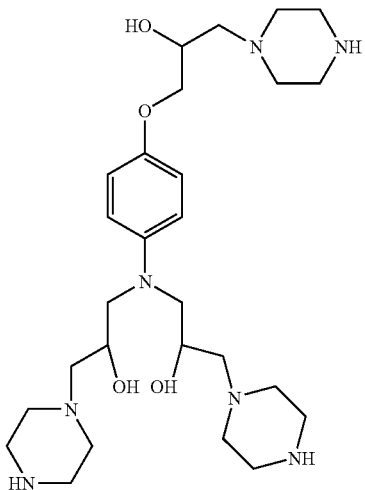

The following examples illustrate G=2, 2.5 and 3 PEHAM dendrimers.

EXAMPLE 68

Addition of Trifunctional Acrylate Branch Cell TMPTA to the Piperazine Dendrimer from Example 20: Poly(esteramine)dendrimer, G=1

[(C)=TMPTA; (FF)=Et; (EX1)=PIPZ; (BR1)=TMPTA; (EX2)=PIPZ; (BR2)=TMPTA; (TF)=Acrylate; G=2]

To a 50-mL round bottom flask with a stir bar wrapped with aluminum foil was added TMPTA (3.64 g, 12.3 mmol, 4 equiv. per NH) (Aldrich) and 8 mL of MeOH. To this stirred mixture was added poly(esteramine)dendrimer, G=1, TMPTA core, PIPZ surface (1.0 g, 0.51 mmol, 3.1 mmol NH) (made by Example 20) in 6 mL of MeOH over about 5 mins. This mixture was stirred for 24 hours at 25° C. This mixture was extracted with hexanes (3×30 mL). The methanol layer was added over 10 mins. to a mixture of PIPZ (3.0 g, 34.8 mmol, about 6 equiv. per acrylate) in 10 g of MeOH, cooled at 4° C. The resulting mixture was stirred at 25° C. for about 2 hours. This mixture was diluted with MeOH to about a 5% w/w solids and dialyzed in methanol using a 1K regenerated cellulose membrane for 36 hours with 5 changes of dialyzate. Removal of volatiles from the retentate gave the desired product (900 mg; 47% yield). TLC (10% $NH_4OH$ in MeOH) of this material showed only one spot; and its spectra are as follows:

$^1$H NMR (500 MHz, $CDCl_3$): δ 0.82-0.94 (m, 30H), 1.34 (q, 2H), 1.38 (q, 6H), 1.49 (bq, 12H), 2.42 (m, 84H), 2.51 (t, J=7 Hz, 60H), 2.65 (t, J=7 Hz, 60H), 2.86 (bs, 84H), 4.05 (bs, 60H); and $^{13}$C NMR (125 MHz, $CDCl_3$): δ 7.36, 7.44, 22.40, 22.71, 31.97, 32.11, 32.18, 32.30, 32.38, 40.81, 40.87, 40.92, 45.73, 45.84, 52.63, 52.70, 52.74, 53.40, 54.05, 54.10, 63.50, 64.06, 64.47, 171.88, 171.95, 172.03.

EXAMPLE 69

Addition of Trifunctional Epoxide TMPTGE to G=1, PIPZ Terminated PEHAM Dendrimer, Followed by Capping with Piperazine to Give PEHAM Dendrimer, G=2

[(C)=TMPTGE; (FF)=Et; (IF1)=OH; (EX1)=PIPZ; (IF2)=OH; (BR1)=TMPTGE; (IF3)=OH; (EX2)=PIPZ; (IF4)=OH; (BR2)=TMPTGE; (IF5)=OH; (EX3)=PIPZ; (TF)=Secondary NH; G=2.5]

To a 25-mL round bottom flask with a stir bar was added TMPTGE (2.3 g, 7.6 mmol, 10 equiv. per NH) and 12 g of MeOH. To this stirred mixture, cooled to 4° C., was added PEHAM dendrimer, G=1, PIPZ terminated (250 mg, 0.126 mmol, 0.75 mmol NH) (made by Example 22) in 3 g of MeOH over 5 mins. This mixture was stirred under a $N_2$ atmosphere in a sealed vessel for 24 hours at 25° C. This mixture was added over 10 mins. to a mixture of PIPZ (10.0 g, 116.0 mmol, 5 equiv. per epoxide) in 30 g of MeOH. This mixture was stirred for 18 hours at 25° C. The volatiles of this mixture were removed by rotary evaporator to give a white solid. PIPZ was removed using a bulb-to-bulb Kugelrohr distillation at high vacuum and 140° C. for one hour to give a clear, colorless viscous material (6.0 g). This material was dissolved in 100 g of MeOH and dialyzed in a 1K regenerated cellulose membrane in 4 L of MeOH with 2 changes of dialyzate over 24 hours to give the product (1.4 g). TLC ($NH_4OH$ in MeOH) showed some lower molecular weight material present. Further dialysis for another 24 hours under the same conditions gave the purified product (360 mg; 59% yield). TLC showed the absence of lower molecular weight impurities. Its spectra are as follows:

$^1$H NMR (500 MHz, $CD_3OD$): δ 0.86 (t, J=7.0 Hz, 12H), 1.41 (q, J=7.0 Hz, 8H), 2.32-2.45 (m, H), 2.5 (bs, H), 2.60 (bs, H), 2.84 (t, J=7.0 Hz, H), 3.33-3.35 (bs, H), 3.64 (bs, H), 3.37 (bs, H), 3.89 (m, H); and $^{13}$C NMR (125 MHz, $CD_3OD$): δ 8.04, 8.07, 23.91, 44.59, 46.21, 54.61, 55.49, 62.66, 63.28, 68.49, 68.67, 72.68, 75.43.

EXAMPLE 70

Addition of Tetrafunctional Epoxide Branch Cell Reagent to Piperazine Functionalized: Poly(aminoalcoholether)Dendrimer

[(C)=PETGE; (IF1)=OH; (EX1)=PIPZ; (IF2)=OH; (BR1)=PETGE; (IF3)=OH; (EX2)=PIPZ; (IF4)=OH; (BR2)=PETGE; (IF5)=OH; (EX3)=PIPZ; (TF)=Secondary NH; G=2.5]

To a 25 mL round bottom flask containing a stir bar was added 2.8 g of PETGE (7.8 mmol, 10 equivalents per NH) (made by Example 3) and 8 g of MeOH. To this stirred mixture was added 200 mg of poly(aminoalcoholether)dendrimer, pentaerythritol core, G=1, piperazine surface (6.3× $10^{-5}$ mol, 7.6×$10^{-4}$ mol NH) (made by Example 25) in 3 g of MeOH over about 5 mins. This mixture was stirred for 24 hours at 25° C. under a $N_2$ atmosphere. This mixture was added dropwise over about 5 mins. to a stirred mixture of 40 g of piperazine (464 mmol, 15 equivalents per epoxide) dissolved in 80 mL of MeOH at 25° C. This mixture was stirred for 24 hours. The volatiles of this resulting mixture were removed on a rotary evaporator to give a white solid residue. Piperazine was removed from the crude residue using a bulb-to-bulb distillation apparatus at high vacuum and 140° C. for 1 hour until the pot residue was a clear viscous material. This crude residue weighing 5.65 g was dissolved in 20 g of MeOH and added to a Sephadex™ LH-20 column in MeOH. Void volume fractions of 500 mL and 3×25 mL were taken. Product was observed in the last two void volume fractions as observed by TLC (30% $NH_4OH$ in MeOH) with no visible low molecular material present. After the void volume a total of 49 fractions were taken of 15 mL each. Pure product was observed in fractions 1-7, combined with the two void volumes and stripped of volatiles to give 390 mg of product. Lower molecular weight material was mixed with the product in fractions 8-21. These were combined, stripped of volatiles and dialyzed in a 1K regenerated cellulose membrane with 3 changes of dialyzate (2 L each). The retentate was stripped of volatiles to give 200 mg of product. Fractions 22-49 contained no product and only lower molecular weight material. These fractions were stripped of volatiles to give 4.5 g. The total weight of product came to 590 mg (88% yield). A PAGE of this product on a 15% homogeneous gel with 0.1% SDS showed a band corresponding to a G=4, EDA core, TRIS PAMAM dendrimer (MW=18000) (Dendritic Nanotechnologies, Inc.) from a PAMAM dendrimer ladder G=2-6 and the dimer of G=1. Another band was observed that migrated in the gel to a spot that corresponded to the center between G=5 and 6 on the ladder. This band is probably a dimer of G=2. More material was observed at the top of the lane that had not migrated. Its spectra are as follows:

$^{13}$C NMR (125 MHz, $CDCl_3$): δ 46.28, 46.98, 54.69, 55.58, 62.66, 63.28, 68.52, 68.72, 71.32, 75.30, 75.61.

EXAMPLE 71

Addition of Tetrafunctional Epoxide Branch Cell Reagent to Piperazine Functional G=2 with Piperazine Capping: Poly(aminoalcoholether) Dendrimer, G=3

[(C)=PETGE; (IF1)=OH; (EX1)=PIPZ; (IF2)=OH; (BR1)= PETGE; (IF3)=OH; (EX2)=PIPZ; (IF4)=OH; (BR2)=PETGE; (IF5)=OH; (EX3)=PIPZ; (IF6)=OH; (BR3)=PETGE; (IF7)=OH; (EX4)=PIPZ; (TF)=Secondary NH; G=3.5]

To a 50-mL round bottom flask containing a stir bar was added 5.2 g of PETGE (made by Example C) in 15 mL of MeOH. To this stirred mixture was added dropwise over about 5 mins. 200 mg of poly(aminoalcoholether)dendrimer, G=2, piperazine surface ($1.88\times10^{-5}$ mol, $6.7\times10^{-4}$ mol NH) (made by Example 70) in 3 g of MeOH. This mixture was stirred for 24 hours at 25° C. under a $N_2$ atmosphere. This resulting mixture was added dropwise over about 10 mins. to a mixture of 73 g of piperazine (847 mmol, 15 equiv. per epoxide) in 140 mL of MeOH at 25° C. After 24 hours, the methanol was removed using a rotary evaporator to give a white solid residue. The piperazine was removed using a bulb-to-bulb distillation apparatus at high vacuum and 140° C. for one hour or until the pot residue was clear and viscous. The weight of this material came to 10.2 g. This material was dissolved in 30 g of MeOH and added to a Sephadex™ LH-20 column in MeOH. After the void volume, the first 9 fractions were found to contain product uncontaminated by lower molecular weight material as determined by TLC (30% $NH_4OH$ in MeOH). These collected fractions were stripped of volatiles to give 820 mg (80% yield) of product. Fractions 10-22 contained product that was contaminated by lower molecular weight material. Its spectra are as follows:

$^{13}C$ NMR (125 MHz, $CDCl_3$): δ 46.29, 46.89, 47.00, 54.70, 55.59, 62.67, 63.29, 68.53, 68.73, 70.41, 71.34, 74.06, 75.45, 75.62.

EXAMPLE 72

Addition of Tetrafunctional Epoxide Branch Cell Reagent to Piperazine Functional G=1 from with Piperazine Capping: Poly(aminoalcoholether) Dendrimer, G=2 [Removal of Excess Epoxide with Dialysis]

[(C)=PETGE; (IF1)=OH; (EX1)=PIPZ; (IF2)=OH; (BR1)= PETGE; (IF3)=OH; (EX2)=PIPZ; (IF4)=OH; (BR2)=PETGE; (IF5)=OH; (EX3)=PIPZ; (IF6)=OH; (BR3)=PETGE; (IF7)=OH; (EX4)=PIPZ; (TF)=Secondary NH; G=2.5]

To a 50 mL round bottom flask containing a stir bar was added 5.7 g of PETGE (15.8 mmol, 16 equivalents per NH (made by Example C) and 20 g of MeOH. To this stirred mixture was added, dropwise over 5 mins., 260 mg of poly (aminoalcoholether) dendrimer, G=1, piperazine surface ($8.2\times10^{-5}$ mol, $9.8\times10^{-4}$ mmol NH) (made by Example 25) in 5 g of MeOH. This mixture was stirred for 24 hours at 25° C. This mixture was diluted to about 100 mL with MeOH to give a 5% solids solution that was placed in a regenerated cellulose membrane, 1K, and dialyzed for 24 hours in 2L of MeOH with two changes of dialyzate. This retentate mixture was added to 75 g of PIPZ (848 mmol, 341 equiv. per epoxide) in 140 g of MeOH. This resulting mixture was stirred for 18 hours at RT. The volatiles were removed by a rotary evaporator to give a white solid. PIPZ was removed by a bulb-to-bulb distillation at high vacuum at 140° C. for one hour to give an opaque viscous material that was not very soluble in MeOH. Stirring this mixture in MeOH for 16 hours followed by filtration and evaporation of volatiles from the filtrate gave 360 mg (theoretical 1.2 g) of desired material.

EXAMPLE 73

Addition of Tetrafunctional Epoxide Branch Cell Reagent to Piperazine Functional G=1 with Piperazine Capping: Poly(aminoalcoholether)dendrimer, G=2, (C)=pentaerythritol, (TF)=piperazine [Quenching]

[(C)=PETGE; (IF1)=OH; (EX1)=PIPZ; (IF2)=OH; (BR1)= PETGE; (IF3)=OH; (EX2)=PIPZ; (IF4)=OH; (BR2)=PETGE; (IF5)=OH; (EX3)=PIPZ; (IF6)=OH; (BR3)=PETGE; (IF7)=OH; (EX4)=PIPZ; (TF)=Secondary NH; G=2.5]

To a 50-mL round bottom flask containing a stir bar was added 4.9 g of PETGE (13.6 mmol, 10 equiv. per epoxide) (made by Example C) and 20 g of MeOH. To this rapidly stirred mixture was added 360 mg of poly(aminoalcoholether)dendrimer, G=1, piperazine surface ($1.13\times10^{-4}$ mol, 1.36 mmol NH) (made by Example 25) in 3 g of MeOH over about 5 mins. This mixture was sealed under a $N_2$ atmosphere and stirred at 25° C. for 6 hours. This mixture was added to 250 g of piperazine (2.9 mol, 50 equiv. per epoxide) in 250 g of MeOH over about 10 mins. This mixture was stirred for 18 hours at 25° C. under a $N_2$ atmosphere. Volatiles were removed by a rotary evaporator to give a white solid. Piperazine was removed using a bulb-to-bulb distillation apparatus at 140° C. with a high vacuum to give 10 g of a clear viscous material. This material was dissolved in 30 g of MeOH and purified on a Sephadex™ LH-20 column in MeOH. Fractions 1-9 were found to contain pure product and fractions 1-9 were mixed product and low molecular weight material as determined by TLC (30% $NH_4OH$ in MeOH). The collected fractions 1-9 were stripped of volatiles with a rotary evaporator and high vacuum to give 950 mg (80% yield) of a clear viscous material. The collected fractions 10-19 were stripped of volatiles to give 1.6 g. This material was dialyzed in methanol using a 1K regenerated cellulose membrane until low molecular weight material was removed to give 150 mg of pure product.

EXAMPLE 74

Addition of Tetrafunctional Epoxide Branch Cell Reagent to Piperazine Functionalized G=1 with Piperazine Capping: Poly(aminoalcoholether)dendrimer, G=2 [ultrafiltration to remove excess epoxide]

[(C)=PETGE; (IF1)=OH; (EX1)=PIPZ; (IF2)=OH; (BR1)= PETGE; (IF3)=OH; (EX2)=PIPZ; (IF4)=OH; (BR2)=PETGE; (IF5)=OH; (EX3)=PIPZ; (IF6)=OH; (BR3)=PETGE; (IF7)=OH; (EX4)=PIPZ; (TF)=Secondary NH; G=2.5]

To a 50-mL round bottom flask containing a stir bar was added 4.2 g of PETGE (11.6 mmol, 16 equiv. per NH) (made by Example C) and 15 g of MeOH. To this homogenous mixture was added 200 mg of poly(aminoalcoholether)dendrimer, pentaerythritol core, G=1, piperazine surface ($6.29\times10^{-5}$ mol, $7.55\times10^{-4}$ mol NH) (made by Example 25) in 3 g of MeOH, dropwise over about 5 mins. This mixture was stirred for 4 hours at 25° C. This mixture was diluted with 100 mL of MeOH to give a 5% w/w solution and ultrafiltered in a stainless steel tangential flow UF apparatus in MeOH at 20 psi (137.9 kPa) with temperature stabilizing at 35° C. Permeate was collected for 2.75 hours to a volume of 225 mL for 0.4 recirculations. This mixture was then added dropwise over 10 mins. to 75 g of piperazine (871 mmol) in 140 g of MeOH. This mixture was stirred for 18 hours at 25° C. The volatiles were removed on a rotary evaporator to give a white solid residue. Piperazine was removed by a bulb-to-bulb distillation at 140° C. and high vacuum for one hour to give a clear viscous residue of 6 g. The residue was not a clear viscous liquid but a porous solid that was not soluble in MeOH after a few mins. of stirring. This mixture was stirred in 100 mL of MeOH for 20 hours at 25° C. The clear liquid was decanted off and evaporated of volatiles to give 360 mg. This material was purified using Sephadex™ LH-20 in MeOH with monitoring fractions of 8 mL each with TLC (30% NH$_4$OH in MeOH). Fractions 1-9 contained the desired product as determined by PAGE amounting to 260 mg with considerable oligomeric material present on the baseline of the PAGE.

EXAMPLE 75

Addition of Tetrafunctional Epoxide Branch Cell Reagent to Piperazine Functional G=1 with Piperazine Capping [Retentate Temperature Control]

[(C)=PETGE; (IF1)=OH; (EX1)=PIPZ; (IF2)=OH; (BR1)= PETGE; (IF3)=OH; (EX2)=PIPZ; (IF4)=OH; (BR2)=PETGE; (IF5)=OH; (EX3)=PIPZ; (IF6)=OH; (BR3)=PETGE; (IF7)=OH; (EX4)=PIPZ; (TF)=Secondary NH; G=2.5]

To a 50-mL round bottom flask containing a stir bar was added 3.80 g of PETGE (10.5 mmol, 15 equiv. per NH) (made by Example C) and 12 g of MeOH. To this homogeneous, rapidly stirred mixture was added 180 mg of poly(aminoalcoholether) dendrimer, G=1, pentaerythritol core (5.66×10$^{-5}$ mol, 6.8×10$^{-4}$ mol NH) (made by Example 25) in 3 g of MeOH. This mixture was stirred for 4 hours at 25° C. in a sealed vessel under a N$_2$ atmosphere. This mixture was added to a tangential flow UF apparatus containing 1K regenerated cellulose membranes in MeOH, maintaining the volume of the retentate at 80 mL, about 5% w/w, and the temperature between 25-27° C. A total of 280 mL of permeate were obtained (4.5 hours) for 3.4 recirculations. The permeate was stripped of volatiles to give 1.9 g (50% recovery). The retentate was removed and the UF device was washed 3×80 mL with MeOH. The combined solutions were added dropwise over 15 mins. to a mixture of 75 g of PIPZ (871 mmol) in 140 g of MeOH. This resulting mixture was stirred at 25° C. for 18 hours. The volatiles were removed from this mixture to give a white solid. Piperazine was removed from the mixture using a bulb-to-bulb distillation at 140° C. and high vacuum for one hour to give 4 g of a clear viscous residue. This mixture was dissolved in 9 g of MeOH, purified on a Sephadex™ LH-20 size exclusion column in MeOH. After a void volume of 575 mL was taken, 48 fractions of 8 mL each were collected. Pure product was observed in fractions 1-12 and stripped of volatiles to give 540 mg (90% yield) of product. Mixed fractions of product and pentaerythritol tetra(2-hydroxypropyl-3-piperazine)ether in fractions 13-22 were collected and dialyzed in MeOH with a regenerated cellulose membrane to give 40 mg (6%). Essentially pure pentaerythritol tetra(2-hydroxypropyl-3-piperazine)ether in fractions 23-32 were collected for recycle.

EXAMPLE 76

Reaction of the Product from Example 41 with Diethanolamine (DEA) to Produce PEHAM Dendrimer G=2 with a Four-Arm Core and Hydroxyl Surface

[(C)=PETGE; (IF1)=OH; (EX1)=Triazole; (BR1)=PETriGE; (IF2)=OH; (BR2)=DEA; (TF)=OH; G=2]

Crude product 4 was quenched with DEA (1.07 g, 10.26 mmol, 3 equiv. per epoxide) (Aldrich) in 3 mL of t-butanol. The reaction mixture was stirred at RT for 1 day, then heated at 45° C. for 3 days. After cooling to RT, the reaction mixture was diluted with 300 mL of MeOH, and a few undissolved inorganic solids were filtered off. The filtrate was further purified by UF through a 1K size exclusion membrane. After collecting 900 mL of permeate, the retentate was withdrawn from the UF and the UF washed with MeOH (3×50 mL). The solvent was removed by rotary evaporation to give a tan colored liquid, which was dried under high vacuum to give the desired G=2 dendrimer 5 as a foam-like solid (850 mg, 99% yield). Its spectra are as follows:

$^1$H NMR (300 MHz, CD$_3$OD): δ 2.49-2.80 (m, H), 3.40-3.50 (m, H), 3.52-3.70 (m, H), 3.81 (bs, H), 4.10-4.20 (m, H), 4.38-4.50 (m, H), 4.588 (bs, H), 7.99 (s, 4H); and $^{13}$C NMR (75 MHz, CD$_3$OD): δ 29.99, 45.51, 45.68, 53.39, 57.47, 58.46, 59.63, 64.32, 68.44, 69.03, 69.35, 70.12, 72.85, 73.84, 125.04, 144.82.

The following Scheme 73 illustrates this reaction.

Scheme 73

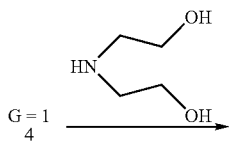

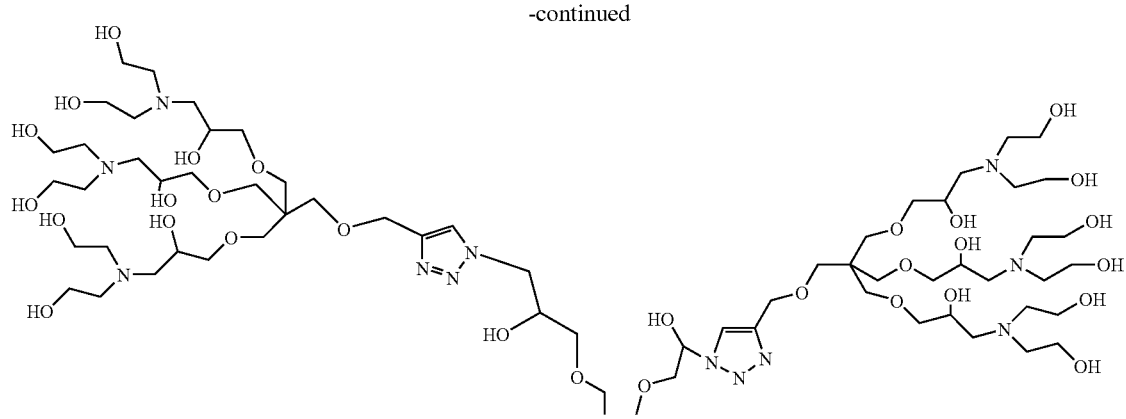

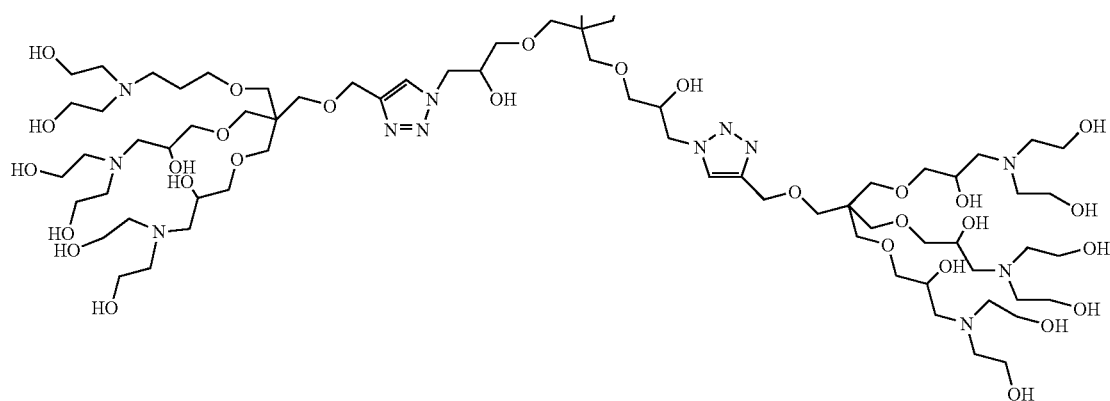

G = 2
5

EXAMPLE 77

Ester Derivatives from Primary Amines

[(C)=PETGE; (IF1)=OH; (BR1)=DETA; (BR2) in situ=Methylacrylate; (TF)=Methyl ester; G=2.5]

A solution of the octa amine (made by Example 27) in MeOH was added to the solution of methyl acrylate (Acros) in MeOH dropwise at 0° C. (1.5 equiv. per NH). After the addition, the reaction was allowed to warm to RT. The mixture was then heated to 40° C. for 24 hours. Then the solvent was removed to give the product as an yellow oil, having the following spectra:

MALDI-TOF: Calc. 2146; found 2169.662 (M+Na) amu.
Scheme 74 illustrates this reaction:

Scheme 74

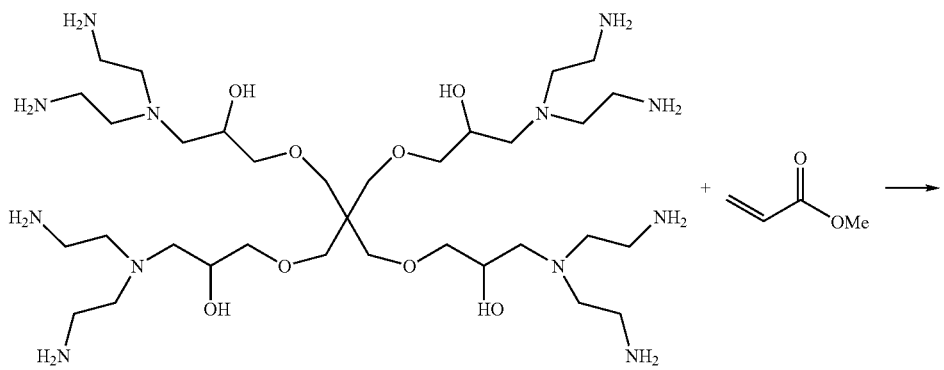

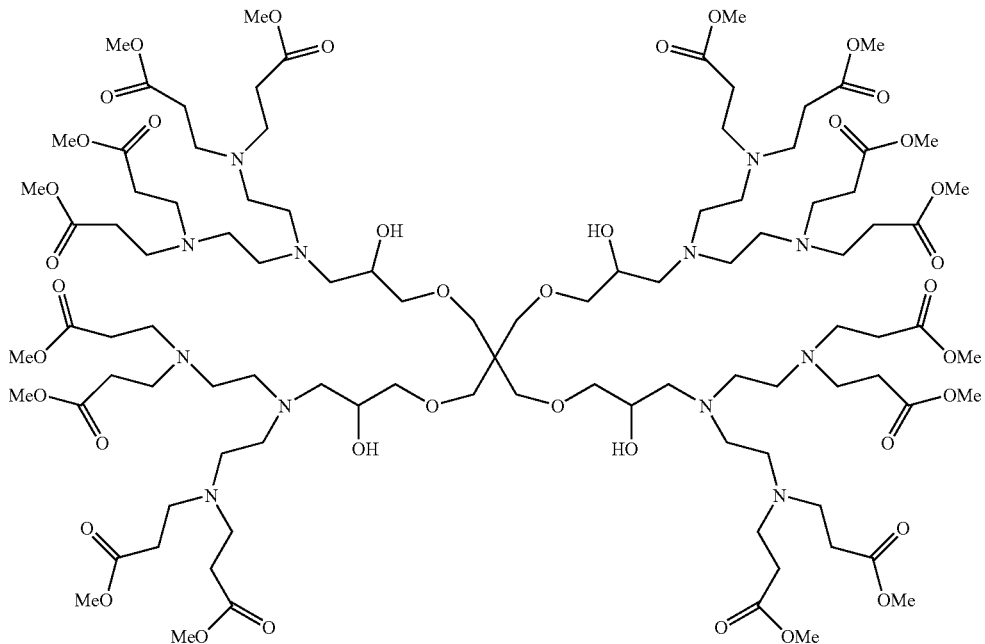

EXAMPLE 78

Synthesis of PEHAM Dendrimer (G=2) from Dendrimer (G=1) and PETGE [(C)=PETGE; (IF1)=OH; (EX1)=PIPZ; (IF2)=OH; (BR1)=PETGE; (IF3)=OH; (EX2)=PIPZ; (IF4)=OH; (BR2)=PETGE; (IF5)=OH; (EX3)=PIPZ; (TF)=Secondary NH; G=2.5]

PETGE (4.40 g, 12.24 mmol) (made by Example C) was taken in 20 mL of MeOH and the flask was cooled to 4° C. in an ice bath. A G=1 dendrimer (0.54 g, 0.17 mmol, 2.04—(NH)—mmol) (made by Example 26B) was dissolved in 10 mL of MeOH and added to the above stirring solution dropwise over a period of 15 mins. The ice-bath was removed and the mixture allowed to stir at RT for 20 hours. The reaction mixture was made a 5% solution in MeOH and subjected to UF (1K cut off). After five cycles (5×120 mL) the retentate was withdrawn from UF. The UF filtrate was washed with MeOH (2×20 mL) and quenched with EPC (3.38 g, 21.44 mmol, 3.5 equiv. per epoxide) and concentrated to 15 mL on a rotary evaporator under reduced pressure with minimal heat.

The reaction mixture was allowed to stir at RT for 16 hours. Excess of EPC was separated through UF (1K cut off) (2.33 g of EPC was recovered from permeate). The solvent was removed on a rotary evaporator and dried under high vacuum, which gives 2.3 g of ester surface dendrimer.

Ester surface G=2 dendrimer (2.3 g) was dissolved in 21 mL of MeOH. Aqueous KOH (6.9 g of 90% was dissolved in 14 mL of water) solution was added to the above stirring solution dropwise over a period of 5 mins. The flask was arranged with a refluxing condenser and placed in a pre-heated oil bath (85-90° C.) and heated for 20 hours. MeOH was removed on a rotary evaporator and the resulting aqueous reaction mixture was further diluted with 20 mL of water, cooled to 10° C. with an ice bath and neutralized with 6N HCl with constant mixing. The pH was adjusted to 9, concentrated on a rotary evaporator, which gave a solid. The solid was re-dissolved in 120 mL of MeOH with gentle heat (by a heat-gun) and allowed to stand at RT. The solids were filtered through a Büchner funnel, and washed with MeOH. The filtrate was concentrated on a rotary evaporator to give solid material (3 g). This material was subjected to UF (1K cut off) (5×120 mL) to remove traces of KCl. Evaporation of the solvent from the retentate gave PIPZ surface, G=2 dendrimer (1.66 g, 91.76% yield) as a pale yellow solid that has the following spectra:

$^1$H NMR: (300 MHz, CD$_3$OD): δ 2.37-2.42 (m, 144H), 2.51 (bs, 144H), 2.58 (bs, 136H), 2.83 (bs, 128H), 3.30 (bs, 68H, —OH), 3.34 (s, 36H, —NH), 2.37 (d, J=4.50 Hz, 136H), 3.42-3.45 (bs, 136H), 3.90 (bs, 68H); and $^{13}$C NMR: (75 MHz, CD$_3$OD): δ 45.09, 45.80, 53.50, 54.40, 61.47, 62.10, 67.35, 67.55, 69.24, 70.12, 72.85, 74.20, 74.42; and IR (Neat): $\lambda_{max}$ 3385, 2929, 2924, 2817, 1649, 1557, 1454, 1362, 1321, 1367, 1106, 1029, 1004, 860, 825, 784 $cm^{-1}$; and MALDI-TOF: $C_{497}H_{996}N_{104}O_{136}$ Calc. 10605; found 4000-10000 amu; and Polydispersity was measured from AFM gives 1.091.

EXAMPLE 79

PEHAM Dendrimer (G=3) from Dendrimer (G=2) and PETGE

[(C)=PETGE; (IF1)=OH; (EX1)=PIPZ; (IF2)=OH; (BR1)= PETGE; (IF3)=OH; (EX2)=PIPZ; (IF4)=OH; (BR2)=PETGE; (IF5)=OH; (EX3)=PIPZ; (IF6)=OH; (BR3)=PETGE; (IF7)=OH; (EX4)=PIPZ; (TF)=Secondary NH; G=0.5, 1.5, 2.5, 3.5]

A single necked, 100-mL, round bottom flask was charged with PETGE (15.55 g, 43.2 mmol) (made by Example C) and 35 mL of MeOH. The flask was cooled to 10° C. with an ice-bath. Dendrimer, G=2.5 (1.06 g, 0.1 mmol, 3.6—(NH)—mmol) (made by Example 78) was dissolved in 15 mL of MeOH and added to the above stirring solution over a period of 20 min. through a dropping funnel. The ice-bath was removed and allowed to stir at RT for 42 hours. The reaction mixture was diluted with 320 mL of MeOH to provide a 5% methanolic solution and subjected to UF (1K cut off). After five recycles (5×120 mL), TLC indicated only traces of PETGE with retentate (11.78 g of PETGE was recovered from the permeate).

The retentate was drawn from the ultrafiltrate; the ultrafiltrate was washed with methanol (2×20 mL). The total amount of the retentate was 150 mL, which was quenched with EPC (23 g, 145.56 mmol, 13.47 equiv. per epoxide) and stirred for 4 days at RT. The reaction mixture was diluted with MeOH to provide a 5% methanolic solution and excess of EPC was separated by UF (1K cut off) (14×120 mL) (19.15 g of EPC was recovered from the permeate). Evaporation of solvent from the retentate gave 5.57 g of ester surface G=3.5 dendrimer as a foamy solid.

Ester surface G=3.5 dendrimer (5.38 g) was taken in a 250-mL, round bottom flask and dissolved in 48 mL of MeOH. Aqueous KOH (45%) (16.14 g of 90% KOH was dissolved in 32 mL of water) was added to the above stirring solution over 5 mins. The flask was arranged with a refluxing condenser and placed in a preheated (85-90° C.) oil-bath and heated for 36 hours. TLC indicated no G=0 ester was left, which was expected to form as a side product. The reaction mixture was cooled to RT and concentrated on a rotary evaporator. The aqueous reaction mixture was cooled to 10° C. with an ice-bath. 6N HCl was added with occasional shaking. After adding 40 mL, a change of pH from basic to acidic was observed by pH paper. Another 6 mL of HCl was added to adjust to pH5. The solution was then concentrated on a rotary evaporator under reduced pressure (bath temperature is 70° C.). After evaporating half of the solution, formation of solids in the flask was observed. Water was completely removed to dry. The flask was removed from the rotary evaporator and the residue dissolved in 150 mL of MeOH with gentle heating with a heat gun. The flask was allowed to stand on bench top for few mins. Solid material was filtered though Büchner funnel, washed thoroughly with 100 mL of MeOH. Solid was not completely dissolved in MeOH and the rate of UF was found to be very slow. After six recycles through 1K membranes, the retentate was concentrated on a rotary evaporator, which give PIPZ surface 5.36 g of pale yellow color foamy solid (theoretical yield is 3.206 g).

$^1$H NMR in $CD_3OD$ revealed that all the protons from surface PIPZ were moved to down field by 0.55 ppm. The material was not completely dissolved in MeOH. This possibly could be a result of trapping of guest molecules inside the cavities/interior. This is also evident from final yields >100%.

The above sample was dialyzed through 1K membrane in water and dialyzed for 21 hours with two changes of dialyzate. Water was evaporated from the retentate on a rotary evaporator and dried under high vacuum, which gave 2.34 g (71% yield) of G=3 dendrimer as a pale yellow solid. Concentration of first dialyzate gave a solid.

MALDI-TOF analysis on dialyzate showed that guest molecules are G=0.5 dendrimer, traces of G=0 ester and few other unidentified compounds.

$^1$H NMR of the compound from retentate was recorded and it was found that protons from surface PIPZ were moved to up-field by 0.55 ppm.

Its spectra are as follows:

$^1$H NMR: (300 MHz, $CD_3OD$): δ 2.53 (bs, H), 2.81 (bs, H), 3.23 (bs, H), 3.30 (bs, H), 3.45 (bs, H), 3.90 (bs, H), 4.07 (bs, H); and $^{13}$C NMR: (75 MHz, $CD_3OD$+3 drops of $D_2O$): δ 43.53, 45.77, 50.22, 51.46, 58.47, 59.74, 60.62, 66.16, 67.45, 69.18, 70.17, 72.83, 74.09; and MALDI-TOF: $C_{1541}H_{3094}N_{320}O_{424}$ Calc. 32882; found 49617 amu; and Polydispersity was measured from AFM gives 1.117.

TABLE I

PEHAM dendrimer

| Generation | Molecular formula | Molecular weight | Surface groups | Core |
|---|---|---|---|---|
| 0 | $C_{33}H_{68}N_8O_8$ | 704 | 4 | PETGE |
| 1 | $C_{149}H_{300}N_{32}O_{40}$ | 3180 | 12 | PETGE |
| 2 | $C_{497}H_{996}N_{104}O_{136}$ | 10605 | 36 | PETGE |
| 3 | $C_{1541}H_{3084}N_{320}O_{424}$ | 32882 | 108 | PETGE |

EXAMPLE 80

Reaction of 4,4'-methylene bis(N,N'-diglycidyl aniline) (MBDGA) with Diethanolamine (DEA)

[(C)=MBDGA; (IF1)=OH; (BR1)=DEA; (TF)=OH; G=2]

Glycidyl aniline, I-b (0.844 g, 2 mmol) and 30 mL of MeOH were placed in a 100-mL single necked round bottom flask and equipped with a stir bar. DEA (1.68 g, 16 mmol) was dissolved in 10 mL of MeOH and added to the above stirring solution at RT. The flask was arranged with a refluxing condenser and heated at 60° C. for 2 days under a $N_2$ atmosphere. After 2 days, TLC indicated complete consumption of starting material I-b and MALDI-TOF MS indicated molecular ion peaks for octa hydroxyl terminated (G=1) dendrimer III-f and hexa hydroxyl terminated product. Solvent was removed on a rotary evaporator, which gives a transparent liquid. Spectra for III-f are as follows:

MALDI-TOF: $C_{41}H_{74}N_6O_{12}$ Calc. 843; found 866 ($M^+Na$) and 761 ($M^+Na$) amu for tri addition product.

The following Scheme 75 illustrates this reaction:

Scheme 75

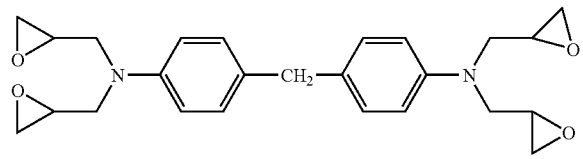

I-b

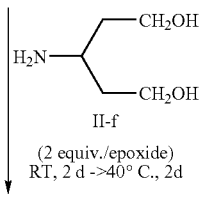

II-f (2 equiv./epoxide)
RT, 2 d ->40° C., 2d

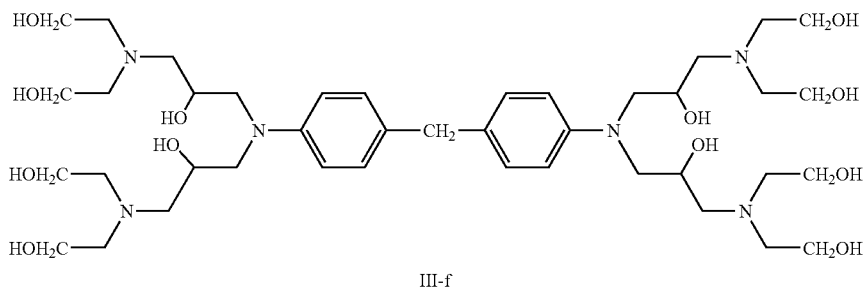

III-f

EXAMPLE 81

Reaction of Glycidyl Aniline I-b with Diethyliminodiacetate

[(C)=MBDGA; (IF1)=OH; (BR1)=DEIDA; (TF)=Ethyl ester; G=2.5]

DEIDA (1.512 g, 8 mmol) was taken in a single necked 100-mL, round bottom flask and 12 mL of MeOH added. MBDGA I-b (0.422 g, 1 mmol) was dissolved in a mixture of solvents (3 mL of DCM and 5 mL of MeOH) and added to the above reaction mixture over a period of 30 mins. After stirring the reaction mixture at RT for 2 days, MALDI-TOF mass spectrometry indicated molecular ion peaks for mono- and bis-addition products. The flask was arranged with a refluxing condenser and heated for 3 days at 40° C. Solvents were removed on a rotary evaporator, which gives a pale yellow color liquid. The entire reaction mixture was subjected to column chromatography on silica gel (7"×1.5") (17.8 cm×3.8 cm). First, 40% ethyl acetate/hexanes were used to elute the excess of DEIDA followed by 5% methanol/chloroform used to elute the octa-ester terminated (G=1) dendrimer III-g, 0.92 g (78% yield) that has the following spectra:

$^1$H NMR (300 MHz, CDCl$_3$): δ 2.40-3.80 (m, H), 3.90-4.3 (m, 16H), 4.7 (m, 4H), 6.60-6.76 (m, 4H), 6.90-7.10 (m, 4H); and $^{13}$C NMR (75 MHz, CDCl$_3$): δ 14.43, 21.29, 39.90, 45.57, 45.71, 45.91, 50.64, 50.79, 50.88, 51.18, 51.97, 52.06, 53.22, 53.03, 53.54, 53.97, 54.23, 54.62, 55.00, 55.88, 56.07, 56.48, 56.59, 56.92, 58.68, 58.98, 59.28, 59.63, 60.63, 60.99, 61.11, 66.60, 66.92, 67.13, 67.62, 112.33, 112.76, 112.98, 113.12, 113.33, 129.67, 129.79, 129.91, 167.37, 169.66, 171.92, 171.97, 172.02 (The number of carbons found indicated trans-esterification products); and MALDI-TOF: C$_{57}$H$_{90}$N$_6$O$_{20}$ Calc. 1178; found 1201 (M$^+$Na) amu.

Scheme 76 illustrates this reaction:

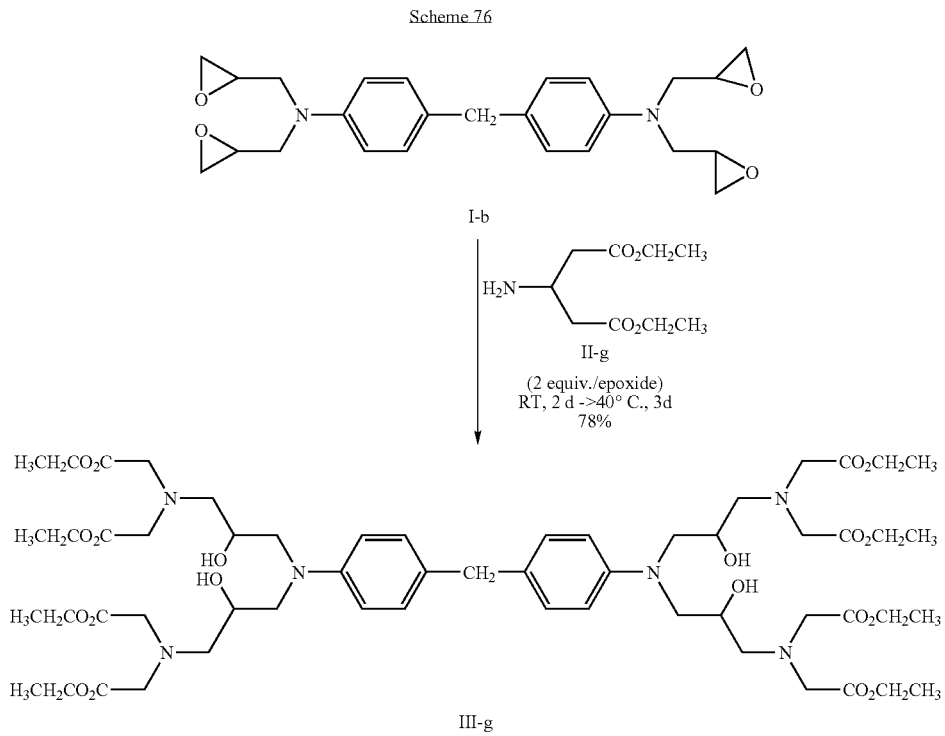

EXAMPLE 82

Synthesis of Octaamine Terminated (G=1) Dendrimer from Ester Terminated (G=1) Dendrimer

[(C)=MBDGA; (IF1)=OH; (BR1)=DEIDA; (EX1)=EDA; (TF)=Primary NH$_2$; G=2]

EDA (66 g, 200 mol. Equiv.) was placed in a oven dried 500-mL single necked round bottom flask, equipped with a stir bar and closed with a rubber septum and cooled to 0° C. with an ice-bath. Ester surface dendrimer III-g (0.65 g, 0.55 mmol) (from Example 81) was dissolved in 10 mL of MeOH and added to the above solution through a pressure equalizing funnel over a period of 20 mins. The funnel was removed and the flask flushed with N$_2$ gas and closed with a rubber septum and stored at 0° C. in a refrigerator for 2 days. After 2 days the reaction mixture was allowed to warm to RT. Excess EDA was removed on a rotary evaporator under reduced pressure, which gives a waxy colorless compound. The entire reaction mixture was dissolved in 30 mL of MeOH and 70 mL of toluene added and then evaporated on a rotary evaporator. This process was repeated three times in order to remove residual amount of EDA, which gives a light yellow color solid, amine surface dendrimer IV (0.825 g, 98% yield) that has the following spectra:

$^{13}$C NMR (125 MHz, DMSO-d6): δ 41.97, 42.53, 49.27, 52.96, 54.09, 56.76, 57.56, 59.90, 60.44, 66.76, 112.57, 112.71, 129.71, 171.16; and IR (Neat): $v_{max}$ 3291 (br), 2933, 1653, 1545, 1517, 1440, 1358, 1232, 1189, 1000, 962, 799, 7322 cm$^{-1}$; and MALDI-TOF: C$_{57}$H$_{106}$N$_{22}$O$_{12}$ Calc. 1290; found 1313 (M$^+$Na) amu.

Scheme 77 illustrates this reaction:

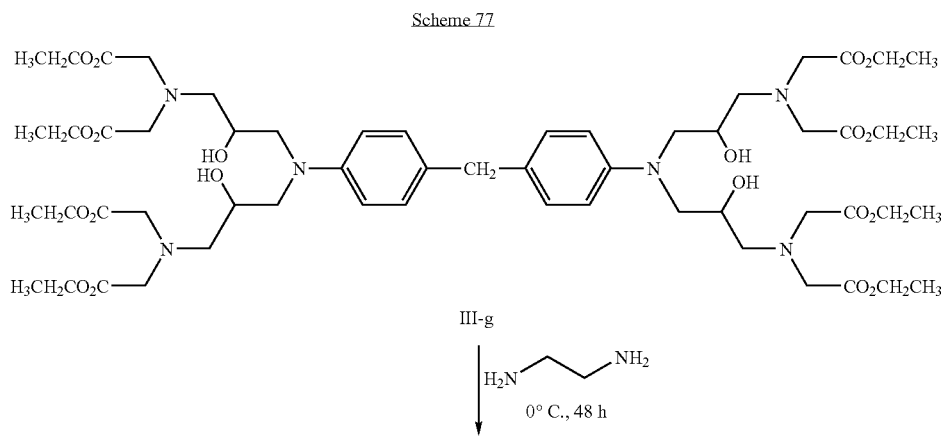

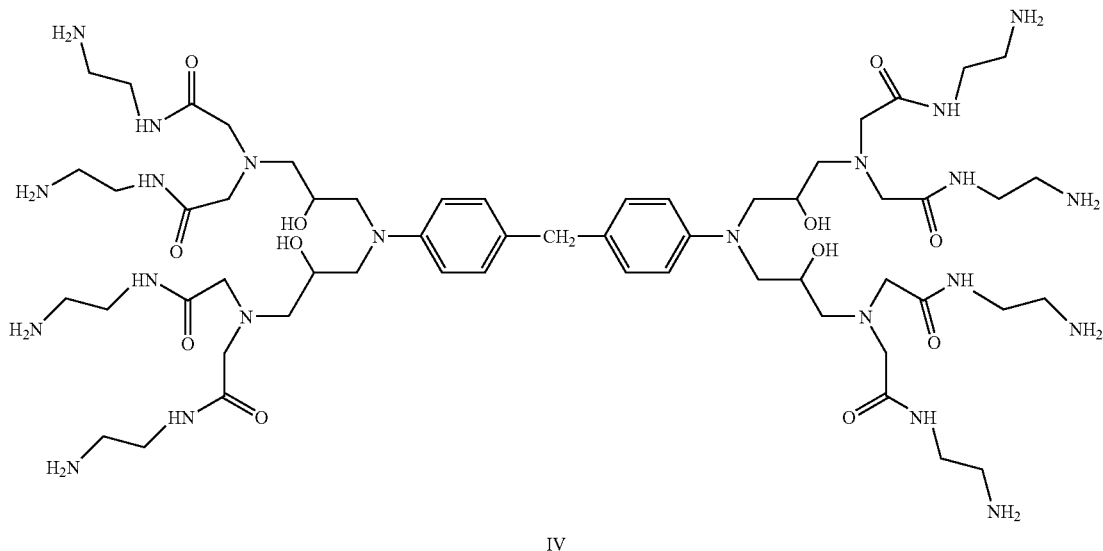

IV

EXAMPLE 83

The Dendronization of an Allyl Terminated Dendrimer

[(C)=PETGE; (IF1)=OH; (BR1)=BAA; (BR2)=PAMAM type branch cell; (IF2)=Allyl; (TF)=pyrrolidone; G=2.5]

Generation zero (G=0), cystamine core PAMAM dendrimer with a pyrrolidone surface (571 mg, 0.5129 mmol) (Dendritic Nanotechnologies, Inc.) was dissolved in 1.5 mL of anhydrous MeOH (Acros). Then DTT (71 mg, 0.462 mmol, 0.9 equiv. of disulfide bond) was added. The reduction reaction was stirred at RT under argon overnight. To another flask was added the octa-allyl product (57 mg, 0.0761 mmol) (made by Example 28) and AIBN (17 mg, 0.104 mmol) (Aldrich) to 3 mL of anhydrous THF (Acros). To this solution was added the reduced dendron solution under argon. Then the reaction mixture was heated to 65° C. overnight. Then the solvent was removed to give the crude product as a foam solid (631 mg, >100% because of the excess of dendron that was used) that has the following spectra:

MALDI-TOF: Calc. 3002.68 (M$^+$Na); found 3003.43, (M$^+$Na) amu.

Scheme 78 illustrates this reaction:

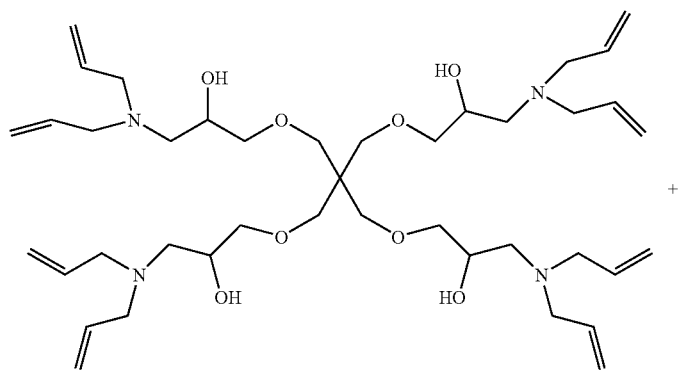

Scheme 78

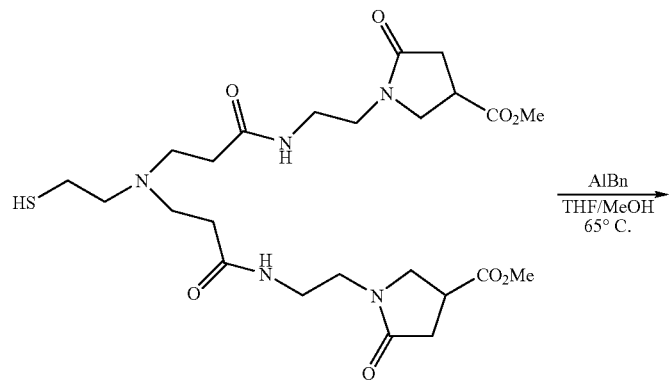
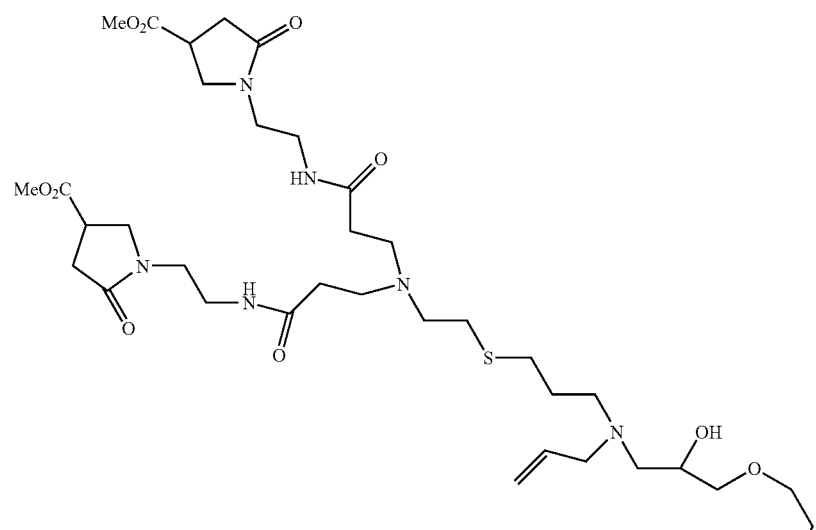
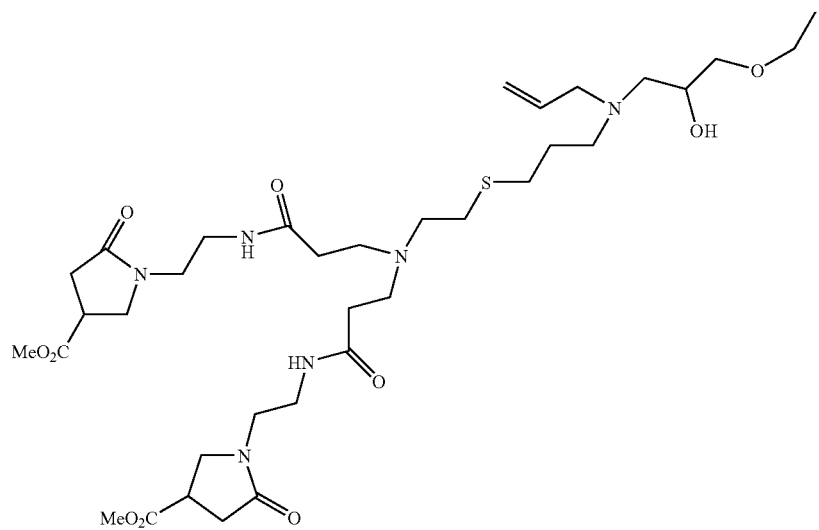

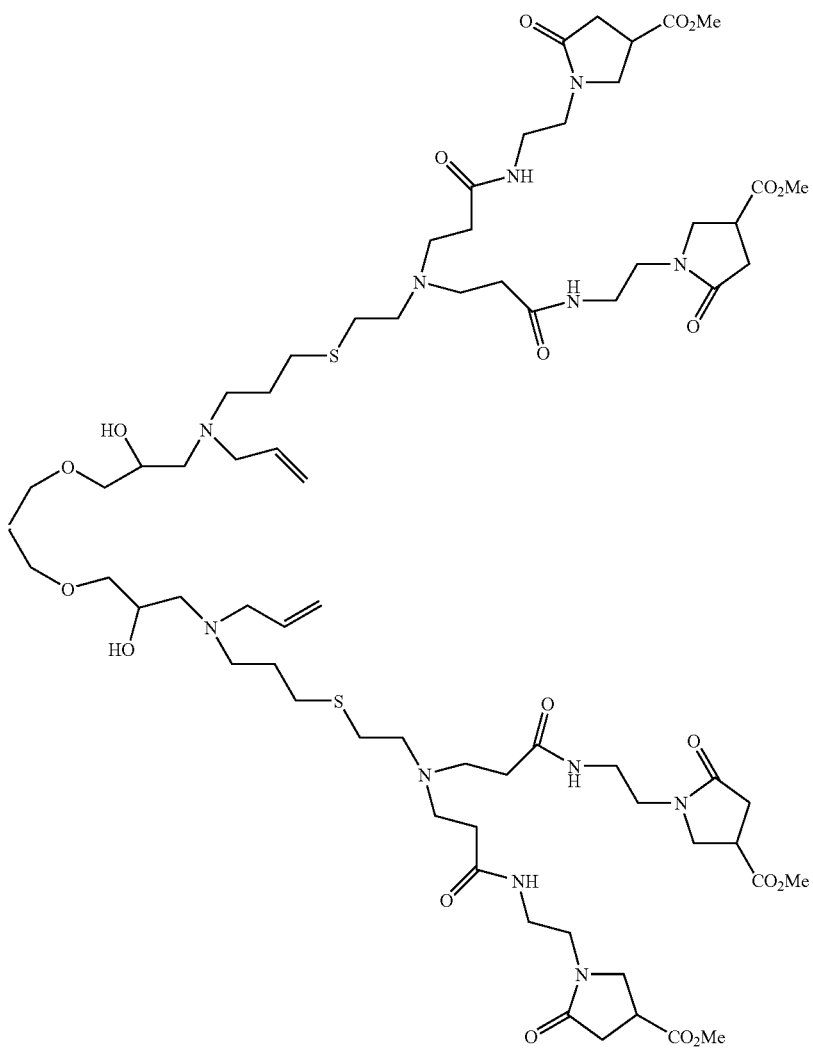

EXAMPLE 84

Reaction of the Product from Trimethylolpropane Triglycidylether Reacting with Diethyliminodiacetate (DEIDA) with tris(2-aminoethyl)amine (TREN) to Produce PEHAM Dendrimer G=2 with a Three-Arm Core and Primary Amine Surface for DNA Compaction and Antibacterial Activity

[(C)=TMPTGE; (FF)=Et; (IF1)=OH; (BR1)=DEIDA; (BR2)=TREN; (TF)=Primary $NH_2$; G=2]

A 100-mL round bottom flask was charged with TREN 2 (17.05 g, 116.82 mmol, 60 $NH_2$ equiv. per ester) and 40 mL of MeOH (Fisher Scientific) and a magnetic stir bar. After the exothermic mixing reaction had stopped, (20 minutes), a solution of G=1 ester C4 (0.846 g, 0.97 mmol, 5.84 ester mmol; made from Example 23B) in 10 mL of MeOH was added dropwise over a period of 1 hour at RT. The mixture was then placed in an oil-bath and heated at 50° C. for 3 days. Progress of the reaction was monitored by IR spectroscopy, i.e., the disappearance of the ester vibration at 1740 $cm^{-1}$ and the appearance of the amide vibration at 1567 $cm^{-1}$. MALDI-TOF MS analysis indicated the mass for the desired G=2.0 product accompanied by looped compounds at 1348 $[M+Na]^+$ and 1201 $[M+Na]^+$ (one and two loops). The reaction mixture was diluted with 700 mL of MeOH and subjected to UF using a 1K size exclusion membrane. After collecting 1.8 liters of permeate, the retentate was withdrawn from the UF and the solvent removed by rotary evaporation, giving a pale yellow colored, viscous liquid, which was further dried under high vacuum to give the desired G=2 dendrimer 3 (1.41 g, 98.94% yield). Its spectra are as follows:

$^1$H NMR (300 MHz, $CD_3OD$): δ 0.86 (3H, bt), 1.38 (2H, bs), 2.32-2.60 (H, m), 2.67-2.76 (H, m), 3.29-3.34 (H, m), 3.82 (3H, bs); and $^{13}$C NMR (125 MHz, $CD_3OD$): δ 8.14, 24.06, 38.57, 38.63, 39.98, 40.16, 44.59, 54.00, 55.09, 55.28, 57.21, 58.02, 60.19, 63.05, 63.28, 69.38, 69.94, 72.52, 72.96, 75.00, 173.76, 173.86, 174.03; and IR (Neat): $v_{max}$ 3298, 2934, 2842, 1659, 1572, 1536, 1470, 1388, 1357, 1311, 1116, 973, 819 $cm^{-1}$; and MALDI-TOF MS: $C_{63}H_{143}N_{27}O_{12}$ Calc. 1470.9843; found 1494.2270 $[M+Na]^+$, 1348.022 $[M+Na]^+$ (one looped), 1201.0970 $[M+Na]^+$ (two looped) amu.

The following Scheme 79 illustrates this reaction.
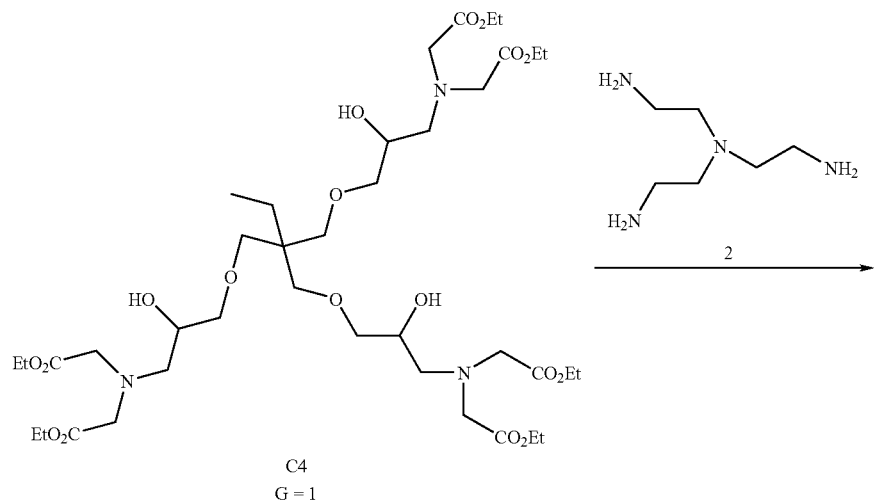
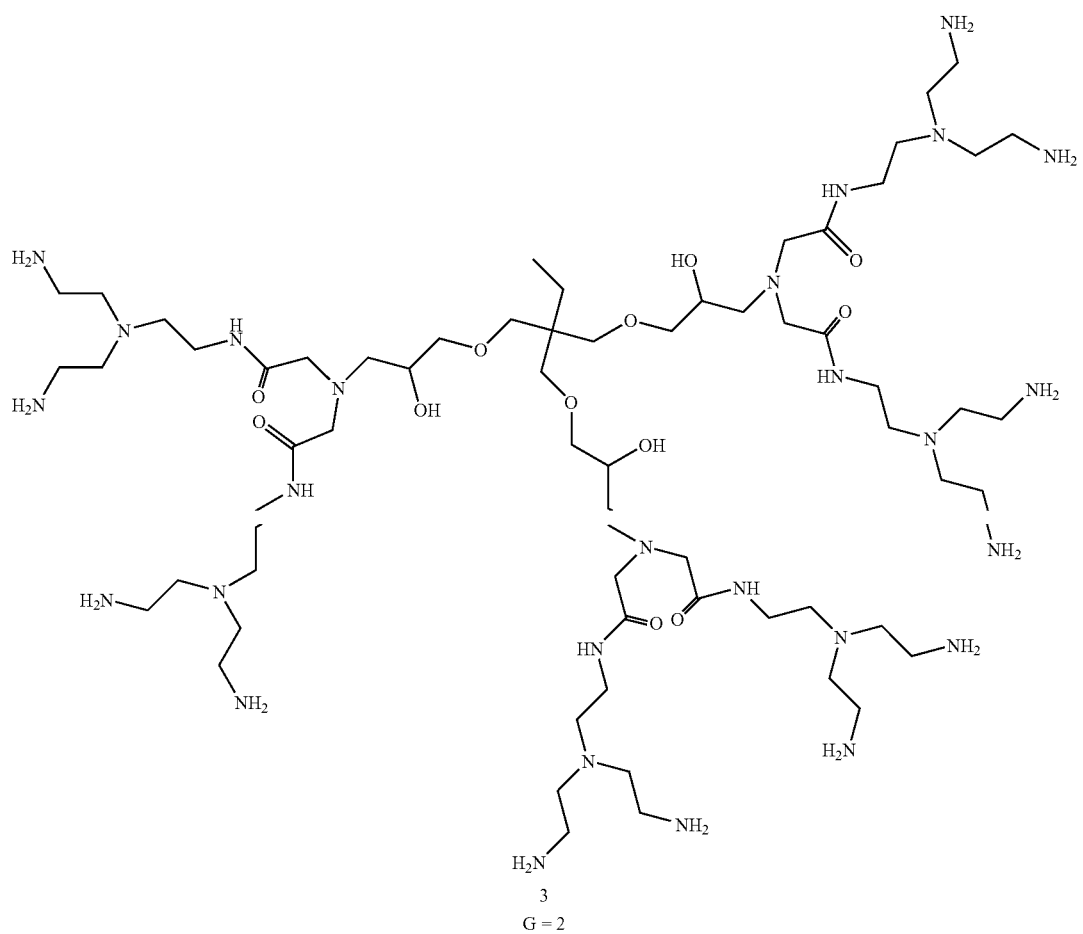

EXAMPLE 85

Reaction of the Product from Example 84 with Dimethylitaconate (DMI) to Produce PEHAM Dendrimer G=2.5 with a Three-Arm Core and Biocompatible Pyrrolidone Surface

[(C)=TMPTGE; (FF)=Et; (IF1)=OH; (BR1)=DEIDA; (BR2)=TREN; (EX1)=DMI; (TF)=Methyl ester; G=2.5]

To a cold (10° C.) solution of DMI (2.84 g, 18.0 mmol, 3 equiv. per $NH_2$) (Acros Organics) was added a solution of G=2 dendrimer 3 (0.7435 g, 0.5 mmol, 6 $NH_2$ mmol; made from Example 84) in 5 mL of MeOH dropwise over a period of 30 mins. After complete addition, the flask was closed with a septum and allowed to warm to RT and remained under mechanical stirring for 60 hours. MALDI-TOF MS analysis showed the expected mass for the desired product and mass peaks for by-products with one, two, three looped pyrrolidone surface compounds. Another 1.42 g of DMI was added and allowed to stir for 36 hours. The reaction mixture was diluted to 2.5-5% w/w in MeOH and subjected to UF using a 1K size exclusion membrane at a pressure of 20-22 psi (137.9 kPa). After collecting 800 mL of permeate, the retentate was withdrawn from the ultrafiltration apparatus and washed with MeOH (3×50 mL). The solvent was removed from the retentate by rotary evaporation to give a liquid, which was further dried under high vacuum to give the pyrrolidone surface G=2.5 dendrimer 4 as a hygroscopic solid (1.166 g, 74.8% yield). Its spectra are as follows:

$^1$H NMR (300 MHz, $CD_3OD$): δ 0.83 (3H, bt), 1.37 (2H, bq), 2.65 (H, bs), 3.30-3.35 (H, t, J=5.10 Hz), 3.65 (H, s), 3.68-3.73 (H, bs), 3.84-3.96 (H, bs); and $^{13}$C NMR (75 MHz, $CD_3OD$): δ 8.17, 24.05, 34.97, 35.06, 38.16, 38.39, 41.65, 41.96, 44.61, 50.96, 51.98, 52.55, 54.05, 54.68, 60.25, 62.50, 69.34, 72.86, 75.01, 173.69, 174.99, 175.19; and IR (Neat): $\nu_{max}$ 3308, 2955, 2883, 2842, 1736, 1675, 1541, 1495, 1439, 1362, 1275, 1203, 1173, 1106, 1024, 932, 855, 753, 697 $cm^{-1}$; and MALDI-TOF MS: $C_{135}H_{215}N_{27}O_{48}$; Calc. 2984.3, found 3007.3 $[M+Na]^+$ amu.

The following Scheme 80 illustrates this reaction.

Scheme 80

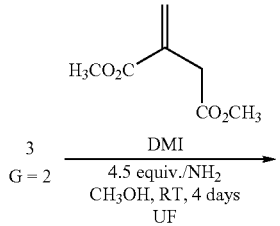
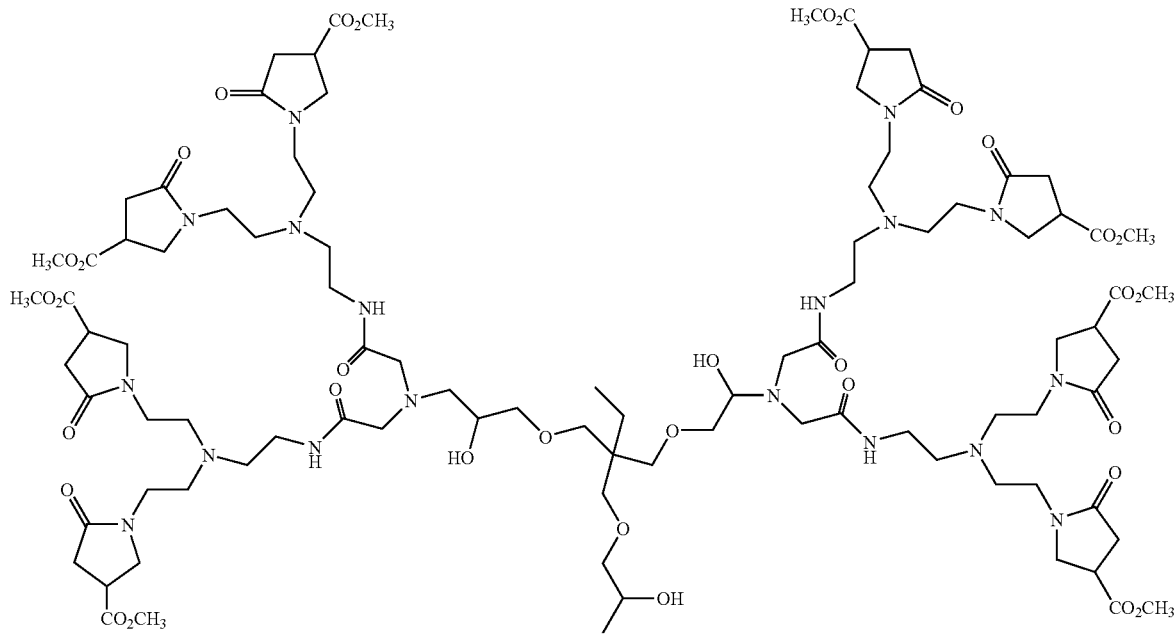

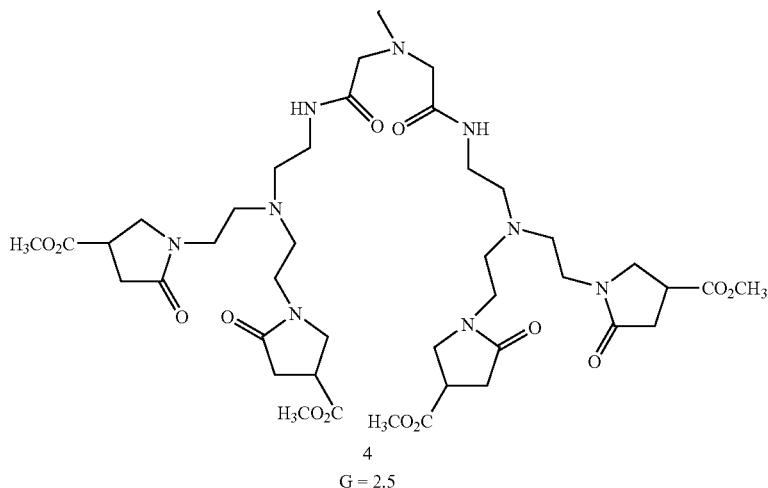

4
G = 2.5

EXAMPLE 86

Reaction of the Product from Pentaerythritol Tetraglycidylether Reacting with Diethyliminodiacetate (DEIDA) with tris(2-aminoethyl)amine (TREN) to Produce PEHAM Dendrimer G=2 with a Four-Arm Core and Primary Amine Surface for DNA Compaction and Antibacterial Activity

[(C)=PETGE; (IF1)=OH; (BR1)=DEIDA; (BR2)=TREN; (TF)=Primary $NH_2$; G=2]

A 250-mL round bottom flask was charged with TREN 2 (52.26 g, 358.0 mmol, 120 $NH_2$ equiv. per ester), 50 mL OF MeOH (Fisher Scientific) and a stir bar. After the exothermic mixing reaction had stopped (30 minutes), a solution of G=1 ester C5 (1.25 g, 1.12 mmol, 8.95 ester mmol; made from Example 51) in 10 mL of MeOH was added dropwise over a period of 1 hour at RT, and the mixture stirred for overnight. MALDI-TOF MS analysis showed the expected mass peak for the desired product as well as mass peaks for by-products with one and two loops. An IR spectrum was recorded and showed the presence of the amide vibration at 1575 $cm^{-1}$ and the absence of the ester vibration at 1740 $cm^{-1}$. Stirring was continued for additional 36 hours. Then the reaction mixture was diluted to 5% w/w solution in MeOH and subjected to UF using a 1K size exclusion membrane. After collecting 3.5 liters of permeate, the retentate was withdrawn from the UF, the solvent was removed by rotary evaporation, and the remaining product dried under high vacuum to give a pale yellow colored, foamy solid 3 (2.02 g, 94% yield). Its spectra are as follows:

$^1H$ NMR (500 MHz, $CD_3OD$): δ 2.49-2.59 (H, m), 2.62 (H, bt), 2.66 (H, s), 2.68 (H, s), 2.69 (H, s), 2.70 (H, s), 2.73-2.82 (H, m), 3.29-3.47 (H, m), 3.82 (H, bs); and $^{13}C$ NMR (125 MHz, $CD_3OD$): δ 38.64, 40.19, 48.48, 49.85, 53.94, 55.10, 55.29, 57.66, 58.10, 60.23, 63.06, 69.33, 71.41, 75.11, 173.70, 173.80, 173.97; and IR (Neat): $v_{max}$ 3313, 3078, 2934, 2868, 1649, 1557, 1541, 1475, 1449, 1362, 1306, 1163, 1101, 978, 818 $cm^{-1}$; and MALDI-TOF MS: $C_{81}H_{184}N_{36}O_{16}$; Calc. 1918.6, found 1941.8 $[M+Na]^+$ amu.

The following Scheme 81 illustrates this reaction.

Scheme 81

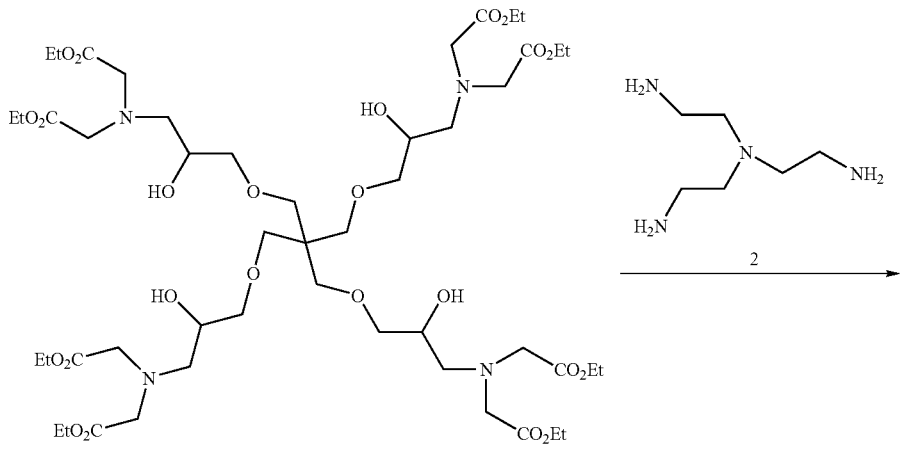

C5

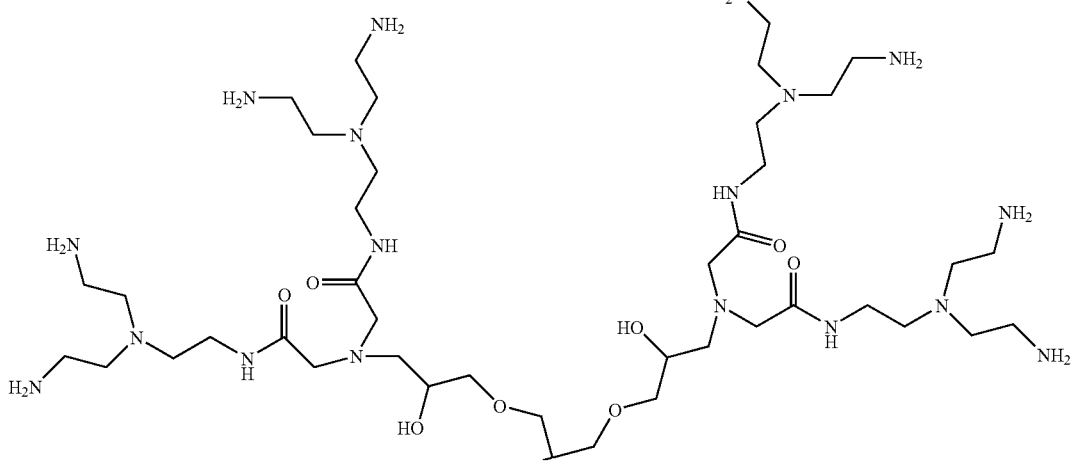

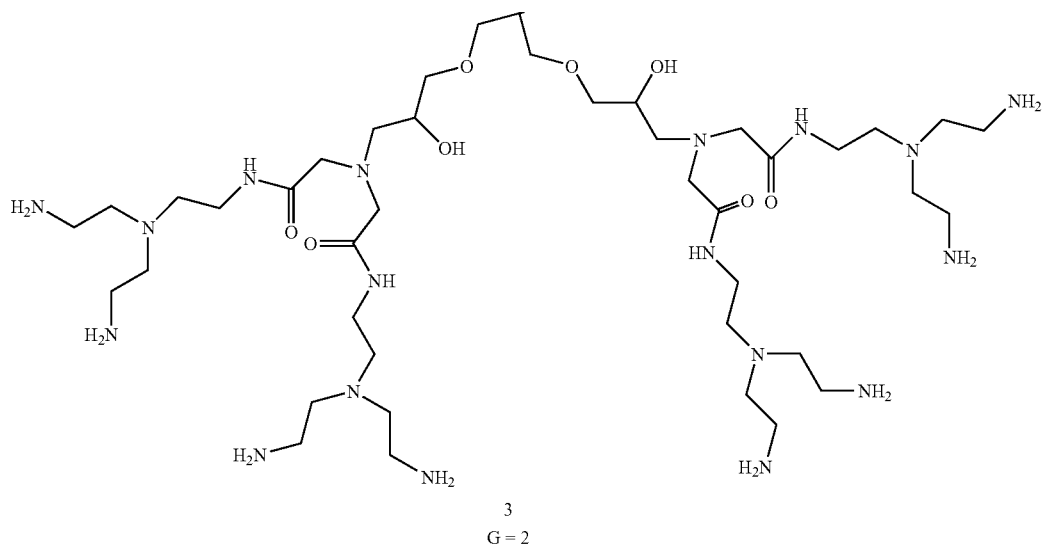

3
G = 2

EXAMPLE 87

Reaction of the Product from Example 86 with Dimethylitaconate (DMI) to Produce PEHAM Dendrimer G=2.5 with a Four-Arm Core and Biocompatible Pyrrolidone Surface

[(C)=PETGE; (IF1)=OH; (BR1)=DEIDA; (BR2)=TREN; (EX1)=DMI ; (TF)=Methyl ester; G=2.5]

To a cold (10° C.) solution of DMI (3.792 g, 24.0 mmol) (Acros Organics) in 15 mL of MeOH (Fisher Scientific) was added a solution of G=2 dendrimer 3 (0.959 g, 0.5 mmol, 8 $NH_2$ mmol, made from Example 86) in 15 mL of MeOH dropwise over a period of 30 mins. After complete addition, the reaction mixture was gradually allowed to warm to RT and stirred for 2 days. Analysis by MALDI-TOF MS spectroscopy showed the expected mass for the desired product and some looped material. Another 1.896 g (12.0 mmol) DMI in 2.0 mL of MeOH were added and stirred for 24 hours. The reaction mixture was diluted to 2.5-5% w/w in MeOH and subjected to UF using a 1K size exclusion membrane at a pressure of 20-22 psi (137.9 kPa). After collecting 1 liter permeate, the retentate was withdrawn from the UF device and the UF device washed with MeOH (3×50 mL). The solvent was removed from the retentate by rotary evaporation to give a viscous liquid, which was further dried under high vacuum, yielding the pyrrolidone surface G=2.5 dendrimer as a hygroscopic solid 4 (1.56 g, 79.27% yield). Its spectra are as follows:

$^1$H NMR (500 MHz, $CD_3OD$): δ 2.65 (H, bs), 3.30-3.47 (H, bs), 3.65-3.68 (H, m), 3.72-3.74 (H, m), 3.88 (H, m); and $^{13}$C NMR (125 MHz, $CD_3OD$): δ 34.96, 35.06, 38.16, 38.40, 41.65, 41.96, 42.18, 46.95, 49.85, 50.95, 51.98, 52.24, 52.84, 52.94, 54.05, 54.69, 60.22, 69.35, 71.43, 75.11, 173.65, 175.01, 175.15; and IR (Neat): $v_{max}$ 3308, 2950, 2878, 2817, 1736, 1675, 1536, 1495, 1434, 1362, 1265, 1203, 1168, 1106, 1019, 937, 855, 753, 702 $cm^{-1}$; and MALDI-TOF MS: $C_{177}H_{280}N_{36}O_{64}$; Calc. 3936.3, found 3957.7 $[M+Na]^+$ amu.

The following Scheme 82 illustrates this reaction.

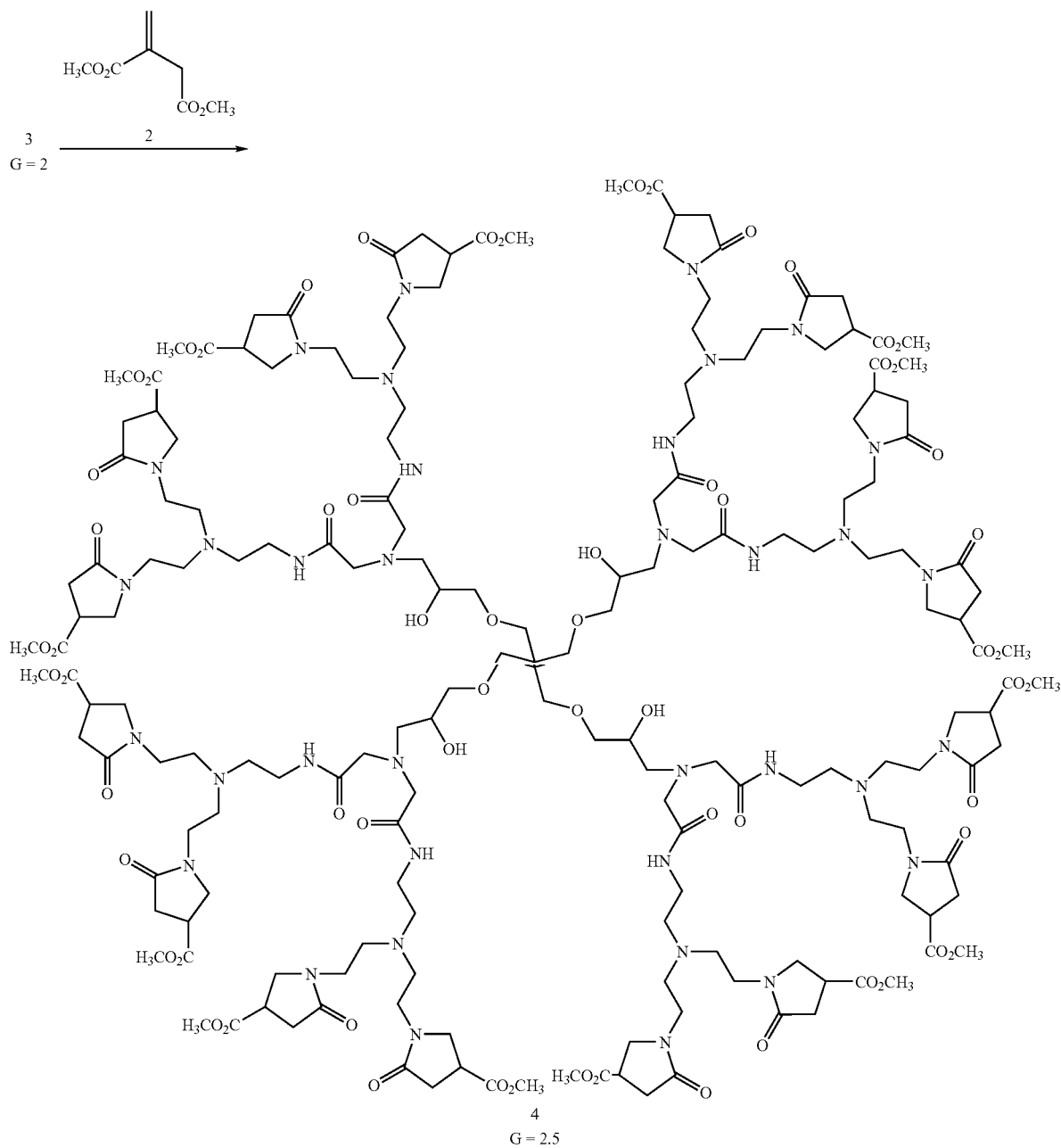

EXAMPLE 88

Reaction of the Product from Example 56 with tris(2-aminoethyl)amine (TREN) to Produce PEHAM Dendrimer G=2 with an Aromatic Four-Arm Core and Primary Amine Surface for DNA Compaction and Antibacterial Activity

[(C)=TPEGE; (IF1)=OH; (BR1)=DETA; (EX1)=DMI; (BR2)=TREN; (TF)=Primary $NH_2$; G=2]

In a 250-mL round bottom flask TREN (11.42 g, 78.22 mmol, 51.0 equiv. per ester) (Dow Chemical) was dissolved into 10 mL of MeOH under mechanical stirring and cooled to 4° C. Dendrimer II (0.392 g, 0.192 mmol; made from Example 56) was added as 7.5% solution in MeOH via a 60-mL addition funnel over 25 mins. An additional 15 mL of MeOH was used as washings. The reaction was monitored by FT-IR through the consumption of the methyl ester vibration at 1736 $cm^{-1}$. An aliquot of 30.06 g was removed from the reaction and placed in a 1,000 Dalton dialysis membrane (38 mm diameter, 4 cm in length, Spectra/Por®, Spectrum Laboratories) in 1000 mL of MeOH. The bulk MeOH was changed after 5 hours, 16 hours, and another 8 hours. The product was transferred to a 100-mL round bottom flask and the solvent removed by rotary evaporation. The residue was placed under high vacuum for 24 hours to yield a dark yellow, amorphous, hygroscopic product III (0.230 g, 88% yield, 0.261 g theoretical yield). Its spectra are as follows:
$^1$H NMR (500 MHz, CD$_3$OD): δ 2.52 (8H, s), 2.72 (8H, s), 3.14 (2H, s), 3.53 (2H, s), 4.89 (16H, s), 6.68 (1H, s), 7.15 (1H, s); and
$^{13}$C NMR (75 MHz, CD$_3$OD): δ 35.94, 38.07, 38.93, 40.75, 41.92, 69.25, 115.17, 149.32, 156.29, 162.48, 168.36, 157.09, 175.49; and
MALDI-TOF: C$_{142}$H$_{250}$N$_{44}$O$_{24}$; Calc. 2957.8, found 2981.4 [M+Na]$^+$ amu.
The following Scheme 83 illustrates this reaction.
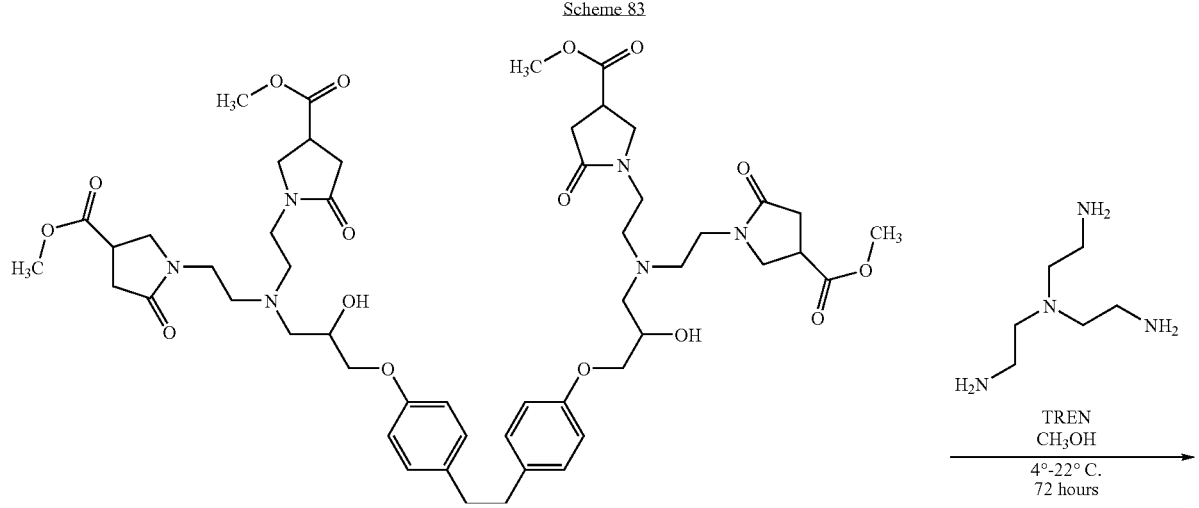
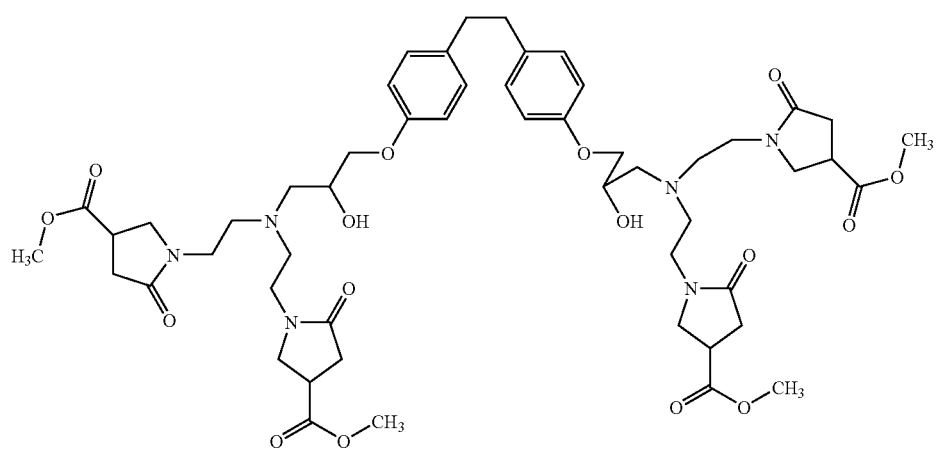

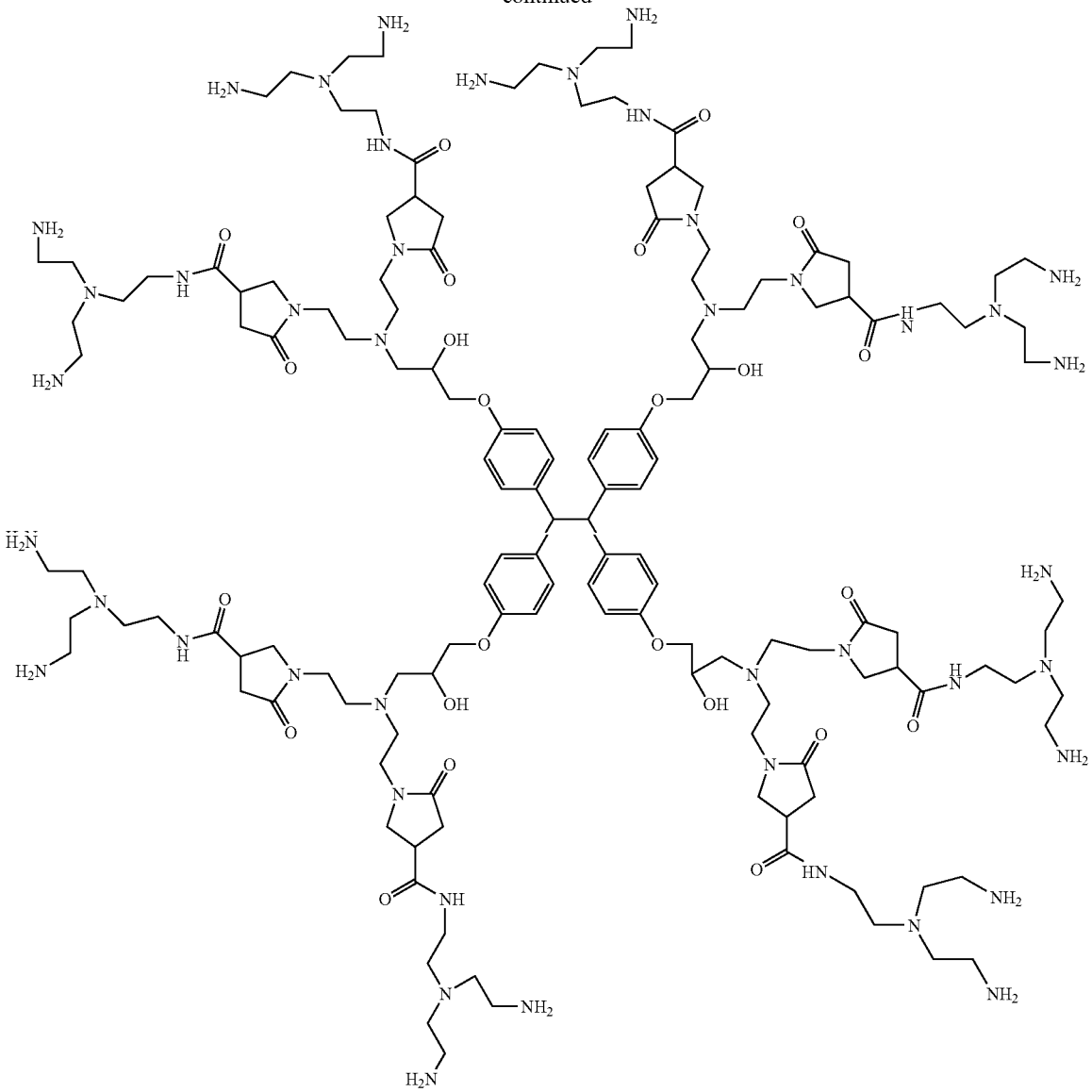

III

EXAMPLE 89

Reaction of the Product from Example 56 with tris(hydroxymethyl)aminomethane (TRIS) to Produce PEHAM Dendrimer G=2 with an Aromatic Four-Arm Core and Biocompatible Hydroxyl Surface

[(C)=TPEGE; (IF1)=OH; (BR1)=DETA; (EX1)=DMI; (BR2)=TRIS; (TF)=OH; G=2]

In a 100-mL round bottom flask TRIS (0.722 g, 5.97 mmol, 3.22 equiv. per ester) was dissolved into 25 mL of DMSO (Acros Organics). Dendrimer II (0.472 g, 0.231 mmol; made from Example 56) was added to the stirred reaction mixture via a powder funnel, which was washed with an additional 10 mL of DMSO. Then potassium carbonate (0.011 g, 0.104 mmol) (Acros Organics) was added via a powder funnel and residual powder washed with 10 mL of DMSO. The reaction was monitored by FT-IR. Upon complete consumption of the ester vibration at 1736 cm$^{-1}$, the reaction was diluted to 1000 mL with water and subjected to UF using a 3K size exclusion membrane. Upon completion of the UF, the retentate was transferred into a 500-mL round bottom flask and the solvent was removed by rotary evaporation. The remaining yellow paste was dried under high vacuum for 24 hours to yield the desired product IV (0.520 g, 78.5% yield, 0.662 g theoretical yield). Its spectra are as follows:

$^1$H NMR: (500 MHz, D$_2$O): δ 2.46 (1H, s), 2.53 (1H, s), 2.66 (1H, s), 2.84 (1H,s), 3.06 (1H, s), 3.16 (1H, s), 3.52 (2H, J=3.0 Hz), 4.77 (10H, s), 7.05 (1H, s), 7.41 (1H, s); and $^{13}$C NMR: (75 MHz, D$_2$O): δ33.64, 35.07, 37.55, 39.57, 43.28, 51.49, 53.42, 59.07, 63.23, 64.86, 117.28, 132.05, 177.92, 181.75; and MALDI-TOF: C$_{134}$H$_{210}$N$_{20}$O$_{48}$; Calc. 2757.0, found 2781.3 [M+Na]$^+$ amu.

The following Scheme 84 illustrates this reaction.
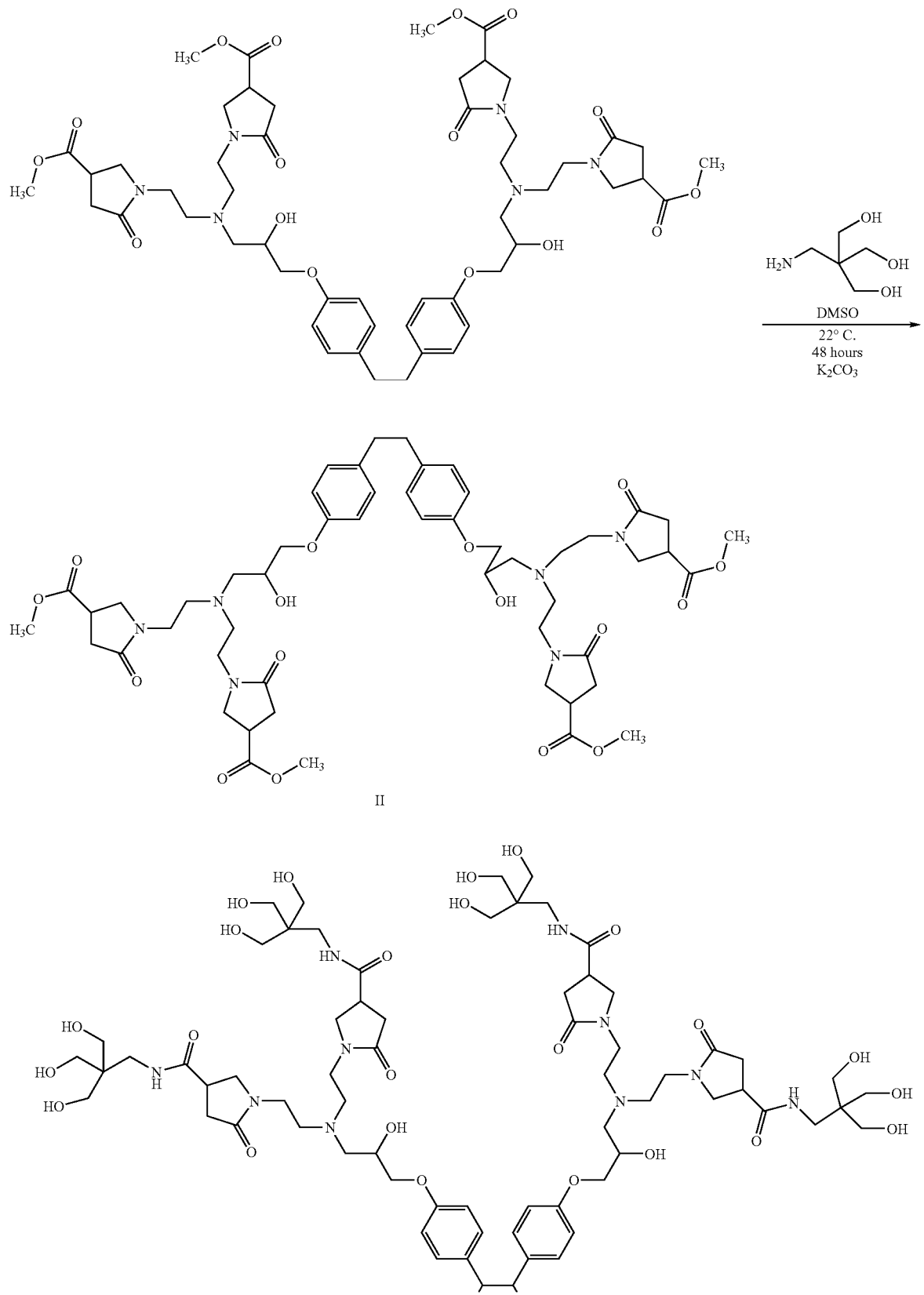
Scheme 84

-continued

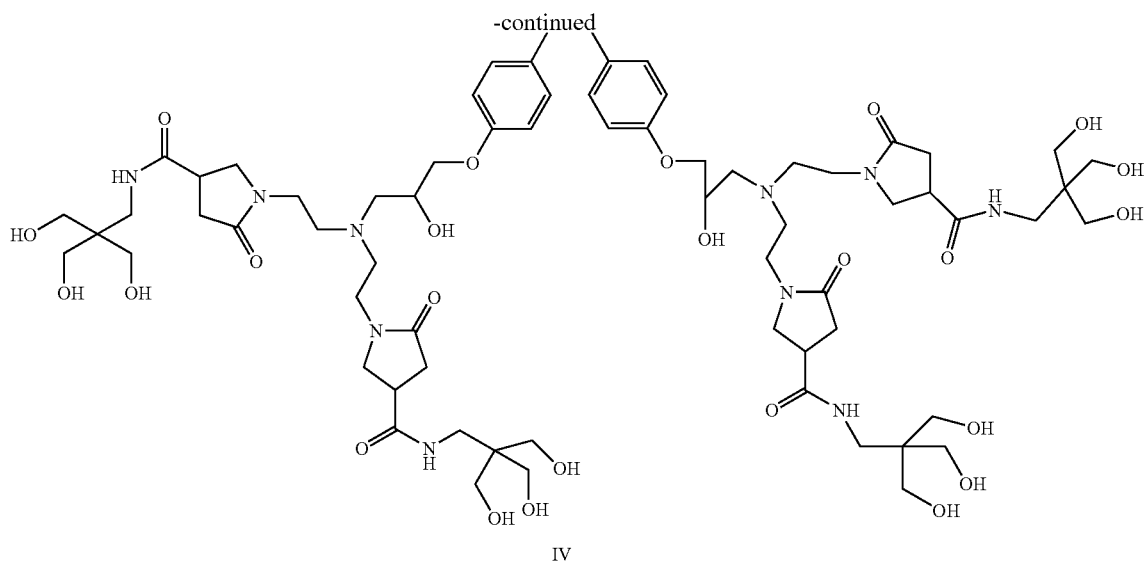

IV

EXAMPLE 90

Reaction of the Product from Tetraphenylolethane Glycidylether with tris(2-aminoethyl)amine (TREN) with Methyl Acrylate to Produce PEHAM Dendrimer G=2.5 with a Four-Arm Core and Ester Surface

[(C)=TPEGE; (IF1)=OH; (BR1)=TREN; (EX1)=Methyl acrylate; (TF)=Methyl ester; G=2.5]

To a 50-mL round bottom flask was added methyl acrylate (4.0 g, 46.0 mmol, 2 equiv. per NH) in 6 mL of MeOH. To this mixture, cooled at 4° C., was added dropwise over 3 mins. a mixture of tetraphenylolethane tetra(2-hydroxypropyl-3-(bis-aminoethyl)amine G1 (1.6 g, 1.5 mmol, 12.4 mmol $NH_2$; made from Example 58) in 10 mL of MeOH under mechanical stirring. The mixture was allowed to warm and was stirred at 25° C. for 48 hours sealed under a blanket of a $N_2$ atmosphere. Volatile material was removed by rotary evaporation, the residue redissolved in 50 mL of MeOH and again rotary evaporated. Redissolution and evaporation were repeated another 3 times. The resulting residue was dried under high vacuum for 5 hours at 25° C. to give the desired product II (2.4 g, 67% yield). Its spectra are as follows:

$^{13}C$ NMR (125 MHz, $CDCl_3$): δ 49.80, 51.01, 52.08, 52.67, 53.88, 58.04, 68.19, 70.25, 114.55, 129.73, 136.90, 157.13, 173.36; and MALDI-TOF MS: $C_{118}H_{186}N_{12}O_{40}$; Calc. 2411.3, found 2413 [M]$^+$ amu.

The following Scheme 85 illustrates this reaction.

Scheme 85

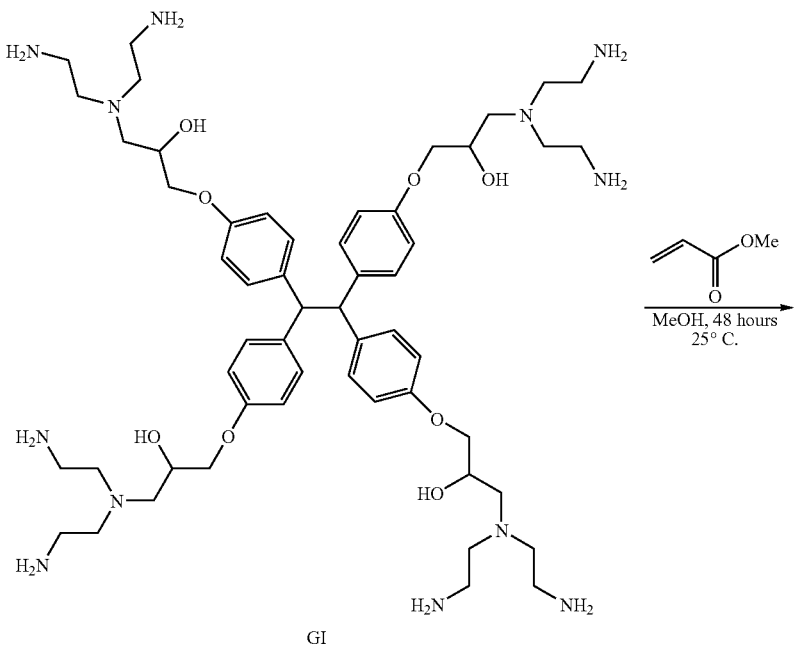

GI

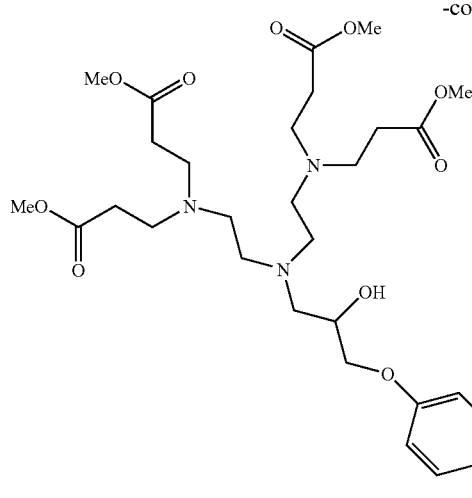
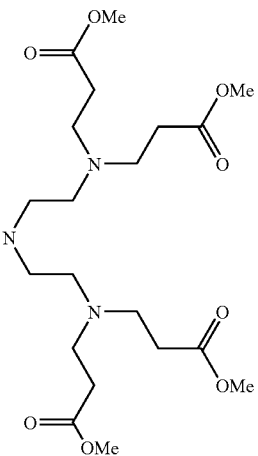
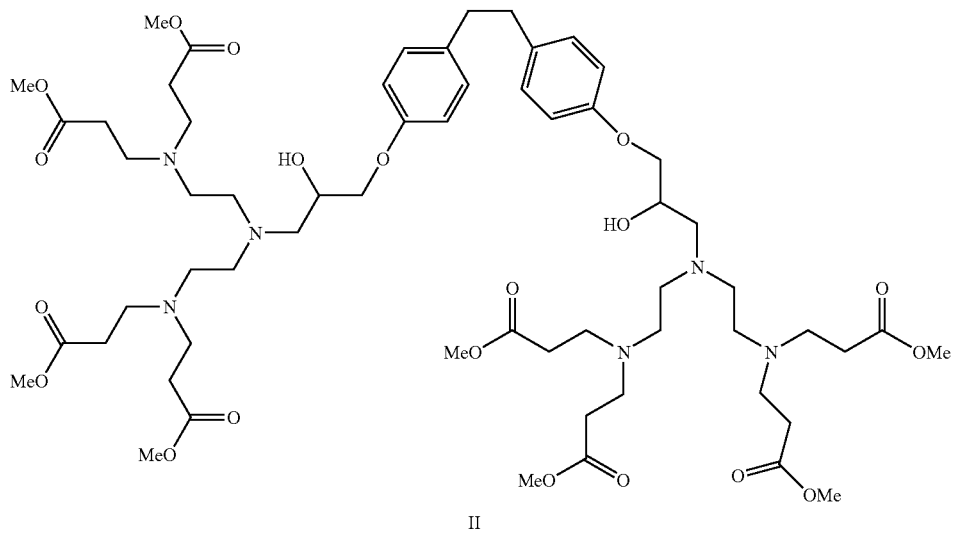

II

EXAMPLE 91

Reaction of the Product from Example 90 with Potassium Carbonate to Produce PEHAM Dendrimer G=2.5 with an Aromatic Four-Arm Core and Biocompatible Anionic Sodium Carboxylate Surface

[(C)=TPEGE; (IF1)=OH; (BR1)=TREN; (EX1)=Methyl acrylate; (TF)=COONa; G=2.5]

To a 50-mL round bottom flask was added sodium carboxylate (700 mg, 6.53 mmol, 1.9 equiv. per ester) and 20 mL of DI water under mechanical stirring. To this homogeneous solution was added the G=2 methyl ester surface dendrimer II (518 mg, 21.0 mmol, 3.44 mmol ester; made from Example 90) in 20 mL of MeOH. The mixture was stirred at 25° C. for three days under a blanket of $N_2$ atmosphere (cloudy at first, the mixture became clear after 2.5 hours of stirring). Then the mixture was diluted with 150 mL of DI water and ultrafiltered with a tangential flow UF device containing 1K regenerated cellulose membranes at a pressure of 20 psi (137.9 kPa) to give a total of 1 liter of permeate. Volatile materials were removed using a rotary evaporator. The residue was dissolved in MeOH and volatiles were removed on the rotary evaporator twice, followed by drying under high vacuum to give the desired product III (540 mg, 98% yield). Its spectra are as follows:

$^{13}$C NMR (125 MHz, $D_2O$): δ 34.38, 47.16, 52.68, 58.15, 70.21, 72.02, 117.44, 132.12, 140.60, 158.88, 181.51; and MALDI-TOF MS: $C_{102}H_{138}N12Na_{16}O_{40}$; Calc. 2540.1, found 2352 [M-2 sodium acrylates]$^+$ amu.

The following Scheme 86 illustrates this reaction.

Scheme 86

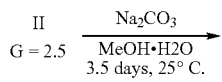

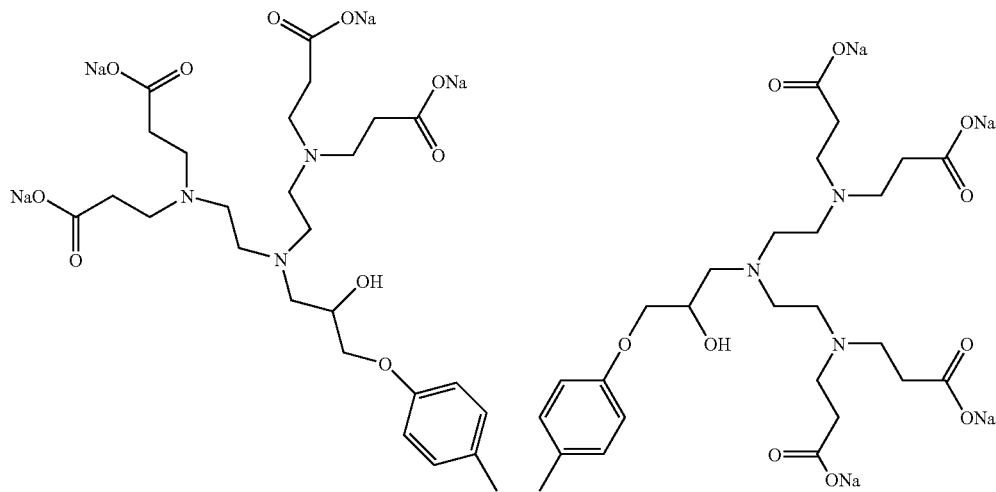

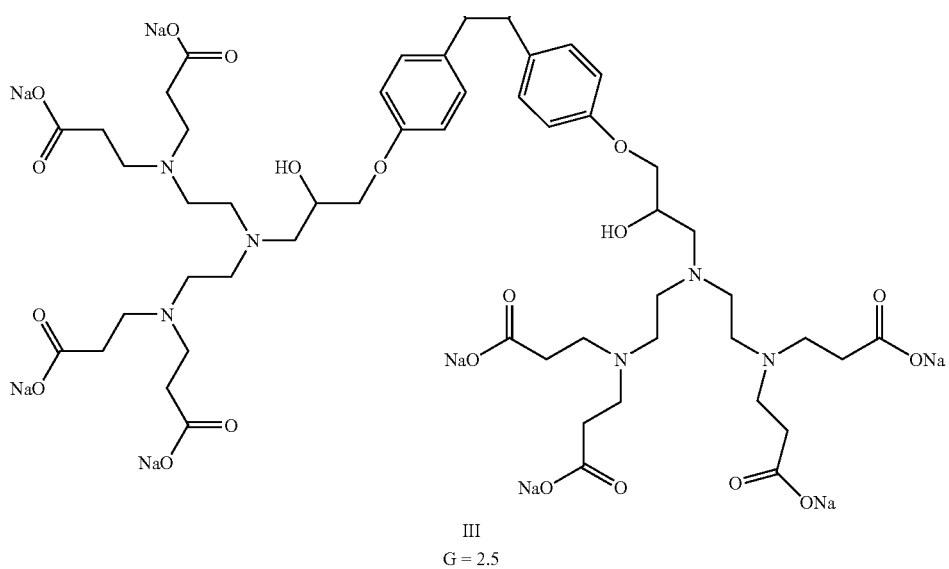

III
G = 2.5

EXAMPLE 92

Reaction of the Product from Example 90 with tris(hydroxymethyl)amino Methane (TRIS) to Produce PEHAM Dendrimer G=3 with an Aromatic Four-Arm Core and Biocompatible Hydroxyl Surface

[(C)=TPEGE; (IF1)=OH; (BR1)=TREN; (EX1)=Methyl acrylate; (BR2)=TRIS; (TF)=OH; G=3]

A 100-mL round bottom flask containing a stir bar and fitted with a septum was flame-dried under a flow of $N_2$ gas. Upon cooling to 25° C., a solution of the G=2 methyl ester surface dendrimer II (2.4 g, 1.0 mmol, 16 mmol ester; made from Example 90) in 30 mL anhydrous DMSO was added via a syringe. To this mixture was added TRIS (3.2 g, 26.4 mmol, 2 equiv.), followed by anhydrous potassium carbonate (4.0 g, 28.9 mmol, 1.1 equiv. per ester). The resulting mixture was rapidly stirred for 24 hours under a $N_2$ atmosphere. An IR of the crude mixture indicated the disappearance of the carbonyl vibration at 1736 $cm^{-1}$ after this time. The reaction mixture was diluted to 3% w/w mixture (1000 mL) with DI water and then filtered to give 900 mL of permeate. After another 600 mL permeate were ultrafiltered (6 recirculations), the retentate was concentrated by rotary evaporation to give a light yellow solid. The solid was dissolved in 50 mL of MeOH and reconcentrated on the rotary evaporator 3 times to give a fluffy powder. This powder was further dried under high vacuum to give the desired product IV (3.54 g, 93% yield). Its spectra are as follows:

$^{13}C$ NMR (125 MHz): δ 35.51, 51.78, 52.45, 54.45, 63.31, 64.83, 70.21, 117.23, 131.99, 140.05, 159.50, 177.84; and MALDI-TOF MS: $C166N_{298}N_{28}O_{72}$; Calc. 3838.1, found 3855 [M+Na]$^+$ amu.

The following Scheme 87 illustrates this reaction.

Scheme 87

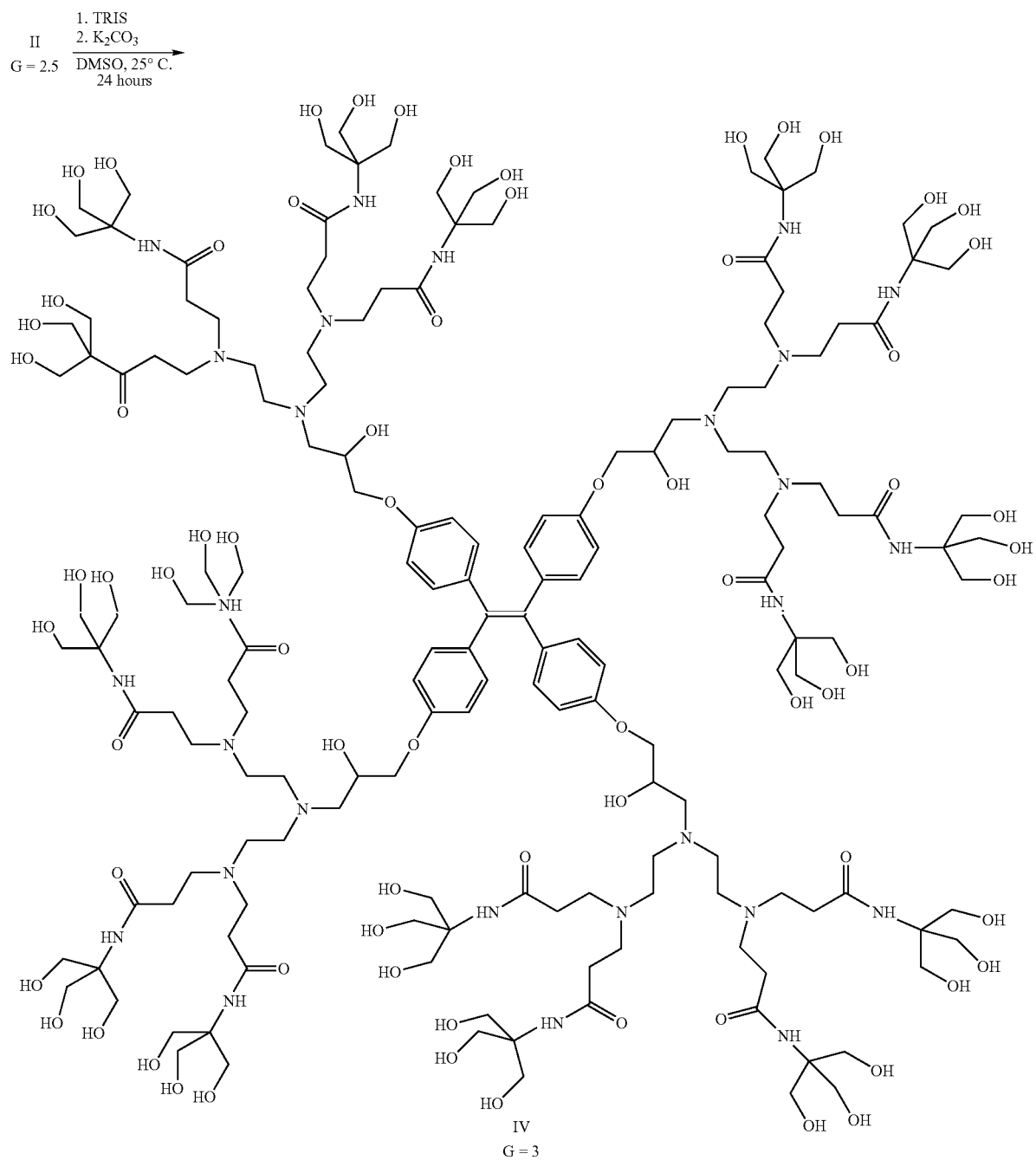

EXAMPLE 93

Reaction of Pentaerythritol Tetraglycidylether and the Product from Example 10B in Water to Produce PEHAM Dendrimer G=1 with a Four-Arm Core and Piperazine Surface

[(C)=PETGE; (IF1)=OH; (EX1)=PIPZ; (IF2)=OH; (BR1)=PETGE; (IF3)=OH; (EX2)=PIPZ; (TF)=Secondary NH; G=1.5]

To a 500-mL round bottom flask was added 0=0 PEHAM dendrimer A5 (5.88 g, 8.34 mmol, 6 equiv. per PETGE; made from Example 10B) and 57.0 g of water along with potassium carbonate (1.27 g, 9.19 mmol, 1.11 equiv. per NH) (Acros Organics) under mechanical stirring. To this solution was added dropwise PETGE (0.499 g, 1.34 mmol), dissolved in 8.0 g water, via a pipette over 10 mins. The reaction was allowed to stir at 22° C. for 24 hours under a $N_2$ atmosphere and then heated to 45° C. for another 24 hours. After 48 hours, the reaction was cooled to 22° C. and diluted to 1000 mL with water. The product was subjected to 3K UF, collecting 14 liters of permeate. The water was removed by rotary evapo ration and the residue dried under high vacuum for 24 hours to give the G=1 dendrimer I (1.51 g, 64.5% yield, 2.34 g theoretical). Its spectra are as follows:
$^1$H NMR: (300 MHz, D$_2$O): δ 2.36, (m, 8H), 2.74 (s, 2H), 3.374 (m, 6H), 3.92 (s, 1H), 4.68 (dd, J=5.85 Hz, 5H); and
$^{13}$C NMR: (75 MHz, D$_2$O): δ 44.03, 45.57, 50.83, 52.52, 53.26, 60.69, 61.25, 67.25, 70.15, 74.47, 78.96; and
MALDI-TOF: C$_{149}$H$_{300}$O$_{32}$; Calc. 3180, found 3181 [M]$^+$ amu.
The following Scheme 88 illustrates this reaction.
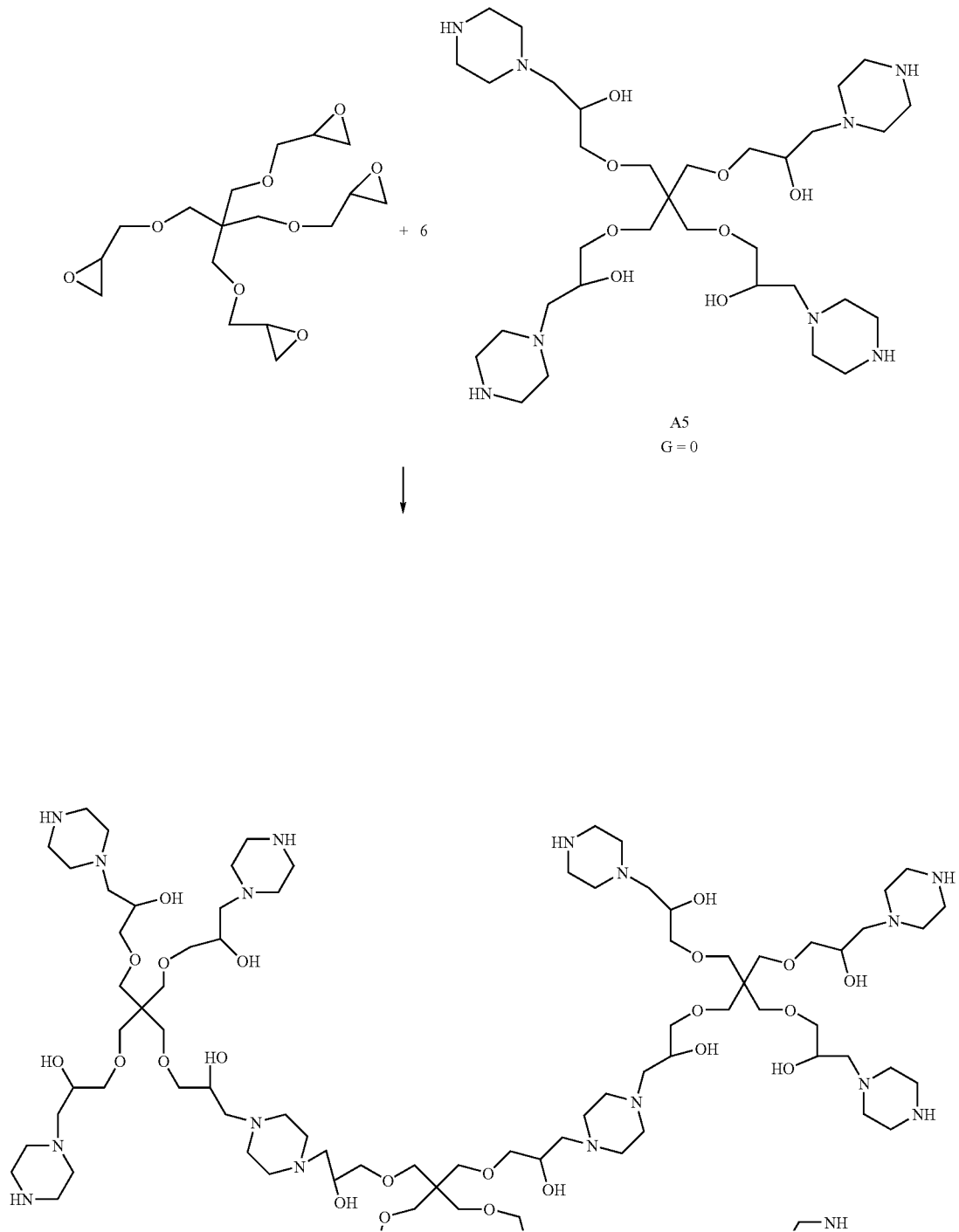

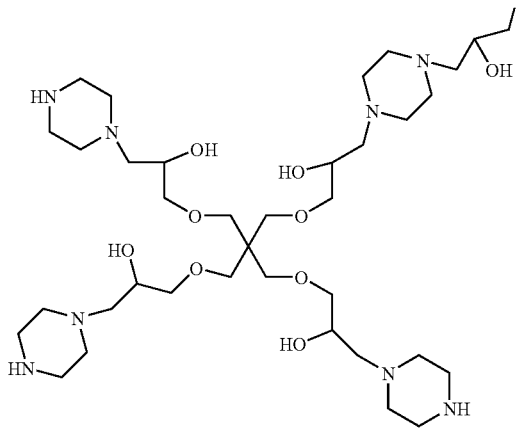

I
G = 1

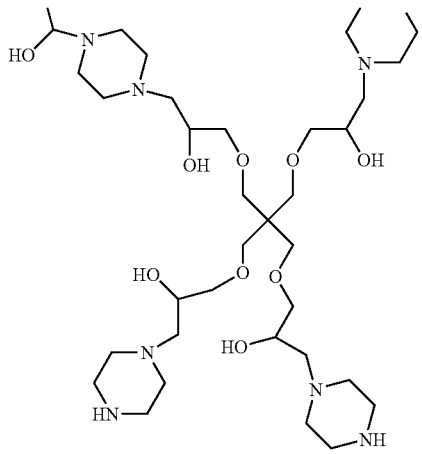

EXAMPLE 94

Reaction of the Product from Example 93 with Glycidol to Produce PEHAM Dendrimer G=2 with a Four-Arm Core and Hydroxyl Surface

[(C)=PETGE; (IF1)=OH; (EX1)=PIPZ; (IF2)=OH; (BR1)= PETGE; (IF3) OH; (EX2)=PIPZ; (BR2)=Glycidol; (TF)=OH; G=2]

In a 100-mL round bottom flask glycidol (237 mg, 3.2 mmol, 2.12 equiv per NH) (Aldrich) was dissolved into 8 mL of water. The G=1 PEHAM dendrimer I (400 mg, 0.126 mmol, 1.51 mmol of NH; made from Example 93) was dissolved into 12 mL of water, followed by addition of potassium carbonate (220 mg, 1.59 mmol, 1.06 equiv. per NH) (Acros Organics). The clear solution of dendrimer and base was added dropwise via a pipette to the glycidol solution under mechanical stirring. After 72 hours, MALDI-TOF showed consumption of the glycidol and reaction with dendrimer I. The mixture was subjected to 3K UF with 8 liters of permeate collected. The retentate was collected and water removed by rotary evaporation. The residue was further dried under high vacuum overnight to yield the desired dendrimer II (760 mg, 100% yield). Its spectra are as follows:

$^1$H NMR (500 MHz, D$_2$O): δ 2.48 (3H, s), 2.58 (2H, s), 2.87 (2H, s), 3.49 (2H, s), 3.90 (1H, s), 4.03 (2H, s), 4.80 (4H, s, J=7.8 Hz); and $^{13}$C NMR (75 MHz, D$_2$O): δ 46.52, 48.10, 55.01, 55.65, 61.81, 63.21, 63.73, 65.27, 67.22, 69.76, 71.32, 72.67, 73.11, 74.79, 76.58, 76.99; and MALDI-TOF: C$_{183}$H$_{368}$N$_{32}$O$_{64}$; Calc. 4041.1, found 4080.5 [M+K]$^+$ amu.

The following Scheme 89 illustrates this reaction.

Scheme 89

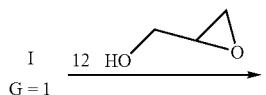

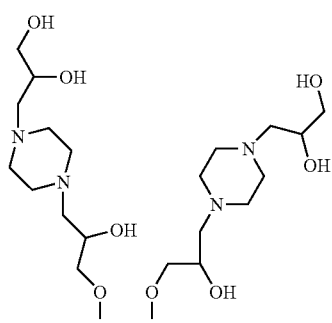

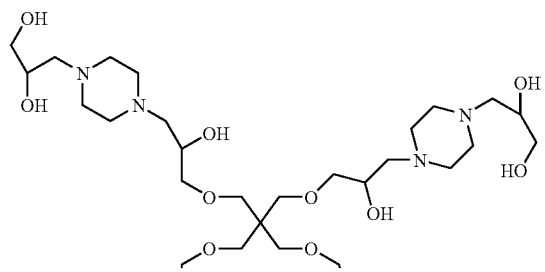

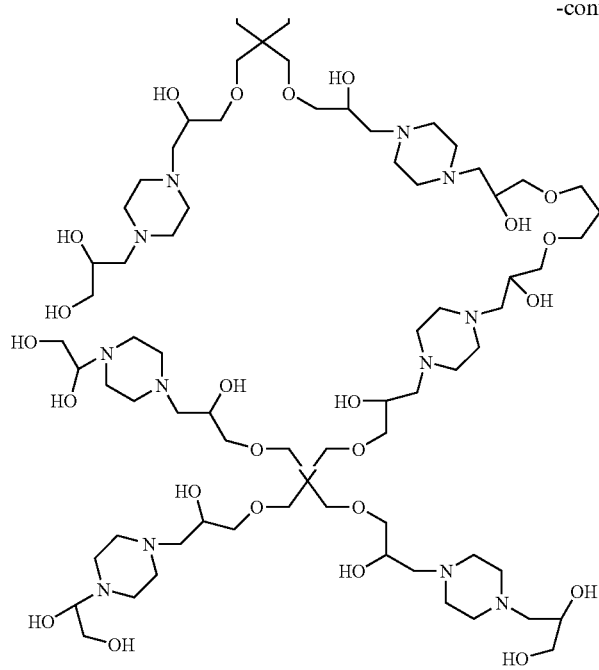
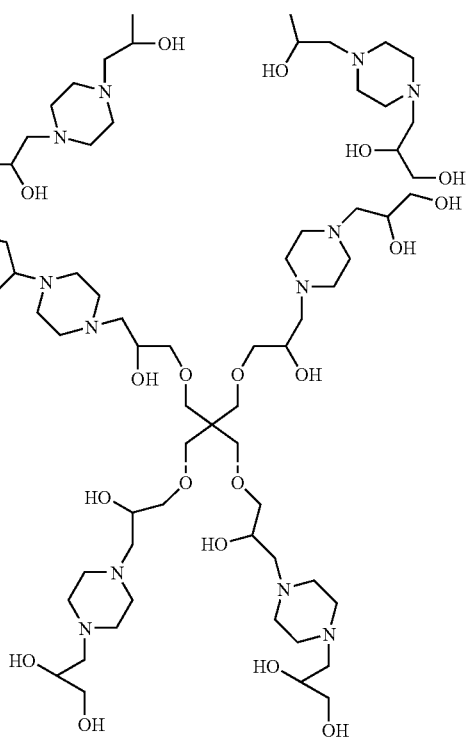

II
G = 2

EXAMPLE 95

Single Focal Point PAMAM Dendron Cystamine Core Generation Tetraacetamide Surface

[(C) or (BR)=Single site reactive dendron; G=0.5]

Generation=0, cystamine core, amine surface dendrimer 2.315 g (3.80 mmol) was dissolved in 5 mL of MeOH. Then 1.847 g (18.25 mmol) of TEA was added to the solution. This mixture was cooled to 0° C. using an ice-bath. Then 1.725 mL (18.25 mmol) of acetic anhydride was added dropwise. The reaction was then allowed to warm to RT and stirred overnight. TLC showed that all starting material was consumed. Then the solvent was removed and the residue was put on high vacuum to give crude product as a brown solid, 3.47 g. The crude (1.27 g) was purified by $SiO_2$ chromatograph using a solvent of 6:1:0.02 $CHCl_3$:MeOH:$NH_4OH$ to give 593.3 mg product as a white solid, mp 141.0-142.0° C.; and its spectra are as follows:

$^1$H NMR (300 MHz, $D_2O$): δ 1.82 (s, 12H), 2.25 (m, 8H), 2.64 (m, 16H), 3.19 (t, 16H), 4.67 (s, 8H); and $^{13}$C NMR: δ 21.92, 32.52, 34.39, 38.60, 38.66, 48.77, 51.43, 174.14, 175.01.

1. The Reduction of [Cystamine]; Gen=0; Dendri-PAMAM; (acetamide)$_4$ Dendrimer:

148.8 mg (0.1915 mmol) Dendrimer was dissolved in 2 mL of MeOH. MeOH was purged with nitrogen for 15 mins. prior to use. Then 28 mg (0.182, 0.95 equiv. of dendrimer) of DTT was added to the solution. The reaction mixture was stirred for two days at RT under a $N_2$ atmosphere. TLC showed that all DTT was consumed and the spot was positive to Ellman's reagent on TLC plate. The product was used in the next reaction without further purification.

2. Reaction of Focal Point, Thiol Functionalized PAMAM Dendron with Methyl Acrylate:

To the reaction solution of step 2 was added 117 mg (1.36 mmol) methylacrylate. Then the reaction was heated to 40° C. for two hours. TLC showed that there was starting material left. Then another 117 mg of methylacrylate was added. TLC showed that after 4 hours the reaction was completed. The solvent was removed by a rotary evaporator. The residue was purified by silica gel chromatography to give 104 mg of product as a pale white solid: mp 128.0-129.5° C.

$^1$H NMR (300 MHz, $CDCl_3$): δ 1.93 (s, 6H), 2.32 (m, 8H), 2.65 (m, 12H), 3.29 (m, 4H), 3.65 (s, 3H); and $^{13}$C NMR (75 MHz, $CDCl_3$): δ 23.10, 27.13, 29.80, 33.69, 34.58, 39.22, 39.78, 49.86, 51.84, 53.03, 171.27, 172.33, 173.00.

3. Reaction of Focal Point, Thiol Functionalized PAMAM Dendron with 2-Isopropenyl Oxazoline:

To the reaction solution of step 2 was added 15.4 mg (0.136 mmol) isopropenyl oxazoline. Then the reaction was heated to 40° C. for 2.5 hours. TLC showed that there was starting material left. Then another 3.0 mg of isopropenyl oxazoline was added. TLC showed that after 4 hours the reaction was completed. The solvent was removed by a rotary evaporator. The residue was purified by silica gel chromatography to give 58 mg of product as a waxy white solid (85%); mp 92.0-95.0° C.; having the following spectra:

$^1$H NMR (300 MHz, $CDCl_3$): δ 1.17 (d, J=6.6 Hz, 3H), 1.89 (s, 6H), 2.27 (t, J=6.0 Hz, 6H), 2.47-2.78 (m, 17H), 3.74 (t, J=9.6 Hz, 2H), 4.14 (t, J=9.6 Hz), 7.32 (s, 2H), 7.87 (s, 2H); and $^{13}$C NMR (75 MHz, $CDCl_3$): δ 17.17, 23.07, 29.98, 33.70, 34.08, 36.11, 39.12, 39.77, 49.91, 52.92, 53.97, 67.37, 170.29, 171.19, 172.99.

Scheme 90 illustrates the above reaction:
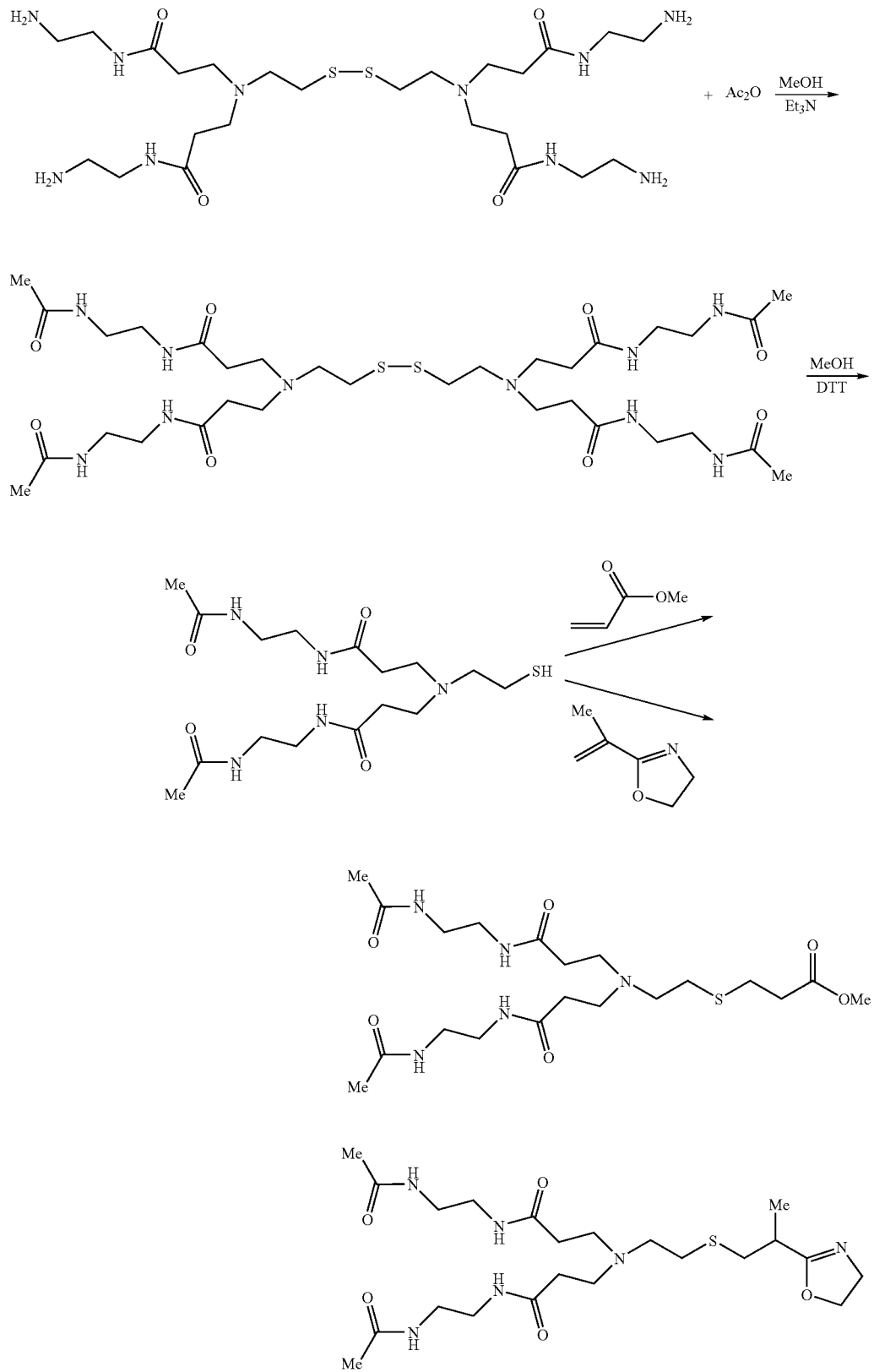

EXAMPLE 96

PEHAM Dendrimer Build Around a Cleavable Disulfide (S—S) Core, Allowing Separation of the Dendrimer into Two Dendrons with Active Focal Point Functionality

[(C)=BPEDS; (IF1)=OH; (BR1)=PETGE; (EX1)=PEA; (TF)=Secondary NH; G=1]

A. Preparation of bis(2-piperazinoethyl)disulfide Core.

To a 100-mL three-neck round bottom flask containing a stir bar and fitted with an addition funnel, a condenser and a glass stopper was added piperazine (5.8 g, 67.0 mmol) in 40 mL of benzene. This mixture was heated to a gentle reflux under $N_2$ gas, then ethylene sulfide (1.0 g, 1.0 mL, 16.8 mmol) (Aldrich) in 20 mL of benzene was added dropwise over 30 mins. The resulting mixture was further gently refluxed for 2 hours under $N_2$ gas. Volatile materials were removed by rotary evaporation to give a crude residue (7.0 g). This residue was purified by silica gel chromatography, using a mixture comprised of concentrated ammonium, methanol and chloroform (5:25:75) as the eluant and giving the purified product (1.76 g, 72% yield). TLC (5:25:75, concentrated ammonium, methanol and chloroform) analysis revealed a mixture of two compounds with $R_f$=0.3 for excess ethylene sulfide and $R_f$=0.5 for the desired product. $^{13}$CNMR spectroscopy revealed a roughly 1:1 mixture of both compounds. Therefore, this mixture was further heated in refluxing benzene for 7 hours, followed by bubbling with air for 2 hours. $^{13}$CNMR spectroscopy of this material indicated 90% of the desired product. Its spectra are as follows:

$^{13}$CNMR (75 MHz, acetone-4): δ 36.93, 46.70, 55.21, 59.04; and

MALDI-TOF MS: $C_{12}H_{26}N_4S_2$; Calc. 290.2, found 291 [M]$^+$ amu.

The following Scheme 91 illustrates this reaction.

Scheme 91

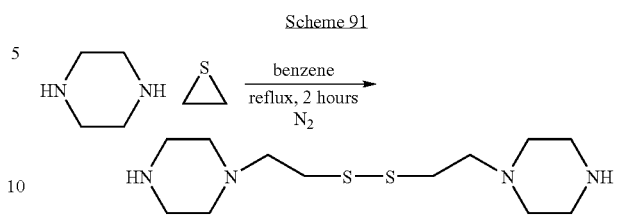

B. Reaction of bis(2-piperazinylethyl)disulfide Core with Excess Pentaerythritol Tetraglycidylether (PETGE) Branch Cell [BR] to form PEHAM Dendrimer G=0 with Epoxide Surface.

To a 50-mL round bottom flask containing a stir bar was added PETGE (8.5 g, 23.6 mmol, 6 equiv. per NH) and 25 mL of MeOH. To this mixture, BPEDS (550 mg, 1.89 mmol, 3.8 mmol NH) in 2.0 mL of MeOH was added over 5 mins. at 25° C. under mechanical stirring. The resulting mixture was further stirred for 18 hours under a $N_2$ atmosphere. One-half of this mixture was treated with UF in MeOH to remove excess PETGE, using a tangential flow UF apparatus containing 1K regenerated cellulose membranes as a 125-mL retentate solution to give 600 mL of permeate (5 recirculations). MALDI-TOF mass spectrum revealed the desired product (~960 mg, 0.95 mmol yield). Its spectra are as follows:

MALDI-TOF MS: $C_{46}H_{82}N_4O_{16}S_2$; Calc. 1010.5, found 1011 [M]$^+$ amu.

The following Scheme 92 illustrates this reaction.

Scheme 92

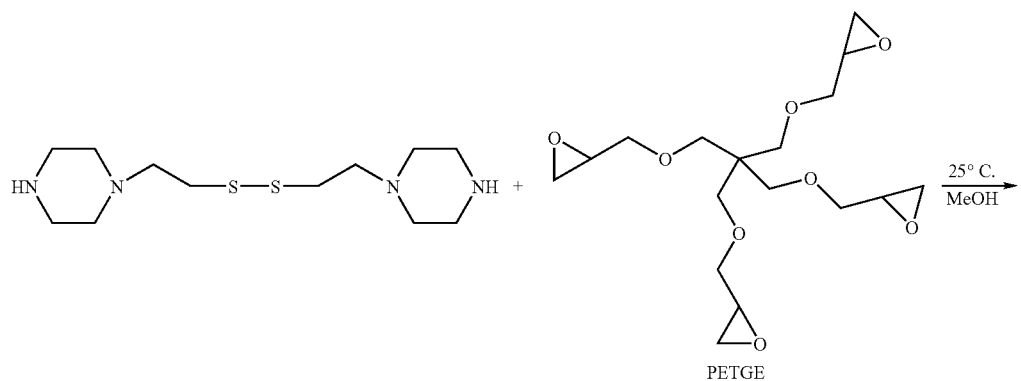

PETGE

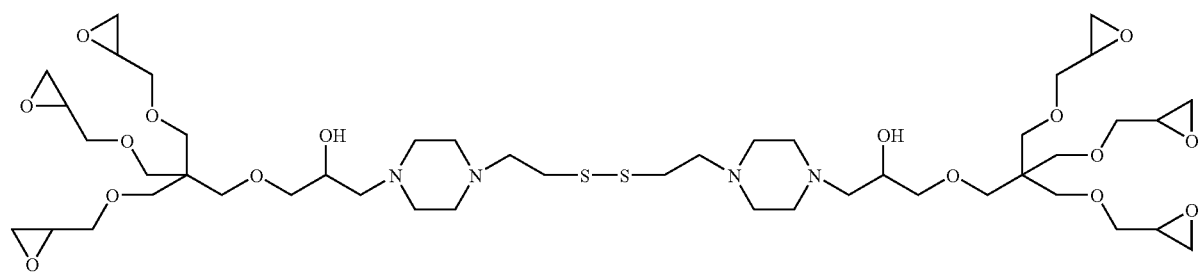

C. Reaction of PEHAM Dendrimer with bis(2-piperazinyl-ethyl)disulfide Core (BPEDS) and Pentaerythritol Tetraglycidylether (PETGE) Branch Cell [BR] and Epoxide Terminal Functionality [TF] with Excess Methylisopropyliminoethylpiperazine to Produce a Primary Amine Surface.

In a 100-mL round bottom flask, MIPIEP (6.5 g, 33.0 mmol) and 250 mL of the retentate solution from part B (960 mg, 0.95 mmol) were mixed under mechanical stirring and heated at 50° C. for 24 hours. The solvent was removed by rotary evaporation and the crude product further purified by UF in MeOH to remove excess MIPIEP, using a tangential flow UF apparatus containing 1K regenerated cellulose membranes. The desired product was identified by MALDI-TOF mass spectroscopy as follows:

MALDI-TOF MS: $C_{82}H_{172}N_{22}O_{16}S_2$; Calc. 1786, found 1785 $[M]^+$ amu.

The following Scheme 93 illustrates this reaction.

mL of MeOH. To this stirred mixture, cooled to 4° C., was added PEI (250.0 mg, 5.8 mmol NH, DP=21, peak signal by MALDI-TOF mass spectrometry) in 4 mL of MeOH. The mixture was allowed to warm to 25° C. and was stirred for 24 hours under a blanket of $N_2$ atmosphere. MALDI-TOF mass spectrum of the reaction mixture revealed a peak mass of 4591 amu (theory: 8482 amu), indicating 54% grafting of the glycidylether onto the polymer backbone. To this mixture was added EPC (39.0 g, 246.0 mmol, 1.5 equiv. per epoxide) in 39 mL of MeOH. The mixture was stirred at 40° C. for 24 hours. Then volatile materials were removed by rotary evaporation. Excess piperazine of this crude product was removed using a bulb-to-bulb Kugelrohr distillation at high vacuum and heating to 170-200° C., giving a residue of 37.0 g. MALDI-TOF analysis of the residue revealed a peak at 6245 amu, indicating 60% grafting. The residue was dissolved in 40 mL of MeOH and placed onto a column containing silica gel (150 g, Scheme 93

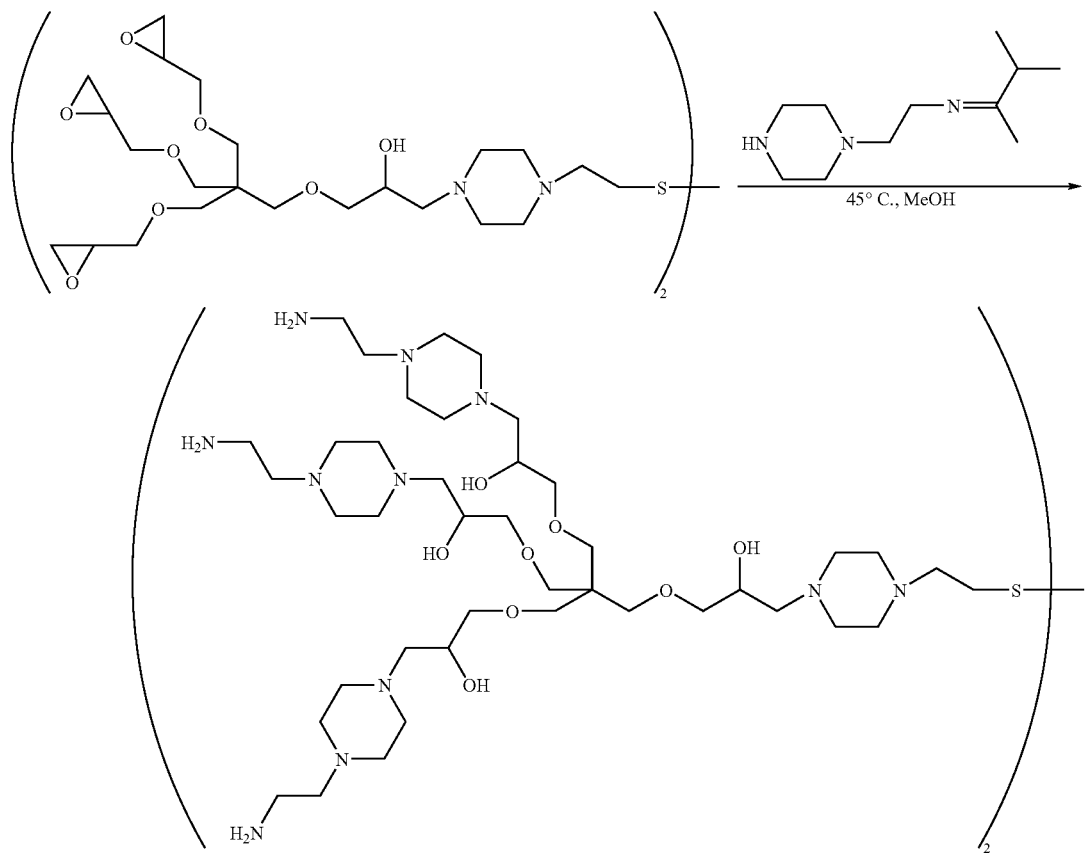

EXAMPLE 97

Rod-Shaped Dendrimer (G=1) from poly(ethyleneimine) and Pentaerythritol Tetraglycidylether Surface-Capped with Piperazine

[(C)=PEI; (BR1)=PETGE; (IF1)=OH; (EX1)=PIPZ; (TF)= Secondary NH; G=1.5]

A. Reaction of Poly(Ethyleneimine) with Pentaerythritol Tetraglycidylether Followed by Ethyl-N-Piperazine Carboxylate To a 250-mL round bottom flask containing a stir bar was added PETGE (14.5 g, 40.3 mmol, 6.9 equiv. per NH) and 39

60 angstrom, 200-430 mesh) in MeOH. The not grafted product of tetraglycidyl-ether and mono-protected piperazine was removed by elution with 15 100-mL fractions of MeOH. The product was eluted using 20% ammonium hydroxide in MeOH with 8 100-mL fractions. These fractions were concentrated by rotary evaporation to give the desired product (1.55 g, 60% recovery based on a theory of 3 g). Its spectra are as follows:

$^{13}C$ NMR (125 MHz, $CD_3OD$): δ 14.95, 15.06, 44.72, 46.99, 54.62, 62.47, 62.71, 68.74, 71.36, 75.48, 75.58157.10 (final product reacted with ethyl 1-piperazine carboxylate); and MALDI-TOF MS: $C_{399}H_{693}N_{21}O_{168}$; Calc. 8482 (100% grafting), found 6245 (60% grafting) amu (epoxide intermediate).

B. Hydrolysis of the Protective Groups of the G=1 Poly(Ethyleneimine) Rod-Shaped Dendrimer To a 50-mL round bottom flask containing a stir bar was added KOH (4.7 g, 71.0 mmol, 16 equiv. per carbamate) and 10 mL of DI water. To this homogeneous solution was added dropwise the poly(ethyleneimine) rod (1.47 g, 14 mmol, 1.6 mmol carbamate) (made in Example 97A) in 14 mL of MeOH. This mixture was heated at 75° C. for 16 hours under $N_2$ atmosphere. The mixture was cooled to RT and acidified with 12N HCl to pH 3, then made basic with potassium hydroxide to pH 10.5. Volatile materials were removed by rotary evaporation, followed by drying under high vacuum at 50° C. The remaining solid was stirred in 100 mL of MeOH at 25° C. for 3 hours. Not dissolved salts were allowed to settle, and the methanol solution was decanted. This procedure was repeated two more times. Then the combined methanol washes were concentrated by rotary evaporation, followed by drying of the residue under high vacuum to give 1.2 g of a light brown solid. This material was placed on a Sephadex™ LH-20 column in MeOH and eluted, collecting 30 2-mL fractions. Fractions 1-7 were combined and concentrated by rotary evaporation to give the desired product (540 mg). Its spectra are as follows:

$^{13}C$ NMR (125 MHz, $CD_3OD$): δ 46.29, 47.04, 55.57, 63.30, 68.53, 71.39, 75.68; and MALDI-TOF: $C_{609}H_{1218}N_{126}O_{168}$; Calc. 13908 (100% grafting), found 6245 (~45% total grafting) amu.

The following Scheme 94 illustrates this reaction.

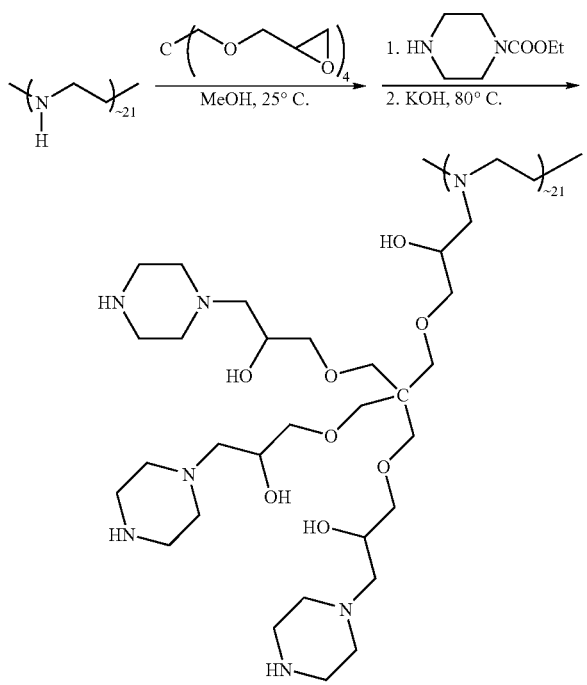

Scheme 94

EXAMPLE 98

Random hyperbranched dendrimers

The reaction of amines and epoxides to form epoxy polymers is the basis of a large class of commercially available monomers. In general the monomer is polymerized for the particular application. These polymers are widely used as protective coatings, glues, binders and are generally attractive because of their high thermal stability and toughness (high tensile strength). The introduction of dendrimers to this class of polymers via the PEHAM repeat unit should provide more versatility. A broader range of physical and chemical properties should be available with careful tuning of the degree of polymerization, utilizing the 'dendritic state'. Dendrimer-based polymers should also have a more compact structure as a result of their dendritic growth.

[(C)=Oligo(neopentyldiglycidyl ether); (IF1)=OH; (BR1)= DETA; (TF)=Amine]

A. Preparation of $AB_2$ Monomer from Bis(Methylisobutyl-iminoethyl)Amine and Neopentylglycidyl Ether To a 25-mL round bottom flask was added 10 mL of a 0.633 M solution of bis(methylisobutyliminoethyl)amine in MIBK. Volatile material was removed by evacuation under high vacuum and heating. The residue (1.7 g, 6.3 mmol) was added dropwise over 1-2 minutes to a 50-mL flask with a stir bar containing neopentyldiglycidyl ether (Aldrich) (8.2 g, 38 mmol, 6 equiv.) and 20 mL of MeOH. This mixture was stirred at 25° C. for 18 hours under a $N_2$ atmosphere. A MALDI-TOF mass spectrum of the reaction mixture revealed a peak at 319 amu for the desired product. A TLC (30% $NH_4OH$-MeOH) indicated a large spot at $R_f=0.85$ and a small spot $R_f=0.2$. This mixture was concentrated by rotary evaporation. The resulting residue was bulb-to-bulb distilled of excess diepoxide at 160-190° C. for ~20 minutes using a Kugelrohr apparatus to give a pot the desired monomer (3.4 g, theory 3.1 g). This monomer was dissolved in MIBK and sealed under a $N_2$ atmosphere during storage. A 500 mg sample of this monomer was purified on a Sephadex™ LH-20 column in MeOH. Collected fractions 15-23 were concentrated to give 250 mg of the monomer, showing a MALDI-TOF mass spectrum for 319 amu, with most of the higher molecular weight impurities removed. A TLC (30% $NH_4OH$ in MeOH) of this material showed one spot at $R_f=0.85$. Its spectra are as follows:

$^{13}C$ NMR ($CDCl_3$, 500 MHz): δ 17.59, 22.05, 22.1, 26.09, 36.44, 44.08, 44.18, 50.02, 50.92, 51.58, 68.51, 70.71, 71.13, 73.80, 71.91, 78.03, 170.73; and MALDI-TOF: $C_{15}H_{33}N_3O_4$; Calc. 319.44, found 319 [M⁺] amu.

The following Scheme 95 illustrates this reaction.

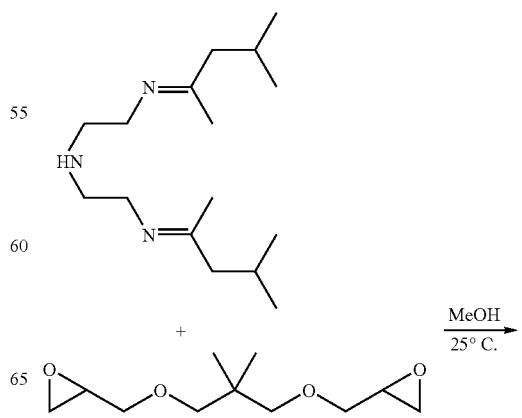

Scheme 95

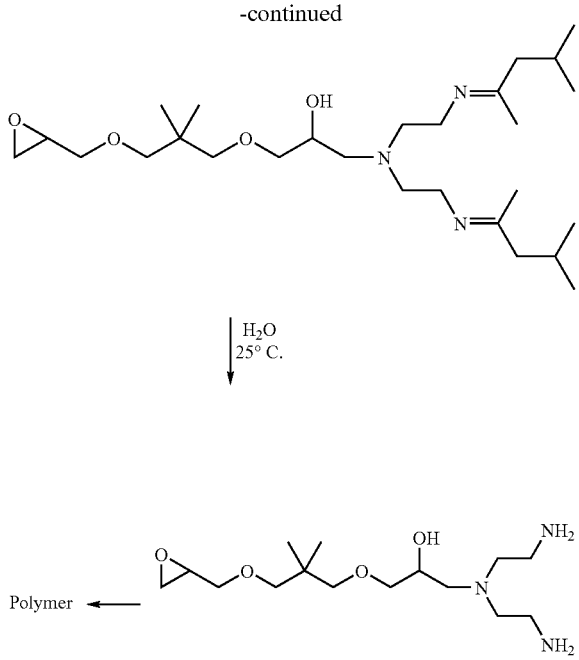

B. Polymerization Reaction of AB$_2$ Monomer

To a 25-mL round bottom flask containing a stir bar was added an aliquot of the monomer (made from Example 98A) in MIBK. The volatiles were removed by high vacuum (1.0 g. 3.2 mmol). To this flask was added 25 mL of MeOH and 120 mg of water. This mixture was heated at 55° C. and stirred for 48 hours under a N$_2$ atmosphere. A TLC (50% NH$_4$OH in MeOH) of the reaction mixture indicated a slow decrease in the monomer concentration (R$_f$=0.85) and an increase in a spot on the baseline, corresponding to high molecular weight material. A MALDI-TOF mass spectrum of the crude polymer mixture showed peaks for oligomers up to ~4000 amu. Its spectra are as follows:

MALDI-TOF: found oligomeric peaks (multiples of 319 amu) up to 4000 amu.

EXAMPLE 99

Dendrigraft Polymer Based on Poly(2-Ethyl-2-Oxazoline) (PEOX) as the Core, PEHAM Dendrimer G=0 with a Four-Arm Core as the Branching Unit and Piperazine as the Surface

[(C)=PEOX; (IF1)=OH; (BR1)=PEHAM dendrimer G=0; (EX1)=PIPZ; (Th)=Amine]

A. Preparation of the PEOX Core

To a 250-mL round bottom flask containing a large stir bar was added methyl p-toluenesulfonate (1.85 g, 9.93 mmol) and 125 mL of toluene. This flask was fitted with a Dean-Stark trap and a condenser connected to a N$_2$ gas line and a bubbler. This mixture was refluxed for ~30 minutes, distilling about 25% of the toluene volume into the trap to thoroughly dry the apparatus, and then cooled to 90° C., while the trap was replaced with a septum to exclude moisture. Ethyl oxazoline (19.5 g, 196.7 mmol) was freshly distilled from calcium hydride powder under vacuum into a separate flask, fitted with a septum to exclude moisture. The content of this flask was transferred through a flame-dried 18-gauge needle over a time period of 5-8 minutes into the toluene/methyl p-toluenesulfonate solution. The resulting mixture was fitted with a reflux condenser and heated to a gentle reflux (~110° C.) for 16 hours under a N$_2$ atmosphere. A MALDI-TOF mass spectrum of this material indicated a degree of polymerization (DP) of 20. Its spectra are as follows:

MALDI-TOF: found multiple peaks between 900-3700 amu, with a maximum at 2100 amu (corresponding to DP=20).

B. Grafting of PEHAM Dendrimer G=0 onto the PEOX Backbone

To the above mixture, cooled to ~90° C., was added all at once a solution of the PEHAM G=0 core, pentaerythritol tetra(2-hydroxypropyl-3-piperazine)ether (483 mg, 0.686 mmol, 2.7 mmol NH) in 2.0 mL of MeOH. The resulting mixture was refluxed for 24 hours under a N$_2$ atmosphere. Then remaining ungrafted poly(2-ethyl-2-oxazoline) was quenched with morpholine (2.0 g, 23.0 mmol, ~2 equivalents per living polymer end), and the mixture refluxed for another 24 hours. The mixture was cooled to 25° C. and volatile materials were removed by rotary evaporation, followed by further drying under high vacuum to give the crude dendrigraft product (25 g). The residue was dissolved in 50 mL of MeOH and a 3 g aliquot (corresponding to ~1 g crude product) was purified on a Sephadex™ LH-20 column in MeOH, taking a total of 40 fractions of 2 mL each. Fractions 1-7 were collected and the solvent removed by rotary evaporation to give the purified product (300 mg). This yield would indicate a grafting yield of 90-100% for a 4:1 adduct (i.e., four PEOX units per PEHAM G=0 dendrimer) based on mass balance. However, a MALDI-TOF mass spectrum of the purified product indicated in average a 1:1 adduct. This conclusion was supported by the carbon NMR spectrum of combined fractions 1-7. The characteristic signals for the PEHAM dendrimer G=0 portion of the dendrigraft were clearly present at 74.30, 70.61, 60.63 and 53.35 ppm. The signal at 53.35 ppm is broad and indicative of the piperazine functional group that often broadens as the second nitrogen gets substituted. Its spectra are as follows:

$^{13}$C NMR (125 MHz, CDCl$_3$) δ 9.35, 25.96, 43.56, 45.54, 53.35, 59.14, 60.63, 70.61, 74.30, 173.92, 174.41, 174.52; and MALDI-TOF MS: found multiple peaks with a maximum at 2240 amu.

The following Scheme 96 illustrates this reaction.

Scheme 96

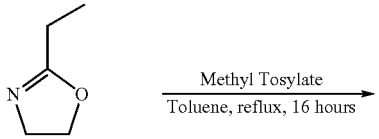

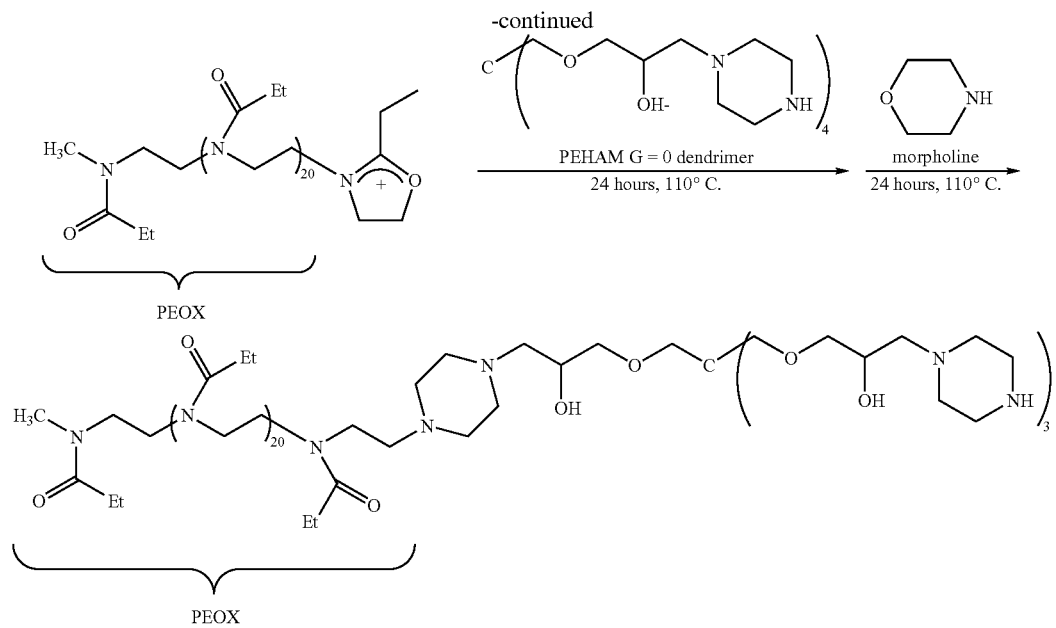

EXAMPLE 100

Core-Shell Tectodendrimer with G=4 PAMAM Core and G=1 PEHAM Shell CORE: G=4 PAMAM Shell: G=1 PEHAM [(C)=TMPTGE; (IF1)=OH; (BR1)= DEIDA; (TF)=Ethyl ester]

To a pressure tube was added a solution of G=1 PEHAM dendrimer with ethyl ester surface (2.17 g, 2.5 mmol, 50 mole equiv. per G=4 PAMAM core; made from Example 23B) in 11.0 mL of MeOH as the shell unit. To this solution was added lithium chloride (0.21 g, 5.0 mmol, 2 mole equiv. per G=1 ester) (Acros) all at once, and the tube was equipped with a stir bar and stopper. After stirring for 10 mins. at RT, a solution of G=4 STARBURST® PAMAM dendrimer with EDA core and primary amine surface groups (0.71 g, 0.5 mmol, 12.3% w/w solution in MeOH) was added as the core unit, and the tube was closed with stopper and heated at 45° C. for overnight. An aliquot of the reaction mixture was analyzed by MALDI-TOF MS and it showed mass peaks at 26,809 (corresponding to approx. 14 G=1 PEHAM dendrimers as the shell) and 54,142 amu (corresponding to approx. 46 G=1 PEHAM dendrimers as the shell). Peaks of low intensities at 80,175 and 106,191 amu indicated the presence of small amounts of cross-linked by-products. Heating was continued for 3 days and progress of the reaction was analyzed by MALDI-TOF MS, showing the same peak intensity ratio. After 6 days, the reaction mixture was allowed to cool to RT and transferred into a 100-mL, single neck round bottom flask. Then a solution of AEP (2.42 g, 18.75 mmol; 1.25 equiv. per starting G=1 ester group) (Acros) in 10.0 mL of MeOH was added and the mixture heated to 75-80° C. After 22 hours, progress of the reaction was analyzed by IR, revealing the absence of the ester vibration at 1740 cm$^{-1}$ and the presence of a strong amide vibration band at 1645 cm$^{-1}$. The MALDI-TOF mass spectroscopy was in good agreement with the conversion of all ester groups into amide functionality. The reaction mixture was allowed to cool to RT, diluted to 2.5-5% w/w solution in MeOH, and subjected to UF, using a 5K size exclusion membrane at a pressure of 15-20 psi (about 135-137.9 kPa) for purification. Its spectra are as follows:

MALDI-TOF (PAMAM-PEHAM tectodendrimer with ester shell surface): 26,809 (PAMAM core with 14 G=1 PEHAM surface dendrimers added) and 54,142 amu (PAMAM core with 46 G=1 PEHAM surface dendrimers added); and MALDI-TOF PAMAM-PEHAM tectodendrimer with piperazine shell surface): 37,329 (PAMAM core with 14 G=1 PEHAM surface dendrimers added) and 71,904 amu (PAMAM core with 46 G=1 PEHAM surface dendrimers added).

The following Scheme 97 illustrates this reaction.

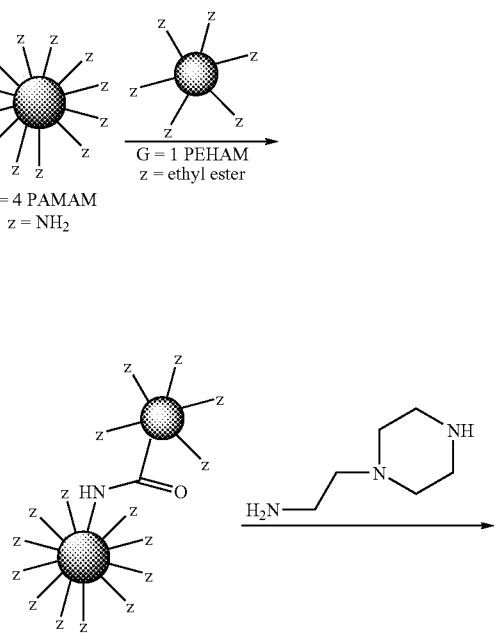

Scheme 97

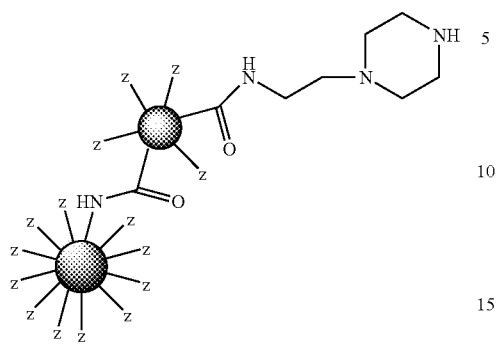

EXAMPLE 101

Core-Shell Tectodendrimer with G=2 PEHAM Core and G=1 PEHAM Shell Core: G=2 PEHAM [(C)=TMPTGE; (IF1)=OH; (BR1)=DEIDA; (BR2)=TREN; (TF)=Amine]

Shell: G=1 PEHAM [(C)=TMPTGE; (IF1)=OH; (BR1)=DCEA; (TF)=Ethyl Ester]

To an oven dried 100-mL round bottom flask was added G=2 PEHAM dendrimer with primary amine surface (390 mg, 0.265 mmol; made from Example 84) dissolved in 4 mL of dry MeOH (Aldrich) as the core unit. The flask was equipped with a stir bar. Then G=1 PEHAM dendrimer with ethyl ester surface (4.6 g, 5.3 mmol, 20 moles equiv. per G=2; made from Example 23B) dissolved in 11.0 mL of MeOH was added as the shell unit. After stirring for 2 hours at RT, lithium chloride (0.42 g, 10 mmol) (Acros) was added all at once. The reaction flask was arranged with a refluxing condenser and heated at 45° C. overnight under a $N_2$ atmosphere. Analysis of an aliquot of the sample by MALDI-TOF MS indicated mass peaks for one, two, three, four and five G=1 PEHAM shell units attached to the core, with peak intensities in decreasing order. Heating was continued for 6 days, then the reaction mixture was allowed to cool to RT. A solution of AEP (5.13 g, 39.75 mmol; 1.25 equiv. per starting G=1 ester) (Acros) in 20 mL of MeOH was added, and the mixture heated to 75-80° C. for 22 hours. Progress of the reaction was monitored by IR revealed the absence of the ester vibration 1740 $cm^{-1}$ and the presence of a strong amide vibration at 1649 $cm^{-1}$ after this time period. MALDI-TOF mass spectroscopy supported the complete conversion of ester bonds into amide functionality. The reaction mixture was diluted to 2.5-5% w/w solution in MeOH and subjected to UF using a 3K size exclusion membrane at a pressure of 20-25 psi (about 137.9 kPa) for purification.

MALDI-TOF MS (PEHAM-PEHAM tectodendrimer with ester shell surface): 2349.3, 3232.1, 4011.8 and 4816.8 amu (core unit with 1-4 G=1 shell units added); and MALDI-TOF MS (PEHAM-PEHAM tectodendrimer with PIPZ shell surface): 2609.4, 3739.7, 4682.3 and 5968.2 amu (core unit with 1-4 G=1 shell units added).

The following Scheme 98 illustrates this reaction.

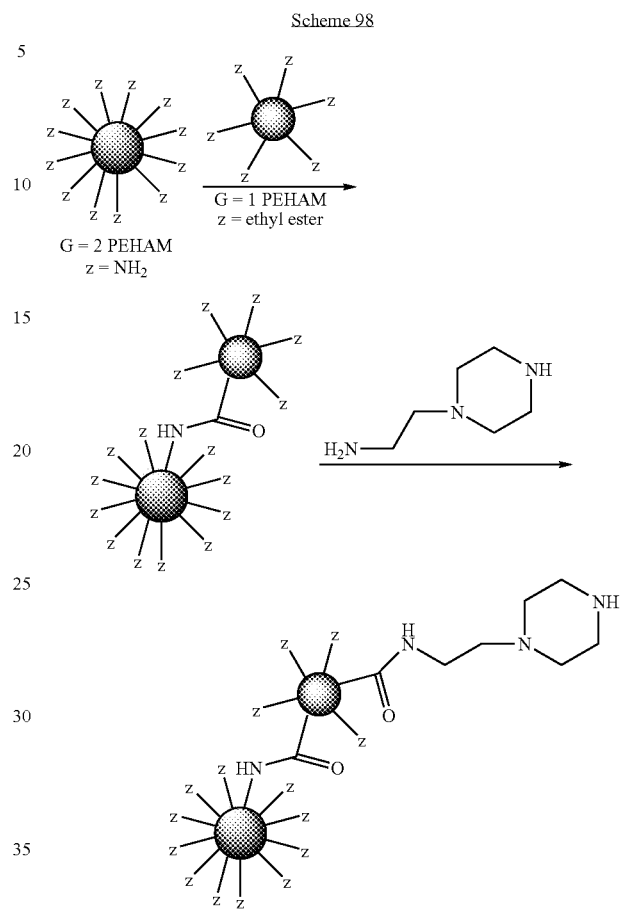

Scheme 98

Life Science Applications of PEHAM Dendrimers

The following Examples illustrate exemplarily life science applications of PEHAM dendrimers and disclose their use in areas such as drug encapsulation, detoxification, prodrug formation, surface conjugation, membrane permeation, nucleic acid—especially siRNA—transport, and antibacterial effect of dendrimers.

EXAMPLE 102

Drug Encapsulation by PEHAM Dendrimers, Using the Non-Steroidal Anti-Inflammatory Drug (NSAID) Indomethacin as a Model Drug General method: Encapsulation efficiency of indomethacin was examined in the presence of the respective PEHAM dendrimer (~0.2% w/v) in 5.0 mL of DI water. An excess (~15 mg) of indomethacin (Alfa Aesar, lot# c7517A) was added to vials containing the aqueous dendrimer solutions. These suspensions were briefly exposed to ultrasonication, then incubated overnight at 37° C. and 100 rpm in a shaking water bath, and allowed to equilibrate at RT. The dendrimer-indomethacin suspensions were filtered through a 0.2 μm, 13-mm in diameter nylon syringe filter to remove excess drug. The samples were analyzed for dendrimer-encapsulated indomethacin by UV spectroscopy at a light wavelength of 320 nm using a Perkin Elmer™ Lambda 2 UV/VIS Spectrophotometer. The results are summarized in Table n below. The results indicate an encapsulation dependency for indomethacin on dendrimer size (generation), hydrophobicity of the core, and functionality of the dendrimer branches and surface.

TABLE II

| Compounds from Example # | Size (Generation) | Core Functionality | Surface Functionality | Indomethacin[a] [mole drug/mole dendr.] |
|---|---|---|---|---|
| 10B | 1.5 | 4 | piperazine | 2.3 (0.022) |
| 47 | 1 | 3 | OH (TRIS) | 1.1 (0.007) |
| 48 | 1 | 4 | OH (TRIS) | 1.5 (0.027) |
| 23A | 1 | 3 | OH (DEA) | 1.0 (0.077) |
| 55 | 1 | 4 (aromatic) | $NH_2$ (DETA) | 4.0 (0.14) |
| 61 | 1.5 | 4 | piperazine | 3.8 (0.06) |
| 84 (C4 + TREN) | 2 | 3 | $NH_2$ (TREN) | 1.9 (0.152) |
| 85 (Ex 82 + DMI) | 2.5 | 3 | pyrrolidone | 0.6 (0.008) |
| 86 (C5 + TREN) | 2 | 4 | $NH_2$ (TREN) | 2.5 (0.196) |
| 87 (Ex 84 + DMI) | 2.5 | 4 | pyrrolidone | 0.6 (0.048) |
| 92 | 3 | 4 (aromatic) | OH (TRIS) | 5.2 (0.14) |
| 93 | 1.5 | 4 | piperazine | 5.7 (0.155) |
| 94 | 2 | 4 | OH | 4.8 (0.175) |

[a]Numbers in parenthesis indicate standard deviation (±SD).

EXAMPLE 103

Encapsulation of Copper(0) Atoms by PEHAM Dendrimers for Use as Biomarker Nanocomposites A PEHAM dendrimer generation G=2.5 with pyrrolidone surface (15.0 mg, 0.0038 mmol; made from Example 87) was dissolved in 3.81 Ml of DI water as a dendrimer stock solution. Copper(II) acetate (9.0 mg, 0.0734 mmol) (Aldrich) was dissolved in 4.52 mL of DI water. The reducing agent hydrazine monohydrate (0.1 mL, 99%) (Aldrich) was mixed with 0.1 mL of water. A control solution containing DI water but no dendrimers was prepared at the same time. Then 1.0 mL of dendrimer stock solution was mixed with 0.5 mL copper(II) acetate solution. This mixture was stirred at RT for 20 minutes. The color of the dendrimer-copper(II) solution changed to bright blue, while the water-copper(II) control was very light blue. Then 5.0 μL of hydrazine solution was slowly added to both mixtures, using a 20-μL syringe (Hamilton). The color of the dendrimer-copper(II) solution became very light, indication the formation of copper(0) nanoparticles inside the dendrimers, while the water-copper(II) control solution turned immediately yellow and copper(0) particles formed and precipitated. The dendrimer-copper(0) complex was stable at RT in the presence of air and light for at least 6 hours. UV-V is spectra were recorded for the copper-free dendrimer solution, the dendrimer-copper(II) solution, and the dendrimer-copper(0) solution. The dendrimer solution showed a maximum absorption at 280 nm, which shifted for the dendrimer-copper(II) solution to 632 nm. After reduction with hydrazine monohydrate, this maximum absorption shifted to 432 nm, suggesting the formation of stabilized copper(0) nanoparticles inside the PEHAM dendrimers.

EXAMPLE 104

Pharmaceutical injectable formulations of selected PEHAM dendrimers containing the model drug indomethacin in physiological saline solution. The following example discloses the ability of PEHAM dendrimers to function as drug carriers in injectable pharmaceutical formulations Physiological saline (0.9% w/v) was prepared in DI water. Then PEHAM solutions (0.2% w/v) were prepared in 5.0 mL of saline. An excess of indomethacin (15.0 mg) (Alfa Aesar) was added to vials containing the PEHAM solutions, and the resulting suspensions were briefly treated with ultrasonication, then incubated overnight at 37° C. and 100 rpm in a shaking water bath. After cooling to RT, the suspensions were filtered through 0.2 μm, 13-mm in diameter nylon syringe filters to remove excess drug. The samples were analyzed for dendrimer-encapsulated indomethacin by UV spectroscopy at 320 nm on a Perkin Elmer™ Lambda 2 UV/VIS Spectrophotometer. The results are shown in Table III below. All formulations had a water-like consistency and could be applied using a standard 24-gauge syringe needle.

TABLE III

| Compounds from Example # | Indomethacin[a] Physiological saline [mole drug/mole dendr.] | Indomethacin[a] DI water [mole drug/mole dendr.] |
|---|---|---|
| 61 | 4.8 (0.01) | 3.8 (0.06) |
| 92 | 5.6 (0.16) | 5.2 (0.14) |
| 94 | 9.1 (0.047) | 4.8 (0.175) |

[a]Numbers in parenthesis indicate standard deviation (±SD).

EXAMPLE 105

Drug Encapsulation by PEHAM Dendrimers, Using the Anti-Cancer Drug Cisplatin as a Model Drug A G=3 PEHAM dendrimer (61.5 mg, 0.024 mM; made from Example 92) was added to 60.0 mL of DI water in a round bottom flask under mechanical shaking. The anti-cancer drug cisplatin (226.0 mg, 0.75 mM) (Strem Chemicals) was added to the aqueous dendrimer solution, followed by ultrasonication for 5 mins. and heating at 50° C. for 20 mins. After cooling to RT, the reaction mixture was stirred for 20 hours. Non-encapsulated cisplatin was removed by dialysis ((MWCO-1000) against 500 mL of DI water for 30 mins. at 4° C. The dialysis bag content was dried by lyophilization, and the cisplatin content measured by inductively coupled plasma spectroscopy (ICP) (Anderson Analytical, Texas). The cisplatin content was found to be 44.9±1.89% (w/w) (N=2), disclosing that PEHAM dendrimers with carboxylate surface can be utilized in this drug delivery application.

EXAMPLE 106

Drug Encapsulation by PEHAM Dendrimers, Using the Magnetic Resonance Imaging (MRI) Agent Magnevist® as a Model Drug A. Sample Preparation Two reactions were set up to encapsulate diethylenetriaminepentaacetic acid, gadolinium(III) (DTPA-Gd(III), Magnevist®) (Aldrich) into PEHAM dendrimers. In reaction 1, G=1 PEHAM dendrimer (200 mg, 0.0495 mmol; made from Example 93) in water was added to a 10-mL round bottom flask. To this solution, DTPA-Gd(III) (867.2 mg, 1.584 mmol, 32 equiv. per dendrimer) were added under mechanical stirring until a clear solution formed. In reaction 2, G=1 PEHAM dendrimer (200 mg, 0.0495 mmol; made from Example 93) in water was added to a 10-mL round bottom flask. Then DTPA-Gd(III) (433.4 mg, 0.791 mmol, 16 equiv. per dendrimer) were added under mechanical stirring until a clear solution formed. Both mixtures were stirred at RT for 4½ days. Then each mixture was transferred into a separate dialysis bag (1K cut-off regenerated cellulose dialysis tubes, Spectrum Laboratories Inc.). The flasks were rinsed with DI water (3×1.0 mL) and the rinsing solutions were added to the respective dialysis tubes. The dialysis tubes were put into 1-L beakers containing 900 mL of DI water and stirred at moderate speed. The dialysis was carried out for 2½ hours. At the end of 0.5, 1.0, 1.5 and 2.0 hours, the water was changed. After 2.5 hours, the reaction mixtures were transferred to pre-weighed 100-mL round bottom flasks. The dialysis tubes were rinsed using DI water (3×1.0 mL), which was also added to the round bottom flasks. The water was removed by rotary evaporation, and the remaining residue dried under high vacuum for 4-6 hours to remove remaining traces of water. The resulting products were cream colored solids on the wall of the flasks. The weight per sample was 761 mg (reaction 1) and 537 mg (reaction 2). Aliquots were removed for analysis, and the main products were transferred to small vials and stored at −12° C.

B. Sample Analysis

The Gd(III) content of the solutions was determined on a sequential, radially viewed Varian™ Liberty Series II ICPOES inductively coupled plasma optical emission spectrophotometer (Anderson Analytical, TX). Relaxivity analysis was performed using a variable field T1-T2 analyzer (University of Pittsburgh). The field strength was varied from 1-64 MHz. Data from the analysis of these materials is shown in Table IV. Reaction 1, set up to encapsulate a higher number of DTPA-Gd(III) molecules, did show higher Gd(M) content; however, this increase in DTPA-Gd(III) did not result in an increase in relaxivity. Relaxivity values for DTPA-Gd(III)-encapsulated dendrimers were similar to free DTPA-Gd(III).

TABLE IV

| Sample | Gd content (ppm) | DTPA-Gd:PEHAM | Relaxivity (r1) |
|---|---|---|---|
| Reaction 1 | 240389 | 37.8 | 4.0 |
| Reaction 2 | 213683 | 21.4 | 4.6 |
| DTPA-Gd | | | 4.2 |

EXAMPLE 107

Encapsulation of DTPA-Gd with G=1 Dendrimer

[(C)=PETGE; (IF1)=OH; (EX1)-PIPZ; (IF2)=OH; (BR2)= PETGE; (IF3)=OH; (EX2)=PIPZ; (TF)=Primary $NH_2$; (M)=DTPA-Gd; G=1.5]

A G=1 dendrimer (50 mg, 0.0157 mmol) (made by Example 26B) was dissolved in 7 mL DI. Then DTPA-Gd (275 mg, 0.503 mmol) (Aldrich) was added. The reaction mixture was stirred at RT for 2 days. Trace undissolved solid was filtered off. Then the mixture was dialysis against DI water using a 1K cut-off membrane for 5 hours with several water changes. The water was removed by a rotary-evaporator to give the products as a slightly yellow solid. (164 mg, weight gain 114 mg, dendrimer: DTPA-Gd=1:13.2, molar ratio).

EXAMPLE 108

Encapsulation of DTPA-Gd with G=2 Dendrimer

[(C)=PETGE; (IF1)=OH; (EX1)=PIPZ; (IF2)=OH; (BR1)= PETGE; (IF3)=OH; (EX2)=PIPZ; (IF4)=OH; (BR2)=PETGE; (IF5)=OH; (EX3)=PIPZ; (TF)=Primary $NH_2$; (M)=DTPA-Gd; G=2.5]

A G=2 dendrimer (100 mg, 0.00943 mmol) (made by Example 78) was dissolved in 7 mL of DI water. Then DTPA-Gd (537 mg, 0.981 mmol) (Aldrich) was added. The reaction mixture was stirred at RT for 2 days. Trace undissolved solid was filtered off. Then the mixture was dialysis against DI water using a 1K cut-off membrane for 5 hours with several water changes. The water was removed by a rotary-evaporator to give the products as a slightly yellow solid (318 mg, weight gain 218 mg, dendrimer: DTPA-Gd=1:42, molar ratio).

EXAMPLE 109

Encapsulation of DTPA-Gd with G=3.5 Dendrimer

[(C)=PETGE; (IF1)=OH; (EX1)=PIPZ; (IF2)=OH; (BR1)= PETGE; (IF3)=OH; (EX2)=PIPZ; (IF4)=OH; (BR2)=PETGE; (IF5)=OH; (EX3)=PIPZ; (IF6)=OH; (BR3)=PETGE; (IF7)=OH; (EX4)=PIPZ; (TF)=Primary $NH_2$; (M)=DTPA-Gd; G=3.5]

A G=3 dendrimer (120 mg, 0.00366 mmol) (made by Example 79) was dissolved in 7 mL of DI water. Then DTPA-Gd (313 mg, 0.5703 mmol) (Aldrich) was added. The reaction mixture was stirred at RT for 2 days. Trace undissolved solid was filtered off. Then the mixture was dialysis against DI water using a 1K cut-off membrane for 5 hours with several water changes. The water was removed by a rotary-evaporator to give the products as a slightly yellow solid (294 mg, weight gain 174 mg, dendrimer: DTPA-Gd=1:86, molar ratio).

EXAMPLE 110

Drug encapsulation by PEHAM dendrimers, using a near infrared active dye as a model drug. Combining PEHAM dendrimers with near infrared active materials will allow visualization of objects in this spectral wavelength regime with applications, for example, in tumor imaging or night-readable maps A. Synthesis of the Near Infrared Active Dye CyTE-807

To a 10-mL round bottom flask were added the dye IR-806 (112.0 mg, 0.1523 mmol) (Aldrich) and 2.0 mL of anhydrous DMF (Acros Organics) under mechanical stirring and under a $N_2$ atmosphere. Then 3-mercaptoproprionic acid (14.7 μL, 0.168 mmol, 1.10 equiv) (Acros Organics) was added via a 25-μL syringe, followed by addition of TEA (24.7 μL, 0.176 mmol, 1.15 equiv.) (Acros Organics) via a 100-μL syringe. The reaction mixture was purged with argon gas and allowed to stir at 22° C. overnight. Volatile materials were removed by rotary evaporation and the crude product analyzed using HPLC with a mixture of 0.1% acetic acid and acetonitrile (75:25% v/v) as the eluant and UV light at λ=480 nm as the detector. The starting material, IR-806, had a retention time of 7:05 mins. and the product, CyTE-807, was found at 5:20 mins. The crude product, CyTE-807, was further purified by recrystallization from 5.0 mL tert-butylmethylether (Fisher Scientific), followed by filtration through a 30-mL fine glass frit and wash (3×5 mL) with tert-butylmethylether, giving the desired product CyTE-807 (111.5 mg, 93.5% yield, 119.3 mg theoretical mass balance). Its spectra are as follows:

$^1$H NMR (500 MHz, DMSO-d6): δ 1.18 (2H, t, 3-2.5 Hz), 1.65-1.83 (10H, m), 2.51-2.56 (4H, m), 2.72 (2H, s), 2.94 (4H, s), 3.03 (3H, m), 4.17 (2H, s), 6.19 (1H, d J=7.0 Hz), 7.23 (1H, t, J=4.83 Hz), 7.42 (2H, s, J=8.67 Hz), 7.58 (1H, d, J=3.5 Hz), 8.03 (1H, d, J=6.5 Hz); and $^{13}$C NMR (75 MHz, DMSO-d6): δ 8.50, 22.49, 26.07, 27.48, 30.78, 35.10, 35.80, 43.60, 45.43, 48.68, 50.70, 102.57, 111.28, 124.69, 128.57, 136.96, 142.30, 162.35, 170.22, 172.27; and MALDI-TOF: $C_{40}H_{51}N_2O_8S_3$; Calc. 783.3, found 783.6 [M]$^+$ and 805.6 [M+Na]$^+$ amu.

The following Scheme 99 illustrates this reaction.

using a mixture of 0.1% acetic acid and acetonitrile (75:25% v/v) as the eluant and identified by its UV activity at $\lambda_{max}$=806 nm. The PEHAM dendrimer is UV inactive and the UV activity resulted from the dye associated with the dendrimer.

C. Encapsulation of CyTE-807

To a 100-mL round bottom flask, equipped with a stir bar, was added the dye CyTE-807 (20.0 mg, 0.0265 mmol, 1.5 equiv. per dendrimer) dissolved into 2.0 mL of water. To this solution, PEHAM G=1 dendrimer (1.36 g, 4.18% aqueous solution containing 56.8 mg, 0.0179 mmol dendrimer) was added. The reaction was allowed to stir for 96 hours, then diluted with 35 mL of water and placed into a 2K dialysis membrane (38-mm diameter, 4 cm in length, Spectra/Por®, Spectrum Laboratories) with 1000 mL of water as the bulk solvent. The bulk was changed after 24 hours. Upon completion of the dialysis, the content was transferred to a 250-mL round bottom flask and volatile materials removed by rotary evaporation to yield a dark blue solid (59 mg). HPLC analysis using 0.1% acetic acid and acetonitrile (75:25% v/v) as the eluant revealed the absence of free dye, expected to eluate

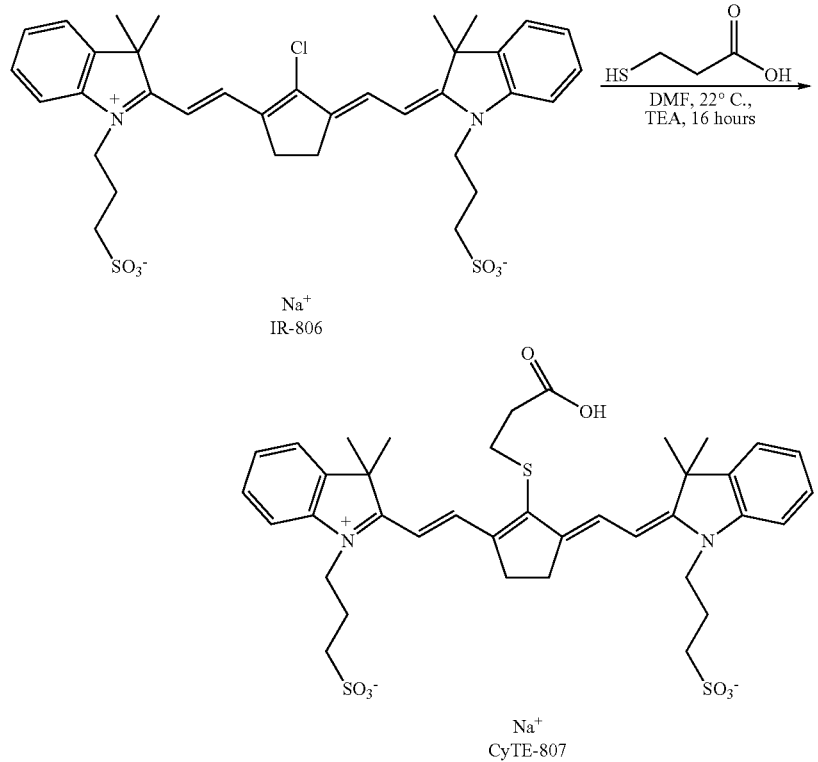

Scheme 99

B. Encapsulation of IR-806

To a 10-mL round bottom flask, equipped with magnetic stir bar, was added PEHAM G=1 dendrimer (1.08 g, 4.189% aqueous solution containing 0.045 mg, 0.0142 mmol dendrimer; made from Example 93). To this solution, an excess of dye IR-806 was added as a powder, resulting in the formation of a very dark green solution, which was placed under $N_2$ atmosphere and stirred for 24 hours. The reaction was diluted with 60 mL water and placed into a 2K dialysis membrane (38-mm diameter, 4 cm in length, Spectra/Por®, Spectrum Laboratories) in 1000 mL water. Volatile materials were removed by rotary evaporation, giving the desired product as a dark red solid (114 mg). The product was purified by HPLC after 5:20 minutes. The UV-VIS spectrum showed a maximum at λ=672 nm, a down shift from the λ=807 nm found for the free dye, which can be attributed to the micro-environment created by the PEHAM dendrimer.

EXAMPLE 111

PEHAM Dendrimer Build Around a Gold (Au—S) Core

[(C)=Gold; (EX1)=PIPZ; (IF1)=OH; (BR1)=PETGE; (IF2)=OH; (EX2)=PEA; (Ex3)=DMI; (TF)=Methyl Ester]

The PEHAM dendrimer G=1 with disulfide core, made from Example 96C, was capped with DMI to produce a pyrrolidone surface. This dendrimer (108 mg) was dissolved in 0.70 mL of DI water. Then a solution of DTT in DI water (0.128 mL, solution made from 23 mg DTT in 0.5 mL of DI water) was added under mechanical stirring. The DI water used in this example was purged with argon gas for 10 to 15 mins. prior to use. The mixture was stirred at RT overnight. The 5-nm gold nanoparticles were made using the following procedure. First, 1 mL of a 4% chloroauric acid solution in DI water was prepared. Second, 375 μL of the chloroauric acid solution and 500 μL of aqueous potassium carbonate (0.2 M) were added to 100 mL of DI water and cooled on ice to 4° C. under vigorous stirring. Third, sodium borohydride (0.5 mg/mL) was freshly prepared in 5 mL of DI water. Fourth, five 1-mL aliquots of the sodium borohydride solution were added to the chloroauric acid/carbonate suspension under rapid stirring. The color of the mixture changed from bluish-purple to reddish-orange during the mixing. Last, the final mixture was stirred for 5 mins. on ice after complete sodium borohydride addition. To this pre-made gold nanoparticle solution, the reduced dendron solution with SH focal functionality was added at 0° C. under vigorous stirring. After the addition, the reaction mixture was stirred at 0° C. for another 10 mins. and then allowed to warm to RT. The mixture was stirred at RT under dark overnight. Water was removed by rotary evaporation until there was about 1 mL of solution left. One third of the crude product was purified using a Sephadex™ G-50 column (diameter 1.6 cm, length 22 cm) with water as the eluant. A sharp band was eluded from the column. 27 fractions were collected at 2 drops per fraction. The first 9 fractions were checked by PAGE (4% acrylamide gel, 0.1% SDS), revealing the formation of gold nanoparticles coated with thio-dendrons.

Figure 10:
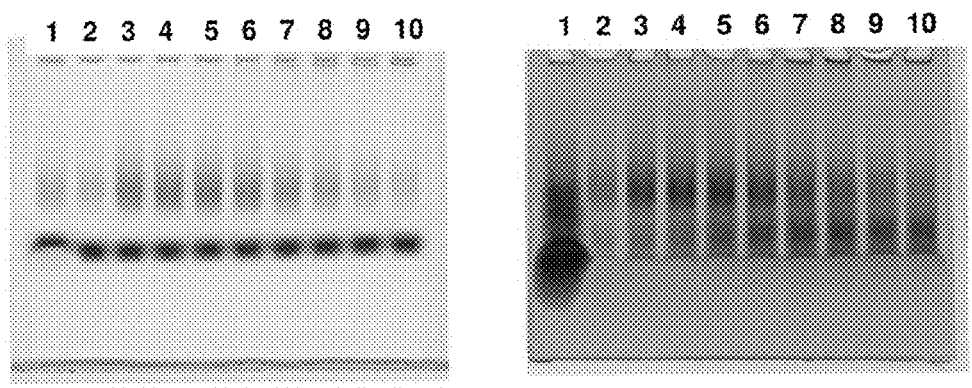
FIG. 10 illustrates the PAGE results for Au nanoparticles coated with (FF) thio-functionalized dendrons. Before staining, the left panel shows by the brownish color of the coated Au nanoparticles whereas the purple color is the loading dye. After staining with Coomassie blue, the right panel shows by the blue color the dendron shells around the Au nanoparticle core. Lane 1 contains crude product with excess dendrons; lanes 2-10 show fractions 1-9 from the Sephadex™ G-50 separation.

FIG. 10 illustrates the formation of these gold nanoparticles coated with thio-dendrons. PAGE was done for the gold nanoparticles coated with PEHAM dendrons. Before stain (left panel), the brownish color represents the coated gold nanoparticles (the purple color is the loading dye). After stain (right panel) with Coomassie blue dye, the blue color indicates the presence of the dendron shells around the gold. Lane 1 contains the crude product with excess dendrons, while Lanes 2 to 10 contain fractions 1-9 from the Sephadex™ G-50 separation.

The following Scheme 100 illustrates the dendron reaction.

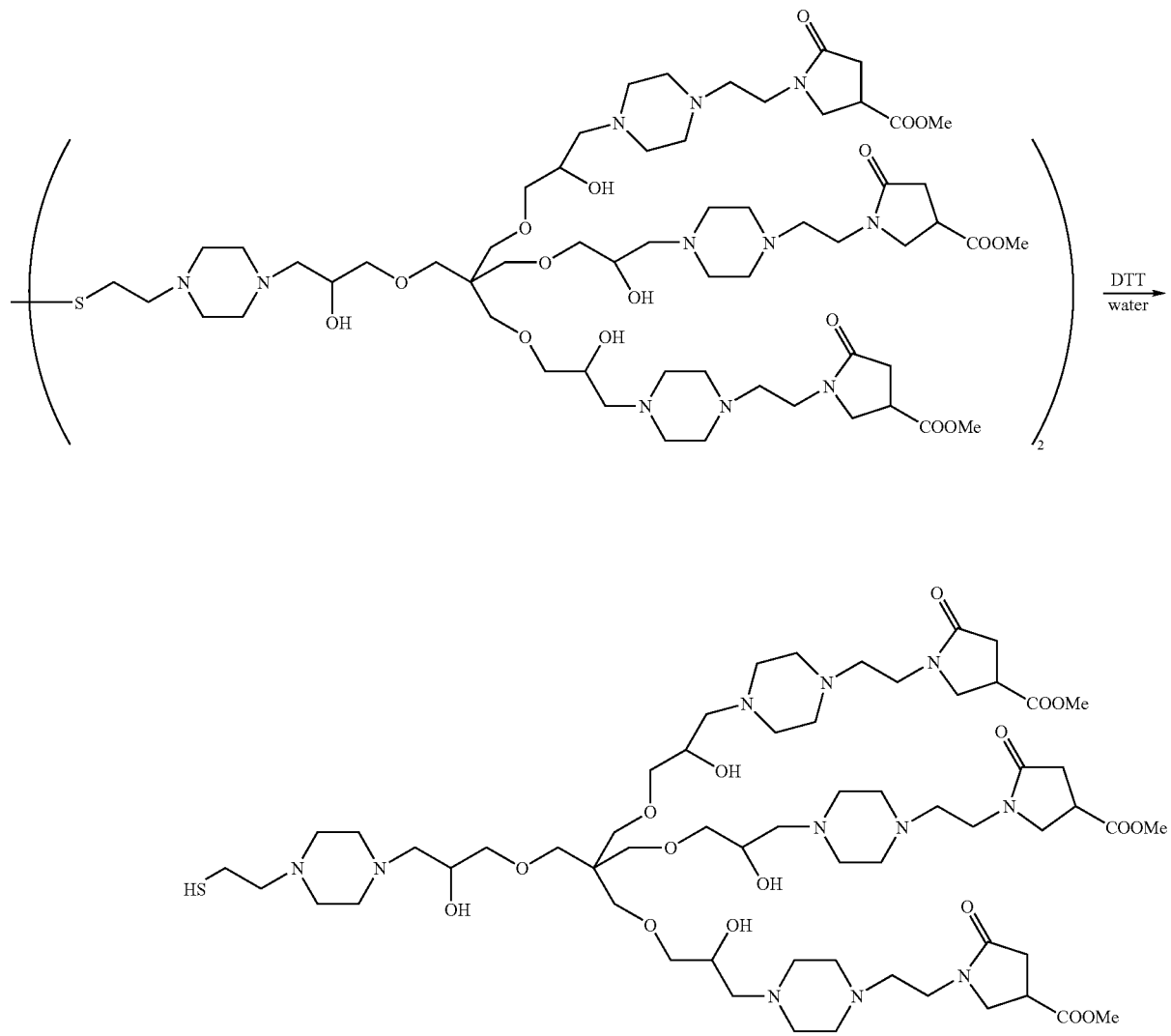

EXAMPLE 112

Figure 11:
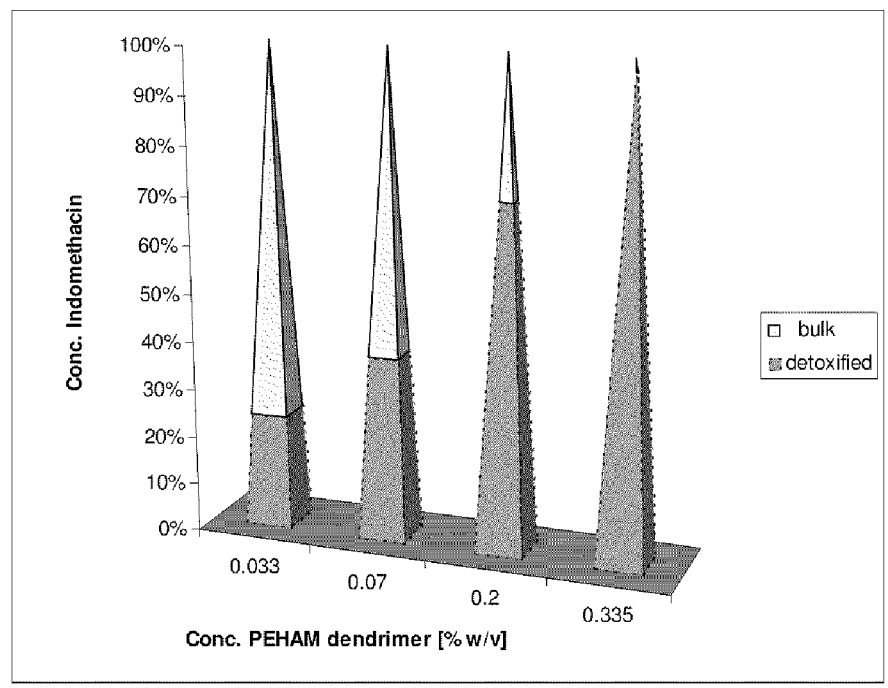
FIG. 11 shows the results of encapsulation of indomethacin as a model toxin in four different concentrations of a PEHAM dendrimer. The PEHAM dendrimer was able to encapsulate the model toxin and remove it from solution.

Detoxification behavior of PEHAM dendrimers, for example, removal of indomethacin as model toxin from solution. This example discloses the ability of PEHAM dendrimers to remove a drug overdose from a body or remove toxins from the environment The simulated detoxification of indomethacin was studied in the presence of PEHAM dendrimer (made from Example 93) in DI water. Four different concentrations (0.033, 0.070, 0.200, 0.335% w/v) of PEHAM dendrimers (in duplicate) were prepared by adding the respective aliquots of dendrimer to 5 mL of DI water. An equal amount of 10 mg indomethacin (Alfa Aesar) was added to each vial containing an aqueous dendrimer solution. The resulting suspensions were briefly treated by ultrasonication, then incubated overnight at 37° C. and 100 rpm in a shaking water bath, and allowed to equilibrate at RT. The suspensions were filtered with 0.2 μm, 13-mm in diameter nylon syringe filter to remove the excess of not encapsulated drug. Excess undissolved indomethacin from the filter material and the mixing vials dissolved in MeOH. The indomethacin content encapsulated into PEHAM dendrimers as well as the excess drug per sample was analyzed for by UV spectroscopy at a light wavelength of 320 nm using a Perkin Elmer™ Lambda 2 UV/VIS Spectrophotometer. The results are shown in FIG. 11, revealing the amount of indomethacin encapsulated and not encapsulated, clearly indicating the removal of the model toxin from solution.

EXAMPLE 113

PEHAM dendrimers as carriers in prodrug approach. The model drug indomethacin has been chemically bound to interior hydroxyl groups of a PEHAM dendrimer, creating a prodrug. Hydrolysis of the dendrimer-indomethacin complex and release of the unaltered drug disclose the ability of PEHAM dendrimers to be employed in prodrug delivery applications A. Protection of Terminal Piperazine NH Groups to Prevent Surface Attachment of Indomethacin PEHAM dendrimer (50 mg, 0.016 mmol; made from Example 93) and tri(ethyleneglycol)methylether p-nitrophenyl carbonate (250 mg, 0.064 mmol, 4 equiv.) were mixed in 3 mL of MeOH and stirred for 4 days. The reaction mixture was transferred into a dialysis bag (1,000 Dalton dialysis membrane, 18 mm diameter, 10 cm in length, Spectra/Por®, Spectrum Laboratories) and dialyzed in water. The purified product was isolated by lyophilization to give a yellow solid (41 mg, 36% yield). Its spectra are as follows:

$^1$H NMR (CDCl$_3$): δ 4.30-4.15 (18H, br), 4.00-3.80 (31H, br), 3.70-3.20 (267H, br), 2.75-2.20 (152H, br); and $^{13}$C NMR (125 MHz, CDCl$_3$): δ 156.2, 155.4, 152.4, 145.2, 125.4, 122.5, 73.4, 72.1, 70.8, 69.8, 66.8, 66.6, 66.5, 64.8, 61.0, 60.9, 59.3, 53.4, 45.8, 44.9, 44.3, 44.0; and MALDI-TOF: C$_{245}$H$_{468}$N$_{32}$O$_{100}$; Calc. 5459, found 5471 [M]$^+$ amu (broad signals).

B. Reaction of Surface Protected PEHAM Dendrimer with Indomethacin

The triethyleneglycol-protected PEHAM dendrimer (80.0 mg, 0.015 mmol) and indomethacin (95.0 mg, 0.27 mmol, 18 equiv.) were dissolved in 5 mL of methylene-chloride, then DCC (60.0 mg, 0.3 mmol, 20 equiv) was added under mechanical stirring. After 24 hours, the solvent was removed, the remaining solid residue suspended in a small amount of acetone, and the suspension separated by centrifugation. The yellow solution was decanted and the solvent removed by rotary evaporation. The yellow residue was dissolved in MeOH and DMF (9:1) and first dialyzed in MeOH containing 5% DMF to improve the solubility, followed by dialysis in neat MeOH (1,000 Dalton dialysis membrane, 18 mm diameter, 10 cm in length, Spectra/Por®, Spectrum Laboratories). Evaporation of the dialysis bag content gave the desired product as a yellow solid (98 mg, 86% yield). Its spectra are as follows:

$^1$H NMR (CDCl$_3$): δ 8.01, 7.67-7.63 (m), 7.48-7.44 (m), 7.00-6.95 (m), 6.83-6.79 (m), 6.66-6.62 (m), 5.20-5.12 (br), 4.30-4.15 (m), 4.10-3.10 (m), 2.75-2.10 (m).

C. Hydrolysis of PEHAM Dendrimer-Indomethacin Prodrug

The PEHAM-indomethacin prodrug (98 mg, 0.013 mmol) was dissolved in 10 mL of MeOH and 0.5 mL concentrated HCl under mechanical stirring. After 3 hours, the reaction was quenched with aqueous sodium hydrogen carbonate and dialyzed in water (1,000 Dalton dialysis membrane, 38 mm diameter, 5 cm in length, Spectra/Por®, Spectrum Laboratories). The content of the dialysis bag was filtered and the solid residue dried in an air stream to give a yellow solid (17 mg, fraction A). The filtrate was concentrated by rotary evaporation, decanted and solid parts removed by centrifugation. The supernatant yellow solution was the dried by rotary evaporation to give a yellow solid (57 mg, fraction C). The insoluble product from the flask was dissolved in acetone and dried by rotary evaporation to give a yellow solid (21 mg, fraction B). Fractions A-C were analyzed by $^1$H NMR spectroscopy and MALDI-TOF MS. The desired product, i.e., the PEHAM dendrimer without attached indomethacin, was identified in fraction C by the peak in MALDI-TOF MS at m/z 5464 [M]$^+$ and by its $^1$H NMR spectrum, which was virtually identical to that of the starting material. Weight of fraction C is consistent with recovery of 83% of the PEHAM dendrimer. Fraction A was identified by $^1$H NMR spectroscopy as indomethacin, contaminated with a minor organic impurity. The weight of fraction A is consistent with recovery of 58% of indomethacin. Fraction B was identified by MALDI-TOF MS as a mixture of fractions A and C and their spectra are as follows:

Fraction A (recovered indomethacin):

$^1$H NMR (CDCl$_3$): δ 7.67-7.63 (m), 7.48-7.45 (m), 6.97-6.95 (m), 6.83-6.80 (m), 4.05-3.95 (m, impurity), 3.82, 3.70-3.60 (m), 2.38, 2.00-1.00 (impurity).

Fraction C (recovered PEHAM dendrimer):

$^1$H NMR (CDCl$_3$): δ 4.25-4.18 (br), 4.00-3.20 (br), 2.70-2.20 (br); and

MALDI-TOF: C$_{245}$H$_{468}$N$_{32}$O$_{100}$; Calc. 5459, found 5464 [M]$^+$ amu (broad signals).

The following Scheme 101 illustrates this reaction.
Scheme 101
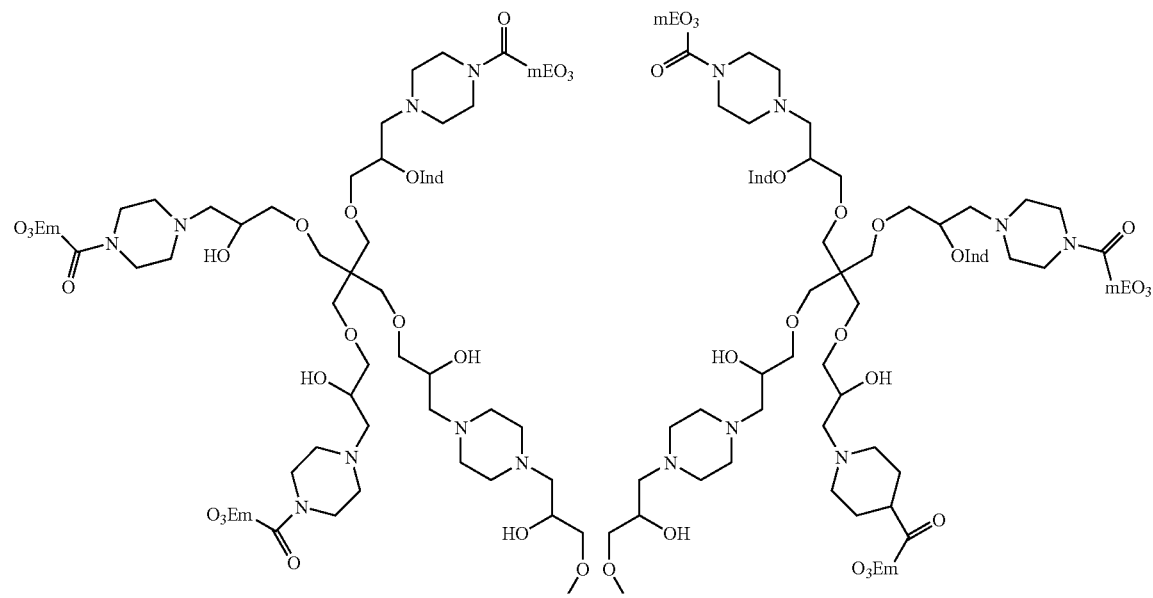
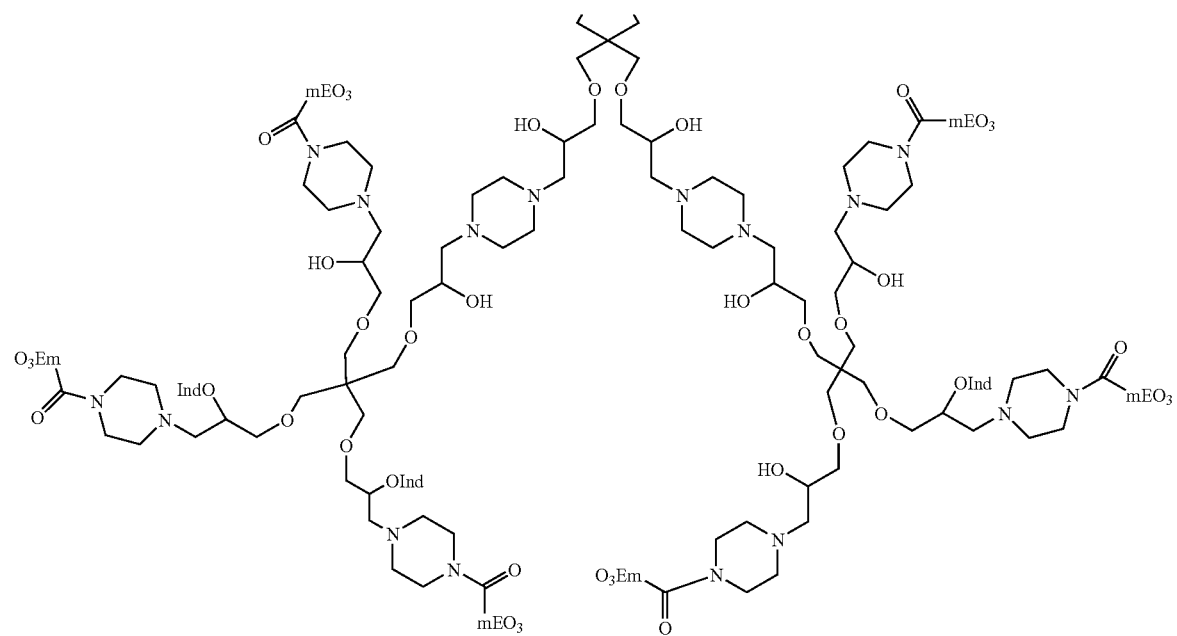
OInd = Indomethacin
mEO₃ = 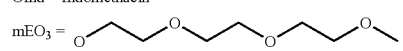

EXAMPLE 114

Surface conjugation of bioactives onto PEHAM dendrimers. The dye fluorescein isothiocyanate (FITC) as a model for a bioactive has been chemically bound to the surface of a PEHAM dendrimer. Surface conjugation was studied by poly(acrylamide) gel electrophoresis (PAGE), disclosing the ability of PEHAM dendrimers to be employed in standard life science conjugation techniques A. Equimolar Reaction Between FITC and PEHAM Dendrimer The equimolar reaction was set up by pipetting PEHAM dendrimer G=1 (239 µL, 10.0 mg, $3.145 \times 10^{-3}$ mmol; made from Example 93) into a 1.5-mL microcentrifuge tube. A FITC (Molecular Probes) solution was prepared by dissolving 187 mg of FITC in 50 µL of DMSO (Aldrich). From this solution, 3.27 µL (1.22 mg, $3.145 \times 10^{-3}$ mmol) was added to the PEHAM solution and mixed by a Vortex mixer for 10 seconds. The reaction became slightly cloudy and orange. Addition of a 10 N aqueous sodium hydroxide solution (2.5 µL) turned the solution clear orange, and the reaction was mixed on a rocking mixer in the dark at RT overnight.

B. Saturating Reaction Between Fluorescein Isothiocyanate (FITC) and PEHAM Dendrimer The saturating reaction was set up by pipetting PEHAM dendrimer G=1 (239 µL, (10.0 mg, $3.145 \times 10^{-3}$ mmol; made from Example 94) into a 1,5-ml microcentrifuge tube. To this solution, FITC (39.27 µL, 14.6 mg, $3.773 \times 10^{-2}$ mmol, 12-fold molar excess to PEHAM in order to conjugate to the theoretical 12 surface amines) was added and mixed by a Vortex mixer for 10 seconds. The solution turned cloudy and orange, and a large piece of orange precipitate formed instantly. Addition of a 10 N aqueous sodium hydroxide solution (5.0 µL) turned the solution clear orange, but the large piece of dark orange precipitate remained. The reaction was mixed on a rocking mixer in the dark at RT overnight.

C. PAGE Analysis of Both Surface-Conjugated PEHAM Dendrimer Products

A fraction of reactions A and B was run by SDS-PAGE for analysis. Two STARBURST™ (Dendritic Nanotechnologies, Inc.) gel control ladders, one containing PAMAM dendrimers G=2-6 with TRIS surface (5.0 µL) and the other PAMAM dendrimers G=0-6 with amine surface (2.5 µL, mixed with the same volume of SDS loading dye) were run as control samples. The third control, unaltered PEHAM dendrimer, and the conjugation reactions were prepared by using 1.0 µL of each solution, mixing with 4.0 µL of water and 5.0 µL of SDS loading dye (only the soluble portion was used for the saturating reaction). The FITC control sample was prepared by mixing 0.2 µL with 4.8 µL of water and 5.0 µL of SDS loading dye. Samples were loaded from left to right (lane number): (2) $NH_2$ surface ladder, (3) Tris surface ladder, (4) PEHAM dendrimer G=1, (5) saturated FITC reaction, (6) equimolar FITC reaction, and (7) FITC control. The 10% gel (30:1 acrylamide:bis-acrylamide) in [50.0 mM TRIS, 50 mM 2-4-morpholino)-ethane sulfonic acid (MES), 0.1% SDS] buffer was run at a constant 150 V from negative to positive until the bromophenyl blue loading dye had migrated ~¾ of the way down the gel. The gel was subsequently observed with UV light and after staining with Coomassie blue dye. These results are shown in FIG. 12.

Figure 12:
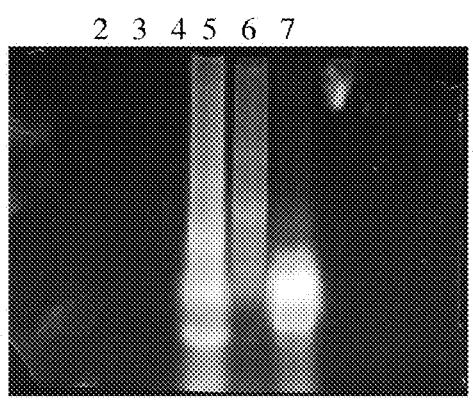
FIG. 12 shows the results obtained from surface binding of FITC for conjugation to PEHAM dendrimers. The left panel (A) shows the control in lane 7 and the PEHAM dendrimers conjugated with FITC in lanes 5 and 6. The right panel (B) shows Coomassie blue staining of the gel where all bands that showed fluorescence had PEHAM dendrimers present except for the free dye band.
Figure 12:
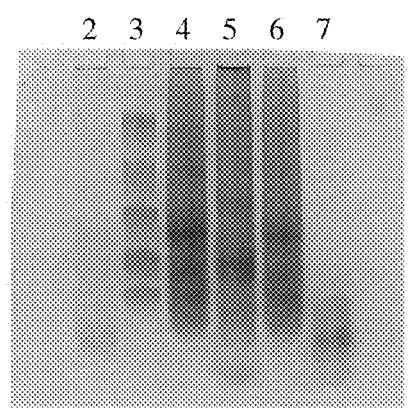

Under UV light (left panel) FIG. 12, distinct fluorescence bands can be seen on top of the background fluorescence in lanes 5-7. Several distinct bands of dendrimer-FITC conjugates are visible besides the band for free FITC in both reactions (lanes 5 and 6) that migrated in the same way as the control FITC (Lane 7). Coomassie blue staining of the gel (right panel) FIG. 12 revealed that PEHAM dendrimers were present in all bands that showed fluorescence, with the exception of the bands caused by free dye. Dendrimers from the equimolar reaction (Lane 6) revealed a similar pattern to not conjugated PEHAM dendrimer, indicating single or low number of FITC conjugation. The different pattern observed for the saturated reaction (Lane 5) is indicative of higher conjugation levels with larger change in size and/or net charge of the dendrimers after conjugation to FITC.

EXAMPLE 115

Figure 13:
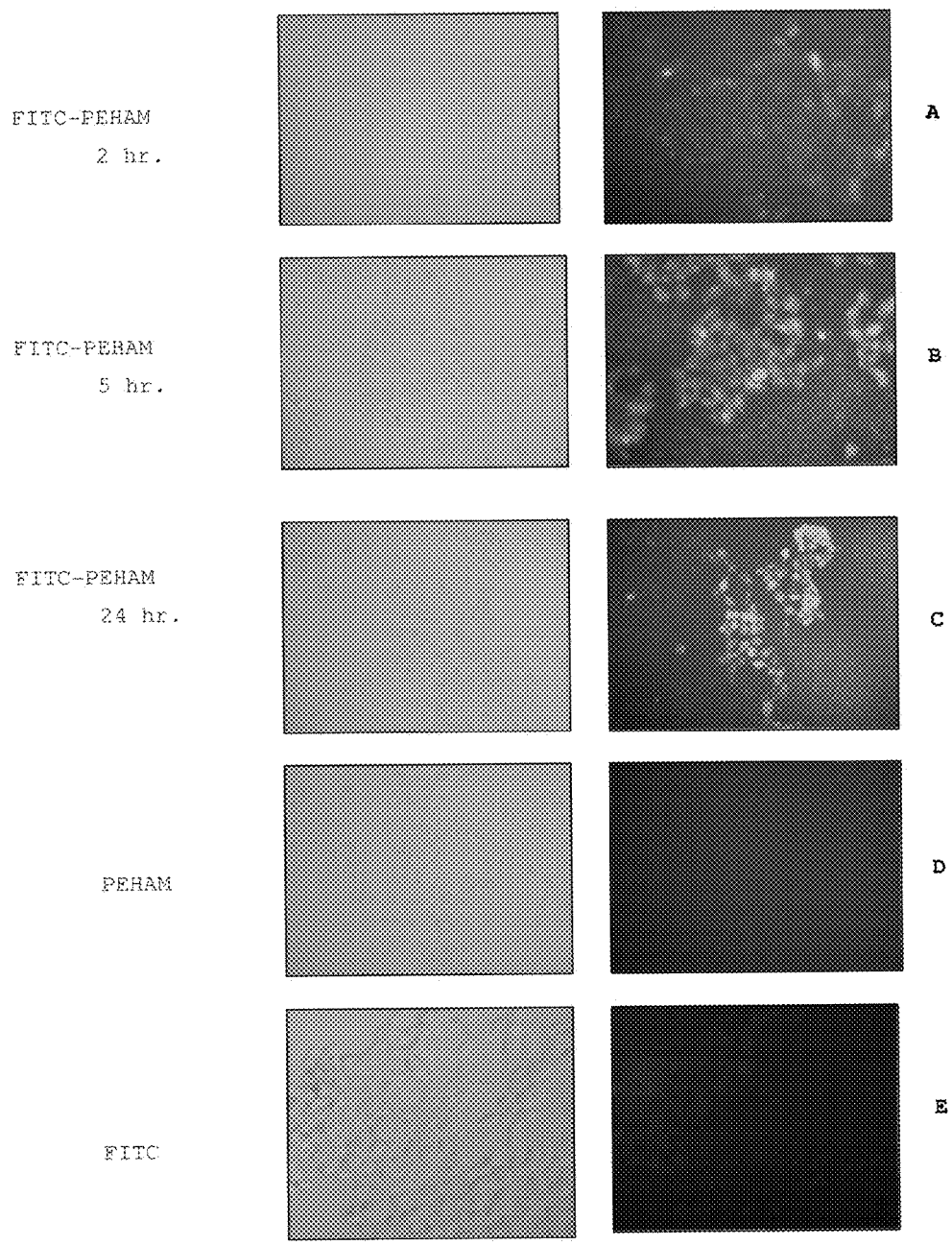
FIG. 13 shows the fluorescence microscopy results in the right column panels after 2, 5 and 24 hours of incubation of PEHAM dendrimer conjugated to FITC, and controls of PEHAM dendrimer and FITC, each alone, in HEK 293 cells. The presence of fluorescence inside the cells indicates that the conjugated PEHAM dendrimer was capable of cell permeation. The left column panels show the phase contrast images as reference points.

Membrane permeation of surface-conjugated PEHAM dendrimers. For practical uses in life science applications, it is necessary to demonstrate that PEHAM dendrimers have the ability to permeate cellular membranes. This is important for both in vitro and in vivo applications, as the transport of materials into cells is an important aspect of dendrimer-mediated delivery HEK 293 cells were plated at 40% confluency in a 96-well plate (Becton Dickinson) in MEM (Fisher), containing 10% FBS (ISC BioExpress). After 24 hours, 1.0 µL of FITC-conjugated G=1 PEHAM dendrimer (0.128 mM stock; made from Example 114) was added to the cells. Control wells included G=1 PEHAM dendrimer and FITC dye alone, at equivalent concentrations. The cells were incubated with the conjugate for 24 hours, with monitoring via fluorescence microscopy at 2, 5, and 24 hours. Prior to examination under the microscope, the cells to be analyzed were rinsed 2 times with PBS. A Nikon™ Diaphot-TMD microscope equipped with Nikon™ TMD-EF for fluorescence was used for the study, along with a Nikon™ CoolPix 990 digital camera to capture the results. The microscopy results indicated that the FITC-conjugated PEHAM dendrimers permeated the 293 cell membranes. Some fluorescent cells could be seen after 2 hours (FIG. 13, right panel), and this effect significantly increased after 5 and 24 hours, clearly indicating that PEHAM conjugates can be utilized in membrane permeation applications. The PEHAM and FITC controls showed no intracellular fluorescence. Phase contrast images (FIG. 13, left panel) have been included as reference points.

EXAMPLE 116

PEHAM dendrimers G=1 (piperazine surface; made from Example 93) as nucleic acid transfection agents. For practical uses in life science applications, it is necessary to demonstrate that PEHAM dendrimers have the ability to transfect nucleic acids, for example siRNA. This is important for both in vitro and in vivo applications, as the transfection of nucleic acids is an important aspect of dendrimer-mediated delivery A. Cell Preparations HEK 293 cells and MDCK cells were grown in 100-mm dishes in MEM with penicillin and streptomycin antibiotics, sodium pyruvate and 10% FBS (complete media) at 37° C. with 5% $CO_2$. When confluent, cultures were split either 1:3 or 1:4 to maintain active growth. Prior to transfection, one 100-mm dish of cells was split for each 10 35-mm dishes used to achieve ~85% confluency at the time of transfection. For transfection, lyophilized dendrimers were brought up to 250 µL in complete media. In a separate Eppendorf tube, Cyclophilin B siRNA (Human PPIB; siGENOME duplex) (Dharmacon, Inc.) was brought up to 250 µL in complete media for a final concentration of 150 nM. Both tubes were allowed to incubate at RT for 15 mins. before mixing together, followed by incubation for an additional 20 mins. Another 500 µL of media was added to each tube after incubation, bringing the total volume to 1.0 mL. This mixture was then added to 85% confluent HEK 293 and MDCK cells, whose media had been completely aspirated. The cells were incubated with the PEHAM dendrimer-siRNA complexes for 6 hours before replacing with fresh media. The cells were fed 48 hours later, and then harvested after 72 hours for protein analysis. The tissue culture plates were rinsed with PBS, then scraped in 150 µL Western Lysis Buffer (15 mM Tris HCl, pH 7.4-8.0, 150 mM NaCl, 1% Triton X-100, and 1 mM $NaVO_4$) and transferred to Eppendorf tubes. The samples were then mixed using a Vortex mixer and frozen at −20° C. until protein analysis. The control Lipofectamine 2000 (Invitrogen) transfections were performed per the manufacturer's protocol as directed for 293 transfections. Basically, the same procedure as above was performed, however the media during complex formation was free from FBS and antibiotics. Complexes were formed with 2 µg/mL Lipofectamine™ 2000.

B. Protein Quantitation and Western Blots

Protein samples were thawed and vortexed, then centrifuged at 12,000 rpm. Samples were analyzed for protein content using the BioRad™ Protein Assay (BioRad) per manufacturer's protocol. Basically, 2 µL of protein sample were added to a 96-well microplate, followed by 200 µL of diluted BioRad™ reagent. The plate was read at 570 nm wave length on a Multiskan™ MCC/340 microplate reader (ThermoLabsystems). BSA was used as the standard. Calculations were performed on the resulting data to determine protein quantitation of the samples. For Western blots, 25 µg protein samples were run on 15%/5% SDS PAGE. The gels were run at 30 mA per gel. Following electrophoresis, the gels were assembled in a gel transfer apparatus and transferred to nitrocellulose membrane in 2.2 g/L sodium bicarbonate at 200 mA for 2 hours. The membranes were then removed, probed with Ponceau Red to monitor transfer efficacy, rinsed with TBS, and blocked in a 5% milk solution for 1 hour. After blocking, the membranes were incubated at RT with anti-Cyclophilin B antibody (1:3000 dilution) for 2 hours (Abcam, Inc.), followed by 2 5-min. rinses with TBS+ 0.05% Tween. Alkaline phosphatase-conjugated anti-rabbit secondary antibody (1:5000 dilution) was then incubated with the membranes for 1 hour, followed by 3 5-minute rinses with TBS+ 0.05% Tween. The membranes were then developed using 1-Step™ NBT/BCIP solution from Pierce. For a loading control, the membranes were incubated with anti-β actin antibody (1:3000 dilution) for 1 hour (Abcam, Inc.). Alkaline phosphatase-conjugated anti-mouse antibody (1:5000 dilution) was used as the secondary antibody as per the anti-rabbit described above. Washes were performed as described above as well. Images were captured digitally and analyzed for band density using ImageJ software (NIH).

C. PEHAM Dendrimer Experiments

Figure 14:
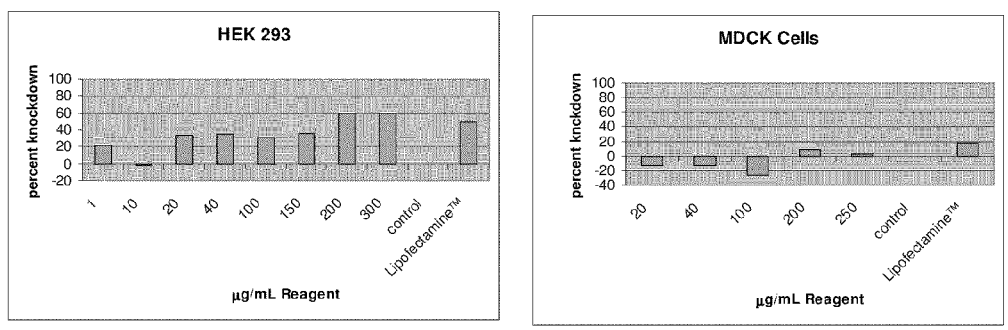
FIG. 14 shows the results of testing G=1 PEHAM dendrimers as a siRNA delivery vehicle at varying concentrations in HEK 293 cells and MDCK cells. A general trend that an increase in PEHAM dendrimer concentration in HEK 293 cells shows an increase in gene product knockdown is shown in the figure on the left. The MDCK cells, the figure on the right, shows a moderate reduction of Cyclophilin B expression at the highest doses of PEHAM dendrimer tested.

In order to determine the concentration at which G-1 PEHAM dendrimers (made from Example 94) effectively function as an siRNA delivery vehicle, a range of concentrations from 1 µg/mL to 300 µg/mL in HEK 293 cells and 20 µg/mL to 250 µg/mL in MDCK cells were used for complex formation. The data are shown in FIG. 14 for the HEK 293 and MDCK cells. In HEK 293 cells, there is a general trend that an increase in the PEHAM dendrimer concentration shows an increase in gene product knockdown. The MDCK cells show moderate reduction of Cyclophilin B expression at the highest doses of PEHAM used in this assay. In both HEK 293 and MDCK cells, the highest percentage of Cyclophilin B knockdown by siRNA delivery was seen when using 200 µg/ml of PEHAM dendrimer to deliver the siRNA to cells. While the knockdown observed in MDCK cells was modest (8.5%), the knockdown in HEK 293 cells was significant (60.2%), surpassing the effect seen for the control, Lipofectamine™ 2000 (49.2%). This observation clearly indicates that PEHAM dendrimers have potential to transfect, at least some cell lines, efficiently at the concentrations tested. Many transfection agents work differently in different cell lines. For this reason the wide range of concentrations was used for this experiment. It is possible that for MDCK cells the concentration to achieve efficient delivery of siRNA by PEHAM dendrimers lies outside the range tested, or other parameters not yet tested, such as cell density, presence of serum, need to be optimized.

Figure 15:
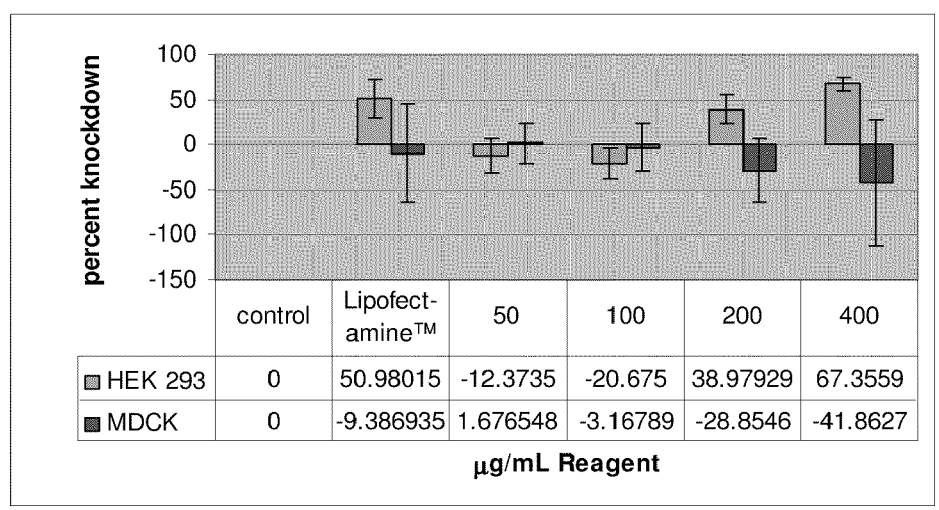
FIG. 15 shows the results of validating the results from FIG. 14 where 50, 100, 200, and 400 µg/mL of G=0 PEHAM dendrimer were tested in triplicate. As before HEK 293 cells showed increasing silencing of Cyclophilin B with increasing concentration of PEHAM dendrimer. However, the PEHAM dendrimer was less effective as a transfection reagent in MDCK cells, showing highly variable results.

In order to validate the findings of the first experiment, HEK 293 and MDCK cells were transfected with siRNA-targeting Cyclophilin B using 50, 100, 200 and 400 µg/mL G=1 PEHAM dendrimer in triplicate. The results from this experiment are shown in FIG. 15. Error bars show the standard deviation of the three experiments for the PEHAM samples, and the deviation between two gels for Lipofectamine™ 2000. Again, the HEK 293 cells showed increasing silencing of Cyclophilin B with increasing PEHAM dendrimer concentration used as a delivery agent. In this experiment, however, percent knockdown continued to increase beyond the 200 µg/mL concentration, showing a maximum of 67.4% knockdown using 400 µg/mL. The transfection ability and subsequent target knockdown was again superior to the control transfection agent, Lipofectamine™ 2000. Conversely, both the PEHAM dendrimer and Lipofectamine™ 2000 are ineffective transfection reagents in MDCK cells. While PEHAM dendrimers showed some ability to deliver siRNA in order to knockdown Cyclophilin B expression in some single assays, this ability was highly variable as is seen by the high standard deviation. This is consistent with a failure to deliver siRNA to induce significant gene knockdown. Any of the observed small amounts of knockdown in a single sample is likely a difference in natural gene expression between samples. However, as is seen for all cellular transfection agents, PEHAM dendrimers function as efficient delivery vehicles for siRNA at certain concentrations for particular cells lines. Observing successful delivery in one cell line, therefore, indicates that PEHAM dendrimers can function as a transfection agent and suggests that other conditions may need to be modified for individual cell lines to find conditions that work for each.

EXAMPLE 117

PEHAM Dendrimers G=2 (Primary Amine Surface; Made from Examples 82 and 84) as Nucleic Acid Transfection Agents A. Cell Preparations MDCK and HEK 293 cells were split 1:300 from a confluent 10-cm culture dish to 22 wells of a 96-well plate for each cell line to achieve ~85% confluency at the time of transfection. To determine the effectiveness of PEHAM dendrimer G=2 with a three-arm core and primary amine surface (made from Example 84) and PEHAM dendrimer G=2 with a four-arm core and primary amine surface (made from Example 86), a concentration range from 1 µg/mL to 500

μg/mL was used for siRNA transfection in both cell lines. For transfection, lyophilized dendrimers were brought up to 50 μL in complete media. In a separate Eppendorf tube, Cyclophilin B siRNA (Human PPIB; siGENOME duplex) (Dharmacon, Inc.) was brought up to 50 μL in complete media for a final concentration of 150 nM. Both tubes were allowed to incubate at RT for 15 mins. before mixing together, followed by incubation for an additional 20 mins. This mixture was then added to 85% confluent HEK 293 and MDCK cells, whose media had been completely aspirated. The cells were incubated with the PEHAM dendrimer-siRNA complexes for 11 hours before replacing with fresh media. After 48 hours, cells were harvested and RNA expression quantitated for specific gene knockdown using a branched DNA (bDNA) assay, Quantigene® Explore Kit from Genospectra, per the manufacturer's protocol. Briefly, 50 μL of Lysis Mixture (proprietary formula, Genospectra) was added to the 100 μL of media in each well and incubated at 37° C. for 15 mins. Visual inspection of the cells under the microscope verified cell lysis. Cell lysates were frozen at −20° C. until the quantitation assay was performed.

B. Quantitation Assays

Prior to the assay probe sets were prepared. Probe sets for actin (HUMAN ACTB, 5× concentration) (Genospectra) and Cyclophilin (HUMAN PPIB, 5× concentration) (Genospectra) were prepared by diluting the probe set components (CE, LE, and BL) to IX concentration in TE (10 mM TRIS, 1 mM ethylenediamine tetraacetate disodium) by adding 52 μL of probe into 208 μL TE. Lysis working reagent was prepared for both actin and Cyclophilin by mixing 3.7 mL of Lysis mixture with 37 μL of each 1× concentration probe set component. The remaining IX probe set components were stored at −20° C. For the quantitation assay cell extracts were thawed at RT and 20 μL of each was pipetted into two wells of a capture plate (white 96-well plate with proprietary DNA sequences conjugated to the surface) (Genospectra). To one well 80 μL of lysis working reagent with the actin probes was added and in the second well 80 μL of lysis working reagent with the Cyclophilin probes was added. The plate was sealed with an aluminum plate sealer (Costar) and incubated at 50° C. overnight in a zip lock aluminum bag (Genospectra) with a wet paper towel inside to minimize evaporation. Working solutions were prepared the next morning per Quantigene® Explore Kit (Genospectra) instructions. Wash buffer was prepared by diluting 20 mL of 10× Wash Buffer (10×SSC (1.5 M NaCl and 0.15 M sodium citrate at pH 7.0), 1% lithium laurylsulfate) (Genospectra) to 1× with 180 mL of water. Amplification working solution and label probe working solution were prepared by adding 9 μL of Amplifier (proprietary branched DNA sequence) (Genospectra) and 9 μL of label probe (proprietary DNA sequence coupled to luciferase) (Genospectra) respectively to 9 mL of Amplifier/label Probe Diluent (proprietary solution) (Genospectra). Substrate working reagent was prepared by adding 27 μL of 10% lithium laurylsulfate to 9 mL substrate (proprietary mixture) (Genospectra).

To each well, 250 mL of wash buffer was added and the entire plate contents were poured off. Each well was washed 3 times with 350 μL wash buffer and after the last wash the plate was dried by inverting and pounding on a paper towel. To each well 100 mL of amplification working solution was added. The plate was resealed and incubated at 50° C. for one hour. The amplification working solution was poured off and the wells washed 3 times as above. To each well 100 mL of label probe working solution was added. The plate was resealed and incubated at 50° C. for one hour. The label probe working solution was poured off and the wells washed 3 times as above. To each well 100 mL of substrate working solution was added. The plate was resealed and incubated at 50° C. for 15 mins. and then cooled to RT for 15 mins. The sealing foil was removed from the plate and the relative light units for each well were measured on a GloRunner™ luminometer (Turner BioSystems).

C. PEHAM Dendrimer Experiments

Figure 16:
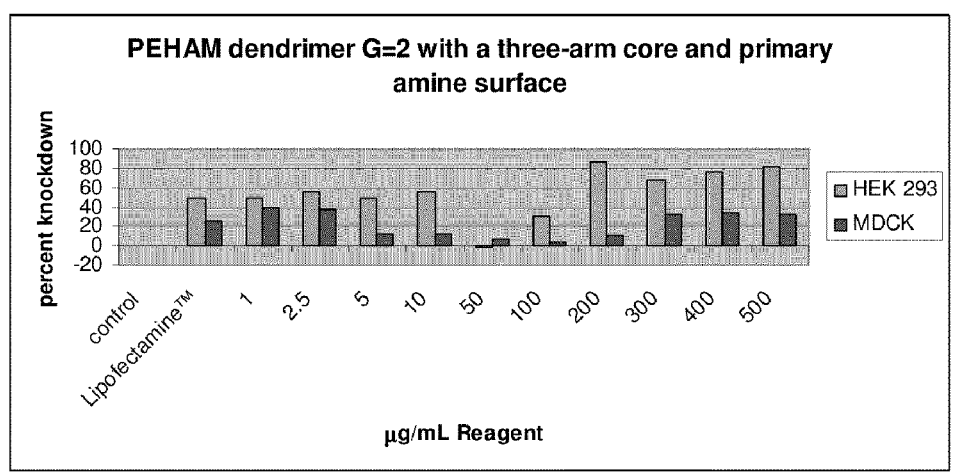
FIG. 16 shows the results of testing G=2 PEHAM dendrimer of Example 82 as a siRNA delivery vehicle at varying concentrations in HEK 293 cells and MDCK cells. A general trend that an increase in G=2 PEHAM dendrimer concentration in HEK 293 and MDCK cells shows an increase in gene product knockdown and both values are higher than those for Lipofectamine™ 2000.
Figure 17:
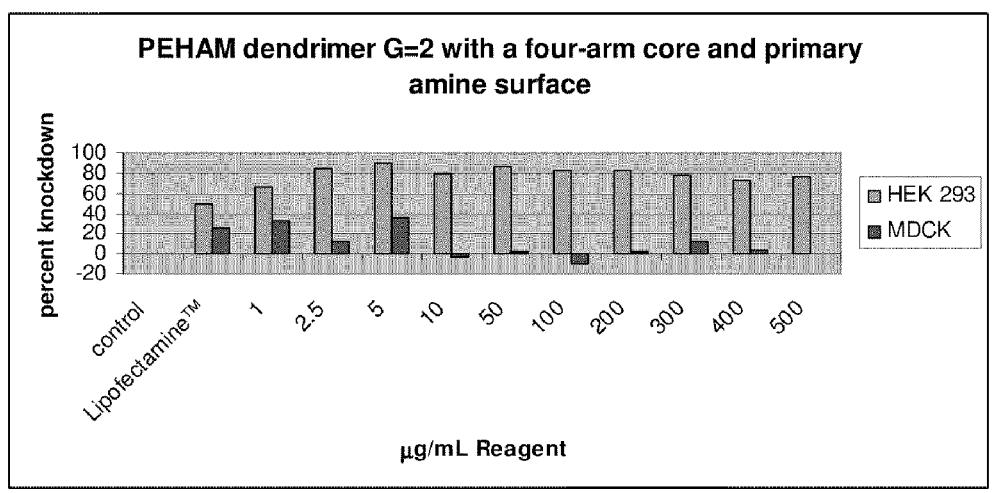
FIG. 17 shows the results of testing G=2 PEHAM dendrimer of Example 84 as a siRNA delivery vehicle at varying concentrations in HEK 293 cells and MDCK cells. The results showed effective silencing of Cyclophilin B expression across the range of concentrations in HEK cells and at low concentrations in MDCK cells.

In both the HEK 293 and the MDCK cells, the PEHAM dendrimer G=2 with a three-arm core and primary amine surface (Example 84) showed effective silencing at low concentrations (1 μg/mL to 10 μg/mL) and at high concentrations (200 μg/mL to 500 μg/mL), with a decrease in effectiveness at 50 μg/mL to 100 μg/mL. The highest percent of Cyclophilin B silencing in HEK 293 cells, 86%, was observed at 200 μg/mL. For MDCK cells, the highest percent of Cyclophilin B silencing (39%) was observed at 1 μg/ml. Both of these values are higher than those observed for Lipofectamine™ 2000 (49% HEK 293, 26% MDCK), showing that the PEHAM dendrimer G=2 with a three-arm core and primary amine surface (Example 84) can function as an efficient vehicle for siRNA delivery in multiple cell lines (See FIG. 16). The PEHAM dendrimer G=2 with a four-arm core and primary amine surface (Example 86) showed effective silencing of Cyclophilin B across the entire range of concentrations tried in HEK 293 cells and at low concentrations in MDCK cells. The peak silencing was seen at 5 μg/mL for both cell lines, with HEK 293 cells showing 89% knockdown and MDCK cells having 35% knockdown. Both of these values are higher than those observed for Lipofectamine™ 2000 (49% HEK 293, 26% MDCK), demonstrating that the PEHAM dendrimer G=2 with a four-arm core and primary amine surface (Example 86) also can function as an efficient transfection agent for siRNA in multiple cell lines (See FIG. 17).

EXAMPLE 118

Antibacterial Activity of PEHAM Dendrimers

To determine the antibacterial properties of PEHAM dendrimers, a method adapted from Paul Goldenheim's 1993 *Postgradate Medical Journal* [Goldenheim P., *Postgrad Med. Journal*, S62-S-65 (1993)] was used. A 5-ml culture of L-Broth (LB) media (TEKnova) was inoculated with 10 μL *E. coli* (obtained from the Schisa laboratory, Central Michigan University, Department of Biology) and grown overnight at 37° C. with shaking at 225 rpm. To a fresh 5-mL batch of LB media, 10 μL of the overnight culture was added and grown for 2 hours at 37° C. with shaking to get bacteria to their logarithmic growth phase. G=1 PEHAM dendrimer samples (made from Example 93) at concentrations of 3.35%, 0.0335% (1:100), and 0.00335% (1:1000) in water were prepared. To each test sample, ¹/₁₀th volume of actively growing *E. coli* was added and 10 μL samples taken after min. These samples were inoculated into 5 mL LB media. The antibacterial agent Povidone-iodine (PVP-iodine from Triadine) was used as a positive control at the same concentrations. The cultures were grown overnight at 37° C. with shaking. The absorbance at 600 nm was read on a PerkinElmer Lambda 2 UV/Vis Spectrophotometer to measure culture density, and then multiplied by $1.4 \times 10^8$ to calculate cells/mL. The calculations of cells/ml to determine the antimicrobial efficacy are shown in Table V.

TABLE IV

| Sample | Cells/mL |
|---|---|
| PEHAM G1 1:1 (3.35%) Example 93 | 4.48E+06 |
| PEHAM G1 1:100 Example 93 | 2.73E+08 |
| PEHAM G1 1:1000 Example 93 | 2.74E+08 |
| Povidone-iodine 1:1 (3.35%) | 7.00E+05 |
| Povidone-iodine 1:100 | 2.69E+08 |
| Povidone-iodine 1:100 | 2.69E+08 |
| PEHAM G = 2 TREN 3-arm (5%) Example 84 | 2.69E+08 |
| PEHAM G = 2 TREN 4-arm (5%) Example 86 | 1.40E+05 |

The result of this experiment indicated that the PEHAM dendrimer killed *E. coli* bacteria at its highest concentration (i.e., 3.35%) with a similar efficiency as the control sample. To further investigate the antibacterial activity of PEHAM dendrimers, two additional compounds derived from TREN surfaces were studied. These G=2 PEHAM dendrimers, a three-arm dendrimer made from Example 84, and a four-arm dendrimer made from Example 86, were used at a 5% concentration. As shown in Table V, the four-arm PEHAM dendrimer killed bacteria, while the three-arm dendrimer was not effective under the experimental conditions. This behavior may be due to the lower number of total amines on the molecule surface. However, these studies indicate that PEHAM dendrimers can be employed in antibacterial applications.

COMPARATIVE EXAMPLES

Dendrimers of Formula (I) Compared with PAMAM Dendrimers

Example I

Thermal Stability

Figure 18:
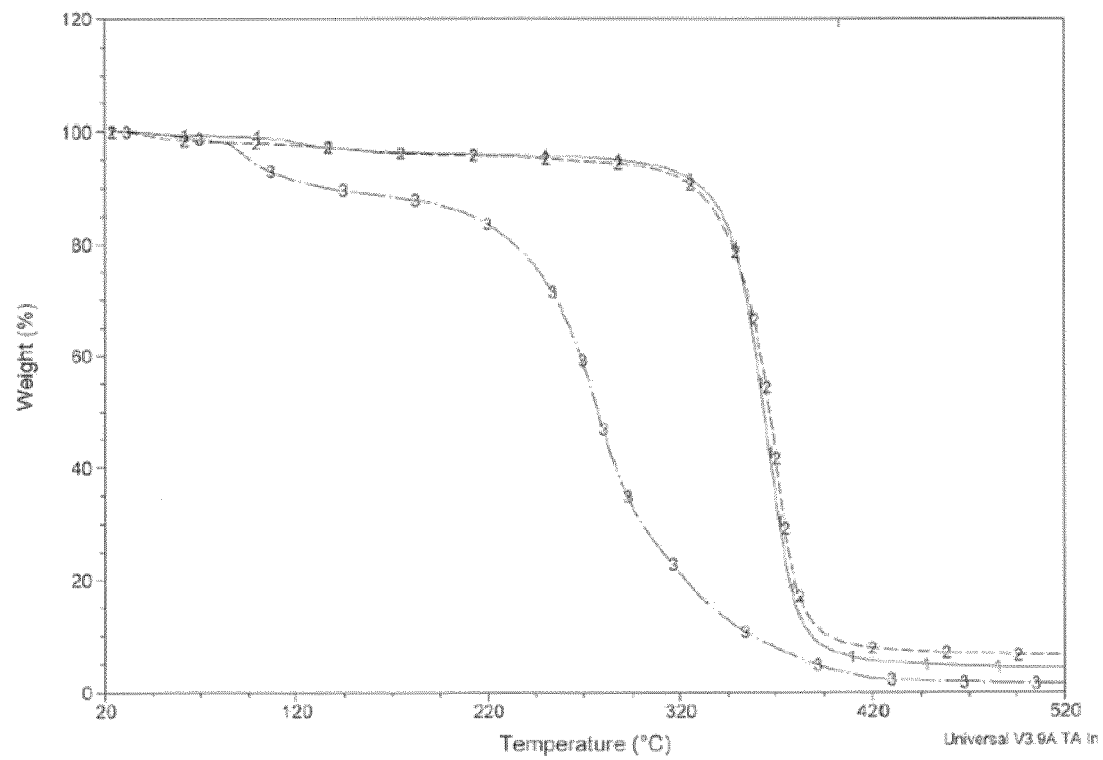
FIG. 18 shows the enhanced thermal stability of dendrimers of Formula (I) compared with traditional PAMAM dendrimers. In this FIG. 18 the numbered lines represent the data for these dendrimers: 1 is Example 25B, 2 is Example 76, and 3 is PAMAM, G=3, (C)=DAB, (TF)=amine.

The present dendrimers of Formula (I) have significantly increased thermal stability (about 100° C. greater) compared with PAMAM dendrimers as determined by TGA. This data is shown in FIG. 18. Curve 3 in FIG. 18 shows the thermal degradation profile in nitrogen of a typical PAMAM [poly (amidoamine), G=3 dendrimer], diaminobutane core amine surface polymer (Dendritic Nanotechnologies, Inc.). In comparison, curves 1 and 2 in FIG. 18 show the thermal degradation profiles of products of Examples 26B and 78, respectively. As can be seen from the data, the products from Examples 26B and 78 show similar thermal profiles and demonstrate significant superior thermal stability compared to the PAMAM polymer of a similar generation. The polymers of these examples show that a much higher temperature of onset of thermal degradation occurs and higher residual mass is present than that known previously for the comparative polymers.

This data shows that the present dendrimers of Formula (I) have greater thermal stability compared with PAMAM dendrimers.

Example II

TGA Under Same Conditions as Comparative Example I for Various Dendrimers of Formula (I) and PAMAM are Shown in Table VI Below

TABLE VI

| Sample | Onset Temp. (° C.) | Temp. (° C.) at 50% wt loss | Temp. (° C.) at Residue |
|---|---|---|---|
| PAMAM G = 3, diaminobutane core, amine surface | 245 | 280 | 400 |
| Example 26B | 345 | 370 | 418 |
| Example 78 | 345 | 370 | 418 |
| *(C) = TMPTGE; (IF1) = OH; (EX1) = PIPZ; (IF2) = OH; (BR1) = TMPGE; (IF3) = OH; (EX2) = PIPZ; (TF) = 2° NH | 380 | 397 | 450 |
| **(C) = TMPTGE; (IF1) = OH; (EX1) = PIPZ; (IF2) = OH; (BR1) = TMPGE; (IF3) = OH; (EX2) = PIPZ; (IF4) = OH; (BR2) = TMPTGE; (IF5) = OH; (EX3) = PIPZ; (TF) = 2° NH | 380 | 400 | 452 |
| ***(C) = TMPTGE; (IF1) = OH; (EX1) = PIPZ; (IF2) = OH; (BR1) = TMPGE; (IF3) = OH; (EX2) = PIPZ; (IF4) = OH; (BR2) = TMPTGE; (IF5) = OH; (EX3) = PIPZ; (IF6) = OH; (BR3) = TMPTGE; (IF7) = OH; (EX4) = PIPZ; (TF) = 2° NH | 385 | 405 | 420 |
| Example 34 | 320 | 407 | 500+ |

*made by a repeating the process of Examples 26A and 26B with appropriate change of reagents;
**made by a repeating the process of Example 78 with appropriate change of reagents;
***made by a repeating the process of Example 79 with appropriate change of reagents.

These above results show that the dendrimers of Formula (I) show significant higher thermal stability compared to PAMAM.

EXAMPLE III

Cost-Benefit Arguments

The dendrimers of Formula (I) are cheaper to prepare than the PAMAM dendrimers because there are:

Fewer processing steps due to higher functionality of intermediates

Fewer reaction by-products due to ring opening or addition reactions

Lower cost for reagents, and

Higher process capacity due to lesser reagent excesses.

The following comparison of formula weights and number of surface groups for epoxide ring opening, piperazine dendrimers with $N_c=4$ and $N_b=3$ of Formula (I) dendrimers versus typical PAMAM dendrimers with in situ branch cell formation is shown by the following Table VII.

TABLE VII

| Generation | $N_c = 4$, $N_b = 3$ Formula (I) Weight | Formula (I) Number of Surface Groups | PAMAM EDA Core - Formula Weight | PAMAM EDA Core - Number of Surface Groups |
| --- | --- | --- | --- | --- |
| G = 0 | 705 | 4 | 517 | 4 |
| G = 1 | 3180 | 12 | 1430 | 8 |
| G = 2 | 10606 | 36 | 3250 | 16 |
| G = 3 | 32854 | 108 | 6909 | 32 |
| G = 4 | 99691 | 324 | 14214 | 64 |
| G = 5 | 305153 | 972 | 28825 | 128 |

This Table VII shows why the invention allows rapid building of surface functionality, rapid increases in molecular weight and attainment of de Gennes surface packing and therefore container properties in fewer generations than for PAMAM. Since each generational addition adds significant costs due to increases in unit operations, the attainment of high molecular weights and surface functionality in fewer steps indicates significant cost reduction potential.

Dendrimers of Formula (I) Compared with Hyperbranched Dendrimers

EXAMPLE IV

Polydispersity

Narrower Polydispersity is observed for the dendrimers of Formula (I) when compared to Hyperbranched Polymers by Less Controlled Random Ring Opening.

The AFM data give very narrow polydispersity numbers for Examples 78 and 79 of 1.091 and 1.117, respectively. These numbers are very narrow and indicate that the particles are highly monodispersed and not aggregated. Typical polydispersities of hyperbranched polymers were never found below 1.3-1.5 and are typically much broader about 3-8.

EXAMPLE V

Size Exclusion Chromatography (SEC)

Figure 19:
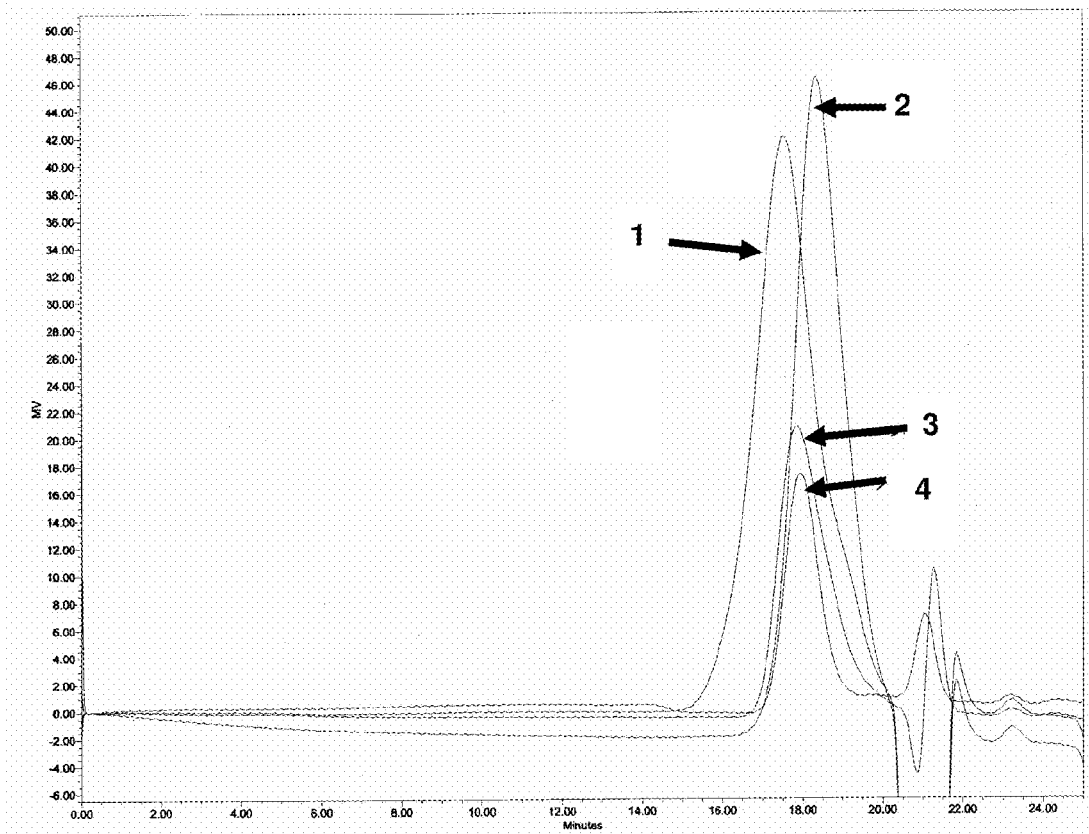
FIG. 19 shows the size exclusion chromatography (SEC) for representative products of Formula (I) [i.e., Examples 76 (4) and 77 (3)] compared to two related hyperbranched dendritic polyglycidols with average molecular weight of 5000 (2) and 8000 (1) molecular weight. The band widths shown indicate narrow polydispersity for 3 and 4.

FIG. 19 shows the SEC of the products of Examples 26B and 78 in comparison to the data for two similar average molecular weight hyperbranched dendritic polyglycidols of 5000 and 8000 molecular weight. The SEC curves numbers 1 and 2 show the lower polydispersity of the unoptimized products of Examples 26B and 78 relative to the typical broad polydispersity of hyperbranched materials. The calculated polydispersity numbers are indicated in the Table VIII below.

TABLE VIII

| Curve Number | Polymer | Polydispersity |
| --- | --- | --- |
| 1 | Hyperbranched Polyglycidol (HB)-5000 | 3.20 |
| 2 | Hyperbranched Polyglycidol (HB)-8000 | 8.80 |
| 3 | Example 26B | 1.59 |
| 4 | Example 78 | 2.90 |

Dendrimers of Formula (I) Compared with Hyperbranched Dendrimers

EXAMPLE VI

CPK Models

Figure 20:
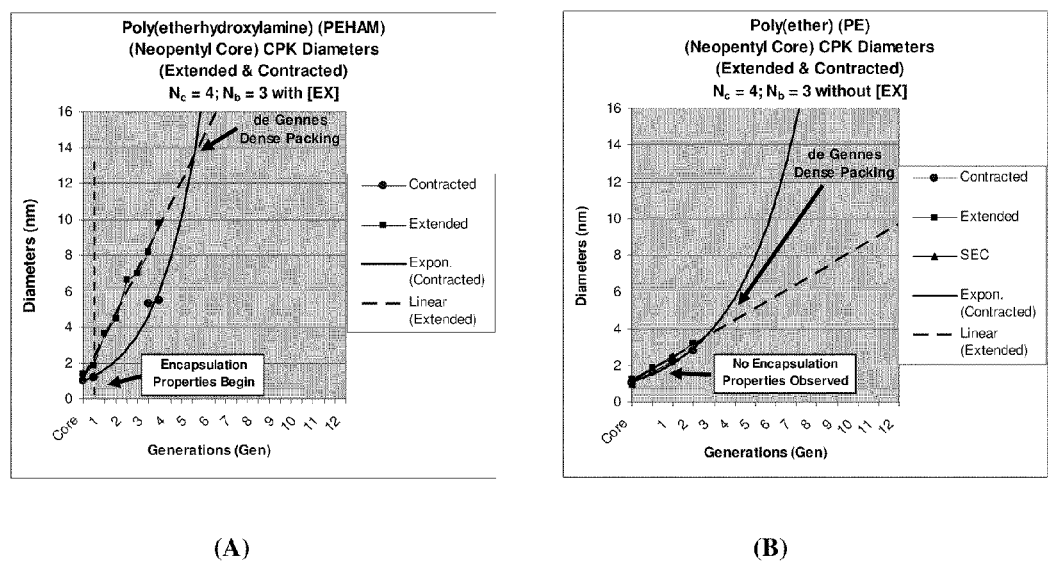
FIG. 20 (A) shows the diameter dimensions (nm) obtained from CPK models illustrating contracted (by circles) and extended (squares) values for poly(etherhydroxylamine) (PEHAM) dendrimers [(C)=neopentyl; (IF)=OH; (BR)=PETGE; (Ex)=PIPZ; (TF)=NH; G=0.5 to 6.5]. The black linear curve (by solid line) shows ideal extended behavior. The black exponential curve (by solid line) indicates contracted dimensions. This difference between the contracted and extended dimensions indicates available void space in the interior of the dendrimer. Note that encapsulation begins at approximately G1. Whereas, encapsulation properties are not observed for classical poly(ether)dendrimers as shown in FIG. 20(B). The cross over point at about G=5.5 illustrates the de Gennes dense packing point for this dendrimer family.

FIG. 20 shows the dimensions obtained from CPK models showing contracted and extended PEHAM dendrimer [(C)=PETGE; (IF)=OH; (EX)=PIPZ; (BR)=PETGE); (TF)=PIPZ; G=0.5, 1.5, 2.5, 3.5, 4.5, 5.5, 6.5]. The crossover points indicate where the de Gennes dense packing is absolute. The space between the contracted and the extended versions of the model indicates available interior void volumes available for encapsulation. SEC volumes in water will give a line between these two boundaries.

Figure 21:
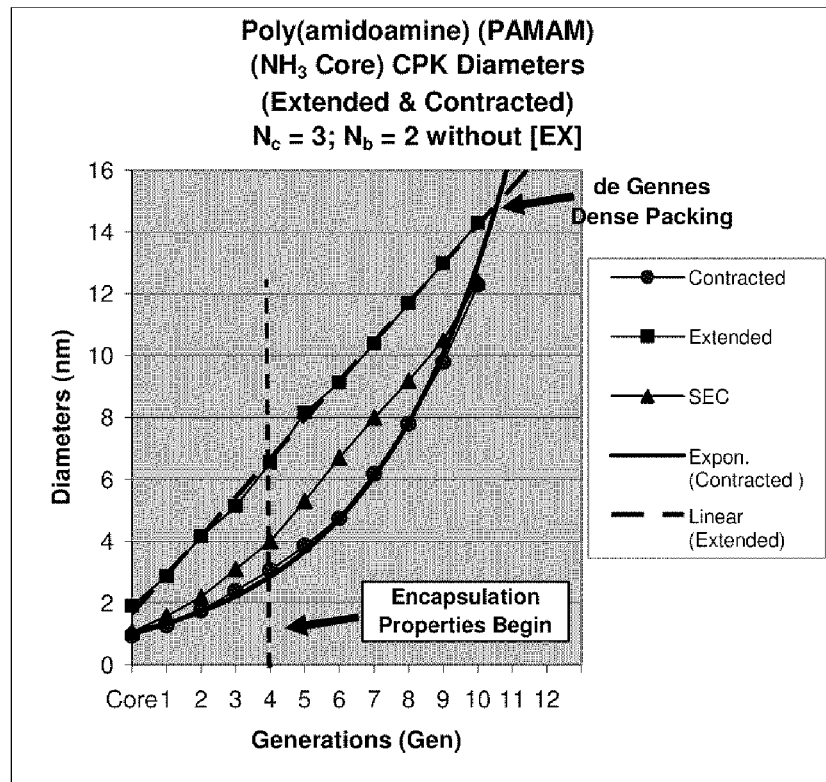
FIG. 21 shows the diameter dimensions (nm) obtained from CPK models illustrating contracted (by circles) and extended (by squares) values for the classical poly(amidoamine) (PAMAM) dendrimers [(C)=NH$_3$]; G=1-10. The actual SEC values (shown by triangles) reside between the contracted and extended dimension values. This dendrimer family has no (EX) and no (IF) and a de Gennes dense packing cross-over point at G=10. Note that encapsulation properties do not begin until G=4 compared to G=1-1.5 for PEHAM dendrimers as shown in FIG. 20(A).

FIG. 21 compares a prior polyether dendrimer [(C)=neopentyl; (BR)=neopentyl; (TF)=OH)] dimensions obtained from CPK models. With these prior dendrimers that have no extenders or internal functionality, there is no interior void volume.

EXAMPLE VII

Theory Discussion for N-SIS

While not wishing to be bound by theory, the following discussion is provided to assist in understanding the possible steric factors and reasons for their effects on PEHAM dendrimer reactions and formation. Two math models were constructed to estimate the maximum number of branch reagents (BR) that can fit around a core reagent (C). The first model treats all reagents as ideal spheres, whereas the second one considers branch reagents (BR) as cone shaped and the core reagents as spheres. All other chemistry parameters such as bond angles, actual molecular shapes, solvent, etc. are not considered. Several core reagents and branch reagents are tested with these models, and results showed that the models are quite accurate when compared with results obtained from actual reactions.

There are several parameters to fine tune the synthesis of perfect dendrimer structure without defects. Among them, steric induced stoichiometry (SIS) plays one of the most important roles. For example, de Gennes predicts that at a given generation ideal branching can no longer occur since available surface space becomes too limited for the mathematically calculated number of surface groups to occupy [P. G. de Gennes and Hervet, H. J. *J. Physique-Lett.* (*Paris*), 44, 351 (1983)]. Ingrid van Baal et al. [Ingrid van Baal et al. *Angew. Chem. Int. Ed.* 44, 2 (2005)] observed sub-saturated substituted molecules along with the perfect structure when they tried to surface modify a G3 dendrimer with peptide. Tomalia et al. mathematically calculated the saturation number of shell dendrimer molecules ($r_1$) that may be placed around a core dendrimer molecule ([2] for the construction of core-shell tecto(dendrimers) [M. L. Mansfield; L. Rakesh; and D. A. Tomalia, *J. Chem. Phys.*, 105, 3245 (1996)]. The ratio of the core and branch radii determines the maximum number of the branch reagents that are theoretically possible for linkage around the core using the Mansfield-Tomalia-Rakesh equation [M. L. Mansfield; L. Rakesh; and D. A. Tomalia, *J. Chem. Phys.*, 105, 3245 (1996)]. These theoretical calculations were proven and experimentally demonstrated by S. Uppuluri. et al., [*Adv. Mater.*, 12, 796 (2000)] in the synthesis of core-shell tecto (dendrimers) which were analyzed by MALDI-TOF and PAGE to demonstrate that the calculations are fairly close to reality [D. A. Tomalia, et al., *Pure Appl. Chem.*, 72, 2343 (2000) and D. A. Tomalia et al., *Proc. Natl. Acad. Sci.*, 99(8), 5081-5087 (2002)].

During the course of synthesizing PEHAM dendrimers by a divergent iterative process, defective structures have been observed. It is believed that these defective structures are due to N-SIS effects manifested by the interaction of the nanoscale cores (C) and the nanoscale branch cell reagents (BR). These following models attempt to explain and predict maximum allowable numbers of branch reagents that may be covalently linked around a core, considering the branch reagents to be simple geometric shapes. This analysis ignores hydrogen bonding and solvent effects. Two kinds of branch reagent (BR) shapes will be considered, namely, spherical and conical.

Figure 22:
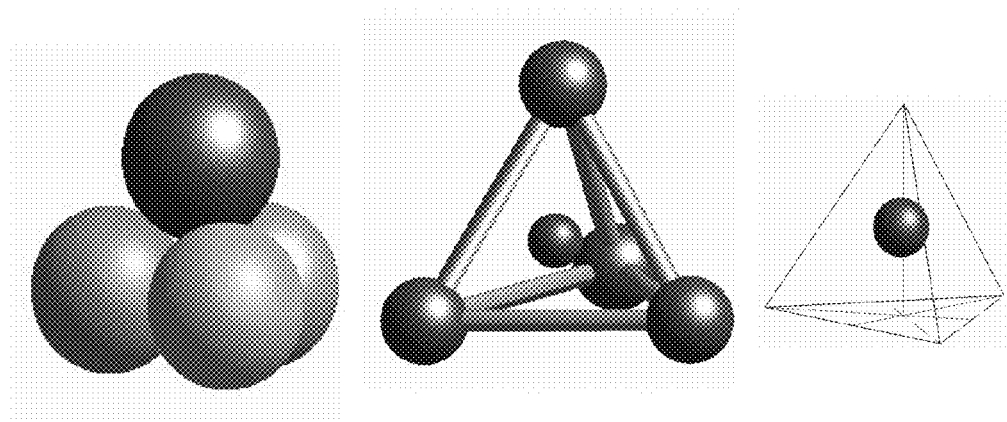
FIG. 22 illustrates a model of four identical spherical branch cell reagents that touch each other with a spherical core inserted to fit in the available space in the center of the tetrahedron formed by the four spherical reagents indicating the relative volumes (diameters) of the core and branch cell spheres that establish space boundaries for N-SIS issues and predictions.

Part I, Sphere Model:

All reagents are considered as ideal spheres. At this stage, other shapes such as cones, cylinders and wedges will not be used in order to simplify calculations. Tether points of core reagent (e.g., PETGE) are considered as a regular tetrahedron shape. 3-D drawings are performed by a program named 3D Shop Shareware by C4W. In FIG. 22 the red ball represents a core reagent, and the other colored balls represent branch reagents. Different colors are used just for aesthetical reasons.

1. Conditions Necessary for Four Branch Reagent (BR) Substituents

First, four larger balls (i.e., branch reagents) are allowed to touch each other's surface. By connecting their four centers one defines a regular tetrahedron. (FIG. 22) The space defined in the interior of this regular tetrahedron describes the volume available for an acceptable core reagent. In the equation below let the radius of the branch reagent be r and the radius of the core be R. The length of the sides of the tetrahedron should be 2r. The maximum radius for the interior core space can be calculated from equation 1 below.

$$R = \frac{1}{4}\sqrt{6} \cdot 2r - r = \left(\frac{1}{2}\sqrt{6} - 1\right)r \approx 0.225r \quad \text{Equation 1}$$

Then $$r = \frac{R}{\frac{1}{2}\sqrt{6} - 1} = \frac{2}{\sqrt{6} - 2}R \approx 4.45R \quad \text{Equation 2}$$

As long as $r \leq 4.45\,R$, then there is sufficient space to allow four branch reagent substituents with radius r to surround the core with radius R. When $r > 4.45\,R$, then N-SIS effects begin to occur, thus reducing the number of substituents possible around core (C) to a number less than four.

2. Conditions Necessary to Allow Three Branch Reagent (BR) Substituents

Three spherical branch reagents (BR) with radii r are allowed to assemble around a core reagent (C) with radius R. If bond angles are ignored and one arranges the centers of the four spheres so they are located in a same plane, then, the length of the sides of the regular triangle defined is 2r. The maximum radius R for the (C) that may fit in the center space defined by the touching branch reagents (BR) is calculated using equation 3.

$$R = \left(\frac{2}{3}\sqrt{3} - 1\right)r \approx 0.155r \quad \text{Equation 3}$$

Then $$r = \frac{1}{\frac{2}{3}\sqrt{3} - 1}R \approx 6.46R \quad \text{Equation 4}$$

The results are summarized in Table IX below.

TABLE IX

Maximum number of spherical branch reagents (BR) arranged around a core (C)

| Branch reagents radii range | Maximum substituent numbers |
|---|---|
| r ≦ 4.45 R | 4 |
| 4.45 R < r ≦ 6.46 R | 3 |
| r > 6.46 R | 2 |

Part II, Cone Shaded (BR) Model:

1. Conditions Necessary for Four Conical Branch Reagent Substituents (BR)

Figure 23:
FIG. 23 shows three views of N-SIS model illustrating a spherically shaped core and three conical shaped branch cell reagents surrounding the core for examination of N-SIS issues and predictions. There are three parameters in this model: the size of core (radius=R), the height of cone (h) and the base radius of cone (r).

There are three parameters in this model. They are radius of spherical core (R), the height of cone (h) and the base radius of cone (r). See FIG. 23.

Figure 24:
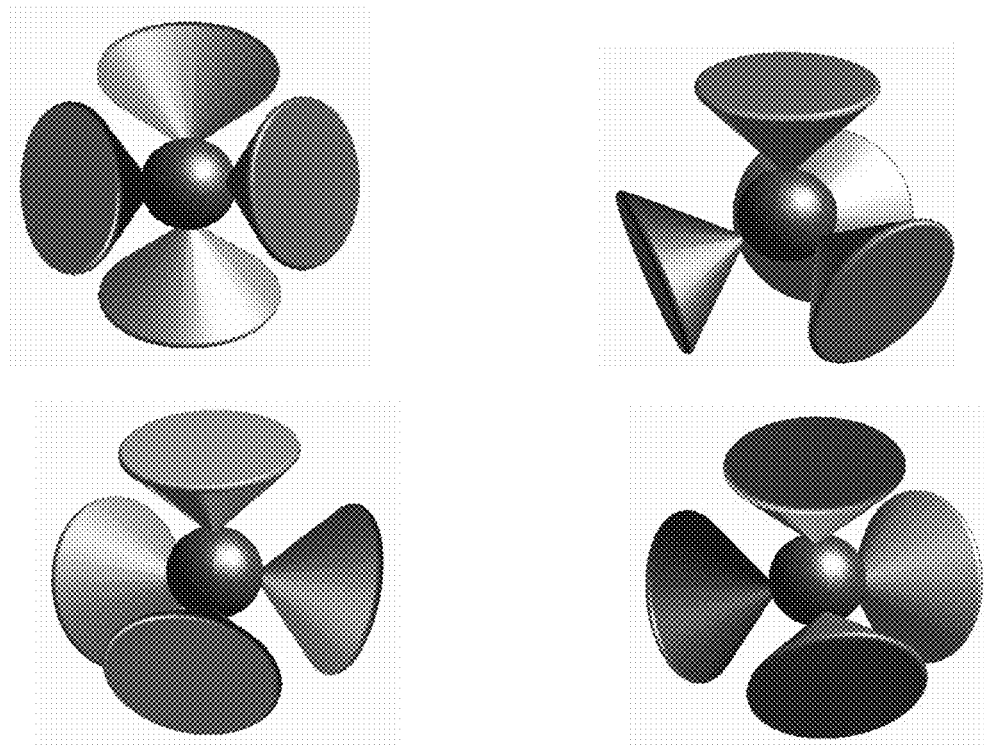
FIG. 24 shows four views of an N-SIS model illustrating a spherical shaped core surrounded by four cone shaped branch cell reagents for examination of N-SIS issues and predictions. The base of each of the four cone shaped branch cell reagents are inscribed in the four faces of a tetrahedron surrounding the spherical core reagent located at the center of the tetrahedron.

The bases of the four conical shaped branch reagents are fitted into the four faces of a tetrahedron, as shown for one conical base in FIG. 24. The core reagent (C) is located at the center of the tetrahedron.

R=radius of core h=height of conical branch reagents r=radius of conical branch reagent base r'=R+h a=length of sides of tetrahedron $$r' = h + R = \frac{1}{12}\sqrt{6}\,a \quad \text{Equation 5}$$

Then, $$a = 2\sqrt{6}\,(h + R) \quad \text{Equation 6}$$

Thus, $$r = \frac{1}{6}\sqrt{3}\,a = \frac{1}{6}\sqrt{3} * 2\sqrt{6}\,(h + R) = \sqrt{2}\,(h + R) \quad \text{Equation 7}$$

If $r \leq \sqrt{2}(h+R)$, four branch reagents can be arranged around the core (C), ($N_{max}=4$).

2. Conditions Necessary for Three Conical Branch Reagent Substituents (BR)

Figure 25:
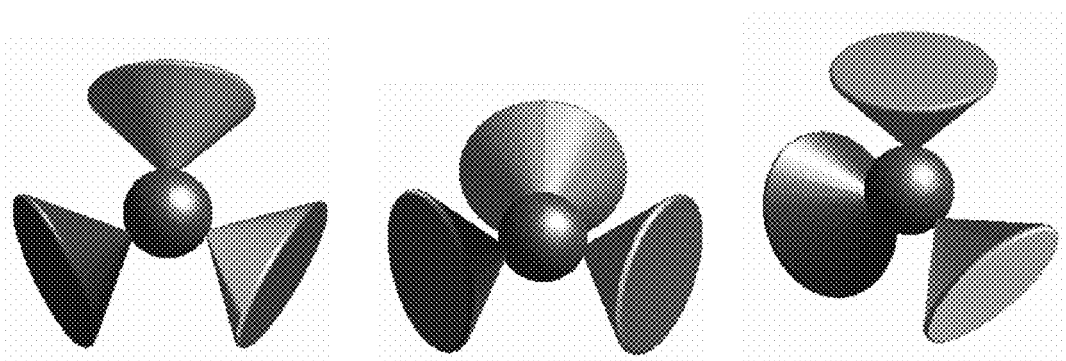
FIG. 25 illustrates the use of three cone shaped branch cell reagents assembled around a spherical core where there is one surface of the tetrahedron without a cone shaped branch cell reagent present.

When three cones are arranged around a spherical core (C) and bond angles are not considered as a parameter, the center of the four objects can be located in the same plane, as described by the equations below. (FIG. 25)

$$r^2 + (h+R)^2 = 4(h+R)^2 \qquad \text{Equation 8}$$
Then,
$$r = \sqrt{3}\,(h+R) \qquad \text{Equation 9}$$

Based on these mathematical results, the maximum numbers of conical shaped branch reagents around a spherical core (C) can be calculated as summarized in Table X.

TABLE X

The maximum number of conical shape branch reagents that can be fitted around a core

| Conditions | Maximum Substituent numbers |
|---|---|
| $r \leq 1.414\,(h+R)$ | 4 |
| $1.414\,(h+R) < r \leq 1.732\,(h+R)$ | 3 |
| $r > 1.732\,(h+R)$ | 2 |

Part III, Methods and Examples

The sizes of all reagents are estimated from Chem3D™ (CambridgeSoft) after energy minimization (MM2), and not verified by other methods. The three-dimensional drawings shown as the figures supporting this discussion are created using share software (3D Shop Shareware by C4W). All reagents are being treated as simple geometric shapes. Sizes of small molecules are determined as follows: Chemical structures have been drawn in ChemDraw™. Bond lengths and angles have been corrected using the clean-up function in ChemDraw™. These structures have been copied into Chem3D™, cleaned-up again and subjected to MM2 energy minimization. Finally, the measured sizes were obtained. See chemical structures below.

Size of Core Reagents:

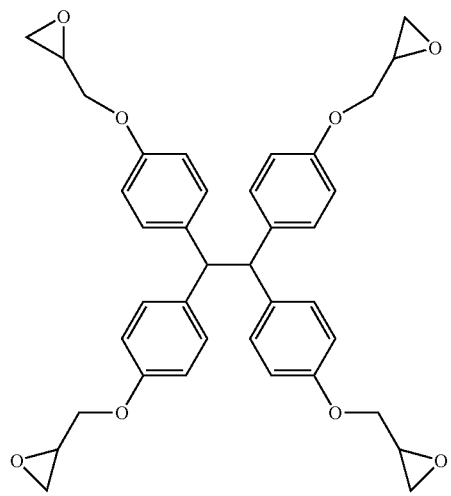

R = 0.80

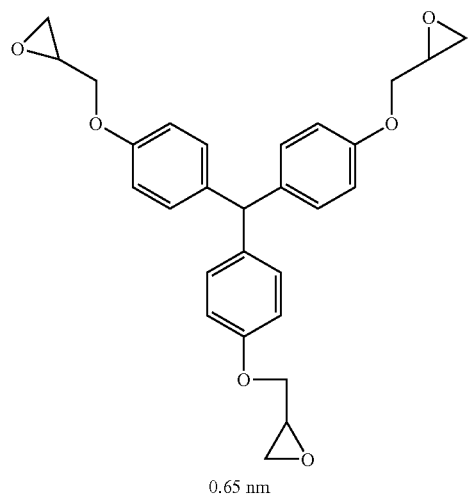

0.65 nm

-continued

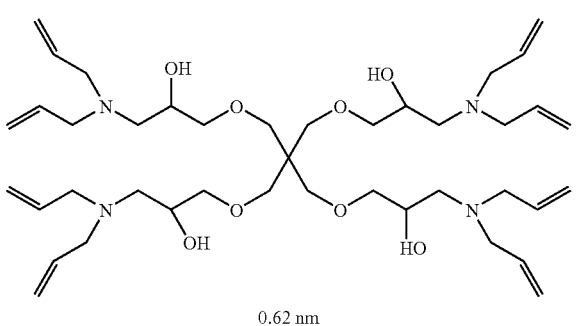

0.62 nm

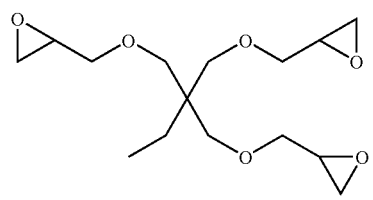

R = 0.45 nm

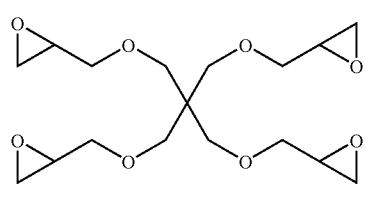

0.45 nm

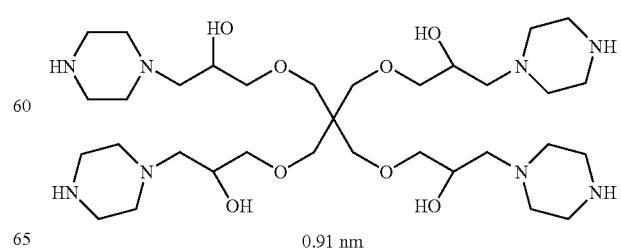

0.91 nm

From these considerations the following Tables XI, XII and XIII were prepared.

TABLE XI

Size of branch reagents

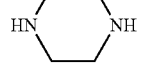

| | | A | B | C | D | E |
|---|---|---|---|---|---|---|
| As sphere | r (nm) | 0.14 | 0.21 | 0.22 | 0.15 | 0.16 |
| As cone | r (nm) | — | 0.31 | 0.61 | 0.33 | 0.32 |
| | h (nm) | — | 0.30 | 0.25 | 0.30 | 0.29 |

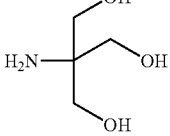

|  |  | F | G | H | I G=0-cys-dendron Pyrrol surface | J G=1-cys-dendron Pyrrol surface |
|---|---|---|---|---|---|---|
| As sphere | r (nm) | 0.30 | 0.34 | 0.45 | 0.56 | 1.10 |
| As cone | r (nm) | 0.93 | 0.33 | 0.50 | 1.20 | 1.42 |
|  | h (nm) | 0.32 | 0.41 | 0.65 | 0.61 | 1.31 |

TABLE XII

Maximum substituent number (method 1, spherical model)
($r \leq 4.45$ R, N = 4; 4.45 R < r $\leq$ 6.46 R, N = 3; r > 6.46 R, N = 2)

| | A | B | C | D | E | F | G | H | I | J |
|---|---|---|---|---|---|---|---|---|---|---|
| 1 | 4 | 4 | 4 | 4 | 4 | 4 | 4 | — | — | — |
| 2 | 4 | 4 | 4 | 4 | 4 | 4 | 4 | — | — | — |
| 4 | 4 | 4 | 4 | 4 | 4 | 4 | 4 | — | — | — |
| 5 | 4 | 4 | 4 | 4 | 4 | 4 | 4 | — | — | — |

TABLE XIII

Maximum substituent number (method 2, cone model)

| | A | B | C | D | E | F | G | H | I | J |
|---|---|---|---|---|---|---|---|---|---|---|
| 1 | — | 4 | 4 | 4 | 4 | 3 or 4 | 4 | — | — | — |
| 2 | — | 4 | 4 | 4 | 4 | 3 or 4 | 4 | — | — | — |
| 4 | — | 4 | 4 | 4 | 4 | 3 | 4 | — | — | — |
| 5 | — | 4 | 4 | 4 | 4 | 3 | 4 | — | — | — |
| 7 | — | — | — | — | — | — | — | — | 4 | 4 |
| 8 | — | — | — | — | — | — | — | 4 | — | — |

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter.

What is claimed is:

1. A dendritic polymer of Formula (I):

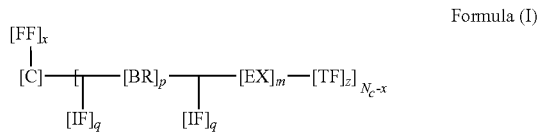

Formula (I)

wherein:
(C) means a core;
(FF) means a focal point functionality component of the core;
x is independently 0 or an integer from 1 to $N_c-1$, provided that $N_c-x$ must be at least 1;
(BR) means a branch cell, which, if p is greater than 1, then (BR) may be the same or a different moiety;
p is the total number of branch cells (BR) in the dendrimer and is an integer from 1 to 2000 derived by the following equation $$p = \text{Total \# of } [BR] = \left(\frac{N_b^1}{N_b} + \frac{N_b^2}{N_b} + \frac{N_b^3}{N_b} + \ldots \frac{N_b^G}{N_b}\right)[N_c] = \left(\sum_{i=0}^{i=G-1} N_b^i\right)[N_c]$$

where: G is number of concentric branch cell shells (generation) surrounding the core; where the upper limit is attained at the deGennes dense-packed stage; i is the final generation G;

$N_b$ is branch cell multiplicity; and $N_c$ is core multiplicity and is an integer from 1 to 1000;

(IF) means interior functionality, which, if q is greater than 1, then (IF) may be the same or a different moiety;

q is independently 0 or an integer from 1 to 4000;

(EX) means an extender, which, if m is greater than 1, then (EX) may be the same or a different moiety; (EX) may occur prior to or after the (BR) moiety or both prior to and after the (BR) moiety; and (EX) may also have an (IF) moiety present;

m is independently 0 or an integer from 1 to 2000;

(TF) means a terminal functionality, which, if z is greater than 1, then (TF) may be the same or a different moiety;

z means the number of surface groups from 1 to the theoretical number possible for (C) and (BR) for a given generation G and is derived by the following equation $$z = N_c N_b^G;$$

where: G, $N_b$ and $N_c$ are defined as above; and with the proviso that at least one of (EX) or (IF) is present.

2. The dendritic polymer of claim 1 wherein:

$N_c$ is an integer from 1 to 20; q is 0 or an integer from 1 to 250; p is an integer from 1 to 250; and m is 0 or an integer from 1 to 250; and one of q or m must be at least 1; and when both q and m are greater then 1, (BR) and (EX) may occur alternately with the other moiety or sequentially with multiple groups of (BR) or (EX) occurring in succession.

3. The dendritic polymer of claim 1 wherein x=0, m=0, which provides a dendritic polymer of Formula (II):

Formula (II)

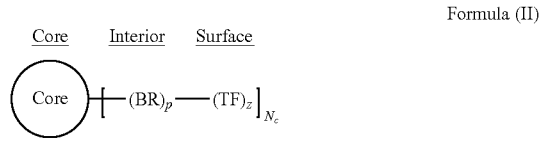

wherein:

$$p = \text{Total \# of } [BR] = \left(\frac{N_b^1}{N_b} + \frac{N_b^2}{N_b} + \frac{N_b^3}{N_b} + \ldots \frac{N_b^G}{N_b}\right)[N_c] = \left(\sum_{i=0}^{i=G-1} N_b^i\right)[N_c]$$

core=(C), (TF), G, $N_c$, $N_b$, i, z and p are defined as in claim 1, and (BR) must have an (IF) moiety present or be able to generate an (IF) in situ.

4. The dendritic polymer of claim 1, 2 or 3 wherein (C) is a simple core.

5. The dendritic polymer of claim 4 wherein the simple core is poly(glycidyl ethers) [e.g., bis-phenol glycidyl ether, pentaerythritol tetraglycidyl ether (PETGE), tetraphenylolethane glycidyl ether (TPEGE), triphenylolmethane triglycidyl ether (TPMTGE), trimethylolpropane triglycidyl ether (TMPTGE), bis(4-glycidyloxyphenyl)methane (BGPM)], tetra(epoxypropyl)cyanurate (TEPC), tris(2,3-epoxypropyl) isocyanurate (TGIC), tris[2-(acryloyloxy)ethyl]isocyanurate, 4,4'-methylene bis(N,N'-diglycidyl aniline) (MBDGA), diglycidyl aniline, N,N'-diglycidyl-4-glycidoxyaniline (DGGA), sorbitol, glycerol, neopentyl, oligoneopentyl diglycidyl ether, tert-butylglycidylether, allylglycidyl ether, pentaerythritol triglycidyl ether (PETriGE), pentaerythritol triallyl ether (PETriAE), pentaerythritol tetraazide (PETAZ), neopentyl tetrapropargyl ethers, monoalkyl neopentyl tripropargyl ethers, triazides, tetraazides, aminoethanol, ammonia, polyamines [e.g., ethylenediamine (EDA), PAMAM, hexamethylenediamine (HMDA), diethylenetriamine, methylisopropylidine, alkylene bis(2-haloethylamines), arylmethyl halides (e.g., benzylic halides), piperazine, aminoethylpiperazine, hyperbranched (e.g., polylysine, poly(ethyleneimine), poly(propyleneimine), tris-2-(aminoethylamine)], linear poly(ethyleneimine), water, hydrogen sulfide, alkylene/arylene dithiols, bis(2-piperazinylethyl)disulfide (BPEDS), cystamine, 4,4'-dithiodibutyric acid, dimethyldithiobutyrate (DMDTB), mercaptoalkylamines, thioether alkylamines, isocyanurate, heterocycles, 1,4,7,10-tetraazacyclododecane-1,4,7-tris(acetic acid) (DO3A), 1,4,7,10-tetraazacyclododecane-1,4,7,10-tetra(acetic acid) (DOTA), macrocycles (e.g., crown ethers), multicarbon cores (ethylene, butane, hexane, dodecane), polyglycidylmethacrylate, poly(functional acrylates) (e.g., trimethylolpropane triacrylate (TMPTA), diallyl amine), diethylaminodiacetate, tris(hydroxymethyl)aminomethane, phosphine, porphines (e.g., porphyrins), oxiranes, thioranes [e.g., tetrathiorane (TES)], oxetanes, aziridines, azetidines, multiazido functionalities (e.g., tetra-azido adduct derived from PETGE), siloxanes, oxazolines [e.g. poly(2-ethyl-2-oxazoline) (PEOX)], carbamates, or caprolactones.

6. The dendritic polymer of claim 5 wherein the simple core is cystamine, diamine disulfides, diazido disulfides, disulfide diacetylenes, propargyl pentaerythritol triallyl ether, propargyl pentaerythritol triglycidyl ether, pentaerythritol tetraazide, pentaerythritol tetraglycidyl ether, tetraphenylolethane glycidyl ether, triphenylolmethane triglycidyl ether, trimethylolpropane triglycidyl ether, tris(2,3-epoxypropyl) isocyanurate, trimethylolpropane triacrylate, isocyanurate, heterocycles, poly(2-ethyl-2-oxazoline), multicarbon cores (ethylene, butane, hexane, and dodecane), phosphine, or linear, branched or cyclic moieties with single or multiple functional epoxides, multifunctional alkenes, alkynes or aryls, or multi-azido functionalities.

7. The dendritic polymer of claim 1, 2 or 3 wherein (C) is a scaffolding core.

8. The dendritic polymer of claim 7 wherein the scaffolding core is a capped material, such as trimethylolpropane triacrylate, or pentaerythritol tetraglycidyl ether (PETGE) or trimethylolpropane triglycidyl ether (TMPTGE) or tetraphenylolethane glycidyl ether (TPEGE) or triphenylolmethane triglycidyl ether (TPMTGE) each capped with one or more of aminoethylpiperazine, azides, propargyl functionalities, piperazine, di-iminodiacetic acids, or epoxide surface PEHAMS, or mixtures thereof.

9. The dendritic polymer of claim 1, 2 or 3 wherein (C) is a super core.

10. The dendritic polymer of claim 9 wherein the super core is either a dendrimer that serves as the core functionality or zero valent metal particles (e.g., Au, Ag, Cu, Pd, Pt), gold nanoparticles, gold nanorods, colloids, latex particles, metal oxides, nanocrystals, quantum dots, micelles, vesicles, liposomes, buckyballs, carbon nanotubes (single and multi wall), carbon fibers, silica, or bulk metal surfaces, and where other structures are attached to or grown from the core surface.

11. The dendritic polymer of claim 9 where (C) is a super core comprising the following components wherein: PAMAM is the core with PEHAM grown on or attached to its surface; PEHAM is the core with PEHAM grown on or attached to its surface; PEHAM is the core with PEHAM and PAMAM grown on or attached to its surface; PAMAM is the core with PEHAM and PAMAM grown on or attached to its surface; PEHAM is the core with PAMAM grown on or attached to its surface; polylysine dendritic polymer is the core and PEHAM grown on or attached to its surface; PPI is the core and PEHAM grown on or attached to its surface; or polyols is the core and PEHAM grown on or attached to its surface.

12. The dendritic polymer of claim 1, 2 or 3 wherein (C) is at least one nucleophilic (Nu), one electrophilic (E), or one other (O) moiety; or a polyvalent core bonded to at least two ordered dendritic branches; or a core atom or molecule that may be any monovalent or monofunctional moiety or any polyvalent or polyfunctional moiety, preferably a polyfunctional moiety having 2-25000 valence bonds of functional sites available for bonding with dendritic branches.

13. The dendritic polymer of claim 12 wherein (C) is nucleophilic (Nu) and is ammonia, water, hydrogen sulfide, phosphine, poly(alkylenediamines) such as ethylenediamine, hexamethylenediamine, dodecyl diamines, polyalkylene polyamines such as diethylenetriamine, triethylenetetraamine, tetraethylenepentaamine, pentaethylenehexamine, poly(propyleneimine), linear and branched poly(ethyleneimine) and poly(amidoamines), primary amines such as methylamine, hydroxyethylamine, octadecylamine, poly(methylenediamines), macrocyclic/cryptand polyamines, poly (aminoalkylarenes), tris(aminoalkyl)amines, methylisopropylidine diethylenetriamine, alkylene bis(2-haloethylamines), arylmethyl halides (e.g., benzylic halides), hyperbranched (e.g., polylysine), poly(propyleneimine), tris-2-(aminoethylamine), heterocyclic amines, star/comb-branched polyamines, piperazine and its derivatives (e.g., aminoalkyl piperazines), ethylene glycol, polyalkylene polyols, polyalkylene polymercaptans, thiophenols, phenols, or any of these cores as capped cores [e.g., tert-butoxycarbonyl (BOC)] where at least one $N_c$ valence is uncapped.

14. The dendritic polymer of claim 12 wherein (C) is electrophilic (E) or is converted to an (E) with Brönsted/Lewis acids or alkylation/acylation agents and is cyclic ethers (e.g., epoxides), oxiranes, cyclic sulfides (e.g., epichlorosulfide), aziridines, azetidines, siloxanes, oxetanes, oxazolines, oxazines, carbamates, caprolactones, carboxyanhydrides, thiolactones, sultones, β-lactams, α,β-ethylenically unsaturated carboxylic esters such as ($C_2$-$C_{18}$ alkyl)acrylate esters (e.g., methyl acrylate, ethyl acrylate), ($C_2$-$C_{18}$ alkyl)methacrylate esters, acrylonitrile, methyl itaconate, dimethyl fumarates, maleic anhydride, or amides such as acrylamide, or any of these cores as capped cores where at least one $N_c$ valence is uncapped.

15. The dendritic polymer of claim 12 wherein (C) is an other (O) moiety and is polyfunctional initiator cores that are compounds capable of generating a polyvalent core or free-radical receptor groups (e.g., olefinics), or 1,3-dipolar cyclo-addition moieties (e.g., polyalkynes and polyazides).

16. The dendritic polymer of claim 12 wherein (C) is triacrylate, tetraacrylate, triaziridine, tetraaziridine, triazide, tetraazide, trithiorane, tetrathiorane, trioxazoline, tetraoxazoline, triepoxide, tetraepoxide, diglycidyl aniline, neopentyl alcohols, aminoalkylol, alkylenediamine, tetraarylmethane, triarylmethane, triglycidylether, tetraarylmethane, tetraglycidylether, bis(glycidoxyphenyl)alkane, tetraepisulfide, trisglycidylisocyanurate, tris(2,3-epoxypropyl)isocyanurate, methylene bis(diglycidylaniline), or tetraepisulfide.

17. The dendritic polymer of claim 12 wherein (C) is cystamine, isocyanurate, heterocycles, multicarbon cores (e.g., ethylene, butane, hexane, dodecane), phosphine, or linear, branched or cyclic moieties with single or multiple functional epoxides.

18. The dendritic polymer of claim 1 or 2 wherein (FF) is any moiety that enables a dendron to be used as a core, enables the joining of two or more dendrons together, or enables reaction with a (C), (BR), or (EX) and (BR).

19. The dendritic polymer of claim 18 wherein (FF) is hydrogen, thiols, amines, carboxylic acids, esters, ethers, cyclic ethers (e.g., crown ethers, cryptands), porphyrins, hydroxyl, maleimides, alkyls, alkenyls,alkynyls, alkyl halides, arylalkyl halides, phosphinos, phosphines, boranes, alcohols, aldehydes, acrylates, cyclic anhydrides, aziridines, pyridines, nitriles, itaconates, cyclic thiolactones, thioranes, azetidines, cyclic lactones, macrocyclics [e.g., 1,4,7,10-tetraazacyclododecane- 1,4,7,10-tetra(acetic acid) (DOTA), 1,4,7,10-tetraazacyclododecane-1,4,7-tris(acetic acid) (DO3A)], chelating ligands [e.g., diethylenetriaminepentaacetic acid (DTPA)], mercapto, amino, carboxy and carboxy esters, epoxy, orthoester, methacrylates, styrenyl, vinylbenzylic moieties, isocyanates, isothiocyanates, oligonucleotides, amino acids, peptides, cyclopeptides, proteins, antibodies or fragments, aptamers, imidazoles, azides, mercaptoamines, silanes, oxazolines, oxirane, oxetane, oxazines, imines, tosylates, metals, biotin, streptavidin, avidin, protecting groups (e.g., tert-butoxycarbonyl (BOC) or ketone solvent protected), siloxanes or its derivatives, or substituted derivatives or combinations thereof, or groups suitable for click chemistry (e.g., polyazido or polyalkyne functionality).

20. The dendritic polymer of claim 1, 2 or 3 wherein (BR) is any nucleophilic (Nu), electrophilic (E) or other (O) reagent, or may be formed from a precursor of a (BR) in situ, which (BR) is capable of reacting with (C), an extender (EX), with another branch cell or branch cell reagent (BR), or terminal functional group (TF), which results in a multiplicity or amplification of reactive groups present for the next generation G of the dendritic polymer of Formula (I), and when (BR) occurs in more than one generation, it may be the same or different (BR) moiety.

21. The dendritic polymer of claim 20 wherein (BR) is used with a co-reactant to form a core adduct and then further reacted with a second co-reactant.

22. The dendritic polymer of claim 20 wherein (BR) is an uncapped or partially capped either branched or linear, or primary or secondary polyamine, diethylenetriamine (DETA), 2-imidazolidyl-1- aminoethane (IMAE), diethanolamine (DEA), dibenzylamine (DBA), triethylenetetraamine (TETA), tetraethylenepentaamine, poly(ethyleneimine), methylamine, bis(allyl)amine (BAA), hydroxyethylamine, octadecylamine, diethyliminodiacetate (DEIDA), poly(methylenediamines) such as hexamethylenediamine (HMDA), polyaminoalkylarenes, tris(aminoalkyl)amines such as tris (aminoethyl)amine (TREN), tris(hydroxymethyl)aminomethane (TRIS), linear and branched poly(ethyleneimines), linear and branched poly(amidoamines), heterocyclic amines such as imidazolines, piperidines (PIPZ), aminoalkyl piperazines, methyl isobutyl protected 1-(2-aminoethyl)piperazine (PEA), pentaerythritol tetraglycidyl ether (PETGE); or various other amines such as hydroxyethylaminoethylamine, (2-hydroxyethyl)ethylenediamine (HEDA), mercaptoalkylamines, mercaptoethylamine, iminodialkynes, iminodialkenes, substituted piperazine, amino derivatives of polyvinylbenzyl chloride and other benzylic amines such as tris(1,3,5-aminomethyl)benzene; or polyols such as pentaerythritol, ethylene glycol, polyalkylene polyols such as polyethylene glycol, polypropylene glycol, 1,2-dimercaptoethane or polyalkylene polymercaptans; thiophenols or phenols; or acetylenic polyepoxides, hydroxyalkyl azides, alkyl azides, tri- and tetra-aziridines, tri- and tetra-oxazolines, triazoles, thiol alkyls, thiol (FF) dendrons, allyl groups, acrylates, methacrylates, or olefinic functionality or capped moieties of any of the above.

23. The dendritic polymer of claim 20 wherein (BR) is one or more of cyclic ethers (epoxides), oxiranes, sulfides (epichlorosulfide), aziridines, azetidines, siloxanes, oxetanes, oxazolines, oxazines, carbamates, caprolactones, carboxyanhydrides, thiolactones, β-lactams, or derivatives thereof.

24. The dendritic polymer of claim 20 wherein the (BR) is triacrylate, tetraacrylates, triepoxide, tetraepoxide, triazides, tetraazides, diallyl amine (BAA), diethanol amine (DEA), bis(2- haloalkyl)amine, N-(2-hydroxyethyl)ethylenediamine (AEEA), imino bis(methylphosphonic acid) (IMPA),diethyliminodiacetate (DEIDA) tris(hydroxymethylamine), pentaerythritol tetraglycidyl ether (PETGE), pentaerythritol triglycidyl ether (PETriGE), pentaerythritol triallyl ether (PETriAE), (2-hydroxyethyl)ethylenediamine (HEDA), methyl isobutyl protected 1-(2-aminoethyl)piperazine (PEA), 2-methyl-2-imidazoline (MIA), 2,3-iminodiacetonitrile (IDAN), tris(2-aminoethyl)amine (TREN), tris(hydroxymethyl)aminomethane (TRIS),dimethyliminodiacetate, protected diethylenetriamine (DETA) (with ketonic solvents), or methyl acrylate, including in situ.

25. The dendritic polymer of claim 1 or 2 wherein (IF) is any active moiety formed from a ring-opening reaction resulting in interior reactive sites.

26. The dendritic polymer of claim 25 wherein (IF) is hydroxyl, thiol, amine, phosphine, alkylsilane, silane, boranes, carboxy, carboxy ester, an alkylene ester, chloro, bromo, alkene, alkyne, or alkyl- or aryl-amide.

27. The dendritic polymer of claim 1 or 2 wherein (EX) is a moiety capable of lengthening the distance in the interior of the dendrimer before the growth of the next G, may occur in the dendritic polymer before or after the (BR) moiety or both before and after a (BR) and such second (EX) may be the same or different from the first (EX), may have an (IF) moiety present, and must have at least two reactive sites.

28. The dendritic polymer of claim 27 wherein (EX) is amino acids such as lysine, poly(amino acids) such as polylysine, oligoethyleneglycols, diethylenetetraamine and higher amine analogs, oligoalkylenamines protected as 5-membered imidazolidyl derivatives, fatty acids with di- or greater heterogeneous or homogenous functionality, unsaturated aliphatic and aromatic difunctional or polyfunctional moieties, ethanolamine (EA), morpholine, dicarboxylic acids, ethyl-N-piperazinecarboxylate (EPC), 2-imidazolidyl-1-aminoethane (IMAE), aryl dimercaptans, dimercaptoalkanes, triazoles, dimethylitaconate (DMI), diazides, diacetylenes, pyrrolidone, pyrrolidone esters, aminoalkyl imidazolines, imidazolidines, poly(alkyleneimidazolidines), mercaptoalkylamines, hydroxyalkylamines or heterogeneous unsaturated aliphatic and aromatic difunctional or polyfunctional moieties.

29. The dendritic polymer of claim 27 wherein (EX) is diaminoalkanes, diphenols, dithiophenols, aromatic poly (carboxylic acids), mercaptoamines, mercaptoethanol, allylamines, methyl isobutyl protected 1-(2-aminoethyl)piperazine (PEA), piperazine (PIPZ), aminoalkyl piperazines, polypiperazines, amino ethyl piperazine (AEP), methylisopropyliminoethylpiperazine (MIPIEP). poly(alkylenepiperazines),diamines possessing disulfide moieties, bis (piperazinoalkyl) disulfides, piperazine derivatives, cyclic pyrrolidine derivatives,ethylenediamine (EDA), diethyliminodiacetate (DEIDA), methyl acrylate, 1,2,3-triazoles, or hyperbranched dendritic polymers such as poly(esteramide), poly(amidoamine), poly(ethyleneimine) or poly(propyleneimine) moieties.

30. The dendritic polymer of claim 1, 2 or 3 wherein (TF) is any functionally active moiety or suitable for 1,3-dipolar addition reactions that is sufficiently reactive to undergo addition or substitution reactions, or ring-opening, polymer initiation group, or any functionally active moiety that can be used to propagate the dendritic branch to the next generation G, wherein some but not all (TF) moieties may react to form the next generation G dendrimer, the (TF) groups may be the same or different, and when the (TF) moiety is the last G, then the (TF) may be unreactive.

31. The dendritic polymer of claim 30 wherein (TF) is amino groups, [including primary and secondary amino groups, which may be capped but has at least one uncapped amino group present, (e.g., methylamino, ethylamino, hydrazino groups, benzylamino, glucosamine, an amino acid, mercaptoethylamino), tertiary amino, (e.g., dimethylamino, diethylamino, bis(hydroxyethyl)amino), quaternary amino groups, trialkyl ammonium, bis(hydroxyethyl)amino, bis(2-haloethyl)amino, N-alkylated, N-arylated, and N-acylated derivatives]; hydroxy, epoxy, mercpato, carboxy, carboxy esters, alkenyl, allyl, aryl, methalkyl, vinyl, amido, halo, urea, oxiranyl, aziridinyl, oxazolinyl, azalactone, lactam, lactone, imidazolinyl, sulfonato, phosphonato, boronato, organosilanes, tetramethylsilane (TMS),isocyanato, isothiocyanato, α-haloacyl groups, hydroxy alkylazido piperazine and its derivatives, alkyl piperazine, aminoalkyl piperazine, 1,2,3-triazoles, 2-imidazolidyl-1-aminoethane (IMAE), acrylate, methacrylate. Acrylamides, hydroxyl, epoxide, oxazoline, alkyleneimines, lactones, azalactone, polyethylene oxides, amino ethyl imines, carboxylates, alkyl, aziridine, azides, ethyl imines, alkyl esters, epoxides, alcohols, alkylthiols, thioranes, morpholines, amines, hydrazinyl, carboxyl, allyl, azidyl, alkenyl, alkynyl, hydroxyalkylamino, protected diethylenetriamine (DETA), carboxyalkyl, pyrrolidone (and its esters), or succimidyl esters.

32. The dendritic polymer of claim 30 wherein (TF) or (M) is present and is polyethyleneglycol, pyrrolidone, pyrrolidone esters, carboxypiperidines, piperidines, piperazines, substituted piperazines, aminoalkyl piperazines, hexylamides, aldehydes, azides, oxetanes, dyes [e.g., near infrared fluorchromes (e.g, cyanine derivatives, FITC), colorimetric (e.g., Nile red)], tris(hydroxymethyl)amidomethane, photochromic moieties (e.g., sydnones, porphines), amidoethylethanolamine, carbomethoxypyrrolidinone, succinamic acid, amidoethanol, amino acids, protected amino acids, antibodies and fragments, proteins, peptides, cyclopeptides, cationic steroids, macrocyclic groups, azacrown ethers, antibiotics/antibacterials [e.g., aminoglycosides, amphenicols, ansamycins, β-lactams (such as penicillin, cephalosporins, cephamycins, oxacephems, carbapenems), tetracyclines, macrolides, lincosamides, 2,4-diaminopyrimidines, nitrofurans, quinolones, sulfonamides, sulfones], antineoplastics [e.g., alkyl sulfonates, aziridines, epoxides, ethylenimines and methylmelamines, nitrogen mustards, nitroureas, purine analogs, androgens, antiadrenals, antiandrogens, antiestrogens, estrogens, LH-RH analogs, progestogens, and others], folic acid and analogs, epoxides, acrylates, methacrylates, amines, carboxylates, cationic, anionic, neutral, aromatic, glucosamine or other amino sugars, biotin, avidin, streptavidin, growth factors, hormones, aptamers, 1,4,7,10-tetraazacyclododecane-1,4,7,10-tetra(acetic acid) (DOTA), diethylene-triaminepentaacetic acid (DTPA), metal chelates, naphthyl sulfonates, alkyl sulfonates, aryl sulfonates, targeting groups (e.g., CD19, CD22, aptamers), hyaluronic acid, polyoxometalates, organic chromophores, polyvalent attached compounds, carbon nanotubes, fullerenes, nanocomposites, all metal nanoparticles, all semiconductor nanoparticles with all varieties of cores and shells, radioactive materials and their chelated analogues, fluorescent molecules (metal salts, organic compounds), electrically conductive molecules, light or electromagnetic energy absorbing or emitting molecules (e.g., UV, VIS (visible), IR, and microwave), radioactive analogues of drugs or diagnostic agents, silanes, siloxanes, silsesquioxane, poly(aryl-alkyl)poly(iodides), quantum dots, nanocrystals (e.g., Au, Ag, Cu, etc.), polyfluorinated molecules, surfactants, dendrons, differentiated dendrons, dendrimers, methoxy ethoxy ethoxy, polyimides (e.g., maleimide), herbicides (e.g., trifluralin, 2-phosphonomethylamino acetic acid), polyazo compounds, polyphosphazine, polyfluorinated sulfonates, heteroatoms chains and branches, lipids, starches, simple sugars (e.g., mannose, dextrose), oligonucleotides, complex sugars, drugs, such as anti-cancer agents (e.g., doxorubicin, methotrexate, and others), acetylsalicylic acid, salicylic acid, vitamins (e.g. vitamin E and C), cofactors (e.g. NADH), or antioxidants.

33. The dendritic polymer of claim 1, 2 or 3 wherein (TF) and/or (IF) can be associated with any carried material (M) which may be from one (M) to: for (TF) the maximum possible number of z present on the surface, or for (IF) the maximum void volume and q for (IF) present in the interior.

34. The dendritic polymer of claim 30 where some or all of (TF) can be further reacted with (BR) or (EX) to further grow the dendrimer or dendron surface.

35. The dendritic polymer of claim 1 or 2 wherein (FF) is further reacted to provide: amides; esters; alkyl-, alkenyl-, alkynyl- or aryl-ethers, optionally substituted with one or more halogens; cyclic ethers (e.g., azacrown ethers, cryptands); porphyrins; thioether; thioester; disulfide; maleimides; phosphines; boranes; carboxylic acids and esters and salts; hydrazides; alcohols; aldehydes; acrylates; cyclic anhydrides; aziridines; pyridines; nitriles; alkynes; imidazoles; azides; mercaptoamines; silanes; oxazolines; oxirane; oxetane; oxazines; imines; tosylates; pyrrolidone; cyclic thiolactones; thioranes; azetidines; lactones; azalactones; macrocyclics [e.g., 1,4,7,10-tetraazacyclododecane-1,4,7,10-tetra (acetic acid) (DOTA), 1,4,7,10-tetraazacyclododecane-1,4,7-tris(acetic acid) (DO3A)]; chelating ligands [e.g., diethylenetriaminepentaacetic acid (DTPA)]; isocyanates; isothiocyanates; oligonucleotides; aptamers; amino acids; proteins, peptides, cyclopeptides, antibodies and antibody fragments; nucleotides; nucleosides; metals; biotin; streptavidin; avidin; capping groups (e.g., tert-butoxycarbonyl (BOC) or solvent capped); siloxanes or derivatives; substituted derivatives or combinations thereof of the above; or groups suitable for click chemistry (e.g., polyazido or polyalkyne functionality).

36. The dendritic polymer of claim 1 or 2 wherein the dendritic polymer has the physical shape, as determined by CPK models, electron microscopy, or solution characterization, of a sphere, rod, random hyperbranched, dendrigraft or core-shell(tecto)dendrimer or dendron.

37. The dendritic polymer of claim 1 or 2 wherein (TF) provides a positive overall charge to the surface.

38. The dendritic polymer of claim 37 wherein $N_c=4$, (TF)= piperazine, and G=1.

39. The dendritic polymer of claim 37 wherein (BR)=tris (2-aminoethyl)amine (TREN), $N_c=4$, and G=2.

40. The dendritic polymer of claim 1 or 2 wherein:
  (C) is pentaerythritol triglycidyl ether (PETriGE), pentaerythritol tetraazide (PETAZ), tetraphenylolethane glycidyl ether (TPEGE), or triphenylolmethane triglycidyl ether (TPMTGE); or
  (BR) is 3,3-iminodiacetonitrile (IDAN), imino bis(methylphosphonic acid) (IMPA), bis(allyl)amine (BAA), diethylenetriamine (DETA), methyl isobutyl protected 1-(2-aminoethyl)piperazine (PEA), tris(2-aminoethyl) amine (TREN), N-(2-hydroxyethyl)ethylenediamine (AEEA), or 2-methyl-2-imidazoline (MIA); or
  (TF) is tetramethylsilane (TMS); or
  (EX) is triazole.

41. The dendritic polymer of claim 1 or 2 wherein (EX)= piperazine (PIPZ) or its derivatives, or triazole or its derivatives and G=0, 1, 2, 3 or 4.

42. The dendritic polymer of claim 1, 2 or 41 wherein when $N_c=3$ or 4, then (BR)=diethyliminodiacetate (DEIDA), bis (allyl)amine (BAA), diethanolamine (DEA), diethylenetriamine (DETA), methyl isobutyl protected 1-(2-aminoethyl) piperazine (PEA), N-(2-hydroxyethyl)ethylenediamine (AEEA), tris(hydroxymethyl)-aminomethane (TRIS) or tris (2-aminoethyl)amine (TREN).

43. The dendritic polymer of claim 1, 2 or 41 wherein the core is an aliphatic moiety where (C)=pentaerythritol tetraglycidyl ether (PETGE), pentaerythritol triglycidyl ether (PETriGE), pentaerythritol triallyl ether (PETriAE), trimethylolpropane triglycidyl ether (TMPTGE), pentaerythritol tetrazide (PETAZ), tetra(epoxypropyl)cyanurate (TEPC), or tris(2,3-epoxypropyl)isocyanurate (TGIC).

44. The dendritic polymer of claim 1, 2 or 41 wherein the core is an aromatic moiety where (C)=tetraphenylolethane glycidyl ether (TPEGE) or triphenylolmethane triglycidyl ether (TPMTGE).

45. The dendritic polymer of claim 1 or 2 wherein the polymer is any one of the following:
  [(C)=tetraphenylolethane glycidyl ether (TPEGE); (IF1)= OH; (EX1) =piperazine (PIPZ); (TF) =NH; G=0.5];
  [(C)=triphenylolmethane triglycidyl ether (TPMTGE); (IF1)=OH; (EX1)=piperazine (PIPZ); (TF)=NH; G=0.5];
  [(C)=triphenylolmethane triglycidyl ether (TMPTGE); (FF)=Et; (IF1)=OH; (EX1)=piperazine (PIPZ); (TF)= NH; G=0.5];
  [(C)=pentaerythritol tetraglycidyl ether (PETGE); (IF1)= OH; (EX1) =piperazine (PIPZ); (TF)=NH; G=0.5];
  [(C)=pentaerythritol tetraglycidyl ether (PETGE); (IF1)= OH; (EX1) =piperazine (PIPZ); (EX2)=Acryloxymethyl; (TF)=tetramethylsilane (TMS); G=0.5];
  [(C)=pentaerythritol tetraglycidyl ether (PETGE); (IF1)= sulfonic acid; G=0.5];
  [(C)=trimethylolpropane triglycidyl ether (TMPTGE); (FF)=Et; (IF1)=OH; (BR1)=imino bis(methylphosphonic acid) (IMPA); (TF)=$PO_2Na$; G=1.5];
  [(C)=pentaerythritol tetraglycidyl ether (PETGE); (IF1)= OH; (EX1) =Triazole; (BR1)=pentaerythritol triglycidyl ether (PETriGE); (TF)=epoxide; G=1];
  [(C)=pentaerythritol tetraglycidyl ether (PETGE); (IF1)= OH; (BR1) =triazole; (TF)=$CO_2Me$; G=1.5];

[(C)=tetraphenylolethane glycidyl ether (TPEGE); (IF1)= OH; (BR1)=tris(hydroxymethyl)aminomethane (TRIS); (TF)=OH; G=1];
[(C)=tetraphenylolethane glycidyl ether (TPEGE); (IF1)= OH; (BR1)=diethyliminodiacetate (DEIDA); (TF)= $CO_2Et$; G=1.5];
[(C)=triphenylolmethane triglycidyl ether (TPMTGE); (FF)=H; (IF1)=OH; (BR1)=diethyliminodiacetate (DEIDA); (TF)=$CO_2Et$; G=1.5];
[(C)=tris(2,3-epoxypropyl)isocyanurate (TGIC); (IF1)= OH; (BR1) =bis(allyl)amine (BAA); (TF)=(=$CH_2$); G=1];
[(C)=pentaerythritol tetraglycidyl ether (PETGE); (IF1)= OH; (BR1)=bis(allyl)amine (BAA); (TF)=(=$CH_2$); G=1];
[(C)=triphenylolmethane triglycidyl ether (TPMTGE); (FF)=H; (IF1)=OH; (BR1)=diethanolamine (DEA); (TF)=OH; G=1];
[(C)=tetraphenylolethane glycidyl ether (TPEGE); (IF1)= OH; (BR1)=diethylenetriamine (DETA); (EX1)=dimethylitaconate (DMI); (TF)=$CO_2Me$; G=1.5];
[(C)=pentaerythritol tetraglycidyl ether (PETGE); (IF1)= OH; (BR1)=tris(2-aminoethyl)amine (TREN); (TF)= $NH_2$; G=1];
[(C)=tetraphenylolethane glycidyl ether (TPEGE); (IF1)= OH; (BR1)=methyl isobutyl protected 1-(2-aminoethyl) piperazine (PEA); (TF) =$NH_2$; G=1];
[(C)=pentaerythritol tetraglycidyl ether (PETGE); (IF1)= OH; (EX1)=dibenzylamine (DBA); (TF)=benzyl; G=1];
[(C)=pentaerythritol tetraglycidyl ether (PETGE); (IF1)= OH; (BR1)=N-(2-hydroxyethyl)ethylenediamine (AEEA); (TF)=$NH_2$; G=1];
[(C)=pentaerythritol tetraglycidyl ether (PETGE); (IF1)= OH; (EX1)=2-methyl-2-imidazoline (MIA); (TF)=imidazoline; G=1];
[(C)=pentaerythritol tetraglycidyl ether (PETGE); (IF1)= OH; (EX1)=Triazole; (BR1)=pentaerythritol triglycidyl ether (PETriGE); (IF2)=OH; (BR2)=diethanolamine (DEA); (TF)=OH; G=2];
[(C)=tetraphenylolethane glycidyl either (TPEGE); (IF1)= OH; (BR1)=diethylenetriamine (DETA); (EX1)=dimethylitaconate (DMI); (BR2)=tris(2-aminoethyl)amine (TREN); (TF)=$NH_2$;G=2];
[(C)=tetraphenylolethane glycidyl either (TPEGE); (IF1)= OH; (BR1)=diethylenetriamine (DETA); (EX1)=dimethylitaconate (DMI); (BR2)=tris(hydroxymethyl)aminomethane (TRIS); (TF)=OH; G=2];
[(C)=tetraphenylolethane glycidyl ether (TPEGE);(IF1)= OH; (BR1)=tris(2-aminoethyl)amine (TREN); (EX1)= Me acrylate; (TF)=$CO_2Na$; G=2.5];
[(C)=pentaerythritol tetraglycidyl ether (PETGE); (IF1)= OH; (EX1)=piperazine (PIPZ); (IF2)=OH; (BR1)= PETGE; (IF3)=OH; (EX2)=PIPZ; (TF)=NH; G=1.5];
[(C)=bis(2-piperazinylethyl)disulfide (BPEDS); (IF1)= OH; (BR1) =pentaerythritol tetraglycidyl ether (PETGE); (EX1)=methyl isobutyl protected 1-(2-aminoethyl)piperazine(PEA); (TF)=NH; G=1];
[(C)=pentaerythritol tetraglycidyl ether (PETGE); (IF1)= OH; (BR1)=tris(hydroxymethyl)aminomethane(TRIS); (TF)=OH; G=1];
[(C)=trimethylolpropane triglycidyl ether (TMPTGE); (FF)=Et; (IF1)=OH; (BR1)=diethyliminodiacetate (DEIDA); (BR2)=tris 2-aminoethyl)amine (TREN); (TF)=$NH_2$; G=2];
[(C)=pentaerythritol tetraglycidyl ether (PETGE); (IF1)= OH; (BR)=diethyliminodiacetate (DEIDA); (BR2)=tris(2-aminoethyl)amine (TREN); (EX1)=dimethylitaconate (DMI); (TF)=$CO_2Me$; G=2.5];
[(C)=tetraphenylolethane glycidyl ether (TPEGE); (IF1)= OH; (BR1)=diethylenetriamine (DETA); (TF)=$NH_2$; G=1];
[(C)=trimethylolpropane triglycidyl ether (TMPTGE); (FF)=Et; (IF1)=OH; (BR1)=diethyliminodiacetate (DEIDA); (BR2)=tris (2-aminoethyl)amine(TREN); (EX1)=dimethylitaconate (DMI); (TF)=$CO_2Me$; G=2.5];
[(C)=pentaerythritol tetraglycidyl ether (PETGE); (IF1)= OH; (BR1)=diethyliminodiacetate (DEIDA); (BR2)= tris(2-aminoethyl)amine (TREN); (TF)=$NH_2$; G=2];
[(C)=trimethylolpropane triglycidyl ether (TMPTGE); (FF)=H; (IF1)=OH; (BR1)=tris(hydroxymethyl)aminomethane (TRIS); (TF)=OH; G=1];
[(C)=tetraphenylolethane glycidyl ether (TPEGE); (IF1)= OH; (BR1)=tris(2-aminoethyl)amine (TREN); (EX)= Me acrylate; (BR2)=tris(hydroxymethyl)aminomethane (TRIS); (TF)=OH; G=3];
[(C)=tetraphenylolethane glycidyl ether (TPEGE); (IF1)= OH; (BR1)=tris(2-aminoethyl)amine (TREN); (EX1)= Me acrylate; (TF)=$CO_2Me$; G=2.5];
[(C)=pentaerythritol tetraglycidyl ether (PETGE); (IF1)= OH; (EX1)=piperazine (PIPZ); (IF2)=OH; (BR1)=pentaerythritol tetraglycidyl ether (PETGE); (IF3)=OH; (EX2)=PIPZ; (BR2)=glycidol; (TF)=OH; G=2];
[(C)=BPEDS; (IF)=OH; (BR1)=pentaerythritol tetraglycidyl ether (PETGE); (EX1)=methyl isobutyl protected 1-(2-aminoethyl)piperazine (PEA); (TF)=epoxy; G=1];
[(C)=BPEDS; (FF)=SH; (IF1)=OH; (BR1)=pentaerythritol tetraglycidyl ether (PETGE); (EX1)=methyl isobutyl protected 1-(2-aminoethyl) piperazine (PEA); (TF)= $NH_2$; G=1];
[(C)=pentaerythritol tetraglycidyl ether (PETGE); (IF1)= OH; (EX1)=methyl isobutyl protected 1-(2-aminoethyl) piperazine (PEA); (TF)=NH; G=1.5];
[(C)=tetraphenylolethane glycidyl ether (TPEGE); (IF1)= OH; (BR1)=tris(2-aminoethyl)amine (TREN);(TF)= $NH_2$; G=1]; and
[(C)=pentaerythritol tetraglycidyl ether (PETGE); (IF1)= OH; (BR1)=diethyliminodiacetate (DEIDA); (TF)= $CO_2Et$; G=1.5].

46. The dendritic polymer of claim 1 or 2 wherein the polymer has enhanced thermal stability, improved chemical stability, and/or a narrow polydispersity range.

47. The dendritic polymer of claim 1, 2 or 3 wherein a carried material (M) is associated with the dendritic polymer on either its interior or surface or both.

48. The dendritic polymer of claim 47 wherein the carried material (M) is associated with the interior (IF) moiety of the dendritic polymer.

49. The dendritic polymer of claim 48 wherein the carried material is a pharmaceutically active agent or pro-drug.

50. A formulation which comprises a dendritic polymer of claim 49 having at least one pharmaceutically-acceptable diluent or carrier present.

51. The dendritic polymer of claim 47 wherein the carried material is an agriculturally active agent.

52. A formulation which comprises a dendritic polymer of claim 51 having at least one agriculturally-acceptable diluent or carrier present.

53. The dendritic polymer of claim 1 wherein (FF) has x=$N_c$-1 and a dendron is formed.

54. A dendritic polymer of Formula (I) as claimed in any one of claims 1-3, 5, 6, 8, 10, 11, 13-17, 19, 21, 22, 23, 24, 26, 28, 29, 31, 32, 34, 38, 39, 48 and 53 for use as an energy and 55. A dendritic polymer of Formula (I) as claimed in any one of claims 1-3, 5, 6, 8, 10, 11, 13-17, 19, 21, 22, 23, 24, 26, 28, 29, 31, 32, 34, 38, 39, 48 and 53 for use as toner compositions either with solvent or dry formulations.

56. A dendritic polymer of Formula (I) as claimed in any one of claims 1-3, 5, 6, 8, 10, 11, 13-17, 19, 21, 22, 23, 24, 26, 28, 29, 31, 32, 34, 38, 39, 48 and 53 for use with dyes (such as anionic dyes, photochromic dyes, thermochromic dyes, liquid crystal), salts, antistatics, surfactants, antioxidants, solvents (such as water) or neat; and with other desired components to yield a precipitate free ink that can be deposited on paper or another printing surface; to coat or permeate synthetic and natural fibers useful in many applications for cloth, patterns in cloth, carpets, and other such items.

57. A dendritic polymer of Formula (I) as claimed in any one of claims 1-3, 5, 6, 8, 10, 11, 13-17, 19, 21, 22, 23, 24, 26, 28, 29, 31, 32, 34, 38, 39, 48 and 53 for use as a coating, caulking and filler formulations such as for paper, latex, pigments, polymers, fiberoptics, glass, metal surfaces, fiberglass, ceramics, rubber, wood, concrete, stone, fibers, and cloth.

58. A dendritic polymer of Formula (I) as claimed in any one of claims 1-3, 5, 6, 8, 10, 11, 13-17, 19, 21, 22, 23, 24, 26, 28, 29, 31, 32, 34, 38, 39, 48 and 53 for use as a coating for containers, stents, medical devices, catheters, implants, microarray slides, cell culture plates, electrodes and sensors.

59. A dendritic polymer of Formula (I) as claimed in any one of claims 1-3, 5, 6, 8, 10, 11, 13-17, 19, 21, 22, 23, 24, 26, 28, 29, 31, 32, 34, 38, 39, 48 and 53 for use as supports for use in separations or filtrations or in size calibrations.

60. A dendritic polymer of Formula (I) as claimed in any one of claims 1-3, 5, 6, 8, 10, 11, 13-17, 19, 21, 22, 23, 24, 26, 28, 29, 31, 32, 34, 38, 39, 48 and 53 for use as compositions for dental composites, photocurable materials, rheological modifiers, polymer adhesion agents, polymer additives, electromagnetic radiation absorbers, anticounterfeiting media, porosity modifiers, disinfectants, antibacterials, flavorings, deodorants, anti-amyloidogenic agents, to increase performance, reduce shrinkage, and/or improve adhesion.

61. A dendritic polymer of Formula (I) as claimed in any one of claims 1-3, 5, 6, 8, 10, 11, 13-17, 19, 21, 22, 23, 24, 26, 28, 29, 31, 32, 34, 38, 39, 48 and 53 for use as manufacturing computer memory systems, magnetic storage systems, and electronic and photonic transistors.

62. A dendritic polymer of Formula (I) as claimed in any one of claims 1-3, 5, 6, 8, 10, 11, 13-17, 19, 21, 22, 23, 24, 26, 28, 29, 31, 32, 34, 38, 39, 48 and 53 for use as carriers for metal ions, metal particles, magnetic and paramagnetic particles, alloys, catalysts, reuseable catalysts, metal cell foams, nanoreactors, semiconductor particles, and quantum dots.

63. A dendritic polymer of Formula (I) as claimed in any one of claims 48-50 and 53 for use as a carrier for a prodrug, drug (e.g., small organic drug, polymer drug, biomacromolecular drug, antirestinosis agent, cardiovascular agent, angiostatin, statin, antibacterial agent, antiviral agent, microbicide, amino acid, peptide, protein, oligonucleotides, nucleotides), vaccines, diagnostic agent, imaging agent, biomarker agent, oncology agent, ocular agent, nonsteriodal anti-inflammatory agent, antigen, vitamin, α-hydroxy acid, detoxification agent, and immunosuppressant agent.

64. A dendritic polymer of Formula (I) as claimed in any one of claims 1-3, 5, 6, 8, 10, 11, 13-17, 19, 21, 22, 23, 24, 26, 28, 29, 31, 32, 34, 38, 39, 48 and 53 for use as a biomarker, a molecular probe, a transfection reagent, or an environmental assay reagent in in vitro, ex vivo, or in vivo applications.

65. A dendritic polymer of Formula (I) as claimed in any one of claims 1-3, 5, 6, 8, 10, 11, 13-17, 19, 21, 22, 23, 24, 26, 28, 29, 31, 32, 34, 38, 39, 48-50 and 53 for use as personal care, cosmetic or neutraceutical carrier or additive.

66. A method of treating a disease in an animal which comprises administering to the animal an effective amount of a dendritic polymer of Formula (I) as claimed in any one of claims 1-3, 5, 6, 8, 10, 11, 13-17, 19, 21, 22, 23, 24, 26, 28, 29, 31, 32, 34, 38, 39, 48-50, and 53 or the pharmaceutically-acceptable salts thereof.

67. A method of coating a solid substrate with a solution containing a dendritic polymer of Formula (I) as claimed in any one of claims 1-3, 5, 6, 8, 10, 11, 13-17, 19, 21, 22, 23, 24, 26, 28, 29, 31, 32, 34, 38, 39, 48 and 53 which comprises dipping, spraying, spin-coating, wiping, or otherwise applying the solution of the dendritic polymer to the outer surface and exposed inner surface of the substrate, removing the substrate from contact with the solution, and allowing the excess solution to evaporate in air or heat dried.

68. The method of claim 67 wherein the solution contains a mixture of solvents, surfactant, emulsifier, and/or detergent to aid the coating process, and the weight of dendritic polymer in the solution is from about 0.0001% by weight to about 50% by weight.

69. A method of transfecting eukaryotic cells by electroporation or applying to the surface of the cells a solution comprising (a) a dendritic polymer of Formula (I) as claimed in any one of claims 1-3, 5, 6, 8, 10, 11, 13-17, 19, 21, 22, 23, 24, 26, 28, 29, 31, 32, 34, 38, 39, 48 and 53 where (TF) is sufficient to have a cationic dendritic surface at a concentration of about 1 picogram to 100 mg/mL and (b) the desired oligonucleotides or polynucleic acids, and exposing the cells to the solution for a sufficient time to allow transfection.

70. A method of delivering genetic material to eukaryotic cells of plants and animals with a gene gun comprising (a) a dendritic polymer of Formula (I) as claimed in any one of claims 1-3, 5, 6, 8, 10, 11, 13-17, 19, 21, 22, 23, 24, 26, 28, 29, 31, 32, 34, 38, 39, 48 and 53 where (TF) is sufficient to have a cationic dendritic surface and conjugating a Au, Ag, Cu, Mg, or Ca particle, gold sols, gold atoms, gold containing complexes or molecules, and clusters or mixtures thereof to form a polymer-metal conjugate, wherein the maximum dimension of the conjugate is from about 1 nm to about 1000 nm as (M) or (C) and (b) the desired genetic material, oligonucleotides or polynucleic acids, which forms a gene transfection particle; and accelerating the gene transfection particle toward a plant or animal cell with sufficient motive force to cause the gene transfection particle to penetrate and enter the cell.

71. A method of drug delivery, including therapeutic and/or diagnostic agents as drugs, to an animal using a dendritic polymer of Formula (I) as claimed in any one of claims 1-3, 5, 6, 8, 10, 11, 13-17, 19, 21, 22, 23, 24, 26, 28, 29, 31, 32, 34, 38, 39, 48 and 53 which comprises administering to an animal in need of such treatment, an effective amount of the drug in a pharmaceutically-acceptable excipient, carrier or diluent.

72. The method of claim 71 wherein the effective amount of drug is that known for that drug and the dose administered is the same as previously known or less to obtain the same effect from the drug.

73. The method of claim 71 wherein the drug and dendritic polymer are administered by an oral route, ampoule, intravenous injection, intramuscular injection, transdermal application, intranasal application, intraperitoneal administration, subcutaneous injection, ocular application, as wipes, sprays, gauze or other means for use at a surgical incision, near scar formation sites, or site of a tumor growth or removal or near or within a tumor.

74. A method of rheological modification of a polymer which comprises admixing the polymer, either neat or in a solvent, with a dendritic polymer of Formula (I) as claimed in any one of claims 1-3, 5, 6, 8, 10, 11, 13-17, 19, 21, 22, 23, 24, 26, 28, 29, 31, 32, 34, 38, 39, 48 and 53 in a polymer melt or solvent to modify the rheological properties of the first polymer in either the molten, solid, dissolved or dry phase by known methods and wherein (M) if present is a flame retardant, dye, UV absorber, antimicrobial agent, polymeric initiator, antistatic agent and/or antioxidant, and wherein the solution or dry mixture has a weight of dendritic polymer from about 0.0001% by weight to about 50% by weight.

75. A method of treating the skin, hair, and/or nails of an animal for cosmetic applications which comprises admixing a dendritic polymer of Formula (I) as claimed in any one of claims 1-3, 5, 6, 8, 10, 11, 13-17, 19, 21, 22, 23, 24, 26, 28, 29, 31, 32, 34, 38, 39, 48-50 and 53 in a cosmetic formulation by known methods for use as a lotion, cream, toner, powder or solvent, and then brushing, smoothing, rubbing or otherwise applying the formulation to the skin, hair and/or nails of the animal wherein the formulation contains the weight of dendritic polymer in the formulation from about 0.0001% by weight to about 50% by weight.

76. A method of calibrating a substrate which comprises preparing a solution (about 1 picogram/mL to about 100 mg/mL) of a dendritic polymer of Formula (I) as claimed in any one of claims 1-3, 5, 6, 8, 10, 11, 13-17, 21, 22, 23, 24, 26, 28, 29, 31, 32, 34, 38, 39, 48 and 53, applying the solution to a nanometer substrate for size comparison standards, and visualizing the substrate by optical, force or electron microscopy to reference the unknown substrate's size relative to the dendritic polymer and/or determining the pore size of the substrate or filter by determining which size dendritic polymer passes through the pore or filter of the substrate.

77. A method of applying a disinfectant to a surface which comprises spraying, wiping, or applying to the surface a dendritic polymer of Formula (I) as claimed in any one of claims 1-3, 5, 6, 8, 10, 11, 13-17, 19, 21, 22, 23, 24, 26, 28, 29, 31, 32, 34, 38, 39, and 53 as solution or in solvent, with or without the presence of other additives for (M) such as dyes, fragrances, antibacterials, surfactants and/or demulsifiers.

78. A kit comprising a dendritic polymer of Formula (I) as claimed in any one of claims 1-3, 5, 6, 8, 10, 11, 13-17, 19, 21, 22, 23, 24, 26, 28, 29, 31, 32, 34, 38, 39, 48 and 53 for use in an assay as a biomarker reagent, molecular probe, transfection reagent, or environmental assay reagent together with any other components required for such assay either in separate containers or obtained separately and with instructions on use.

79. A dendritic polymer of Formula (I) as claimed in claim 1 or 2 wherein the core (C) is a spherical shape and is reacted with four reagents having an (EX) or (BR) or both a (EX) and (BR) that are spherical shapes such that the following number of reagents can react:

$$R = \frac{1}{4}\sqrt{6} \cdot 2r - r = \left(\frac{1}{2}\sqrt{6} - 1\right)r \approx 0.225r \qquad \text{Equation 1}$$

Then $$r = \frac{R}{1/2\sqrt{6} - 1} = \frac{2}{\sqrt{6} - 2}R \approx 4.45R \qquad \text{Equation 2}$$

Where: r is radius of shell reagent; R is radius of core; the length of the sides of tetrahedron=2r; wherein maximum radius for the smaller ball that can fit in the center space can be calculated from equation 1 above; and as long as r≦4.45 R, there is enough space to put four or more shell reagents around the core.

80. A dendritic polymer of Formula (I) as claimed in claim 1 or 2 wherein the core (C) is a spherical shape and is reacted with four reagents of a conical shape having an (EX) or (BR) or both a (EX) and (BR) such that the following number of reagents can react:
Where, in the equations below:
R=radius of core
h=height of cone (shell reagents)
r=radius of cone (shell reagents) base=the in-radius of tetrahedron base
r'=in-radius of tetrahedron=R+h
a=length of side of tetrahedron $$r' = h + R = \frac{1}{12}\sqrt{6}\, a \qquad \text{Equation 1}$$

Then, $$a = 2\sqrt{6}\,(h + R) \qquad \text{Equation 2}$$

Thus, $$r = \frac{1}{6}\sqrt{3}\, a = \frac{1}{6}\sqrt{3} * 2\sqrt{6}\,(h + R) = \sqrt{2}\,(h + R) \qquad \text{Equation 3}$$

If, r≦√2(h+R), there will be enough space to put four or more shell reagents around the core.

81. A process for preparing the dendritic polymers of Formula (I) as defined in claim 1 which comprises:
A. Reacting, as a one pot reaction, (C) with reactive (BR) precursors (for example iminodiacetic acid, primary amine protected diethylenetriamine (DETA), iminodialkyl nitriles, iminodialkyl phosphonic acids, imino dialkyl halides [e.g. bis(2-chloroethyl)amine], diethanol amine, secondary diamines such as dialkylamines, diallylamines, diarylamines, iminodialkynes, iminoalkyleneamines [e.g., bis(hexamethylenetriamine)]) or preformed (BR) reagents [for example tris(2-aminoethyl) amine (TREN), tris(hydroxymethyl)aminomethane (TRIS), acetylene di- or tri-epoxy moieties], or hydroxy, mercapto or amino (FF) dendrons, in a solvent, at a temperature from about 0° to 100° C. until completion of the reaction, to provide the dendritic polymers of Formula (I) where m=0 and q=1-4000;
B. Reacting the dendritic polymer made in Step A by using orthogonal chemistry on the (TF) to add additional (BR) moieties to provide higher generations of homo/hetero compositional (BR) containing dendritic polymers of Formula (I), where m=0 or 1-2000 and q=1-4000;
C. Protecting, by ketone solvent protection, of either reactive (BR) precursors or (BR) possessing secondary and/or primary amines, allowing reaction of only secondary amine sites with reactive (C) or reactive (TF), or when only primary amines are present in the preformed (BR), one or more of these primary amine moieties may be protected with ketone solvent and the other unprotected primary amines may be allowed to react with appropriate (C) or (TF) to provide the dendritic polymers of Formula (I), where m=0 or 1-2000 and q=1 -4000;

D. Reacting the dendritic polymer made in Step A by nucleophilic reaction (Michael's addition) of an alkylamine with an alkyl acrylate (such as methyl acrylate) to form aminoalkyl ester linkages, followed by reaction of the ester with alkleneamines or (EX) or other (BR) of Formula (I) to provide the dendritic polymers of Formula (I), where m=0 or 1-2000 and q=14000;

E. Reacting the dendritic polymer made in Step A by converting either (C) or (BR) possessing primary amine (TF) groups into pyrrolidone ester groups by reaction with dimethylitaconate (DMI); followed by reaction of this ester with primary amines or partially protected primary polyamines to provide linkages to (BR) or (TF) moieties of Formula (I), to provide the dendritic polymers of Formula (I) where m=0 or 1 -2000 and q=14000;

F. Reacting the dendritic polymer made in Step A by free radical addition of thiol containing preformed (BR) reagents or reactive (BR) precursors to provide (C) or (BR) possessing allylic or olefinic groups of Formula (I), to provide the dendritic polymers of Formula (I), where m=0 or 1-2000 and q=14000;

G. Reacting, either by sequential or concurrent addition, by 1,3-dipolar cyclo-addition of (C) containing from 1 to $N_c$ azides or alkynes and (BR) containing from 1 to $N_b$–1 azides or alkynes where the (C) and (BR) have only one of an azide or alkyne present per (C) or (BR) and must have both an azide and alkyne present between them, and the azide containing (C) and (BR) are produced by nucleophilic ring-opening of epoxy rings with azide ions, followed by reaction of these reactive groups to provide triazole linkages to new (BR) or (TF) moieties of Formula (I), to provide the dendritic polymers of Formula (I) where m=1-2000 and q=0 or 1-4000; and H. Reacting (EX) as a part of Steps B-G to insert (EX) after any (BR) or (C) to provide the dendritic polymers of Formula (I), where m=1-2000.

82. A process to prepare the dendritic polymers of Formula (I) as defined in claim 1 or 2 by an acrylate-amine reaction system which comprises:
A. Reacting an acrylate functional core with an amine functional extender, such as shown below:

(C)+(EX)→(C)(EX)(TF)

where (C)=an acrylate functional core such as trimethylolpropane triacrylate (TMPTA); (EX)=an amine functional extender such as piperazine (PIPZ); and (TF)= amine; and B. Reacting an amine functional extended core reagent of (C) (EX) (TF1) with an acrylate functional branch cell reagent (BR) as shown below (C)(EX)(TF1)+(BR)→(C)(EX)(BR)(TF2)

where (C)=trimethylolpropane triacrylate (TMPTA); (EX)= piperazine (PIPZ); (TF1)=Amine; (BR)=trimethylolpropane triacrylate (TMPTA); and (TF2)=Acrylate; and wherein for both Steps A and B:
the addition of an extender (EX) group to a core, the mole ratio of (EX)/(C) is defined as the moles of extender molecules (EX) to the moles of reactive functional groups on the simple core, scaffolding core, super core, or current generation structure (i.e. $N_c$) where an excess of (EX) is used when full coverage is desired;
the addition of a branch cell (BR) to a simple core, scaffolding core, super core, or current generation structure (BR)/(C) is defined as the moles of branch cell molecules (BR) to the moles of reactive functional groups on the simple core, scaffolding core, super core, or current generation structure (i.e. $N_c$) where an excess of (BR) is used when full coverage is desired; and
the level of addition of branch cells (BR) or extenders (EX) to a core, scaffolding core, super core or current generational product can be controlled by the mole ratio added or by N-SIS.

83. A process to prepare the dendritic polymers of Formula (I) as defined in claim 1 or 2 by ring-opening reaction system which comprises:
A. Reacting an epoxy functional core with an amine functional extender, such as shown below:

(C)+(EX)→(C)(IF1)(EX)(TF1)

where (C)=an epoxy functional core such as pentaerythritol tetraglycidyl ether (PETGE); (IF1)=Internal hydroxyl (OH); (EX)=piperazine (PIPZ); (TF1)= Amine; and B. Reacting an amine functional extended core reagent (C) (IF1) (EX) (TF1) with an epoxy functional branch cell reagent such as shown below:

(C)(IF1)(EX)(TF1)+(BR)→(C)(IF1)(EX)(IF2)(BR) (TF2)

where (C)=pentaerythritol tetraglycidyl ether (PETGE); (IF1)=Internal functionality moiety as defined in claim 1 such as OH; (EX)=an extender moiety as defined in claim 1 such as piperazine (PIPZ); (TF1)=Amine; (BR)= an epoxy functional branch cell reagent such as pentaerythritol tetraglycidyl ether (PETGE); and (IF2)= Internal functionality moiety as defined in claim 1 such as OH; (TF2)=Amine; and wherein for both Steps A and B:
the addition of an extender (EX) group to a core, the mole ratio of (EX)/(C) is defined as the moles of extender molecules (EX) to the moles of reactive functional groups on the simple core, scaffolding core, super core, or current generation structure (i.e. $N_c$) where an excess of (EX) is used when full coverage is desired;
the addition of a branch cell (BR) to a simple core, scaffolding core, super core, or current generation structure (BR)/(C) is defined as the moles of branch cell molecules (BR) to the moles of reactive functional groups on the simple core, scaffolding core, super core, or current generation structure (i.e. $N_c$) where an excess of (BR) is used when full coverage is desired; and
the level of addition of branch cells (BR) or extenders (EX) to a core, scaffolding core, super core or current generational product can be controlled by the mole ratio added or by N-SIS.

84. A process to prepare the dendritic polymers of Formula (I) as defined in claim 81 wherein:
$N_c$=1 to 20; q=1 to 250; p=1 to 250; and m=1 to 250; and if more than 1 q, p, or m are present, the (IF), (BR), and (EX) moieties may be the same or different; and
(BR) or (EX) may occur alternately with the other moiety or sequentially with multiple groups of (BR) or (EX) occurring in succession.

85. A pharmacuetical preparation comprising a dendritic polymer of Formula (I) as claimed in any one of claims 1-3, 5, 6, 8, 10, 11, 13-17, 19, 21, 22, 23 24, 26, 28, 29, 31, 32, 34, 38, 39, 48-50 and 53 or the pharmaceutically-acceptable salts thereof.

86. The dendritic polymer of claim 1 wherein (G) is from 0 to 5.

* * * * *

UNITED STATES PATENT AND TRADEMARK OFFICE
CERTIFICATE OF CORRECTION

PATENT NO. : 7,985,424 B2
APPLICATION NO. : 11/630044
DATED : July 26, 2011
INVENTOR(S) : Donald A. Tomalia et al.

It is certified that error appears in the above-identified patent and that said Letters Patent is hereby corrected as shown below:

Column 290, line 4, claim 16, delete the word "tetraarylmethane";

Column 291, line 17, claim 23, change "moreof" to read -- more of --;

Column 291, line 47, claim 27, after the term "(BR)" insert the word -- moiety --;

Column 292, line 8, claim 29, change the words "derivatives,ethylenediamine" to read
-- derivatives, ethylenediamine --;

Column 292, line 36, claim 31, change the words "(TMS),isocyanato" to read -- (TMS), isocyanato --;

Column 292, line 37, claim 31, after the word "alkylazido" to read -- alkylazido, --;

Column 292, line 40, claim 31, change "methacrylate. Acrylamides," to read -- methylacrylate, acrylamides, --;

Column 292, line 43, claim 31, after the word "alkylthiols," insert the word -- thiols, --;

Column 294, line 21, claim 41, the terms "claim 1 or 2" should be changed to read -- claim 1 --;

Column 294, lines 58-59, claim 45, change only the terms in the name that read "(IF1 )=sulfonic acid;" to be corrected to read -- (IF1)=OH; (TF)=sulfonic acid; --;

Column 295, line 64, claim 45, in the term "(BR2)=tris 2-aminoethyl)amine" change that portion to read -- (BR2)=tris(2-aminoethyl)amine --;

Column 296, lines 28 and 31, change the portion that reads "[(C)=BPEDS;" to read
-- [(C)=bis(2-piperazinylethyl) disulfide (BPEDS); --;

Signed and Sealed this
Twenty-first Day of February, 2012

David J. Kappos
*Director of the United States Patent and Trademark Office*

CERTIFICATE OF CORRECTION (continued)
U.S. Pat. No. 7,985,424 B2

Column 297, line 4, claim 54, change the words "diodes,displays" to read -- diodes, displays --;

Column 297, line 16, claim 56, change the numbers "31,32" to read -- 31, 32 --;

Column 299, line 51, claim 77, after the number "39," insert the number -- 48 --;

Column 302, line 11, claim 83, change the word "system" to read -- systems --;

Column 302, line 25, claim 83, move the term "(TF2)" to the end of the formula on line 25 so the entire formula is together; and Column 302, line 60, claim 85, change the numbers "2324" to read -- 23, 24 --.